US009982045B2

(12) United States Patent
Bialucha et al.

(10) Patent No.: US 9,982,045 B2
(45) Date of Patent: May 29, 2018

(54) ANTI-CDH6 ANTIBODY DRUG CONJUGATES

(71) Applicants: Carl Uli Bialucha, Arlington, MA (US); Scott Collins, Quincy, MA (US); Clemens Dürr, Weil am Rhein (DE); Tiancen Hu, Cambridge, MA (US); Mary Jo Janatpour, Castro Valley, CA (US); Matthew John Meyer, Framingham, MA (US)

(72) Inventors: Carl Uli Bialucha, Arlington, MA (US); Scott Collins, Quincy, MA (US); Clemens Dürr, Weil am Rhein (DE); Tiancen Hu, Cambridge, MA (US); Mary Jo Janatpour, Castro Valley, CA (US); Matthew John Meyer, Framingham, MA (US)

(73) Assignee: Novartis AG, Basel (CH)

( * ) Notice: Subject to any disclaimer, the term of this patent is extended or adjusted under 35 U.S.C. 154(b) by 54 days.

(21) Appl. No.: 14/820,897

(22) Filed: Aug. 7, 2015

(65) Prior Publication Data

US 2016/0046711 A1 Feb. 18, 2016

Related U.S. Application Data

(60) Provisional application No. 62/036,382, filed on Aug. 12, 2014.

(51) Int. Cl.

| | |
|---|---|
| ***A61K 47/48*** | (2006.01) |
| ***C07K 16/28*** | (2006.01) |
| ***G01N 33/574*** | (2006.01) |
| ***A61K 45/06*** | (2006.01) |
| ***A61K 31/4738*** | (2006.01) |
| ***A61K 47/68*** | (2017.01) |
| *A61K 39/00* | (2006.01) |

(52) U.S. Cl.

CPC .......... *C07K 16/28* (2013.01); *A61K 31/4738* (2013.01); *A61K 45/06* (2013.01); *A61K 47/6803* (2017.08); *A61K 47/6849* (2017.08); *A61K 47/6889* (2017.08); *G01N 33/57492* (2013.01); *A61K 2039/505* (2013.01); *C07K 2317/21* (2013.01); *C07K 2317/34* (2013.01); *C07K 2317/40* (2013.01); *C07K 2317/55* (2013.01); *C07K 2317/56* (2013.01); *C07K 2317/73* (2013.01); *C07K 2317/92* (2013.01); *G01N 2333/705* (2013.01)

(58) Field of Classification Search

None

See application file for complete search history.

(56) References Cited

U.S. PATENT DOCUMENTS

| | | | |
|---|---|---|---|
| 3,896,111 | A | 7/1975 | Kupchan et al. |
| 4,137,230 | A | 1/1979 | Hamhimoto et al. |
| 4,151,042 | A | 4/1979 | Higashide et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 5,208,020 | A | 5/1993 | Chari et al. |
| 5,624,821 | A | 4/1997 | Winter |
| 5,648,260 | A | 7/1997 | Winter |
| 5,677,425 | A | 10/1997 | Bodmer |
| 6,165,745 | A | 12/2000 | Ward |
| 6,194,551 | B1 | 2/2001 | Idusogie |
| 6,333,410 | B1 | 12/2001 | Chari et al. |
| 6,411,163 | B1 | 6/2002 | Enriquez |
| 7,368,565 | B2 | 5/2008 | Chari et al. |
| 7,811,572 | B2 | 10/2010 | Dai et al. |
| 8,163,888 | B2 | 4/2012 | Steeves et al. |

(Continued)

FOREIGN PATENT DOCUMENTS

| | | |
|---|---|---|
| CU | 20150128 A7 | 5/2016 |
| WO | WO 00/42072 | 7/2000 |

(Continued)

OTHER PUBLICATIONS

Zhao et al., "Synthesis and Evalulation of Hydrophlic Linkers for Antibody-Maytansinoid Conjugates" Journal of Medicial Chemistry 54(10):3606-3623, May 26, 2011.
Yutaka Shimoyama et al., "Isolation and Sequence Analysis of Human Cadherin-6 Complementary DNA for the Full Coding Sequence and Its Expression in Human Carcinoma Cells1" Cancer Research 55(10):2206-2211, May 15, 1995.
Inoue et al., "Cadherin-6 Gene Regulatory Patterns in the Postnatal Mouse Brain" Molecular and Cellular Neuroscience 39(1):95-104, Sep. 2008.
Jessica A. Osterhout et al.,"Cadherin-6 Mediates Axon-Target Matching in a Non-Image-Forming Visual Circuit" Neuron 71(4):632-639, 2011.
Nakagawa et al., "Defects in Ultrasonic Vocalization of Cadherin-6 Knockout Mice" PLOS One 7(11):e349233, Nov. 2012.
Paul et al., "Cadherin-6: A New Prognostic Marker for Renal Cell Carcinoma" Journal of Urology 171:97-101, 2004.

(Continued)

*Primary Examiner* — Misook Yu
*Assistant Examiner* — Kauser M Akhoon
(74) *Attorney, Agent, or Firm* — David A. Carpenter

(57) ABSTRACT

The present invention relates to anti-CDH6 antibodies, antibody fragments, antibody drug conjugates, and their uses for the treatment of cancer.

20 Claims, 26 Drawing Sheets

(56) References Cited

U.S. PATENT DOCUMENTS

| | | | |
|---|---|---|---|
| 2003/0153043 | A1 | 8/2003 | Carr |
| 2006/0182750 | A1 | 8/2006 | Chari et al. |
| 2008/0145374 | A1 | 6/2008 | Steeves |
| 2011/0003969 | A1 | 1/2011 | Kellogg et al. |
| 2011/0166319 | A1 | 7/2011 | Dai et al. |
| 2012/0253021 | A1 | 10/2012 | Li et al. |
| 2012/0259100 | A1 | 10/2012 | Jin |

FOREIGN PATENT DOCUMENTS

| | | | |
|---|---|---|---|
| WO | 2005/001092 | 1/2005 | |
| WO | WO 2014/150937 | 9/2014 | |
| WO | WO 2014134483 A2 * | 9/2014 | ....... A61K 47/48384 |

OTHER PUBLICATIONS

Shimazui et al., "Expression of Cadherin-6 as a Novel Diagnostic Tool to Predict Prognosis of Patients with E-Cadherin-Absent Renal Cell Carcinoma" Clinical Cancer Research 4:2419-2424, Oct. 1998.

Sancisi et al., "Cadherin 6 Is a New RUNX2 Target in TGF-β Signalling Pathway" 8(9):e75489, Sep. 2013.

Kobel et al., "Ovarian Carcinoma Subtypes Are Different Diseases: Implications for Biomarker Studies" PLoS One 5 (12):e232, Dec. 2008.

Lambert, "Drug-Conjugated Monoclonal Antibodies for the Treatment of Cancer" Current Opinion in Pharmacology 5 (5):543-549, Oct. 2005.

Kawai et al., "Chemical Modification of Ansamitocins. III. Synthesis and Biological Effects of 3-Acyl Esters of Maytansinol" Chem Pharm Bull 32(9):3441-3451, 1984.

Chari et al., "Immunoconjugates Containing Novel Maytansinoids: Promising Anticancer Drugs" Cancer Research 52:127-131, Jan. 1, 1992.

Liu et al., "Eradication of Large Colon Tumor Xenografts by Targeted Delivery of Maytansinoids" Proc. Natl. Acad. Sci. 93(16):8618-8623, Aug. 1996.

Trouet et al., "A Covalent Linkage Between Daunorubicin and Proteins that is Stable in Serum and Reversible by Lysosomal Hydrolases, as Required for a Lysosomotropic Drug-Carrier Conjugate: in vitro and in vivo Studies" Proc. Natl. Acad.Sci. USA, 79(2):626-629, Jan. 1982.

Umemoto et al.,"Preparation and in Vitro Cytotoxicit of Methotrexazte-Anti-MM46 Monoclonal Antibody Conjugate Via an Oligopeptide Spacer" Int. J. Cancer 43:677-684, 1989.

Knappik et al., "Fully Synthetic Human Combinatorial Antibody Libraries (HuCAL) Based on Modular Consensus Frameworks and CDRs Randomized with Trinucleotides1" J. Mol. Biol. 296(1):57-86, 2000.

Prassler et al., "HuCAL Platinum, a Synthetic Fab Library Optimized for Sequence Diversity and Superior Performance in Mammalian Expression Systems" J Mol Biol. 413(1):261-278, 2011.

Rothe et al., "The Human Combinatorial Antibody Library HuCAL Gold Combines Diversification of All Six CDRs According to the Natural Immune System with a Novel Display Method for Efficient Selection of High-Affinity Antibodies" J Mol Biol. 376(4):1182-1200, 2008.

Lehar et al., "Synergistic Drug Combinations Tend to Improve Therapeutically Relevant Selectivity" Nature Biotechnology 27(7):659-666, 2009.

Zimmermann et al., "Multi-Target Therapeutics: When the Whole is Greater than the Sum of the Parts" Drug Discovery Today 12(1/2):34-42, Jan. 2007.

Saito et al., "Drug Delivery Strategy Utilizing Conjugation via Reversible Disulfide Linkages: Role and Site of Cellular Reducing Activities" Advanced Drug Delivery Reviews 55(2):199-215, Feb. 10, 2003.

Trail et al., "Monoclonal Antibody Drug Immunoconjugates for Targeted Treatment of Cancer" Cancer Immunol Immunother 52:328-337, 2003.

Payne, "Progress in Immunoconjugate Cancer Therapeutics" Cancer Cell 3(3):207-212, Mar. 2003.

Allen, "Ligand-Targeted Therapeutics in Anticancer Therapy" Nature Review Cancer 2:750-763, 2002.

Pastan and Kreitman, "Immunotoxins in Cancer Therapy" Current Opinion in Investigation Drugs 3(7):1089-1091, 2002.

Senter and Springer, "Selective Activation of Anticancer Prodrugs by Monoclonal Antibody—Enzyme Conjugates" Advanced Drug Delivery Reviews 52:247-264, 2001.

Chalmers et al., "Probing Protein Ligand Interactions by Automated Hydrogen/Deuterium Exchange Mass Spectrometry" *Anal Chem. 78*(4):1005-1014, 2006.

Cowtan, "The Buccaneer Software for Automated Model Building. 1. Tracing Protein Chains" *Acta Cryst. D62*(9):1002-1011, 2006.

Emsley and Cowtan, "Coot: Model-Building Tools for Molecular Graphics" *Acta Cryst. D60*:2126-2132, 2004.

Krissinel et al., "Inference of Macromolecular Assemblies from Crystalline State" *J. Mol. Biol. 372*:774-797, 2007.

McCoy et al., "Phaser Crystallographic Software" *J. Appl. Cryst. 40*:658-674, 2007.

Winn et al., "Overview of the CCP4 suite and current developments" *Acta. Cryst. D67*:235-242, 2011.

Woods et al., "High Resolution, High-Throughput Amide DeuteriumExchange-Mass Spectrometry (DXMS) Determination of Protein Binding Site Structure and Dynamics: Utility in Pharmaceutical Design" *Journal of Cellular Biochemistry S37*:89-98, 2001.

* cited by examiner

Determination of cellular binding EC50 of CDH6 IgGs by FACS on OVCAR3 cells

FIGURE 2

Epitope binning of anti-CDH6 antibodies using competitive binding assay on Biacore

| | NOV1126 | NOV1127 | NOV1132 | NOV0692 | NOV0710 | NOV0712 | NOV0719 |
|---|---|---|---|---|---|---|---|
| NOV1126 | 8.59 | 16.47 | 23.7 | 7.829 | 15 | 9.506 | 25.42 |
| NOV1127 | 56.62 | 36.74 | 39.28 | 50.79 | 32.73 | 24.73 | 46.9 |
| NOV1132 | 30.06 | 17.82 | 1.08 | 23.2 | 10.62 | 6.004 | 20.71 |
| NOV0692 | 18.7 | 25.45 | 17.87 | -2.84 | 8.84 | 5.12 | 13.48 |
| NOV0710 | 36.93 | 30.92 | 17.84 | 17.89 | -3.562 | -3.264 | 16.15 |
| NOV0712 | 26.66 | 22.38 | 14.3 | 14.14 | -2.167 | -1.821 | 11.05 |
| NOV0719 | 61.59 | 51.5 | 33.65 | 35.53 | 21.94 | 16.48 | -2.356 |

hCDH6(54-615) ion-exchange data summary

Overlay of CDH6 EC5/NOV0712 and CDH6 EC5/NOV0710 complex structures onto the full-length ECD structure of CDH2 by superposition of EC5 domains. The lighter-colored ribbon is NOV0710, the darker one is NOV0712

<u>Upper panel:</u> Structure of NOV0712 binding to CDH6. Upper panel: overall structure of NOV0712 binding to CDH6 EC5 (left) and detailed view of NOV0712 epitope residues on CDH6 (right, shown as sticks and labeled). <u>Lower panel:</u> NOV0712 binds the majority of a Ca2+-binding loop in CDH6 EC5 (residues 571-579) and induces an "out" conformation of the loop Upper panel: Structure of NOV0710 binding to CDH6. Upper panel: overall structure of NOV0710 binding to CDH6 EC5 (left) and detailed view of NOV0710 epitope residues on CDH6 (right, shown as sticks and labeled). Lower panel: NOV0710 binds the majority of a Ca2+-binding loop in CDH6 EC5 (residues 571-579) and induces an "out" conformation of the loop ELISA assay to evaluate binding of CDH6 antibodies to wild-type and mutant forms of CDH6

FIGURE 8

Cellular binding of of CDH6-targeting antibodies in either non-conjugated form or as a sulfo-SPDB-DM4 antibody drug conjugate in a panel of CHO cell lines expressing either human, cynomolgus, rat or mouse CDH6

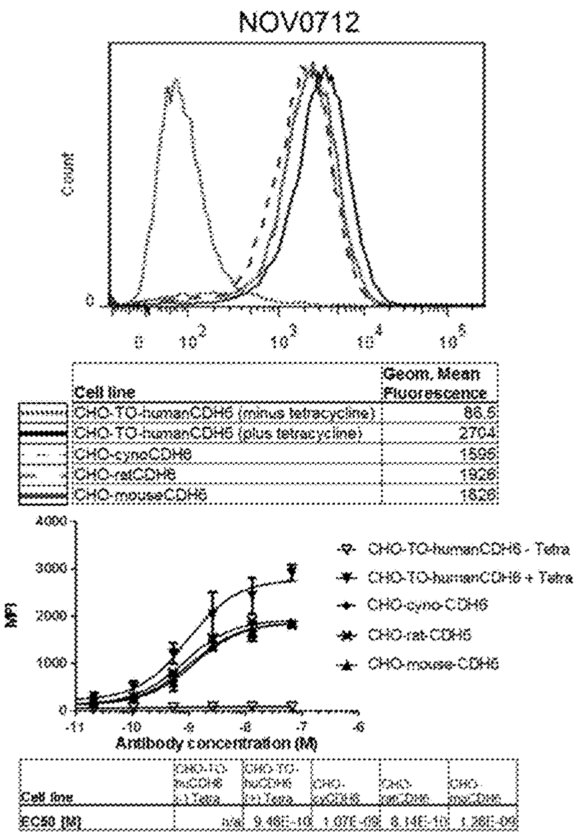

| Cell line | Geom. Mean Fluorescence |
|---|---|
| CHO-TO-humanCDH6 (minus tetracycline) | 86.5 |
| CHO-TO-humanCDH6 (plus tetracycline) | 2704 |
| CHO-cynoCDH6 | 1596 |
| CHO-ratCDH6 | 1926 |
| CHO-mouseCDH6 | 1826 |

| Cell line | CHO-TO-huCDH6 (-) Tetra | CHO-TO-huCDH6 (+) Tetra | CHO-cyCDH6 | CHO-ratCDH6 | CHO-msCDH6 |
|---|---|---|---|---|---|
| EC50 [M] | n/a | 9.46E-10 | 1.07E-09 | 8.14E-10 | 1.28E-09 |

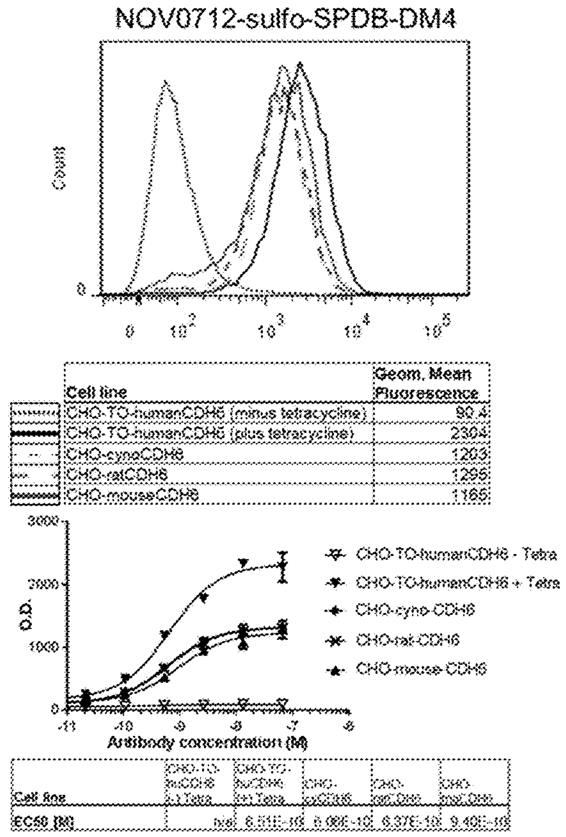

| Cell line | Geom. Mean Fluorescence |
|---|---|
| CHO-TO-humanCDH6 (minus tetracycline) | 90.4 |
| CHO-TO-humanCDH6 (plus tetracycline) | 2304 |
| CHO-cynoCDH6 | 1203 |
| CHO-ratCDH6 | 1295 |
| CHO-mouseCDH6 | 1166 |

| Cell line | CHO-TO-huCDH6 (-) Tetra | CHO-TO-huCDH6 (+) Tetra | CHO-cyCDH6 | CHO-ratCDH6 | CHO-msCDH6 |
|---|---|---|---|---|---|
| EC50 [M] | n/a | 6.51E-10 | 6.08E-10 | 6.37E-10 | 9.40E-10 |

FACS analysis of CDH6 expression in ovarian cancer cell lines OVCAR3, OVCAR3_CDH6_shRNA, OVCAR8 and OVCAR8_engineered_CDH6+

Cellular binding of of CDH6-targeting antibodies or control IgG in either non-conjugated form or as a sulfo-SPDB-DM4 antibody drug conjugate in a panel of ovarian cancer cell lines In vitro cellular activity of anti-CDH6 ADCs as SMCC-DM1 and SPDB-DM4 conjugates on ovarian cancer cell lines In vitro cellular activity of CDH6-targeting antibodies or control IgG in either non-conjugated form or as a sulfo-SPDB-DM4 antibody drug conjugate

| | IC50 [nM] | | |
|---|---|---|---|
| Treatment | OVCAR3 | OVCAR8 | OVCAR8-CDH6+ |
| NOV0712-sulfo-SPDB-DM4 | 1.28E-03 | 1.65E+01 | 5.28E-03 |
| NOV0712 | >333 | >333 | >333 |
| hIgG1 | >333 | >333 | >333 |
| hIgG1-sulfo-SPDB-DM4 | 3.34E-01 | 1.88E+01 | 1.48E+01 |

In vivo efficacy of anti-CDH6 antibodies as SMCC-DM1 conjugates in a xenograft mouse model of ovarian cancer In vivo efficacy of anti-CDH6 antibodies as SMCC-DM1 conjugates in a xenograft mouse model of ovarian cancer In vivo efficacy of anti-CDH6 antibodies as SPDB-DM4 conjugates in a xenograft mouse model of ovarian cancer In vivo efficacy of anti-CDH6 antibodies as SPDB-DM4 and SMCC-DM1 conjugates in a xenograft mouse model of ovarian cancer In vivo efficacy of anti-CDH6 ADCs with different linker/payload formats in a patient-derived primary tumor xenograft mouse model of ovarian cancer (serous carcinoma)

In vivo efficacy of anti-CDH6 ADCs with different linker/payload formats in a xenograft mouse model of ovarian cancer In vivo efficacy of anti-CDH6 ADCs with different linker/payload formats in a patient-derived primary tumor xenograft mouse model of ovarian cancer (serous carcinoma)

In vivo efficacy of an anti-CDH6 ADC (NOV0712-sulfo-SPDB-DM4; 5 mg/kg Q14D, i.v.) in a panel of patient-derived primary tumor xenograft mouse models of ovarian cancer In vivo efficacy of an anti-CDH6 ADC (NOV0712-sulfo-SPDB-DM4), dosed either at 2.5 mg/kg Q14D or 5 mg/kg Q14D in a patient-derived primary tumor xenograft mouse model of renal cancer (renal cell carcinoma)

In vivo efficacy of an anti-CDH6 ADC (NOV0712-sulfo-SPDB-DM4), dosed either at 2.5 mg/kg, Q14D or 5 mg/kg Q14D in a patient-derived primary tumor xenograft mouse model of renal cancer (metastatic lesion of renal cell carcinoma, clear cell type)

In vivo efficacy of an anti-CDH6 ADC (NOV0712-sulfo-SPDB-DM4), dosed either at 2.5 mg/kg, Q14D or 5 mg/kg Q14D in a patient-derived primary tumor xenograft mouse model of renal cancer (renal cell carcinoma, clear cell type)

FIGURE 24

Evidence for combination activity of CDH6-targeting ADCs with BCL2/BCL-Xl, BCL-Xl, IAP and MEK inhibitors

| Combination | Loewe Synergy Score | Loewe Excess Average |
|---|---|---|
| CDH6-ADC + CDH6-ADC | 7.79 | 0.078 |
| ABT-263 + ABT-263 | 6.04 | 0.055 |
| WEHI-539 + WEHI-539 | 3.30 | 0.079 |
| NVP-LCL161 + NVP-LCL161 | 0.0 | -0.660 |
| CDH6-ADC + ABT-263 | **41** | **0.364** |
| CDH6-ADC + WEHI-539 | **31.3** | **0.316** |
| CDH6-ADC + NVP-LCL161 | **17.9** | **0.187** |
| CDH6-ADC + trametinib | **26.9** | **0.258** |

CDH6 mRNA expression highlights ovarian cancer, renal cancer, soft tissue cancer, CNS cancers and thyroid cancer as indications with CDH6 over-expression CDH6 protein expression analysis by immuno-histochemistry (IHC) highlights ovarian cancer, endometrial cancer, renal cancer and cholangiocarcinoma as indications with frequent over-expression

ANTI-CDH6 ANTIBODY DRUG CONJUGATES

FIELD OF THE INVENTION

The present disclosure is directed to anti-CDH6 antibodies, antibody fragments, antibody drug conjugates, and their uses for the treatment of cancer.

BACKGROUND OF THE INVENTION

Cadherins are a family of cell adhesion molecules involved in cell-cell contact. There are more than 30 cadherin molecules in the family which consists of subclasses with individual binding specificities. There are well studied classic cadherins such as epithelial (E) cadherin, neural (N) cadherin and placental (P) cadherin which play key roles in the development and maintenance of tissues such as the epithelium. The cadherin family has also been classified by their amino acid similarities, which separate the cadherins into two groups, type I and type II. Then there are tissue specific cadherins such as cadherin-6 (CDH6).

CDH6 was first cloned and characterized in 1995 (Shimoyama et al., Cancer Res. 1995: 55 (10)2206-2211). The CDH6 cDNA isolated by Shimoyama was 4315 nucleotides and coded for a cadherin protein of 790 amino acids and exhibited 97% homology with rat K-cadherin (Shimoyama, supra). CDH6 is a type II cadherin with five extracellular cadherin repeats, a transmembrane domain and a cytoplasmic domain. In probing for normal tissue expression, CDH6 was detected in brain, cerebellum and kidney, with weaker expression in the lung, pancreas and gastric mucosa. In the nervous system, CDH6 was found to demarcate the auditory and somatosensory systems (Inoue et al., Mol. Cell Neuro. 2008: (39) 95-104). It was demonstrated that CDH6 is expressed by a subset of retinal ganglion cells (RGCs) in the eye responsible for such vision qualities as brightness, direction of motion or edges (Osterhout et al., Neuron 2011: 71(4)632-639). In the CDH6 knockout mouse, the absence of CDH6 cause loss of axon targeting. The CDH6 mutant axons elongated properly and were appropriately guided to their targets, but then grew through and past their connections (Osterhout, supra). In another study, CDH6 knockout mice demonstrated defects in vocalization (Nakagawa et al., PLOS 2012: 7(11) e49233).

Turning to its expression in cancer, the CDH6 cDNA was cloned from a hepatocellular carcinoma cell line, which was an early indication it may be involved in this type of cancer (Shimoyama, supra). The early work found CDH6 expression in several hepatoma lines, but no expression in normal liver. In later work, a group analyzed 216 patients with renal cell carcinoma and found that CDH6 expression correlated with this type of cancer (Paul et al., J Urology 2004 (171): 97-101). Shimazui found that renal cell carcinoma patients who expressed CDH6 and lacked E-cadherin expression had a poor prognosis (Shimazui et al., Clin. Cancer Res. 1998 (4): 2419-2424). It was also discovered that CDH6 was a TGF-B target and plays a role in thyroid cancer (Sancisi et al., PLoS One 2013; 8(9): e75489). Lastly, CDH6 was shown to be a biomarker for ovarian cancer (Kobel et al., PLoS One 2008 5(12): e232).

Antibody drug conjugates ("ADCs") have been used for the local delivery of cytotoxic agents in the treatment of cancer (see e.g., Lambert, Curr. Opinion In Pharmacology 5:543-549, 2005). ADCs allow targeted delivery of the drug moiety where maximum efficacy with minimal toxicity may be achieved. As more ADCs show promising clinical results, there is an increased need to develop new therapeutics for cancer therapy.

SUMMARY OF THE INVENTION

An antibody drug conjugate of the formula:

$$Ab\text{-}(L\text{-}(D)_m)_n$$

or a pharmaceutically acceptable salt thereof; wherein

Ab is an antibody or antigen binding fragment thereof that specifically binds to an epitope of human CDH6;

L is a linker;

D is a drug moiety;

m is an integer from 1 to 8; and n is an integer from 1 to 10.

The antibody drug conjugate according of any of the preceding embodiments, wherein said n is 3 or 4.

The antibody drug conjugate of any of the preceding embodiments, wherein said antibody or antigen binding fragment thereof specifically binds the extracellular domain of CDH6 (SEQ ID NO:4).

The antibody drug conjugate of any of the preceding embodiments, wherein said antibody or antigen binding fragment specifically binds to an epitope of human CDH6 at SEQ ID NO:534.

The antibody drug conjugate of any of the preceding embodiments, wherein said antibody or antigen binding fragment thereof comprises:

(i) a light chain variable region that comprises (a) a LCDR1 (CDR-Complementarity Determining Region) of SEQ ID NO:224, (b) a LCDR2 of SEQ ID NO:225, (c) a LCDR3 of SEQ ID NO:226; and a heavy chain variable region that comprises: (d) a HCDR1 of SEQ ID NO: 227, (e) a HCDR2 of SEQ ID NO: 228, and (f) a HCDR3 of SEQ ID NO:229;

(ii) a light chain variable region that comprises (a) a LCDR1 (CDR-Complementarity Determining Region) of SEQ ID NO:210, (b) a LCDR2 of SEQ ID NO:211, (c) a LCDR3 of SEQ ID NO:212; and a heavy chain variable region that comprises: (d) a HCDR1 of SEQ ID NO:213, (e) a HCDR2 of SEQ ID NO: 214, and (f) a HCDR3 of SEQ ID NO:215;

(iii) a light chain variable region that comprises (a) a LCDR1 (CDR-Complementarity Determining Region) of SEQ ID NO:266, (b) a LCDR2 of SEQ ID NO:267, (c) a LCDR3 of SEQ ID NO:268; and a heavy chain variable region that comprises: (d) a HCDR1 of SEQ ID NO: 269, (e) a HCDR2 of SEQ ID NO:270, and (f) a HCDR3 of SEQ ID NO: 271;

(iv) a light chain variable region that comprises (a) a LCDR1 (CDR-Complementarity Determining Region) of SEQ ID NO:308, (b) a LCDR2 of SEQ ID NO:309, (c) a LCDR3 of SEQ ID NO:310; and a heavy chain variable region that comprises: (d) a HCDR1 of SEQ ID NO:311, (e) a HCDR2 of SEQ ID NO:312, and (f) a HCDR3 of SEQ ID NO:313;

(v) a light chain variable region that comprises (a) a LCDR1 (CDR-Complementarity Determining Region) of SEQ ID NO:14, (b) a LCDR2 of SEQ ID NO:15, (c) a LCDR3 of SEQ ID NO:16; and a heavy chain variable region that comprises: (d) a HCDR1 of SEQ ID NO:17, (e) a HCDR2 of SEQ ID NO:18, and (f) a HCDR3 of SEQ ID NO:19;

(vi) a light chain variable region that comprises (a) a LCDR1 (CDR-Complementarity Determining Region) of SEQ ID NO:28, (b) a LCDR2 of SEQ ID NO:29, (c) a LCDR3 of SEQ ID NO:30; and a heavy chain variable region that comprises: (d) a HCDR1 of SEQ ID NO:31, (e) a HCDR2 of SEQ ID NO:32, and (f) a HCDR3 of SEQ ID NO:33;

(vii) a light chain variable region that comprises (a) a LCDR1 (CDR-Complementarity Determining Region) of SEQ ID NO:42, (b) a LCDR2 of SEQ ID NO:43, (c) a LCDR3 of SEQ ID NO:44; and a heavy chain variable region that comprises: (d) a HCDR1 of SEQ ID NO:45, (e) a HCDR2 of SEQ ID NO:46, and (f) a HCDR3 of SEQ ID NO:47;

(viii) a light chain variable region that comprises (a) a LCDR1 (CDR-Complementarity Determining Region) of SEQ ID NO:56, (b) a LCDR2 of SEQ ID NO:57, (c) a LCDR3 of SEQ ID NO:58; and a heavy chain variable region that comprises: (d) a HCDR1 of SEQ ID NO:59, (e) a HCDR2 of SEQ ID NO:60, and (f) a HCDR3 of SEQ ID NO:61;

(ix) a light chain variable region that comprises (a) a LCDR1 (CDR-Complementarity Determining Region) of SEQ ID NO:70, (b) a LCDR2 of SEQ ID NO:71, (c) a LCDR3 of SEQ ID NO:72; and a heavy chain variable region that comprises: (d) a HCDR1 of SEQ ID NO:73, (e) a HCDR2 of SEQ ID NO:74, and (f) a HCDR3 of SEQ ID NO:75;

(x) a light chain variable region that comprises (a) a LCDR1 (CDR-Complementarity Determining Region) of SEQ ID NO:84, (b) a LCDR2 of SEQ ID NO:85, (c) a LCDR3 of SEQ ID NO:86; and a heavy chain variable region that comprises: (d) a HCDR1 of SEQ ID NO:87, (e) a HCDR2 of SEQ ID NO: 88, and (f) a HCDR3 of SEQ ID NO: 89;

(xi) a light chain variable region that comprises (a) a LCDR1 (CDR-Complementarity Determining Region) of SEQ ID NO:98, (b) a LCDR2 of SEQ ID NO:99, (c) a LCDR3 of SEQ ID NO:100; and a heavy chain variable region that comprises: (d) a HCDR1 of SEQ ID NO:101, (e) a HCDR2 of SEQ ID NO:102, and (f) a HCDR3 of SEQ ID NO:103;

(xii) a light chain variable region that comprises (a) a LCDR1 (CDR-Complementarity Determining Region) of SEQ ID NO:112, (b) a LCDR2 of SEQ ID NO:113, (c) a LCDR3 of SEQ ID NO:114; and a heavy chain variable region that comprises: (d) a HCDR1 of SEQ ID NO:115, (e) a HCDR2 of SEQ ID NO:116, and (f) a HCDR3 of SEQ ID NO:117;

(xiii) a light chain variable region that comprises (a) a LCDR1 (CDR-Complementarity Determining Region) of SEQ ID NO:126, (b) a LCDR2 of SEQ ID NO:127, (c) a LCDR3 of SEQ ID NO:128; and a heavy chain variable region that comprises: (d) a HCDR1 of SEQ ID NO:129, (e) a HCDR2 of SEQ ID NO:130, and (f) a HCDR3 of SEQ ID NO:131;

(xiv) a light chain variable region that comprises (a) a LCDR1 (CDR-Complementarity Determining Region) of SEQ ID NO:140, (b) a LCDR2 of SEQ ID NO:141, (c) a LCDR3 of SEQ ID NO:142; and a heavy chain variable region that comprises: (d) a HCDR1 of SEQ ID NO:143, (e) a HCDR2 of SEQ ID NO:144, and (f) a HCDR3 of SEQ ID NO:145;

(xv) a light chain variable region that comprises (a) a LCDR1 (CDR-Complementarity Determining Region) of SEQ ID NO:154, (b) a LCDR2 of SEQ ID NO:155, (c) a LCDR3 of SEQ ID NO:156; and a heavy chain variable region that comprises: (d) a HCDR1 of SEQ ID NO:157, (e) a HCDR2 of SEQ ID NO:158, and (f) a HCDR3 of SEQ ID NO:159;

(xvi) a light chain variable region that comprises (a) a LCDR1 (CDR-Complementarity Determining Region) of SEQ ID NO:168, (b) a LCDR2 of SEQ ID NO:169, (c) a LCDR3 of SEQ ID NO:170; and a heavy chain variable region that comprises: (d) a HCDR1 of SEQ ID NO:171, (e) a HCDR2 of SEQ ID NO:172, and (f) a HCDR3 of SEQ ID NO:173;

(xvii) a light chain variable region that comprises (a) a LCDR1 (CDR-Complementarity Determining Region) of SEQ ID NO:182, (b) a LCDR2 of SEQ ID NO:183, (c) a LCDR3 of SEQ ID NO:184; and a heavy chain variable region that comprises: (d) a HCDR1 of SEQ ID NO:185, (e) a HCDR2 of SEQ ID NO:186, and (f) a HCDR3 of SEQ ID NO:187;

(xviii) a light chain variable region that comprises (a) a LCDR1 (CDR-Complementarity Determining Region) of SEQ ID NO:196, (b) a LCDR2 of SEQ ID NO:197, (c) a LCDR3 of SEQ ID NO:198; and a heavy chain variable region that comprises: (d) a HCDR1 of SEQ ID NO:199, (e) a HCDR2 of SEQ ID NO:200, and (f) a HCDR3 of SEQ ID NO:201;

(xix) a light chain variable region that comprises (a) a LCDR1 (CDR-Complementarity Determining Region) of SEQ ID NO:238, (b) a LCDR2 of SEQ ID NO:239, (c) a LCDR3 of SEQ ID NO:240; and a heavy chain variable region that comprises: (d) a HCDR1 of SEQ ID NO:241, (e) a HCDR2 of SEQ ID NO:242, and (f) a HCDR3 of SEQ ID NO:243;

(xx) a light chain variable region that comprises (a) a LCDR1 (CDR-Complementarity Determining Region) of SEQ ID NO:252, (b) a LCDR2 of SEQ ID NO:253, (c) a LCDR3 of SEQ ID NO:254; and a heavy chain variable region that comprises: (d) a HCDR1 of SEQ ID NO:255, (e) a HCDR2 of SEQ ID NO:256, and (f) a HCDR3 of SEQ ID NO:257;

(xxi) a light chain variable region that comprises (a) a LCDR1 (CDR-Complementarity Determining Region) of SEQ ID NO:280, (b) a LCDR2 of SEQ ID NO:281, (c) a LCDR3 of SEQ ID NO:282; and a heavy chain variable region that comprises: (d) a HCDR1 of SEQ ID NO:283, (e) a HCDR2 of SEQ ID NO:284, and (f) a HCDR3 of SEQ ID NO:285;

(xxii) a light chain variable region that comprises (a) a LCDR1 (CDR-Complementarity Determining Region) of SEQ ID NO:294, (b) a LCDR2 of SEQ ID NO:295, (c) a LCDR3 of SEQ ID NO:296; and a heavy chain variable region that comprises: (d) a HCDR1 of SEQ ID NO:297, (e) a HCDR2 of SEQ ID NO:298, and (f) a HCDR3 of SEQ ID NO:299; or (xxiii) a light chain variable region that comprises (a) a LCDR1 (CDR-Complementarity Determining Region) of SEQ ID NO:322, (b) a LCDR2 of SEQ ID NO:323, (c) a LCDR3 of SEQ ID NO:324; and a heavy chain variable region that comprises: (d) a HCDR1 of SEQ ID NO:325, (e) a HCDR2 of SEQ ID NO:326, and (f) a HCDR3 of SEQ ID NO:327.

The antibody drug conjugate of any of the preceding embodiments, in which at least one amino acid within a CDR is substituted by a corresponding residue of a corresponding CDR of another anti-CDH6 antibody in Table 5 or 6.

The antibody drug conjugate of any of the preceding embodiments, in which one or two amino acids within a CDR have been modified, deleted or substituted.

The antibody drug conjugate of any of the preceding embodiments, wherein said antibody or antigen binding fragment thereof comprises:

(i) a heavy chain variable region (vH) that comprises SEQ ID NO: 230, and a light chain variable region (vL) that comprises SEQ ID NO:231;

(ii) a heavy chain variable region (vH) that comprises SEQ ID NO: 216, and a light chain variable region (vL) that comprises SEQ ID NO:217;

(iii) a heavy chain variable region (vH) that comprises SEQ ID NO: 272, and a light chain variable region (vL) that comprises SEQ ID NO:273;

(iv) a heavy chain variable region (vH) that comprises SEQ ID NO:314, and a light chain variable region (vL) that comprises SEQ ID NO:315;

(v) a heavy chain variable region (vH) that comprises SEQ ID NO:20, and a light chain variable region (vL) that comprises SEQ ID NO:21;

(vi) a heavy chain variable region (vH) that comprises SEQ ID NO: 34, and a light chain variable region (vL) that comprises SEQ ID NO:35;

(vii) a heavy chain variable region (vH) that comprises SEQ ID NO:48, and a light chain variable region (vL) that comprises SEQ ID NO:49;

(viii) a heavy chain variable region (vH) that comprises SEQ ID NO:62, and a light chain variable region (vL) that comprises SEQ ID NO:63;

(ix) a heavy chain variable region (vH) that comprises SEQ ID NO:76, and a light chain variable region (vL) that comprises SEQ ID NO:77;

(x) a heavy chain variable region (vH) that comprises SEQ ID NO:90, and a light chain variable region (vL) that comprises SEQ ID NO:91;

(xi) a heavy chain variable region (vH) that comprises SEQ ID NO:104, and a light chain variable region (vL) that comprises SEQ ID NO:105;

(xii) a heavy chain variable region (vH) that comprises SEQ ID NO: 118, and a light chain variable region (vL) that comprises SEQ ID NO:119;

(xiii) a heavy chain variable region (vH) that comprises SEQ ID NO: 132, and a light chain variable region (vL) that comprises SEQ ID NO:133;

(xiv) a heavy chain variable region (vH) that comprises SEQ ID NO: 146, and a light chain variable region (vL) that comprises SEQ ID NO:147;

(xv) a heavy chain variable region (vH) that comprises SEQ ID NO:160, and a light chain variable region (vL) that comprises SEQ ID NO:161;

(xvi) a heavy chain variable region (vH) that comprises SEQ ID NO: 174, and a light chain variable region (vL) that comprises SEQ ID NO:175;

(xvii) a heavy chain variable region (vH) that comprises SEQ ID NO: 188, and a light chain variable region (vL) that comprises SEQ ID NO:189;

(xviii) a heavy chain variable region (vH) that comprises SEQ ID NO: 202, and a light chain variable region (vL) that comprises SEQ ID NO:203;

(xix) a heavy chain variable region (vH) that comprises SEQ ID NO: 244, and a light chain variable region (vL) that comprises SEQ ID NO:245;

(xx) a heavy chain variable region (vH) that comprises SEQ ID NO:258, and a light chain variable region (vL) that comprises SEQ ID NO:259;

(xxi) a heavy chain variable region (vH) that comprises SEQ ID NO:286, and a light chain variable region (vL) that comprises SEQ ID NO:287;

(xxii) a heavy chain variable region (vH) that comprises SEQ ID NO:300, and a light chain variable region (vL) that comprises SEQ ID NO:301; or (xxiii) a heavy chain variable region (vH) that comprises SEQ ID NO:328, and a light chain variable region (vL) that comprises SEQ ID NO:329.

The antibody drug conjugate of any of the preceding embodiments, wherein said antibody or antigen binding fragment thereof comprises:

(i) a heavy chain that comprises SEQ ID NO: 234, and a light chain that comprises SEQ ID NO:235;

(ii) a heavy chain that comprises SEQ ID NO: 220, and a light chain that comprises SEQ ID NO:221;

(iii) a heavy chain that comprises SEQ ID NO: 276, and a light chain that comprises SEQ ID NO:277;

(iv) a heavy chain that comprises SEQ ID NO:318, and a light chain that comprises SEQ ID NO:319;

(v) a heavy chain that comprises SEQ ID NO:24, and a light chain that comprises SEQ ID NO:25;

(vi) a heavy chain that comprises SEQ ID NO: 38, and a light chain that comprises SEQ ID NO:39;

(vii) a heavy chain that comprises SEQ ID NO:52, and a light chain that comprises SEQ ID NO:53;

(viii) a heavy chain that comprises SEQ ID NO:66, and a light chain that comprises SEQ ID NO:67;

(ix) a heavy chain that comprises SEQ ID NO:80, and a light chain that comprises SEQ ID NO:81;

(x) a heavy chain that comprises SEQ ID NO:94, and a light chain that comprises SEQ ID NO:95;

(xi) a heavy chain that comprises SEQ ID NO:108, and a light chain that comprises SEQ ID NO:109;

(xii) a heavy chain that comprises SEQ ID NO: 122, and a light chain that comprises SEQ ID NO:123;

(xiii) a heavy chain that comprises SEQ ID NO:136, and a light chain that comprises SEQ ID NO:137;

(xiv) a heavy chain that comprises SEQ ID NO:150, and a light chain that comprises SEQ ID NO:151;

(xv) a heavy chain that comprises SEQ ID NO:164, and a light chain that comprises SEQ ID NO:165;

(xvi) a heavy chain that comprises SEQ ID NO:178, and a light chain that comprises SEQ ID NO:179;

(xvii) a heavy chain that comprises SEQ ID NO:192, and a light chain that comprises SEQ ID NO:193;

(xviii) a heavy chain that comprises SEQ ID NO:206, and a light chain that comprises SEQ ID NO:207;

(xix) a heavy chain that comprises SEQ ID NO:248, and a light chain that comprises SEQ ID NO:249;

(xx) a heavy chain that comprises SEQ ID NO:262, and a light chain that comprises SEQ ID NO:263;

(xxi) a heavy chain that comprises SEQ ID NO:290, and a light chain that comprises SEQ ID NO:291;

(xxii) a heavy chain that comprises SEQ ID NO:304, and a light chain that comprises SEQ ID NO:305; or (xxiii) a heavy chain that comprises SEQ ID NO:332, and a light chain that comprises SEQ ID NO:333.

The antibody drug conjugate of any of the preceding embodiments that retains at least 90, 91, 92, 93, 94, 95, 96, 97, 98 or 99% identity over either the variable light or variable heavy region.

The antibody drug conjugate of any of the preceding embodiments, wherein the antibody is a monoclonal antibody, a chimeric antibody, a humanized antibody, a human engineered antibody, a human antibody, a single chain antibody(scFv) or an antibody fragment.

The antibody drug conjugate according to any of the preceding embodiments, wherein said linker (L) is selected from the group consisting of a cleavable linker, a non-cleavable linker, a hydrophilic linker, a procharged linker and a dicarboxylic acid based linker.

The antibody drug conjugate according to any of the preceding embodiments, wherein the linker is derived from a cross-linking reagent selected from the group consisting of: N-succinimidyl-4-(2-pyridyldithio)2-sulfo-butanoate (sulfo-SPDB), N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl iodoacetate (SIA), N-succinimidyl (4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

The antibody drug conjugate according to any of the preceding embodiments, wherein said linker is derived from N-succinimidyl-4-(2-pyridyldithio)2-sulfo-butanoate (sulfo-SPDB).

The antibody drug conjugate of any of the preceding embodiments, wherein said drug moiety (D) is selected from a group consisting of: a maytansinoid, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

The antibody drug conjugate of any of the preceding embodiments, wherein the drug moiety is a maytansinoid.

The antibody drug conjugate of any of the preceding embodiments, wherein the maytansinoid is N(2')-deacetyl-N2-(4-mercapto-4-methyl-1-oxopentyl)-maytansine (DM4) or N(2')-deacetyl-N(2')-(3-mercapto-1-oxopropyl)-maytansine (DM1).

The antibody drug conjugate of any of the preceding embodiments in combination with another therapeutic agent.

The antibody drug conjugate of any of the preceding embodiments in combination with a therapeutic agent listed in Table 18.

The antibody drug conjugate of any of the preceding embodiments in combination with a BCL2 inhibitor, a BCL-XL inhibitor, a BCL2/BCL-XL inhibitor, an IAP inhibitor or a MEK inhibitor.

The antibody drug conjugate of any of the preceding embodiments in combination with an immune modulatory molecule.

An antibody drug conjugate of the formula:

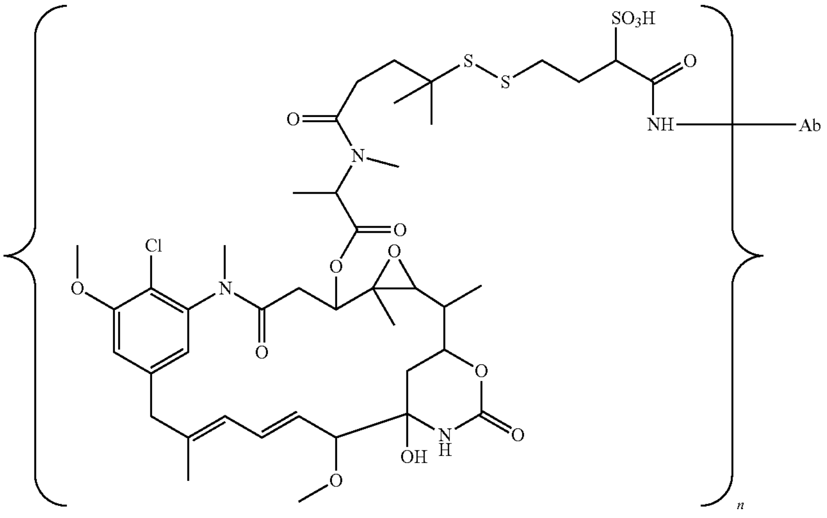

Ab-sulfo-SPDB-DM4 or a pharmaceutically acceptable salt thereof; wherein;

Ab is an antibody or antigen binding fragment thereof that specifically binds to human CDH6, and n is an integer from 1 to 10.

The antibody drug conjugate of any of the preceding embodiments, wherein said antibody or antigen binding fragment specifically binds to an epitope of human CDH6 at (SEQ ID NO:4).

The antibody drug conjugate of any of the preceding embodiments, wherein said antibody or antigen binding fragment thereof specifically binds human CDH6 at (SEQ ID NO:534).

The antibody drug conjugate of any of the preceding embodiments, wherein said Ab is an antibody or antigen binding fragment thereof comprises:

(i) a light chain variable region that comprises (a) a LCDR1 (CDR-Complementarity Determining Region) of SEQ ID NO:224, (b) a LCDR2 of SEQ ID NO:225, (c) a LCDR3 of SEQ ID NO:226; and a heavy chain variable region that comprises: (d) a HCDR1 of SEQ ID NO: 227, (e) a HCDR2 of SEQ ID NO: 228, and (f) a HCDR3 of SEQ ID NO:229;

(ii) a light chain variable region that comprises (a) a LCDR1 (CDR-Complementarity Determining Region) of SEQ ID NO:210, (b) a LCDR2 of SEQ ID NO:211, (c) a LCDR3 of SEQ ID NO:212; and a heavy chain variable region that comprises: (d) a HCDR1 of SEQ ID NO:213, (e) a HCDR2 of SEQ ID NO: 214, and (f) a HCDR3 of SEQ ID NO:215;

(iii) a light chain variable region that comprises (a) a LCDR1 (CDR-Complementarity Determining Region) of SEQ ID NO:266, (b) a LCDR2 of SEQ ID NO:267, (c) a LCDR3 of SEQ ID NO:268; and a heavy chain variable region that comprises: (d) a HCDR1 of SEQ ID NO: 269, (e) a HCDR2 of SEQ ID NO:270, and (f) a HCDR3 of SEQ ID NO: 271;

(iv) a light chain variable region that comprises (a) a LCDR1 (CDR-Complementarity Determining Region) of SEQ ID NO:308, (b) a LCDR2 of SEQ ID NO:309, (c) a LCDR3 of SEQ ID NO:310; and a heavy chain variable region that comprises: (d) a HCDR1 of SEQ ID NO:311, (e) a HCDR2 of SEQ ID NO:312, and (f) a HCDR3 of SEQ ID NO:313;

(v) a light chain variable region that comprises (a) a LCDR1 (CDR-Complementarity Determining Region) of SEQ ID NO:14, (b) a LCDR2 of SEQ ID NO:15, (c) a LCDR3 of SEQ ID NO:16; and a heavy chain variable region that comprises: (d) a HCDR1 of SEQ ID NO:17, (e) a HCDR2 of SEQ ID NO:18, and (f) a HCDR3 of SEQ ID NO:19;

(vi) a light chain variable region that comprises (a) a LCDR1 (CDR-Complementarity Determining Region) of SEQ ID NO:28, (b) a LCDR2 of SEQ ID NO:29, (c) a LCDR3 of SEQ ID NO:30; and a heavy chain variable region that comprises: (d) a HCDR1 of SEQ ID NO:31, (e) a HCDR2 of SEQ ID NO:32, and (f) a HCDR3 of SEQ ID NO:33;

(vii) a light chain variable region that comprises (a) a LCDR1 (CDR-Complementarity Determining Region) of SEQ ID NO:42, (b) a LCDR2 of SEQ ID NO:43, (c) a LCDR3 of SEQ ID NO:44; and a heavy chain variable region that comprises: (d) a HCDR1 of SEQ ID NO:45, (e) a HCDR2 of SEQ ID NO:46, and (f) a HCDR3 of SEQ ID NO:47;

(viii) a light chain variable region that comprises (a) a LCDR1 (CDR-Complementarity Determining Region) of SEQ ID NO:56, (b) a LCDR2 of SEQ ID NO:57, (c) a LCDR3 of SEQ ID NO:58; and a heavy chain variable region that comprises: (d) a HCDR1 of SEQ ID NO:59, (e) a HCDR2 of SEQ ID NO:60, and (f) a HCDR3 of SEQ ID NO:61;

(ix) a light chain variable region that comprises (a) a LCDR1 (CDR-Complementarity Determining Region) of SEQ ID NO:70, (b) a LCDR2 of SEQ ID NO:71, (c) a LCDR3 of SEQ ID NO:72; and a heavy chain variable region that comprises: (d) a HCDR1 of SEQ ID NO:73, (e) a HCDR2 of SEQ ID NO:74, and (f) a HCDR3 of SEQ ID NO:75;

(x) a light chain variable region that comprises (a) a LCDR1 (CDR-Complementarity Determining Region) of SEQ ID NO:84, (b) a LCDR2 of SEQ ID NO:85, (c) a LCDR3 of SEQ ID NO:86; and a heavy chain variable region that comprises: (d) a HCDR1 of SEQ ID NO:87, (e) a HCDR2 of SEQ ID NO: 88, and (f) a HCDR3 of SEQ ID NO: 89;

(xi) a light chain variable region that comprises (a) a LCDR1 (CDR-Complementarity Determining Region) of SEQ ID NO:98, (b) a LCDR2 of SEQ ID NO:99, (c) a LCDR3 of SEQ ID NO:100; and a heavy chain variable region that comprises: (d) a HCDR1 of SEQ ID NO:101, (e) a HCDR2 of SEQ ID NO:102, and (f) a HCDR3 of SEQ ID NO:103;

(xii) a light chain variable region that comprises (a) a LCDR1 (CDR-Complementarity Determining Region) of SEQ ID NO:112, (b) a LCDR2 of SEQ ID NO:113, (c) a LCDR3 of SEQ ID NO:114; and a heavy chain variable region that comprises: (d) a HCDR1 of SEQ ID NO:115, (e) a HCDR2 of SEQ ID NO:116, and (f) a HCDR3 of SEQ ID NO:117;

(xiii) a light chain variable region that comprises (a) a LCDR1 (CDR-Complementarity Determining Region) of SEQ ID NO:126, (b) a LCDR2 of SEQ ID NO:127, (c) a LCDR3 of SEQ ID NO:128; and a heavy chain variable region that comprises: (d) a HCDR1 of SEQ ID NO:129, (e) a HCDR2 of SEQ ID NO:130, and (f) a HCDR3 of SEQ ID NO:131;

(xiv) a light chain variable region that comprises (a) a LCDR1 (CDR-Complementarity Determining Region) of SEQ ID NO:140, (b) a LCDR2 of SEQ ID NO:141, (c) a LCDR3 of SEQ ID NO:142; and a heavy chain variable region that comprises: (d) a HCDR1 of SEQ ID NO:143, (e) a HCDR2 of SEQ ID NO:144, and (f) a HCDR3 of SEQ ID NO:145;

(xv) a light chain variable region that comprises (a) a LCDR1 (CDR-Complementarity Determining Region) of SEQ ID NO:154, (b) a LCDR2 of SEQ ID NO:155, (c) a LCDR3 of SEQ ID NO:156; and a heavy chain variable region that comprises: (d) a HCDR1 of SEQ ID NO:157, (e) a HCDR2 of SEQ ID NO:158, and (f) a HCDR3 of SEQ ID NO:159;

(xvi) a light chain variable region that comprises (a) a LCDR1 (CDR-Complementarity Determining Region) of SEQ ID NO:168, (b) a LCDR2 of SEQ ID NO:169, (c) a LCDR3 of SEQ ID NO:170; and a heavy chain variable region that comprises: (d) a HCDR1 of SEQ ID NO:171, (e) a HCDR2 of SEQ ID NO:172, and (f) a HCDR3 of SEQ ID NO:173;

(xvii) a light chain variable region that comprises (a) a LCDR1 (CDR-Complementarity Determining Region) of SEQ ID NO:182, (b) a LCDR2 of SEQ ID NO:183, (c) a LCDR3 of SEQ ID NO:184; and a heavy chain variable region that comprises: (d) a HCDR1 of SEQ ID NO:185, (e) a HCDR2 of SEQ ID NO:186, and (f) a HCDR3 of SEQ ID NO:187;

(xviii) a light chain variable region that comprises (a) a LCDR1 (CDR-Complementarity Determining Region) of SEQ ID NO:196, (b) a LCDR2 of SEQ ID NO:197, (c) a LCDR3 of SEQ ID NO:198; and a heavy chain variable region that comprises: (d) a HCDR1 of SEQ ID NO:199, (e) a HCDR2 of SEQ ID NO:200, and (f) a HCDR3 of SEQ ID NO:201;

(xix) a light chain variable region that comprises (a) a LCDR1 (CDR-Complementarity Determining Region) of SEQ ID NO:238, (b) a LCDR2 of SEQ ID NO:239, (c) a LCDR3 of SEQ ID NO:240; and a heavy chain variable region that comprises: (d) a HCDR1 of SEQ ID NO:241, (e) a HCDR2 of SEQ ID NO:242, and (f) a HCDR3 of SEQ ID NO:243;

(xx) a light chain variable region that comprises (a) a LCDR1 (CDR-Complementarity Determining Region) of SEQ ID NO:252, (b) a LCDR2 of SEQ ID NO:253, (c) a LCDR3 of SEQ ID NO:254; and a heavy chain variable region that comprises: (d) a HCDR1 of SEQ ID NO:255, (e) a HCDR2 of SEQ ID NO:256, and (f) a HCDR3 of SEQ ID NO:257;

(xxi) a light chain variable region that comprises (a) a LCDR1 (CDR-Complementarity Determining Region) of SEQ ID NO:280, (b) a LCDR2 of SEQ ID NO:281, (c) a LCDR3 of SEQ ID NO:282; and a heavy chain variable region that comprises: (d) a HCDR1 of SEQ ID NO:283, (e) a HCDR2 of SEQ ID NO:284, and (f) a HCDR3 of SEQ ID NO:285;

(xxii) a light chain variable region that comprises (a) a LCDR1 (CDR-Complementarity Determining Region) of SEQ ID NO:294, (b) a LCDR2 of SEQ ID NO:295, (c) a LCDR3 of SEQ ID NO:296; and a heavy chain variable region that comprises: (d) a HCDR1 of SEQ ID NO:297, (e) a HCDR2 of SEQ ID NO:298, and (f) a HCDR3 of SEQ ID NO:299; or (xxiii) a light chain variable region that comprises (a) a LCDR1 (CDR-Complementarity Determining Region) of SEQ ID NO:322, (b) a LCDR2 of SEQ ID NO:323, (c) a LCDR3 of SEQ ID NO:324; and a heavy chain variable region that comprises: (d) a HCDR1 of SEQ ID NO:325, (e) a HCDR2 of SEQ ID NO:326, and (f) a HCDR3 of SEQ ID NO:327.

The antibody drug conjugate of any of the preceding embodiments in which at least one amino acid within a CDR is substituted by a corresponding residue of a corresponding CDR of another anti-CDH6 antibody in Table 5 or 6.

The antibody drug conjugate of any of the preceding embodiments in which one or two amino acids within a CDR have been modified, deleted or substituted.

The antibody drug conjugate of any of the preceding embodiments, wherein said antibody or antigen binding fragment thereof comprises:

(i) a heavy chain variable region (vH) that comprises SEQ ID NO: 230, and a light chain variable region (vL) that comprises SEQ ID NO:231;

(ii) a heavy chain variable region (vH) that comprises SEQ ID NO: 216, and a light chain variable region (vL) that comprises SEQ ID NO:217;

(iii) a heavy chain variable region (vH) that comprises SEQ ID NO: 272, and a light chain variable region (vL) that comprises SEQ ID NO:273;

(iv) a heavy chain variable region (vH) that comprises SEQ ID NO:314, and a light chain variable region (vL) that comprises SEQ ID NO:315;

(v) a heavy chain variable region (vH) that comprises SEQ ID NO:20, and a light chain variable region (vL) that comprises SEQ ID NO:21;

(vi) a heavy chain variable region (vH) that comprises SEQ ID NO: 34, and a light chain variable region (vL) that comprises SEQ ID NO:35;

(vii) a heavy chain variable region (vH) that comprises SEQ ID NO:48, and a light chain variable region (vL) that comprises SEQ ID NO:49;

(viii) a heavy chain variable region (vH) that comprises SEQ ID NO:62, and a light chain variable region (vL) that comprises SEQ ID NO:63;

(ix) a heavy chain variable region (vH) that comprises SEQ ID NO:76, and a light chain variable region (vL) that comprises SEQ ID NO:77;

(x) a heavy chain variable region (vH) that comprises SEQ ID NO:90, and a light chain variable region (vL) that comprises SEQ ID NO:91;

(xi) a heavy chain variable region (vH) that comprises SEQ ID NO:104, and a light chain variable region (vL) that comprises SEQ ID NO:105;

(xii) a heavy chain variable region (vH) that comprises SEQ ID NO: 118, and a light chain variable region (vL) that comprises SEQ ID NO:119;

(xiii) a heavy chain variable region (vH) that comprises SEQ ID NO: 132, and a light chain variable region (vL) that comprises SEQ ID NO:133;

(xiv) a heavy chain variable region (vH) that comprises SEQ ID NO: 146, and a light chain variable region (vL) that comprises SEQ ID NO:147;

(xv) a heavy chain variable region (vH) that comprises SEQ ID NO:160, and a light chain variable region (vL) that comprises SEQ ID NO:161;

(xvi) a heavy chain variable region (vH) that comprises SEQ ID NO: 174, and a light chain variable region (vL) that comprises SEQ ID NO:175;

(xvii) a heavy chain variable region (vH) that comprises SEQ ID NO: 188, and a light chain variable region (vL) that comprises SEQ ID NO:189;

(xviii) a heavy chain variable region (vH) that comprises SEQ ID NO: 202, and a light chain variable region (vL) that comprises SEQ ID NO:203;

(xix) a heavy chain variable region (vH) that comprises SEQ ID NO: 244, and a light chain variable region (vL) that comprises SEQ ID NO:245;

(xx) a heavy chain variable region (vH) that comprises SEQ ID NO:258, and a light chain variable region (vL) that comprises SEQ ID NO:259;

(xxi) a heavy chain variable region (vH) that comprises SEQ ID NO:286, and a light chain variable region (vL) that comprises SEQ ID NO:287;

(xxii) a heavy chain variable region (vH) that comprises SEQ ID NO:300, and a light chain variable region (vL) that comprises SEQ ID NO:301; or (xxiii) a heavy chain variable region (vH) that comprises SEQ ID NO:328, and a light chain variable region (vL) that comprises SEQ ID NO:329.

The antibody drug conjugate of any of the preceding embodiments that retains at least 90, 91, 92, 93, 94, 95, 96, 97, 98 or 99% identity over either the variable light or variable heavy region.

The antibody drug conjugate of any of the preceding embodiments, wherein the antibody is a monoclonal antibody, a chimeric antibody, a humanized antibody, a human engineered antibody, a human antibody, a single chain antibody(scFv) or an antibody fragment.

The antibody drug conjugate of any of the preceding embodiments, wherein said n is an integer from 2 to 8.

The antibody drug conjugate of any of the preceding embodiments, wherein said n is an integer from 3 to 4.

The antibody drug conjugate of any of the preceding embodiments in combination with another therapeutic agent.

The antibody drug conjugate of any of the preceding embodiments in combination with a therapeutic agent listed in Table 18.

The antibody drug conjugate of any of the preceding embodiments in combination with a BCL2 inhibitor, a BCL-XL inhibitor, a BCL2/BCL-XL inhibitor, an IAP inhibitor or a MEK inhibitor.

The antibody drug conjugate of any of the preceding embodiments in combination with an immune modulatory molecule.

A pharmaceutical composition comprising the antibody drug conjugate of any of the preceding embodiments and a pharmaceutically acceptable carrier.

The pharmaceutical composition of any of the preceding embodiments wherein said composition is prepared as a lyophilisate.

The pharmaceutical composition of any of the preceding embodiments, wherein said lyophilisate comprises the antibody drug conjugate of any of the preceding embodiments, sodium succinate, and polysorbate 20.

A method of treating an CDH6 positive cancer in a patient in need thereof, comprising administering to said patient the antibody drug conjugate or the pharmaceutical composition.

The method wherein said cancer is selected from the group consisting of: ovarian cancer, renal cancer, hepatic cancer, soft tissue cancer, CNS cancers, thyroid cancer and cholangiocarcinoma.

The method wherein the antibody drug conjugate or the pharmaceutical composition is administered in combination with another therapeutic agent.

The method wherein the antibody drug conjugate or the pharmaceutical composition is administered in combination with a therapeutic listed in Table 18.

The antibody drug conjugate of any of the preceding embodiments in combination with a BCL2 inhibitor, a BCL-XL inhibitor, a BCL2/BCL-XL inhibitor, an IAP inhibitor or a MEK inhibitor.

The antibody drug conjugate of any of the preceding embodiments in combination with an immune modulatory molecule.

The antibody drug conjugate of any of the preceding embodiments for use as a medicament.

The antibody drug conjugate or the pharmaceutical composition thereof, for use in the treatment of a CDH6 positive cancer.

The antibody drug conjugate of any of the preceding embodiments, administered in combination with another therapeutic agent.

The antibody drug conjugate of any of the preceding embodiments administered in combination with a therapeutic agent listed in Table 18.

The antibody drug conjugate of any of the preceding embodiments in combination with a BCL2 inhibitor, a BCL-XL inhibitor, a BCL2/BCL-XL inhibitor, an IAP inhibitor or a MEK inhibitor.

The antibody drug conjugate of any of the preceding embodiments in combination with an immune modulatory molecule.

A nucleic acid that encodes the antibody or antigen binding fragment of any of the preceding embodiments.

A vector comprising the nucleic acid of any of the preceding embodiments.

A host cell comprising the vector according to any of the preceding embodiments.

A process for producing an antibody or antigen binding fragment comprising cultivating the host cell and recovering the antibody from the culture.

A process for producing an anti-CDH6 antibody drug conjugate, the process comprising:

(a) chemically linking N-succinimidyl-4-(2-pyridyldithio)2-sulfo-butanoate (sulfo-SPDB) to a drug moiety DM-4;

(b) conjugating said linker-drug to the antibody recovered from the cell culture; and (c) purifying the antibody drug conjugate.

The antibody drug conjugate made according to any of the preceding embodiments having an average maytansinoid to antibody ratio (MAR), measured with a UV spectrophotometer, about 3.5.

An antibody or antigen binding fragment thereof that comprises:

(i) a light chain variable region that comprises (a) a LCDR1 (CDR-Complementarity Determining Region) of SEQ ID NO:224, (b) a LCDR2 of SEQ ID NO:225, (c) a LCDR3 of SEQ ID NO:226; and a heavy chain variable region that comprises: (d) a HCDR1 of SEQ ID NO: 227, (e) a HCDR2 of SEQ ID NO: 228, and (f) a HCDR3 of SEQ ID NO:229;

(ii) a light chain variable region that comprises (a) a LCDR1 (CDR-Complementarity Determining Region) of SEQ ID NO:210, (b) a LCDR2 of SEQ ID NO:211, (c) a LCDR3 of SEQ ID NO:212; and a heavy chain variable region that comprises: (d) a HCDR1 of SEQ ID NO:213, (e) a HCDR2 of SEQ ID NO: 214, and (f) a HCDR3 of SEQ ID NO:215;

(iii) a light chain variable region that comprises (a) a LCDR1 (CDR-Complementarity Determining Region) of SEQ ID NO:266, (b) a LCDR2 of SEQ ID NO:267, (c) a LCDR3 of SEQ ID NO:268; and a heavy chain variable region that comprises: (d) a HCDR1 of SEQ ID NO: 269, (e) a HCDR2 of SEQ ID NO:270, and (f) a HCDR3 of SEQ ID NO: 271;

(iv) a light chain variable region that comprises (a) a LCDR1 (CDR-Complementarity Determining Region) of SEQ ID NO:308, (b) a LCDR2 of SEQ ID NO:309, (c) a LCDR3 of SEQ ID NO:310; and a heavy chain variable region that comprises: (d) a HCDR1 of SEQ ID NO:311, (e) a HCDR2 of SEQ ID NO:312, and (f) a HCDR3 of SEQ ID NO:313;

(v) a light chain variable region that comprises (a) a LCDR1 (CDR-Complementarity Determining Region) of SEQ ID NO:14, (b) a LCDR2 of SEQ ID NO:15, (c) a LCDR3 of SEQ ID NO:16; and a heavy chain variable region that comprises: (d) a HCDR1 of SEQ ID NO:17, (e) a HCDR2 of SEQ ID NO:18, and (f) a HCDR3 of SEQ ID NO:19;

(vi) a light chain variable region that comprises (a) a LCDR1 (CDR-Complementarity Determining Region) of SEQ ID NO:28, (b) a LCDR2 of SEQ ID NO:29, (c) a LCDR3 of SEQ ID NO:30; and a heavy chain variable region that comprises: (d) a HCDR1 of SEQ ID NO:31, (e) a HCDR2 of SEQ ID NO:32, and (f) a HCDR3 of SEQ ID NO:33;

(vii) a light chain variable region that comprises (a) a LCDR1 (CDR-Complementarity Determining Region) of SEQ ID NO:42, (b) a LCDR2 of SEQ ID NO:43, (c) a LCDR3 of SEQ ID NO:44; and a heavy chain variable region that comprises: (d) a HCDR1 of SEQ ID NO:45, (e) a HCDR2 of SEQ ID NO:46, and (f) a HCDR3 of SEQ ID NO:47;

(viii) a light chain variable region that comprises (a) a LCDR1 (CDR-Complementarity Determining Region) of SEQ ID NO:56, (b) a LCDR2 of SEQ ID NO:57, (c) a LCDR3 of SEQ ID NO:58; and a heavy chain variable region that comprises: (d) a HCDR1 of SEQ ID NO:59, (e) a HCDR2 of SEQ ID NO:60, and (f) a HCDR3 of SEQ ID NO:61;

(ix) a light chain variable region that comprises (a) a LCDR1 (CDR-Complementarity Determining Region) of SEQ ID NO:70, (b) a LCDR2 of SEQ ID NO:71, (c) a LCDR3 of SEQ ID NO:72; and a heavy chain variable region that comprises: (d) a HCDR1 of SEQ ID NO:73, (e) a HCDR2 of SEQ ID NO:74, and (f) a HCDR3 of SEQ ID NO:75;

(x) a light chain variable region that comprises (a) a LCDR1 (CDR-Complementarity Determining Region) of SEQ ID NO:84, (b) a LCDR2 of SEQ ID NO:85, (c) a LCDR3 of SEQ ID NO:86; and a heavy chain variable region that comprises: (d) a HCDR1 of SEQ ID NO:87, (e) a HCDR2 of SEQ ID NO: 88, and (f) a HCDR3 of SEQ ID NO: 89;

(xi) a light chain variable region that comprises (a) a LCDR1 (CDR-Complementarity Determining Region) of SEQ ID NO:98, (b) a LCDR2 of SEQ ID NO:99, (c) a LCDR3 of SEQ ID NO:100; and a heavy chain variable region that comprises: (d) a HCDR1 of SEQ ID NO:101, (e) a HCDR2 of SEQ ID NO:102, and (f) a HCDR3 of SEQ ID NO:103;

(xii) a light chain variable region that comprises (a) a LCDR1 (CDR-Complementarity Determining Region) of SEQ ID NO:112, (b) a LCDR2 of SEQ ID NO:113, (c) a LCDR3 of SEQ ID NO:114; and a heavy chain variable region that comprises: (d) a HCDR1 of SEQ ID NO:115, (e) a HCDR2 of SEQ ID NO:116, and (f) a HCDR3 of SEQ ID NO:117;

(xiii) a light chain variable region that comprises (a) a LCDR1 (CDR-Complementarity Determining Region) of SEQ ID NO:126, (b) a LCDR2 of SEQ ID NO:127, (c) a LCDR3 of SEQ ID NO:128; and a heavy chain variable region that comprises: (d) a HCDR1 of SEQ ID NO:129, (e) a HCDR2 of SEQ ID NO:130, and (f) a HCDR3 of SEQ ID NO:131;

(xiv) a light chain variable region that comprises (a) a LCDR1 (CDR-Complementarity Determining Region) of SEQ ID NO:140, (b) a LCDR2 of SEQ ID NO:141, (c) a LCDR3 of SEQ ID NO:142; and a heavy chain variable region that comprises: (d) a HCDR1 of SEQ ID NO:143, (e) a HCDR2 of SEQ ID NO:144, and (f) a HCDR3 of SEQ ID NO:145;

(xv) a light chain variable region that comprises (a) a LCDR1 (CDR-Complementarity Determining Region) of SEQ ID NO:154, (b) a LCDR2 of SEQ ID NO:155, (c) a LCDR3 of SEQ ID NO:156; and a heavy chain variable region that comprises: (d) a HCDR1 of SEQ ID NO:157, (e) a HCDR2 of SEQ ID NO:158, and (f) a HCDR3 of SEQ ID NO:159;

(xvi) a light chain variable region that comprises (a) a LCDR1 (CDR-Complementarity Determining Region) of SEQ ID NO:168, (b) a LCDR2 of SEQ ID NO:169, (c) a LCDR3 of SEQ ID NO:170; and a heavy chain variable region that comprises: (d) a HCDR1 of SEQ ID NO:171, (e) a HCDR2 of SEQ ID NO:172, and (f) a HCDR3 of SEQ ID NO:173;

(xvii) a light chain variable region that comprises (a) a LCDR1 (CDR-Complementarity Determining Region) of SEQ ID NO:182, (b) a LCDR2 of SEQ ID NO:183, (c) a LCDR3 of SEQ ID NO:184; and a heavy chain variable region that comprises: (d) a HCDR1 of SEQ ID NO:185, (e) a HCDR2 of SEQ ID NO:186, and (f) a HCDR3 of SEQ ID NO:187;

(xviii) a light chain variable region that comprises (a) a LCDR1 (CDR-Complementarity Determining Region) of SEQ ID NO:196, (b) a LCDR2 of SEQ ID NO:197, (c) a LCDR3 of SEQ ID NO:198; and a heavy chain variable region that comprises: (d) a HCDR1 of SEQ ID NO:199, (e) a HCDR2 of SEQ ID NO:200, and (f) a HCDR3 of SEQ ID NO:201;

(xix) a light chain variable region that comprises (a) a LCDR1 (CDR-Complementarity Determining Region) of SEQ ID NO:238, (b) a LCDR2 of SEQ ID NO:239, (c) a LCDR3 of SEQ ID NO:240; and a heavy chain variable region that comprises: (d) a HCDR1 of SEQ ID NO:241, (e) a HCDR2 of SEQ ID NO:242, and (f) a HCDR3 of SEQ ID NO:243;

(xx) a light chain variable region that comprises (a) a LCDR1 (CDR-Complementarity Determining Region) of SEQ ID NO:252, (b) a LCDR2 of SEQ ID NO:253, (c) a LCDR3 of SEQ ID NO:254; and a heavy chain variable region that comprises: (d) a HCDR1 of SEQ ID NO:255, (e) a HCDR2 of SEQ ID NO:256, and (f) a HCDR3 of SEQ ID NO:257;

(xxi) a light chain variable region that comprises (a) a LCDR1 (CDR-Complementarity Determining Region) of SEQ ID NO:280, (b) a LCDR2 of SEQ ID NO:281, (c) a LCDR3 of SEQ ID NO:282; and a heavy chain variable region that comprises: (d) a HCDR1 of SEQ ID NO:283, (e) a HCDR2 of SEQ ID NO:284, and (f) a HCDR3 of SEQ ID NO:285;

(xxii) a light chain variable region that comprises (a) a LCDR1 (CDR-Complementarity Determining Region) of SEQ ID NO:294, (b) a LCDR2 of SEQ ID NO:295, (c) a LCDR3 of SEQ ID NO:296; and a heavy chain variable region that comprises: (d) a HCDR1 of SEQ ID NO:297, (e) a HCDR2 of SEQ ID NO:298, and (f) a HCDR3 of SEQ ID NO:299; or (xxiii) a light chain variable region that comprises (a) a LCDR1 (CDR-Complementarity Determining Region) of SEQ ID NO:322, (b) a LCDR2 of SEQ ID NO:323, (c) a LCDR3 of SEQ ID NO:324; and a heavy chain variable region that comprises: (d) a HCDR1 of SEQ ID NO:325, (e) a HCDR2 of SEQ ID NO:326, and (f) a HCDR3 of SEQ ID NO:327.

The antibody or antigen binding fragment thereof of any of the preceding embodiments in which at least one amino acid within a CDR is substituted by a corresponding residue of a corresponding CDR of another anti-CDH6 antibody in Table 5 or 6.

The antibody or antigen binding fragment thereof of any of the preceding embodiments, wherein said antibody or antigen binding fragment thereof comprises:

(i) a heavy chain variable region (vH) that comprises SEQ ID NO: 230, and a light chain variable region (vL) that comprises SEQ ID NO:231;

(ii) a heavy chain variable region (vH) that comprises SEQ ID NO: 216, and a light chain variable region (vL) that comprises SEQ ID NO:217;

(iii) a heavy chain variable region (vH) that comprises SEQ ID NO: 272, and a light chain variable region (vL) that comprises SEQ ID NO:273;

(iv) a heavy chain variable region (vH) that comprises SEQ ID NO:314, and a light chain variable region (vL) that comprises SEQ ID NO:315;

(v) a heavy chain variable region (vH) that comprises SEQ ID NO:20, and a light chain variable region (vL) that comprises SEQ ID NO:21;

(vi) a heavy chain variable region (vH) that comprises SEQ ID NO: 34, and a light chain variable region (vL) that comprises SEQ ID NO:35;

(vii) a heavy chain variable region (vH) that comprises SEQ ID NO:48, and a light chain variable region (vL) that comprises SEQ ID NO:49;

(viii) a heavy chain variable region (vH) that comprises SEQ ID NO:62, and a light chain variable region (vL) that comprises SEQ ID NO:63;

(ix) a heavy chain variable region (vH) that comprises SEQ ID NO:76, and a light chain variable region (vL) that comprises SEQ ID NO:77;

(x) a heavy chain variable region (vH) that comprises SEQ ID NO:90, and a light chain variable region (vL) that comprises SEQ ID NO:91;

(xi) a heavy chain variable region (vH) that comprises SEQ ID NO:104, and a light chain variable region (vL) that comprises SEQ ID NO:105;

(xii) a heavy chain variable region (vH) that comprises SEQ ID NO: 118, and a light chain variable region (vL) that comprises SEQ ID NO:119;

(xiii) a heavy chain variable region (vH) that comprises SEQ ID NO: 132, and a light chain variable region (vL) that comprises SEQ ID NO:133;

(xiv) a heavy chain variable region (vH) that comprises SEQ ID NO: 146, and a light chain variable region (vL) that comprises SEQ ID NO:147;

(xv) a heavy chain variable region (vH) that comprises SEQ ID NO:160, and a light chain variable region (vL) that comprises SEQ ID NO:161;

(xvi) a heavy chain variable region (vH) that comprises SEQ ID NO: 174, and a light chain variable region (vL) that comprises SEQ ID NO:175;

(xvii) a heavy chain variable region (vH) that comprises SEQ ID NO: 188, and a light chain variable region (vL) that comprises SEQ ID NO:189;

(xviii) a heavy chain variable region (vH) that comprises SEQ ID NO: 202, and a light chain variable region (vL) that comprises SEQ ID NO:203;

(xix) a heavy chain variable region (vH) that comprises SEQ ID NO: 244, and a light chain variable region (vL) that comprises SEQ ID NO:245;

(xx) a heavy chain variable region (vH) that comprises SEQ ID NO:258, and a light chain variable region (vL) that comprises SEQ ID NO:259;

(xxi) a heavy chain variable region (vH) that comprises SEQ ID NO:286, and a light chain variable region (vL) that comprises SEQ ID NO:287;

(xxii) a heavy chain variable region (vH) that comprises SEQ ID NO:300, and a light chain variable region (vL) that comprises SEQ ID NO:301; or (xxiii) a heavy chain variable region (vH) that comprises SEQ ID NO:328, and a light chain variable region (vL) that comprises SEQ ID NO:329.

A diagnostic reagent comprising the antibody or antigen binding fragment thereof of any of the preceding embodiments which is labeled.

The diagnostic reagent of any of the preceding embodiments, wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262: 732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to a polypeptide including one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000.

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)). A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an antibody drug conjugate of the present disclosure. In some aspects, the phrase "consisting essentially of" expressly excludes the inclusion of one or more additional active agents other than an antibody drug conjugate of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term “nucleic acid” is used herein interchangeably with the term “polynucleotide” and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term “operably linked” in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms “polypeptide” and “protein” are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "immunoconjugate" or "antibody drug conjugate" as used herein refers to the linkage of an antibody or an antigen binding fragment thereof with another agent, such as a payload, drug moiety, chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "toxin," "cytotoxin" or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment, and can include any therapeutic or diagnostic agent, for example, an anti-cancer, anti-inflammatory, anti-infective (e.g., anti-fungal, antibacterial, anti-parasitic, anti-viral), or an anesthetic agent. In certain aspects, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the present disclosure are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "maytansinoid drug moiety" means the substructure of an antibody-drug conjugate that has the structure of a maytansinoid compound. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451, each of which are expressly incorporated by reference. Specific examples of maytansinoids useful for conjugation include DM1, DM3 and DM4.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of tumor cells, tumor size stasis or tumor size reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "Cadherin 6" or "CDH6" refers to a cell adhesion molecule that is a member of the cadherin family of cell-cell adhesion molecules. The nucleic acid and amino acid sequences of CDH6 are known, and have been published in GenBank Accession Nos. AK291290 (protein accession number BAF83979.1) See also SEQ ID NO:1 for the human CDH6 cDNA sequence and SEQ ID NO:2 for the human CDH6 protein sequence. Structurally, CDH6 receptor is a type II cadherin with five extracellular cadherin repeats and has over its full length at least about 90%, 91%, 92%, 93%, 94%, 95%, 96%, 97%, 98%, 99%, or 100% sequence identity with the amino acid sequence of SEQ ID NO:2. Structurally, a CDH6 nucleic acid sequence has over its full length at least about 90%, 91%, 92%, 93%, 94%, 95%, 96%, 97%, 98%, 99%, or 100% sequence identity with the nucleic acid sequence of SEQ ID NO 1.

The terms "CDH6 expressing cancer" or "CDH6 positive cancer" refers to a cancer that express CDH6 and/or a mutant form of CDH6 on the surface of cancer cells.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat,"

"treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both. In yet another aspect, "treat," "treating," or "treatment" refers to preventing or delaying the onset or development or progression of the disease or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated with cancer.

The term "co-administer" refers to the simultaneous presence of two active agents in the blood of an individual. Active agents that are co-administered can be concurrently or sequentially delivered.

BRIEF DESCRIPTION OF THE DRAWINGS

FIG. 2 shows epitope binning of anti-CDH6 antibodies.

FIG. 8 is FACS data of anti-CDH6 antibodies either unconjugated or conjugated with a sulfo-SPDB-DM4 linker/payload binding to CHO cell lines expressing human, cynomolgus, rat or mouse CDH6.

FIG. 24 provides the Loewe Synergy scores for combination activity of CDH6-targeting ADCs with BCL2/BCL-Xl, BCL-Xl, IAP and MEK inhibitors.

DETAILED DESCRIPTION

Figure 1:
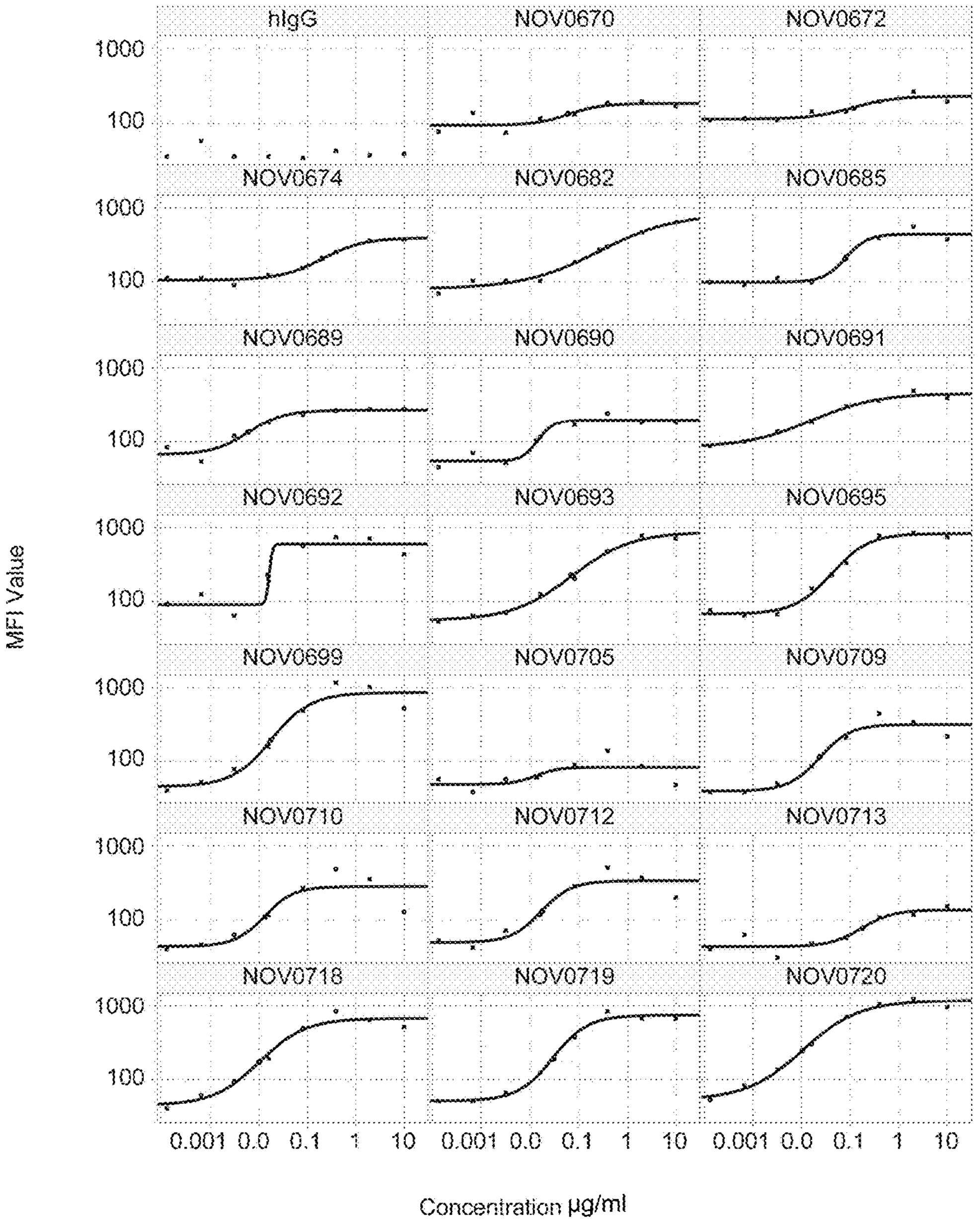
FIG. 1 is a graphic depiction of anti-CDH6 antibodies cellular binding EC50 on OVCAR3 cells.

The present disclosure provides for antibodies, antibody fragments (e.g., antigen binding fragments), and antibody drug conjugates that bind to CDH6. In particular, the present disclosure is directed to antibodies and antibody fragments (e.g., antigen binding fragments) that bind to CDH6, and internalize upon such binding. The antibodies and antibody fragments (e.g., antigen binding fragments) of the present disclosure can be used for producing antibody drug conjugates. Furthermore, the present disclosure provides antibody drug conjugates that have desirable pharmacokinetic characteristics and other desirable attributes, and thus can be used for treating cancer expressing CDH6, without limitation, for example: ovarian cancer, renal cancer, hepatic cancer, soft tissue cancer, CNS cancers, thyroid cancer and cholangiocarcinoma. The present disclosure further provides pharmaceutical compositions comprising the antibody drug conjugates, and methods of making and using such pharmaceutical compositions for the treatment of cancer.

Antibody Drug Conjugates

The present disclosure provides antibody drug conjugates, where an antibody, antigen binding fragment or its functional equivalent that specifically binds to CDH6 is linked to a drug moiety. In one aspect, the antibodies, antigen binding fragments or their functional equivalents are linked, via covalent attachment by a linker, to a drug moiety that is an anti-cancer agent. The antibody drug conjugates can selectively deliver an effective dose of an anti-cancer agent (e.g., a cytotoxic agent) to tumor tissues expressing CDH6, whereby greater selectivity (and lower efficacious dose) may be achieved.

In one aspect, the disclosure provides for an immunoconjugate of Formula (I):

$$Ab\text{-}(L\text{-}(D)_m)_n$$

Wherein Ab represents an CDH6 binding antibody or antibody fragment (e.g., antigen binding fragment) described herein;

L is a linker;

D is a drug moiety;

m is an integer from 1-8; and n is an integer from 1-20. In one aspect, n is an integer from 1 to 10, 2 to 8, or 2 to 5. In a specific aspect, n is 3 to 4. In some aspects, m is 1. In some aspects, m is 2, 3 or 4.

While the drug moiety to antibody ratio has an exact integer value for a specific conjugate molecule (e.g., n multiplied by m in Formula (I)), it is understood that the value will often be an average value when used to describe a sample containing many molecules, due to some degree of inhomogeneity, typically associated with the conjugation step. The average loading for a sample of an immunoconjugate is referred to herein as the drug moiety to antibody ratio, or "DAR." In the aspect of maytansinoids, this can be referred to as maytansinoid to antibody ratio or "MAR." In some aspects, the DAR is between about 1 and about 5, and typically is about 3, 3.5, 4, 4.5, or 5. In some aspects, at least 50% of a sample by weight is compound having the average DAR plus or minus 2, and preferably at least 50% of the sample is a conjugate that contains the average DAR plus or minus 1. Other aspects include immunoconjugates wherein the DAR is about 3.5. In some aspects, a DAR of 'about n' means the measured value for DAR is within 20% of n.

The present disclosure provides immunoconjugates comprising the antibodies, antibody fragments (e.g., antigen binding fragments) and their functional equivalents as disclosed herein, linked or conjugated to a drug moiety. In one aspect, the drug moiety D is a maytansinoid drug moiety, including those having the structure:

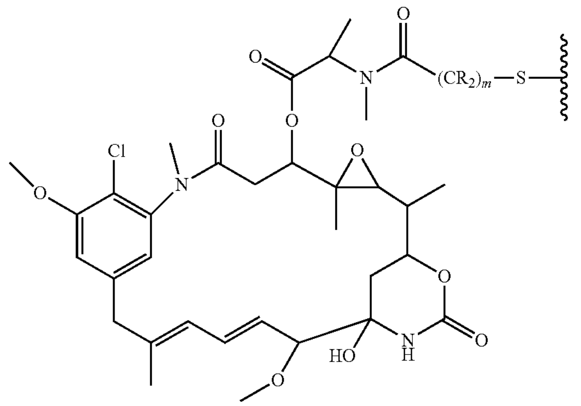

where the wavy line indicates the covalent attachment of the sulfur atom of the maytansinoid to a linker of an antibody drug conjugate. R at each occurrence is independently H or a $C_1$-$C_6$ alkyl. The alkylene chain attaching the amide group to the sulfur atom may be methanyl, ethanyl, or propanyl, i.e. m is 1, 2, or 3. (U.S. Pat. No. 633,410, U.S. Pat. No. 5,208,020, Chari et al. (1992) Cancer Res. 52; 127-131, Lui et al. (1996) Proc. Natl. Acad. Sci. 93:8618-8623).

All stereoisomers of the maytansinoid drug moiety are contemplated for the immunoconjugates disclosed, i.e. any combination of R and S configurations at the chiral carbons of the maytansinoid. In one aspect the maytansinoid drug moiety has the following stereochemistry.

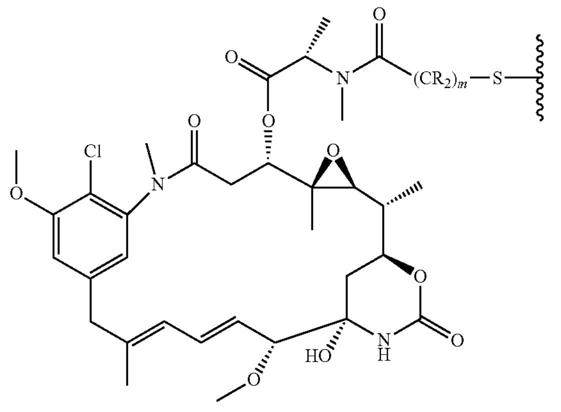

In one aspect, the maytansinoid drug moiety is $N^{2'}$-deacetyl-$N^{2'}$-(3-mercapto-1-oxopropyl)-maytansine (also known as DM1). DM1 is represented by the following structural formula.

DM1

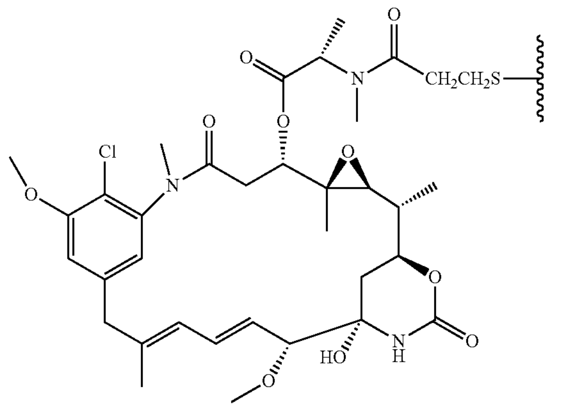

In another aspect the maytansinoid drug moiety is $N^{2'}$-deacetyl-$N^{2'}$-(4-mercapto-1-oxopentyl)-maytansine (also known as DM3). DM3 is represented by the following structural formula.

DM3

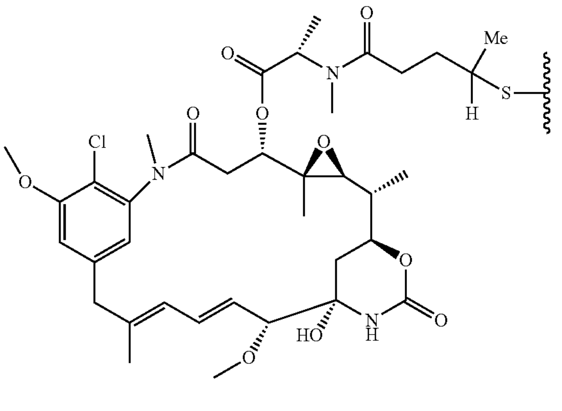

In another aspect the maytansinoid drug moiety is $N^{2'}$-deacetyl-$N^{2'}$-(4-methyl-4-mercapto-1-oxopentyl)-maytansine (also known as DM4). DM4 is represented by the following structural formula.

DM4

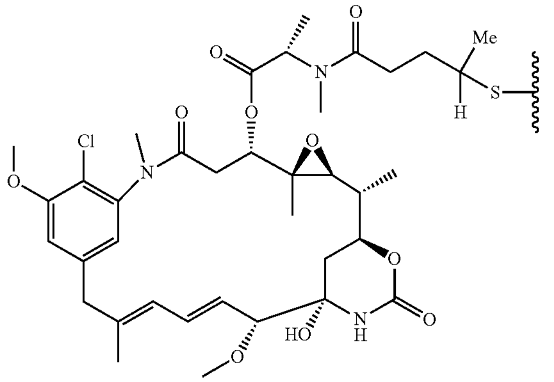

The drug moiety D can be linked to the antibody Ab through a linker L. L is any chemical moiety that is capable of linking the antibody Ab to the drug moiety D. The linker, L attaches the antibody Ab to the drug moiety D through covalent bond(s). The linker reagent is a bifunctional or multifunctional moiety which can be used to link a drug moiety D and an antibody Ab to form antibody drug conjugates. Antibody drug conjugates can be prepared using a linker having a reactive functionality for binding to the drug moiety D and to the antibody Ab. A cysteine, thiol or an amine, e.g. N-terminus or amino acid side chain such as lysine of the antibody can form a bond with a functional group of a linker reagent.

In one aspect, L is a cleavable linker. In another aspect, L is a non-cleavable linker. In some aspects, L is an acid-labile linker, photo-labile linker, peptidase cleavable linker, esterase cleavable linker, a disulfide bond reducible linker, a hydrophilic linker, a procharged linker, or a dicarboxylic acid based linker.

Suitable cross-linking reagents that form a non-cleavable linker between the drug moiety D, for example maytansinoid, and the antibody Ab are well known in the art, and can form non-cleavable linkers that comprise a sulfur atom (such as SMCC) or those that are without a sulfur atom. Preferred cross-linking reagents that form non-cleavable linkers between the drug moiety D, for example maytansinoid, and the antibody Ab comprise a maleimido- or haloacetyl-based moiety. According to the present disclosure, such non-cleavable linkers are said to be derived from maleimido- or haloacetyl-based moieties.

Cross-linking reagents comprising a maleimido-based moiety include but not limited to, N-succinimidyl-4-(maleimidomethyl)cyclohexanecarboxylate (SMCC), sulfosuccinimidyl 4-(N-maleimidomethyl) cyclohexane-1-carboxylate (sulfo-SMCC), N-succinimidyl-4-(maleimidomethyl) cyclohexane-1-carboxy-(6-amidocaproate), which is a “long chain” analog of SMCC (LC-SMCC), κ-maleimidoundecanoic acid N-succinimidyl ester (KMUA), γ-maleimidobutyric acid N-succinimidyl ester (GMBS), ϵ-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethythene glycol spacer, such as MAL-PEG-NHS. These cross-linking reagents form non-cleavable linkers derived from maleimido-based moieties. Representative structures of maleimido-based cross-linking reagents are shown below.

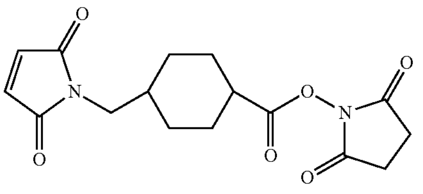

SMCC

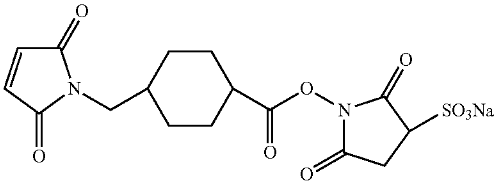

Sulfo-SMCC

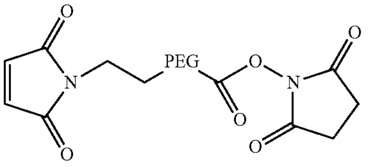

MAL-PEG-NHS

In another aspect, the linker L is derived from N-succinimidyl-4-(maleimidomethyl)cyclohexanecarboxylate (SMCC), sulfosuccinimidyl 4-(N-maleimidomethyl) cyclohexane-1-carboxylate (sulfo-SMCC) or MAL-PEG-NHS.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

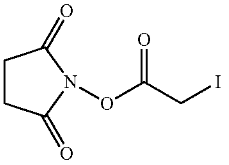 or

SIA

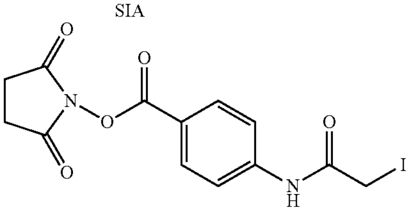

SIAB

In one aspect, the linker L is derived from N-succinimidyl iodoacetate (SIA) or N-succinimidyl(4-iodoacetyl)aminobenzoate (SIAB).

Suitable cross-linking reagents that form a cleavable linker between the drug moiety D, for example maytansinoid, and the antibody Ab are well known in the art.

Disulfide containing linkers are linkers cleavable through disulfide exchange, which can occur under physiological conditions. According to the present disclosure, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)2-sulfo-butanoate (sulfo-SPDB), the structures of which are shown below. These disulfide cross-linking reagents form a cleavable linker derived from disulfide-based moieties.

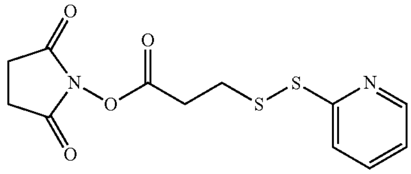
,

N-succinimidyl-3-(2-pyridyldithio)propionate (SPDP)

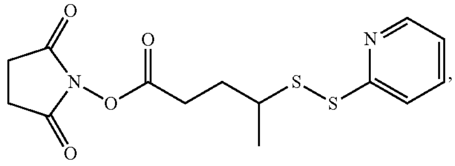
,

N-succinimidyl-4-(2-pyridyldithio)pentanoate (SPP)

-continued

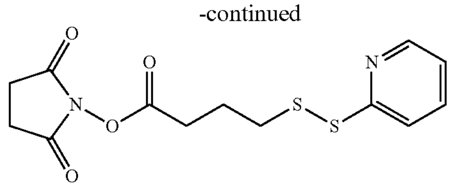

N-succinimidyl-4-(2-pyridyldithio)butanoate (SPDB) and

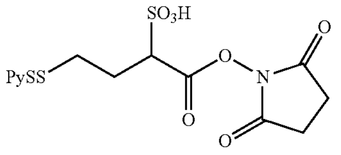

N-succinimidyl-4-(2-pyridyldithio)2-sulfo-butanoate (sulfo-SPDB)

In one aspect, the linker L is derived from N-succinimidyl-4-(2-pyridyldithio)2-sulfo-butanoate (sulfo-SPDB).

Suitable cross-linking reagents that form a charged linker between the drug moiety D, for example maytansinoid, and the antibody Ab are known as procharged cross-linking reagents. In one aspect, the linker L is derived from the procharged cross-linking reagent is CX1-1. The structure of CX1-1 is below.

(CX1-1)

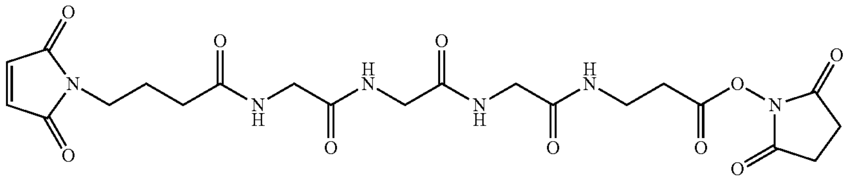

2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate In one aspect provided by the disclosure, the conjugate is represented by any one of the following structural formulae:

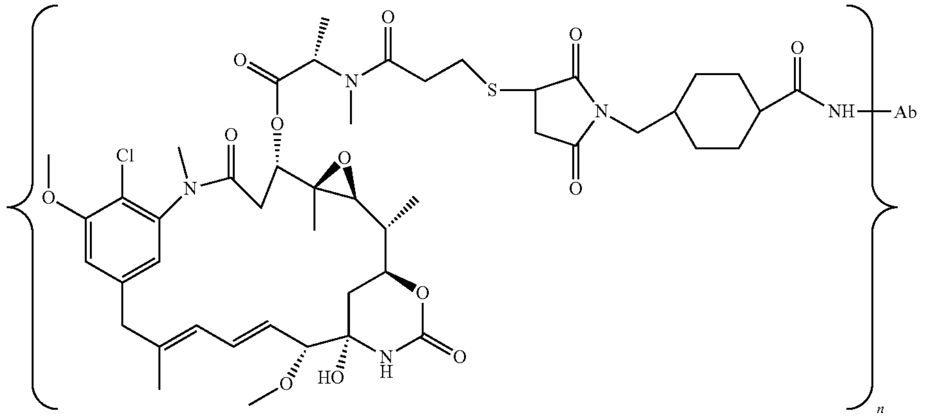

Ab-MCC-DM1

-continued

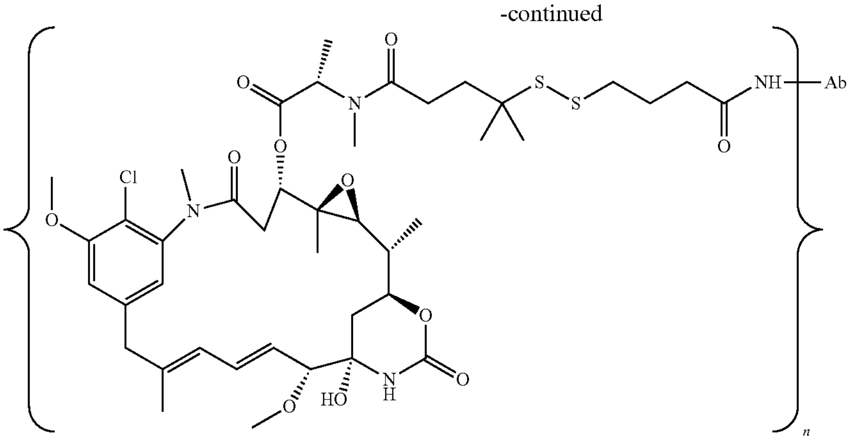

Ab-SPDB-DM4

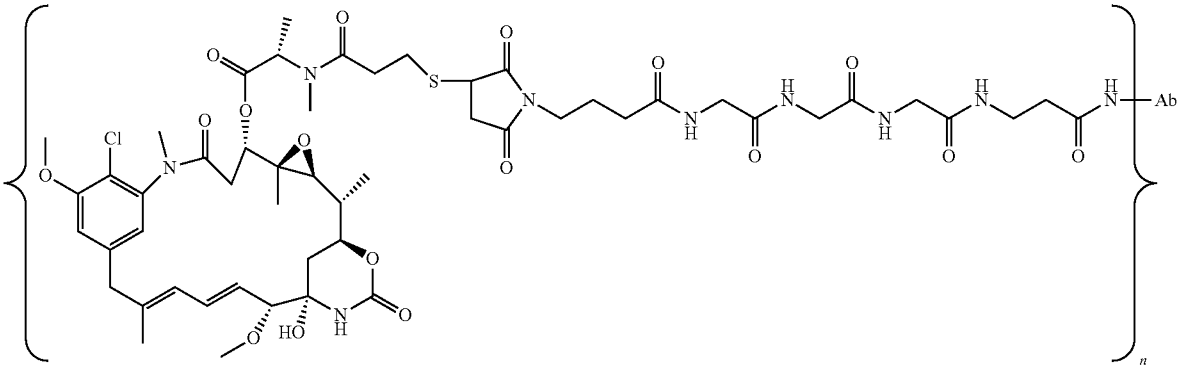

Ab-CX1-1-DM1

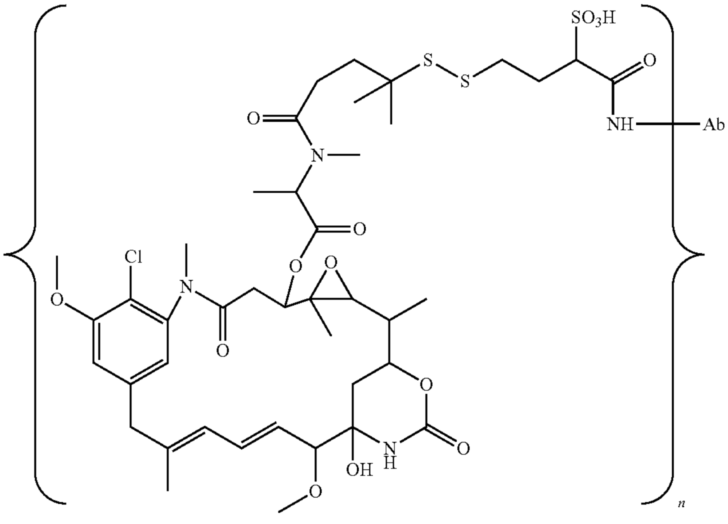

Ab-sulfo-SPDB-DM4 wherein:

Ab is an antibody or antigen binding fragment thereof that specifically binds to human CDH6;

n, which indicates the number of D-L groups attached the Ab through the formation of an amide bond with a primary amine of the Ab, is an integer from 1 to 20. In one aspect, n is an integer from 1 to 10, 2 to 8 or 2 to 5. In a specific aspect, n is 3 or 4.

In one aspect, the average molar ratio of drug moiety (e.g., DM1 or DM4) to the antibody in the conjugate (i.e., average w value, also known as Maytansinoid Antibody Ratio (MAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In one aspect provided by the disclosure, the conjugate has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug moiety (e.g., DM1 or DM4) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent).

As used herein, the term "unconjugated linker" refers to the antibody that is covalently linked with a linker derived from a cross-linking reagent (e.g., SMCC, Sulfo-SMCC, SPDB, Sulfo-SPDB or CX1-1), wherein the antibody is not covalently coupled to the drug moiety (e.g., DM1 or DM4) through a linker (i.e., the "unconjugated linker" can be represented by Ab-SMCC, Ab-SPDB, Ab-sulfo-SPDB, or Ab-CX1-1).

1. Drug Moiety

The present disclosure provides immunoconjugates that specifically bind to CDH6. The immunoconjugates of the present disclosure comprise anti-CDH6 antibodies, antibody fragments (e.g., antigen binding fragments) or functional equivalents that are conjugated to a drug moiety, e.g., an anti-cancer agent, anti-hematological disorder agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents can be conjugated to several identical or different drug moieties using any methods known in the art.

In certain aspects, the drug moiety of the immunoconjugates of the present disclosure is selected from a group consisting of: a maytansinoid, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a MetAP (methionine aminopeptidase), an inhibitor of nuclear export of proteins CRM1, a DPPIV inhibitor, proteasome inhibitors, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In one aspect, the drug moiety of the immunoconjugates of the present disclosure is a maytansinoid drug moiety, such as but not limited to, DM1, DM3, or DM4.

Further, the antibodies, antibody fragments (e.g., antigen binding fragments) or functional equivalents of the present disclosure may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one aspect, the antibodies, antibody fragments (e.g., antigen binding fragments) or functional equivalents of the present disclosure are conjugated to a drug moiety, such as a cytotoxin, a drug (e.g., an immunosuppressant) or a radiotoxin. Examples of cytotoxin include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood 2003 15; 102(4):1458-65), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the present disclosure include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present disclosure can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies disclosed herein. In certain aspects, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present disclosure can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the present disclosure provides fusion proteins comprising an antibody fragment (e.g., antigen binding fragment) described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the present disclosure or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2): 76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present disclosure can be conjugated to marker sequences, such as a peptide, to facilitate purification. In preferred aspects, the marker amino acid sequence is a hexa-histidine peptide, such as the tag provided in a pQE vector (QIAGEN, Chatsworth, Calif.), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). As described in the present disclosure, antibodies or antigen binding fragments can also be conjugated to tumor-penetrating peptides in order to enhance their efficacy.

In other aspects, the antibodies, antibody fragments (e.g., antigen binding fragments) or functional equivalents of the present disclosure are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{193}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the present disclosure may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In another aspect, the linker used is derived from a cross-linking agent such as N-succinimidyl-3-(2-pyridyldithio)propionate (SPDP), N-succinimidyl 4-(maleimidomethyl) cyclohexanecarboxylate (SMCC), N-sulfosuccinimidyl 4-(maleimidomethyl) cyclohexanecarboxylate (sulfo-SMCC), N-succinimidyl-4-(2-pyridyldithio)-2-sulfo-butanoate (sulfo-SPDB) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug moiety, such as a maytansinoid, to an antibody in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug moiety, such as maytansinoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the ϵ-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

3. Conjugation and Preparation of ADCs

The conjugates of the present disclosure can be prepared by any methods known in the art, such as those described in U.S. Pat. Nos. 7,811,572, 6,411,163, 7,368,565, and 8,163,888, and US application publications 2011/0003969, 2011/0166319, 2012/0253021 and 2012/0259100. The entire teachings of these patents and patent application publications are herein incorporated by reference.

One-Step Process

In one aspect, the conjugates of the present disclosure can be prepared by a one-step process. The process comprises combining the antibody, drug and cross-linking agent in a substantially aqueous medium, optionally containing one or more co-solvents, at a suitable pH. In one aspect, the process comprises the step of contacting the antibody of the present disclosure with a drug (e.g., DM1 or DM4) to form a first mixture comprising the antibody and the drug, and then contacting the first mixture comprising the antibody and the drug with a cross-linking agent (e.g., SMCC, Sulfo-SMCC, SPDB, Sulfo-SPDB or CX1-1) in a solution having a pH of about 4 to about 9 to provide a mixture comprising (i) the conjugate (e.g., Ab-MCC-DM1, Ab-SPDB-DM4, Sulfo-SPDB-DM4, or Ab-CX1-1-DM1), (ii) free drug (e.g., DM1 or DM4), and (iii) reaction by-products.

In one aspect, the one-step process comprises contacting the antibody with the drug (e.g., DM1 or DM4) and then the cross-linking agent (e.g., SMCC, Sulfo-SMCC, SPDB, Sulfo-SPDB or CX1-1) in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the process comprises contacting a cell-binding agent with the drug (DM1 or DM4) and then the cross-linking agent (e.g., SMCC, Sulfo-SMCC, SPDB, Sulfo-SPDB or CX1-1) in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In another aspect, the process comprises contacting a cell-binding agent with the drug (e.g., DM1 or DM4) and then the cross-linking agent (e.g., SMCC, Sulfo-SMCC, SPDB, Sulfo-SPDB or CX1-1) in a solution having a pH of about 7.8 (e.g., a pH of 7.6 to 8.0 or a pH of 7.7 to 7.9).

The one-step process (i.e., contacting the antibody with the drug (e.g., DM1 or DM4) and then the cross-linking agent (e.g., SMCC, Sulfo-SMCC, SPDB, Sulfo-SPDB or CX1-1) can be carried out at any suitable temperature known in the art. For example, the one-step process can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one aspect, the one-step process occurs at a temperature of about 16° C. to about 24° C. (e.g., about 16° C., about 17° C., about 18° C., about 19° C., about 20° C., about 21° C., about 22° C., about 23° C., about 24° C., or about 25° C.). In another aspect, the one-step process is carried out at a temperature of about 15° C. or less (e.g., about −10° C. to about 15° C., or about 0° C. to about 15° C.). For example, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the cross-linking agent (e.g., SMCC, Sulfo-SMCC, Sulfo-SPDB SPDB, or CX1-1). In one aspect, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another aspect, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 10° C. (e.g., a temperature of 8° C. to 12° C. or a temperature of 9° C. to 11° C.).

In one aspect, the contacting described above is effected by providing the antibody, then contacting the antibody with the drug (e.g., DM1 or DM4) to form a first mixture comprising the antibody and the drug (e.g., DM1 or DM4), and then contacting the first mixture comprising the antibody and the drug (e.g., DM1 or DM4) with the cross-linking agent (e.g., SMCC, Sulfo-SMCC, SPDB, Sulfo-SPDB or CX1-1). For example, in one aspect, the antibody is provided in a reaction vessel, the drug (e.g., DM1 or DM4) is added to the reaction vessel (thereby contacting the antibody), and then the cross-linking agent (e.g., SMCC, Sulfo-SMCC, SPDB, Sulfo-SPDB or CX1-1) is added to the mixture comprising the antibody and the drug (e.g., DM1 or DM4) (thereby contacting the mixture comprising the antibody and the drug). In one aspect, the antibody is provided in a reaction vessel, and the drug (e.g., DM1 or DM4) is added to the reaction vessel immediately following providing the antibody to the vessel. In another aspect, the antibody is provided in a reaction vessel, and the drug (e.g., DM1 or DM4) is added to the reaction vessel after a time interval following providing the antibody to the vessel (e.g., about 5 minutes, about 10 minutes, about 20 minutes, about 30 minutes, about 40 minutes, about 50 minutes, about 1 hour, about 1 day or longer after providing the cell-binding agent to the space). The drug (e.g., DM1 or DM4) can be added quickly (i.e., within a short time interval, such as about 5 minutes, about 10 minutes) or slowly (such as by using a pump).

The mixture comprising the antibody and the drug (e.g., DM1 or DM4) can then be contacted with the cross-linking agent (e.g., SMCC, Sulfo-SMCC, SPDB, Sulfo-SPDB or CX1-1) either immediately after contacting the antibody with the drug (e.g., DM1 or DM4) or at some later point (e.g., about 5 minutes to about 8 hours or longer) after contacting the antibody with the drug (e.g., DM1 or DM4). For example, in one aspect, the cross-linking agent (e.g., SMCC, Sulfo-SMCC, SPDB, Sulfo-SPDB or CX1-1) is added to the mixture comprising the antibody and the drug (e.g., DM1 or DM4) immediately after the addition of the drug (e.g., DM1 or DM4) to the reaction vessel comprising the antibody. Alternatively, the mixture comprising the antibody and the drug (e.g., DM1 or DM4) can be contacted with the cross-linking agent (e.g., SMCC, Sulfo-SMCC, SPDB, Sulfo-SPDB or CX1-1) at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the antibody with the drug (e.g., DM1 or DM4).

After the mixture comprising the antibody and the drug (e.g., DM1 or DM4) is contacted with the cross-linking agent (e.g., SMCC, Sulfo-SMCC, SPDB, Sulfo-SPDB or CX1-1) the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

In one aspect, the one-step process further comprises a quenching step to quench any unreacted drug (e.g., DM1 or DM4) and/or unreacted cross-linking agent (e.g., SMCC, Sulfo-SMCC, SPDB, Sulfo-SPDB or CX1-1). The quenching step is typically performed prior to purification of the conjugate. In one aspect, the mixture is quenched by contacting the mixture with a quenching reagent. As used herein, the "quenching reagent" refers to a reagent that reacts with the free drug (e.g., DM1 or DM4) and/or cross-linking agent (e.g., SMCC, Sulfo-SMCC, SPDB, Sulfo-SPDB or CX1-1). In one aspect, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the drug (e.g., DM1 or DM4) is quenched. The quenching step can help prevent the dimerization of the drug (e.g., DM1). The dimerized DM1 can be difficult to remove. Upon quenching with polar, charged thiol-quenching reagents (such as 4-maleimidobutyric acid or 3-maleimidopropionic acid), the excess, unreacted DM1 is converted into a polar, charged, water-soluble adduct that can be easily separated from the covalently-linked conjugate during the purification step. Quenching with non-polar and neutral thiol-quenching reagents can also be used. In one aspect, the mixture is quenched by contacting the mixture with a quenching reagent that reacts with the unreacted cross-linking agent (e.g., SMCC, Sulfo-SMCC, SPDB, Sulfo-SPDB or CX1-1). For example, nucleophiles can be added to the mixture in order to quench any unreacted SMCC. The nucleophile preferably is an amino group containing nucleophile, such as lysine, taurine and hydroxylamine.

In another aspect, the reaction (i.e., contacting the antibody with the drug (e.g., DM1 or DM4) and then cross-linking agent (e.g., SMCC, Sulfo-SMCC, SPDB, Sulfo-SPDB or CX1-1)) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

Alternatively, the mixture is quenched by lowering the pH of the mixture to about 5.0 (e.g., 4.8, 4.9, 5.0, 5.1 or 5.2). In another aspect, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one aspect, the mixture is quenched by lowering the pH of the mixture to 4.8. In another aspect, the mixture is quenched by lowering the pH of the mixture to 5.5.

In one aspect, the one-step process further comprises a holding step to release the unstably bound linkers from the antibody. The holding step comprises holding the mixture prior to purification of the conjugate (e.g., after the reaction step, between the reaction step and the quenching step, or after the quenching step). For example, the process comprises (a) contacting the antibody with the drug (e.g., DM1 or DM4) to form a mixture comprising the antibody and the drug (e.g., DM1 or DM4); and then contacting the mixture comprising the antibody and drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate (e.g., Ab-MCC-DM1, Ab-SPDB-DM4, Sulfo-SPDB-DM4 or Ab-CX1-1-DM1), (ii) free drug (e.g., DM1 or DM4), and (iii) reaction by-products, (b) holding the mixture prepared in step (a) to release the unstably bound linkers from the cell-binding agent, and (c) purifying the mixture to provide a purified conjugate.

In another aspect, the process comprises (a) contacting the antibody with the drug (e.g., DM1 or DM4) to form a mixture comprising the antibody and the drug (e.g., DM1 or DM4); and then contacting the mixture comprising the antibody and the drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate, (ii) free drug (e.g., DM1 or DM4), and (iii) reaction by-products, (b) quenching the mixture prepared in step (a) to quench any unreacted drug (e.g., DM1 or DM4) and/or unreacted cross-linking agent (e.g., SMCC, Sulfo-SMCC, SPDB, Sulfo-SPDB or CX1-1), (c) holding the mixture prepared in step (b) to release the unstably bound linkers from the cell-binding agent, and (d) purifying the mixture to provide a purified conjugate (e.g., Ab-MCC-DM1, Ab-SPDB-DM4, Ab-Sulfo-SPDB-DM4 or Ab-CX1-1-DM1).

Alternatively, the holding step can be performed after purification of the conjugate, followed by an additional purification step.

In another aspect, the reaction is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the antibody while not substantially releasing the stably bound linkers from the antibody. In one aspect, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one aspect, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another aspect, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another aspect, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one aspect, the holding step comprises maintaining the solution at a temperature of about 2° C. to about 8° C. for a period of at least about 12 hours for up to a week. In another aspect, the holding step comprises maintaining the solution at a temperature of about 2° C. to about 8° C. overnight (e.g., about 12 to about 24 hours, preferably about 20 hours).

The pH value for the holding step preferably is about 4 to about 10. In one aspect, the pH value for the holding step is about 4 or more, but less than about 6 (e.g., 4 to 5.9) or about 5 or more, but less than about 6 (e.g., 5 to 5.9). In another aspect, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In other aspects, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The one-step process can optionally include the addition of sucrose to the reaction step to increase solubility and recovery of the conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one aspect, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

The one-step process can further comprise the step of purifying the mixture to provide purified conjugate (e.g., Ab-MCC-DM1, Ab-SPDB-DM4, Ab-Sulfo-SPDB-DM4 or Ab-CX1-1-DM1). Any purification methods known in the art can be used to purify the conjugates of the present disclosure. In one aspect, the conjugates of the present disclosure use tangential flow filtration (TFF), non-adsorptive chromatography, adsorptive chromatography, adsorptive filtration, selective precipitation, or any other suitable purification process, as well as combinations thereof. In another aspect, prior to subjecting the conjugates to purification process described above, the conjugates are first filtered through one or more PVDF membranes. Alternatively, the conjugates are filtered through one or more PVDF membranes after subjecting the conjugates to the purification process described above. For example, in one aspect, the conjugates are filtered through one or more PVDF membranes and then purified using tangential flow filtration. Alternatively, the conjugates are purified using tangential flow filtration and then filtered through one or more PVDF membranes.

Any suitable TFF systems may be utilized for purification, including a Pellicon® type system (Millipore, Billerica, Mass.), a Sartocon® Cassette system (Sartorius AG, Edgewood, N.Y.), and a Centrasette® type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel® hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel® resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep® Methyl and Macro-Prep® t-Butyl resins (Biorad Laboratories, Hercules, Calif.). Examples of suitable ion exchange resins include SP-Sepharose®, Sepharose®, and Q-Sepharose® resins (all from GE Healthcare, Piscataway, N.J.), and Unosphere® S resin (Bio-Rad Laboratories, Hercules, Calif.). Examples of suitable mixed mode ion exchangers include Bakerbond® ABx resin (JT Baker, Phillipsburg N.J.). Examples of suitable IMAC resins include Chelating Sepharose® resin (GE Healthcare, Piscataway, N.J.) and Profinity® IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.) and lectin affinity resins, e.g. Lentil Lectin Sepharose® resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Two-Step Process and One-Pot Process

In one aspect, the conjugates of the present disclosure can be prepared as described in the U.S. Pat. No. 7,811,572 and U.S. Patent Application Publication No. 2006/0182750. The process comprises the steps of (a) contacting the antibody of the present disclosure with the cross-linking agent (e.g., SMCC, Sulfo-SMCC, SPDB, Sulfo-SPDB or CX1-1) to covalently attach the linker (i.e., Ab-SMCC, Ab-SPDB or Ab-CX1-1) to the antibody and thereby prepare a first mixture comprising the antibody having the linker bound thereto; (b) optionally subjecting the first mixture to a purification process to prepare a purified first mixture of the antibody having the linker bound thereto; (c) conjugating the drug (e.g., DM1 or DM4) to the antibody having the linker bound thereto in the first mixture by reacting the antibody having the linker bound thereto with the drug (e.g., DM1 or DM4) in a solution having a pH of about 4 to about 9 to prepare a second mixture comprising (i) conjugate (e.g., Ab-MCC-DM1, Ab-SPDB-DM4, Ab-Sulfo-SPDB-DM4 or Ab-CX1-1-DM1), (ii) free drug (e.g., DM1 or DM4); and (iii) reaction by-products; and (d) subjecting the second mixture to a purification process to purify the conjugate from the other components of the second mixture. Alternatively, the purification step (b) can be omitted. Any purification methods described herein can be used for steps (b) and (d). In one embodiment, TFF is used for both steps (b) and (d). In another embodiment, TFF is used for step (b) and absorptive chromatography (e.g., CHT) is used for step (d).

One-Step Reagent and In-Situ Process

In one aspect, the conjugates of the present disclosure can be prepared by conjugating pre-formed drug-linker compound (e.g., SMCC-DM1, Sulfo-SMCC-DM1, SPDB-DM4, Sulfo-SPDB-DM4 or CX1-1-DM1) to the antibody of the present disclosure, as described in U.S. Pat. No. 6,441,163 and U.S. Patent Application Publication Nos. 2011/0003969 and 2008/0145374, followed by a purification step. Any purification methods described herein can be used. The drug-linker compound is prepared by reacting the drug (e.g., DM1 or DM4) with the cross-linking agent (e.g., SMCC, Sulfo-SMCC, SPDB, Sulfo-SPDB or CX1-1). The drug-linker compound (e.g., SMCC-DM1, Sulfo-SMCC-DM1, SPDB-DM4, Sulfo-SPDB-DM4 or CX1-1-DM1) is optionally subjected to purification before being conjugated to the antibody.

4. Characterization and Selection of Desirable Antibodies and Antibody Drug Conjugates The antibodies, antibody fragments (e.g., antigen binding fragments) or antibody drug conjugates of the present disclosure can be characterized and selected for their physical/chemical properties and/or biological activities by various assays known in the art.

For example, an antibody of the present disclosure can be tested for its antigen binding activity by known methods such as ELISA, FACS, Biacore or Western blot.

Transgenic animals and cell lines are particularly useful in screening antibody drug conjugates (ADCs) that have potential as prophylactic or therapeutic treatments of cancer overexpression of tumor-associated antigens and cell surface receptors. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. The candidate ADC may be screened serially and individually, or in parallel under medium or high-throughput screening format.

One aspect is a screening method comprising (a) transplanting cells from a stable cancer cell line or human patient tumor expressing CDH6 (e.g., an ovarian cell line or tumor fragment, a renal cell line or tumor fragment, a hepatic cell line or tumor fragment, a thyroid cell line or tumor fragment, a CNS cancer cell line or tumor fragment, a cholangiocarcinoma cancer cell line or tumor fragment, ovarian, renal, hepatic, soft tissue, CNS, thyroid, or cholangiocarcinoma primary cells) into a non-human animal, (b) administering an ADC drug candidate to the non-human animal and (c) determining the ability of the candidate to inhibit the growth of tumors from the transplanted cell line. The present disclosure also encompasses a method of screening ADC candidates for the treatment of a disease or disorder characterized by the overexpression of CDH6 comprising (a) contacting cells from a stable cancer cell line expressing CDH6 with a drug candidate, and (b) evaluating the ability of the ADC candidate to inhibit the growth of the stable cell line.

A further aspect is a screening method comprising (a) contacting cells from a stable cancer cell line expressing CDH6 with an ADC drug candidate and (b) evaluating the ability of the ADC candidate to induce cell death. In one aspect the ability of the ADC candidate to induce apoptosis is evaluated.

Candidate ADC can be screened by being administered to the transgenic animal over a range of doses, and evaluating the animal's physiological response to the compounds over time. In some cases, it can be appropriate to administer the compound in conjunction with co-factors that would enhance the efficacy of the compound. If cell lines derived from the subject transgenic animals are used to screen for ADCs useful in treating various disorders associated with overexpression of CDH6, the test ADCs are added to the cell culture medium at an appropriate time, and the cellular response to the ADCs is evaluated over time using the appropriate biochemical and/or histological assays.

Thus, the present disclosure provides assays for identifying ADC which specifically target and bind to CDH6, and CDH6 expressed on tumor cells.

CDH6 Antibodies

The present disclosure provides for antibodies or antibody fragments (e.g., antigen binding fragments) that specifically bind to human CDH6. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind CDH6, said antibodies or antibody fragments (e.g., antigen binding fragments) comprise a VH domain having an amino acid sequence of SEQ ID NO: 20, 34, 48, 62, 76, 90, 104, 118, 132, 146, 160, 174, 188, 202, 216, 230, 244, 258, 272, 286, 300, 314 or 328 (Table 5 and 6). The present disclosure also provides antibodies or antibody fragments (e.g., antigen binding fragments) that specifically bind to CDH6, said antibodies or antibody fragments (e.g., antigen binding fragments) comprise a VH CDR having an amino acid sequence of any one of the VH CDRs listed in Table 5 and 6. In particular aspects, the present disclosure provides antibodies or antibody fragments (e.g., antigen binding fragments) that specifically bind to CDH6, said antibodies comprising (or alternatively, consist of) one, two, three, four, five or more VH CDRs having an amino acid sequence of any of the VH CDRs listed in Table 5 and 6.

The present disclosure provides antibodies or antibody fragments (e.g., antigen binding fragments) that specifically bind to CDH6, said antibodies or antibody fragments (e.g., antigen binding fragments) comprise a VL domain having an amino acid sequence of SEQ ID NO: 21, 35, 49, 63, 77, 91, 105, 119, 133, 147, 161, 175, 189, 203, 217, 231, 245, 259, 273, 287, 301, 315 or 329 (Table 5 and 6). The present disclosure also provides antibodies or antibody fragments (e.g., antigen binding fragments) that specifically bind to CDH6, said antibodies or antibody fragments (e.g., antigen binding fragments) comprise a VL CDR having an amino acid sequence of any one of the VL CDRs listed in Table 5 and 6, infra. In particular, the disclosure provides antibodies or antibody fragments (e.g., antigen binding fragments) that specifically bind to CDH6, said antibodies or antibody fragments (e.g., antigen binding fragments) comprise (or alternatively, consist of) one, two, three or more VL CDRs having an amino acid sequence of any of the VL CDRs listed in Table 5 and 6.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 5 and 6. In some aspects, it includes mutant amino acid sequences wherein no more than 1, 2, 3, 4 or 5 amino acids have been mutated in the CDR regions when compared with the CDR regions depicted in the sequence described in Table 5 and 6.

The present disclosure also provides nucleic acid sequences that encode VH, VL, the full length heavy chain, and the full length light chain of the antibodies that specifically bind to CDH6. Such nucleic acid sequences can be optimized for expression in mammalian cells.

Other antibodies of the present disclosure include those where the amino acids or nucleic acids encoding the amino acids have been mutated, yet have at least 60, 70, 80, 90 or 95 percent identity to the sequences described in 5 and 6. In some aspects, it includes mutant amino acid sequences wherein no more than 1, 2, 3, 4 or 5 amino acids have been mutated in the variable regions when compared with the variable regions depicted in the sequence described in 5 and 6, while retaining substantially the same therapeutic activity.

Since each of these antibodies can bind to CDH6, the VH, VL, full length light chain, and full length heavy chain sequences (amino acid sequences and the nucleotide sequences encoding the amino acid sequences) can be "mixed and matched" to create other CDH6-binding antibodies. Such "mixed and matched" CDH6-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NO: 20, 34, 48, 62, 76, 90, 104, 118, 132, 146, 160, 174, 188, 202, 216, 230, 244, 258, 272, 286, 300, 314 or 328 (Table 5 and 6); and a light chain variable region comprising an amino acid sequence selected from the group consisting of SEQ ID NO: 21, 35, 49, 63, 77, 91, 105, 119, 133, 147, 161, 175, 189, 203, 217, 231, 245, 259, 273, 287, 301, 315 or 329 (Table 5 and 6); wherein the antibody specifically binds to CDH6.

In another aspect, the disclosure provides (i) an isolated monoclonal antibody having: a full length heavy chain comprising an amino acid sequence that has been optimized for expression in the cell of a mammalian selected from the group consisting of SEQ ID NO: 24, 38, 52, 66, 80, 94, 108, 122, 136, 150, 164, 178, 192, 206, 220, 234, 248, 262, 276, 290, 304, 318 or 332; and a full length light chain comprising an amino acid sequence that has been optimized for expression in the cell of a mammalian selected from the group consisting of SEQ ID NO: 25, 39, 53, 67, 81, 95, 109, 123, 137, 151, 165, 179, 193, 207, 221, 235, 249, 263, 277, 291, 305, 319 or 333; or (ii) a functional protein comprising an antigen binding portion thereof.

In another aspect, the present disclosure provides CDH6-binding antibodies that comprise the heavy chain and light chain CDR1s, CDR2s and CDR3s as described in Table 5 and 6, or combinations thereof. The amino acid sequences of the VH CDR1s of the antibodies are shown in SEQ ID NOs: 17, 31, 45, 59, 73, 87, 101, 115, 129, 143, 157, 171, 185, 199, 213, 227, 241, 255, 269, 283, 297, 311 and 325. The amino acid sequences of the VH CDR2s of the antibodies and are shown in SEQ ID NOs: 18, 32, 46, 60, 74, 88, 102, 116, 130, 144, 158, 172, 186, 200, 214, 228, 242, 256, 270, 284, 298, 312 and 326. The amino acid sequences of the VH CDR3s of the antibodies are shown in SEQ ID NOs: 19, 33, 47, 61, 75, 89, 103, 117, 131, 145, 159, 173, 187, 201, 215, 229, 243, 257, 271, 285, 299, 313 and 327. The amino acid sequences of the VL CDR1s of the antibodies are shown in SEQ ID NOs: 14, 28, 42, 56, 70, 84, 98, 112, 126, 140, 154, 168, 182, 196, 210, 224, 238, 252, 266, 280, 294, 308 and 322. The amino acid sequences of the VL CDR2s of the antibodies are shown in SEQ ID NOs: 15, 29, 43, 57, 71, 85, 99, 113, 127, 141, 155, 169, 183, 197, 211, 225, 239, 253, 267, 281, 295, 309 and 323. The amino acid sequences of the VL CDR3s of the antibodies are shown in SEQ ID NOs: 16, 30, 44, 58, 72, 86, 100, 114, 128, 142, 156, 170, 184, 198, 212, 226, 240, 254, 268, 282, 296, 310 and 324.

Given that each of these antibodies can bind to CDH6 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other CDH6-binding binding molecules. Such "mixed and matched" CDH6-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 17, 31, 45, 59, 73, 87, 101, 115, 129, 143, 157, 171, 185, 199, 213, 227, 241, 255, 269, 283, 297, 311 and 325; a heavy chain CDR2 comprising an amino acid sequence selected from the group consisting of SEQ ID NOs: 18, 32, 46, 60, 74, 88, 102, 116, 130, 144, 158, 172, 186, 200, 214, 228, 242, 256, 270, 284, 298, 312 and 326; a heavy chain CDR3 comprising an amino acid sequence selected from the group consisting of SEQ ID NOs: 19, 33, 47, 61, 75, 89, 103, 117, 131, 145, 159, 173, 187, 201, 215, 229, 243, 257, 271, 285, 299, 313 and 327; a light chain CDR1 comprising an amino acid sequence selected from the group consisting of SEQ ID NOs: 14, 28, 42, 56, 70, 84, 98, 112, 126, 140, 154, 168, 182, 196, 210, 224, 238, 252, 266, 280, 294, 308 and 322; a light chain CDR2 comprising an amino acid sequence selected from the group consisting of SEQ ID NOs: 15, 29, 43, 57, 71, 85, 99, 113, 127, 141, 155, 169, 183, 197, 211, 225, 239, 253, 267, 281, 295, 309 and 323; and a light chain CDR3 comprising an amino acid sequence selected from the group consisting of SEQ ID NOs: 16, 30, 44, 58, 72, 86, 100, 114, 128, 142, 156, 170, 184, 198, 212, 226, 240, 254, 268, 282, 296, 310 and 324; wherein the antibody specifically binds CDH6.

In a specific aspect, an antibody or antibody fragment (e.g., antigen binding fragments) that specifically binds to CDH6 comprising:

(i) a light chain variable region that comprises (a) a LCDR1 (CDR-Complementarity Determining Region) of SEQ ID NO:224, (b) a LCDR2 of SEQ ID NO:225, (c) a LCDR3 of SEQ ID NO:226; and a heavy chain variable region that comprises: (d) a HCDR1 of SEQ ID NO: 227, (e) a HCDR2 of SEQ ID NO: 228, and (f) a HCDR3 of SEQ ID NO:229;

(ii) a light chain variable region that comprises (a) a LCDR1 (CDR-Complementarity Determining Region) of SEQ ID NO:210, (b) a LCDR2 of SEQ ID NO:211, (c) a LCDR3 of SEQ ID NO:212; and a heavy chain variable region that comprises: (d) a HCDR1 of SEQ ID NO:213, (e) a HCDR2 of SEQ ID NO: 214, and (f) a HCDR3 of SEQ ID NO:215;

(iii) a light chain variable region that comprises (a) a LCDR1 (CDR-Complementarity Determining Region) of SEQ ID NO:266, (b) a LCDR2 of SEQ ID NO:267, (c) a LCDR3 of SEQ ID NO:268; and a heavy chain variable region that comprises: (d) a HCDR1 of SEQ ID NO: 269, (e) a HCDR2 of SEQ ID NO:270, and (f) a HCDR3 of SEQ ID NO: 271;

(iv) a light chain variable region that comprises (a) a LCDR1 (CDR-Complementarity Determining Region) of SEQ ID NO:308, (b) a LCDR2 of SEQ ID NO:309, (c) a LCDR3 of SEQ ID NO:310; and a heavy chain variable region that comprises: (d) a HCDR1 of SEQ ID NO:311, (e) a HCDR2 of SEQ ID NO:312, and (f) a HCDR3 of SEQ ID NO:313;

(v) a light chain variable region that comprises (a) a LCDR1 (CDR-Complementarity Determining Region) of SEQ ID NO:14, (b) a LCDR2 of SEQ ID NO:15, (c) a LCDR3 of SEQ ID NO:16; and a heavy chain variable region that comprises: (d) a HCDR1 of SEQ ID NO:17, (e) a HCDR2 of SEQ ID NO:18, and (f) a HCDR3 of SEQ ID NO:19;

(vi) a light chain variable region that comprises (a) a LCDR1 (CDR-Complementarity Determining Region) of SEQ ID NO:28, (b) a LCDR2 of SEQ ID NO:29, (c) a LCDR3 of SEQ ID NO:30; and a heavy chain variable region that comprises: (d) a HCDR1 of SEQ ID NO:31, (e) a HCDR2 of SEQ ID NO:32, and (f) a HCDR3 of SEQ ID NO:33;

(vii) a light chain variable region that comprises (a) a LCDR1 (CDR-Complementarity Determining Region) of SEQ ID NO:42, (b) a LCDR2 of SEQ ID NO:43, (c) a LCDR3 of SEQ ID NO:44; and a heavy chain variable region that comprises: (d) a HCDR1 of SEQ ID NO:45, (e) a HCDR2 of SEQ ID NO:46, and (f) a HCDR3 of SEQ ID NO:47;

(viii) a light chain variable region that comprises (a) a LCDR1 (CDR-Complementarity Determining Region) of SEQ ID NO:56, (b) a LCDR2 of SEQ ID NO:57, (c) a LCDR3 of SEQ ID NO:58; and a heavy chain variable region that comprises: (d) a HCDR1 of SEQ ID NO:59, (e) a HCDR2 of SEQ ID NO:60, and (f) a HCDR3 of SEQ ID NO:61;

(ix) a light chain variable region that comprises (a) a LCDR1 (CDR-Complementarity Determining Region) of SEQ ID NO:70, (b) a LCDR2 of SEQ ID NO:71, (c) a LCDR3 of SEQ ID NO:72; and a heavy chain variable region that comprises: (d) a HCDR1 of SEQ ID NO:73, (e) a HCDR2 of SEQ ID NO:74, and (f) a HCDR3 of SEQ ID NO:75;

(x) a light chain variable region that comprises (a) a LCDR1 (CDR-Complementarity Determining Region) of SEQ ID NO:84, (b) a LCDR2 of SEQ ID NO:85, (c) a LCDR3 of SEQ ID NO:86; and a heavy chain variable region that comprises: (d) a HCDR1 of SEQ ID NO:87, (e) a HCDR2 of SEQ ID NO: 88, and (f) a HCDR3 of SEQ ID NO: 89;

(xi) a light chain variable region that comprises (a) a LCDR1 (CDR-Complementarity Determining Region) of SEQ ID NO:98, (b) a LCDR2 of SEQ ID NO:99, (c) a LCDR3 of SEQ ID NO:100; and a heavy chain variable region that comprises: (d) a HCDR1 of SEQ ID NO:101, (e) a HCDR2 of SEQ ID NO:102, and (f) a HCDR3 of SEQ ID NO:103;

(xii) a light chain variable region that comprises (a) a LCDR1 (CDR-Complementarity Determining Region) of SEQ ID NO:112, (b) a LCDR2 of SEQ ID NO:113, (c) a LCDR3 of SEQ ID NO:114; and a heavy chain variable region that comprises: (d) a HCDR1 of SEQ ID NO:115, (e) a HCDR2 of SEQ ID NO:116, and (f) a HCDR3 of SEQ ID NO:117;

(xiii) a light chain variable region that comprises (a) a LCDR1 (CDR-Complementarity Determining Region) of SEQ ID NO:126, (b) a LCDR2 of SEQ ID NO:127, (c) a LCDR3 of SEQ ID NO:128; and a heavy chain variable region that comprises: (d) a HCDR1 of SEQ ID NO:129, (e) a HCDR2 of SEQ ID NO:130, and (f) a HCDR3 of SEQ ID NO:131;

(xiv) a light chain variable region that comprises (a) a LCDR1 (CDR-Complementarity Determining Region) of SEQ ID NO:140, (b) a LCDR2 of SEQ ID NO:141, (c) a LCDR3 of SEQ ID NO:142; and a heavy chain variable region that comprises: (d) a HCDR1 of SEQ ID NO:143, (e) a HCDR2 of SEQ ID NO:144, and (f) a HCDR3 of SEQ ID NO:145;

(xv) a light chain variable region that comprises (a) a LCDR1 (CDR-Complementarity Determining Region) of SEQ ID NO:154, (b) a LCDR2 of SEQ ID NO:155, (c) a LCDR3 of SEQ ID NO:156; and a heavy chain variable region that comprises: (d) a HCDR1 of SEQ ID NO:157, (e) a HCDR2 of SEQ ID NO:158, and (f) a HCDR3 of SEQ ID NO:159;

(xvi) a light chain variable region that comprises (a) a LCDR1 (CDR-Complementarity Determining Region) of SEQ ID NO:168, (b) a LCDR2 of SEQ ID NO:169, (c) a LCDR3 of SEQ ID NO:170; and a heavy chain variable region that comprises: (d) a HCDR1 of SEQ ID NO:171, (e) a HCDR2 of SEQ ID NO:172, and (f) a HCDR3 of SEQ ID NO:173;

(xvii) a light chain variable region that comprises (a) a LCDR1 (CDR-Complementarity Determining Region) of SEQ ID NO:182, (b) a LCDR2 of SEQ ID NO:183, (c) a LCDR3 of SEQ ID NO:184; and a heavy chain variable region that comprises: (d) a HCDR1 of SEQ ID NO:185, (e) a HCDR2 of SEQ ID NO:186, and (f) a HCDR3 of SEQ ID NO:187;

(xviii) a light chain variable region that comprises (a) a LCDR1 (CDR-Complementarity Determining Region) of SEQ ID NO:196, (b) a LCDR2 of SEQ ID NO:197, (c) a LCDR3 of SEQ ID NO:198; and a heavy chain variable region that comprises: (d) a HCDR1 of SEQ ID NO:199, (e) a HCDR2 of SEQ ID NO:200, and (f) a HCDR3 of SEQ ID NO:201;

(xix) a light chain variable region that comprises (a) a LCDR1 (CDR-Complementarity Determining Region) of SEQ ID NO:238, (b) a LCDR2 of SEQ ID NO:239, (c) a LCDR3 of SEQ ID NO:240; and a heavy chain variable region that comprises: (d) a HCDR1 of SEQ ID NO:241, (e) a HCDR2 of SEQ ID NO:242, and (f) a HCDR3 of SEQ ID NO:243;

(xx) a light chain variable region that comprises (a) a LCDR1 (CDR-Complementarity Determining Region) of SEQ ID NO:252, (b) a LCDR2 of SEQ ID NO:253, (c) a LCDR3 of SEQ ID NO:254; and a heavy chain variable region that comprises: (d) a HCDR1 of SEQ ID NO:255, (e) a HCDR2 of SEQ ID NO:256, and (f) a HCDR3 of SEQ ID NO:257;

(xxi) a light chain variable region that comprises (a) a LCDR1 (CDR-Complementarity Determining Region) of SEQ ID NO:280, (b) a LCDR2 of SEQ ID NO:281, (c) a LCDR3 of SEQ ID NO:282; and a heavy chain variable region that comprises: (d) a HCDR1 of SEQ ID NO:283, (e) a HCDR2 of SEQ ID NO:284, and (f) a HCDR3 of SEQ ID NO:285;

(xxii) a light chain variable region that comprises (a) a LCDR1 (CDR-Complementarity Determining Region) of SEQ ID NO:294, (b) a LCDR2 of SEQ ID NO:295, (c) a LCDR3 of SEQ ID NO:296; and a heavy chain variable region that comprises: (d) a HCDR1 of SEQ ID NO:297, (e) a HCDR2 of SEQ ID NO:298, and (f) a HCDR3 of SEQ ID NO:299; or (xxiii) a light chain variable region that comprises (a) a LCDR1 (CDR-Complementarity Determining Region) of SEQ ID NO:322, (b) a LCDR2 of SEQ ID NO:323, (c) a LCDR3 of SEQ ID NO:324; and a heavy chain variable region that comprises: (d) a HCDR1 of SEQ ID NO:325, (e) a HCDR2 of SEQ ID NO:326, and (f) a HCDR3 of SEQ ID NO:327.

In certain aspects, an antibody that specifically binds to CDH6 is an antibody or antibody fragment (e.g., antigen binding fragment) that is described in Table 5 and/or 6.

1. Identification of Epitopes and Antibodies that Bind to the Same Epitope

The present disclosure provides antibodies and antibody fragments (e.g., antigen binding fragments) that bind to an epitope of within the extracellular domain of CDH6. In certain aspects the antibodies and antibody fragments can bind to epitopes within domains of the CDH6 extracellular domain.

The present disclosure also provides antibodies and antibody fragments (e.g., antigen binding fragments) that bind to the same epitope as do the anti-CDH6 antibodies described in Table 5 and 6. Additional antibodies and antibody fragments (e.g., antigen binding fragments) can therefore be identified based on their ability to cross-compete (e.g., to competitively inhibit the binding of, in a statistically significant manner) with other antibodies in CDH6 binding assays. The ability of a test antibody to inhibit the binding of antibodies and antibody fragments (e.g., antigen binding fragments) of the present disclosure to a CDH6 protein (e.g., human CDH6) demonstrates that the test antibody can compete with that antibody or antibody fragment (e.g., antigen binding fragments) for binding to CDH6; such an antibody may, according to non-limiting theory, bind to the same or a related (e.g., a structurally similar or spatially proximal) epitope on the CDH6 protein as the antibody or antibody fragment (e.g., antigen binding fragments) with which it competes. In a certain aspect, the antibody that binds to the same epitope on CDH6 as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure provides site-specific labeled immunoconjugates. These immunoconjugates can comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered Clq binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγR1, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in “Fc silent” antibodies that have minimal interaction with effector cells. In general, the “IgG Fc region” is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950. Examples of silent Fc IgG1 antibodies are the LALA mutant comprising L234A and L235A mutation in the IgG1 Fc amino acid sequence. Another example of a silent IgG1 antibody is the DAPA (D265A, P329A) mutation (U.S. Pat. No. 6,737,056). Another silent IgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis, No ADCC activity means that the Fc silent antibody exhibits an ADCC activity (specific cell lysis) that is below 1%.

3. Production of the CDH6 Antibodies

Anti-CDH6 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 22, 36, 50, 64, 78, 92, 106, 120, 134, 148, 162, 176, 190, 204, 218, 232, 246, 260, 274, 288, 302, 316, and 330. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 23, 37, 51, 65, 79, 93, 107, 121, 135, 149, 163, 177, 191, 205, 219, 233, 247, 261, 275, 289, 303, 317, and 331.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 26, 40, 54, 68, 82, 96, 110, 124, 138, 152, 166, 180, 194, 208, 222, 236, 250, 264, 278, 292, 306, 320, and 334. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 27, 41, 55, 69, 83, 97, 111, 125, 139, 153, 167, 181, 195, 209, 223, 237, 251, 265, 279, 293, 307, 321, and 335.

The polynucleotides of the present disclosure can encode only the variable region sequence of an anti-CDH6 antibody. They can also encode both a variable region and a constant region of the antibody. Some of the polynucleotide sequences encode a polypeptide that comprises variable regions of both the heavy chain and the light chain of one of an exemplified anti-CDH6 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-CDH6 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing the anti-CDH6 antibodies described above. Various expression vectors can be employed to express the polynucleotides encoding the anti-CDH6 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-CDH6 polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-CDH6 antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-CDH6 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-CDH6 antibody sequences. More often, the inserted anti-CDH6 antibody sequences are linked to a signal sequences before inclusion in the vector. Vectors to be used to receive sequences encoding anti-CDH6 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-CDH6 antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-CDH6 polypeptides. Insect cells in combination with baculovirus vectors can also be used.

In other aspects, mammalian host cells are used to express and produce the anti-CDH6 polypeptides of the present disclosure. For example, they can be either a hybridoma cell line expressing endogenous immunoglobulin genes (e.g., a myeloma hybridoma clone) or a mammalian cell line harboring an exogenous expression vector (e.g., SP2/0 myeloma cells). These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-CDH6 antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments), and antibody drug conjugates of the present disclosure are useful in a variety of applications including, but not limited to, treatment of cancer, such as solid cancers. In certain aspects, the antibodies, antibody fragments (e.g., antigen binding fragments), and antibody drug conjugates are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates are useful for detecting the presence of CDH6 in a biological sample. The term "detecting" as used herein encompasses quantitative or qualitative detection. In certain aspects, a biological sample comprises a cell or tissue. In certain aspects, such tissues include normal and/or cancerous tissues that express CDH6 at higher levels relative to other tissues.

In one aspect, the present disclosure provides a method of detecting the presence of CDH6 in a biological sample. In certain aspects, the method comprises contacting the biological sample with an anti-CDH6 antibody under conditions permissive for binding of the antibody to the antigen, and detecting whether a complex is formed between the antibody and the antigen.

Also included is a method of diagnosing a disorder associated with increased expression of CDH6. In certain aspects, the method comprises contacting a test cell with an anti-CDH6 antibody; determining the level of expression (either quantitatively or qualitatively) of CDH6 on the test cell by detecting binding of the anti-CDH6 antibody to the CDH6 antigen; and comparing the level of expression of CDH6 in the test cell with the level of expression of CDH6 in a control cell (e.g., a normal cell of the same tissue origin as the test cell or a cell that expresses CDH6 at levels comparable to such a normal cell), wherein a higher level of expression of CDH6 on the test cell as compared to the control cell indicates the presence of a disorder associated with increased expression of CDH6. In certain aspects, the test cell is obtained from an individual suspected of having a disorder associated with increased expression of CDH6. In certain aspects, the disorder is a cell proliferative disorder, such as a cancer or a tumor.

In certain aspects, a method of diagnosis or detection, such as those described above, comprises detecting binding of an anti-CDH6 antibody to CDH6 expressed on the surface of a cell or in a membrane preparation obtained from a cell expressing CDH6 on its surface. An exemplary assay for detecting binding of an anti-CDH6 antibody to CDH6 expressed on the surface of a cell is a "FACS" assay.

Certain other methods can be used to detect binding of anti-CDH6 antibodies to CDH6. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-CDH6 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-CDH6 antibodies are immobilized on an insoluble matrix. Immobilization entails separating the anti-CDH6 antibody from any CDH6 proteins that remains free in solution. This conventionally is accomplished by either insolubilizing the anti-CDH6 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-CDH6 antibody after formation of a complex between the anti-CDH6 antibody and CDH6 protein, e.g., by immunoprecipitation.

Any of the above aspects of diagnosis or detection can be carried out using an immunoconjugate of the present disclosure in place of or in addition to an anti-CDH6 antibody.

In one aspect, the disclosure provides for a method of treating, preventing or ameliorating a disease comprising administering the antibodies, antibody fragments (e.g., antigen binding fragments), and antibody drug conjugates to a patient, thereby treating the disease. In certain aspects, the disease treated with the antibodies, antibody fragments (e.g., antigen binding fragments), and antibody drug conjugates is a cancer. Examples of diseases which can be treated and/or prevented include, but are not limited to, ovarian cancer, renal cancer, hepatic cancer, soft tissue cancer, CNS cancers, thyroid cancer and cholangiocarcinoma. In certain aspects, the cancer is characterized by CDH6 expressing cells to which the antibodies, antibody fragments (e.g., antigen binding fragments), and antibody drug conjugates can specifically bind.

The present disclosure provides for methods of treating cancer comprising administering a therapeutically effective amount of the antibodies, antibody fragments (e.g., antigen binding fragments), or antibody drug conjugates. In certain aspects, the cancer is a solid cancer. In certain aspects, the subject is a human.

In certain aspects, the method of inhibiting tumor growth comprises administering to a subject a therapeutically effective amount of the antibodies, antibody fragments (e.g., antigen binding fragments), or antibody drug conjugates. In certain aspects, the subject is a human. In certain aspects, the subject has a tumor or has had a tumor removed.

In certain aspects, the tumor expresses the CDH6 to which the anti-CDH6 antibody binds. In certain aspects, the tumor overexpresses the human CDH6.

For the treatment of the disease, the appropriate dosage of the antibodies, antibody fragments (e.g., antigen binding fragments), or antibody drug conjugates depend on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody, antibody fragment (e.g., antigen binding fragment), or antibody drug conjugate of the present disclosure is given once every two weeks or once every three weeks. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present disclosure is combined with other therapeutic agents, such as other anti-cancer agents, anti-allergic agents, anti-nausea agents (or anti-emetics), pain relievers, cytoprotective agents, and combinations thereof.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan®), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®)), topotecan hydrochloride for injection (Hycamptin®), vinblastine (Velban®), vincristine (Oncovin®), and vinorelbine (Navelbine®)).

In one aspect, an antibody, antibody fragment (e.g., antigen binding fragment), or antibody drug conjugate of the present disclosure is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present disclosure can be administered in combination with, but not limited to, a chemotherapeutic agent, a tyrosine kinase inhibitor, for example, Imatinib.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating cancer by administering to a subject in need thereof an antibody drug conjugate in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); nilotinib (Tasigna®); Regorafenib (Stivarga®) and Imatinib or Imatinib mesylate (Gilvec® and Gleevec®).

Epidermal growth factor receptor (EGFR) inhibitors include but are not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (HER2 receptor) (also known as Neu, ErbB-2, CD340, or p185) inhibitors include but are not limited to, Trastuzumab (Herceptin®); Pertuzumab (Omnitarg®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-01 (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)-N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)-N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and BI836845. See e.g., Yee, JNCI, 104; 975 (2012) for review.

In another aspect, the present disclosure provides a method of treating cancer by administering to a subject in need thereof an antibody drug conjugate in combination with one or more FGF downstream signaling pathway inhibitors, including but not limited to, MEK inhibitors, Braf inhibitors, PI3K/Akt inhibitors, SHP2 inhibitors, and also mTor inhibitors.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

Phosphoinositide 3-kinase (PI3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran- 2,7,10(1H)-trione (PX866, CAS 502632-66-8); and 8-Phenyl-2-(morpholin-4-yl)-chromen-4-one (LY294002, CAS 154447-36-6).

mTor inhibitors include but are not limited to, Temsirolimus (Torisel®); Ridaforolimus (formally known as deferolimus, (1R,2R,4S)-4-[(2R)-2 [(1R,9S,12S,15R,16E,18R, 19R,21R,23S,24E,26E,28Z,30S,32S,35R)-1,18-dihydroxy-19,30-dimethoxy-15,17,21,23,29,35-hexamethyl-2,3,10,14, 20-pentaoxo-11,36-dioxa-4-azatricyclo[30.3.1.$0^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

In yet another aspect, the present disclosure provides a method of treating cancer by administering to a subject in need thereof an antibody drug conjugate in combination with one or more pro-apoptotics, including but not limited to, IAP inhibitors, Bcl2 inhibitors, MCl1 inhibitors, Trail agents, Chk inhibitors.

For examples, IAP inhibitors include but are not limited to, NVP-LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl] phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl) methyl]-1-piperazinyl]-N-[[4-[[(1R)-3-(dimethylamino)-1-[(phenylthio)methyl]propyl]amino]-3-nitrophenyl] sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo [1,5-a]pyrimidin-7-amine (SCH900776, CAS 891494-63-6); 5-(3-Fluorophenyl)-3-ureidothiophene-2-carboxylic acid N-[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7,4-Methylsulfinylbutyl isothiocyanate); 9,10,11,12-Tetrahydro-9,12-epoxy-1H-diindolo [1,2,3-fg:3',2',1'-kl]pyrrolo[3,4-i][1,6]benzodiazocine-1,3 (2H)-dione (SB-218078, CAS 135897-06-2); and TAT-S216A (Sha et al., Mol. Cancer. Ther 2007; 6(1):147-153), and CBP501.

In one aspect, the present disclosure provides a method of treating cancer by administering to a subject in need thereof an antibody drug conjugate in combination with one or more FGFR inhibitors. For example, FGFR inhibitors include but are not limited to, Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Vargatef (BIBF1120, CAS 928326-83-4); Dovitinib dilactic acid (TKI258, CAS 852433-84-2); 3-(2,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and (PD173074, CAS 219580-11-7). In a specific aspect, the present disclosure provides a method of treating cancer by administering to a subject in need thereof an antibody drug conjugate in combination with an FGFR2 inhibitor, such as 3-(2,6-dichloro-3,5-dimethoxyphenyl)-1-(6((4-(4-ethylpiperazin-1-yl)phenyl)amino)pyrimidin-4-yl)-1-methylurea (also known as BGJ-398); or 4-amino-5-fluoro-3-(5-(4-methylpiperazin1-yl)-1H-benzo[d]imidazole-2-yl)quinolin-2(1H)-one (also known as dovitinib or TKI-258). AZD4547 (Gavine et al., 2012, Cancer Research 72, 2045-56, N-[5-[2-(3,5-Dimethoxyphenyl)ethyl]-2H-pyrazol-3-yl]-4-(3R,5S)-diemthylpiperazin-1-yl)benzamide), Ponatinib (AP24534; Gozgit et al., 2012, Mol Cancer Ther., 11; 690-99; 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide, CAS 943319-70-8)

Pharmaceutical Compositions

To prepare pharmaceutical or sterile compositions including immunoconjugates, the immunoconjugates of the present disclosure are mixed with a pharmaceutically acceptable carrier or excipient. The compositions can additionally contain one or more other therapeutic agents that are suitable for treating or preventing cancer, for example, ovarian cancer, renal cancer, hepatic cancer, soft tissue cancer, CNS cancers, thyroid cancer and cholangiocarcinoma.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the clinical service form (CSF) of the antibody drug conjugates of the present disclosure is a lyophilisate in vial containing the ADC, sodium succinate, and polysorbate 20. The lyophilisate can be reconstitute with water for injection, the solution comprises the ADC, sodium succinate, sucrose, and polysorbate 20 at a pH of about 5.0. For subsequent intravenous administration, the obtained solution will usually be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions antibody drug conjugates can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the present disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the immunoconjugates the can be repeated and the administrations may be separated by at least 1 day, 2 days, 3 days, 5 days, 10 days, 15 days, 30 days, 45 days, 2 months, 75 days, 3 months, or at least 6 months. In a specific aspect, doses of the immunoconjugates of the present disclosure are repeated every 3 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the immunoconjugates include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the immunoconjugates of the present disclosure are administered by infusion. In another aspect, the immunoconjugates are administered subcutaneously.

If the immunoconjugates of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the immunoconjugates (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the disclosure are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the present disclosure. The two or more therapies may be administered within one same patient visit.

In certain aspects, immunoconjugates can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol.

29:685). Exemplary targeting moieties include folate or biotin (see, e.g., U.S. Pat. No. 5,416,016 to Low et al.); mannosides (Umezawa et al., (1988) Biochem. Biophys. Res. Commun 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising immunoconjugates alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the immunoconjugates can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Identification of CDH6 Antibodies by Phage-Display Technology

HuCAL PLATINUM® Pannings

Antibodies were identified by the selection of clones that bound to CDH6-ECD. As a source of antibody variants a commercially available phage display library, the Morphosys HuCAL PLATINUM® library, was used. The phagemid library is based on the HuCAL® concept (Knappik et al., J Mol Biol. 2000: 296(1):57-86; Prassler et al., J Mol Biol. 2011: 413(1):261-78 2011) and employs the CysDisplay™ technology for displaying the Fab on the phage surface (Rothe et al., J Mol Biol. 2008: 376(4):1182-200). For isolation of anti-CDH6 antibodies, standard panning strategies were performed using solid phase and solution panning approaches.

Overview of Antigen (Recombinant Protein and Cell Lines) and Antibody Reagents Used for Pannings and Screenings Pannings were done on various forms of CDH6 antigens. An overview of recombinant CDH6 proteins and CDH6-expressing cell lines used as antigens for pannings and subsequent screening and characterization is given in Table 1.

Human, mouse and rat CDH6 extracellular domains were gene synthesized based on amino acid sequences from the GenBank or Uniprot databases (see Table 1). Cynomolgus CDH6 cDNA template was gene synthesized based on amino acid sequences and homology information generated using mRNA from various cyno tissues (e.g. Zyagen Laboratories, San Diego, Calif.). All synthesized DNA fragments were cloned into appropriate expression vectors listed affinity tags to allow for purification or expression vectors Zyagen Laboratories for mammalian cell surface expression.

For the generation of a stable CHO cell line exogenously expressing human CDH6 the TREX expression system (Invitrogen, Carlsbad, Calif.) was used according to the manufacturer's instructions. Briefly, CHO-TREx cells (Invitrogen, R718-07, Carlsbad, Calif.) were grown in DMEM media (Invitrogen 11995-085) with 00% FBS (Invitrogen, 10082-147, Carlsbad, Calif.), and 10 μg/ml Blasticidin (Invitrogen A11139-02, Carlsbad, Calif.). Transfection was performed in 6 well plates when cell reach 90% confluence. 4 μg of linearized CDH6 plasmid DNA was mixed with 100 μl DMEM media (no FBS) in a sterile Eppendorf tube, 12 μl of Lipofectamine® 2000 (Invitrogen 11668-019, Carlsbad, Calif.) were mixed with 100 μl DMEM media in another sterile Eppendorf tube. DNA and Lipofectamine® were mixed together, and incubated in room temperature for 15 min. The culture media of CHO-TREx cells was changed to 1 ml DMEM media without FBS for each well; half above DNA/Lipofectamine® mix were added into each well, incubated for 2 hours. Then 2 ml growth media (with FBS) were added into each well, and the cells were incubated overnight. The transfected cells were split from 6 well plate to T175 flask next day and grew in selection DMEM media with 10% FBS, 10 μg/ml Blasticidin, 800-1000 μg/ml Geneticin (Invitrogen 10131-027). CDH6 expression was induced with final 1 μg/ml Tetracycline in selection media for 20-24 hours. Positive cells were labeled with final 5 μg/ml anti-CDH6 primary monoclonal antibody (MAB2715 from R&D Systems, Minneapolis, Minn.), and then labeled with PE conjugated anti-mouse secondary antibody (cat #12-4010-87, eBioscience, San Diego, Calif.) and sorted by FACS.

Stable CHO cell lines featuring exogenous expression of CDH6 from mouse, rat and cynomolgus origin were generated by transfection of CHO-K1 cells (Invitrogen, Carlsbad, Calif.) with the respective cDNAs cloned into a mammalian expression vector (pcDNA6.1, Invitrogen, Carlsbad, Calif.). Transfection was performed in 6 well plates when cell reach 90% confluence. 4 μg of linearized CDH6 plasmid DNA were mixed with 100 μl DMEM media without FBS in a sterile Eppendorf tube, 12 μl of Lipofectamine® 2000 (Invitrogen 11668-019, Carlsbad, Calif.) were mixed with 100 μl DMEM media in another sterile Eppendorf tube. The DNA and Lipofectamine® solution were mixed together, and incubated at room temperature for 15 min. The culture media of CHO cells was changed to 1 ml DMEM media without FBS for each well; half above DNA/Lipofectamine® mix were added into each well, incubated for 2 hours. Then 2 ml growth media (with FBS) were added into each well, and the cells were incubated overnight. The transfected cells were split from 6 well plate to T175 flask next day and grew in selection DMEM media with 10% FBS, 10 μg/ml Blasticidin, 800-1000 μg/ml Geneticin (Invitrogen 10131-027 Carlsbad, Calif.). CDH6 expression was induced with final 1 μg/ml Tetracycline in selection media for 20-24 hours. Positive cells were labeled with final 5 μg/ml anti-CDH6 primary monoclonal antibody (MAB2715 from R&D Systems, Minneapolis, Minn.), and then labeled with PE conjugated anti-mouse secondary antibody (cat #12-4010-87, eBioscience, San Diego, Calif.) and sorted by FACS. An alternative commercially available anti-CDH6 antibody is the 2B6 antibody (#GWB-E8FDF3-Genway, San Diego, Calif.). This antibody was also used to confirm CDH6 expression in cells.

TABLE 1

Overview of antigen, antibody and cell line reagents for pannings and screenings

| Antigen/ Antibody | Accession/ Source | Description | Mature sequence |
|---|---|---|---|
| His6-SUMO-CDH6 aa54-260-APP-Avi | NM_004932.3 | human EC 1/2 domain variant (SEQ ID NO: 3) | SWMWNQFFLLEEYTGSDYQYVGKLHSD QDRGDGSLKYILSGDGAGDLFIINENTGD IQATKRLDREEKPVYILRAQAINRRTGRP VEPESEFIIKIHDINDNEPIFTKEVYTATVP EMSDVGTFVVQVTATDADDPTYGNSAK VVYSILQGQPYFSVESETGIIKTALLNMD RENREQYQVVIQAKDMGGQMGGLSGTT TVNITLTDGGGGSEFRHDSGLNDIFEAQK IEWHE |
| hCDH6aa54-615 APPavi | NM_004932.3 | human full-length ECD (SEQ ID NO: 4) | SWMWNQFFLLEEYTGSDYQYVGKLHSD QDRGDGSLKYILSGDGAGDLFIINENTGD IQATKRLDREEKPVYILRAQAINRRTGRP VEPESEFIIKIHDINDNEPIFTKEVYTATVP EMSDVGTFVVQVTATDADDPTYGNSAK VVYSILQGQPYFSVESETGIIKTALLNMD RENREQYQVVIQAKDMGGQMGGLSGTT TVNITLTDVNDNPPRFPQSTYQFKTPESSP PGTPIGRIKASDADVGENAEIEYSITDGEG LDMFDVITDQETQEGIITVKKLLDFEKKK VYTLKVEASNPYVEPRFLYLGPFKDSAT VRIVVEDVDEPPVFSKLAYILQIREDAQIN TTIGSVTAQDPDAARNPVKYSVDRHTDM DRIFNIDSGNGSIFTSKLLDRETLLWHNIT VIATEINNPKQSSRVPLYIKVLDVNDNAP EFAEFYETFVCEKAKADQLIQTLHAVDK DDPYSGHQFSFSLAPEAASGSNFTIQDNK DNTAGILTRKNGYNRHEMSTYLLPVVIS DNDYPVQSSTGTVTVRVCACDHHGNMQ SCHAEALIHPTGLSTGA |
| hCDH6aa54-615 APPavi biotin | NM_004932.3 | human full-length ECD, biotinylated (SEQ ID NO: 5) | SWMWNQFFLLEEYTGSDYQYVGKLHSD QDRGDGSLKYILSGDGAGDLFIINENTGD IQATKRLDREEKPVYILRAQAINRRTGRP VEPESEFIIKIHDINDNEPIFTKEVYTATVP EMSDVGTFVVQVTATDADDPTYGNSAK VVYSILQGQPYFSVESETGIIKTALLNMD RENREQYQVVIQAKDMGGQMGGLSGTT TVNITLTDVNDNPPRFPQSTYQFKTPESSP PGTPIGRIKASDADVGENAEIEYSITDGEG LDMFDVITDQETQEGIITVKKLLDFEKKK VYTLKVEASNPYVEPRFLYLGPFKDSAT VRIVVEDVDEPPVFSKLAYILQIREDAQIN TTIGSVTAQDPDAARNPVKYSVDRHTDM DRIFNIDSGNGSIFTSKLLDRETLLWHNIT VIATEINNPKQSSRVPLYIKVLDVNDNAP EFAEFYETFVCEKAKADQLIQTLHAVDK DDPYSGHQFSFSLAPEAASGSNFTIQDNK DNTAGILTRKNGYNRHEMSTYLLPVVIS DNDYPVQSSTGTVTVRVCACDHHGNMQ SCHAEALIHPTGLSTGAGSEFRHDSGLND IFEAQK(BIOTIN)IEWHE |

TABLE 1-continued

Overview of antigen, antibody and cell line reagents for pannings and screenings

| Antigen/ Antibody | Accession/ Source | Description | Mature sequence |
|---|---|---|---|
| hCDH6aa54-615 Fc | NM_004932.3 | human full-length ECD, dimerized (SEQ ID NO: 6) | SWMWNQFFLLEEYTGSDYQYVGKLHSD<br>QDRGDGSLKYILSGDGAGDLFIINENTGD<br>IQATKRLDREEKPVYILRAQAINRRTGRP<br>VEPESEFIIKIHDINDNEPIFTKEVYTATVP<br>EMSDVGTFVVQVTATDADDPTYGNSAK<br>VVYSILQGQPYFSVESETGIIKTALLNMD<br>RENREQYQVVIQAKDMGGQMGGLSGTT<br>TVNITLTDVNDNPPRFPQSTYQFKTPESSP<br>PGTPIGRIKASDADVGENAEIEYSITDGEG<br>LDMFDVITDQETQEGIITVKKLLDFEKKK<br>VYTLKVEASNPYVEPRFLYLGPFKDSAT<br>VRIVVEDVDEPPVFSKLAYILQIREDAQIN<br>TTIGSVTAQDPDAARNPVKYSVDRHTDM<br>DRIFNIDSGNGSIFTSKLLDRETLLWHNIT<br>VIATEINNPKQSSRVPLYIKVLDVNDNAP<br>EFAEFYETFVCEKAKADQLIQTLHAVDK<br>DDPYSGHQFSFSLAPEAASGSNFTIQDNK<br>DNTAGILTRKNGYNRHEMSTYLLPVVIS<br>DNDYPVQSSTGTVTVRVCACDHHGNMQ<br>SCHAEALIHPTGLSTGAGSDKTHTCPPCP<br>APELLGGPSVFLFPPKPKDTLMISRTPEVT<br>CVVVDVSHEDPEVKFNWYVDGVEVHNA<br>KTKPREEQYNSTYRVVSVLTVLHQDWL<br>NGKEYKCKVSNKALPAPIEKTISKAKGQP<br>REPQVYTLPPSREEMTKNQVSLTCLVKG<br>FYPSDIAVEWESNGQPENNYKTTPPVLDS<br>DGSFFLYSKLTVDKSRWQQGNVFSCSVM<br>HEALHNHYTQKSLSLSPGK |
| cynoCDH6 FL | See above description on cynomolgus sequence derivation | Cynomolgus (*Macaca fascicularis*) full-length CDH6 (SEQ ID NO: 7) | SWMWNQFFLLEEYTGSDYQYVGKLHSD<br>QDRGDGSLKYILSGDGAGDLFIINENTGD<br>IQATKRLDREEKPVYILRAQAINRRTGRP<br>VEPESEFIIKIHDINDNEPIFTKEVYTATVP<br>EMSDVGTFVVQVTATDADDPTYGNSAK<br>VVYSILQGQPYFSVESETGIIKTALLNMD<br>RENREQYQVVIQAKDMGGQMGGLSGTT<br>TVNITLTDVNDNPPRFPQSTYQFKTPESSP<br>PGTPIGRIKASDADVGENAEIEYSITDGEG<br>LDMFDVITDQETQEGIITVKKLLDFEKKK<br>VYTLKVEASNPHVEPRFLYLGPFKDSAT<br>VRIVVEDVDEPPVFSKLAYILQIREDAQIN<br>TTIGSVTAQDPDAARNPVKYSVDRHTDM<br>DRIFNIDSGNGSIFTSKLLDRETLLWHNIT<br>VIATEINNPKQSSRVPLYIKVLDVNDNAP<br>EFAEFYETFVCEKAKADQLIQTLRAVDK<br>DDPYSGHQFSFSLAPEAASGSNFTIQDNK<br>DNTAGILTRKNGYNRHEMSTYLLPVVIS<br>DNDYPVQSSTGTVTVRVCACDHHGNMQ<br>SCHAEALIHPTGLSTGAGSEFRHDSGLND<br>IFEAQKIEWHE |
| moCDH6 FL | NM_007666.3 | Mouse (*Mus musculus*) full-length CDH6 (SEQ ID NO: 8) | SWMWNQFFLLEEYTGSDYQYVGKLHSD<br>QDRGDGSLKYILSGDGAGDLFIINENTGD<br>IQATKRLDREEKPVYILRAQAVNRRTGRP<br>VEPESEFIIKIHDINDNEPIFTKDVYTATVP<br>EMADVGTFVVQVTATDADDPTYGNSAK<br>VVYSILQGQPYFSVESETGIIKTALLNMD<br>RENREQYQVVIQAKDMGGQMGGLSGTT<br>TVNITLTDVNDNPPRFPQSTYQFKTPESSP<br>PGTPIGRIKASDADVGENAEIEYSITDGEG<br>HEMFDVITDQETQEGIITVKKLLDFEKKK<br>VYTLKVEASNPHVEPRFLYLGPFKDSAT<br>VRIVVDDVDEPPVFSKLAYILQIREDARIN<br>TTIGSVAAQDPDAARNPVKYSVDRHTD<br>MDRIFNIDSGNGSIFTSKLLDRETLLWHNI<br>TVIATEINNPKQSSRVPLYIKVLDVNDNA<br>PEFAEFYETFVCEKAKADQLIQTLRAVD<br>KDDPYSGHQFSFSLAPEAASSSNFTIQDN<br>KDNTAGILTRKNGYNRHEMSTYLLPVVI<br>SDNDYPVQSSTGTVTVRVCACDHHGNM<br>QSCHAEALIHPTGLSTGAGSEFRHDSGLN<br>DIFEAQKIEWHE |

TABLE 1-continued

Overview of antigen, antibody and cell line reagents for pannings and screenings

| Antigen/ Antibody | Accession/ Source | Description | Mature sequence |
|---|---|---|---|
| ratCDH6 FL | NM_012927.1 | Rat (*Rattus norvegicus*) full-length CDH6 (SEQ ID NO: 9) | SWMWNQFFLLEEYTGSDYQYVGKLHSD QDRGDGSLKYILSGDGAGDLFIINENTGD IQATKRLDREEKPVYILRAQAINRRTGRP VEPESEFIIKIHDINDNEPIFTKDVYTATVP EMADVGTFVVQVTATDADDPTYGNSAK VVYSILQGQPYFSVESETGIIKTALLNMD RENREQYQVVIQAKDMGGQMGGLSGTT TVNITLTDVNDNPPRFPQSTYQFKTPESSP PGTPIGRIKASDADVGENAEIEYSITDGEG HDMFDVITDQETQEGIITVKKLLDFEKKR VYTLKVEASNPHIEPRFLYLGPFKDSATV RIVVDDVDEPPVFSKLAYILQIREDAQINT TIGSVAAQDPDAARNPVKYSVDRHTDM DRIFNIDSGNGSIFTSKLLDRETLLWHNIT VIATEINNPKQSSRVPLYIKVLDVNDNAP EFAEFYETFVCEKAKADQLIQTLHAVDK DDPYSGHQFSFSLAPEAASGSNFTIQDNK DNTAGILTRKNGYNRHEMSTYLLPVVIS DNDYPVQSSTGTVTVRVCACDHHGNMQ SCHAEALIHPTGLSTGAGSEFRHDSGLND IFEAQKIEWHE |

Recombinant Protein Expression and Purification:
His6-SUMO-CDH6 aa54-260-APP-Avi Protein was expressed in Rosetta® 2 De3 pLysS cells (Millipore, Billerica, Mass.) in pET vector using 2×YT+50 μg/ml Kanamycin and 30 μg/ml chloramphenicol. Cells were induced with 0.1 mM IPTG at 30° C. The pellet resuspended in 400 ml 20 mM Tris-Cl, pH 8.0, 150 mM NaCl, 3 mM CaCl2, 20 mM Imidazole, +PI tabs (1 per 50 ml)+1 mg/ml lysozyme added fresh, homogenized to break up clumps and passed through microfluidizer 3 times. Following centrifugation at 20K×g for 30 min the soluble fraction of supernatant was used for purification over a 2 ml Ni-NTA (Qiagen superflow resin, Qiagen, Venlo, Netherlands). The lysate was passed over the column at 2.0 ml/min, washed with 10 CV (column volume) 20 mM Tris-Cl, pH 8.0, 150 mM NaCl, 3 mM CaCl2, 20 mM Imidazole and protein was eluted with 4×3.0 ml elution fractions using 20 mM Tris-Cl, pH 8.0, 500 mM NaCl, 3 mM CaCl2, 250 mM Imidazole. Fractions were pooled. 200 units of SUMO Protease (Invitrogen) were added with ~15 ml protein (~20 mgs) and dialyzed into 5 L of 20 mM Tris-Cl, pH 8.0, 150 mM NaCl, 3 mM CaCl2 overnight at 4° C. using Snakeskin® pleated tubing with 10K cutoff (Thermo Scientific, Rockford, Ill.). Dialyzed material was collected and re-purified over 2.0 ml Ni-NTA resin to remove uncleaved protein and SUMO Protease. Cleaved protein was collected from flow through and wash fractions. Concentrated flow through and wash from reverse Ni-NTA to 5 ml volume, added NaCl to final concentration of 500 mM and injected onto S200 column, buffer=20 mM Tris-Cl, pH 8.0, 150 mM NaCl, 3 mM CaCl2.

hCDH6aa54-615 APPavi, hCDH6aa54-615 Fc, cynoCDH6 FL, moCDH6 FL, ratCDH6 FL

The protein was expressed in HEK293 (ATCC CRL-1573) derived cell lines previously adapted to suspension culture and grown in a Novartis proprietary serum-free medium. Small scale expression verification was undertaken in transient 6-well-plate transfection assays on the basis of lipofection. Large-scale protein production via transient transfection and was performed at the 10-20 L scale in the Wave™ bioreactor system (GE Healthcare, Pittsburgh, Pa.). DNA Polyethylenimine (Polysciences, Warrington, Pa.) was used as a plasmid carrier at a ratio of 1:3 (w:w). The cell culture supernatants were harvested 7-10 days post transfection and concentrated by cross-flow filtration and diafiltration prior to purification.

For purification, clarified and filtered conditioned supernatant from the transient transfection was passed over a 20 ml affinity column at 5 ml/min. Wash 20 CV PBS, 1% TX100, 0.3% t-n-butylphospate buffer, 20CV PBS. Elute using 100 mM sodium citrate, 150 mM NaCl pH3.0, protein collecting 2 ml fractions. Pooled fractions were neutralized and then dialyzed overnight at 4° C. with 5 L 50 mM Tris, 150 mM NaCl pH 7.4, 3 mM CaCl2. Sample was then subjected to size exclusion chromatography on a Superdex® S200 16/60 column (GE Healthcare, Pittsburgh, Pa.) equilibrated with dialysis buffer.

An overview of the various panning strategies is indicated in Table 2

TABLE 2

Overview of panning strategies

| Pancode | Phage subpool | Target and conditions |
|---|---|---|
| 1038.1 | VH1A/B/5 λ + κ | SP on hCDH6aa54-615 |
| 1038.2 | VH3 λ + κ | APPavi, without $CaCl_2$ |
| 1038.3 | VH2/6 λ + κ | |
| 1038.4 | VH6, κ | |
| 1038.5 | VH1A/B/5 λ + κ | SP on hCDH6aa54-615 |
| 1038.6 | VH3 λ + κ | APPavi, with $CaCl_2$ |
| 1038.7 | VH2/6 λ + κ | |
| 1038.8 | VH6, κ | |
| 1038.9 | VH1A/B/5 λ + κ | SP on His6-SUMO-CDH6 aa54- |
| 1038.10 | VH3 λ + κ | 260-APP-Avi, with 1 mM $CaCl_2$ |
| 1038.11 | VH2/6 λ + κ | |
| 1038.12 | VH6, κ | |
| 1038.13 | VH1A/B/5 λ + κ | SP on His6-SUMO-CDH6 aa54- |
| 1038.14 | VH3 λ + κ | 260-APP-Avi, with 1 mM $CaCl_2$ |
| 1038.15 | VH2/6 λ + κ | Binding competition using |
| 1038.16 | VH6, κ | tool antibody MAB2715 |
| 1038.17 | VH1A/B/5 λ + κ | LP on biotinylated hCDH6aa54- |
| 1038.18 | VH3 λ + κ | 615 APPavi |
| 1038.19 | VH2/6 λ + κ | |
| 1038.20 | VH1A/B/5 λ + κ | LP on hCDH6aa54-615 APPavi |

TABLE 2-continued

| Overview of panning strategies | | |
|---|---|---|
| Pancode | Phage subpool | Target and conditions |
| 1038.21 | VH3 λ + κ | Pull-down panning using |
| 1038.22 | VH2/6 λ + κ | biotinylated tool antibody 2B6 |
| 1038.23 | VH1A/B/5 λ + κ | LP on Biotinylated hCDH6aa54- |
| 1038.24 | VH3 λ + κ | 615-Fc |
| 1038.25 | VH2/6 λ + κ | |
| 1038.26 | VH1A/B/5 λ + κ | SP on hCDH6aa54-615-Fc |
| 1038.27 | VH3 λ + κ | |
| 1038.28 | VH2/6 λ + κ | |

Biotinylation of Proteins

Avi-tagged proteins were biotinylated using BirA enzyme following manufacture (Avidity, Aurora, Colo.) standard protocol for protein biotinylation on an Avi-tagged protein. After biotinylation the protein was subjected to size exclusion chromatography on a Superdex® S200 16/60 column into 50 mM Tris, 150 mM NaCl pH 7.4, 3 mM CaCl2.

Non-Avi-tagged proteins were dialyzed using Slide-A-Lyzer Mini Dialysis units, 10000 MWCO (#69576 Thermo Scientific, Rockford, Ill.) twice for 2 h against 5 L of 1×PBS under stirring at room temperature prior to biotinylation. EZ-link Sulfo-NHS-LC-biotin (#21327 Thermo Scientific, Rockford, Ill.) was reconstituted according to the manufacturer's protocol. The proteins were incubated with a 20-fold molar excess of biotin reagent for 30 min at room temperature. To remove non-reacted biotin reagent the sample was again dialyzed twice for 2 h against 5 L of 1×PBS under stirring at room temperature. Protein concentrations were determined by means of the Nanodrop® device (Thermo Scientific, Rockford, Ill.). Samples were stored at 4° C. until usage.

Solid Phase Panning

In solid phase pannings the Fab fragment displaying phages are incubated with antigen that has been bound to a surface support by direct immobilization.

Prior to the antigen selection process, a coating check ELISA was performed to determine the optimal antigen coating concentration. For this purpose a 2 fold dilution series of hCDH6aa54-615 APPavi (see Table 1) covering 24 to 0.19 μg/mL was generated. The individual dilutions were used to coat wells on a 96-well Maxisorp™ plate (#442404 Nunc, Rochester, N.Y.) via direct immobilization. After coating the plate was washed thrice with 300 μL PBS and subsequently blocked with 1× blocking buffer (2.5% milk, 2.5% BSA, 0.05% Tween 20) for 2 h at room temperature.

To detect bound antigen, an anti-APP antibody (generated in-house) was added to 1 μM, 0.18 μM or 0.04 μM. Secondary detection was done using AP-labeled anti-mouse IgG-F(ab)2 specific antibody in a 1:5000 dilution Ref. 115-056-006 Jackson-Immunoresearch, West Grove, Pa.). The antigen concentration at which signal saturation was observed was chosen as coating concentrations for SP pannings.

Pancodes 1038.1-8

For SP pannings 1038.1-8 (see Table 2) hCDH6aa54-615 APPavi (see Table 1, SEQ ID NO:4) was coated on a 96-well Maxisorp™ plate (Nunc) via direct immobilization. Two wells were coated with 300 μL antigen solution (10 μg/mL in PBS) per phage subpool combination. Coating was done at 4° C. overnight with (pannings 1038.1-4) or without (pannings 1038.4-8) the presence of 1 mM CaCl2. The wells were subsequently washed twice with 400 μL PBS and blocked with 400 μL blocking buffer for 2 h at room temperature at 400 rpm. After blocking the cells were washed twice with 400 μL PBS.

Prior to binding phage subpools were blocked and depleted with unrelated FLT2-APPavi at 10 μg/mL for 1 h at room temperature to eliminate unspecific and tag binders. 300 μL of blocked and depleted phage pools were transferred per coated well and incubated for 2 h at room temperature and 400 rpm. Non-specific bound phages were removed by the washing steps listed below in Table 3.

TABLE 3

| First Round | Second Round | Third round (only pancodes 1038.9-16) |
|---|---|---|
| 3x PBST (quick) | 1x PBST (quick) | 10x PBST (quick) |
| 2x PBST/5 min | 4x PBST/5 min | 5x PBST/5 min |
| 3x PBS (quick) | 1x PBS (quick) | 10x PBS (quick) |
| 2x PBS/5 min | 4x PBS/5 min | 5x PBS/5 min |

The specifically bound phages were eluted with 300 μL elution buffer for 10 min at room temperature. Eluted phages were used to reinfect 14 mL of *E. coli* TG1F+ (Stratagene/Agilent, Santa Clara, Calif.), at an optical density of OD600=0.6-0.8. The mix of *E. coli* TG1F+ and phage eluate was incubated for 45 min in a water bath at 37° C. for phage infection. The bacterial pellets were re-suspended in 2×YT medium, plated on LB agar plates supplemented with 34 μg/mL chloramphenicol and incubated overnight at 37° C. Colonies were scraped off the plates and were used for polyclonal amplification of enriched clones and phage production. With purified phage the next panning round was started. The second round of pannings was performed according to the protocol of the first round except for a more stringent washing condition. A third panning round was omitted due to the low second round output titers of ~104 cfu/mL.

Pancodes 1038.9-16

For SP pannings 1038.9-16 (Table 2) His6-SUMO-CDH6 aa54-260-APP-Avi (see Table 1) was coated on a 96-well Maxisorp™ plate (Nunc) via direct immobilization as described for pancodes 1038.1-8. For pannings 1038.13-16 300 μL of a 100 nM solution of tool antibody MAB2715 was added per well and incubated for 1 h at room temperature to avoid selection of binders recognizing the same epitope as MAB2715. Besides the antigen coated and a third panning round the pannings were done as described for pancodes 1038.1-8.

Pancodes 1038.26-28

For SP pannings 1038.26-28 (see Table 2) hCDH6aa54-615-Fc (see Table 1, SEQ ID NO:6) was coated on a 96-well Maxisorp™ plate (Nunc) via direct immobilization as described for pancodes 1038.1-8. Besides the antigen coated and the washing stringencies the pannings were done as described for pancodes 1038.1-8.

Liquid Phase Panning

During solution panning, the Fab fragment displaying phage and biotinylated antigens are incubated in solution which is expected to increase accessibility of the antigen by the phage. Antigen biotinylation was done as described above.

Pancodes 1038.17-22

Each phage library subpool was blocked with an equal volume of 2× Chemiblocker for 2 h at room temperature on a turning wheel. To avoid selection of antibodies against the APPavi and biotin tag unrelated FLT3-APPAvi and biotinylated anti-Cyclosporin msIgG was added to 7.5 and 18 μg/mL in the blocking step, respectively. For removal of phage particles binding to Streptavidin-beads, pre-adsorption of blocked phage particles was performed using blocked Streptavidin beads (#112.06D Invitrogen, Carlsbad, Calif.). Blocked and pre-adsorbed phages were incubated with biotinylated hCDH6aa54-615 APPavi (see Table 1, SEQ ID NO:4) for 1 h at room temperature on a turning wheel. Phage-antigen complexes were captured either with washed beads (Pancodes 1038.17-19) or with beads precoated with biotinylated anti-CDH6 antibody 2B6 (Genway, San Diego, Calif.) to enrich binders for non-2B6 epitopes (Pancodes 1038.20-22). Non-specific phage particles were removed by several washing steps (see below). Elution of specifically bound phage particles, infection, and amplification were done as described for pancodes 1038.1-8.

TABLE 4

Washing conditions Pancodes 1038.17-25

| First Round | Second Round | Third round (only pancodes 1038.9-16) |
| --- | --- | --- |
| 5x PBST (quick) | 10x PBST (quick) | 10x PBST (quick) |
| 2x PBST/5 min | 3x PBST/5 min | 5x PBST/5 min |
| 3x PBS (quick) | 5x PBS (quick) | 5x PBS (quick) |

Pancodes 1038.23-25

Pannings were done as described for pancodes 1038.1-8 but using biotinylated hCDH6aa54-615-Fc (see Table 1, SEQ ID NO:6) as antigen.

Subcloning

Conversion for FAB-FH Expression

To facilitate rapid expression of soluble Fab fragments, the Fab encoding inserts of the selected HuCAL® PLATINUM phage particles were subcloned from the pMORPH®30 display vector into the pMORPH®11_FH expression vector. Glycerol stocks containing *E. coli* that were infected with the final panning round output phages were used to inoculate cultures for pMORPH®30 DNA purification using the Nucleobond® Xtra Midi Plus kit according to the manufacturers manual (#740.412.50 Machery Nagel, Bethlehem, Pa.). 5 μg of each pMORPH®30 DNA output pool was triple digested via EcoRI/XbaI/BmtI (all restriction enzymes were purchased from New England Biolabs, Ipswich, Mass.). The resulting EcoRI/XbaI Fab encoding 1485 bp fragment was gel purified using the Wizard SV Gel/PCR clean-up kit according to the manufacturers manual (A9282, Promega, Madison, Wis.) and ligated into the EcoRI/XbaI cut pMORPH®11_FH vector backbone.

Conversion for IgG Expression

In order to express full length IgG, variable domain fragments of VH and VL were subcloned from Fab expression vectors into pMORPH®4_hIgG1f vectors following the RapCLONE® protocol (Morphosys, Martinsried/Planegg, Germany). RapCLONE® is a two-step cloning method for the batch conversion of a large amount of Fab expression vectors into IgG expression vectors. In a first cloning step, a eukaryotic expression cassette was introduced into the pMORPH®11 expression vectors via BsiWI/MfeI (for κ pools) or HpaI/MfeI (for λ pools) digestion and subsequent ligation. This was followed by a second cloning step, in which the Fab pools containing the expression cassette were digested using EcoRV/BlpI (both κ and λ pools) and subsequently cloned into the pMORPH®4_IgG1f acceptor vector for expression in mammalian cells.

Expression and Purification of Fab Fragments

Transformation of *E. coli* TG1F

Electroporation-competent *E. coli* TG1F-aliquots of 50 μL were thawed on ice, mixed with 50 pg/μl pMORPH®11_FH plasmid DNA and transferred into pre-cooled electroporation cuvettes. The cells were electroporated (Bio-Rad Gene Pulser; settings: 1.75 kV, 200Ω, and 25 μF (Bio-Rad, Hercules, Calif.), transferred into 950 μl pre-warmed SOB medium and incubated for 1 h at 37° C. shaking at 220 rpm. An appropriate volume of the transformation samples were plated onto LB agar plates supplemented with 34 μg/mL Chloramphenicol and incubated overnight at 37° C. to obtain single colonies.

Generation of Master Plates

Chloramphenicol resistant single clones were picked into the wells of a sterile 384-well microtiter plate (Nunc) pre-filled with 60 μl 2×YT medium supplemented with 34 μg/ml of Chloramphenicol and 1% glucose and grown overnight at 37° C. Next morning, 20 μl sterile 2×YT media containing 60% glycerol and 1% glucose were added into each well of the master plates. Plates were sealed with aluminum foil and stored at −8° C.

Generation of Fab-Containing Bacterial Lysates for ELISA Screening

5 μl of each well of a Master plate was transferred to a sterile 384-well microtiter plate pre-filled with 40 μl 2×YT medium per well supplemented with 34 μg/ml of Chloramphenicol and 0.1% glucose. Plates were incubated at 37° C. at 480 rpm and 80% humidity until the cultures were slightly turbid. 10 μl of 2×YT medium supplemented with 34 μg/ml Chloramphenicol and 5 mM IPTG were added per well for induction of Fab fragment expression. Plates were sealed with a gas-permeable tape and incubated overnight at 22° C. at 500 rpm and 80% humidity. The next day 15 μl BEL lysis buffer (2.5 mg/ml lysozyme (#10837059001, Roche, Nutley, N.J.), 4 mM EDTA, 10 U/μl Benzonase (#1.01654.0001 Merck, White House Station, N.J.) was added to each well and plates were incubated for 1 h at 500 rpm and 80% humidity. Resulting Fab lysates were blocked by adding 15 μL of 2× Chemiblocker per well followed by incubation for 30 min at 22° C., 500 rpm and 80% humidity.

Generation of Fab-Containing Bacterial Lysates for FACS Screening

5 μl of each well of a compression plate was transferred to a sterile 96-well round bottom microtiter plate pre-filled with 100 μl 2×YT medium per well supplemented with 34 μg/ml of Chloramphenicol. Plates were incubated at 37° C. at 500 rpm and 80% humidity until the cultures were slightly turbid. 10 μl of 2×YT medium supplemented with 34 μg/ml Chloramphenicol and 5 mM IPTG were added per well for induction of Fab fragment expression. Plates were sealed with a gas-permeable tape and incubated overnight at 22° C. at 500 rpm and 80% humidity. The next day the plate was centrifuged for 10 min at 1200 g and the supernatant discarded. The bacterial pellets were frozen overnight at −20° C. to facilitate the lysis step. The thawed pellets were re-suspended in 200 μL of BEL lysis buffer (see above) and incubated for 1 h at 22° C. and 250 rpm. Resulting Fab lysates were centrifuged to remove cellular debris for 10 min at 1200 g. Fab containing supernatants were used for screening purposes.

Expression and Purification of His6-Tagged Fab Fragments in *E. coli*

*E. coli* TG1F-transformants containing pMORPH®11 Fab FH DNA were singled out on 2×YT supplemented with 34 μg/mL Chloramphenicol and 1% glucose. Individual clones were picked and transferred into 3 mL 2×YT seed cultures supplemented with 34 μg/mL Chloramphenicol and 1% glucose and incubated at 37° C., 220 rpm for 4 h. The seed culture was used to inoculate 50 mL main cultures with 2×YT supplemented with 34 μg/mL Chloramphenicol and 1% glucose and incubated in 250 mL shake flasks at 30° C. until the OD600 reached a value of 0.6. Fab expression was induced by addition of IPTG to a final concentration of 0.75 mM and cultures were further incubated overnight at 25° C.

and 220 rpm. The next day cells were harvested and the cell pellets frozen overnight at −20° C. Cells pellets were disrupted by re-suspending and incubating in lysis buffer ((25 mM TRIS/pH=8, 500 mM NaCl, 2 mM $MgCl_2$, 10 U/μl Benzonase (#1.01654.0001 Merck), 0.1% Lysozyme (#10837059001, Roche), Protease Inhibitor Complete w/o EDTA 1 tablet/50 mL of buffer (#11873580001 Roche)) for 1 h at room temperature on a rocking table. Lysates were clarified by centrifugation for 30 min at 15000 g and filtration of the supernatant through a 200 nm pore sized filter. His6-tagged Fab fragments were isolated via immobilized metal ion affinity chromatography (Ni-NTA Superflow® beads, #30430 Qiagen, Venlo, Netherlands) and eluted using imidazole. Buffer exchange to 1×PBS was performed using PD-10 columns (#17-0851-01 GE Healthcare, Pittsburgh, Pa.). Samples were sterile-filtered and the protein concentrations were determined by UV-spectrophotometry. The purity of the samples was analyzed in denaturing, reducing 15% SDS-PAGE. The identity of the samples was confirmed by MS.

Expression and Purification of IgGs

Expression of IgGs at Screening Scale

Eukaryotic HEK293c18 cells (ATCC CRL-10852) were used in a 96-well expression system for the generation of conditioned cell culture supernatants containing full-length IgG for the subsequent use in specificity and/or functional assays. Eukaryotic HEK293 c18 cells were re-suspended in transfection medium (D-MEM supplemented with 2% L-glutamine (#25030-024 Gibco, Grand Island, N.Y.) 10% FCS (#3302 PAN Biotech, Aidenbach, Germany) and 1% penicillin/streptomycin (#15140-122 Gibco, Grand Island, N.Y.)) and seeded in 96-well F-bottom plates to a density of approximately $4\times10^4$ cells in 50 μl per well the day before. A transfection master mix was prepared by mixing 0.6 μl Lipofectamine® 2000 (#11668 Invitrogen, Carlsbad, Calif.) per well with 25 μL Opti-MEM® I medium. (#31985-047 Invitrogen, Carlsbad, Calif.). The master mix was incubated for 15 min at room temperature. On a new plate 20 μL of Opti-MEM® I medium was added to wells containing 300 ng DNA and gently mixed. After that, the DNA was combined with the pre-incubated Lipofectamine® 2000, mixed gently and incubated for 20 min at room temperature. 100 μl of the pre-incubated Lipofectamine® 2000/DNA complexes were then transferred to each well of the plates with the cells and gently mixed. Plates were incubated for 40 h at 37° C. and 6% CO2 for transient expression. The culture supernatants were transferred to 96-well V-bottom plates and cleared by centrifugation. The resulting IgG-containing supernatants were tested by an anti-Fd capture ELISA for assessment of IgG protein concentration in reference to a known standard and stored at −80° C. for later use.

IgG Expression Check by Anti-Fd ELISA

To assess IgG levels in screening scale derived supernatants Maxisorp® 96-well plates (#437111 Nunc) were coated with 50 μl/well Fd-fragment-specific sheep anti-human IgG (#PC075 The Binding Site, San Diego, Calif.) diluted 1:1000 in PBS. After coating, the plates were washed twice with TBST and blocked for 1 h with 5% skim milk powder in TBST. In the meantime the IgG containing supernatants were diluted 1:50 in 2.5% skim milk powder in TBST. After washing the ELISA plates three times with TBST, 100 μL of the diluted supernatants were transferred per well and plates were incubated for 1 h at room temperature. Subsequently, the plates were washed five times with TBST and the captured IgGs were detected by incubation with 50 μl F(ab')2-specific goat anti-human IgG (#109-055-097 Dianova, Hamburg, Germany) (diluted 1:5000) in 0.5% skim milk powder in TBST for 1 h. After washing the plates five times with TBST the AttoPhos fluorescence substrate (#1484281 Roche, Nutley, N.J.) was added according to the manufacturer's instructions and the fluorescence emission at 535 nm was recorded with excitation at 430 nm with an ELISA reader.

Expression and Purification of IgGs in Microscale

CAP-T® cells (CEVEC Pharmaceuticals, Cologne, Germany) were transiently transfected with pMORPH®4 IgG expression plasmid in FreeStyle293® expression medium (#12338 Invitrogen, Carlsbad, Calif.) using 40 kDa linear PEI ((PEI Max (#24765-2 Polysciences Warrington, Pa.)) as gene delivery vehicle.

One day prior to the transfection cells were diluted to ~0.8E+06 cells/ml to ensure exponential growth. At the day of transfection cells were diluted in 9 mL pre-warmed Freestyle® (Invitrogen, Carlsbad, Calif.) medium to $\sim0.5\times10^7$ cells/ml and transferred into a 125 ml shake flask. 30 μg DNA was diluted in 500 μl OptiMEM. 1200 μg PEI Max (#24765-2 Polysciences Warrington, Pa.) was diluted in 8.80 mL OptiMEM medium. The DNA solution was added drop wise to the cells and gently mixed. After that, 500 μL PEI Max solution was added to the cells and gently mixed.

The cells were incubated at 37° C., 6% CO2, 85% humidity with agitation at 100 rpm. After 4 h 10 mL pre-warmed PEM supplemented with 4 mM L-Glutamine and 5 μg/ml blasticidin (#R21001 Invitrogen, Carlsbad, Calif.) was added. Simultaneously, 400 μL valproic acid (#P4543-25G Sigma Aldrich, St. Louis, Mo.) was added to a final concentration of 4 mM. Cells were incubated for 6 days at 37° C., 6% CO2, 85% humidity with agitation at 100 rpm.

After centrifugation for 5 min at 1200 g at 4° C. the supernatant was sterile-filtered (0.2 μm pore size) and subjected to a Protein A affinity chromatography (MabSelect® SURE, GE Healthcare, Pittsburgh, Pa.) using a liquid handling station. Buffer exchange was performed to 1×PBS and samples were sterile filtered (0.2 μm pore size). Protein concentrations were determined by UV spectrophotometry and purity of IgGs was analyzed under denaturing, reducing conditions in SDS-PAGE.

Screening of Fab-Containing Raw Bacterial Lysates

ELISA Screening

Using ELISA screening, single Fab clones were identified from panning outputs for binding to the target antigen. Fab fragments were tested using Fab containing crude *E. coli* lysates.

ELISA Screening on Directly Coated Antigen

Maxisorp® (#442404 Nunc, Rochester, N.Y.) 384-well plates were coated overnight at 4° C. with huCDH6 proteins at a concentration of 3 μg/ml in PBS. After washing plates were blocked for 2 h with 5% skimmed milk in 1×PBST. Fab-containing *E. coli* lysates were added and binding allowed for 1 h at room temperature.

To detect bound Fab fragments plates were washed 5× with TBST and AP-anti human IgG F(ab')2 (#109-055-097 Jackson Immunoresearch, West Grove, Pa.) was added in a 1/2500 dilution. After 1 h at room temperature plates were washed 5× with TBST and AttoPhos substrate was added according to the manufacturer's specifications. Plates were read in an ELISA reader 5 minutes after adding the substrate.

ELISA Screening on Biotinylated Antigen Using NeutrAvidin® Plates

Maxisorp® (#442404 Nunc, Rochester, N.Y.) 384-well plates were coated overnight at 4° C. with NeutrAvidin® (#31000 Thermo Scientific, Rockford, Ill.) at a concentration of 10 μg/ml in PBS. After washing, plates were blocked for 2 h with 1× Chemiblocker. Fab-containing *E. coli* lysates were dispensed into a fresh 384-well microtiter plate and biotinylated CDH6 antigens added at a concentration of 2.5 μg/mL. Fab-antigen complexes were then transferred to the NeutrAvidin® coated plates and capturing allowed for 1 h at room temperature and detected as described above.

FACS Screening

In FACS screening, Fab fragments binding to cell surface expressed CDH6 antigen were identified from the panning output. $1\times10^5$ cells/well were transferred into U bottom 96 well plates and mixed with 40 μl/well of the Fab-containing bacterial lysates. Plates were incubated shaking at 4° C. for 1 h. After the incubation, 100 μl/well ice-cold FACS buffer (3% FCS, 0.02% $NaN_3$, 2 mM EDTA in PBS) was added, cells were spun down at 4° C. for 5 min at 250 g and washed twice with 180 μl/well ice-cold FACS buffer. After each washing step, cells were centrifuged and carefully re-suspended. After the last washing step cells were re-suspended in 50 μL of 1/200 diluted secondary detection antibody (PE-conjugated goat anti-human IgG (#109-116-088, Jackson Immunoresearch, West Grove, Pa.). After 1 h incubation at 4° C. cells were again washed twice in 180 μL/well ice-cold FACS buffer. Finally, cell pellets were re-suspended in 120 μl/well FACS buffer with 0.4% paraformaldehyde and analyzed in a FACSCalibur® (BD Biosciences, San Jose, Calif.) equipped with an HTS plate reader.

Clone Sequencing

Fab Clone Sequencing

Confirmed cell binding Fab hits were subjected to VL and VH sequencing. 1.2 mL 2×YT supplemented with 34 μg/mL Chloramphenicol and 1% glucose were inoculated with 5 μL of bacterial glycerol stock deriving from the compression plates and grown in 96-well deep well microtiter plates overnight at 37° C. and 500 rpm. The next day the bacteria were harvested and the pMORPH®11 FH plasmids purified using a 96-well DNA purification kit (Nucleospin® 96 Plasmid Purification Kit #740625.24, Machery Nagel, Bethlehem, Pa.) according to the manufacturers protocol. To sequence the VL and VH primers M13rev (5' CAGGAAACAGCTATGAC 3' (SEQ ID NO:10) and HuCAL_VH_ for GATAAGCATGCGTAGGAGAAA 3 (SEQ ID NO:11)) were used, respectively.

IgG Clone Sequencing

Unique cell binding Fab clones were converted in the IgG1 format in a polyclonal manner and afterwards retrieved by VL and VH sequencing. 1.5 mL 2×YT medium supplemented with 100 μg/mL Amp and 1% glucose were inoculated with single clones and grown in 96-well deep well microtiter plates overnight at 37° C., 450 rpm and 80% humidity. The next day the bacteria were harvested and the IgG encoding pMORPH®4 plasmids purified using a 96-well DNA purification kit according to the manufacturer's protocol (Nucleospin® 96 Plasmid Purification Kit #740625.24, Machery Nagel, Bethlehem, Pa.). To sequence the VL and VH primers ((T7 5' TAATACGACTCACTATAGGG 3' (SEQ ID NO:12) and CMV HC for (5' CTCTAGCGCCACCATGAAACA 3' (SEQ ID NO:13)) were used, respectively.

In Vitro Assays

Affinity Assessment Using Octet® QK

Affinity assessments by determining kinetic parameters were performed via Bio-Layer Interferometry technology. All Fab samples were measured using Streptavidin Dip and Read biosensors (#18-0009 ForteBio, Menlo Park, Calif.). The plate was placed in an Octet® QK instrument (ForteBio, Menlo Park, Calif.) and allowed to equilibrate to 27° C. in the chamber. The run was initiated by placing the sensors in the wells containing 150 nM of biotinylated CDH6 protein for 300s. After that the sensors were placed in the wells containing 250 nM Fab sample. Fab association and dissociation were each recorded for 600s by measuring the change in layer thickness (in nanometers, nm) with time, all under computer control. Data were processed automatically using the Octet® User Software version 3.0.

Assessment of Antibody Cellular Internalization Propensity

Cell Internalization of IgGs by target mediated endocytosis was assessed by microscopy using a VTI ArrayScan® HC reader (ThermoFischer, Waltham, Mass.) as described below. The underlying analysis protocol was the Spot Detector V4 algorithm (ThermoScientific Cellomics®, Thermo Scientific, Rockford, Ill.). In brief, this analysis protocol provides a fast and generic spot analysis that identifies intracellular punctuate objects, such as IgG containing lysosomal vesicles after immunofluorescent staining. The total punctuate fluorescent intensity can then be averaged over the number of cells analyzed.

OVCAR3 cells (ATCC HTB-161) were grown in T150 tissue culture flasks to approximately 90% confluency. Media was discarded and cells flushed with 10 mL PBS. Cells were detached by incubation with 4 mL cell dissociation buffer for 5 min at 37° C. Detached cells were re-suspended thoroughly in growth medium and transferred to a 50 mL tube. After counting the cells on a Vi-Cell® analyzer (Beckman Coulter, Brea, Calif.) the suspension was adjusted to $10^5$ cells/mL in growth medium. 100 μL of the cell suspension was seeded per well of a 96-well microtiter plate with transparent bottom. Plates were incubated for 24 h at 37° C. in 5% CO2 to allow the cells to adhere and to expand.

IgG containing cell culture supernatants were generated as described and diluted in PBS in a fourfold dilution series covering dilutions ranging from 1:4 to 1:128. 100 μl of each sample dilution was dispensed per well of the cell containing microtiter plate and incubated for 2 h at 37° C. to permit IgG internalization. Subsequently, cells were fixed by adding 100 μl 1× CellFix® reagent (#340181 BD Biosciences, San Jose, Calif.) per well. After 10 minutes plates were washed twice with PBS and cells then permeabilized by adding 100 μl 0.1% Triton X-100 per well. After 10 min plates were washed again twice with PBS and blocked with 100 μl 1× Odyssey blocking buffer (#927-40000 LiCor, Lincoln, Nebr.) for 2 hours at room temperature. To detect internalized IgGs 100 μl of a 1:000 dilution of secondary antibody Alexa Fluor® 488 goat anti-human IgG (#11001 Molecular Probes, Grand Island, N.Y.) supplemented with a 1:10000 dilution of Hoechst nucleus staining reagent (#B2261 Sigma, St. Louis, Mo.) were added per well and incubated for 1 hours at room temperature in the dark. Cells were then washed twice with PBS without final aspiration. Plates were then loaded into the Cellomics® VTI ArrayScan HC reader (ThermoFischer, Waltham, Mass.) and analyzed. The extent of IgG internalization was assessed by the mean average spot intensity (MSAI) per cell.

Surrogate ADC Assay Using Anti-Human FAB-DM1 Conjugate

To test the ability of CDH6 antibodies to internalize after receptor binding and deliver cytotoxic payload, a surrogate ADC assay was performed mixing anti-human Fab-DM1 reagent (AffiniPure® Fab Fragment Goat Anti-Human IgG H+L conjugated with SMCC-DM1) with purified IgGs at a fixed 1:2 ratio. Cytotoxic potential was tested on the cancer cell line OVCAR3 (ovarian serous carcinoma, cultured in McCoys+20% FCS) as these cells show high expression of CDH6.

Cells in culture were counted and diluted in medium to a concentration of $1\times10^5$ cells/ml. 1000 cells/well were transferred to 384-well plates (Corning Costar#3707, Corning, Tewksbury, Mass.). Primary antibody/Fab-DM1 solution was prepared in 1.4 ml Matrix tubes (Thermo, #3790, Rockford, Ill.) by combining 666 nM Fab-DM1 with 333 nM primary human IgG diluted in cell culture media and incubated at 37° C. for 30 minutes. A 10-point, 1:3 serial dilution was prepared in a 384-well deep-well plate (Brandtech Scientific Inc #701355, Essex, Conn.) and 25 μl were transferred per assay plate (triplicates) to yield a highest starting concentration of FAB-DM1/human IgG of 66 nM and 33 nM, respectively. For controls, wells with cells only (=100% viability control) and cells only incubated with Fab-DM1 (to check for unspecific killing of the secondary reagent) were prepared. Plates were incubated for 120 h at 37° C. and 5% CO2. Cellular activity of the primary antibody/Fab-DM1 complexes was determined using CellTiter-Glo® reagent (#G7571 Promega, Madison, Wis.) according to the manufacturer's instructions. Viability was normalized to the cells only control.

Antibody Screening Summary

The HuCAL® PLATINUM phagemid library was used to select specific Fab fragments against human CDH6-ECD antigens. Recombinant human APPAvi and Fc fusion as well as truncated domain APPAvi fusion proteins were used for the pannings. HuCAL® PLATINUM antibody-phage particles were subjected in different subpool combinations to a total of 8 different panning strategies resulting in 28 panning output pools. In summary, six out of eight strategies have been productive and resulted in 771 ELISA positive screening hits.

FACS screening on CHO cells expressing human CDH6 as well as OVCAR3 cells resulted in 271 confirmed cell binding hits. To consolidate these cell binding hits VL and VH sequencing was performed leading to the identification of 53 unique Fab antibody clones.

To allow for the functional characterization, the Fab antibody clones were converted into the IgG format, yielding 47 unique IgG clones of which 44 were successfully expressed at screening scale. The purified, unique IgGs were subjected to a series of characterization assays including human/cyno/rat/mouse cross-reactivity by FACS, affinity ranking by Octet, cellular internalization assays as well as surrogate ADC assays using an anti-human IgG Fab-SMCC-DM1 secondary reagent. Based on these assays, human IgGs were selected for scaled up production, subsequent direct conjugation to ADC linker/payloads and testing as ADCs in in vitro and in vivo experiments.

The sequence information for the anti-CDH6 IgGs selected for further in-depth characterization are shown in Table 5.

TABLE 5

Sequence information of the IgGs selected for in-depth characterization.

| NOV ID | Category | Value |
|---|---|---|
| NOV0670 | LCDR1 (Kabat) (SEQ ID NO: 14) | SGSSSNIGSQYVY |
| | LCDR2 (Kabat) (SEQ ID NO: 15) | YNSERPS |
| | LCDR3 (Kabat) (SEQ ID NO: 16) | QTWDASSQSFV |
| | HCDR1 (Kabat) (SEQ ID NO: 17) | SYAIS |
| | HCDR2 (Kabat) (SEQ ID NO: 18) | GIIPIFGTANYAQKFQG |
| | HCDR3 (Kabat) (SEQ ID NO: 19) | KFPGRGPFAY |
| | vH full sequence (SEQ ID NO: 20) | QVQLVQSGAEVKKPGSSVKVSCKASGGTFSSYAISWVRQAPG QGLEWMGGIIPIFGTANYAQKFQGRVTITADESTSTAYMELSSL RSEDTAVYYCARKFPGRGPFAYWGQGTLVTVSS |
| | vL full sequence (SEQ ID NO:21) | DIVLTQPPSVSGAPGQRVTISCSGSSSNIGSQYVYWYQQLPGTA PKLLIYYNSERPSGMPDRFSGSKSGTSASLAITGLQAEDEADYY CQTWDASSQSFVFGGGTKLTVL |
| | vH DNA sequence (SEQ ID NO: 22) | CAGGTGCAATTGGTGCAGAGCGGTGCCGAAGTGAAAAAAC CGGGCAGCAGCGTGAAAGTTAGCTGCAAAGCATCCGGAGG GACGTTTTCTTCTTACGCTATCTCTTGGGTGCGCCAGGCCCC GGGCCAGGGCCTCGAGTGGATGGGCGGTATCATCCCGATCT TCGGCACTGCGAACTACGCCCAGAAATTTCAGGGCCGGGTG ACCATTACCGCCGATGAAAGCACCAGCACCGCCTATATGGA ACTGAGCAGCCTGCGCAGCGAAGATACGGCCGTGTATTATT GCGCGCGTAAATTCCCGGGTCGTGGTCCGTTCGCTTACTGGG GCCAAGGCACCCTGGTGACTGTTAGCTCA |

TABLE 5-continued

Sequence information of the IgGs selected for in-depth characterization.

| NOV ID | Category | Value |
|---|---|---|
| | vL DNA sequence (SEQ ID NO: 23) | GATATCGTGCTGACCCAGCCGCCGAGCGTGAGCGGTGCACC GGGCCAGCGCGTGACCATTAGCTGTAGCGGCAGCAGCAGCA ACATTGGTTCTCAGTACGTGTACTGGTACCAGCAGCTGCCG GGCACGGCGCCGAAACTGCTGATCTACTACAACTCTGAACG CCCGAGCGGCATGCCGGATCGCTTTAGCGGATCCAAAAGCG GCACCAGCGCCAGCCTGGCGATTACCGGCCTGCAAGCAGAA GACGAAGCGGATTATTACTGCCAGACTTGGGACGCTTCTTCT CAGTCTTTCGTGTTTGGCGGCGGCACGAAGTTAACCGTCCTA |
| | HC full sequence (SEQ ID NO: 24) | QVQLVQSGAEVKKPGSSVKVSCKASGGTFSSYAISWVRQAPG QGLEWMGGIIPIFGTANYAQKFQGRVTITADESTSTAYMELSSL RSEDTAVYYCARKFPGRGPFAYWGQGTLVTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDKR VEPKSCDKTHTCPPCPAPELLGGPSVFLFPPKPKDTLMISRTPEV TCVVVDVSHEDPEVKFNWYVDGVEVHNAKTKPREEQYNSTY RVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSV MHEALHNHYTQKSLSLSPGK |
| | LC full sequence (SEQ ID NO: 25) | DIVLTQPPSVSGAPGQRVTISCSGSSSNIGSQYVYWYQQLPGTA PKLLIYYNSERPSGMPDRFSGSKSGTSASLAITGLQAEDEADYY CQTWDASQSFVFGGGTKLTVLGQPKAAPSVTLFPPSSEELQA NKATLVCLISDFYPGAVTVAWKADSSPVKAGVETTTPSKQSNN KYAASSYLSLTPEQWKSHRSYSCQVTHEGSTVEKTVAPTECS |
| | HC DNA sequence (SEQ ID NO: 26) | CAGGTGCAATTGGTGCAGAGCGGTGCCGAAGTGAAAAAAC CGGGCAGCAGCGTGAAAGTTAGCTGCAAAGCATCCGGAGG GACGTTTTCTTCTTACGCTATCTCTTGGGTGCGCCAGGCCCC GGGCCAGGGCCTCGAGTGGATGGGCGGTATCATCCCGATCT TCGGCACTGCGAACTACGCCCAGAAATTTCAGGGCCGGGTG ACCATTACCGCCGATGAAAGCACCAGCACCGCCTATATGGA ACTGAGCAGCCTGCGCAGCGAAGATACGGCCGTGTATTATT GCGCGCGTAAATTCCCGGGTCGTGGTCCGTTCGCTTACTGGG GCCAAGGCACCCTGGTGACTGTTAGCTCAGCCTCCACCAAG GGTCCATCGGTCTTCCCCCTGGCACCCTCCTCCAAGAGCACC TCTGGGGGCACAGCGGCCCTGGGCTGCCTGGTCAAGGACTA CTTCCCCGAACCGGTGACGGTGTCGTGGAACTCAGGCGCCC TGACCAGCGGCGTGCACACCTTCCCGGCTGTCCTACAGTCCT CAGGACTCTACTCCCTCAGCAGCGTGGTGACCGTGCCCTCC AGCAGCTTGGGCACCCAGACCTACATCTGCAACGTGAATCA CAAGCCCAGCAACACCAAGGTGGACAAGAGAGTTGAGCCC AAATCTTGTGACAAAACTCACACATGCCCACCGTGCCCAGC ACCTGAACTCCTGGGGGGACCGTCAGTCTTCCTCTTCCCCCC AAAACCCAAGGACACCCTCATGATCTCCCGGACCCCTGAGG TCACATGCGTGGTGGTGGACGTGAGCCACGAAGACCCTGAG GTCAAGTTCAACTGGTACGTGGACGGCGTGGAGGTGCATAA TGCCAAGACAAAGCCGCGGGAGGAGCAGTACAACAGCACG TACCGGGTGGTCAGCGTCCTCACCGTCCTGCACCAGGACTG GCTGAATGGCAAGGAGTACAAGTGCAAGGTCTCCAACAAA GCCCTCCCAGCCCCCATCGAGAAAACCATCTCCAAAGCCAA AGGGCAGCCCCGAGAACCACAGGTGTACACCCTGCCCCCAT CCCGGGAGGAGATGACCAAGAACCAGGTCAGCCTGACCTGC CTGGTCAAAGGCTTCTATCCCAGCGACATCGCCGTGGAGTG GGAGAGCAATGGGCAGCCGGAGAACAACTACAAGACCACG CCTCCCGTGCTGGACTCCGACGGCTCCTTCTTCCTCTACAGC AAGCTCACCGTGGACAAGAGCAGGTGGCAGCAGGGGAACG TCTTCTCATGCTCCGTGATGCATGAGGCTCTGCACAACCACT ACACGCAGAAGAGCCTCTCCCTGTCTCCGGGTAAA |
| | LC DNA sequence (SEQ ID NO: 27) | GATATCGTGCTGACCCAGCCGCCGAGCGTGAGCGGTGCACC GGGCCAGCGCGTGACCATTAGCTGTAGCGGCAGCAGCAGCA ACATTGGTTCTCAGTACGTGTACTGGTACCAGCAGCTGCCG GGCACGGCGCCGAAACTGCTGATCTACTACAACTCTGAACG CCCGAGCGGCATGCCGGATCGCTTTAGCGGATCCAAAAGCG GCACCAGCGCCAGCCTGGCGATTACCGGCCTGCAAGCAGAA GACGAAGCGGATTATTACTGCCAGACTTGGGACGCTTCTTCT CAGTCTTTCGTGTTTGGCGGCGGCACGAAGTTAACCGTCCTA GGTCAGCCCAAGGCTGCCCCCTCGGTCACTCTGTTCCCGCCC TCCTCTGAGGAGCTTCAAGCCAACAAGGCCACACTGGTGTG TCTCATAAGTGACTTCTACCCGGGAGCCGTGACAGTGGCCT GGAAGGCAGATAGCAGCCCCGTCAAGGCGGGAGTGGAGAC CACCACACCCTCCAAACAAAGCAACAACAAGTACGCGGCCA GCAGCTATCTGAGCCTGACGCCTGAGCAGTGGAAGTCCCAC AGAAGCTACAGCTGCCAGGTCACGCATGAAGGGAGCACCGT GGAGAAGACAGTGGCCCCTACAGAATGTTCA |

TABLE 5-continued

| Sequence information of the IgGs selected for in-depth characterization. | | |
|---|---|---|
| NOV ID | Category | Value |
| NOV0672 | LCDR1 (Kabat) (SEQ ID NO: 28) | TGTSSDVGAYNYVS |
| | LCDR2 (Kabat) (SEQ ID NO: 29) | GVSKRPS |
| | LCDR3 (Kabat) (SEQ ID NO: 30) | QSYDHLLHVV |
| | HCDR1 (SEQ ID NO: 31) | TYGIH |
| | HCDR2 (Kabat) (SEQ ID NO: 32) | YIHYSGSSTYYADSVKG |
| | HCDR3 (Kabat) (SEQ ID NO: 33) | HAYGYMDF |
| | vH full sequence (SEQ ID NO: 34) | QVQLLESGGGLVQPGGSLRLSCAASGFTFNTYGIHWVRQAPG KGLEWVSYIHYSGSSTYYADSVKGRFTISRDNSKNTLYLQMNS LRAEDTAVYYCARHAYGYMDFWGQGTLVTVSS |
| | vL full sequence (SEQ ID NO: 35) | DIALTQPASVSGSPGQSITISCTGTSSDVGAYNYVSWYQQHPGK APKLMIYGVSKRPSGVSNRFSGSKSGNTASLTISGLQAEDEADY YCQSYDHLLHVVFGGGTKLTVL |
| | vH DNA sequence (SEQ ID NO: 36) | CAGGTGCAATTGCTGGAAAGCGGCGGTGGCCTGGTGCAGCC GGGTGGCAGCCTGCGTCTGAGCTGCGCGGCGTCCGGATTCA CCTTTAACACTTACGGTATCCATTGGGTGCGCCAGGCCCCGG GCAAAGGTCTCGAGTGGGTTTCCTACATCCATTACTCTGGTT CTTCTACCTACTATGCGGATAGCGTGAAAGGCCGCTTTACCA TCAGCCGCGATAATTCGAAAAACACCCTGTATCTGCAAATG AACAGCCTGCGTGCGGAAGATACGGCCGTGTATTATTGCGC GCGTCATGCTTACGGTTACATGGATTTCTGGGGCCAAGGCA CCCTGGTGACTGTTAGCTCA |
| | vL DNA sequence (SEQ ID NO: 37) | GATATCGCGCTGACCCAGCCGGCGAGCGTGAGCGGTAGCCC GGGCCAGAGCATTACCATTAGCTGCACCGGCACCAGCAGCG ATGTGGGCGCTTACAACTACGTGTCTTGGTACCAGCAGCAT CCGGGCAAGGCGCCGAAACTGATGATCTACGGTGTTTCTAA ACGTCCGAGCGGCGTGAGCAACCGTTTTAGCGGATCCAAAA GCGGCAACACCGCGAGCCTGACCATTAGCGGCCTGCAAGCG GAAGACGAAGCGGATTATTACTGCCAGTCTTACGACCATCT GCTGCATGTTGTGTTTGGCGGCGGCACGAAGTTAACCGTCCT A |
| | HC full sequence (SEQ ID NO: 38) | QVQLLESGGGLVQPGGSLRLSCAASGFTFNTYGIHWVRQAPG KGLEWVSYIHYSGSSTYYADSVKGRFTISRDNSKNTLYLQMNS LRAEDTAVYYCARHAYGYMDFWGQGTLVTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDKR VEPKSCDKTHTCPPCPAPELLGGPSVFLFPPKPKDTLMISRTPEV TCVVVDVSHEDPEVKFNWYVDGVEVHNAKTKPREEQYNSTY RVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSV MHEALHNHYTQKSLSLSPGK |
| | LC full sequence (SEQ ID NO: 39) | DIALTQPASVSGSPGQSITISCTGTSSDVGAYNYVSWYQQHPGK APKLMIYGVSKRPSGVSNRFSGSKSGNTASLTISGLQAEDEADY YCQSYDHLLHVVFGGGTKLTVLGQPKAAPSVTLFPPSSEELQA NKATLVCLISDFYPGAVTVAWKADSSPVKAGVETTTPSKQSNN KYAASSYLSLTPEQWKSHRSYSCQVTHEGSTVEKTVAPTECS |
| | HC DNA sequence (SEQ ID NO: 40) | CAGGTGCAATTGCTGGAAAGCGGCGGTGGCCTGGTGCAGCC GGGTGGCAGCCTGCGTCTGAGCTGCGCGGCGTCCGGATTCA CCTTTAACACTTACGGTATCCATTGGGTGCGCCAGGCCCCGG GCAAAGGTCTCGAGTGGGTTTCCTACATCCATTACTCTGGTT CTTCTACCTACTATGCGGATAGCGTGAAAGGCCGCTTTACCA TCAGCCGCGATAATTCGAAAAACACCCTGTATCTGCAAATG AACAGCCTGCGTGCGGAAGATACGGCCGTGTATTATTGCGC GCGTCATGCTTACGGTTACATGGATTTCTGGGGCCAAGGCA CCCTGGTGACTGTTAGCTCAGCCTCCACCAAGGGTCCATCG |

TABLE 5-continued

| Sequence information of the IgGs selected for in-depth characterization. | | |
|---|---|---|
| NOV ID | Category | Value |
| | | GTCTTCCCCCTGGCACCCTCCTCCAAGAGCACCTCTGGGGGC ACAGCGGCCCTGGGCTGCCTGGTCAAGGACTACTTCCCCGA ACCGGTGACGGTGTCGTGGAACTCAGGCGCCCTGACCAGCG GCGTGCACACCTTCCCGGCTGTCCTACAGTCCTCAGGACTCT ACTCCCTCAGCAGCGTGGTGACCGTGCCCTCCAGCAGCTTG GGCACCCAGACCTACATCTGCAACGTGAATCACAAGCCCAG CAACACCAAGGTGGACAAGAGAGTTGAGCCCAAATCTTGTG ACAAAACTCACACATGCCCACCGTGCCCAGCACCTGAACTC CTGGGGGGACCGTCAGTCTTCCTCTTCCCCCCAAAACCCAA GGACACCCTCATGATCTCCCGGACCCCTGAGGTCACATGCG TGGTGGTGGACGTGAGCCACGAAGACCCTGAGGTCAAGTTC AACTGGTACGTGGACGGCGTGGAGGTGCATAATGCCAAGAC AAAGCCGCGGGAGGAGCAGTACAACAGCACGTACCGGGTG GTCAGCGTCCTCACCGTCCTGCACCAGGACTGGCTGAATGG CAAGGAGTACAAGTGCAAGGTCTCCAACAAAGCCCTCCCAG CCCCCATCGAGAAAACCATCTCCAAAGCCAAAGGGCAGCCC CGAGAACCACAGGTGTACACCCTGCCCCCATCCCGGGAGGA GATGACCAAGAACCAGGTCAGCCTGACCTGCCTGGTCAAAG GCTTCTATCCCAGCGACATCGCCGTGGAGTGGGAGAGCAAT GGGCAGCCGGAGAACAACTACAAGACCACGCCTCCCGTGCT GGACTCCGACGGCTCCTTCTTCCTCTACAGCAAGCTCACCGT GGACAAGAGCAGGTGGCAGCAGGGGAACGTCTTCTCATGCT CCGTGATGCATGAGGCTCTGCACAACCACTACACGCAGAAG AGCCTCTCCCTGTCTCCGGGTAAA |
| | LC DNA sequence (SEQ ID NO: 41) | GATATCGCGCTGACCCAGCCGGCGAGCGTGAGCGGTAGCCC GGGCCAGAGCATTACCATTAGCTGCACCGGCACCAGCAGCG ATGTGGGCGCTTACAACTACGTGTCTTGGTACCAGCAGCAT CCGGGCAAGGCGCCGAAACTGATGATCTACGGTGTTTCTAA ACGTCCGAGCGGCGTGAGCAACCGTTTTAGCGGATCCAAAA GCGGCAACACCGCGAGCCTGACCATTAGCGGCCTGCAAGCG GAAGACGAAGCGGATTATTACTGCCAGTCTTACGACCATCT GCTGCATGTTGTGTTTGGCGGCGGCACGAAGTTAACCGTCCT AGGTCAGCCCAAGGCTGCCCCCTCGGTCACTCTGTTCCCGCC CTCCTCTGAGGAGCTTCAAGCCAACAAGGCCACACTGGTGT GTCTCATAAGTGACTTCTACCCGGGAGCCGTGACAGTGGCC TGGAAGGCAGATAGCAGCCCCGTCAAGGCGGGAGTGGAGA CCACCACACCCTCCAAACAAAGCAACAACAAGTACGCGGCC AGCAGCTATCTGAGCCTGACGCCTGAGCAGTGGAAGTCCCA CAGAAGCTACAGCTGCCAGGTCACGCATGAAGGGAGCACC GTGGAGAAGACAGTGGCCCCTACAGAATGTTCA |
| NOV0674 | LCDR1 (Kabat) (SEQ ID NO: 42) | SGSSSNIGYNYVS |
| | LCDR2 (Kabat) (SEQ ID NO: 43) | RDNQRPS |
| | LCDR3 (SEQ ID NO: 44) | AAWTSGSIGWV |
| | HCDR1 (Kabat) (SEQ ID NO: 45) | SYAMT |
| | HCDR2 (Kabat) (SEQ ID NO: 46) | GISGGGSNTYYADSVKG |
| | HCDR3 (Kabat) (SEQ ID NO: 47) | GGGQYFDY |
| | vH full sequence (SEQ ID NO: 48) | QVQLLESGGGLVQPGGSLRLSCAASGFTFSSYAMTWVRQAPG KGLEWVSGISGGGSNTYYADSVKGRFTISRDNSKNTLYLQMNS LRAEDTAVYYCARGGGQYFDYWGQGTLVTVSS |
| | vL full sequence (SEQ ID NO: 49) | DIVLTQPPSVSGAPGQRVTISCSGSSSNIGYNYVSWYQQLPGTA PKLLIYRDNQRPSGVPDRFSGSKSGTSASLAITGLQAEDEADYY CAAWTSGSIGWVFGGGTKLTVL |

TABLE 5-continued

Sequence information of the IgGs selected for in-depth characterization.

| NOV ID | Category | Value |
|---|---|---|
| | vH DNA sequence (SEQ ID NO: 50) | CAGGTGCAATTGCTGGAAAGCGGCGGTGGCCTGGTGCAGCC<br>GGGTGGCAGCCTGCGTCTGAGCTGCGCGGCGTCCGGATTCA<br>CCTTTTCTTCTTACGCTATGACTTGGGTGCGCCAGGCCCCGG<br>GCAAAGGTCTCGAGTGGGTTTCCGGTATCTCTGGTGGTGGTT<br>CTAACACCTACTATGCGGATAGCGTGAAAGGCCGCTTTACC<br>ATCAGCCGCGATAATTCGAAAAACACCCTGTATCTGCAAAT<br>GAACAGCCTGCGTGCGGAAGATACGGCCGTGTATTATTGCG<br>CGCGTGGTGGTGGTCAGTACTTCGATTACTGGGGCCAAGGC<br>ACCCTGGTGACTGTTAGCTCA |
| | vL DNA sequence (SEQ ID NO: 51) | GATATCGTGCTGACCCAGCCGCCGAGCGTGAGCGGTGCACC<br>GGGCCAGCGCGTGACCATTAGCTGTAGCGGCAGCAGCAGCA<br>ACATTGGTTACAACTACGTGTCTTGGTACCAGCAGCTGCCG<br>GGCACGGCGCCGAAACTGCTGATCTACCGTGACAACCAGCG<br>CCCGAGCGGCGTGCCGGATCGCTTTAGCGGATCCAAAAGCG<br>GCACCAGCGCCAGCCTGGCGATTACCGGCCTGCAAGCAGAA<br>GACGAAGCGGATTATTACTGCGCTGCTTGGACTTCTGGTTCT<br>ATCGGTTGGGTGTTTGGCGGCGGCACGAAGTTAACCGTCCT<br>A |
| | HC full sequence (SEQ ID NO: 52) | QVQLLESGGGLVQPGGSLRLSCAASGFTFSSYAMTWVRQAPG<br>KGLEWVSGISGGGSNTYYADSVKGRFTISRDNSKNTLYLQMNS<br>LRAEDTAVYYCARGGGQYFDYWGQGTLVTVSSASTKGPSVFP<br>LAPSSKSTSGGTAALGCLVKDYFPEPVTVSWNSGALTSGVHTF<br>PAVLQSSGLYSLSSVVTVPSSSLGTQTYICNVNHKPSNTKVDKR<br>VEPKSCDKTHTCPPCPAPELLGGPSVFLFPPKPKDTLMISRTPEV<br>TCVVVDVSHEDPEVKFNWYVDGVEVHNAKTKPREEQYNSTY<br>RVVSVLTVLHQDWLNGKEYKCKVSNKALPAPIEKTISKAKGQ<br>PREPQVYTLPPSREEMTKNQVSLTCLVKGFYPSDIAVEWESNG<br>QPENNYKTTPPVLDSDGSFFLYSKLTVDKSRWQQGNVFSCSV<br>MHEALHNHYTQKSLSLSPGK |
| | LC full sequence (SEQ ID NO: 53) | DIVLTQPPSVSGAPGQRVTISCSGSSSNIGYNYVSWYQQLPGTA<br>PKLLIYRDNQRPSGVPDRFSGSKSGTSASLAITGLQAEDEADYY<br>CAAWTSGSIGWVFGGGTKLTVLGQPKAAPSVTLFPPSSEELQA<br>NKATLVCLISDFYPGAVTVAWKADSSPVKAGVETTTPSKQSNN<br>KYAASSYLSLTPEQWKSHRSYSCQVTHEGSTVEKTVAPTECS |
| | HC DNA sequence (SEQ ID NO: 54) | CAGGTGCAATTGCTGGAAAGCGGCGGTGGCCTGGTGCAGCC<br>GGGTGGCAGCCTGCGTCTGAGCTGCGCGGCGTCCGGATTCA<br>CCTTTTCTTCTTACGCTATGACTTGGGTGCGCCAGGCCCCGG<br>GCAAAGGTCTCGAGTGGGTTTCCGGTATCTCTGGTGGTGGTT<br>CTAACACCTACTATGCGGATAGCGTGAAAGGCCGCTTTACC<br>ATCAGCCGCGATAATTCGAAAAACACCCTGTATCTGCAAAT<br>GAACAGCCTGCGTGCGGAAGATACGGCCGTGTATTATTGCG<br>CGCGTGGTGGTGGTCAGTACTTCGATTACTGGGGCCAAGGC<br>ACCCTGGTGACTGTTAGCTCAGCCTCCACCAAGGGTCCATC<br>GGTCTTCCCCCTGGCACCCTCCTCCAAGAGCACCTCTGGGGG<br>CACAGCGGCCCTGGGCTGCCTGGTCAAGGACTACTTCCCCG<br>AACCGGTGACGGTGTCGTGGAACTCAGGCGCCCTGACCAGC<br>GGCGTGCACACCTTCCCGGCTGTCCTACAGTCCTCAGGACTC<br>TACTCCCTCAGCAGCGTGGTGACCGTGCCCTCCAGCAGCTTG<br>GGCACCCAGACCTACATCTGCAACGTGAATCACAAGCCCAG<br>CAACACCAAGGTGGACAAGAGAGTTGAGCCCAAATCTTGTG<br>ACAAAACTCACACATGCCCACCGTGCCCAGCACCTGAACTC<br>CTGGGGGGACCGTCAGTCTTCCTCTTCCCCCCAAAACCCAA<br>GGACACCCTCATGATCTCCCGGACCCCTGAGGTCACATGCG<br>TGGTGGTGGACGTGAGCCACGAAGACCCTGAGGTCAAGTTC<br>AACTGGTACGTGGACGGCGTGGAGGTGCATAATGCCAAGAC<br>AAAGCCGCGGGAGGAGCAGTACAACAGCACGTACCGGGTG<br>GTCAGCGTCCTCACCGTCCTGCACCAGGACTGGCTGAATGG<br>CAAGGAGTACAAGTGCAAGGTCTCCAACAAAGCCCTCCCAG<br>CCCCCATCGAGAAAACCATCTCCAAAGCCAAAGGGCAGCCC<br>CGAGAACCACAGGTGTACACCCTGCCCCCATCCCGGGAGGA<br>GATGACCAAGAACCAGGTCAGCCTGACCTGCCTGGTCAAAG<br>GCTTCTATCCCAGCGACATCGCCGTGGAGTGGGAGAGCAAT<br>GGGCAGCCGGAGAACAACTACAAGACCACGCCTCCCGTGCT<br>GGACTCCGACGGCTCCTTCTTCCTCTACAGCAAGCTCACCGT<br>GGACAAGAGCAGGTGGCAGCAGGGGAACGTCTTCTCATGCT<br>CCGTGATGCATGAGGCTCTGCACAACCACTACACGCAGAAG<br>AGCCTCTCCCTGTCTCCGGGTAAA |
| | LC DNA sequence (SEQ ID NO: 55) | GATATCGTGCTGACCCAGCCGCCGAGCGTGAGCGGTGCACC<br>GGGCCAGCGCGTGACCATTAGCTGTAGCGGCAGCAGCAGCA<br>ACATTGGTTACAACTACGTGTCTTGGTACCAGCAGCTGCCG<br>GGCACGGCGCCGAAACTGCTGATCTACCGTGACAACCAGCG<br>CCCGAGCGGCGTGCCGGATCGCTTTAGCGGATCCAAAAGCG<br>GCACCAGCGCCAGCCTGGCGATTACCGGCCTGCAAGCAGAA<br>GACGAAGCGGATTATTACTGCGCTGCTTGGACTTCTGGTTCT<br>ATCGGTTGGGTGTTTGGCGGCGGCACGAAGTTAACCGTCCT |

TABLE 5-continued

Sequence information of the IgGs selected for in-depth characterization.

| NOV ID | Category | Value |
| --- | --- | --- |
| | | AGGTCAGCCCAAGGCTGCCCCCTCGGTCACTCTGTTCCCGCC CTCCTCTGAGGAGCTTCAAGCCAACAAGGCCACACTGGTGT GTCTCATAAGTGACTTCTACCCGGGAGCCGTGACAGTGGCC TGGAAGGCAGATAGCAGCCCCGTCAAGGCGGGAGTGGAGA CCACCACACCCTCCAAACAAAGCAACAACAAGTACGCGGCC AGCAGCTATCTGAGCCTGACGCCTGAGCAGTGGAAGTCCCA CAGAAGCTACAGCTGCCAGGTCACGCATGAAGGGAGCACC GTGGAGAAGACAGTGGCCCCTACAGAATGTTCA |
| NOV0682 | LCDR1 (Kabat) (SEQ ID NO: 56) | RASQTINSYLN |
| | LCDR2 (Kabat) (SEQ ID NO: 57) | RASNLQS |
| | LCDR3 (SEQ ID NO: 58) | QQGDSSWT |
| | HCDR1 (Kabat) (SEQ ID NO: 59) | SYAIS |
| | HCDR2 (Kabat) (SEQ ID NO: 60) | FIKSNADGYTTNYAAPVKG |
| | HCDR3 (Kabat) (SEQ ID NO: 61) | IRYFRNWDY |
| | vH full sequence (SEQ ID NO: 62) | QVQLVESGGGLVKPGGSLRLSCAASGFTFSSYAISWVRQAPGK GLEWVGFIKSNADGYTTNYAAPVKGRFTISRDDSKNTLYLQM NSLKTEDTAVYYCARIRYFRNWDYWGQGTLVTVSS |
| | vL full sequence (SEQ ID NO: 63) | DIQMTQSPSSLSASVGDRVTITCRASQTINSYLNWYQQKPGKA PKLLIYRASNLQSGVPSRFSGSGSGTDFTLTISSLQPEDFATYYC QQGDSSWTFGQGTKVEIK |
| | vH DNA sequence (SEQ ID NO: 64) | CAGGTGCAATTGGTGGAAAGCGGCGGTGGCCTGGTGAAACC AGGCGGCAGCCTGCGCCTGAGCTGCGCCGCCTCCGGATTCA CCTTTTCTTCTTACGCTATCTCTTGGGTGCGCCAGGCCCCGG GCAAAGGTCTCGAGTGGGTGGGCTTCATCAAATCTAACGCT GACGGTTACACTACTAACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTATCCGTTACTTCCGTAACTGGGATTACTGGG GCCAAGGCACCCTGGTGACTGTTAGCTCA |
| | vL DNA sequence (SEQ ID NO: 65) | GATATCCAGATGACCCAGAGCCCGAGCAGCCTGAGCGCCAG CGTGGGCGATCGCGTGACCATTACCTGCAGAGCCAGCCAGA CTATTAACTCTTACCTGAACTGGTACCAGCAGAAACCGGGC AAAGCGCCGAAACTATTAATCTACCGTGCTTCTAACCTGCA AAGCGGCGTGCCGAGCCGCTTTAGCGGCAGCGGATCCGGCA CCGATTTCACCCTGACCATTAGCTCTCTGCAACCGGAAGACT TTGCGACCTATTATTGCCAGCAGGGTGACTCTTCTTGGACCT TTGGCCAGGGCACGAAAGTTGAAATTAAA |
| | HC full sequence (SEQ ID NO: 66) | QVQLVESGGGLVKPGGSLRLSCAASGFTFSSYAISWVRQAPGK GLEWVGFIKSNADGYTTNYAAPVKGRFTISRDDSKNTLYLQM NSLKTEDTAVYYCARIRYFRNWDYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRVEPKSCDKTHTCPPCPAPELLGGPSVFLFPPKPKDTLMISR TPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| | LC full sequence (SEQ ID NO: 67) | DIQMTQSPSSLSASVGDRVTITCRASQTINSYLNWYQQKPGKA PKLLIYRASNLQSGVPSRFSGSGSGTDFTLTISSLQPEDFATYYC QQGDSSWTFGQGTKVEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC |

TABLE 5-continued

| Sequence information of the IgGs selected for in-depth characterization. | | |
|---|---|---|
| NOV ID | Category | Value |
| | HC DNA sequence (SEQ ID NO: 68) | CAGGTGCAATTGGTGGAAAGCGGCGGTGGCCTGGTGAAACC AGGCGGCAGCCTGCGCCTGAGCTGCGCCGCCTCCGGATTCA CCTTTTCTTCTTACGCTATCTCTTGGGTGCGCCAGGCCCCGG GCAAAGGTCTCGAGTGGGTGGGCTTCATCAAATCTAACGCT GACGGTTACACTACTAACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTATCCGTTACTTCCGTAACTGGGATTACTGGG GCCAAGGCACCCTGGTGACTGTTAGCTCAGCCTCCACCAAG GGTCCATCGGTCTTCCCCCTGGCACCCTCCTCCAAGAGCACC TCTGGGGGCACAGCGGCCCTGGGCTGCCTGGTCAAGGACTA CTTCCCCGAACCGGTGACGGTGTCGTGGAACTCAGGCGCCC TGACCAGCGGCGTGCACACCTTCCCGGCTGTCCTACAGTCCT CAGGACTCTACTCCCTCAGCAGCGTGGTGACCGTGCCCTCC AGCAGCTTGGGCACCCAGACCTACATCTGCAACGTGAATCA CAAGCCCAGCAACACCAAGGTGGACAAGAGAGTTGAGCCC AAATCTTGTGACAAAACTCACACATGCCCACCGTGCCCAGC ACCTGAACTCCTGGGGGGACCGTCAGTCTTCCTCTTCCCCCC AAAACCCAAGGACACCCTCATGATCTCCCGGACCCCTGAGG TCACATGCGTGGTGGTGGACGTGAGCCACGAAGACCCTGAG GTCAAGTTCAACTGGTACGTGGACGGCGTGGAGGTGCATAA TGCCAAGACAAAGCCGCGGGAGGAGCAGTACAACAGCACG TACCGGGTGGTCAGCGTCCTCACCGTCCTGCACCAGGACTG GCTGAATGGCAAGGAGTACAAGTGCAAGGTCTCCAACAAA GCCCTCCCAGCCCCCATCGAGAAAACCATCTCCAAAGCCAA AGGGCAGCCCCGAGAACCACAGGTGTACACCCTGCCCCCAT CCCGGGAGGAGATGACCAAGAACCAGGTCAGCCTGACCTGC CTGGTCAAAGGCTTCTATCCCAGCGACATCGCCGTGGAGTG GGAGAGCAATGGGCAGCCGGAGAACAACTACAAGACCACG CCTCCCGTGCTGGACTCCGACGGCTCCTTCTTCCTCTACAGC AAGCTCACCGTGGACAAGAGCAGGTGGCAGCAGGGGAACG TCTTCTCATGCTCCGTGATGCATGAGGCTCTGCACAACCACT ACACGCAGAAGAGCCTCTCCCTGTCTCCGGGTAAA |
| | LC DNA sequence (SEQ ID NO: 69) | GATATCCAGATGACCCAGAGCCCGAGCAGCCTGAGCGCCAG CGTGGGCGATCGCGTGACCATTACCTGCAGAGCCAGCCAGA CTATTAACTCTTACCTGAACTGGTACCAGCAGAAACCGGGC AAAGCGCCGAAACTATTAATCTACCGTGCTTCTAACCTGCA AAGCGGCGTGCCGAGCCGCTTTAGCGGCAGCGGATCCGGCA CCGATTTCACCCTGACCATTAGCTCTCTGCAACCGGAAGACT TTGCGACCTATTATTGCCAGCAGGGTGACTCTTCTTGGACCT TTGGCCAGGGCACGAAAGTTGAAATTAAACGTACGGTGGCC GCTCCCAGCGTGTTCATCTTCCCCCCCAGCGACGAGCAGCTG AAGAGCGGCACCGCCAGCGTGGTGTGCCTGCTGAACAACTT CTACCCCCGGGAGGCCAAGGTGCAGTGGAAGGTGGACAAC GCCCTGCAGAGCGGCAACAGCCAGGAAAGCGTCACCGAGC AGGACAGCAAGGACTCCACCTACAGCCTGAGCAGCACCCTG ACCCTGAGCAAGGCCGACTACGAGAAGCACAAGGTGTACG CCTGCGAGGTGACCCACCAGGGCCTGTCCAGCCCCGTGACC AAGAGCTTCAACCGGGGCGAGTGT |
| NOV0685 | LCDR1 (Kabat) (SEQ ID NO: 70) | SGSSSNIGSYYVS |
| | LCDR2 (Kabat) (SEQ ID NO: 71) | YNTKRPS |
| | LCDR3 (Kabat) (SEQ ID NO: 72) | QSWDKLGKGYV |
| | HCDR1 (Kabat) (SEQ ID NO: 73) | GNSAAWN |
| | HCDR2 (Kabat) (SEQ ID NO: 74) | IIYYRSKWYNDYAVSVKS |
| | HCDR3 (Kabat) (SEQ ID NO: 75) | SSYSGGFDY |

TABLE 5-continued

Sequence information of the IgGs selected for in-depth characterization.

| NOV ID | Category | Value |
|---|---|---|
| | vH full sequence (SEQ ID NO: 76) | QVQLQQSGPGLVKPSQTLSLTCAISGDSVSGNSAAWNWIRQSP SRGLEWLGIIYYRSKWYNDYAVSVKSRITINPDTSKNQFSLQLN SVTPEDTAVYYCARSSYSGGFDYWGQGTLVTVSS |
| | vL full sequence (SEQ ID NO: 77) | DIVLTQPPSVSGAPGQRVTISCSGSSSNIGSYYVSWYQQLPGTA PKLLIYYNTKRPSGVPDRFSGSKSGTSASLAITGLQAEDEADYY CQSWDKLGKGYVFGGGTKLTVL |
| | vH DNA sequence (SEQ ID NO: 78) | CAGGTGCAATTGCAGCAGAGCGGTCCGGGCCTGGTGAAACC GAGCCAGACCCTGAGCCTGACCTGCGCGATTTCCGGAGATA GCGTGAGCGGTAACTCTGCTGCTTGGAACTGGATTCGTCAG AGCCCGAGCCGTGGCCTCGAGTGGCTGGGCATCATCTACTA CCGTAGCAAATGGTACAACGACTATGCCGTGAGCGTGAAAA GCCGCATTACCATTAACCCGGATACTTCGAAAAACCAGTTT AGCCTGCAACTGAACAGCGTGACCCCGGAAGATACGGCCGT GTATTATTGCGCGCGTTCTTCTTACTCTGGTGGTTTCGATTAC TGGGGCCAAGGCACCCTGGTGACTGTTAGCTCA |
| | vL DNA sequence (SEQ ID NO: 79) | GATATCGTGCTGACCCAGCCGCCGAGCGTGAGCGGTGCACC GGGCCAGCGCGTGACCATTAGCTGTAGCGGCAGCAGCAGCA ACATTGGTTCTTACTACGTGTCTTGGTACCAGCAGCTGCCGG GCACGGCGCCGAAACTGCTGATCTACTACAACACTAAACGC CCGAGCGGCGTGCCGGATCGCTTTAGCGGATCCAAAAGCGG CACCAGCGCCAGCCTGGCGATTACCGGCCTGCAAGCAGAAG ACGAAGCGGATTATTACTGCCAGTCTTGGGACAAACTGGGT AAAGGTTACGTGTTTGGCGGCGGCACGAAGTTAACCGTCCT A |
| | HC full sequence (SEQ ID NO: 80) | QVQLQQSGPGLVKPSQTLSLTCAISGDSVSGNSAAWNWIRQSP SRGLEWLGIIYYRSKWYNDYAVSVKSRITINPDTSKNQFSLQLN SVTPEDTAVYYCARSSYSGGFDYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK RVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPGK |
| | LC full sequence (SEQ ID NO: 81) | DIVLTQPPSVSGAPGQRVTISCSGSSSNIGSYYVSWYQQLPGTA PKLLIYYNTKRPSGVPDRFSGSKSGTSASLAITGLQAEDEADYY CQSWDKLGKGYVFGGGTKLTVLGQPKAAPSVTLFPPSSEELQA NKATLVCLISDFYPGAVTVAWKADSSPVKAGVETTTPSKQSNN KYAASSYLSLTPEQWKSHRSYSCQVTHEGSTVEKTVAPTECS |
| | HC DNA sequence (SEQ ID NO: 82) | CAGGTGCAATTGCAGCAGAGCGGTCCGGGCCTGGTGAAACC GAGCCAGACCCTGAGCCTGACCTGCGCGATTTCCGGAGATA GCGTGAGCGGTAACTCTGCTGCTTGGAACTGGATTCGTCAG AGCCCGAGCCGTGGCCTCGAGTGGCTGGGCATCATCTACTA CCGTAGCAAATGGTACAACGACTATGCCGTGAGCGTGAAAA GCCGCATTACCATTAACCCGGATACTTCGAAAAACCAGTTT AGCCTGCAACTGAACAGCGTGACCCCGGAAGATACGGCCGT GTATTATTGCGCGCGTTCTTCTTACTCTGGTGGTTTCGATTAC TGGGGCCAAGGCACCCTGGTGACTGTTAGCTCAGCCTCCAC CAAGGGTCCATCGGTCTTCCCCCTGGCACCCTCCTCCAAGAG CACCTCTGGGGGCACAGCGGCCCTGGGCTGCCTGGTCAAGG ACTACTTCCCCGAACCGGTGACGGTGTCGTGGAACTCAGGC GCCCTGACCAGCGGCGTGCACACCTTCCCGGCTGTCCTACA GTCCTCAGGACTCTACTCCCTCAGCAGCGTGGTGACCGTGCC CTCCAGCAGCTTGGGCACCCAGACCTACATCTGCAACGTGA ATCACAAGCCCAGCAACACCAAGGTGGACAAGAGAGTTGA GCCCAAATCTTGTGACAAAACTCACACATGCCCACCGTGCC CAGCACCTGAACTCCTGGGGGGACCGTCAGTCTTCCTCTTCC CCCCAAAACCCAAGGACACCCTCATGATCTCCCGGACCCCT GAGGTCACATGCGTGGTGGTGGACGTGAGCCACGAAGACCC TGAGGTCAAGTTCAACTGGTACGTGGACGGCGTGGAGGTGC ATAATGCCAAGACAAAGCCGCGGGAGGAGCAGTACAACAG CACGTACCGGGTGGTCAGCGTCCTCACCGTCCTGCACCAGG ACTGGCTGAATGGCAAGGAGTACAAGTGCAAGGTCTCCAAC AAAGCCCTCCCAGCCCCCATCGAGAAAACCATCTCCAAAGC CAAAGGGCAGCCCCGAGAACCACAGGTGTACACCCTGCCCC CATCCCGGGAGGAGATGACCAAGAACCAGGTCAGCCTGACC TGCCTGGTCAAAGGCTTCTATCCCAGCGACATCGCCGTGGA GTGGGAGAGCAATGGGCAGCCGGAGAACAACTACAAGACC ACGCCTCCCGTGCTGGACTCCGACGGCTCCTTCTTCCTCTAC AGCAAGCTCACCGTGGACAAGAGCAGGTGGCAGCAGGGGA ACGTCTTCTCATGCTCCGTGATGCATGAGGCTCTGCACAACC ACTACACGCAGAAGAGCCTCTCCCTGTCTCCGGGTAAA |

TABLE 5-continued

Sequence information of the IgGs selected for in-depth characterization.

| NOV ID | Category | Value |
|---|---|---|
| | LC DNA sequence (SEQ ID NO: 83) | GATATCGTGCTGACCCAGCCGCCGAGCGTGAGCGGTGCACC GGGCCAGCGCGTGACCATTAGCTGTAGCGGCAGCAGCAGCA ACATTGGTTCTTACTACGTGTCTTGGTACCAGCAGCTGCCGG GCACGGCGCCGAAACTGCTGATCTACTACAACACTAAACGC CCGAGCGGCGTGCCGGATCGCTTTAGCGGATCCAAAAGCGG CACCAGCGCCAGCCTGGCGATTACCGGCCTGCAAGCAGAAG ACGAAGCGGATTATTACTGCCAGTCTTGGGACAAACTGGGT AAAGGTTACGTGTTTGGCGGCGGCACGAAGTTAACCGTCCT AGGTCAGCCCAAGGCTGCCCCCTCGGTCACTCTGTTCCCGCC CTCCTCTGAGGAGCTTCAAGCCAACAAGGCCACACTGGTGT GTCTCATAAGTGACTTCTACCCGGGAGCCGTGACAGTGGCC TGGAAGGCAGATAGCAGCCCCGTCAAGGCGGGAGTGGAGA CCACCACACCCTCCAAACAAAGCAACAACAAGTACGCGGCC AGCAGCTATCTGAGCCTGACGCCTGAGCAGTGGAAGTCCCA CAGAAGCTACAGCTGCCAGGTCACGCATGAAGGGAGCACC GTGGAGAAGACAGTGGCCCCTACAGAATGTTCA |
| NOV0689 | LCDR1 (Kabat) (SEQ ID NO: 84) | SGSSSNIGSNFVS |
| | LCDR2 (Kabat) (SEQ ID NO: 85) | DNSNRPS |
| | LCDR3 (Kabat) (SEQ ID NO: 86) | SSYDSFDHSWV |
| | HCDR1 (Kabat) (SEQ ID NO: 87) | SFAMN |
| | HCDR2 (Kabat) (SEQ ID NO: 88) | VISSSGSNTNYADSVKG |
| | HCDR3 (Kabat) (SEQ ID NO: 89) | PSYFQAMDY |
| | vH full sequence (SEQ ID NO: 90) | QVQLLESGGGLVQPGGSLRLSCAASGFTFSSFAMNWVRQAPG KGLEWVSVISSSGSNTNYADSVKGRFTISRDNSKNTLYLQMNS LRAEDTAVYYCARPSYFQAMDYWGQGTLVTVSS |
| | vL full sequence (SEQ ID NO: 91) | DIVLTQPPSVSGAPGQRVTISCSGSSSNIGSNFVSWYQQLPGTAP KLLIYDNSNRPSGVPDRFSGSKSGTSASLAITGLQAEDEADYYC SSYDSFDHSWVFGGGTKLTVL |
| | vH DNA sequence (SEQ ID NO: 92) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTTCTTTCGCTATGAACTGGGTGCGCCAGGCCCCGG GCAAAGGTCTCGAGTGGGTTTCCGTTATCTCTTCTTCTGGTT CTAACACCAACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTCCGTCTTACTTCCAGGCTATGGATTACTGGGGCCAAG GCACCCTGGTGACTGTTAGCTCA |
| | vL DNA sequence (SEQ ID NO: 93) | GATATCGTGCTGACCCAGCCGCCGAGCGTGAGCGGTGCACC GGGCCAGCGCGTGACCATTAGCTGTAGCGGCAGCAGCAGCA ACATTGGTTCTAACTTCGTGTCTTGGTACCAGCAGCTGCCGG GCACGGCGCCGAAACTGCTGATCTACGACAACTCTAACCGC CCGAGCGGCGTGCCGGATCGCTTTAGCGGATCCAAAAGCGG CACCAGCGCCAGCCTGGCGATTACCGGCCTGCAAGCAGAAG ACGAAGCGGATTATTACTGCTCTTCTTACGACTCTTTCGACC ATTCTTGGGTGTTTGGCGGCGGCACGAAGTTAACCGTCCTA |
| | HC full sequence (SEQ ID NO: 94) | QVQLLESGGGLVQPGGSLRLSCAASGFTFSSFAMNWVRQAPG KGLEWVSVISSSGSNTNYADSVKGRFTISRDNSKNTLYLQMNS LRAEDTAVYYCARPSYFQAMDYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK RVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWESN |

TABLE 5-continued

Sequence information of the IgGs selected for in-depth characterization.

| NOV ID | Category | Value |
|---|---|---|
| | | GQPENNYKTTPPVLDSDGSFFLYSKLTVDKSRWQQGNVFSCSV MHEALHNHYTQKSLSLSPGK |
| | LC full sequence (SEQ ID NO: 95) | DIVLTQPPSVSGAPGQRVTISCSGSSSNIGSNFVSWYQQLPGTAP KLLIYDNSNRPSGVPDRFSGSKSGTSASLAITGLQAEDEADYYC SSYDSFDHSWVFGGGTKLTVLGQPKAAPSVTLFPPSSEELQAN KATLVCLISDFYPGAVTVAWKADSSPVKAGVETTTPSKQSNNK YAASSYLSLTPEQWKSHRSYSCQVTHEGSTVEKTVAPTECS |
| | HC DNA sequence (SEQ ID NO: 96) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTTCTTTCGCTATGAACTGGGTGCGCCAGGCCCCGG GCAAAGGTCTCGAGTGGGTTTCCGTTATCTCTTCTTCTGGTT CTAACACCAACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTCCGTCTTACTTCCAGGCTATGGATTACTGGGGCCAAG GCACCCTGGTGACTGTTAGCTCAGCCTCCACCAAGGGTCCA TCGGTCTTCCCCCTGGCACCCTCCTCCAAGAGCACCTCTGGG GGCACAGCGGCCCTGGGCTGCCTGGTCAAGGACTACTTCCC CGAACCGGTGACGGTGTCGTGGAACTCAGGCGCCCTGACCA GCGGCGTGCACACCTTCCCGGCTGTCCTACAGTCCTCAGGA CTCTACTCCCTCAGCAGCGTGGTGACCGTGCCCTCCAGCAGC TTGGGCACCCAGACCTACATCTGCAACGTGAATCACAAGCC CAGCAACACCAAGGTGGACAAGAGAGTTGAGCCCAAATCTT GTGACAAAACTCACACATGCCCACCGTGCCCAGCACCTGAA CTCCTGGGGGGACCGTCAGTCTTCCTCTTCCCCCCAAAACCC AAGGACACCCTCATGATCTCCCGGACCCCTGAGGTCACATG CGTGGTGGTGGACGTGAGCCACGAAGACCCTGAGGTCAAGT TCAACTGGTACGTGGACGGCGTGGAGGTGCATAATGCCAAG ACAAAGCCGCGGGAGGAGCAGTACAACAGCACGTACCGGG TGGTCAGCGTCCTCACCGTCCTGCACCAGGACTGGCTGAAT GGCAAGGAGTACAAGTGCAAGGTCTCCAACAAAGCCCTCCC AGCCCCCATCGAGAAAACCATCTCCAAAGCCAAAGGGCAGC CCCGAGAACCACAGGTGTACACCCTGCCCCCATCCCGGGAG GAGATGACCAAGAACCAGGTCAGCCTGACCTGCCTGGTCAA AGGCTTCTATCCCAGCGACATCGCCGTGGAGTGGGAGAGCA ATGGGCAGCCGGAGAACAACTACAAGACCACGCCTCCCGTG CTGGACTCCGACGGCTCCTTCTTCCTCTACAGCAAGCTCACC GTGGACAAGAGCAGGTGGCAGCAGGGGAACGTCTTCTCATG CTCCGTGATGCATGAGGCTCTGCACAACCACTACACGCAGA AGAGCCTCTCCCTGTCTCCGGGTAAA |
| | LC DNA sequence (SEQ ID NO: 97) | GATATCGTGCTGACCCAGCCGCCGAGCGTGAGCGGTGCACC GGGCCAGCGCGTGACCATTAGCTGTAGCGGCAGCAGCAGCA ACATTGGTTCTAACTTCGTGTCTTGGTACCAGCAGCTGCCGG GCACGGCGCCGAAACTGCTGATCTACGACAACTCTAACCGC CCGAGCGGCGTGCCGGATCGCTTTAGCGGATCCAAAAGCGG CACCAGCGCCAGCCTGGCGATTACCGGCCTGCAAGCAGAAG ACGAAGCGGATTATTACTGCTCTTCTTACGACTCTTTCGACC ATTCTTGGGTGTTTGGCGGCGGCACGAAGTTAACCGTCCTA GGTCAGCCCAAGGCTGCCCCCTCGGTCACTCTGTTCCCGCCC TCCTCTGAGGAGCTTCAAGCCAACAAGGCCACACTGGTGTG TCTCATAAGTGACTTCTACCCGGGAGCCGTGACAGTGGCCT GGAAGGCAGATAGCAGCCCCGTCAAGGCGGGAGTGGAGAC CACCACACCCTCCAAACAAAGCAACAACAAGTACGCGGCCA GCAGCTATCTGAGCCTGACGCCTGAGCAGTGGAAGTCCCAC AGAAGCTACAGCTGCCAGGTCACGCATGAAGGGAGCACCGT GGAGAAGACAGTGGCCCCTACAGAATGTTCA |
| NOV0690 | LCDR1 (Kabat) (SEQ ID NO: 98) | SGDAIGTKFAH |
| | LCDR2 (Kabat) (SEQ ID NO: 99) | YDHERPS |
| | LCDR3 (Kabat) (SEQ ID NO: 100) | YSRASSNLV |
| | HCDR1 (Kabat) (SEQ ID NO: 101) | DHAID |

TABLE 5-continued

Sequence information of the IgGs selected for in-depth characterization.

| NOV ID | Category | Value |
|---|---|---|
| | HCDR2 (Kabat) (SEQ ID NO: 102) | VIAGDGSITYYADSVKG |
| | HCDR3 (Kabat) (SEQ ID NO: 103) | DTGVYREYMDV |
| | vH full sequence (SEQ ID NO: 104) | QVQLLESGGGLVQPGGSLRLSCAASGFTFSDHAIDWVRQAPGK GLEWVSVIAGDGSITYYADSVKGRFTISRDNSKNTLYLQMNSL RAEDTAVYYCARDTGVYREYMDVWGQGTLVTVSS |
| | vL full sequence (SEQ ID NO: 105) | DIELTQPPSVSVSPGQTASITCSGDAIGTKFAHWYQQKPGQAPV LVIYYDHERPSGIPERFSGSNSGNTATLTISGTQAEDEADYYCY SRASSNLVFGGGTKLTVL |
| | vH DNA sequence (SEQ ID NO: 106) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTGACCATGCTATCGACTGGGTGCGCCAGGCCCCGG GCAAAGGTCTCGAGTGGGTTTCCGTTATCGCTGGTGACGGTT CTATCACCTACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTGACACTGGTGTTTACCGTGAATACATGGATGTTTGG GGCCAAGGCACCCTGGTGACTGTTAGCTCA |
| | vL DNA sequence (SEQ ID NO: 107) | GATATCGAACTGACCCAGCCGCCGAGCGTGAGCGTGAGCCC GGGCCAGACCGCGAGCATTACCTGTAGCGGCGATGCTATCG GTACTAAATTCGCTCATTGGTACCAGCAGAAACCGGGCCAG GCGCCGGTGCTGGTGATCTACTACGACCATGAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCTACTCTCGTGCTTCTTCTAACCTGGTG TTTGGCGGCGGCACGAAGTTAACCGTCCTA |
| | HC full sequence (SEQ ID NO: 108) | QVQLLESGGGLVQPGGSLRLSCAASGFTFSDHAIDWVRQAPGK GLEWVSVIAGDGSITYYADSVKGRFTISRDNSKNTLYLQMNSL RAEDTAVYYCARDTGVYREYMDVWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRVEPKSCDKTHTCPPCPAPELLGGPSVFLFPPKPKDTLMISR TPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| | LC full sequence (SEQ ID NO: 109) | DIELTQPPSVSVSPGQTASITCSGDAIGTKFAHWYQQKPGQAPV LVIYYDHERPSGIPERFSGSNSGNTATLTISGTQAEDEADYYCY SRASSNLVFGGGTKLTVLGQPKAAPSVTLFPPSSEELQANKATL VCLISDFYPGAVTVAWKADSSPVKAGVETTTPSKQSNNKYAA SSYLSLTPEQWKSHRSYSCQVTHEGSTVEKTVAPTECS |
| | HC DNA sequence (SEQ ID NO: 110) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTGACCATGCTATCGACTGGGTGCGCCAGGCCCCGG GCAAAGGTCTCGAGTGGGTTTCCGTTATCGCTGGTGACGGTT CTATCACCTACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTGACACTGGTGTTTACCGTGAATACATGGATGTTTGG GGCCAAGGCACCCTGGTGACTGTTAGCTCAGCCTCCACCAA GGGTCCATCGGTCTTCCCCCTGGCACCCTCCTCCAAGAGCAC CTCTGGGGGCACAGCGGCCCTGGGCTGCCTGGTCAAGGACT ACTTCCCCGAACCGGTGACGGTGTCGTGGAACTCAGGCGCC CTGACCAGCGGCGTGCACACCTTCCCGGCTGTCCTACAGTCC TCAGGACTCTACTCCCTCAGCAGCGTGGTGACCGTGCCCTCC AGCAGCTTGGGCACCCAGACCTACATCTGCAACGTGAATCA CAAGCCCAGCAACACCAAGGTGGACAAGAGAGTTGAGCCC AAATCTTGTGACAAAACTCACACATGCCCACCGTGCCCAGC ACCTGAACTCCTGGGGGGACCGTCAGTCTTCCTCTTCCCCCC AAAACCCAAGGACACCCTCATGATCTCCCGGACCCCTGAGG TCACATGCGTGGTGGTGGACGTGAGCCACGAAGACCCTGAG GTCAAGTTCAACTGGTACGTGGACGGCGTGGAGGTGCATAA TGCCAAGACAAAGCCGCGGGAGGAGCAGTACAACAGCACG TACCGGGTGGTCAGCGTCCTCACCGTCCTGCACCAGGACTG GCTGAATGGCAAGGAGTACAAGTGCAAGGTCTCCAACAAA GCCCTCCCAGCCCCCATCGAGAAAACCATCTCCAAAGCCAA AGGGCAGCCCCGAGAACCACAGGTGTACACCCTGCCCCCAT |

TABLE 5-continued

Sequence information of the IgGs selected for in-depth characterization.

| NOV ID | Category | Value |
|---|---|---|
| | | CCCGGGAGGAGATGACCAAGAACCAGGTCAGCCTGACCTGC CTGGTCAAAGGCTTCTATCCCAGCGACATCGCCGTGGAGTG GGAGAGCAATGGGCAGCCGGAGAACAACTACAAGACCACG CCTCCCGTGCTGGACTCCGACGGCTCCTTCTTCCTCTACAGC AAGCTCACCGTGGACAAGAGCAGGTGGCAGCAGGGGAACG TCTTCTCATGCTCCGTGATGCATGAGGCTCTGCACAACCACT ACACGCAGAAGAGCCTCTCCCTGTCTCCGGGTAAA |
| | LC DNA sequence (SEQ ID NO: 111) | GATATCGAACTGACCCAGCCGCCGAGCGTGAGCGTGAGCCC GGGCCAGACCGCGAGCATTACCTGTAGCGGCGATGCTATCG GTACTAAATTCGCTCATTGGTACCAGCAGAAACCGGGCCAG GCGCCGGTGCTGGTGATCTACTACGACCATGAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCTACTCTCGTGCTTCTTCTAACCTGGTG TTTGGCGGCGGCACGAAGTTAACCGTCCTAGGTCAGCCCAA GGCTGCCCCCTCGGTCACTCTGTTCCCGCCCTCCTCTGAGGA GCTTCAAGCCAACAAGGCCACACTGGTGTGTCTCATAAGTG ACTTCTACCCGGGAGCCGTGACAGTGGCCTGGAAGGCAGAT AGCAGCCCCGTCAAGGCGGGAGTGGAGACCACCACACCCTC CAAACAAAGCAACAACAAGTACGCGGCCAGCAGCTATCTG AGCCTGACGCCTGAGCAGTGGAAGTCCCACAGAAGCTACAG CTGCCAGGTCACGCATGAAGGGAGCACCGTGGAGAAGACA GTGGCCCCTACAGAATGTTCA |
| NOV0691 | LCDR1 (Kabat) (SEQ ID NO: 112) | TGTSSDVGRYNFVS |
| | LCDR2 (Kabat) (SEQ ID NO: 113) | RVSNRPS |
| | LCDR3 (Kabat) (SEQ ID NO: 114) | QSWTTYSNVV |
| | HCDR1 (Kabat) (SEQ ID NO: 115) | SYALN |
| | HCDR2 (Kabat) (SEQ ID NO: 116) | RIKSKTYGGSTDYAAPVKG |
| | HCDR3 (Kabat) (SEQ ID NO: 117) | DRGGYVGFDS |
| | vH full sequence (SEQ ID NO: 118) | QVQLVESGGGLVKPGGSLRLSCAASGFTFSSYALNWVRQAPG KGLEWVGRIKSKTYGGSTDYAAPVKGRFTISRDDSKNTLYLQ MNSLKTEDTAVYYCARDRGGYVGFDSWGQGTLVTVSS |
| | vL full sequence (SEQ ID NO: 119) | DIALTQPASVSGSPGQSITISCTGTSSDVGRYNFVSWYQQHPGK APKLMIYRVSNRPSGVSNRFSGSKSGNTASLTISGLQAEDEADY YCQSWTTYSNVVFGGGTKLTVL |
| | vH DNA sequence (SEQ ID NO:120) | CAGGTGCAATTGGTGGAAAGCGGCGGTGGCCTGGTGAAACC AGGCGGCAGCCTGCGCCTGAGCTGCGCCGCCTCCGGATTCA CCTTTTCTTCTTACGCTCTGAACTGGGTGCGCCAGGCCCCGG GCAAAGGTCTCGAGTGGGTGGGCCGTATCAAATCTAAAACT TACGGTGGTTCTACTGACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTGACCGTGGTGGTTACGTTGGTTTCGATTCTT GGGGCCAAGGCACCCTGGTGACTGTTAGCTCA |
| | vL DNA sequence (SEQ ID NO: 121) | GATATCGCGCTGACCCAGCCGGCGAGCGTGAGCGGTAGCCC GGGCCAGAGCATTACCATTAGCTGCACCGGCACCAGCAGCG ATGTGGGCCGTTACAACTTCGTGTCTTGGTACCAGCAGCATC CGGGCAAGGCGCCGAAACTGATGATCTACCGTGTTTCTAAC CGTCCGAGCGGCGTGAGCAACCGTTTTAGCGGATCCAAAAG CGGCAACACCGCGAGCCTGACCATTAGCGGCCTGCAAGCGG AAGACGAAGCGGATTATTACTGCCAGTCTTGGACTACTTAC TCTAACGTTGTGTTTGGCGGCGGCACGAAGTTAACCGTCCTA |

TABLE 5-continued

Sequence information of the IgGs selected for in-depth characterization.

| NOV ID | Category | Value |
|---|---|---|
| | HC full sequence (SEQ ID NO: 122) | QVQLVESGGGLVKPGGSLRLSCAASGFTFSSYALNWVRQAPG KGLEWVGRIKSKTYGGSTDYAAPVKGRFTISRDDSKNTLYLQ MNSLKTEDTAVYYCARDRGGYVGFDSWGQGTLVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKRVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| | LC full sequence (SEQ ID NO: 123) | DIALTQPASVSGSPGQSITISCTGTSSDVGRYNFVSWYQQHPGK APKLMIYRVSNRPSGVSNRFSGSKSGNTASLTISGLQAEDEADY YCQSWTTYSNVVFGGGTKLTVLGQPKAAPSVTLFPPSSEELQA NKATLVCLISDFYPGAVTVAWKADSSPVKAGVETTTPSKQSNN KYAASSYLSLTPEQWKSHRSYSCQVTHEGSTVEKTVAPTECS |
| | HC DNA sequence (SEQ ID NO: 124) | CAGGTGCAATTGGTGGAAAGCGGCGGTGGCCTGGTGAAACC AGGCGGCAGCCTGCGCCTGAGCTGCGCCGCCTCCGGATTCA CCTTTTCTTCTTACGCTCTGAACTGGGTGCGCCAGGCCCCGG GCAAAGGTCTCGAGTGGGTGGGCCGTATCAAATCTAAAACT TACGGTGGTTCTACTGACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTGACCGTGGTGGTTACGTTGGTTTCGATTCTT GGGGCCAAGGCACCCTGGTGACTGTTAGCTCAGCCTCCACC AAGGGTCCATCGGTCTTCCCCCTGGCACCCTCCTCCAAGAGC ACCTCTGGGGGCACAGCGGCCCTGGGCTGCCTGGTCAAGGA CTACTTCCCCGAACCGGTGACGGTGTCGTGGAACTCAGGCG CCCTGACCAGCGGCGTGCACACCTTCCCGGCTGTCCTACAGT CCTCAGGACTCTACTCCCTCAGCAGCGTGGTGACCGTGCCCT CCAGCAGCTTGGGCACCCAGACCTACATCTGCAACGTGAAT CACAAGCCCAGCAACACCAAGGTGGACAAGAGAGTTGAGC CCAAATCTTGTGACAAAACTCACACATGCCCACCGTGCCCA GCACCTGAACTCCTGGGGGGACCGTCAGTCTTCCTCTTCCCC CCAAAACCCAAGGACACCCTCATGATCTCCCGGACCCCTGA GGTCACATGCGTGGTGGTGGACGTGAGCCACGAAGACCCTG AGGTCAAGTTCAACTGGTACGTGGACGGCGTGGAGGTGCAT AATGCCAAGACAAAGCCGCGGGAGGAGCAGTACAACAGCA CGTACCGGGTGGTCAGCGTCCTCACCGTCCTGCACCAGGAC TGGCTGAATGGCAAGGAGTACAAGTGCAAGGTCTCCAACAA AGCCCTCCCAGCCCCCATCGAGAAAACCATCTCCAAAGCCA AAGGGCAGCCCCGAGAACCACAGGTGTACACCCTGCCCCCA TCCCGGGAGGAGATGACCAAGAACCAGGTCAGCCTGACCTG CCTGGTCAAAGGCTTCTATCCCAGCGACATCGCCGTGGAGT GGGAGAGCAATGGGCAGCCGGAGAACAACTACAAGACCAC GCCTCCCGTGCTGGACTCCGACGGCTCCTTCTTCCTCTACAG CAAGCTCACCGTGGACAAGAGCAGGTGGCAGCAGGGGAAC GTCTTCTCATGCTCCGTGATGCATGAGGCTCTGCACAACCAC TACACGCAGAAGAGCCTCTCCCTGTCTCCGGGTAAA |
| | LC DNA sequence (SEQ ID NO: 125) | GATATCGCGCTGACCCAGCCGGCGAGCGTGAGCGGTAGCCC GGGCCAGAGCATTACCATTAGCTGCACCGGCACCAGCAGCG ATGTGGGCCGTTACAACTTCGTGTCTTGGTACCAGCAGCATC CGGGCAAGGCGCCGAAACTGATGATCTACCGTGTTTCTAAC CGTCCGAGCGGCGTGAGCAACCGTTTTAGCGGATCCAAAAG CGGCAACACCGCGAGCCTGACCATTAGCGGCCTGCAAGCGG AAGACGAAGCGGATTATTACTGCCAGTCTTGGACTACTTAC TCTAACGTTGTGTTTGGCGGCGGCACGAAGTTAACCGTCCTA GGTCAGCCCAAGGCTGCCCCCTCGGTCACTCTGTTCCCGCCC TCCTCTGAGGAGCTTCAAGCCAACAAGGCCACACTGGTGTG TCTCATAAGTGACTTCTACCCGGGAGCCGTGACAGTGGCCT GGAAGGCAGATAGCAGCCCCGTCAAGGCGGGAGTGGAGAC CACCACACCCTCCAAACAAAGCAACAACAAGTACGCGGCCA GCAGCTATCTGAGCCTGACGCCTGAGCAGTGGAAGTCCCAC AGAAGCTACAGCTGCCAGGTCACGCATGAAGGGAGCACCGT GGAGAAGACAGTGGCCCCTACAGAATGTTCA |
| NOV0692 | LCDR1 (Kabat) (SEQ ID NO: 126) | SGDSIGSKYAQ |
| | LCDR2 (Kabat) (SEQ ID NO: 127) | YNSERPS |

TABLE 5-continued

| Sequence information of the IgGs selected for in-depth characterization. | | |
|---|---|---|
| NOV ID | Category | Value |
| | LCDR3 (Kabat) (SEQ ID NO: 128) | QSWDGQSTIRV |
| | HCDR1 (Kabat) (SEQ ID NO: 129) | RYWMD |
| | HCDR2 (Kabat) (SEQ ID NO: 130) | RIKSKANGGITDYAAPVKG |
| | HCDR3 (Kabat) (SEQ ID NO: 131) | GMTFLGI |
| | vH full sequence (SEQ ID NO: 132) | QVQLVESGGGLVKPGGSLRLSCAASGFTFSRYWMDWVRQAP GKGLEWVGRIKSKANGGITDYAAPVKGRFTISRDDSKNTLYLQ MNSLKTEDTAVYYCARGMTFLGIWGQGTLVTVSS |
| | vL full sequence (SEQ ID NO: 133) | DIELTQPPSVSVSPGQTASITCSGDSIGSKYAQWYQQKPGQAPV LVIYYNSERPSGIPERFSGSNSGNTATLTISGTQAEDEADYYCQS WDGQSTIRVFGGGTKLTVL |
| | vH DNA sequence (SEQ ID NO: 134) | CAGGTGCAATTGGTGGAAAGCGGCGGTGGCCTGGTGAAACC AGGCGGCAGCCTGCGCCTGAGCTGCGCCGCCTCCGGATTCA CCTTTTCTCGTTACTGGATGGACTGGGTGCGCCAGGCCCCGG GCAAAGGTCTCGAGTGGGTGGGCCGTATCAAATCTAAAGCT AACGGTGGTATCACTGACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTGGTATGACTTTCCTGGGTATCTGGGGCCAA GGCACCCTGGTGACTGTTAGCTCA |
| | vL DNA sequence (SEQ ID NO: 135) | GATATCGAACTGACCCAGCCGCCGAGCGTGAGCGTGAGCCC GGGCCAGACCGCGAGCATTACCTGTAGCGGCGATTCTATCG GTTCTAAATACGCTCAGTGGTACCAGCAGAAACCGGGCCAG GCGCCGGTGCTGGTGATCTACTACAACTCTGAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTTGGGACGGTCAGTCTACTATC CGTGTGTTTGGCGGCGGCACGAAGTTAACCGTCCTA |
| | HC full sequence (SEQ ID NO: 136) | QVQLVESGGGLVKPGGSLRLSCAASGFTFSRYWMDWVRQAP GKGLEWVGRIKSKANGGITDYAAPVKGRFTISRDDSKNTLYLQ MNSLKTEDTAVYYCARGMTFLGIWGQGTLVTVSSASTKGPSV FPLAPSSKSTSGGTAALGCLVKDYFPEPVTVSWNSGALTSGVH TFPAVLQSSGLYSLSSVVTVPSSSLGTQTYICNVNHKPSNTKVD KRVEPKSCDKTHTCPPCPAPELLGGPSVFLFPPKPKDTLMISRTP EVTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSREEMTKNQVSLTCLVKGFYPSDIAVEWES NGQPENNYKTTPPVLDSDGSFFLYSKLTVDKSRWQQGNVFSCS VMHEALHNHYTQKSLSLSPGK |
| | LC full sequence (SEQ ID NO: 137) | DIELTQPPSVSVSPGQTASITCSGDSIGSKYAQWYQQKPGQAPV LVIYYNSERPSGIPERFSGSNSGNTATLTISGTQAEDEADYYCQS WDGQSTIRVFGGGTKLTVLGQPKAAPSVTLFPPSSEELQANKA TLVCLISDFYPGAVTVAWKADSSPVKAGVETTTPSKQSNNKYA ASSYLSLTPEQWKSHRSYSCQVTHEGSTVEKTVAPTECS |
| | HC DNA sequence (SEQ ID NO: 138) | CAGGTGCAATTGGTGGAAAGCGGCGGTGGCCTGGTGAAACC AGGCGGCAGCCTGCGCCTGAGCTGCGCCGCCTCCGGATTCA CCTTTTCTCGTTACTGGATGGACTGGGTGCGCCAGGCCCCGG GCAAAGGTCTCGAGTGGGTGGGCCGTATCAAATCTAAAGCT AACGGTGGTATCACTGACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTGGTATGACTTTCCTGGGTATCTGGGGCCAA GGCACCCTGGTGACTGTTAGCTCAGCCTCCACCAAGGGTCC ATCGGTCTTCCCCCTGGCACCCTCCTCCAAGAGCACCTCTGG GGGCACAGCGGCCCTGGGCTGCCTGGTCAAGGACTACTTCC CCGAACCGGTGACGGTGTCGTGGAACTCAGGCGCCCTGACC AGCGGCGTGCACACCTTCCCGGCTGTCCTACAGTCCTCAGG ACTCTACTCCCTCAGCAGCGTGGTGACCGTGCCCTCCAGCA GCTTGGGCACCCAGACCTACATCTGCAACGTGAATCACAAG CCCAGCAACACCAAGGTGGACAAGAGAGTTGAGCCCAAAT CTTGTGACAAAACTCACACATGCCCACCGTGCCCAGCACCT GAACTCCTGGGGGGACCGTCAGTCTTCCTCTTCCCCCCAAAA |

TABLE 5-continued

Sequence information of the IgGs selected for in-depth characterization.

| NOV ID | Category | Value |
|---|---|---|
| | | CCCAAGGACACCCTCATGATCTCCCGGACCCCTGAGGTCAC ATGCGTGGTGGTGGACGTGAGCCACGAAGACCCTGAGGTCA AGTTCAACTGGTACGTGGACGGCGTGGAGGTGCATAATGCC AAGACAAAGCCGCGGGAGGAGCAGTACAACAGCACGTACC GGGTGGTCAGCGTCCTCACCGTCCTGCACCAGGACTGGCTG AATGGCAAGGAGTACAAGTGCAAGGTCTCCAACAAAGCCCT CCCAGCCCCCATCGAGAAAACCATCTCCAAAGCCAAAGGGC AGCCCCGAGAACCACAGGTGTACACCCTGCCCCCATCCCGG GAGGAGATGACCAAGAACCAGGTCAGCCTGACCTGCCTGGT CAAAGGCTTCTATCCCAGCGACATCGCCGTGGAGTGGGAGA GCAATGGGCAGCCGGAGAACAACTACAAGACCACGCCTCCC GTGCTGGACTCCGACGGCTCCTTCTTCCTCTACAGCAAGCTC ACCGTGGACAAGAGCAGGTGGCAGCAGGGGAACGTCTTCTC ATGCTCCGTGATGCATGAGGCTCTGCACAACCACTACACGC AGAAGAGCCTCTCCCTGTCTCCGGGTAAA |
| | LC DNA sequence (SEQ ID NO: 139) | GATATCGAACTGACCCAGCCGCCGAGCGTGAGCGTGAGCCC GGGCCAGACCGCGAGCATTACCTGTAGCGGCGATTCTATCG GTTCTAAATACGCTCAGTGGTACCAGCAGAAACCGGGCCAG GCGCCGGTGCTGGTGATCTACTACAACTCTGAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTTGGGACGGTCAGTCTACTATC CGTGTGTTTGGCGGCGGCACGAAGTTAACCGTCCTAGGTCA GCCCAAGGCTGCCCCCTCGGTCACTCTGTTCCCGCCCTCCTC TGAGGAGCTTCAAGCCAACAAGGCCACACTGGTGTGTCTCA TAAGTGACTTCTACCCGGGAGCCGTGACAGTGGCCTGGAAG GCAGATAGCAGCCCCGTCAAGGCGGGAGTGGAGACCACCA CACCCTCCAAACAAAGCAACAACAAGTACGCGGCCAGCAG CTATCTGAGCCTGACGCCTGAGCAGTGGAAGTCCCACAGAA GCTACAGCTGCCAGGTCACGCATGAAGGGAGCACCGTGGAG AAGACAGTGGCCCCTACAGAATGTTCA |
| NOV0693 | LCDR1 (Kabat) (SEQ ID NO: 140) | RASQSISFYLA |
| | LCDR2 (Kabat) (SEQ ID NO: 141) | GASTLQS |
| | LCDR3 (Kabat) (SEQ ID NO: 142) | HQYSYWLRT |
| | HCDR1 (Kabat) (SEQ ID NO: 143) | SYALH |
| | HCDR2 (Kabat) (SEQ ID NO: 144) | YIFYDSSSTYYADSVKG |
| | HCDR3 (Kabat) (SEQ ID NO: 145) | FLYSAYGVAN |
| | vH full sequence (SEQ ID NO: 146) | QVQLLESGGGLVQPGGSLRLSCAASGFTFSSYALHWVRQAPG KGLEWVSYIFYDSSSTYYADSVKGRFTISRDNSKNTLYLQMNS LRAEDTAVYYCARFLYSAYGVANWGQGTLVTVSS |
| | vL full sequence (SEQ ID NO: 147) | DIQMTQSPSSLSASVGDRVTITCRASQSISFYLAWYQQKPGKAP KLLIYGASTLQSGVPSRFSGSGSGTDFTLTISSLQPEDFATYYCH QYSYWLRTFGQGTKVEIK |
| | vH DNA sequence (SEQ ID NO: 148) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTTCTTACGCTCTGCATTGGGTGCGCCAGGCCCCGG GCAAAGGTCTCGAGTGGGTTTCCTACATCTTCTACGACTCTT CTTCTACCTACTATGCGGATAGCGTGAAAGGCCGCTTTACCA TCAGCCGCGATAATTCGAAAAACACCCTGTATCTGCAAATG AACAGCCTGCGTGCGGAAGATACGGCCGTGTATTATTGCGC GCGTTTCCTGTACTCTGCTTACGGTGTTGCTAACTGGGGCCA AGGCACCCTGGTGACTGTTAGCTCA |

TABLE 5-continued

Sequence information of the IgGs selected for in-depth characterization.

| NOV ID | Category | Value |
|---|---|---|
| | vL DNA sequence (SEQ ID NO: 149) | GATATCCAGATGACCCAGAGCCCGAGCAGCCTGAGCGCCAG<br>CGTGGGCGATCGCGTGACCATTACCTGCAGAGCCAGCCAGT<br>CTATTTCTTTCTACCTGGCTTGGTACCAGCAGAAACCGGGCA<br>AAGCGCCGAAACTATTAATCTACGGTGCTTCTACTCTGCAA<br>AGCGGCGTGCCGAGCCGCTTTAGCGGCAGCGGATCCGGCAC<br>CGATTTCACCCTGACCATTAGCTCTCTGCAACCGGAAGACTT<br>TGCGACCTATTATTGCCATCAGTACTCTTACTGGCTGCGTAC<br>CTTTGGCCAGGGCACGAAAGTTGAAATTAAA |
| | HC full sequence (SEQ ID NO: 150) | QVQLLESGGGLVQPGGSLRLSCAASGFTFSSYALHWVRQAPG<br>KGLEWVSYIFYDSSSTYYADSVKGRFTISRDNSKNTLYLQMNS<br>LRAEDTAVYYCARFLYSAYGVANWGQGTLVTVSSASTKGPSV<br>FPLAPSSKSTSGGTAALGCLVKDYFPEPVTVSWNSGALTSGVH<br>TFPAVLQSSGLYSLSSVVTVPSSSLGTQTYICNVNHKPSNTKVD<br>KRVEPKSCDKTHTCPPCPAPELLGGPSVFLFPPKPKDTLMISRTP<br>EVTCVVVDVSHEDPEVKFNWYVDGVEVHNAKTKPREEQYNS<br>TYRVVSVLTVLHQDWLNGKEYKCKVSNKALPAPIEKTISKAK<br>GQPREPQVYTLPPSREEMTKNQVSLTCLVKGFYPSDIAVEWES<br>NGQPENNYKTTPPVLDSDGSFFLYSKLTVDKSRWQQGNVFSCS<br>VMHEALHNHYTQKSLSLSPGK |
| | LC full sequence (SEQ ID NO: 151) | DIQMTQSPSSLSASVGDRVTITCRASQSISFYLAWYQQKPGKAP<br>KLLIYGASTLQSGVPSRFSGSGSGTDFTLTISSLQPEDFATYYCH<br>QYSYWLRTFGQGTKVEIKRTVAAPSVFIFPPSDEQLKSGTASVV<br>CLLNNFYPREAKVQWKVDNALQSGNSQESVTEQDSKDSTYSL<br>SSTLTLSKADYEKHKVYACEVTHQGLSSPVTKSFNRGEC |
| | HC DNA sequence (SEQ ID NO: 152) | CAGGTGCAATTGCTGGAAAGCGGCGGTGGCCTGGTGCAGCC<br>GGGTGGCAGCCTGCGTCTGAGCTGCGCGGCGTCCGGATTCA<br>CCTTTTCTTCTTACGCTCTGCATTGGGTGCGCCAGGCCCCGG<br>GCAAAGGTCTCGAGTGGGTTTCCTACATCTTCTACGACTCTT<br>CTTCTACCTACTATGCGGATAGCGTGAAAGGCCGCTTTACCA<br>TCAGCCGCGATAATTCGAAAAACACCCTGTATCTGCAAATG<br>AACAGCCTGCGTGCGGAAGATACGGCCGTGTATTATTGCGC<br>GCGTTTCCTGTACTCTGCTTACGGTGTTGCTAACTGGGGCCA<br>AGGCACCCTGGTGACTGTTAGCTCAGCCTCCACCAAGGGTC<br>CATCGGTCTTCCCCCTGGCACCCTCCTCCAAGAGCACCTCTG<br>GGGGCACAGCGGCCCTGGGCTGCCTGGTCAAGGACTACTTC<br>CCCGAACCGGTGACGGTGTCGTGGAACTCAGGCGCCCTGAC<br>CAGCGGCGTGCACACCTTCCCGGCTGTCCTACAGTCCTCAG<br>GACTCTACTCCCTCAGCAGCGTGGTGACCGTGCCCTCCAGC<br>AGCTTGGGCACCCAGACCTACATCTGCAACGTGAATCACAA<br>GCCCAGCAACACCAAGGTGGACAAGAGAGTTGAGCCCAAA<br>TCTTGTGACAAAACTCACACATGCCCACCGTGCCCAGCACC<br>TGAACTCCTGGGGGGACCGTCAGTCTTCCTCTTCCCCCCAAA<br>ACCCAAGGACACCCTCATGATCTCCCGGACCCCTGAGGTCA<br>CATGCGTGGTGGTGGACGTGAGCCACGAAGACCCTGAGGTC<br>AAGTTCAACTGGTACGTGGACGGCGTGGAGGTGCATAATGC<br>CAAGACAAAGCCGCGGGAGGAGCAGTACAACAGCACGTAC<br>CGGGTGGTCAGCGTCCTCACCGTCCTGCACCAGGACTGGCT<br>GAATGGCAAGGAGTACAAGTGCAAGGTCTCCAACAAAGCC<br>CTCCCAGCCCCCATCGAGAAAACCATCTCCAAAGCCAAAGG<br>GCAGCCCCGAGAACCACAGGTGTACACCCTGCCCCCATCCC<br>GGGAGGAGATGACCAAGAACCAGGTCAGCCTGACCTGCCTG<br>GTCAAAGGCTTCTATCCCAGCGACATCGCCGTGGAGTGGGA<br>GAGCAATGGGCAGCCGGAGAACAACTACAAGACCACGCCT<br>CCCGTGCTGGACTCCGACGGCTCCTTCTTCCTCTACAGCAAG<br>CTCACCGTGGACAAGAGCAGGTGGCAGCAGGGGAACGTCTT<br>CTCATGCTCCGTGATGCATGAGGCTCTGCACAACCACTACA<br>CGCAGAAGAGCCTCTCCCTGTCTCCGGGTAAA |
| | LC DNA sequence (SEQ ID NO: 153) | GATATCCAGATGACCCAGAGCCCGAGCAGCCTGAGCGCCAG<br>CGTGGGCGATCGCGTGACCATTACCTGCAGAGCCAGCCAGT<br>CTATTTCTTTCTACCTGGCTTGGTACCAGCAGAAACCGGGCA<br>AAGCGCCGAAACTATTAATCTACGGTGCTTCTACTCTGCAA<br>AGCGGCGTGCCGAGCCGCTTTAGCGGCAGCGGATCCGGCAC<br>CGATTTCACCCTGACCATTAGCTCTCTGCAACCGGAAGACTT<br>TGCGACCTATTATTGCCATCAGTACTCTTACTGGCTGCGTAC<br>CTTTGGCCAGGGCACGAAAGTTGAAATTAAACGTACGGTGG<br>CCGCTCCCAGCGTGTTCATCTTCCCCCCCAGCGACGAGCAGC<br>TGAAGAGCGGCACCGCCAGCGTGGTGTGCCTGCTGAACAAC<br>TTCTACCCCCGGGAGGCCAAGGTGCAGTGGAAGGTGGACAA<br>CGCCCTGCAGAGCGGCAACAGCCAGGAAAGCGTCACCGAG<br>CAGGACAGCAAGGACTCCACCTACAGCCTGAGCAGCACCCT<br>GACCCTGAGCAAGGCCGACTACGAGAAGCACAAGGTGTAC<br>GCCTGCGAGGTGACCCACCAGGGCCTGTCCAGCCCCGTGAC<br>CAAGAGCTTCAACCGGGGCGAGTGT |

TABLE 5-continued

Sequence information of the IgGs selected for in-depth characterization.

| NOV ID | Category | Value |
|---|---|---|
| NOV0695 | LCDR1 (Kabat) (SEQ ID NO: 154) | RASQGIFTYLN |
| | LCDR2 (Kabat) (SEQ ID NO: 155) | AASTLQS |
| | LCDR3 (Kabat) (SEQ ID NO: 156) | QQYYSTSLT |
| | HCDR1 (Kabat) (SEQ ID NO: 157) | SNSAAWN |
| | HCDR2 (Kabat) (SEQ ID NO: 158) | RIYYRSKWYNDYAVSVKS |
| | HCDR3 (Kabat) (SEQ ID NO: 159) | ERSYRDYFDY |
| | vH full sequence (SEQ ID NO: 160) | QVQLQQSGPGLVKPSQTLSLTCAISGDSVSSNSAAWNWIRQSP<br>SRGLEWLGRIYYRSKWYNDYAVSVKSRITINPDTSKNQFSLQL<br>NSVTPEDTAVYYCARERSYRDYFDYWGQGTLVTVSS |
| | vL full sequence (SEQ ID NO: 161) | DIQMTQSPSSLSASVGDRVTITCRASQGIFTYLNWYQQKPGKA<br>PKLLISAASTLQSGVPSRFSGSGSGTDFTLTISSLQPEDFATYYC<br>QQYYSTSLTFGQGTKVEIK |
| | vH DNA sequence (SEQ ID NO: 162) | CAGGTGCAATTGCAGCAGAGCGGTCCGGGCCTGGTGAAACC<br>GAGCCAGACCCTGAGCCTGACCTGCGCGATTTCCGGAGATA<br>GCGTGAGCTCTAACTCTGCTGCTTGGAACTGGATTCGTCAGA<br>GCCCGAGCCGTGGCCTCGAGTGGCTGGGCCGTATCTACTAC<br>CGTAGCAAATGGTACAACGACTATGCCGTGAGCGTGAAAAG<br>CCGCATTACCATTAACCCGGATACTTCGAAAAACCAGTTTA<br>GCCTGCAACTGAACAGCGTGACCCCGGAAGATACGGCCGTG<br>TATTATTGCGCGCGTGAACGTTCTTACCGTGACTACTTCGAT<br>TACTGGGGCCAAGGCACCCTGGTGACTGTTAGCTCA |
| | vL DNA sequence (SEQ ID NO: 163) | GATATCCAGATGACCCAGAGCCCGAGCAGCCTGAGCGCCAG<br>CGTGGGCGATCGCGTGACCATTACCTGCAGAGCCAGCCAGG<br>GTATTTTCACTTACCTGAACTGGTACCAGCAGAAACCGGGC<br>AAAGCGCCGAAACTATTAATCTCTGCTGCTTCTACTCTGCAA<br>AGCGGCGTGCCGAGCCGCTTTAGCGGCAGCGGATCCGGCAC<br>CGATTTCACCCTGACCATTAGCTCTCTGCAACCGGAAGACTT<br>TGCGACCTATTATTGCCAGCAGTACTACTCTACTTCTCTGAC<br>CTTTGGCCAGGGCACGAAAGTTGAAATTAAA |
| | HC full sequence (SEQ ID NO: 164) | QVQLQQSGPGLVKPSQTLSLTCAISGDSVSSNSAAWNWIRQSP<br>SRGLEWLGRIYYRSKWYNDYAVSVKSRITINPDTSKNQFSLQL<br>NSVTPEDTAVYYCARERSYRDYFDYWGQGTLVTVSSASTKGP<br>SVFPLAPSSKSTSGGTAALGCLVKDYFPEPVTVSWNSGALTSG<br>VHTFPAVLQSSGLYSLSSVVTVPSSSLGTQTYICNVNHKPSNTK<br>VDKRVEPKSCDKTHTCPPCPAPELLGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALPAPIEKTISK<br>AKGQPREPQVYTLPPSREEMTKNQVSLTCLVKGFYPSDIAVEW<br>ESNGQPENNYKTTPPVLDSDGSFFLYSKLTVDKSRWQQGNVFS<br>CSVMHEALHNHYTQKSLSLSPGK |
| | LC full sequence (SEQ ID NO: 165) | DIQMTQSPSSLSASVGDRVTITCRASQGIFTYLNWYQQKPGKA<br>PKLLISAASTLQSGVPSRFSGSGSGTDFTLTISSLQPEDFATYYC<br>QQYYSTSLTFGQGTKVEIKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGEC |
| | HC DNA sequence (SEQ ID NO: 166) | CAGGTGCAATTGCAGCAGAGCGGTCCGGGCCTGGTGAAACC<br>GAGCCAGACCCTGAGCCTGACCTGCGCGATTTCCGGAGATA<br>GCGTGAGCTCTAACTCTGCTGCTTGGAACTGGATTCGTCAGA<br>GCCCGAGCCGTGGCCTCGAGTGGCTGGGCCGTATCTACTAC<br>CGTAGCAAATGGTACAACGACTATGCCGTGAGCGTGAAAAG<br>CCGCATTACCATTAACCCGGATACTTCGAAAAACCAGTTTA<br>GCCTGCAACTGAACAGCGTGACCCCGGAAGATACGGCCGTG<br>TATTATTGCGCGCGTGAACGTTCTTACCGTGACTACTTCGAT<br>TACTGGGGCCAAGGCACCCTGGTGACTGTTAGCTCAGCCTC |

TABLE 5-continued

Sequence information of the IgGs selected for in-depth characterization.

| NOV ID | Category | Value |
|---|---|---|
| | | CACCAAGGGTCCATCGGTCTTCCCCCTGGCACCCTCCTCCAA<br>GAGCACCTCTGGGGGCACAGCGGCCCTGGGCTGCCTGGTCA<br>AGGACTACTTCCCCGAACCGGTGACGGTGTCGTGGAACTCA<br>GGCGCCCTGACCAGCGGCGTGCACACCTTCCCGGCTGTCCT<br>ACAGTCCTCAGGACTCTACTCCCTCAGCAGCGTGGTGACCG<br>TGCCCTCCAGCAGCTTGGGCACCCAGACCTACATCTGCAAC<br>GTGAATCACAAGCCCAGCAACACCAAGGTGGACAAGAGAG<br>TTGAGCCCAAATCTTGTGACAAAACTCACACATGCCCACCG<br>TGCCCAGCACCTGAACTCCTGGGGGGACCGTCAGTCTTCCTC<br>TTCCCCCCAAAACCCAAGGACACCCTCATGATCTCCCGGAC<br>CCCTGAGGTCACATGCGTGGTGGTGGACGTGAGCCACGAAG<br>ACCCTGAGGTCAAGTTCAACTGGTACGTGGACGGCGTGGAG<br>GTGCATAATGCCAAGACAAAGCCGCGGGAGGAGCAGTACA<br>ACAGCACGTACCGGGTGGTCAGCGTCCTCACCGTCCTGCAC<br>CAGGACTGGCTGAATGGCAAGGAGTACAAGTGCAAGGTCTC<br>CAACAAAGCCCTCCCAGCCCCCATCGAGAAAACCATCTCCA<br>AAGCCAAAGGGCAGCCCCGAGAACCACAGGTGTACACCCT<br>GCCCCCATCCCGGGAGGAGATGACCAAGAACCAGGTCAGCC<br>TGACCTGCCTGGTCAAAGGCTTCTATCCCAGCGACATCGCC<br>GTGGAGTGGGAGAGCAATGGGCAGCCGGAGAACAACTACA<br>AGACCACGCCTCCCGTGCTGGACTCCGACGGCTCCTTCTTCC<br>TCTACAGCAAGCTCACCGTGGACAAGAGCAGGTGGCAGCAG<br>GGGAACGTCTTCTCATGCTCCGTGATGCATGAGGCTCTGCAC<br>AACCACTACACGCAGAAGAGCCTCTCCCTGTCTCCGGGTAA<br>A |
| | LC DNA sequence (SEQ ID NO: 167) | GATATCCAGATGACCCAGAGCCCGAGCAGCCTGAGCGCCAG<br>CGTGGGCGATCGCGTGACCATTACCTGCAGAGCCAGCCAGG<br>GTATTTTCACTTACCTGAACTGGTACCAGCAGAAACCGGGC<br>AAAGCGCCGAAACTATTAATCTCTGCTGCTTCTACTCTGCAA<br>AGCGGCGTGCCGAGCCGCTTTAGCGGCAGCGGATCCGGCAC<br>CGATTTCACCCTGACCATTAGCTCTCTGCAACCGGAAGACTT<br>TGCGACCTATTATTGCCAGCAGTACTACTCTACTTCTCTGAC<br>CTTTGGCCAGGGCACGAAAGTTGAAATTAAACGTACGGTGG<br>CCGCTCCCAGCGTGTTCATCTTCCCCCCCAGCGACGAGCAGC<br>TGAAGAGCGGCACCGCCAGCGTGGTGTGCCTGCTGAACAAC<br>TTCTACCCCCGGGAGGCCAAGGTGCAGTGGAAGGTGGACAA<br>CGCCCTGCAGAGCGGCAACAGCCAGGAAAGCGTCACCGAG<br>CAGGACAGCAAGGACTCCACCTACAGCCTGAGCAGCACCCT<br>GACCCTGAGCAAGGCCGACTACGAGAAGCACAAGGTGTAC<br>GCCTGCGAGGTGACCCACCAGGGCCTGTCCAGCCCCGTGAC<br>CAAGAGCTTCAACCGGGGCGAGTGT |
| NOV0699 | LCDR1 (Kabat) (SEQ ID NO: 168) | SGDNIRKYVVH |
| | LCDR2 (Kabat) (SEQ ID NO: 169) | RDNNRPS |
| | LCDR3 (Kabat) (SEQ ID NO: 170) | QSWDSFLAVV |
| | HCDR1 (Kabat) (SEQ ID NO: 171) | SYAMH |
| | HCDR2 (Kabat) (SEQ ID NO: 172) | FISSLGSYTYYADSVKG |
| | HCDR3 (Kabat) (SEQ ID NO: 173) | ETAGYGYAFDP |
| | vH full sequence (SEQ ID NO: 174) | QVQLLESGGGLVQPGGSLRLSCAASGFTFSSYAMHWVRQAPG<br>KGLEWVSFISSLGSYTYYADSVKGRFTISRDNSKNTLYLQMNS<br>LRAEDTAVYYCARETAGYGYAFDPWGQGTLVTVSS |
| | vL full sequence (SEQ ID NO: 175) | DIELTQPPSVSVSPGQTASITCSGDNIRKYVVHWYQQKPGQAP<br>VLVIYRDNNRPSGIPERFSGSNSGNTATLTISGTQAEDEADYYC<br>QSWDSFLAVVFGGGTKLTVL |

TABLE 5-continued

Sequence information of the IgGs selected for in-depth characterization.

| NOV ID | Category | Value |
|---|---|---|
| | vH DNA sequence (SEQ ID NO: 176) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTTCTTACGCTATGCATTGGGTGCGCCAGGCCCCGG GCAAAGGTCTCGAGTGGGTTTCCTTCATCTCTTCTCTGGGTT CTTACACCTACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTGAAACTGCTGGTTACGGTTACGCTTTCGATCCGTGGG GCCAAGGCACCCTGGTGACTGTTAGCTCA |
| | vL DNA sequence (SEQ ID NO: 177) | GATATCGAACTGACCCAGCCGCCGAGCGTGAGCGTGAGCCC GGGCCAGACCGCGAGCATTACCTGTAGCGGCGATAACATCC GTAAATACGTTGTTCATTGGTACCAGCAGAAACCGGGCCAG GCGCCGGTGCTGGTGATCTACCGTGACAACAACCGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTTGGGACTCTTTCCTGGCTGTT GTGTTTGGCGGCGGCACGAAGTTAACCGTCCTA |
| | HC full sequence (SEQ ID NO: 178) | QVQLLESGGGLVQPGGSLRLSCAASGFTFSSYAMHWVRQAPG KGLEWVSFISSLGSYTYYADSVKGRFTISRDNSKNTLYLQMNS LRAEDTAVYYCARETAGYGYAFDPWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRVEPKSCDKTHTCPPCPAPELLGGPSVFLFPPKPKDTLMISR TPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| | LC full sequence (SEQ ID NO: 179) | DIELTQPPSVSVSPGQTASITCSGDNIRKYVVHWYQQKPGQAP VLVIYRDNNRPSGIPERFSGSNSGNTATLTISGTQAEDEADYYC QSWDSFLAVVFGGGTKLTVLGQPKAAPSVTLFPPSSEELQANK ATLVCLISDFYPGAVTVAWKADSSPVKAGVETTTPSKQSNNKY AASSYLSLTPEQWKSHRSYSCQVTHEGSTVEKTVAPTECS |
| | HC DNA sequence (SEQ ID NO: 180) | CAGGTGCAATTGCTGGAAAGCGGCGGTGGCCTGGTGCAGCC GGGTGGCAGCCTGCGTCTGAGCTGCGCGGCGTCCGGATTCA CCTTTTCTTCTTACGCTATGCATTGGGTGCGCCAGGCCCCGG GCAAAGGTCTCGAGTGGGTTTCCTTCATCTCTTCTCTGGGTT CTTACACCTACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTGAAACTGCTGGTTACGGTTACGCTTTCGATCCGTGGG GCCAAGGCACCCTGGTGACTGTTAGCTCAGCCTCCACCAAG GGTCCATCGGTCTTCCCCCTGGCACCCTCCTCCAAGAGCACC TCTGGGGGCACAGCGGCCCTGGGCTGCCTGGTCAAGGACTA CTTCCCCGAACCGGTGACGGTGTCGTGGAACTCAGGCGCCC TGACCAGCGGCGTGCACACCTTCCCGGCTGTCCTACAGTCCT CAGGACTCTACTCCCTCAGCAGCGTGGTGACCGTGCCCTCC AGCAGCTTGGGCACCCAGACCTACATCTGCAACGTGAATCA CAAGCCCAGCAACACCAAGGTGGACAAGAGAGTTGAGCCC AAATCTTGTGACAAAACTCACACATGCCCACCGTGCCCAGC ACCTGAACTCCTGGGGGGACCGTCAGTCTTCCTCTTCCCCCC AAAACCCAAGGACACCCTCATGATCTCCCGGACCCCTGAGG TCACATGCGTGGTGGTGGACGTGAGCCACGAAGACCCTGAG GTCAAGTTCAACTGGTACGTGGACGGCGTGGAGGTGCATAA TGCCAAGACAAAGCCGCGGGAGGAGCAGTACAACAGCACG TACCGGGTGGTCAGCGTCCTCACCGTCCTGCACCAGGACTG GCTGAATGGCAAGGAGTACAAGTGCAAGGTCTCCAACAAA GCCCTCCCAGCCCCCATCGAGAAAACCATCTCCAAAGCCAA AGGGCAGCCCCGAGAACCACAGGTGTACACCCTGCCCCCAT CCCGGGAGGAGATGACCAAGAACCAGGTCAGCCTGACCTGC CTGGTCAAAGGCTTCTATCCCAGCGACATCGCCGTGGAGTG GGAGAGCAATGGGCAGCCGGAGAACAACTACAAGACCACG CCTCCCGTGCTGGACTCCGACGGCTCCTTCTTCCTCTACAGC AAGCTCACCGTGGACAAGAGCAGGTGGCAGCAGGGGAACG TCTTCTCATGCTCCGTGATGCATGAGGCTCTGCACAACCACT ACACGCAGAAGAGCCTCTCCCTGTCTCCGGGTAAA |
| | LC DNA sequence (SEQ ID NO: 181) | GATATCGAACTGACCCAGCCGCCGAGCGTGAGCGTGAGCCC GGGCCAGACCGCGAGCATTACCTGTAGCGGCGATAACATCC GTAAATACGTTGTTCATTGGTACCAGCAGAAACCGGGCCAG GCGCCGGTGCTGGTGATCTACCGTGACAACAACCGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTTGGGACTCTTTCCTGGCTGTT GTGTTTGGCGGCGGCACGAAGTTAACCGTCCTAGGTCAGCC CAAGGCTGCCCCCTCGGTCACTCTGTTCCCGCCCTCCTCTGA |

TABLE 5-continued

Sequence information of the IgGs selected for in-depth characterization.

| NOV ID | Category | Value |
|---|---|---|
| | | GGAGCTTCAAGCCAACAAGGCCACACTGGTGTGTCTCATAA GTGACTTCTACCCGGGAGCCGTGACAGTGGCCTGGAAGGCA GATAGCAGCCCCGTCAAGGCGGGAGTGGAGACCACCACAC CCTCCAAACAAAGCAACAACAAGTACGCGGCCAGCAGCTAT CTGAGCCTGACGCCTGAGCAGTGGAAGTCCCACAGAAGCTA CAGCTGCCAGGTCACGCATGAAGGGAGCACCGTGGAGAAG ACAGTGGCCCCTACAGAATGTTCA |
| NOV0705 | LCDR1 (Kabat) (SEQ ID NO: 182) | SGSSSNIGLDYVN |
| | LCDR2 (Kabat) (SEQ ID NO: 183) | RNKQRPS |
| | LCDR3 (Kabat) (SEQ ID NO: 184) | QAWAGRTNYVV |
| | HCDR1 (Kabat) (SEQ ID NO: 185) | NYWIG |
| | HCDR2 (Kabat) (SEQ ID NO: 186) | FIDPGVSYTRYSPSFQG |
| | HCDR3 (Kabat) (SEQ ID NO: 187) | VLAHSTEYNWPAF |
| | vH full sequence (SEQ ID NO: 188) | QVQLVQSGAEVKKPGESLKISCKGSGYSFTNYWIGWVRQMPG KGLEWMGFIDPGVSYTRYSPSFQGQVTISADKSISTAYLQWSSL KASDTAMYYCARVLAHSTEYNWPAFWGQGTLVTVSS |
| | vL full sequence (SEQ ID NO: 189) | DIVLTQPPSVSGAPGQRVTISCSGSSSNIGLDYVNWYQQLPGTA PKLLIYRNKQRPSGVPDRFSGSKSGTSASLAITGLQAEDEADYY CQAWAGRTNYVVFGGGTKLTVL |
| | vH DNA sequence (SEQ ID NO: 190) | CAGGTGCAATTGGTGCAGAGCGGTGCGGAAGTGAAAAAAC CGGGCGAAAGCCTGAAAATTAGCTGCAAAGGCTCCGGATAT AGCTTCACTAACTACTGGATCGGTTGGGTGCGCCAGATGCC GGGCAAAGGTCTCGAGTGGATGGGCTTCATCGACCCGGGTG TTAGCTACACCCGTTATAGCCCGAGCTTTCAGGGCCAGGTG ACCATTAGCGCGGATAAAAGCATCAGCACCGCGTATCTGCA ATGGAGCAGCCTGAAAGCGAGCGATACCGCGATGTATTATT GCGCGCGTGTTCTGGCTCATTCTACTGAATACAACTGGCCGG CTTTCTGGGGCCAAGGCACCCTGGTGACTGTTAGCTCA |
| | vL DNA sequence (SEQ ID NO: 191) | GATATCGTGCTGACCCAGCCGCCGAGCGTGAGCGGTGCACC GGGCCAGCGCGTGACCATTAGCTGTAGCGGCAGCAGCAGCA ACATTGGTCTGGACTACGTGAACTGGTACCAGCAGCTGCCG GGCACGGCGCCGAAACTGCTGATCTACCGTAACAAACAGCG CCCGAGCGGCGTGCCGGATCGCTTTAGCGGATCCAAAAGCG GCACCAGCGCCAGCCTGGCGATTACCGGCCTGCAAGCAGAA GACGAAGCGGATTATTACTGCCAGGCTTGGGCTGGTCGTAC TAACTACGTTGTGTTTGGCGGCGGCACGAAGTTAACCGTCCT A |
| | HC full sequence (SEQ ID NO: 192) | QVQLVQSGAEVKKPGESLKISCKGSGYSFTNYWIGWVRQMPG KGLEWMGFIDPGVSYTRYSPSFQGQVTISADKSISTAYLQWSSL KASDTAMYYCARVLAHSTEYNWPAFWGQGTLVTVSSASTKG PSVFPLAPSSKSTSGGTAALGCLVKDYFPEPVTVSWNSGALTSG VHTFPAVLQSSGLYSLSSVVTVPSSSLGTQTYICNVNHKPSNTK VDKRVEPKSCDKTHTCPPCPAPELLGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| | LC full sequence (SEQ ID NO: 193) | DIVLTQPPSVSGAPGQRVTISCSGSSSNIGLDYVNWYQQLPGTA PKLLIYRNKQRPSGVPDRFSGSKSGTSASLAITGLQAEDEADYY CQAWAGRTNYVVFGGGTKLTVLGQPKAAPSVTLFPPSSEELQ ANKATLVCLISDFYPGAVTVAWKADSSPVKAGVETTTPSKQSN NKYAASSYLSLTPEQWKSHRSYSCQVTHEGSTVEKTVAPTECS |

TABLE 5-continued

Sequence information of the IgGs selected for in-depth characterization.

| NOV ID | Category | Value |
|---|---|---|
| | HC DNA sequence (SEQ ID NO: 194) | CAGGTGCAATTGGTGCAGAGCGGTGCGGAAGTGAAAAAAC CGGGCGAAAGCCTGAAAATTAGCTGCAAAGGCTCCGGATAT AGCTTCACTAACTACTGGATCGGTTGGGTGCGCCAGATGCC GGGCAAAGGTCTCGAGTGGATGGGCTTCATCGACCCGGGTG TTAGCTACACCCGTTATAGCCCGAGCTTTCAGGGCCAGGTG ACCATTAGCGCGGATAAAAGCATCAGCACCGCGTATCTGCA ATGGAGCAGCCTGAAAGCGAGCGATACCGCGATGTATTATT GCGCGCGTGTTCTGGCTCATTCTACTGAATACAACTGGCCGG CTTTCTGGGGCCAAGGCACCCTGGTGACTGTTAGCTCAGCCT CCACCAAGGGTCCATCGGTCTTCCCCCTGGCACCCTCCTCCA AGAGCACCTCTGGGGGCACAGCGGCCCTGGGCTGCCTGGTC AAGGACTACTTCCCCGAACCGGTGACGGTGTCGTGGAACTC AGGCGCCCTGACCAGCGGCGTGCACACCTTCCCGGCTGTCC TACAGTCCTCAGGACTCTACTCCCTCAGCAGCGTGGTGACC GTGCCCTCCAGCAGCTTGGGCACCCAGACCTACATCTGCAA CGTGAATCACAAGCCCAGCAACACCAAGGTGGACAAGAGA GTTGAGCCCAAATCTTGTGACAAAACTCACACATGCCCACC GTGCCCAGCACCTGAACTCCTGGGGGGACCGTCAGTCTTCC TCTTCCCCCCAAAACCCAAGGACACCCTCATGATCTCCCGG ACCCCTGAGGTCACATGCGTGGTGGTGGACGTGAGCCACGA AGACCCTGAGGTCAAGTTCAACTGGTACGTGGACGGCGTGG AGGTGCATAATGCCAAGACAAAGCCGCGGGAGGAGCAGTA CAACAGCACGTACCGGGTGGTCAGCGTCCTCACCGTCCTGC ACCAGGACTGGCTGAATGGCAAGGAGTACAAGTGCAAGGT CTCCAACAAAGCCCTCCCAGCCCCCATCGAGAAAACCATCT CCAAAGCCAAAGGGCAGCCCCGAGAACCACAGGTGTACAC CCTGCCCCCATCCCGGGAGGAGATGACCAAGAACCAGGTCA GCCTGACCTGCCTGGTCAAAGGCTTCTATCCCAGCGACATC GCCGTGGAGTGGGAGAGCAATGGGCAGCCGGAGAACAACT ACAAGACCACGCCTCCCGTGCTGGACTCCGACGGCTCCTTCT TCCTCTACAGCAAGCTCACCGTGGACAAGAGCAGGTGGCAG CAGGGGAACGTCTTCTCATGCTCCGTGATGCATGAGGCTCT GCACAACCACTACACGCAGAAGAGCCTCTCCCTGTCTCCGG GTAAA |
| | LC DNA sequence (SEQ ID NO: 195) | GATATCGTGCTGACCCAGCCGCCGAGCGTGAGCGGTGCACC GGGCCAGCGCGTGACCATTAGCTGTAGCGGCAGCAGCAGCA ACATTGGTCTGGACTACGTGAACTGGTACCAGCAGCTGCCG GGCACGGCGCCGAAACTGCTGATCTACCGTAACAAACAGCG CCCGAGCGGCGTGCCGGATCGCTTTAGCGGATCCAAAAGCG GCACCAGCGCCAGCCTGGCGATTACCGGCCTGCAAGCAGAA GACGAAGCGGATTATTACTGCCAGGCTTGGGCTGGTCGTAC TAACTACGTTGTGTTTGGCGGCGGCACGAAGTTAACCGTCCT AGGTCAGCCCAAGGCTGCCCCCTCGGTCACTCTGTTCCCGCC CTCCTCTGAGGAGCTTCAAGCCAACAAGGCCACACTGGTGT GTCTCATAAGTGACTTCTACCCGGGAGCCGTGACAGTGGCC TGGAAGGCAGATAGCAGCCCCGTCAAGGCGGGAGTGGAGA CCACCACACCCTCCAAACAAAGCAACAACAAGTACGCGGCC AGCAGCTATCTGAGCCTGACGCCTGAGCAGTGGAAGTCCCA CAGAAGCTACAGCTGCCAGGTCACGCATGAAGGGAGCACC GTGGAGAAGACAGTGGCCCCTACAGAATGTTCA |
| NOV0709 | LCDR1 (Kabat) (SEQ ID NO: 196) | TGTSSDVGSYNYVS |
| | LCDR2 (Kabat) (SEQ ID NO: 197) | YVSNRPS |
| | LCDR3 (Kabat) (SEQ ID NO: 198) | ASYTHQGSWV |
| | HCDR1 (Kabat) (SEQ ID NO: 199) | TYYMH |
| | HCDR2 (Kabat) (SEQ ID NO: 200) | VISSDGSFTFYADSVKG |
| | HCDR3 (Kabat) (SEQ ID NO: 201) | HGYGAFDY |

TABLE 5-continued

Sequence information of the IgGs selected for in-depth characterization.

| NOV ID | Category | Value |
|---|---|---|
| | vH full sequence (SEQ ID NO: 202) | QVQLLESGGGLVQPGGSLRLSCAASGFTFSTYYMHWVRQAPGKGLEWVSVISSDGSFTFYADSVKGRFTISRDNSKNTLYLQMNSLRAEDTAVYYCARHGYGAFDYWGQGTLVTVSS |
| | vL full sequence (SEQ ID NO: 203) | DIALTQPASVSGSPGQSITISCTGTSSDVGSYNYVSWYQQHPGKAPKLMIYYVSNRPSGVSNRFSGSKSGNTASLTISGLQAEDEADYYCASYTHQGSWVFGGGTKLTVL |
| | vH DNA sequence (SEQ ID NO: 204) | CAGGTGCAATTGCTGGAAAGCGGCGGTGGCCTGGTGCAGCCGGGTGGCAGCCTGCGTCTGAGCTGCGCGGCGTCCGGATTCACCTTTTCTACTTACTACATGCATTGGGTGCGCCAGGCCCCGGGCAAAGGTCTCGAGTGGGTTTCCGTTATCTCTTCTGACGGTTCTTTCACCTTCTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTCATGGTTACGGTGCTTTCGATTACTGGGGCCAAGGCACCCTGGTGACTGTTAGCTCA |
| | vL DNA sequence (SEQ ID NO: 205) | GATATCGCGCTGACCCAGCCGGCGAGCGTGAGCGGTAGCCCGGGCCAGAGCATTACCATTAGCTGCACCGGCACCAGCAGCGATGTGGGCTCTTACAACTACGTGTCTTGGTACCAGCAGCATCCGGGCAAGGCGCCGAAACTGATGATCTACTACGTTTCTAACCGTCCGAGCGGCGTGAGCAACCGTTTTAGCGGATCCAAAAGCGGCAACACCGCGAGCCTGACCATTAGCGGCCTGCAAGCGGAAGACGAAGCGGATTATTACTGCGCTTCTTACACTCATCAGGGTTCTTGGGTGTTTGGCGGCGGCACGAAGTTAACCGTCCTA |
| | HC full sequence (SEQ ID NO: 206) | QVQLLESGGGLVQPGGSLRLSCAASGFTFSTYYMHWVRQAPGKGLEWVSVISSDGSFTFYADSVKGRFTISRDNSKNTLYLQMNSLRAEDTAVYYCARHGYGAFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | LC full sequence (SEQ ID NO: 207) | DIALTQPASVSGSPGQSITISCTGTSSDVGSYNYVSWYQQHPGKAPKLMIYYVSNRPSGVSNRFSGSKSGNTASLTISGLQAEDEADYYCASYTHQGSWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| | HC DNA sequence (SEQ ID NO: 208) | CAGGTGCAATTGCTGGAAAGCGGCGGTGGCCTGGTGCAGCCGGGTGGCAGCCTGCGTCTGAGCTGCGCGGCGTCCGGATTCACCTTTTCTACTTACTACATGCATTGGGTGCGCCAGGCCCCGGGCAAAGGTCTCGAGTGGGTTTCCGTTATCTCTTCTGACGGTTCTTTCACCTTCTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTCATGGTTACGGTGCTTTCGATTACTGGGGCCAAGGCACCCTGGTGACTGTTAGCTCAGCCTCCACCAAGGGTCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGGGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA |

TABLE 5-continued

Sequence information of the IgGs selected for in-depth characterization.

| NOV ID | Category | Value |
|---|---|---|
| | LC DNA sequence (SEQ ID NO: 209) | GATATCGCGCTGACCCAGCCGGCGAGCGTGAGCGGTAGCCCGGGCCAGAGCATTACCATTAGCTGCACCGGCACCAGCAGCGATGTGGGCTCTTACAACTACGTGTCTTGGTACCAGCAGCATCCGGGCAAGGCGCCGAAACTGATGATCTACTACGTTTCTAACCGTCCGAGCGGCGTGAGCAACCGTTTTAGCGGATCCAAAAGCGGCAACACCGCGAGCCTGACCATTAGCGGCCTGCAAGCGGAAGACGAAGCGGATTATTACTGCGCTTCTTACACTCATCAGGGTTCTTGGGTGTTTGGCGGCGGCACGAAGTTAACCGTCCTAGGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTATCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCA |
| NOV0710 | LCDR 1 (Kabat) (SEQ ID NO: 210) | RASQSISLWLN |
| | LCDR2 (Kabat) (SEQ ID NO: 211) | AASTLQS |
| | LCDR3 (Kabat) (SEQ ID NO: 212) | QQYYTSPYT |
| | HCDR 1 (Kabat) (SEQ ID NO: 213) | SYAMS |
| | HCDR2 (Kabat) (SEQ ID NO: 214) | VIRSSGSSTYYADSVKG |
| | HCDR3 (Kabat) (SEQ ID NO: 215) | GGGYFDY |
| | vH full sequence (SEQ ID NO: 216) | QVQLLESGGGLVQPGGSLRLSCAASGFTFSSYAMSWVRQAPGKGLEWVSVIRSSGSSTYYADSVKGRFTISRDNSKNTLYLQMNSLRAEDTAVYYCARGGGYFDYWGQGTLVTVSS |
| | vL full sequence (SEQ ID NO: 217) | DIQMTQSPSSLSASVGDRVTITCRASQSISLWLNWYQQKPGKAPKLLIYAASTLQSGVPSRFSGSGSGTDFTLTISSLQPEDFATYYCQQYYTSPYTFGQGTKVEIK |
| | vH DNA sequence (SEQ ID NO: 218) | CAGGTGCAGCTGCTGGAATCAGGCGGCGGACTGGTGCAACCTGGCGGATCCCTGAGGCTGAGCTGCGCTGCTAGTGGCTTCACCTTCTCTAGCTACGCTATGAGCTGGGTCCGCCAGGCCCCTGGTAAAGGCCTCGAGTGGGTGTCAGTGATTAGATCTAGCGGCTCTAGCACCTACTACGCCGATAGCGTGAAGGGCCGGTTCACTATCTCTAGGGATAACTCTAAGAACACCCTGTACCTGCAGATGAACTCCCTGAGGGCCGAGGACACCGCCGTCTACTACTGCGCTAGAGGCGGAGGCTACTTCGACTACTGGGGTCAAGGCACCCTGGTCACCGTGTCTAGC |
| | vL DNA sequence (SEQ ID NO: 219) | GATATTCAGATGACTCAGTCACCTAGTAGCCTGAGCGCTAGTGTGGGCGATAGAGTGACTATCACCTGTAGAGCCTCTCAGTCTATTAGCCTGTGGCTGAACTGGTATCAGCAGAAGCCCGGTAAAGCCCCTAAGCTGCTGATCTACGCCGCCTCTACCCTGCAGTCAGGCGTGCCCTCTAGGTTTAGCGGTAGCGGTAGTGGCACCGACTTCACCCTGACTATCTCTAGCCTGCAGCCCGAGGACTTCGCTACCTACTACTGTCAGCAGTACTACACTAGCCCCTACACCTTCGGTCAGGGCACTAAGGTCGAGATTAAG |
| | HC full sequence (SEQ ID NO: 220) | QVQLLESGGGLVQPGGSLRLSCAASGFTFSSYAMSWVRQAPGKGLEWVSVIRSSGSSTYYADSVKGRFTISRDNSKNTLYLQMNSLRAEDTAVYYCARGGGYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNG |

TABLE 5-continued

Sequence information of the IgGs selected for in-depth characterization.

| NOV ID | Category | Value |
|---|---|---|
| | | QPENNYKTTPPVLDSDGSFFLYSKLTVDKSRWQQGNVFSCSV MHEALHNHYTQKSLSLSPGK |
| | LC full sequence (SEQ ID NO: 221) | DIQMTQSPSSLSASVGDRVTITCRASQSISLWLNWYQQKPGKA PKLLIYAASTLQSGVPSRFSGSGSGTDFTLTISSLQPEDFATYYC QQYYTSPYTFGQGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| | HC DNA sequence (SEQ ID NO: 222) | CAGGTGCAGCTGCTGGAATCAGGCGGCGGACTGGTGCAACC TGGCGGATCCCTGAGGCTGAGCTGCGCTGCTAGTGGCTTCA CCTTCTCTAGCTACGCTATGAGCTGGGTCCGCCAGGCCCCTG GTAAAGGCCTCGAGTGGGTGTCAGTGATTAGATCTAGCGGC TCTAGCACCTACTACGCCGATAGCGTGAAGGGCCGGTTCAC TATCTCTAGGGATAACTCTAAGAACACCCTGTACCTGCAGA TGAACTCCCTGAGGGCCGAGGACACCGCCGTCTACTACTGC GCTAGAGGCGGAGGCTACTTCGACTACTGGGGTCAAGGCAC CCTGGTCACCGTGTCTAGCGCTAGCACTAAGGGCCCAAGTG TGTTTCCCCTGGCCCCCAGCAGCAAGTCTACTTCCGGCGGAA CTGCTGCCCTGGGTTGCCTGGTGAAGGACTACTTCCCCGAGC CCGTGACAGTGTCCTGGAACTCTGGGGCTCTGACTTCCGGC GTGCACACCTTCCCCGCCGTGCTGCAGAGCAGCGGCCTGTA CAGCCTGAGCAGCGTGGTGACAGTGCCCTCCAGCTCTCTGG GAACCCAGACCTATATCTGCAACGTGAACCACAAGCCCAGC AACACCAAGGTGGACAAGAGAGTGGAGCCCAAGAGCTGCG ACAAGACCCACACCTGCCCCCCCTGCCCAGCTCCAGAACTG CTGGGAGGGCCTTCCGTGTTCCTGTTCCCCCCCAAGCCCAAG GACACCCTGATGATCAGCAGGACCCCCGAGGTGACCTGCGT GGTGGTGGACGTGTCCCACGAGGACCCAGAGGTGAAGTTCA ACTGGTACGTGGACGGCGTGGAGGTGCACAACGCCAAGACC AAGCCCAGAGAGGAGCAGTACAACAGCACCTACAGGGTGG TGTCCGTGCTGACCGTGCTGCACCAGGACTGGCTGAACGGC AAAGAATACAAGTGCAAAGTCTCCAACAAGGCCCTGCCAGC CCCAATCGAAAAGACAATCAGCAAGGCCAAGGGCCAGCCA CGGGAGCCCCAGGTGTACACCCTGCCCCCCAGCCGGGAGGA GATGACCAAGAACCAGGTGTCCCTGACCTGTCTGGTGAAGG GCTTCTACCCCAGCGATATCGCCGTGGAGTGGGAGAGCAAC GGCCAGCCCGAGAACAACTACAAGACCACCCCCCCAGTGCT GGACAGCGACGGCAGCTTCTTCCTGTACAGCAAGCTGACCG TGGACAAGTCCAGGTGGCAGCAGGGCAACGTGTTCAGCTGC AGCGTGATGCACGAGGCCCTGCACAACCACTACACCCAGAA GTCCCTGAGCCTGAGCCCCGGCAAG |
| | LC DNA sequence (SEQ ID NO: 223) | GATATTCAGATGACTCAGTCACCTAGTAGCCTGAGCGCTAG TGTGGGCGATAGAGTGACTATCACCTGTAGAGCCTCTCAGT CTATTAGCCTGTGGCTGAACTGGTATCAGCAGAAGCCCGGT AAAGCCCCTAAGCTGCTGATCTACGCCGCCTCTACCCTGCA GTCAGGCGTGCCCTCTAGGTTTAGCGGTAGCGGTAGTGGCA CCGACTTCACCCTGACTATCTCTAGCCTGCAGCCCGAGGACT TCGCTACCTACTACTGTCAGCAGTACTACACTAGCCCCTACA CCTTCGGTCAGGGCACTAAGGTCGAGATTAAGCGTACGGTG GCCGCTCCCAGCGTGTTCATCTTCCCCCCCAGCGACGAGCA GCTGAAGAGCGGCACCGCCAGCGTGGTGTGCCTGCTGAACA ACTTCTACCCCCGGGAGGCCAAGGTGCAGTGGAAGGTGGAC AACGCCCTGCAGAGCGGCAACAGCCAGGAGAGCGTCACCG AGCAGGACAGCAAGGACTCCACCTACAGCCTGAGCAGCACC CTGACCCTGAGCAAGGCCGACTACGAGAAGCATAAGGTGTA CGCCTGCGAGGTGACCCACCAGGGCCTGTCCAGCCCCGTGA CCAAGAGCTTCAACAGGGGCGAGTGC |
| NOV0712 | LCDR1 (Kabat) (SEQ ID NO: 224) | RASQSISSYLN |
| | LCDR2 (Kabat) (SEQ ID NO: 225) | AVSTLQS |
| | LCDR3 (Kabat) (SEQ ID NO: 226) | QQSGTFPPTT |
| | HCDR1 (Kabat) (SEQ ID NO: 227) | SHGMH |

TABLE 5-continued

Sequence information of the IgGs selected for in-depth characterization.

| NOV ID | Category | Value |
| --- | --- | --- |
| | HCDR2 (Kabat) (SEQ ID NO: 228) | VISGSGSNTGYADSVKG |
| | HCDR3 (Kabat) (SEQ ID NO: 229) | QWGSYAFDS |
| | vH full sequence (SEQ ID NO: 230) | QVQLLESGGGLVQPGGSLRLSCAASGFTFSSHGMHWVRQAPG KGLEWVSVISGSGSNTGYADSVKGRFTISRDNSKNTLYLQMNS LRAEDTAVYYCARQWGSYAFDSWGQGTLVTVSS |
| | vL full sequence (SEQ ID NO: 231) | DIQMTQSPSSLSASVGDRVTITCRASQSISSYLNWYQQKPGKAP KLLIYAVSTLQSGVPSRFSGSGSGTDFTLTISSLQPEDFATYYCQ QSGTFPPTTFGQGTKVEIK |
| | vH DNA sequence (SEQ ID NO: 232) | CAGGTGCAGCTGCTGGAATCAGGCGGCGGACTGGTGCAGCC TGGCGGATCCCTGAGGCTGAGCTGCGCTGCTAGTGGCTTCA CCTTTAGCTCTCACGGAATGCACTGGGTCCGCCAGGCCCCTG GTAAAGGCCTCGAGTGGGTGTCAGTGATTAGCGGTAGCGGC TCTAACACCGGCTACGCCGATAGCGTGAAGGGCCGGTTCAC TATCTCTAGGGATAACTCTAAGAACACCCTGTACCTGCAGA TGAACTCCCTGAGGGCCGAGGACACCGCCGTCTACTACTGC GCTAGACAGTGGGGCTCCTACGCCTTCGATAGCTGGGGTCA AGGCACCCTGGTCACCGTGTCTAGC |
| | vL DNA sequence (SEQ ID NO: 233) | GATATTCAGATGACTCAGTCACCTAGTAGCCTGAGCGCTAG TGTGGGCGATAGAGTGACTATCACCTGTAGAGCCTCTCAGT CTATCTCTAGCTACCTGAACTGGTATCAGCAGAAGCCCGGT AAAGCCCCTAAGCTGCTGATCTACGCCGTGTCTACCCTGCA GTCAGGCGTGCCCTCTAGGTTTAGCGGTAGCGGTAGTGGCA CCGACTTCACCCTGACTATTAGTAGCCTGCAGCCCGAGGAC TTCGCTACCTACTACTGTCAGCAGTCAGGCACCTTCCCCCCT ACTACCTTCGGTCAGGGCACTAAGGTCGAGATTAAG |
| | HC full sequence (SEQ ID NO: 234) | QVQLLESGGGLVQPGGSLRLSCAASGFTFSSHGMHWVRQAPG KGLEWVSVISGSGSNTGYADSVKGRFTISRDNSKNTLYLQMNS LRAEDTAVYYCARQWGSYAFDSWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK RVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPGK |
| | LC full sequence (SEQ ID NO: 235) | DIQMTQSPSSLSASVGDRVTITCRASQSISSYLNWYQQKPGKAP KLLIYAVSTLQSGVPSRFSGSGSGTDFTLTISSLQPEDFATYYCQ QSGTFPPTTFGQGTKVEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC |
| | HC DNA sequence (SEQ ID NO: 236) | CAGGTGCAGCTGCTGGAATCAGGCGGCGGACTGGTGCAGCC TGGCGGATCCCTGAGGCTGAGCTGCGCTGCTAGTGGCTTCA CCTTTAGCTCTCACGGAATGCACTGGGTCCGCCAGGCCCCTG GTAAAGGCCTCGAGTGGGTGTCAGTGATTAGCGGTAGCGGC TCTAACACCGGCTACGCCGATAGCGTGAAGGGCCGGTTCAC TATCTCTAGGGATAACTCTAAGAACACCCTGTACCTGCAGA TGAACTCCCTGAGGGCCGAGGACACCGCCGTCTACTACTGC GCTAGACAGTGGGGCTCCTACGCCTTCGATAGCTGGGGTCA AGGCACCCTGGTCACCGTGTCTAGCGCTAGCACTAAGGGCC CAAGTGTGTTTCCCCTGGCCCCCAGCAGCAAGTCTACTTCCG GCGGAACTGCTGCCCTGGGTTGCCTGGTGAAGGACTACTTC CCCGAGCCCGTGACAGTGTCCTGGAACTCTGGGGCTCTGAC TTCCGGCGTGCACACCTTCCCCGCCGTGCTGCAGAGCAGCG GCCTGTACAGCCTGAGCAGCGTGGTGACAGTGCCCTCCAGC TCTCTGGGAACCCAGACCTATATCTGCAACGTGAACCACAA GCCCAGCAACACCAAGGTGGACAAGAGAGTGGAGCCCAAG AGCTGCGACAAGACCCACACCTGCCCCCCCTGCCCAGCTCC AGAACTGCTGGGAGGGCCTTCCGTGTTCCTGTTCCCCCCCAA GCCCAAGGACACCCTGATGATCAGCAGGACCCCCGAGGTGA CCTGCGTGGTGGTGGACGTGTCCCACGAGGACCCAGAGGTG AAGTTCAACTGGTACGTGGACGGCGTGGAGGTGCACAACGC CAAGACCAAGCCCAGAGAGGAGCAGTACAACAGCACCTAC AGGGTGGTGTCCGTGCTGACCGTGCTGCACCAGGACTGGCT GAACGGCAAAGAATACAAGTGCAAAGTCTCCAACAAGGCC CTGCCAGCCCCAATCGAAAAGACAATCAGCAAGGCCAAGG GCCAGCCACGGGAGCCCCAGGTGTACACCCTGCCCCCCAGC |

TABLE 5-continued

| Sequence information of the IgGs selected for in-depth characterization. | | |
|---|---|---|
| NOV ID | Category | Value |
| | | CGGGAGGAGATGACCAAGAACCAGGTGTCCCTGACCTGTCT GGTGAAGGGCTTCTACCCCAGCGATATCGCCGTGGAGTGGG AGAGCAACGGCCAGCCCGAGAACAACTACAAGACCACCCC CCCAGTGCTGGACAGCGACGGCAGCTTCTTCCTGTACAGCA AGCTGACCGTGGACAAGTCCAGGTGGCAGCAGGGCAACGT GTTCAGCTGCAGCGTGATGCACGAGGCCCTGCACAACCACT ACACCCAGAAGTCCCTGAGCCTGAGCCCCGGCAAG |
| | LC DNA sequence (SEQ ID NO: 237) | GATATTCAGATGACTCAGTCACCTAGTAGCCTGAGCGCTAG TGTGGGCGATAGAGTGACTATCACCTGTAGAGCCTCTCAGT CTATCTCTAGCTACCTGAACTGGTATCAGCAGAAGCCCGGT AAAGCCCCTAAGCTGCTGATCTACGCCGTGTCTACCCTGCA GTCAGGCGTGCCCTCTAGGTTTAGCGGTAGCGGTAGTGGCA CCGACTTCACCCTGACTATTAGTAGCCTGCAGCCCGAGGAC TTCGCTACCTACTACTGTCAGCAGTCAGGCACCTTCCCCCCT ACTACCTTCGGTCAGGGCACTAAGGTCGAGATTAAGCGTAC GGTGGCCGCTCCCAGCGTGTTCATCTTCCCCCCCAGCGACGA GCAGCTGAAGAGCGGCACCGCCAGCGTGGTGTGCCTGCTGA ACAACTTCTACCCCCGGGAGGCCAAGGTGCAGTGGAAGGTG GACAACGCCCTGCAGAGCGGCAACAGCCAGGAGAGCGTCA CCGAGCAGGACAGCAAGGACTCCACCTACAGCCTGAGCAGC ACCCTGACCCTGAGCAAGGCCGACTACGAGAAGCATAAGGT GTACGCCTGCGAGGTGACCCACCAGGGCCTGTCCAGCCCCG TGACCAAGAGCTTCAACAGGGGCGAGTGC |
| NOV0713 | LCDR1 (Kabat) (SEQ ID NO: 238) | SGDNLRSYYVH |
| | LCDR2 (Kabat) (SEQ ID NO: 239) | GNNKRPS |
| | LCDR3 (Kabat) (SEQ ID NO: 240) | GVYTLSSVV |
| | HCDR1 (Kabat) (SEQ ID NO: 241) | SNSAAWN |
| | HCDR2 (Kabat) (SEQ ID NO: 242) | RIYYRSKWYNDYAVSVKS |
| | HCDR3 (Kabat) (SEQ ID NO: 243) | GLVGRYGQPYHFDV |
| | vH full sequence (SEQ ID NO: 244) | QVQLQQSGPGLVKPSQTLSLTCAISGDSVSSNSAAWNWIRQSP SRGLEWLGRIYYRSKWYNDYAVSVKSRITINPDTSKNQFSLQL NSVTPEDTAVYYCARGLVGRYGQPYHFDVWGQGTLVTVSS |
| | vL full sequence (SEQ ID NO: 245) | DIELTQPPSVSVSPGQTASITCSGDNLRSYYVHWYQQKPGQAP VLVIYGNNKRPSGIPERFSGSNSGNTATLTISGTQAEDEADYYC GVYTLSSVVFGGGTKLTVL |
| | vH DNA sequence (SEQ ID NO: 246) | CAGGTGCAATTGCAGCAGAGCGGTCCGGGCCTGGTGAAACC GAGCCAGACCCTGAGCCTGACCTGCGCGATTTCCGGAGATA GCGTGAGCTCTAACTCTGCTGCTTGGAACTGGATTCGTCAGA GCCCGAGCCGTGGCCTCGAGTGGCTGGGCCGTATCTACTAC CGTAGCAAATGGTACAACGACTATGCCGTGAGCGTGAAAAG CCGCATTACCATTAACCCGGATACTTCGAAAAACCAGTTTA GCCTGCAACTGAACAGCGTGACCCCGGAAGATACGGCCGTG TATTATTGCGCGCGTGGTCTGGTTGGTCGTTACGGTCAGCCG TACCATTTCGATGTTTGGGGCCAAGGCACCCTGGTGACTGTT AGCTCA |
| | vL DNA sequence (SEQ ID NO: 247) | GATATCGAACTGACCCAGCCGCCGAGCGTGAGCGTGAGCCC GGGCCAGACCGCGAGCATTACCTGTAGCGGCGATAACCTGC GTTCTTACTACGTTCATTGGTACCAGCAGAAACCGGGCCAG GCGCCGGTGCTGGTGATCTACGGTAACAACAAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCGGTGTTTACACTCTGTCTTCTGTTGTG TTTGGCGGCGGCACGAAGTTAACCGTCCTA |

TABLE 5-continued

Sequence information of the IgGs selected for in-depth characterization.

| NOV ID | Category | Value |
|---|---|---|
| | HC full sequence (SEQ ID NO: 248) | QVQLQQSGPGLVKPSQTLSLTCAISGDSVSSNSAAWNWIRQSP SRGLEWLGRIYYRSKWYNDYAVSVKSRITINPDTSKNQFSLQL NSVTPEDTAVYYCARGLVGRYGQPYHFDVWGQGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSDIA VEWESNGQPENNYKTTPPVLDSDGSFFLYSKLTVDKSRWQQG NVFSCSVMHEALHNHYTQKSLSLSPGK |
| | LC full sequence (SEQ ID NO: 249) | DIELTQPPSVSVSPGQTASITCSGDNLRSYYVHWYQQKPGQAP VLVIYGNNKRPSGIPERFSGSNSGNTATLTISGTQAEDEADYYC GVYTLSSVVFGGGTKLTVLGQPKAAPSVTLFPPSSEELQANKA TLVCLISDFYPGAVTVAWKADSSPVKAGVETTTPSKQSNNKYA ASSYLSLTPEQWKSHRSYSCQVTHEGSTVEKTVAPTECS |
| | HC DNA sequence (SEQ ID NO: 250) | CAGGTGCAATTGCAGCAGAGCGGTCCGGGCCTGGTGAAACC GAGCCAGACCCTGAGCCTGACCTGCGCGATTTCCGGAGATA GCGTGAGCTCTAACTCTGCTGCTTGGAACTGGATTCGTCAGA GCCCGAGCCGTGGCCTCGAGTGGCTGGGCCGTATCTACTAC CGTAGCAAATGGTACAACGACTATGCCGTGAGCGTGAAAAG CCGCATTACCATTAACCCGGATACTTCGAAAAACCAGTTTA GCCTGCAACTGAACAGCGTGACCCCGGAAGATACGGCCGTG TATTATTGCGCGCGTGGTCTGGTTGGTCGTTACGGTCAGCCG TACCATTTCGATGTTTGGGGCCAAGGCACCCTGGTGACTGTT AGCTCAGCCTCCACCAAGGGTCCATCGGTCTTCCCCCTGGCA CCCTCCTCCAAGAGCACCTCTGGGGGCACAGCGGCCCTGGG CTGCCTGGTCAAGGACTACTTCCCCGAACCGGTGACGGTGT CGTGGAACTCAGGCGCCCTGACCAGCGGCGTGCACACCTTC CCGGCTGTCCTACAGTCCTCAGGACTCTACTCCCTCAGCAGC GTGGTGACCGTGCCCTCCAGCAGCTTGGGCACCCAGACCTA CATCTGCAACGTGAATCACAAGCCCAGCAACACCAAGGTGG ACAAGAGAGTTGAGCCCAAATCTTGTGACAAAACTCACACA TGCCCACCGTGCCCAGCACCTGAACTCCTGGGGGGACCGTC AGTCTTCCTCTTCCCCCCAAAACCCAAGGACACCCTCATGAT CTCCCGGACCCCTGAGGTCACATGCGTGGTGGTGGACGTGA GCCACGAAGACCCTGAGGTCAAGTTCAACTGGTACGTGGAC GGCGTGGAGGTGCATAATGCCAAGACAAAGCCGCGGGAGG AGCAGTACAACAGCACGTACCGGGTGGTCAGCGTCCTCACC GTCCTGCACCAGGACTGGCTGAATGGCAAGGAGTACAAGTG CAAGGTCTCCAACAAAGCCCTCCCAGCCCCCATCGAGAAAA CCATCTCCAAAGCCAAAGGGCAGCCCCGAGAACCACAGGTG TACACCCTGCCCCCATCCCGGGAGGAGATGACCAAGAACCA GGTCAGCCTGACCTGCCTGGTCAAAGGCTTCTATCCCAGCG ACATCGCCGTGGAGTGGGAGAGCAATGGGCAGCCGGAGAA CAACTACAAGACCACGCCTCCCGTGCTGGACTCCGACGGCT CCTTCTTCCTCTACAGCAAGCTCACCGTGGACAAGAGCAGG TGGCAGCAGGGGAACGTCTTCTCATGCTCCGTGATGCATGA GGCTCTGCACAACCACTACACGCAGAAGAGCCTCTCCCTGT CTCCGGGTAAA |
| | LC DNA sequence (SEQ ID NO: 251) | GATATCGAACTGACCCAGCCGCCGAGCGTGAGCGTGAGCCC GGGCCAGACCGCGAGCATTACCTGTAGCGGCGATAACCTGC GTTCTTACTACGTTCATTGGTACCAGCAGAAACCGGGCCAG GCGCCGGTGCTGGTGATCTACGGTAACAACAAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCGGTGTTTACACTCTGTCTTCTGTTGTG TTTGGCGGCGGCACGAAGTTAACCGTCCTAGGTCAGCCCAA GGCTGCCCCCTCGGTCACTCTGTTCCCGCCCTCCTCTGAGGA GCTTCAAGCCAACAAGGCCACACTGGTGTGTCTCATAAGTG ACTTCTACCCGGGAGCCGTGACAGTGGCCTGGAAGGCAGAT AGCAGCCCCGTCAAGGCGGGAGTGGAGACCACCACACCCTC CAAACAAAGCAACAACAAGTACGCGGCCAGCAGCTATCTG AGCCTGACGCCTGAGCAGTGGAAGTCCCACAGAAGCTACAG CTGCCAGGTCACGCATGAAGGGAGCACCGTGGAGAAGACA GTGGCCCCTACAGAATGTTCA |
| NOV0718 | LCDR1 (Kabat) (SEQ ID NO: 252) | SGDKIPTYTVH |
| | LCDR2 (Kabat) (SEQ ID NO: 253) | DDNKRPS |

TABLE 5-continued

Sequence information of the IgGs selected for in-depth characterization.

| NOV ID | Category | Value |
|---|---|---|
| | LCDR3 (Kabat) (SEQ ID NO: 254) | QSTASGTVV |
| | HCDR1 (Kabat) (SEQ ID NO: 255) | SYALH |
| | HCDR2 (Kabat) (SEQ ID NO: 256) | RIKSKTNGGTTDYAAPVKG |
| | HCDR3 (Kabat) (SEQ ID NO: 257) | VDATYSYSGYYYPMDY |
| | vH full sequence (SEQ ID NO: 258) | QVQLVESGGGLVKPGGSLRLSCAASGFTFNSYALHWVRQAPG KGLEWVGRIKSKTNGGTTDYAAPVKGRFTISRDDSKNTLYLQ MNSLKTEDTAVYYCARVDATYSYSGYYYPMDYWGQGTLVT VSS |
| | vL full sequence SEQ ID NO: 259) | DIELTQPPSVSVSPGQTASITCSGDKIPTYTVHWYQQKPGQAPV LVIYDDNKRPSGIPERFSGSNSGNTATLTISGTQAEDEADYYCQ STASGTVVFGGGTKLTVL |
| | vH DNA sequence (SEQ ID NO: 260) | CAGGTGCAATTGGTGGAAAGCGGCGGTGGCCTGGTGAAACC AGGCGGCAGCCTGCGCCTGAGCTGCGCCGCCTCCGGATTCA CCTTTAACTCTTACGCTCTGCATTGGGTGCGCCAGGCCCCGG GCAAAGGTCTCGAGTGGGTGGGCCGTATCAAATCTAAAACT AACGGTGGTACTACTGACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTGTTGACGCTACTTACTCTTACTCTGGTTACT ACTACCCGATGGATTACTGGGGCCAAGGCACCCTGGTGACT GTTAGCTCA |
| | vL DNA sequence (SEQ ID NO: 261) | GATATCGAACTGACCCAGCCGCCGAGCGTGAGCGTGAGCCC GGGCCAGACCGCGAGCATTACCTGTAGCGGCGATAAAATCC CGACTTACACTGTTCATTGGTACCAGCAGAAACCGGGCCAG GCGCCGGTGCTGGTGATCTACGACGACAACAAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTACTGCTTCTGGTACTGTTGTG TTTGGCGGCGGCACGAAGTTAACCGTCCTA |
| | HC full sequence (SEQ ID NO: 262) | QVQLVESGGGLVKPGGSLRLSCAASGFTFNSYALHWVRQAPG KGLEWVGRIKSKTNGGTTDYAAPVKGRFTISRDDSKNTLYLQ MNSLKTEDTAVYYCARVDATYSYSGYYYPMDYWGQGTLVT VSSASTKGPSVFPLAPSSKSTSGGTAALGCLVKDYFPEPVTVSW NSGALTSGVHTFPAVLQSSGLYSLSSVVTVPSSSLGTQTYICNV NHKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSRW QQGNVFSCSVMHEALHNHYTQKSLSLSPGK |
| | LC full sequence (SEQ ID NO: 263) | DIELTQPPSVSVSPGQTASITCSGDKIPTYTVHWYQQKPGQAPV LVIYDDNKRPSGIPERFSGSNSGNTATLTISGTQAEDEADYYCQ STASGTVVFGGGTKLTVLGQPKAAPSVTLFPPSSEELQANKAT LVCLISDFYPGAVTVAWKADSSPVKAGVETTTPSKQSNNKYA ASSYLSLTPEQWKSHRSYSCQVTHEGSTVEKTVAPTECS |
| | HC DNA sequence (SEQ ID NO: 264) | CAGGTGCAATTGGTGGAAAGCGGCGGTGGCCTGGTGAAACC AGGCGGCAGCCTGCGCCTGAGCTGCGCCGCCTCCGGATTCA CCTTTAACTCTTACGCTCTGCATTGGGTGCGCCAGGCCCCGG GCAAAGGTCTCGAGTGGGTGGGCCGTATCAAATCTAAAACT AACGGTGGTACTACTGACTATGCCGCCCCAGTGAAAGGCCG CTTTACCATTAGCCGCGATGATTCGAAAAACACCCTGTATCT GCAAATGAACAGCCTGAAAACCGAAGATACGGCCGTGTATT ATTGCGCGCGTGTTGACGCTACTTACTCTTACTCTGGTTACT ACTACCCGATGGATTACTGGGGCCAAGGCACCCTGGTGACT GTTAGCTCAGCCTCCACCAAGGGTCCATCGGTCTTCCCCCTG GCACCCTCCTCCAAGAGCACCTCTGGGGGCACAGCGGCCCT GGGCTGCCTGGTCAAGGACTACTTCCCCGAACCGGTGACGG TGTCGTGGAACTCAGGCGCCCTGACCAGCGGCGTGCACACC TTCCCGGCTGTCCTACAGTCCTCAGGACTCTACTCCCTCAGC AGCGTGGTGACCGTGCCCTCCAGCAGCTTGGGCACCCAGAC CTACATCTGCAACGTGAATCACAAGCCCAGCAACACCAAGG TGGACAAGAGAGTTGAGCCCAAATCTTGTGACAAAACTCAC |

TABLE 5-continued

| Sequence information of the IgGs selected for in-depth characterization. | | |
|---|---|---|
| NOV ID | Category | Value |
| | | ACATGCCCACCGTGCCCAGCACCTGAACTCCTGGGGGGACC GTCAGTCTTCCTCTTCCCCCCAAAACCCAAGGACACCCTCAT GATCTCCCGGACCCCTGAGGTCACATGCGTGGTGGTGGACG TGAGCCACGAAGACCCTGAGGTCAAGTTCAACTGGTACGTG GACGGCGTGGAGGTGCATAATGCCAAGACAAAGCCGCGGG AGGAGCAGTACAACAGCACGTACCGGGTGGTCAGCGTCCTC ACCGTCCTGCACCAGGACTGGCTGAATGGCAAGGAGTACAA GTGCAAGGTCTCCAACAAAGCCCTCCCAGCCCCCATCGAGA AAACCATCTCCAAAGCCAAAGGGCAGCCCCGAGAACCACA GGTGTACACCCTGCCCCCATCCCGGGAGGAGATGACCAAGA ACCAGGTCAGCCTGACCTGCCTGGTCAAAGGCTTCTATCCC AGCGACATCGCCGTGGAGTGGGAGAGCAATGGGCAGCCGG AGAACAACTACAAGACCACGCCTCCCGTGCTGGACTCCGAC GGCTCCTTCTTCCTCTACAGCAAGCTCACCGTGGACAAGAG CAGGTGGCAGCAGGGGAACGTCTTCTCATGCTCCGTGATGC ATGAGGCTCTGCACAACCACTACACGCAGAAGAGCCTCTCC CTGTCTCCGGGTAAA |
| | LC DNA sequence (SEQ ID NO: 265) | GATATCGAACTGACCCAGCCGCCGAGCGTGAGCGTGAGCCC GGGCCAGACCGCGAGCATTACCTGTAGCGGCGATAAAATCC CGACTTACACTGTTCATTGGTACCAGCAGAAACCGGGCCAG GCGCCGGTGCTGGTGATCTACGACGACAACAAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTACTGCTTCTGGTACTGTTGTG TTTGGCGGCGGCACGAAGTTAACCGTCCTAGGTCAGCCCAA GGCTGCCCCCTCGGTCACTCTGTTCCCGCCCTCCTCTGAGGA GCTTCAAGCCAACAAGGCCACACTGGTGTGTCTCATAAGTG ACTTCTACCCGGGAGCCGTGACAGTGGCCTGGAAGGCAGAT AGCAGCCCCGTCAAGGCGGGAGTGGAGACCACCACACCCTC CAAACAAAGCAACAACAAGTACGCGGCCAGCAGCTATCTG AGCCTGACGCCTGAGCAGTGGAAGTCCCACAGAAGCTACAG CTGCCAGGTCACGCATGAAGGGAGCACCGTGGAGAAGACA GTGGCCCCTACAGAATGTTCA |
| NOV0719 | LCDR1 (Kabat) (SEQ ID NO: 266) | RASQSIVSYLN |
| | LCDR2 (Kabat) (SEQ ID NO: 267) | DASSLQS |
| | LCDR3 (Kabat) (SEQ ID NO: 268) | QQSGSHSIT |
| | HCDR1 (Kabat) (SEQ ID NO: 269) | SHWVH |
| | HCDR2 (Kabat) (SEQ ID NO: 270) | VISYMGSSTYYADSVKG |
| | HCDR3 (Kabat) (SEQ ID NO: 271) | GSYDMAFDV |
| | vH full sequence (SEQ ID NO: 272) | QVQLLESGGGLVQPGGSLRLSCAASGFTFSSHWVHWVRQAPG KGLEWVSVISYMGSSTYYADSVKGRFTISRDNSKNTLYLQMNS LRAEDTAVYYCARGSYDMAFDVWGQGTLVTVSS |
| | vL full sequence (SEQ ID NO: 273) | DIQMTQSPSSLSASVGDRVTITCRASQSIVSYLNWYQQKPGKAP KLLIYDASSLQSGVPSRFSGSGSGTDFTLTISSLQPEDFATYYCQ QSGSHSITFGQGTKVEIK |
| | vH DNA sequence (SEQ ID NO: 274) | CAGGTGCAGCTGCTGGAATCAGGCGGCGGACTGGTGCAGCC TGGCGGTAGCCTGAGACTGAGCTGCGCTGCTAGTGGCTTCA CCTTTAGCTCTCACTGGGTGCACTGGGTCAGACAGGCCCCTG GTAAAGGCCTGGAGTGGGTGTCAGTGATTAGCTATATGGGC TCTAGCACCTACTACGCCGATAGCGTGAAGGGCCGGTTCAC TATCTCTAGGGATAACTCTAAGAACACCCTGTACCTGCAGA TGAATAGCCTGAGAGCCGAGGACACCGCCGTCTACTACTGC GCTAGAGGCTCCTACGATATGGCCTTCGACGTGTGGGGTCA GGGCACCCTGGTCACCGTGTCTAGC |

TABLE 5-continued

| Sequence information of the IgGs selected for in-depth characterization. | | |
|---|---|---|
| NOV ID | Category | Value |
| | vL DNA sequence (SEQ ID NO: 275) | GATATTCAGATGACTCAGTCACCTAGTAGCCTGAGCGCTAGTGTGGGCGATAGAGTGACTATCACCTGTAGAGCCTCTCAGTCTATCGTCAGCTACCTGAACTGGTATCAGCAGAAGCCCGGTAAAGCCCCTAAGCTGCTGATCTACGACGCCTCTAGCCTGCAGTCAGGCGTGCCCTCTAGGTTTAGCGGTAGCGGTAGTGGCACCGACTTCACCCTGACTATTAGTAGCCTGCAGCCCGAGGACTTCGCTACCTACTACTGTCAGCAGTCAGGCTCTCACTCTATCACCTTCGGTCAGGGCACTAAGGTCGAGATTAAG |
| | HC full sequence (SEQ ID NO: 276) | QVQLLESGGGLVQPGGSLRLSCAASGFTFSSHWVHWVRQAPGKGLEWVSVISYMGSSTYYADSVKGRFTISRDNSKNTLYLQMNSLRAEDTAVYYCARGSYDMAFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | LC full sequence (SEQ ID NO: 277) | DIQMTQSPSSLSASVGDRVTITCRASQSIVSYLNWYQQKPGKAPKLLIYDASSLQSGVPSRFSGSGSGTDFTLTISSLQPEDFATYYCQQSGSHSITFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | HC DNA sequence (SEQ ID NO: 278) | CAGGTGCAGCTGCTGGAATCAGGCGGCGGACTGGTGCAGCCTGGCGGTAGCCTGAGACTGAGCTGCGCTGCTAGTGGCTTCACCTTTAGCTCTCACTGGGTGCACTGGGTCAGACAGGCCCCTGGTAAAGGCCTGGAGTGGGTGTCAGTGATTAGCTATATGGGCTCTAGCACCTACTACGCCGATAGCGTGAAGGGCCGGTTCACTATCTCTAGGGATAACTCTAAGAACACCCTGTACCTGCAGATGAATAGCCTGAGAGCCGAGGACACCGCCGTCTACTACTGCGCTAGAGGCTCCTACGATATGGCCTTCGACGTGTGGGGTCAGGGCACCCTGGTCACCGTGTCTAGCGCTAGCACTAAGGGCCCAAGTGTGTTTCCCCTGGCCCCCAGCAGCAAGTCTACTTCCGGCGGAACTGCTGCCCTGGGTTGCCTGGTGAAGGACTACTTCCCCGAGCCCGTGACAGTGTCCTGGAACTCTGGGGCTCTGACTTCCGGCGTGCACACCTTCCCCGCCGTGCTGCAGAGCAGCGGCCTGTACAGCCTGAGCAGCGTGGTGACAGTGCCCTCCAGCTCTCTGGGAACCCAGACCTATATCTGCAACGTGAACCACAAGCCCAGCAACACCAAGGTGGACAAGAGAGTGGAGCCCAAGAGCTGCGACAAGACCCACACCTGCCCCCCCTGCCCAGCTCCAGAACTGCTGGGAGGGCCTTCCGTGTTCCTGTTCCCCCCCAAGCCCAAGGACACCCTGATGATCAGCAGGACCCCCGAGGTGACCTGCGTGGTGGTGGACGTGTCCCACGAGGACCCAGAGGTGAAGTTCAACTGGTACGTGGACGGCGTGGAGGTGCACAACGCCAAGACCAAGCCCAGAGAGGAGCAGTACAACAGCACCTACAGGGTGGTGTCCGTGCTGACCGTGCTGCACCAGGACTGGCTGAACGGCAAAGAATACAAGTGCAAAGTCTCCAACAAGGCCCTGCCAGCCCCAATCGAAAAGACAATCAGCAAGGCCAAGGGCCAGCCACGGGAGCCCCAGGTGTACACCCTGCCCCCCAGCCGGGAGGAGATGACCAAGAACCAGGTGTCCCTGACCTGTCTGGTGAAGGGCTTCTACCCCAGCGATATCGCCGTGGAGTGGGAGAGCAACGGCCAGCCCGAGAACAACTACAAGACCACCCCCCCAGTGCTGGACAGCGACGGCAGCTTCTTCCTGTACAGCAAGCTGACCGTGGACAAGTCCAGGTGGCAGCAGGGCAACGTGTTCAGCTGCAGCGTGATGCACGAGGCCCTGCACAACCACTACACCCAGAAGTCCCTGAGCCTGAGCCCCGGCAAG |
| | LC DNA sequence (SEQ ID NO: 279) | GATATTCAGATGACTCAGTCACCTAGTAGCCTGAGCGCTAGTGTGGGCGATAGAGTGACTATCACCTGTAGAGCCTCTCAGTCTATCGTCAGCTACCTGAACTGGTATCAGCAGAAGCCCGGTAAAGCCCCTAAGCTGCTGATCTACGACGCCTCTAGCCTGCAGTCAGGCGTGCCCTCTAGGTTTAGCGGTAGCGGTAGTGGCACCGACTTCACCCTGACTATTAGTAGCCTGCAGCCCGAGGACTTCGCTACCTACTACTGTCAGCAGTCAGGCTCTCACTCTATCACCTTCGGTCAGGGCACTAAGGTCGAGATTAAGCGTACGGTGGCCGCTCCCAGCGTGTTCATCTTCCCCCCCAGCGACGAGCAGCTGAAGAGCGGCACCGCCAGCGTGGTGTGCCTGCTGAACAACTTCTACCCCCGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAGAAGCATAAGGTGTACGCCTGCGAGGTGACCCACCAGGGCCTGTCCAGCCCCGTGACCAAGAGCTTCAACAGGGGCGAGTGC |

TABLE 5-continued

Sequence information of the IgGs selected for in-depth characterization.

| NOV ID | Category | Value |
|---|---|---|
| NOV0720 | LCDR1 (Kabat) (SEQ ID NO: 280) | SGDNIGSMTAH |
| | LCDR2 (Kabat) (SEQ ID NO: 281) | DKNERPS |
| | LCDR3 (Kabat) (SEQ ID NO: 282) | QSWDDSYNSVV |
| | HCDR1 (Kabat) (SEQ ID NO: 283) | SNSAGWN |
| | HCDR2 (Kabat) (SEQ ID NO: 284) | RIYYRSKWYNDYAVSVKS |
| | HCDR3 (Kabat) (SEQ ID NO: 285) | EKYTVSFYDFFDY |
| | vH full sequence (SEQ ID NO: 286) | QVQLQQSGPGLVKPSQTLSLTCAISGDSVSSNSAGWNWIRQSP SRGLEWLGRIYYRSKWYNDYAVSVKSRITINPDTSKNQFSLQL NSVTPEDTAVYYCAREKYTVSFYDFFDYWGQGTLVTVSS |
| | vL full sequence (SEQ ID NO: 287) | DIELTQPPSVSVSPGQTASITCSGDNIGSMTAHWYQQKPGQAPV LVIYDKNERPSGIPERFSGSNSGNTATLTISGTQAEDEADYYCQ SWDDSYNSVVFGGGTKLTVL |
| | vH DNA sequence (SEQ ID NO:288) | CAGGTGCAATTGCAGCAGAGCGGTCCGGGCCTGGTGAAACC GAGCCAGACCCTGAGCCTGACCTGCGCGATTTCCGGAGATA GCGTGAGCTCTAACTCTGCTGGTTGGAACTGGATTCGTCAG AGCCCGAGCCGTGGCCTCGAGTGGCTGGGCCGTATCTACTA CCGTAGCAAATGGTACAACGACTATGCCGTGAGCGTGAAAA GCCGCATTACCATTAACCCGGATACTTCGAAAAACCAGTTT AGCCTGCAACTGAACAGCGTGACCCCGGAAGATACGGCCGT GTATTATTGCGCGCGTGAAAAATACACTGTTTCTTTCTACGA CTTCTTCGATTACTGGGGCCAAGGCACCCTGGTGACTGTTAG CTCA |
| | vL DNA sequence (SEQ ID NO: 289) | GATATCGAACTGACCCAGCCGCCGAGCGTGAGCGTGAGCCC GGGCCAGACCGCGAGCATTACCTGTAGCGGCGATAACATCG GTTCTATGACTGCTCATTGGTACCAGCAGAAACCGGGCCAG GCGCCGGTGCTGGTGATCTACGACAAAAACGAACGTCCGAG CGGCATCCCGGAACGTTTTAGCGGATCCAACAGCGGCAACA CCGCGACCCTGACCATTAGCGGCACCCAGGCGGAAGACGAA GCGGATTATTACTGCCAGTCTTGGGACGACTCTTACAACTCT GTTGTGTTTGGCGGCGGCACGAAGTTAACCGTCCTA |
| | HC full sequence (SEQ ID NO: 290) | QVQLQQSGPGLVKPSQTLSLTCAISGDSVSSNSAGWNWIRQSP SRGLEWLGRIYYRSKWYNDYAVSVKSRITINPDTSKNQFSLQL NSVTPEDTAVYYCAREKYTVSFYDFFDYWGQGTLVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKRVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIAV EWESNGQPENNYKTTPPVLDSDGSFFLYSKLTVDKSRWQQGN VFSCSVMHEALHNHYTQKSLSLSPGK |
| | LC full sequence (SEQ ID NO: 291) | DIELTQPPSVSVSPGQTASITCSGDNIGSMTAHWYQQKPGQAPV LVIYDKNERPSGIPERFSGSNSGNTATLTISGTQAEDEADYYCQ SWDDSYNSVVFGGGTKLTVLGQPKAAPSVTLFPPSSEELQANK ATLVCLISDFYPGAVTVAWKADSSPVKAGVETTTPSKQSNNKY AASSYLSLTPEQWKSHRSYSCQVTHEGSTVEKTVAPTECS |
| | HC DNA sequence (SEQ ID NO: 292) | CAGGTGCAATTGCAGCAGAGCGGTCCGGGCCTGGTGAAACC GAGCCAGACCCTGAGCCTGACCTGCGCGATTTCCGGAGATA GCGTGAGCTCTAACTCTGCTGGTTGGAACTGGATTCGTCAG AGCCCGAGCCGTGGCCTCGAGTGGCTGGGCCGTATCTACTA CCGTAGCAAATGGTACAACGACTATGCCGTGAGCGTGAAAA GCCGCATTACCATTAACCCGGATACTTCGAAAAACCAGTTT AGCCTGCAACTGAACAGCGTGACCCCGGAAGATACGGCCGT GTATTATTGCGCGCGTGAAAAATACACTGTTTCTTTCTACGA |

TABLE 5-continued

Sequence information of the IgGs selected for in-depth characterization.

| NOV ID | Category | Value |
|---|---|---|
| | | CTTCTTCGATTACTGGGGCCAAGGCACCCTGGTGACTGTTAG<br>CTCAGCCTCCACCAAGGGTCCATCGGTCTTCCCCCTGGCACC<br>CTCCTCCAAGAGCACCTCTGGGGGCACAGCGGCCCTGGGCT<br>GCCTGGTCAAGGACTACTTCCCCGAACCGGTGACGGTGTCG<br>TGGAACTCAGGCGCCCTGACCAGCGGCGTGCACACCTTCCC<br>GGCTGTCCTACAGTCCTCAGGACTCTACTCCCTCAGCAGCGT<br>GGTGACCGTGCCCTCCAGCAGCTTGGGCACCCAGACCTACA<br>TCTGCAACGTGAATCACAAGCCCAGCAACACCAAGGTGGAC<br>AAGAGAGTTGAGCCCAAATCTTGTGACAAAACTCACACATG<br>CCCACCGTGCCCAGCACCTGAACTCCTGGGGGGACCGTCAG<br>TCTTCCTCTTCCCCCCAAAACCCAAGGACACCCTCATGATCT<br>CCCGGACCCCTGAGGTCACATGCGTGGTGGTGGACGTGAGC<br>CACGAAGACCCTGAGGTCAAGTTCAACTGGTACGTGGACGG<br>CGTGGAGGTGCATAATGCCAAGACAAAGCCGCGGGAGGAG<br>CAGTACAACAGCACGTACCGGGTGGTCAGCGTCCTCACCGT<br>CCTGCACCAGGACTGGCTGAATGGCAAGGAGTACAAGTGCA<br>AGGTCTCCAACAAAGCCCTCCCAGCCCCCATCGAGAAAACC<br>ATCTCCAAAGCCAAAGGGCAGCCCCGAGAACCACAGGTGTA<br>CACCCTGCCCCCATCCCGGGAGGAGATGACCAAGAACCAGG<br>TCAGCCTGACCTGCCTGGTCAAAGGCTTCTATCCCAGCGAC<br>ATCGCCGTGGAGTGGGAGAGCAATGGGCAGCCGGAGAACA<br>ACTACAAGACCACGCCTCCCGTGCTGGACTCCGACGGCTCC<br>TTCTTCCTCTACAGCAAGCTCACCGTGGACAAGAGCAGGTG<br>GCAGCAGGGGAACGTCTTCTCATGCTCCGTGATGCATGAGG<br>CTCTGCACAACCACTACACGCAGAAGAGCCTCTCCCTGTCTC<br>CGGGTAAA |
| | LC DNA sequence (SEQ ID NO: 293) | GATATCGAACTGACCCAGCCGCCGAGCGTGAGCGTGAGCCC<br>GGGCCAGACCGCGAGCATTACCTGTAGCGGCGATAACATCG<br>GTTCTATGACTGCTCATTGGTACCAGCAGAAACCGGGCCAG<br>GCGCCGGTGCTGGTGATCTACGACAAAAACGAACGTCCGAG<br>CGGCATCCCGGAACGTTTTAGCGGATCCAACAGCGGCAACA<br>CCGCGACCCTGACCATTAGCGGCACCCAGGCGGAAGACGAA<br>GCGGATTATTACTGCCAGTCTTGGGACGACTCTTACAACTCT<br>GTTGTGTTTGGCGGCGGCACGAAGTTAACCGTCCTAGGTCA<br>GCCCAAGGCTGCCCCCTCGGTCACTCTGTTCCCGCCCTCCTC<br>TGAGGAGCTTCAAGCCAACAAGGCCACACTGGTGTGTCTCA<br>TAAGTGACTTCTACCCGGGAGCCGTGACAGTGGCCTGGAAG<br>GCAGATAGCAGCCCCGTCAAGGCGGGAGTGGAGACCACCA<br>CACCCTCCAAACAAAGCAACAACAAGTACGCGGCCAGCAG<br>CTATCTGAGCCTGACGCCTGAGCAGTGGAAGTCCCACAGAA<br>GCTACAGCTGCCAGGTCACGCATGAAGGGAGCACCGTGGAG<br>AAGACAGTGGCCCCTACAGAATGTTCA |

Example 2: Antibody Engineering by Site-Directed Mutagenesis

Site-directed mutagenesis for the removal of the potential sites for post-translational modifications and germlining was performed for a subset of anti-CDH6 antibodies using the QuikChange® Site-Directed Mutagenesis Kit (Agilent Technologies, Santa Clara, Calif.). NOV690 sequence was changed $D_{53}$5 and VL (34-germline) resulting in antibody NOV1126. NOV695 sequence was changed $N_{31}Q$ and $S_{49}Y$, resulting in antibody NOV1127. NOV0720 sequence was changed $N_{31}Q$, $N_{95}Q$ and VL (34-germline), resulting in antibody NOV1132. Sequence information for the engineered antibodies is described in Table 6.

TABLE 6

Sequence information of engineered antibodies

| | | |
|---|---|---|
| NOV1126 | LCDR1 (Kabat) (SEQ ID NO: 294) | SGDAIGTKFAH |
| | LCDR2 (Kabat) (SEQ ID NO: 295) | YDHERPS |
| | LCDR3 (Kabat) (SEQ ID NO: 296) | YSRASSNLV |
| | HCDR1 (Kabat) (SEQ ID NO: 297) | DHAID |

TABLE 6-continued

| Sequence information of engineered antibodies | |
|---|---|
| HCDR2 (Kabat) (SEQ ID NO: 298) | VIAGSGSITYYADSVKG |
| HCDR3 (Kabat) (SEQ ID NO: 299) | DTGVYREYMDV |
| vH full sequence (SEQ ID NO: 300) | EVQLLESGGGLVQPGGSLRLSCAASGFTFSDHAIDWVRQAPGK GLEWVSVIAGSGSITYYADSVKGRFTISRDNSKNTLYLQMNSL RAEDTAVYYCARDTGVYREYMDVWGQGTLVTVSS |
| vL full sequence (SEQ ID NO: 301) | SYELTQPLSVSVALGQTARITCSGDAIGTKFAHWYQQKPGQAP VLVIYYDHERPSGIPERFSGSNSGNTATLTISRAQAGDEADYYC YSRASSNLVFGGGTKLTVL |
| vH DNA sequence (SEQ ID NO: 302) | GAAGTGCAATTGCTGGAAAGCGGCGGTGGCCTGGTGCAGCC GGGTGGCAGCCTGCGTCTGAGCTGCGCGGCGTCCGGATTCA CCTTTTCTGACCATGCTATCGACTGGGTGCGCCAGGCCCCGG GCAAAGGTCTCGAGTGGGTTTCCGTTATCGCTGGTAGCGGTT CTATCACCTACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTGACACTGGTGTTTACCGTGAATACATGGATGTTTGG GGCCAAGGCACCCTGGTGACTGTTAGCTCA |
| vL DNA sequence (SEQ ID NO: 303) | AGCTATGAACTGACCCAGCCGCTGAGCGTGAGCGTGGCGCT GGGCCAGACCGCGCGCATTACCTGTAGCGGCGATGCTATCG GTACTAAATTCGCTCATTGGTACCAGCAGAAACCGGGCCAG GCGCCGGTGCTGGTGATCTACTACGACCATGAACGTCCGAG CGGCATCCCGGAACGTTTTAGCGGATCCAACAGCGGCAACA CCGCGACCCTGACCATTAGCCGCGCGCAGGCGGGCGACGAA GCGGATTATTACTGCTACTCTCGTGCTTCTTCTAACCTGGTG TTTGGCGGCGGCACGAAGTTAACCGTCCTA |
| HC full sequence (SEQ ID NO: 304) | EVQLLESGGGLVQPGGSLRLSCAASGFTFSDHAIDWVRQAPGK GLEWVSVIAGSGSITYYADSVKGRFTISRDNSKNTLYLQMNSL RAEDTAVYYCARDTGVYREYMDVWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKRVEPKSCDKTHTCPPCPAPELLGGPSVFLFPPKPKDTLMISR TPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| LC full sequence (SEQ ID NO: 305) | SYELTQPLSVSVALGQTARITCSGDAIGTKFAHWYQQKPGQAP VLVIYYDHERPSGIPERFSGSNSGNTATLTISRAQAGDEADYYC YSRASSNLVFGGGTKLTVLGQPKAAPSVTLFPPSSEELQANKA TLVCLISDFYPGAVTVAWKADSSPVKAGVETTTPSKQSNNKYA ASSYLSLTPEQWKSHRSYSCQVTHEGSTVEKTVAPTECS |
| HC DNA sequence (SEQ ID NO: 306) | GAAGTGCAATTGCTGGAAAGCGGCGGTGGCCTGGTGCAGCC GGGTGGCAGCCTGCGTCTGAGCTGCGCGGCGTCCGGATTCA CCTTTTCTGACCATGCTATCGACTGGGTGCGCCAGGCCCCGG GCAAAGGTCTCGAGTGGGTTTCCGTTATCGCTGGTAGCGGTT CTATCACCTACTATGCGGATAGCGTGAAAGGCCGCTTTACC ATCAGCCGCGATAATTCGAAAAACACCCTGTATCTGCAAAT GAACAGCCTGCGTGCGGAAGATACGGCCGTGTATTATTGCG CGCGTGACACTGGTGTTTACCGTGAATACATGGATGTTTGG GGCCAAGGCACCCTGGTGACTGTTAGCTCAGCCTCCACCAA GGGTCCATCGGTCTTCCCCCTGGCACCCTCCTCCAAGAGCAC CTCTGGGGGCACAGCGGCCCTGGGCTGCCTGGTCAAGGACT ACTTCCCCGAACCGGTGACGGTGTCGTGGAACTCAGGCGCC CTGACCAGCGGCGTGCACACCTTCCCGGCTGTCCTACAGTCC TCAGGACTCTACTCCCTCAGCAGCGTGGTGACCGTGCCCTCC AGCAGCTTGGGCACCCAGACCTACATCTGCAACGTGAATCA CAAGCCCAGCAACACCAAGGTGGACAAGAGAGTTGAGCCC AAATCTTGTGACAAAACTCACACATGCCCACCGTGCCCAGC ACCTGAACTCCTGGGGGGACCGTCAGTCTTCCTCTTCCCCCC AAAACCCAAGGACACCCTCATGATCTCCCGGACCCCTGAGG TCACATGCGTGGTGGTGGACGTGAGCCACGAAGACCCTGAG GTCAAGTTCAACTGGTACGTGGACGGCGTGGAGGTGCATAA TGCCAAGACAAAGCCGCGGGAGGAGCAGTACAACAGCACG TACCGGGTGGTCAGCGTCCTCACCGTCCTGCACCAGGACTG GCTGAATGGCAAGGAGTACAAGTGCAAGGTCTCCAACAAA GCCCTCCCAGCCCCCATCGAGAAAACCATCTCCAAAGCCAA AGGGCAGCCCCGAGAACCACAGGTGTACACCCTGCCCCCAT CCCGGGAGGAGATGACCAAGAACCAGGTCAGCCTGACCTGC CTGGTCAAAGGCTTCTATCCCAGCGACATCGCCGTGGAGTG GGAGAGCAATGGGCAGCCGGAGAACAACTACAAGACCACG |

TABLE 6-continued

| Sequence information of engineered antibodies | | |
|---|---|---|
| | | CCTCCCGTGCTGGACTCCGACGGCTCCTTCTTCCTCTACAGC<br>AAGCTCACCGTGGACAAGAGCAGGTGGCAGCAGGGGAACG<br>TCTTCTCATGCTCCGTGATGCATGAGGCTCTGCACAACCACT<br>ACACGCAGAAGAGCCTCTCCCTGTCTCCGGGTAAA |
| | LC DNA sequence (SEQ ID NO: 307) | AGCTATGAACTGACCCAGCCGCTGAGCGTGAGCGTGGCGCT<br>GGGCCAGACCGCGCGCATTACCTGTAGCGGCGATGCTATCG<br>GTACTAAATTCGCTCATTGGTACCAGCAGAAACCGGGCCAG<br>GCGCCGGTGCTGGTGATCTACTACGACCATGAACGTCCGAG<br>CGGCATCCCGGAACGTTTTAGCGGATCCAACAGCGGCAACA<br>CCGCGACCCTGACCATTAGCCGCGCGCAGGCGGGCGACGAA<br>GCGGATTATTACTGCTACTCTCGTGCTTCTTCTAACCTGGTG<br>TTTGGCGGCGGCACGAAGTTAACCGTCCTAGGTCAGCCCAA<br>GGCTGCCCCCTCGGTCACTCTGTTCCCGCCCTCCTCTGAGGA<br>GCTTCAAGCCAACAAGGCCACACTGGTGTGTCTCATAAGTG<br>ACTTCTACCCGGGAGCCGTGACAGTGGCCTGGAAGGCAGAT<br>AGCAGCCCCGTCAAGGCGGGAGTGGAGACCACCACACCCTC<br>CAAACAAAGCAACAACAAGTACGCGGCCAGCAGCTATCTG<br>AGCCTGACGCCTGAGCAGTGGAAGTCCCACAGAAGCTACAG<br>CTGCCAGGTCACGCATGAAGGGAGCACCGTGGAGAAGACA<br>GTGGCCCCTACAGAATGTTCA |
| NOV1127 | LCDR1 (Kabat) (SEQ ID NO: 308) | RASQGIFTYLN |
| | LCDR2 (Kabat) (SEQ ID NO: 309) | AASTLQS |
| | LCDR3 (Kabat) (SEQ ID NO: 310) | QQYYSTSLT |
| | HCDR1 (Kabat) (SEQ ID NO: 311) | SQSAAWN |
| | HCDR2 (Kabat) (SEQ ID NO: 312) | RIYYRSKWYNDYAVSVKS |
| | HCDR3 (Kabat) (SEQ ID NO: 313) | ERSYRDYFDY |
| | vH full sequence (SEQ ID NO: 314) | QVQLQQSGPGLVKPSQTLSLTCAISGDSVSSQSAAWNWIRQSP<br>SRGLEWLGRIYYRSKWYNDYAVSVKSRITINPDTSKNQFSLQL<br>NSVTPEDTAVYYCARERSYRDYFDYWGQGTLVTVSS |
| | vL full sequence (SEQ ID NO: 315) | DIQMTQSPSSLSASVGDRVTITCRASQGIFTYLNWYQQKPGKA<br>PKLLIYAASTLQSGVPSRFSGSGSGTDFTLTISSLQPEDFATYYC<br>QQYYSTSLTFGQGTKVEIK |
| | vH DNA sequence (SEQ ID NO: 316) | CAGGTGCAGCTGCAGCAGTCAGGCCCTGGCCTGGTCAAGCC<br>TAGTCAGACCCTGAGCCTGACCTGCGCTATTAGCGGCGATA<br>GTGTGTCTAGTCAGTCAGCCGCCTGGAACTGGATTAGACAG<br>TCACCCTCTAGGGGCCTGGAGTGGCTGGGTAGAATCTACTA<br>TAGGTCTAAGTGGTATAACGACTACGCCGTCAGCGTGAAGT<br>CTAGGATCACTATTAACCCCGACACCTCTAAGAATCAGTTTA<br>GCCTGCAGCTGAATAGCGTGACCCCCGAGGACACCGCCGTC<br>TACTACTGCGCTAGAGAGCGGTCCTATAGAGACTACTTCGA<br>CTACTGGGGTCAGGGCACCCTGGTCACCGTGTCTAGC |
| | vL DNA sequence (SEQ ID NO: 317) | GATATTCAGATGACTCAGTCACCTAGTAGCCTGAGCGCTAG<br>TGTGGGCGATAGAGTGACTATCACCTGTAGAGCCTCTCAGG<br>GAATCTTCACCTACCTGAACTGGTATCAGCAGAAGCCCGGT<br>AAAGCCCCTAAGCTGCTGATCTACGCCGCCTCTACCCTGCA<br>GTCAGGCGTGCCCTCTAGGTTTAGCGGTAGCGGTAGTGGCA<br>CCGACTTCACCCTGACTATCTCTAGCCTGCAGCCCGAGGACT<br>TCGCTACCTACTACTGTCAGCAGTACTACTCTACTAGCCTGA<br>CCTTCGGTCAGGGCACTAAGGTCGAGATTAAG |
| | HC full sequence (SEQ ID NO: 318) | QVQLQQSGPGLVKPSQTLSLTCAISGDSVSSQSAAWNWIRQSP<br>SRGLEWLGRIYYRSKWYNDYAVSVKSRITINPDTSKNQFSLQL<br>NSVTPEDTAVYYCARERSYRDYFDYWGQGTLVTVSSASTKGP<br>SVFPLAPSSKSTSGGTAALGCLVKDYFPEPVTVSWNSGALTSG<br>VHTFPAVLQSSGLYSLSSVVTVPSSSLGTQTYICNVNHKPSNTK<br>VDKRVEPKSCDKTHTCPPCPAPELLGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALPAPIEKTISK |

TABLE 6-continued

| Sequence information of engineered antibodies | | |
|---|---|---|
| | | AKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | LC full sequence (SEQ ID NO: 319) | DIQMTQSPSSLSASVGDRVTITCRASQGIFTYLNWYQQKPGKAPKLLIYAASTLQSGVPSRFSGSGSGTDFTLTISSLQPEDFATYYCQQYYSTSLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | HC DNA sequence (SEQ ID NO: 320) | CAGGTGCAGCTGCAGCAGTCAGGCCCTGGCCTGGTCAAGCCTAGTCAGACCCTGAGCCTGACCTGCGCTATTAGCGGCGATAGTGTGTCTAGTCAGTCAGCCGCCTGGAACTGGATTAGACAGTCACCCTCTAGGGGCCTGGAGTGGCTGGGTAGAATCTACTATAGGTCTAAGTGGTATAACGACTACGCCGTCAGCGTGAAGTCTAGGATCACTATTAACCCCGACACCTCTAAGAATCAGTTTAGCCTGCAGCTGAATAGCGTGACCCCCGAGGACACCGCCGTCTACTACTGCGCTAGAGAGCGGTCCTATAGAGACTACTTCGACTACTGGGGTCAGGGCACCCTGGTCACCGTGTCTAGCGCTAGCACTAAGGGCCCAAGTGTGTTTCCCCTGGCCCCCAGCAGCAAGTCTACTTCCGGCGGAACTGCTGCCCTGGGTTGCCTGGTGAAGGACTACTTCCCCGAGCCCGTGACAGTGTCCTGGAACTCTGGGGCTCTGACTTCCGGCGTGCACACCTTCCCCGCCGTGCTGCAGAGCAGCGGCCTGTACAGCCTGAGCAGCGTGGTGACAGTGCCCTCCAGCTCTCTGGGAACCCAGACCTATATCTGCAACGTGAACCACAAGCCCAGCAACACCAAGGTGGACAAGAGAGTGGAGCCCAAGAGCTGCGACAAGACCCACACCTGCCCCCCCTGCCCAGCTCCAGAACTGCTGGGAGGGCCTTCCGTGTTCCTGTTCCCCCCCAAGCCCAAGGACACCCTGATGATCAGCAGGACCCCCGAGGTGACCTGCGTGGTGGTGGACGTGTCCCACGAGGACCCAGAGGTGAAGTTCAACTGGTACGTGGACGGCGTGGAGGTGCACAACGCCAAGACCAAGCCCAGAGAGGAGCAGTACAACAGCACCTACAGGGTGGTGTCCGTGCTGACCGTGCTGCACCAGGACTGGCTGAACGGCAAAGAATACAAGTGCAAAGTCTCCAACAAGGCCCTGCCAGCCCCAATCGAAAAGACAATCAGCAAGGCCAAGGGCCAGCCACGGGAGCCCCAGGTGTACACCCTGCCCCCCAGCCGGGAGGAGATGACCAAGAACCAGGTGTCCCTGACCTGTCTGGTGAAGGGCTTCTACCCCAGCGATATCGCCGTGGAGTGGGAGAGCAACGGCCAGCCCGAGAACAACTACAAGACCACCCCCCCAGTGCTGGACAGCGACGGCAGCTTCTTCCTGTACAGCAAGCTGACCGTGGACAAGTCCAGGTGGCAGCAGGGCAACGTGTTCAGCTGCAGCGTGATGCACGAGGCCCTGCACAACCACTACACCCAGAAGTCCCTGAGCCTGAGCCCCGGCAAG |
| | LC DNA sequence (SEQ ID NO: 321) | GATATTCAGATGACTCAGTCACCTAGTAGCCTGAGCGCTAGTGTGGGCGATAGAGTGACTATCACCTGTAGAGCCTCTCAGGGAATCTTCACCTACCTGAACTGGTATCAGCAGAAGCCCGGTAAAGCCCCTAAGCTGCTGATCTACGCCGCCTCTACCCTGCAGTCAGGCGTGCCCTCTAGGTTTAGCGGTAGCGGTAGTGGCACCGACTTCACCCTGACTATCTCTAGCCTGCAGCCCGAGGACTTCGCTACCTACTACTGTCAGCAGTACTACTCTACTAGCCTGACCTTCGGTCAGGGCACTAAGGTCGAGATTAAGCGTACGGTGGCCGCTCCCAGCGTGTTCATCTTCCCCCCCAGCGACGAGCAGCTGAAGAGCGGCACCGCCAGCGTGGTGTGCCTGCTGAACAACTTCTACCCCCGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAGAAGCATAAGGTGTACGCCTGCGAGGTGACCCACCAGGGCCTGTCCAGCCCCGTGACCAAGAGCTTCAACAGGGGCGAGTGC |
| NOV1132 | LCDR1 (Kabat) (SEQ ID NO: 322) | SGDNIGSMTAH |
| | LCDR2 (Kabat) (SEQ ID NO: 323) | DKNERPS |
| | LCDR3 (Kabat) (SEQ ID NO: 324) | QSWDDSYTSVV |
| | HCDR1 (Kabat) (SEQ ID NO: 325) | SQSAGWN |

TABLE 6-continued

| Sequence information of engineered antibodies | |
|---|---|
| HCDR2 (Kabat) (SEQ ID NO: 326) | RIYYRSKWYNDYAVSVKS |
| HCDR3 (Kabat) (SEQ ID NO: 327) | EKYTVSFYDFFDY |
| vH full sequence (SEQ ID NO: 328) | QVQLQQSGPGLVKPSQTLSLTCAISGDSVSSQSAGWNWIRQSP SRGLEWLGRIYYRSKWYNDYAVSVKSRITINPDTSKNQFSLQL NSVTPEDTAVYYCAREKYTVSFYDFFDYWGQGTLVTVSS |
| vL full sequence (SEQ ID NO: 329) | SYELTQPLSVSVALGQTARITCSGDNIGSMTAHWYQQKPGQAP VLVIYDKNERPSGIPERFSGSNSGNTATLTISRAQAGDEADYYC QSWDDSYTSVVFGGGTKLTVL |
| vH DNA sequence (SEQ ID NO: 330) | CAGGTGCAATTGCAGCAGAGCGGTCCGGGCCTGGTGAAACC GAGCCAGACCCTGAGCCTGACCTGCGCGATTTCCGGAGATA GCGTGAGCTCTCAGTCTGCTGGTTGGAACTGGATTCGTCAG AGCCCGAGCCGTGGCCTCGAGTGGCTGGGCCGTATCTACTA CCGTAGCAAATGGTACAACGACTATGCCGTGAGCGTGAAAA GCCGCATTACCATTAACCCGGATACTTCGAAAAACCAGTTT AGCCTGCAACTGAACAGCGTGACCCCGGAAGATACGGCCGT GTATTATTGCGCGCGTGAAAAATACACTGTTTCTTTCTACGA CTTCTTCGATTACTGGGGCCAAGGCACCCTGGTGACTGTTAG CTCA |
| vL DNA sequence (SEQ ID NO: 331) | AGCTATGAACTGACCCAGCCGCTGAGCGTGAGCGTGGCGCT GGGCCAGACCGCGCGCATTACCTGTAGCGGCGATAACATCG GTTCTATGACTGCTCATTGGTACCAGCAGAAACCGGGCCAG GCGCCGGTGCTGGTGATCTACGACAAAAACGAACGTCCGAG CGGCATCCCGGAACGTTTTAGCGGATCCAACAGCGGCAACA CCGCGACCCTGACCATTAGCCGCGCGCAGGCGGGCGACGAA GCGGATTATTACTGCCAGTCTTGGGACGACTCTTACACCTCT GTTGTGTTTGGCGGCGGCACGAAGTTAACCGTCCTA |
| HC full sequence (SEQ ID NO: 332) | QVQLQQSGPGLVKPSQTLSLTCAISGDSVSSQSAGWNWIRQSP SRGLEWLGRIYYRSKWYNDYAVSVKSRITINPDTSKNQFSLQL NSVTPEDTAVYYCAREKYTVSFYDFFDYWGQGTLVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKRVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIAV EWESNGQPENNYKTTPPVLDSDGSFFLYSKLTVDKSRWQQGN VFSCSVMHEALHNHYTQKSLSLSPGK |
| LC full sequence (SEQ ID NO: 333) | SYELTQPLSVSVALGQTARITCSGDNIGSMTAHWYQQKPGQAP VLVIYDKNERPSGIPERFSGSNSGNTATLTISRAQAGDEADYYC QSWDDSYTSVVFGGGTKLTVLGQPKAAPSVTLFPPSSEELQAN KATLVCLISDFYPGAVTVAWKADSSPVKAGVETTTPSKQSNNK YAASSYLSLTPEQWKSHRSYSCQVTHEGSTVEKTVAPTECS |
| HC DNA sequence (SEQ ID NO: 334) | CAGGTGCAATTGCAGCAGAGCGGTCCGGGCCTGGTGAAACC GAGCCAGACCCTGAGCCTGACCTGCGCGATTTCCGGAGATA GCGTGAGCTCTCAGTCTGCTGGTTGGAACTGGATTCGTCAG AGCCCGAGCCGTGGCCTCGAGTGGCTGGGCCGTATCTACTA CCGTAGCAAATGGTACAACGACTATGCCGTGAGCGTGAAAA GCCGCATTACCATTAACCCGGATACTTCGAAAAACCAGTTT AGCCTGCAACTGAACAGCGTGACCCCGGAAGATACGGCCGT GTATTATTGCGCGCGTGAAAAATACACTGTTTCTTTCTACGA CTTCTTCGATTACTGGGGCCAAGGCACCCTGGTGACTGTTAG CTCAGCCTCCACCAAGGGTCCATCGGTCTTCCCCCTGGCACC CTCCTCCAAGAGCACCTCTGGGGGCACAGCGGCCCTGGGCT GCCTGGTCAAGGACTACTTCCCCGAACCGGTGACGGTGTCG TGGAACTCAGGCGCCCTGACCAGCGGCGTGCACACCTTCCC GGCTGTCCTACAGTCCTCAGGACTCTACTCCCTCAGCAGCGT GGTGACCGTGCCCTCCAGCAGCTTGGGCACCCAGACCTACA TCTGCAACGTGAATCACAAGCCCAGCAACACCAAGGTGGAC AAGAGAGTTGAGCCCAAATCTTGTGACAAAACTCACACATG CCCACCGTGCCCAGCACCTGAACTCCTGGGGGGACCGTCAG TCTTCCTCTTCCCCCCAAAACCCAAGGACACCCTCATGATCT CCCGGACCCCTGAGGTCACATGCGTGGTGGTGGACGTGAGC CACGAAGACCCTGAGGTCAAGTTCAACTGGTACGTGGACGG CGTGGAGGTGCATAATGCCAAGACAAAGCCGCGGGAGGAG CAGTACAACAGCACGTACCGGGTGGTCAGCGTCCTCACCGT CCTGCACCAGGACTGGCTGAATGGCAAGGAGTACAAGTGCA AGGTCTCCAACAAAGCCCTCCCAGCCCCCATCGAGAAAACC ATCTCCAAAGCCAAAGGGCAGCCCCGAGAACCACAGGTGTA CACCCTGCCCCCATCCCGGGAGGAGATGACCAAGAACCAGG TCAGCCTGACCTGCCTGGTCAAAGGCTTCTATCCCAGCGAC |

TABLE 6-continued

| Sequence information of engineered antibodies | |
|---|---|
| | ATCGCCGTGGAGTGGGAGAGCAATGGGCAGCCGGAGAACA ACTACAAGACCACGCCTCCCGTGCTGGACTCCGACGGCTCC TTCTTCCTCTACAGCAAGCTCACCGTGGACAAGAGCAGGTG GCAGCAGGGGAACGTCTTCTCATGCTCCGTGATGCATGAGG CTCTGCACAACCACTACACGCAGAAGAGCCTCTCCCTGTCTC CGGGTAAA |
| LC DNA sequence (SEQ ID NO: 335) | AGCTATGAACTGACCCAGCCGCTGAGCGTGAGCGTGGCGCT GGGCCAGACCGCGCGCATTACCTGTAGCGGCGATAACATCG GTTCTATGACTGCTCATTGGTACCAGCAGAAACCGGGCCAG GCGCCGGTGCTGGTGATCTACGACAAAAACGAACGTCCGAG CGGCATCCCGGAACGTTTTAGCGGATCCAACAGCGGCAACA CCGCGACCCTGACCATTAGCCGCGCGCAGGCGGGCGACGAA GCGGATTATTACTGCCAGTCTTGGGACGACTCTTACACCTCT GTTGTGTTTGGCGGCGGCACGAAGTTAACCGTCCTAGGTCA GCCCAAGGCTGCCCCCTCGGTCACTCTGTTCCCGCCCTCCTC TGAGGAGCTTCAAGCCAACAAGGCCACACTGGTGTGTCTCA TAAGTGACTTCTACCCGGGAGCCGTGACAGTGGCCTGGAAG GCAGATAGCAGCCCCGTCAAGGCGGGAGTGGAGACCACCA CACCCTCCAAACAAAGCAACAACAAGTACGCGGCCAGCAG CTATCTGAGCCTGACGCCTGAGCAGTGGAAGTCCCACAGAA GCTACAGCTGCCAGGTCACGCATGAAGGGAGCACCGTGGAG AAGACAGTGGCCCCTACAGAATGTTCA |

Example 3: Determination of Anti-CDH6 IgG Binding to Cells Featuring Expression of CDH6 from Human, Cynomolgus, Rat and Mouse Origins To determine anti-CDH6 binding to cells featuring expression of CDH6 from different species, FACS (Fluorescence Activated Cell sorting) analysis was performed on OVCAR3 cells, which express CDH6 endogenously, as well as on CHO cells engineered to express CDH6 from human, cynomolgus, rat and mouse origins.

OVCAR3 (ovarian serous carcinoma,) were obtained from ATCC (#HTB-161). The generation of the CHO cell lines featuring CDH6 expression is described in Example 1 above.

A cell suspension was prepared by treating cells in culture with Accutase® Cell Dissociation Reagent (#A1110501 Gibco, Grand Island, N.Y.) according to the manufacturer's instructions followed by washing the cells in FACS buffer (PBS/1% BSA, Gibco). Cells were resuspended in FACS buffer at $1\times10^6$ cells/ml and aliquoted into a 96-well round bottom plate (Corning #CLS3360 at 100 μl/well. An 8-point, 1:5 serial dilution of the primary antibodies was prepared to yield a highest final starting concentration of 10 μg/ml and 100 μl/well were added to the cell suspension. As a negative control antibody human isotype control IgG (R&D systems #1-001-A Minneapolis, Minn.) was used. Cells were incubated with the primary antibody solutions for 30 minutes on ice, followed by three washes in 200 μl of cold FACS buffer. The cells were resuspended in 100 μl of PE-conjugated anti-human Human Fc used at 1/500 dilution (Jackson Immuno Research #109-116-098 West Grove, Pa.) and cells were incubated for 30 minutes on ice. Following three washes in 200 μl cold FACS buffer, cells were analyzed on a BD FACS Canto II® (BD Biosciences, San Jose, Calif.). Geomean of signal per sample was determined using FlowJo® software and EC50s were determined by plotting the geomean of signal versus concentration and non-linear regression curve fitting using Tibco Spotfire® (Tibco, Boston, Mass.). All of the 20 analyzed anti-CDH6 antibodies displayed dose-dependent, target-specific binding on OVCAR3 cells (FIG. 1) and CHO cells expressing CDH6. No reactivity was observed on wild-type CHO cells, which do not express CDH6. EC50 values are summarized in Table 7.

TABLE 7

Cellular binding affinity (EC50 [nM]) of CDH6 IgGs on OVCAR3 cells and CHO cells negative for CDH6 expression (CHO-TREX) or engineered to express human, cynomolgus, rat or mouse CDH6.

| Antibody | OVCAR3 | CHO-cyCDH6 | CHO-huCDH6 | CHO-moCDH6 | CHO-ratCDH6 | CHO-TREX |
|---|---|---|---|---|---|---|
| hIgG | n.a. | n.a. | n.a. | n.a. | n.a. | n.a. |
| NOV0670 | 4.092 | 0.281 | 0.205 | 0.312 | 0.521 | n.a. |
| NOV0672 | 7.524 | 0.294 | 0.339 | 0.525 | 0.53 | n.a. |
| NOV0674 | 13.398 | 0.32 | 0.494 | 0.527 | 0.537 | n.a. |
| NOV0682 | 17.028 | 0.624 | 0.556 | 0.758 | 0.558 | n.a. |
| NOV0685 | 5.214 | 0.178 | 0.179 | 0.23 | 0.321 | n.a. |
| NOV0689 | 0.396 | 0.116 | 0.257 | 0.177 | 0.12 | n.a. |
| NOV0690 | 0.924 | 0.777 | 0.136 | 3.041 | 16.595 | n.a. |
| NOV0691 | 1.056 | 0.042 | 0.493 | 0.104 | 0.102 | n.a. |
| NOV0692 | 1.056 | 0.08 | 0.107 | 0.221 | 0.155 | n.a. |
| NOV0693 | 4.686 | 0.528 | 0.556 | 0.66 | 0.55 | n.a. |
| NOV0695 | 2.64 | 0.306 | 0.267 | 0.427 | 0.659 | n.a. |
| NOV0699 | 1.188 | 1.254 | 0.972 | 1.554 | 1.43 | n.a. |
| NOV0705 | 0.858 | 0.005 | 0.511 | 0.018 | 0.646 | n.a. |
| NOV0709 | 1.518 | 0.53 | n.a. | 0.669 | 0.531 | n.a. |

TABLE 7-continued

Cellular binding affinity (EC50 [nM]) of CDH6 IgGs on OVCAR3 cells and CHO cells negative for CDH6 expression (CHO-TREX) or engineered to express human, cynomolgus, rat or mouse CDH6.

| Antibody | OVCAR3 | CHO-cyCDH6 | CHO-huCDH6 | CHO-moCDH6 | CHO-ratCDH6 | CHO-TREX |
|---|---|---|---|---|---|---|
| NOV0710 | 0.858 | 0.15 | 0.151 | 0.22 | 0.152 | n.a. |
| NOV0712 | 1.122 | 0.202 | 0.21 | 0.537 | 0.523 | n.a. |
| NOV0713 | 11.22 | 4.779 | 3.115 | 7.034 | 8.369 | n.a. |
| NOV0718 | 0.66 | 0.313 | 0.187 | 0.52 | 0.322 | n.a. |
| NOV0719 | 1.914 | 0.171 | 0.248 | 0.527 | 0.222 | n.a. |
| NOV0720 | 0.66 | 0.543 | 0.428 | 0.338 | 0.493 | n.a. |

Example 4: Determination of Binding Affinity and Cross-Reactivity to Recombinant CDH6 from Human, Cynomolgus, Rat and Mouse by Biacore Measurement Affinity of the antibodies to recombinant CDH6 protein from human, cynomolgus, rat and mouse origin was determined using SPR technology on a Biacore® T100 instrument (GE Healthcare, Pittsburgh, Pa.) and with CM5 sensor chips.

Briefly, HBS-P (0.01 M HEPES, pH 7.4, 0.15 M NaCl, 0.005% Surfactant P20) supplemented with 0.5% Bovine Albumin Fraction V (7.5% solution) (Gibco 15260-037) was used as the running buffer for all the experiments. The immobilization level and analyte interactions were measured by response unit (RU). Pilot experiments were performed to test and confirm the feasibility of the immobilization of the anti-human Fc antibody (Jackson ImmunoResearch 109-006-098 West Grove, Pa.) and the capture of the test antibodies.

For kinetic measurements, the experiments were performed in which the antibodies were captured to the sensor chip surface via the immobilized anti-human Fc antibody and the ability of the CDH6 proteins to bind in free solution was determined. Briefly, 30 μg/ml of anti-human Fc antibody at pH 5 was immobilized on a CM5 sensor chip through amine coupling at flow rate of 12 μl/minute on all four flow cells to reach 7500 RUs. 5-10 μg/ml of test antibodies were then injected at 10 μl/min for 12 seconds to flow cell 2,3 and 4. Subsequently, 0.78-50 nM of CDH6 receptor extracellular domains (ECD) were diluted in a 2-fold series and injected at a flow rate of 80 μl/min for 100 seconds over reference (flow cell 1) and test flow cells 2,3 and 4. Table of tested ECDs is listed below. Dissociation of the binding was followed for 10 minutes. After each injection cycle, the chip surface was regenerated with 10 mM Glycine pH2.0 at 60 μl/min for 30 s. All experiments were performed at 25° C. and the response data were globally fitted with a simple 1:1 interaction model using Biacore® T100 evaluation software version 2.0.3 to obtain estimates of on rate ($k_a$), off-rate ($k_d$) and affinity ($K_D$). The results suggest most of the CDH6 antibodies assayed in this panel are cross-reactive to human, cynomolgus, rat and mouse (Table 8).

TABLE 8

Binding affinity of anti-CDH6 IgGs to recombinant CDH6 from human, cynomolgus, rat and mouse by Biacore measurement.

| Antibody | KD [M] human CDH6 | KD [M] cynomolgus CDH6 | KD [M] rat CDH6 | KD [M] mouse CDH6 |
|---|---|---|---|---|
| NOV0670 | 9.329E−09 | 7.378E−09 | 7.232E−09 | 1.903E−08 |
| NOV0672 | 2.463E−09 | 4.589E−09 | 3.291E−09 | 4.283E−09 |
| NOV0674 | 1.954E−09 | 6.995E−09 | 2.829E−09 | 4.77E−09 |
| NOV0682 | 6.188E−09 | 1.273E−08 | 5.554E−09 | 1.776E−07 |
| NOV0685 | 4.551E−09 | 4.115E−09 | 4.636E−09 | 5.321E−09 |
| NOV0689 | 5.648E−09 | 6.402E−09 | 6.083E−09 | 8.854E−09 |
| NOV0690 | 6.969E−09 | n/a | n/a | 1.111E−09 |
| NOV0691 | 8.343E−09 | 9.797E−09 | 4.332E−09 | n/a |
| NOV0692 | 5.082E−09 | 5.554E−09 | 2.502E−09 | 2.494E−09 |
| NOV0693 | 1.184E−09 | 1.966E−09 | 1.078E−09 | 1.843E−09 |
| NOV0695 | 3.023E−12 | n/a | n/a | 1.67E−11 |
| NOV0705 | 2.479E−09 | n/a | 2.334E−09 | 4.926E−11 |
| NOV0709 | 8.174E−10 | 1.983E−09 | 6.977E−10 | 2.139E−09 |
| NOV0710 | 2.065E−09 | 3.84E−09 | 2.385E−09 | 4.009E−09 |
| NOV0712 | 2.904E−09 | 3.784E−09 | 5.719E−09 | 4.835E−09 |
| NOV0713 | 1.419E−08 | 9.049E−09 | 7.147E−09 | 2.006E−08 |
| NOV0718 | 5.455E−09 | 6.903E−09 | 6.608E−09 | 5.941E−09 |
| NOV0719 | 1.899E−09 | 4.944E−09 | 8.789E−09 | 5.172E−09 |
| NOV0720 | 2.47E−09 | 3.335E−09 | 1.406E−09 | 2.268E−09 |

Example 5: Epitope Binning by Biacore

Epitope Mapping of CDH6 antibodies was determined using Surface Plasmon Resonance (SPR) technology on a Biacore® A-100 instrument (GE Healthcare, Pittsburgh, Pa.) with a CM5 (s) sensor chip. Briefly, HBS-EP buffer (10 mM HEPES pH 7.4, 150 mM NaCl, 3.4 mM; EDTA, 0.005% Surfactant P20 supplemented with 0.25% BSA and 10 mM calcium) was used as the running buffer for all the experiments. The immobilization level and analyte interactions were measured by response unit (RU). Pilot experiments were performed to test and confirm the feasibility of the immobilization of the anti-human Fc antibody (Catalog number Jackson Immuno Research 109-006-098 West Grove, Pa.) and the capture of the test antibodies.

For epitope mapping, anti-human Fc antibody was immobilized on spot 1,2 and 4,5 of all four flow cells at 10,000RU. Spot 5 was used as reference. Each of the primary testing CDH6 antibodies was then captured via the immobilized anti-human Fc on the biosensor chip at a response level greater than 300 RU, followed by injection of the CDH6 protein in spot 1 and 5 at binding levels above 20 RU. Spots 2 and 4 were used as additional reference surface. All five spots of each flow cell were blocked with two injections of human IgG at 1 mg/ml to block any free binding sites of anti-human Fc. Each of the secondary testing antibodies was then injected over spots 1,2 or 4,5 to assess the degree of binding to the complex of primary testing antibody and CDH6 protein. Human IgG isotype control was used as primary and secondary testing negative control antibody. The antibodies were tested in parallel in all four flow cells until all possible combinations of antibody pairs had been evaluated. Regeneration of all flow cell surfaces after each primary and secondary antibody binding cycle was done with injection of 10 mM glycine pH2.0.

The results were evaluated using the epitope mapping module in the Biacore® 4000 evaluation software and presented as a matrix, with primary antibodies in rows and secondary in columns (FIG. 2). Additional binding of the secondary testing antibody to the complex of the primary testing antibody and CDH6 protein is indicated by positive response values. Negative pairs are marked and compare to human IgG isotype control. The matrix is then used to map which antibodies recognize which epitopes based on how they can form pairs with other antibodies. Antibody NOV0710 and NOV0712 compete with each other indicating they recognize and overlapping epitope on the antigen. Antibody NOV1127 shows positive binding when it was used as primary and secondary binding antibody, suggesting it may bind to multiple sites on CDH6 or that initial binding alters the conformation and opens up additional binding sites. NOV0719, NOV0692, NOV1126 and NOV1132 all appear to bind distinct epitopes based on this analysis.

Example 6: Epitope Mapping by Hydrogen-Deuterium Exchange/Mass Spectrometry

Hydrogen-deuterium exchange (HDx) in combination with mass spectrometry (MS) (Woods et al., J. Cell Biochem. 2001 S37: 89-98)) was used to map the binding site of antibodies NOV1127, NOV0719, NOV0710 and NOV0712 on the full-length extra-cellular domain (ECD) of hCDH6 full-length (aa54-615), which includes cadherin domains (EC) 1 through 5 (Table 9). In addition, HDx was also performed on a truncated ECD consisting of EC 1 through 3 using antibodies NOV0710 and NOV0712 (Table 10). In HDx exchangeable amide hydrogens of proteins are replaced by deuterium. This process is sensitive to protein structure/dynamics and solvent accessibility and, therefore, able to report on locations that undergo a decrease in deuterium uptake upon ligand binding. The goal of these experiments was to identify the potential epitopes and understand the dynamics of hCDH6 when bound to our therapeutic antibodies. It is important to note that changes in deuterium uptake are sensitive to both direct binding and allosteric events; in order to precisely determine the epitope HDx has to be combined with orthogonal technologies (e.g. X-ray crystallography).

Automated HDx/MS experiments were performed using methods similar to those described in the literature (Chalmers et al., Anal Chem. 2006: 78(4):1005-14). The experiments were performed on a Waters HDx-MS® platform, which includes a LEAP autosampler, nanoACQUITY UPLC System, and Synapt G2 mass spectrometer (Waters Corp, Milford Mass.). The deuterium buffer used to label the protein backbone of the full length hCDH6(54-615) with deuterium was 50 mM D-Tris, 150 mM NaCl pH 7.4+3 mM CaCl2; the overall percentage of deuterium in the solution was 89.5%. For hCDH6(54-615) deuterium labeling experiments in the absence of hCDH6 antibody, 600 pmol of hCDH6(54-615), volume of 5 μl, was diluted using 45 μl of the deuterium buffer in a chilled tube and incubated for 25 minutes on a rotator at 4° C. The labeling reaction was then quenched with 75 μl of chilled quench buffer on ice for three minutes followed by injected onto the LC-MS system for automated pepsin digestion and peptide analysis. For hCDH6(54-615) deuterium labeling experiments in the presence of bound hCDH6 antibody, 600 pmol of the hCDH6 antibody was first immobilized on Thermo Protein G Plus beads and cross-linked using disuccinimidyl suberate (DSS). To perform the labeling experiments, the antibody beads (containing 600 pmol antibody) were incubated with 600 pmol hCDH6(54-615) for 30 minutes at 4° C. After 30 minutes the beads were washed with 200 μl of Tris buffer (50 mM Tris, 150 mM NaCl pH 7.4+3 mM CaCl2). Then 200 μl of chilled deuterium buffer (80.6% deuterium) was added and the complex was incubated for 25 minutes at 4° C. After 25 minutes, the labeling reaction was quenched with 125 μl of chilled quench buffer on ice for 2.5 minutes. After spinning the sample for 30 seconds in a centrifuge, the quenched solution was injected onto the LC-MS system for automated pepsin digestion and peptide analysis. Similar experiments were also performed on a hCDH6(267-615) construct that contains only EC 3 through 5. In these experiments the buffer was 25 mM HEPES pH=7.4, 150 mM NaCl, 3 mM CaCl2 and a deuterium version of the buffer containing 94.2% deuterium.

All measurements were carried out using a minimum of three analytical triplicates. All deuterium exchange experiments were quenched using 0.5 M TCEP and 3 M urea (pH=2.5). After quenching, the exchanged antigen was subjected to on-line pepsin digestion using a Poroszyme® Immobilized Pepsin column (2.1×30 mm) at 12° C. followed by trapping on a Waters Vanguard® HSS T3 (Waters Corp. Milford Mass.) trapping column. Peptides were eluted from the trapping column and separated on a Waters CSH C18 1×100 mm column (maintained at 1° C.) at a flow rate of 40 μl/min using a binary eight minute gradient of 2 to 35% B (mobile phase A was 99.9% water and 0.1% formic acid; mobile phase B was 99.9% acetonitrile and 0.1% formic acid).

Figure 3:
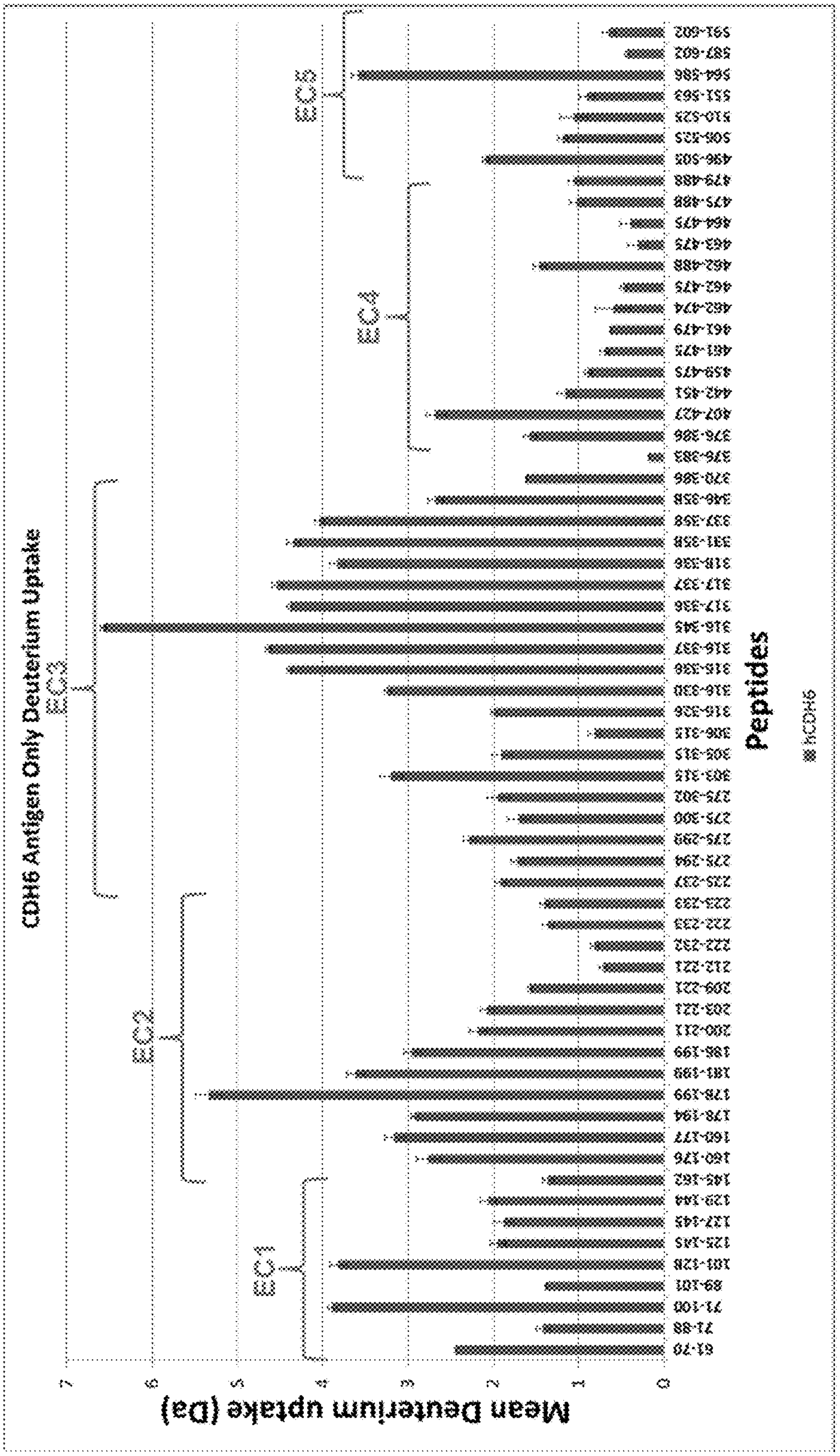
FIG. 3 represents deuterium mapping of the five EC domains of CDH6.

For hCDH6(54-615) protein 73% of the sequence was monitored by the deuterium exchange experiments; a complete list of these peptides appears in Table 9. FIG. 3 provides a summary of the on-exchange characteristics of the hCDH6 (54-615) protein. Regions that have a greater uptake in deuterium, such as EC3, are either more solvent exposed or have a weaker hydrogen bonding network that regions that exhibit less deuterium uptake, such as regions EC4 and EC5. Overall, it is observed that EC1 through EC3 domains have greater on-exchange of deuterium that the EC4 of EC5 domains. For example, the EC2 peptide 181-199 VTATDADDPTYGNSAKVVY (SEQ ID NO:336) mean deuterium uptake is 3.61 Da; in contrast the EC5 peptide 506-525 IQTLHAVDKDDPYSGHQFSF (SEQ ID NO:337) mean deuterium uptake is only 1.18 Da. Limited deuterium uptake can make the determination of protection regions, those that undergo a shift of −0.5 Da or less upon antibody binding, more challenging due to limitations in the dynamic range.

For EC1 (54-159) the only peptides that exhibits a decrease in deuterium uptake upon binding of all four antibodies is 61-70 FLLEEYTGSD (SEQ ID NO:338). In EC1 the antibodies NOV1127 and NOV0719 demonstrate significant destabilization in the structure with changes in deuterium uptake greater or equal to 0.5 Da. Binding of NOV0710 and NOV0712 does not significantly alter the deuterium exchange behavior of the antigen in the EC1 domain.

For EC2 (160-268) the region 195-202 AKVVYSIL (SEQ ID NO:339) has a borderline decrease in deuterium uptake by all antibodies. More interestingly, the region 203-221 QGQPYFSVESETGIIKTAL (SEQ ID NO:340) is destabilized substantially (i.e. undergoes an increase in deuterium uptake) by NOV0719 and slightly less by NOV0712. Neither NOV1127 nor NOV0710 destabilize this region with a change in deuterium incorporation of +0.5 Da or greater. Lastly, the region 225-237 DRENREQYQVVIQ (SEQ ID NO:341) is only destabilized upon NOV0719 binding to hCDH6 antigen.

For EC3 (269-383) the region 275-302 FKTPESSPPGTPIGRIKASDADVGENAE (SEQ ID NO:342) is destabilized by NOV0719. The region 303-315 IEYSITDGEGLDM (SEQ ID NO:343) exhibits a decrease in deuterium uptake by all antibodies, but the decrease is more pronounced by NOV0710 and NOV0712 relative to the others two antibodies. The region 316-330 FDVITDQETQEGIIT (SEQ ID NO:344) exhibits a decrease in deuterium uptake for all antibodies, but the decrease is the least by NOV0719. In contrast, the region 331-336 VKKLLD (SEQ ID NO:345) is destabilized by NOV0719 and less so by NOV0712. The region 337-358 FEKKKVYTLKVEASNPYVEPRF (SEQ ID NO:346) exhibits a decrease in deuterium uptake with all antibodies except NOV0719; in contrast NOV0719 is the only antibody that destabilizes the region 337-345 FEKKKVYTL (SEQ ID NO:347). Lastly, it observed that NOV0719 also destabilizes the region 370-376 VRIVVED (SEQ ID NO:348).

For EC4 (384-486) and EC5 (487-608) the deuterium on-exchange of the antigen (FIG. 3) was overall relatively low making detection of decreases in deuterium uptake challenging. For EC4 the region 407-427 AQDPDAARNPVKYSVDRHTDM (SEQ ID NO:349) exhibits a borderline decrease in deuterium uptake with NOV0710. There are no other regions in EC4 that decrease in deuterium uptake upon binding with any of the four antibodies. Overall, these observations strongly suggest that EC4 is not involved in the epitope. In contrast, 459-488 IATEINNPKQSSRVPLYIKVLDVNDNAPEF (SEQ ID NO:350) exhibits various degrees of destabilization with NOV0719, NOV1127, NOV0712, and NOV0710 (listed in decreasing order of destabilization).

For EC5 only the region 564-586 YLLPVVISDNDYPVQSSTGTVTV (SEQ ID NO:351) exhibits a borderline decrease in deuterium uptake when hCDH6 complexes with either NOV0710 or NOV0712. It should be noted that of the five extracellular domains that only EC5 does not exhibit any regions of destabilization when hCDH6 interacts with any of the four studied antibodies.

HDx experiments were also performed on hCDH6 construct consisting of only EC3-EC5, hCDH6(267-615). In these experiments the antibodies NOV0710 and NOV0712 were studied. This construct is same construct is used in crystallography experiments. The sequence coverage in these experiments was 86%. Table 10 provides a comprehensive list of all the peptides.

With this construct, in EC3 a decrease in deuterium uptake is observed in the region 295-315 ADVGENAEIEYSITDGEGLDM (SEQ ID NO:352) for both NOV0710 and NOV0712; this is very similar behavior to the full-length antigen where the region 303-315 IEYSITDGEGLDM (SEQ ID NO:343) exhibits a decrease in deuterium uptake by all antibodies, but more so by NOV0712 and NOV0710. Interestingly, there are regions in EC3 that exhibit differential behavior between the two constructs. For example, in the hCDH6(54-615) NOV0719 caused significant destabilization in many regions while the other antibodies did not. In contrast, with the hCDH6(267-615) protein both NOV0710 and NOV0712 also exhibit significant destabilization in regions that are very similar to the regions observed to be destabilized by NOV0719 in the full length hCDH6(54-615) protein.

In EC4 a similar trend is observed for destabilizaton. In the hCDH6(54-615) NOV0719 caused the most significant destabilization on the C-terminal side of this domain and NOV0710 and NOV0712 had little effect. In contrast, when using the hCDH6(267-615) construct both NOV0710 and NOV712 significantly destabilize the C-terminal side of EC4. The origins for the differences in destabilization behavior are not well understood. It is important to note that in the EC4 domain neither construct had substantial decrease in deuterium uptake with NOV0710 or NOV0712 suggesting that this region is not involved in binding NOV0710 or NOV0712.

In EC5 we observe the most consistent deuterium exchange behavior between the hCDH6 (54-615) and hCDH6 (267-615) constructs. Neither constructs exhibited significant destabilization with NOV0712 or NOV0710. Moreover, the slight and often insignificant decrease in deuterium uptake (not less than −0.5 Da) with the hCD6 (54-615) becomes more pronounced in hCDH6 (267-615). In the EC5 of hCDH6 (267-615) regions that exhibit the most significant decrease in deuterium uptake upon binding either NOV0710 or NOV0712 include the regions 492-505 YETFVCEKAKADQL (SEQ ID NO:353), 551-563 TRKNGYNRHEMST (SEQ ID NO:354), and 572-586 DNDYPVQSSTGTVTV (SEQ ID NO:355). The substantial protection of 572-586 DNDYPVQSSTGTVTV (SEQ ID NO:355) is in excellent agreement with the epitope data from X-ray crystallography for both NOV0710 and NOV0712. The amino acids N573, D574, and Y575 exhibit a large accessible surface area and upon formation of a complex with either antibody all three are substantially buried. V577 is also buried in both structures indicating further agreement. Crystallography data does not indicate that 492-505 YETFVCEKAKADQL (SEQ ID NO:353) is buried so this protection appears to be allosteric in nature, but the protection of 551-563 TRKNGYNRHEMST (SEQ ID NO:354) appears to be of significance especially in the NOV0712 complex where R552 is substantially buried.

Lastly, it is important to note that there are other regions in the EC5 domain that exhibit significant (−0.5 Da or less) decrease in deuterium uptake upon complex formation with either of the two antibodies. For NOV0710 these regions include 510-525 HAVDKDDPYSGHQFSF (SEQ ID NO:356), 542-550 NKDNTAGIL (SEQ ID NO:357), and 591-604 CDHHGNMQSCHAEA (SEQ ID NO:358). For NOV0712 these regions include 512-522 VDKDDPYSGHQ (SEQ ID NO:359), 542-550 NKDNTAGIL (SEQ ID NO:357), and 591-604 CDHHGNMQSCHAEA (SEQ ID NO:358).

Overall, the HDx data suggest that binding of CDH6 by the identified CDH6-binding antibodies results in several regions of the CDH6 protein becoming more prone to deuterium exchange, likely reflecting conformational changes induced by the binding of the CDH6 antibodies. The regions identified as protected from deuterium exchange in the presence of CDH6 antibodies are consistent with the x-ray crystallography data for NOV0710 and NOV0712 and form part of the epitope of these antibodies.

TABLE 9

Effect of NOV1127, NOV0719, NOV0710, and NOV0712 on hCDH6(54-615) containing cadherin 1-5 domains.

| Peptide Name | Sequence | Change in Deuterium Incorporation (Daltons) NOV 1127 | NOV 0719 | NOV 0710 | NOV 0712 |
|---|---|---|---|---|---|
| 61-70 | FLLEEYTGSD (SEQ ID NO: 338) | -1.1 | -1.2 | -1.1 | -1.3 |
| 63-70 | LEEYTGSD (SEQ ID NO: 360) | -0.1 | -0.3 | -0.4 | -0.2 |
| 71-77 | YQYVGKL (SEQ ID NO: 361) | 0.2 | 0.2 | -0.1 | 0.1 |
| 71-88 | YQYVGKLHSDQDRGDGSL (SEQ ID NO: 362) | 0.2 | 0.2 | -0.1 | 0.1 |
| 71-100 | YQYVGKLHSDQDRGDGSLKYILSGDGAGDL (SEQ ID NO: 363) | 1.0 | 0.9 | -0.1 | 0.2 |
| 90-100 | YILSGDGAGDL (SEQ ID NO: 364) | 0 | 0 | 0 | 0.1 |
| 101-112 | FIINENTGDIQA (SEQ ID NO: 365) | 0.4 | 0.4 | 0.1 | 0.3 |
| 101-124 | FIINENTGDIQATKRLDREEKPVY (SEQ ID NO: 366) | 0.4 | 0.6 | -0.3 | 0 |
| 101-126 | FIINENTGDIQATKRLDREEKPVYIL (SEQ ID NO: 367) | 0.6 | 0.7 | -0.2 | 0 |
| 101-128 | FIINENTGDIQATKRLDREEKPVYILRA (SEQ ID NO: 368) | 1.1 | 1.1 | -0.2 | 0.2 |
| 102-124 | IINENTGDIQATKRLDREEKPVY (SEQ ID NO: 369) | 0.4 | 0.5 | -0.3 | 0.1 |
| 106-124 | NTGDIQATKRLDREEKPVY (SEQ ID NO: 370) | 0.1 | 0.3 | -0.4 | 0 |
| 106-126 | NTGDIQATKRLDREEKPVYIL (SEQ ID NO: 371) | 0.6 | 0.6 | -0.2 | 0 |
| 113-124 | TKRLDREEKPVY (SEQ ID NO: 372) | 0.1 | 0.1 | -0.2 | -0.1 |
| 125-144 | ILRAQAINRRTGRPVEPESE (SEQ ID NO: 373) | 0.3 | 0.4 | -0.2 | 0.1 |
| 125-145 | ILRAQAINRRTGRPVEPESEF (SEQ ID NO: 374) | 0.7 | 0.9 | 0 | 0.3 |
| 127-144 | RAQAINRRTGRPVEPESE (SEQ ID NO: 375) | 0.3 | 0.4 | -0.3 | -0.1 |
| 127-145 | RAQAINRRTGRPVEPESEF (SEQ ID NO: 376 | 0.3 | 0.4 | 0 | 0.2 |
| 129-144 | QAINRRTGRPVEPESE (SEQ ID NO: 377) | 0.1 | 0.2 | -0.3 | -0.2 |
| 129-145 | QAINRRTGRPVEPESEF (SEQ ID NO: 378) | 0.2 | 0.3 | -0.1 | 0.1 |
| 145-159 | FIIKIHDINDNEPIF (SEQ ID NO: 379) | 0.9 | 0.9 | 0.4 | 0.5 |
| 145-162 | FIIKIHDINDNEPIFTKE (SEQ ID NO: 380) | 0.7 | 0.7 | 0 | 0.2 |
| 146-159 | IIKIHDINDNEPIF (SEQ ID NO: 381) | 0.5 | 0.6 | 0.2 | 0.3 |
| 146-160 | IIKIHDINDNEPIFT (SEQ ID NO: 382) | 0.4 | 0.1 | 0.1 | 0.2 |
| 146-162 | IIKIHDINDNEPIFTK (SEQ ID NO: 383) | 0.3 | 0.3 | 0 | 0.1 |
| 160-176 | TKEVYTATVPEMSDVGT (SEQ ID NO: 384) | -0.4 | 0.5 | -0.3 | -0.2 |
| 160-177 | TKEVYTATVPEMSDVGTF (SEQ ID NO: 385) | -0.5 | 0.3 | -0.6 | -0.4 |
| 163-171 | VYTATVPEMSDVGTF (SEQ ID NO: 386) | -0.1 | 0.6 | 0.2 | 0.2 |
| 177-184 | FVVQVTAT (SEQ ID NO: 387) | 0.4 | 0.8 | 0.2 | 0.6 |
| 178-184 | VVQVTAT (SEQ ID NO: 388) | 0.3 | 0.5 | 0.2 | 0.3 |
| 178-194 | VVQVTATDADDPTYGNS (SEQ ID NO: 389) | -0.1 | 0 | -0.2 | -0.1 |
| 178-199 | VVQVTATDADDPTYGNSAKVVY (SEQ ID NO: 390) | -0.6 | -0.1 | -0.8 | -0.5 |

TABLE 9-continued

Effect of NOV1127, NOV0719, NOV0710, and NOV0712 on hCDH6(54-615) containing cadherin 1-5 domains.

| Peptide Name | Sequence | Change in Deuterium Incorporation (Daltons) NOV 1127 | NOV 0719 | NOV 0710 | NOV 0712 |
|---|---|---|---|---|---|
| 181-199 | VTATDADDPTYGNSAKVVY (SEQ ID NO: 336) | -0.7 | -0.3 | -0.9 | -0.6 |
| 185-199 | DADDPTYGNSAKVVY (SEQ ID NO: 391) | -0.3 | -0.5 | -0.4 | -0.4 |
| 200-208 | SILQGQPYF (SEQ ID NO: 392) | -0.3 | -0.1 | -0.3 | -0.3 |
| 203-211 | QGQPYFSVE (SEQ ID NO: 393) | -0.1 | 0.5 | 0 | 0.1 |
| 203-221 | QGQPYFSVESETGIIKTAL (SEQ ID NO 340) | 0.1 | 2.6 | 0.4 | 1.1 |
| 209-211 | SVESETGIIKTAL (SEQ ID NO: 394) | -0.1 | 2.1 | 0.3 | 0.8 |
| 212-221 | SETGIIKTAL (SEQ ID NO: 395) | 0 | 1.9 | 0.4 | 0.8 |
| 214-222 | TGIIKTALL (SEQ ID NO: 396) | 0.1 | 0.8 | -0.1 | 0 |
| 222-232 | LNMDRENREQY (SEQ ID NO: 397) | -0.1 | 0 | -0.1 | -0.1 |
| 222-233 | LNMDRENREQYQ (SEQ ID NO: 398) | -0.2 | 0.1 | -0.2 | -0.1 |
| 225-233 | DRENREQYQ (SEQ ID NO: 399) | -0.4 | -0.3 | -0.4 | -0.4 |
| 225-237 | DRENREQYQVVIQ (SEQ ID NO 341) | -0.4 | 1.1 | -0.1 | 0.2 |
| 275-294 | FKTPESSPPGTPIGRIKASD (SEQ ID NO: 400) | 0.1 | 1.0 | -0.1 | 0.2 |
| 275-300 | FKTPESSPPGTPIGRIKASDADVGEN (SEQ ID NO: 401) | 0.1 | 1.3 | 0 | 0.3 |
| 275-302 | FKTPESSPPGTPIGRIKASDADVGENAE (SEQ ID NO: 342) | 0.1 | 1.4 | 0 | 0.3 |
| 303-315 | IEYSITDGEGLDM (SEQ ID NO: 343) | -0.9 | -1.1 | -1.3 | -1.3 |
| 305-315 | YSITDGEGLDM (SEQ ID NO: 402) | -0.6 | -0.7 | -0.8 | -0.8 |
| 306-315 | SITDGEGLDM (SEQ ID NO: 403) | -0.2 | -0.1 | -0.2 | -0.1 |
| 316-326 | FDVITDQETQE (SEQ ID NO: 404) | -1.0 | -0.6 | -0.9 | -0.8 |
| 316-330 | FDVITDQETQEGIIT (SEQ ID NO: 344) | -1.2 | -0.7 | -1.4 | -1.5 |
| 316-336 | FDVITDQETQEGIITVKKLLD (SEQ ID NO: 405) | -0.6 | 2.2 | -0.8 | -0.2 |
| 316-337 | FDVITDQETQEGIITVKKLLDF (SEQ ID NO: 406) | -0.6 | 2.3 | -0.8 | -0.2 |
| 316-345 | FDVITDQETQEGIITVKKLLDFEKKKVYTL (SEQ ID NO: 407) | -0.2 | 3.3 | -1.1 | -0.5 |
| 317-336 | DVITDQETQEGIITVKKLLD (SEQ ID NO: 408) | -0.2 | 2.2 | -0.1 | 0.6 |
| 317-337 | DVITDQETQEGIITVKKLLDF (SEQ ID NO: 409) | -0.2 | 2.3 | -0.1 | 0.6 |
| 318-337 | VITDQETQEGIITVKKLLDF (SEQ ID NO: 410) | -0.2 | 2.3 | -0.3 | 0.3 |
| 327-336 | GIITVKKLLD (SEQ ID NO: 411) | 0.1 | 0.9 | -0.1 | 0.1 |
| 327-337 | GIITVKKLLDF (SEQ ID NO: 412) | 0.3 | 1.1 | -0.1 | 0.1 |
| 331-358 | VKKLLDFEKKKVYTLKVEASNPYVEPRF (SEQ ID NO: 413) | -0.4 | 1.3 | -1.0 | -0.7 |

TABLE 9-continued

Effect of NOV1127, NOV0719, NOV0710, and NOV0712 on hCDH6(54-615) containing cadherin 1-5 domains.

| Peptide Name | Sequence | Change in Deuterium Incorporation (Daltons) NOV 1127 | NOV 0719 | NOV 0710 | NOV 0712 |
|---|---|---|---|---|---|
| 337-358 | FEKKKVYTLKVEASNPYVEPRF (SEQ ID NO: 346) | -0.9 | 0.5 | -1.1 | -0.9 |
| 338-345 | EKKKVYTL (SEQ ID NO: 414) | -0.1 | -0.6 | -0.2 | -0.2 |
| 346-358 | KVEASNPYVEPRF (SEQ ID NO: 415) | -0.7 | -0.4 | -0.5 | -0.4 |
| 370-376 | VRIVVED (SEQ ID NO: 348) | 0.3 | 1.6 | 0 | 0.2 |
| 370-386 | VRIVVEDVDEPPVFSKL (SEQ ID NO: 416) | 0.3 | 1.6 | 0.1 | 0.4 |
| 376-383 | DVDEPPVF (SEQ ID NO: 417) | 0.2 | 0.3 | 0.1 | 0.1 |
| 376-386 | DVDEPPVFSKL (SEQ ID NO: 418) | -0.1 | 0 | -0.2 | -0.2 |
| 377-383 | VDEPPVF (SEQ ID NO: 419) | 0.3 | 0.6 | 0 | 0.1 |
| 377-386 | VDEPPVFSKL (SEQ ID NO: 420) | -0.2 | -0.1 | -0.4 | -0.3 |
| 407-427 | AQDPDAARNPVKYSVDRHTDM (SEQ ID NO: 349) | -0.3 | -0.3 | -0.6 | -0.4 |
| 413-427 | ARNPVKYSVDRHTDM (SEQ ID NO: 421) | -0.2 | -0.2 | -0.4 | -0.4 |
| 420-427 | SVDRHTDM (SEQ ID NO: 422) | -0.1 | -0.2 | -0.1 | -0.1 |
| 428-441 | DRIFNIDSGNGSIF (SEQ ID NO: 423) | 1.0 | 0.1 | -0.3 | -0.3 |
| 442-451 | TSKLLDRETL (SEQ ID NO: 424) | 0 | -0.2 | -0.1 | -0.1 |
| 446-452 | LDRETLL (SEQ ID NO: 425) | -0.2 | -0.2 | -0.2 | -0.2 |
| 459-475 | IATEINNPKQSSRVPLY (SEQ ID NO: 426) | 0.6 | 1.0 | 0.2 | 0.4 |
| 461-474 | TEINNPKQSSRVPL (SEQ ID NO: 427) | 0.3 | 0.6 | 0.1 | 0.2 |
| 461-475 | TEINNPKQSSRVPLY (SEQ ID NO: 428) | 0.6 | 0.9 | 0.2 | 0.4 |
| 462-474 | EINNPKQSSRVPL (SEQ ID NO: 429) | 0.2 | 0.3 | -0.1 | 0.1 |
| 462-475 | EINNPKQSSRVPLY (SEQ ID NO: 430) | 0.6 | 0.9 | 0.3 | 0.5 |
| 462-488 | EINNPKQSSRVPLYIKVLDVNDNAPEF (SEQ ID NO: 431) | 1.4 | 2.2 | 0.7 | 1.0 |
| 463-475 | INNPKQSSRVPLY (SEQ ID NO: 432) | 0.6 | 0.8 | 0.2 | 0.4 |
| 475-488 | YIKVLDVNDNAPEF (SEQ ID NO: 433) | 0.5 | 0.8 | 0.3 | 0.4 |
| 476-488 | IKVLDVNDNAPEF (SEQ ID NO: 434) | 0.5 | 0.7 | 0.2 | 0.4 |
| 496-505 | VCEKAKADQL (SEQ ID NO: 435) | -0.4 | -0.4 | -0.6 | -0.6 |
| 506-522 | IQTLHAVDKDDPYSGHQ (SEQ ID NO: 436) | 0.1 | 0 | -0.1 | 0 |
| 506-525 | IQTLHAVDKDDPYSGHQFSF (SEQ ID NO: 337) | 0.2 | 0.2 | -0.1 | -0.1 |
| 510-522 | HAVDKDDPYSGHQ (SEQ ID NO: 437) | -0.2 | -0.4 | -0.3 | -0.3 |
| 510-524 | HAVDKDDPYSGHQFS (SEQ ID NO: 438) | -0.3 | -0.5 | -0.3 | -0.3 |
| 510-525 | HAVDKDDPYSGHQFSF (SEQ ID NO: 356) | -0.2 | -0.2 | -0.3 | -0.3 |
| 512-522 | VDKDDPYSGHQ (SEQ ID NO: 359) | -0.2 | -0.4 | -0.3 | -0.4 |
| 512-525 | VDKDDPYSGHQFSF (SEQ ID NO: 439) | -0.1 | -0.1 | -0.3 | -0.3 |

TABLE 9-continued

Effect of NOV1127, NOV0719, NOV0710, and NOV0712 on hCDH6(54-615) containing cadherin 1-5 domains.

| Peptide Name | Sequence | Change in Deuterium Incorporation (Daltons) NOV 1127 | NOV 0719 | NOV 0710 | NOV 0712 |
|---|---|---|---|---|---|
| 551-563 | TRKNGYNRHEMST (SEQ ID NO: 354) | -0.2 | -0.1 | -0.4 | -0.4 |
| 587-602 | RVCACDHHGNMQSCHA (SEQ ID NO: 440) | -0.1 | -0.3 | -0.3 | -0.4 |
| 591-602 | CDHHGNMQSCHA (SEQ ID NO: 441) | -0.2 | -0.6 | -0.4 | -0.6 |

TABLE 10

Effect of NOV0710 and NOV0712 on hCDH6 (267-615) containing cadherin 3-5 domains.

| Peptide Name | Sequence | Change in Deuterium Incorporation (Daltons) NOV0710 | NOV0712 |
|---|---|---|---|
| 274-283 | QFKTPESSPP (SEQ ID NO: 442) | -0.4 | -0.3 |
| 275-294 | FKTPESSPPGTPIGRIKASD (SEQ ID NO: 443) | 0.3 | 0.3 |
| 275-294 | FKTPESSPPGTPIGRIKASDA (SEQ ID NO: 444) | 0.3 | 0.4 |
| 282-294 | PPGTPIGRIKASD (SEQ ID NO: 445) | 0.2 | 0.1 |
| 295-302 | ADVGENAE (SEQ ID NO: 446) | -0.9 | -0.9 |
| 303-312 | IEYSITDGEG (SEQ ID NO: 447) | -0.7 | -0.6 |
| 303-315 | IEYSITDGEGLDM (SEQ ID NO: 343) | -1.1 | -1.1 |
| 306-312 | SITDGEG (SEQ ID NO: 448) | -0.6 | -0.5 |
| 308-315 | TDGEGLDM (SEQ ID NO: 449) | -0.7 | -0.8 |
| 316-323 | FDVITDQE (SEQ ID NO: 450) | 0.1 | 0.1 |
| 316-326 | FDVITDQETQE (SEQ ID NO: 451) | -0.2 | -0.3 |
| 316-336 | FDVITDQETQEGIITVKKLLD (SEQ ID NO: 452) | 2.2 | 2.0 |
| 316-337 | FDVITDQETQEGIITVKKLLDF (SEQ ID NO: 453) | 2.5 | 2.2 |
| 317-330 | DVITDQETQEGIIT (SEQ ID NO: 454) | -0.8 | -0.8 |
| 317-336 | DVITDQETQEGIITVKKLLD (SEQ ID NO: 455) | 2.0 | 1.8 |
| 318-336 | VITDQETQEGIITVKKLLD (SEQ ID NO: 456) | 2.0 | 1.8 |
| 320-326 | TDQETQE (SEQ ID NO: 457) | -0.6 | -0.6 |
| 321-336 | DQETQEGIITVKKLLD (SEQ ID NO: 458) | 2.3 | 2.1 |
| 321-337 | DQETQEGIITVKKLLDF (SEQ ID NO: 459) | 2.5 | 2.3 |
| 323-336 | ETQEGIITVKKLLD (SEQ ID NO: 460) | 2.1 | 1.9 |
| 324-336 | TQEGIITVKKLLD (SEQ ID NO: 461) | 1.8 | 1.8 |
| 327-336 | GIITVKKLLD (SEQ ID NO: 462) | 1.3 | 1.2 |

TABLE 10-continued

Effect of NOV0710 and NOV0712 on hCDH6 (267-615) containing cadherin 3-5 domains.

| Peptide Name | Sequence | Change in Deuterium Incorporation (Daltons) NOV0710 | NOV0712 |
|---|---|---|---|
| 327-337 | GIITVKKLLDF (SEQ ID NO: 463) | 1.5 | 1.4 |
| 328-337 | IITVKKLLDF (SEQ ID NO: 464) | 1.4 | 1.3 |
| 329-336 | ITVKKLLD (SEQ ID NO: 465) | 1.1 | 1.0 |
| 329-337 | ITVKKLLDF (SEQ ID NO: 466) | 1.3 | 1.2 |
| 330-336 | TVKKLLD (SEQ ID NO: 467) | 1.1 | 0.9 |
| 330-337 | TVKKLLDF (SEQ ID NO: 468) | 1.3 | 1.0 |
| 331-337 | VKKLLDF (SEQ ID NO: 469) | 0.5 | 0.5 |
| 337-344 | FEKKKVYT (SEQ ID NO: 470) | -0.2 | -0.1 |
| 337-345 | FEKKKVYTL (SEQ ID NO: 347) | 0.5 | 0.6 |
| 338-345 | EKKKVYTL (SEQ ID NO: 471) | 0.3 | 0.3 |
| 346-358 | KVEASNPYVEPRF (SEQ ID NO: 472) | -0.7 | -0.4 |
| 348-358 | EASNPYVEPRF (SEQ ID NO: 473) | -0.9 | -0.6 |
| 359-369 | LYLGPFKDSAT (SEQ ID NO: 474) | -0.5 | -0.3 |
| 359-370 | LYLGPFKDSATV (SEQ ID NO: 475) | -0.2 | -0.1 |
| 361-369 | LGPFKDSAT (SEQ ID NO: 476) | -0.4 | -0.2 |
| 370-383 | VRIVVEDVDEPPVF (SEQ ID NO: 477) | 1.8 | 1.7 |
| 370-386 | VRIVVEDVDEPPVFSKL (SEQ ID NO: 478) | 2.0 | 1.9 |
| 373-383 | VVEDVDEPPVF (SEQ ID NO: 479) | 0.5 | 0.5 |
| 376-383 | DVDEPPVF (SEQ ID NO: 480) | 0.4 | 0.4 |
| 376-386 | DVDEPPVFSKL (SEQ ID NO: 481) | -0.1 | 0.0 |
| 376-388 | DVDEPPVFSKLAY (SEQ ID NO: 482) | -0.3 | -0.1 |
| 377-383 | VDEPPVF (SEQ ID NO: 483) | 0.4 | 0.4 |
| 377-386 | VDEPPVFSKL (SEQ ID NO: 484) | -0.2 | -0.1 |
| 407-419 | AQDPDAARNPVKY (SEQ ID NO: 485) | -0.1 | 0.1 |
| 407-427 | AQDPDAARNPVKYSVDRHTDM (SEQ ID NO: 349) | -0.2 | -0.1 |
| 413-427 | ARNPVKYSVDRHTDM (SEQ ID NO: 486) | 0.1 | 0 |
| 421-427 | VDRHTDM (SEQ ID NO: 487) | -0.2 | -0.3 |
| 428-441 | DRIFNIDSGNGSIF (SEQ ID NO: 488) | 0.1 | 0.2 |
| 442-451 | TSKLLDRETL (SEQ ID NO: 489) | 0 | 0 |
| 446-452 | LDRETLL (SEQ ID NO: 490) | -0.3 | -0.1 |
| 459-474 | IATEINNPKQSSRVPL (SEQ ID NO: 491) | 1.0 | 1.1 |
| 459-475 | IATEINNPKQSSRVPLY (SEQ ID NO: 492) | 1.2 | 1.4 |
| 461-475 | TEINNPKQSSRVPLY (SEQ ID NO: 493) | 1.0 | 1.0 |

TABLE 10-continued

Effect of NOV0710 and NOV0712 on hCDH6 (267-615) containing cadherin 3-5 domains.

| Peptide Name | Sequence | Change in Deuterium Incorporation (Daltons) NOV0710 | NOV0712 |
|---|---|---|---|
| 461-478 | TEINNPKQSSRVPLYIKV (SEQ ID NO: 494) | 2.5 | 2.6 |
| 462-474 | EINNPKQSSRVPL (SEQ ID NO: 495) | 0.7 | 0.8 |
| 462-475 | EINNPKQSSRVPLY (SEQ ID NO: 496) | 1.1 | 1.2 |
| 463-475 | INNPKQSSRVPLY (SEQ ID NO: 497) | 1.2 | 1.2 |
| 464-474 | NNPKQSSRVPL (SEQ ID NO: 498) | 1.7 | 1.7 |
| 464-476 | NNPKQSSRVPLYI (SEQ ID NO: 499) | 1.2 | 1.2 |
| 475-488 | YIKVLDVNDNAPEF (SEQ ID NO: 500) | 1.1 | 1.3 |
| 476-483 | IKVLDVND (SEQ ID NO: 501) | 1.1 | 1.1 |
| 476-488 | IKVLDVNDNAPEF (SEQ ID NO: 502) | 0.8 | 1.0 |
| 477-488 | KVLDVNDNAPEF (SEQ ID NO: 503) | 0.4 | 0.4 |
| 479-488 | LDVNDNAPEF (SEQ ID NO: 504) | -0.1 | 0.1 |
| 492-505 | YETFVCEKAKADQL (SEQ ID NO 353) | -1.1 | -1.1 |
| 495-505 | FVCEKAKADQL (SEQ ID NO: 505) | -0.7 | -0.6 |
| 496-505 | VCEKAKADQL (SEQ ID NO: 506) | -0.8 | -0.7 |
| 499-505 | KAKADQL (SEQ ID NO: 507) | -0.7 | -0.7 |
| 506-513 | IQTLHAVD (SEQ ID NO: 508) | 0.3 | 0.4 |
| 506-522 | IQTLHAVDKDDPYSGHQ (SEQ ID NO: 509) | 0 | 0.1 |
| 506-524 | IQTLHAVDKDDPYSGHQFS (SEQ ID NO: 510) | 0.1 | 0.1 |
| 506-525 | IQTLHAVDKDDPYSGHQFSF (SEQ ID NO: 511) | -0.1 | 0 |
| 510-522 | HAVDKDDPYSGHQ (SEQ ID NO: 512) | -0.4 | -0.3 |
| 510-524 | HAVDKDDPYSGHQFS (SEQ ID NO: 513) | -0.3 | -0.2 |
| 510-525 | HAVDKDDPYSGHQFSF (SEQ ID NO: 356) | -0.5 | -0.4 |
| 512-522 | VDKDDPYSGHQ (SEQ ID NO: 359) | -0.6 | -0.6 |
| 512-525 | VDKDDPYSGHQFSF (SEQ ID NO: 514) | -0.5 | -0.4 |
| 542-550 | NKDNTAGIL (SEQ ID NO: 357) | -0.5 | -0.6 |
| 549-563 | ILTRKNGYNRHEMST (SEQ ID NO: 515) | -0.5 | -0.4 |
| 551-563 | TRKNGYNRHEMST (SEQ ID NO: 354) | -0.6 | -0.5 |
| 552-563 | RKNGYNRHEMST (SEQ ID NO: 516) | -0.7 | -0.8 |
| 564-571 | YLLPVVIS (SEQ ID NO: 517) | -0.1 | 0.1 |
| 564-575 | YLLPVVISDNDY (SEQ ID NO: 518) | -0.5 | -0.4 |
| 564-578 | YLLPVVISDNDYPVQ (SEQ ID NO: 519) | -1.0 | -1.0 |
| 567-586 | PVVISDNDYPVQSSTGTVTV (SEQ ID NO: 520) | -1.5 | -0.8 |

TABLE 10-continued

Effect of NOV0710 and NOV0712 on hCDH6 (267-615) containing cadherin 3-5 domains.

| Peptide Name | Sequence | Change in Deuterium Incorporation (Daltons) NOV0710 | NOV0712 |
|---|---|---|---|
| 587-600 | RVCACDHHGNMQSC (SEQ ID NO: 521) | -0.5 | -0.5 |
| 587-602 | RVCACDHHGNMQSCHA (SEQ ID NO: 522) | -0.3 | -0.3 |
| 591-600 | CDHHGNMQSC (SEQ ID NO: 523) | -0.7 | -0.7 |
| 591-602 | CDHHGNMQSCHA (SEQ ID NO: 524) | -0.4 | -0.4 |
| 591-604 | CDHHGNMQSCHAEA (SEQ ID NO: 358) | -0.6 | -0.8 |
| 592-602 | DHHGNMQSCHA (SEQ ID NO: 525) | -0.6 | -0.6 |
| 605-618 | LIHPTGLSTGAGSE (SEQ ID NO: 526) | -0.5 | -0.4 |
| 619-625 | FRHDSGL (SEQ ID NO: 527) | -0.3 | -0.2 |
| 619-627 | FRHDSGLND (SEQ ID NO: 528) | -0.4 | -0.4 |
| 630-637 | EAQKIEWH (SEQ ID NO: 529) | -0.6 | -0.5 |
| 630-638 | EAQKIEWHE (SEQ ID NO: 530) | -0.8 | -0.7 |

Example 7: Epitope Mapping by X-Ray Crystallography

The crystal structures of a human CDH6 fragment (extracellular domain 5, or EC5, SEQ ID NO: 443, Table 11) bound to Fab fragment of NOV0712 or NOV0710 (SEQ ID NO: 444-447, Table 12 and 13) were determined. As detailed below, CDH6 EC5 was co-expressed with NOV0712 or NOV0710 Fab in mammalian cells to produce a purified complex. Protein crystallography was then employed to generate atomic resolution data for CDH6 EC5 bound to NOV712 or NOV710 Fab and define the epitopes.

Protein Production for Epitope Mapping

The sequences of CDH6 EC5, NOV0712 Fab and NOV0710 Fab produced for crystallography are shown in Table 9 above. The CDH6 EC5 construct comprises residues 490 to 608 shown as underlined in the context of human CDH6 (UniProt identifier P55285, SEQ ID NO: 533, Table 11), and shown below in Table 11 as SEQ ID NO: 534. The N-terminal signal sequence from mouse IgG kappa light chain is used for secreted expression of CDH6 EC5 and is cleaved during expression, leaving intact N-terminus of CDH6 EC5. The C-terminus of CDH6 EC5 is fused with a purification tag derived from β amyloid (APP tag, amino acids: EFRHDS (SEQ ID NO:531)), preceded by a PreScission® protease (GE Healthcare, Piscataway, N.J.) recognition site (amino acids: LEVLFQGP (SEQ ID NO:532)) to facilitate cleavage and removal of tag after purification. For NOV0712 and NOV0710 Fab, the sequences of heavy and light chains are shown (SEQ ID NO:535-538).

TABLE 11

Proteins used for structural biology studies

| Construct | Amino acid sequence in one letter code | SEQ ID NO |
|---|---|---|
| Human CDH6 (P55285) | MRTYRYFLLLFWVGQPYPTLSTPLSKRTSGFPAKKRALEL SGNSKNELNRSKRSWMWNQFFLLEEYTGSDYQYVGKLHS DQDRGDGSLKYILSGDGAGDLFIINENTGDIQATKRLDREE KPVYILRAQAINRRTGRPVEPESEFIIKIHDINDNEPIFTKEV YTATVPEMSDVGTFVVQVTATDADDPTYGNSAKVVYSIL QGQPYFSVESETGIIKTALLNMDRENREQYQVVIQAKDMG GQMGGLSGTTTVNITLTDVNDNPPRFPQSTYQFKTPESSPP GTPIGRIKASDADVGENAEIEYSITDGEGLDMFDVITDQET QEGIITVKKLLDFEKKKVYTLKVEASNPYVEPRFLYLGPFK DSATVRIVVEDVDEPPVFSKLAYILQIREDAQINTTIGSVTA QDPDAARNPVKYSVDRHTDMDRIFNIDSGNGSIFTSKLLD RETLLWHNITVIATEINNPKQSSRVPLYIKVLDVNDNAPEF AEFYETFVCEKAKADQLIQTLHAVDKDDPYSGHQFSFSLA PEAASGSNFTIQDNKDNTAGILTRKNGYNRHEMSTYLLPV VISDNDYPVQSSTGTVTVRVCACDHHGNMQSCHAEALIHP TGLSTGALVAILLCIVILLVTVVLFAALRRQRKKEPLIISKE DIRDNIVSYNDEGGGEEDTQAFDIGTLRNPEAIEDNKLRRD | (SEQ ID NO: 533) |

TABLE 11-continued

Proteins used for structural biology studies

| Construct | Amino acid sequence in one letter code | SEQ ID NO |
|---|---|---|
| | IVPEALFLPRRTPTARDNTDVRDFINQRLKENDTDPTAPPY DSLATYAYEGTGSVADSLSSLESVTTDADQDYDYLSDWG PRFKKLADMYGGVDSDKDS | |
| CDH6 EC5 construct | EFYETFVCEKAKADQLIQTLHAVDKDDPYSGHQFSFSLAP EAASGSNFTIQDNKDNTAGILTRKNGYNRHEMSTYLLPVV ISDNDYPVQSSTGTVTVRVCACDHHGNMQSCHAEALIHP | (SEQ ID NO: 534) |
| NOV0712 Fab heavy chain | QVQLLESGGGLVQPGGSLRLSCAASGFTFSSHGMHWVRQ APGKGLEWVSVISGSGSNTGYADSVKGRFTISRDNSKNTL YLQMNSLRAEDTAVYYCARQWGSYAFDSWGQGTLVTVS SASTKGPSVFPLAPSSKSTSGGTAALGCLVKDYFPEPVTVS WNSGALTSGVHTFPAVLQSSGLYSLSSVVTVPSSSLGTQTY ICNVNHKPSNTKVDKRVEPKSCDKTH | (SEQ ID NO: 535) |
| NOV0712 Fab light chain | DIQMTQSPSSLSASVGDRVTITCRASQSISSYLNWYQQKPG KAPKLLIYAVSTLQSGVPSRFSGSGSGTDFTLTISSLQPEDF ATYYCQQSGTFPPTTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSS PVTKSFNRGEC | (SEQ ID NO: 536) |
| NOV0710 Fab heavy chain | QVQLLESGGGLVQPGGSLRLSCAASGFTFSSYAMSWVRQ APGKGLEWVSVIRSSGSSTYYADSVKGRFTISRDNSKNTLY LQMNSLRAEDTAVYYCARGGGYFDYWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICN VNHKPSNTKVDKRVEPKSCDKTH | (SEQ ID NO: 537) |
| NOV0710 Fab light chain | DIQMTQSPSSLSASVGDRVTITCRASQSISLWLNWYQQKPG KAPKLLIYAASTLQSGVPSRFSGSGSGTDFTLTISSLQPEDF ATYYCQQYYTSPYTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSS PVTKSFNRGEC | (SEQ ID NO: 538) |
| CDH6-D574A | MRTYRYFLLLFWVGQPYPTLSTPLSKRTSGFPAKKRALEL SGNSKNELNRSKRSWMWNQFFLLEEYTGSDYQYVGKLHS DQDRGDGSLKYILSGDGAGDLFIINENTGDIQATKRLDREE KPVYILRAQAINRRTGRPVEPESEFIIKIHDINDNEPIFTKEV YTATVPEMSDVGTFVVQVTATDADDPTYGNSAKVVYSIL QGQPYFSVESETGIIKTALLNMDRENREQYQVVIQAKDMG GQMGGLSGTTTVNITLTDVNDNPPRFPQSTYQFKTPESSPP GTPIGRIKASDADVGENAEIEYSITDGEGLDMFDVITDQET QEGIITVKKLLDFEKKKVYTLKVEASNPYVEPRFLYLGPFK DSATVRIVVEDVDEPPVFSKLAYILQIREDAQINTTIGSVTA QDPDAARNPVKYSVDRHTDMDRIFNIDSGNGSIFTSKLLD RETLLWHNITVIATEINNPKQSSRVPLYIKVLDVNDNAPEF AEFYETFVCEKAKADQLIQTLHAVDKDDPYSGHQFSFSLA PEAASGSNFTIQDNKDNTAGILTRKNGYNRHEMSTYLLPV VISDNDYPVQSSTGTVTVRVCACDHHGNMQSCHAEALIHP TGLSTGALVAILLCIVILLVTVVLFAALRRQRKKEPLIISKE DIRDNIVSYNDEGGGEEDTQAFDIGTLRNPEAIEDNKLRRD IVPEALFLPRRTPTARDNTDVRDFINQRLKENDTDPTAPPY DSLATYAYEGTGSVADSLSSLESVTTDADQDYDYLSDWG PRFKKLADMYGGVDSDKDS | (SEQ ID NO: 539 |
| CDH6-Y575A | MRTYRYFLLLFWVGQPYPTLSTPLSKRTSGFPAKKRALEL SGNSKNELNRSKRSWMWNQFFLLEEYTGSDYQYVGKLHS DQDRGDGSLKYILSGDGAGDLFIINENTGDIQATKRLDREE KPVYILRAQAINRRTGRPVEPESEFIIKIHDINDNEPIFTKEV YTATVPEMSDVGTFVVQVTATDADDPTYGNSAKVVYSIL QGQPYFSVESETGIIKTALLNMDRENREQYQVVIQAKDMG GQMGGLSGTTTVNITLTDVNDNPPRFPQSTYQFKTPESSPP GTPIGRIKASDADVGENAEIEYSITDGEGLDMFDVITDQET QEGIITVKKLLDFEKKKVYTLKVEASNPYVEPRFLYLGPFK DSATVRIVVEDVDEPPVFSKLAYILQIREDAQINTTIGSVTA QDPDAARNPVKYSVDRHTDMDRIFNIDSGNGSIFTSKLLD RETLLWHNITVIATEINNPKQSSRVPLYIKVLDVNDNAPEF AEFYETFVCEKAKADQLIQTLHAVDKDDPYSGHQFSFSLA PEAASGSNFTIQDNKDNTAGILTRKNGYNRHEMSTYLLPV VISDNDYPVQSSTGTVTVRVCACDHHGNMQSCHAEALIHP | (SEQ ID NO: 540) |

TABLE 11-continued

| Proteins used for structural biology studies | | |
|---|---|---|
| Construct | Amino acid sequence in one letter code | SEQ ID NO |
| | TGLSTGALVAILLCIVILLVTVVLFAALRRQRKKEPLIISKE DIRDNIVSYNDEGGGEEDTQAFDIGTLRNPEAIEDNKLRRD IVPEALFLPRRTPTARDNTDVRDFINQRLKENDTDPTAPPY DSLATYAYEGTGSVADSLSSLESVTTDADQDYDYLSDWG PRFKKLADMYGGVDSDKDS | |
| CDH6-N573A | MRTYRYFLLLFWVGQPYPTLSTPLSKRTSGFPAKKRALEL SGNSKNELNRSKRSWMWNQFFLLEEYTGSDYQYVGKLHS DQDRGDGSLKYILSGDGAGDLFIINENTGDIQATKRLDREE KPVYILRAQAINRRTGRPVEPESEFIIKIHDINDNEPIFTKEV YTATVPEMSDVGTFVVQVTATDADDPTYGNSAKVVYSIL QGQPYFSVESETGIIKTALLNMDRENREQYQVVIQAKDMG GQMGGLSGTTTVNITLTDVNDNPPRFPQSTYQFKTPESSPP GTPIGRIKASDADVGENAEIEYSITDGEGLDMFDVITDQET QEGIITVKKLLDFEKKKVYTLKVEASNPYVEPRFLYLGPFK DSATVRIVVEDVDEPPVFSKLAYILQIREDAQINTTIGSVTA QDPDAARNPVKYSVDRHTDMDRIFNIDSGNGSIFTSKLLD RETLLWHNITVIATEINNPKQSSRVPLYIKVLDVNDNAPEF AEFYETFVCEKAKADQLIQTLHAVDKDDPYSGHQFSFSLA PEAASGSNFTIQDNKDNTAGILTRKNGYNRHEMSTYLLPV VISDNDYPVQSSTGTVTVRVCACDHHGNMQSCHAEALIHP TGLSTGALVAILLCIVILLVTVVLFAALRRQRKKEPLIISKE DIRDNIVSYNDEGGGEEDTQAFDIGTLRNPEAIEDNKLRRD IVPEALFLPRRTPTARDNTDVRDFINQRLKENDTDPTAPPY DSLATYAYEGTGSVADSLSSLESVTTDADQDYDYLSDWG PRFKKLADMYGGVDSDKDS | (SEQ ID NO: 541 |

CDH6 EC5 was co-expressed with NOV0712 or NOV0710 Fab in Expi293® cells to produce complex for crystallography. In detail, 0.5 mg of plasmid encoding CDH6 EC5 was mixed with 0.5 mg of NOV0712 or NOV0710 Fab plasmid, diluted into 50 ml of OptiMEM I medium (Life Technologies, Grand Island, N.Y.), and incubated with 2.5 mg of PEI (Polysciences, Warrington, Pa.) in 50 ml of the same medium for 30 minutes. The mixture was then added into 1 L of Expi293® cells growing in suspension in Expi293® Expression medium (Life Technologies Grand Island, N.Y.) at 1 million cells/ml at 37° C. with 8% of CO2 for transfection. After 72 hours, the medium which contains CDH6 EC5-Fab complex was harvested by centrifugation, and supplemented with CaCl2 to 3 mM. 10 ml of Sepharose® 4B beads (GE Healthcare Pittsburgh, Pa.) conjugated with an anti-APP tag IgG (generated in-house) were then added into the medium and kept stirring at 4° C. overnight. The next day the beads were packed into a gravity column and washed with 25 mM Hepes pH 7.4+150 mM NaCl (HBS), and 3 mM CaCl2. The target complex was eluted with 3 column volumes (CV) of 100 mM glycine pH 2.5, 150 mM NaCl, 3 mM CaCl2, into 1/10 (v/v) of 1 M Tris pH 8.5. The complex was incubated with 1/100 (w/w) GST-tagged PreScission® protease (GE Healthcare, Pittsburgh, Pa.) at 4° C. overnight to cleave APP tag. The next day, PreScission® protease was removed by passing the mixture through a 1 ml GSTrap® HP column (GE Healthcare, Pittsburgh, Pa.). The flow-through was then incubated with 1/10 (w/w) of PNGaseF (purified in house) at 37° C. overnight to remove N-linked glycosylation. After deglycosylation, the mixture was concentrated and loaded onto HiLoad 16/600 Superdex® 200 pg (GE Healthcare, Pittsburgh, Pa.) equilibrated in HBS plus 3 mM CaCl2. Peak fractions containing purified CDH6-Fab complex were analyzed by SDS-PAGE and LCMS, pooled and concentrated for crystallization.

Crystallization and Structure Determination

CDH6 EC5/NOV0712 and CDH6 EC5/NOV0710 complexes were concentrated to 9.3 mg/ml and 14.7 mg/ml, respectively, centrifuged at 20,000 g for 5 minutes, and screened for crystallization. Crystals for data collection were grown by hanging drop vapor diffusion at 20° C. Crystals of CDH6 EC5/NOV0712 complex were grown by mixing 1.2 µl of the complex with 1 µl of reservoir solution containing 20% (v/v) PEG3350 and 0.2 M di-ammonium hydrogen citrate, and equilibrating the drop against 450 µl of the same reservoir solution plus 50 µl water. Crystals of CDH6 EC5/NOV0710 complex are grown by mixing 0.8 µl of the complex with 1 µl of reservoir solution containing 0.7 M tri-sodium citrate and 0.1 M Tris.HCl pH 8.5, and equilibrating the drop against 425 µl of the same reservoir solution plus 75 µl water. Before data collection, the crystals were transferred to 75% of reservoir solutions plus 25% glycerol and flash cooled in liquid nitrogen.

Diffraction data were collected at beamline 17-ID at the Advanced Photon Source (Argonne National Laboratory, USA). Data are processed and scaled using Autoproc (Global Phasing, LTD). The data of CDH6 EC5/NOV0712 was processed to 2.3 Å in space group P212121 with cell dimensions a=78.83 Å, b=88.86 Å, c=186.73 Å, alpha=90°, beta=90°, gamma=90°. The data of CDH6 EC5/NOV0710 complex was processed to 3.5 Å in space group P43212 with cell dimensions a=101.48 Å, b=101.48 Å, c=240.96 Å, alpha=90°, beta=90°, gamma=90°. The structures of the complexes were solved by molecular replacement using Phaser (McCoy et al., (2007) J. Appl. Cryst. 40:658-674) with in-house Fab structures as search models. The structure of CDH6 EC5 was built from scratch using Buccaneer (K. Cowtan (2006) Acta Cryst. D62:1002-1011) in the CCP4 program suite (Winn et al., (2011) Acta. Cryst. D67:235-242). The final models were built in COOT (Emsley & Cowtan (2004) Acta Cryst. D60:2126-2132) and refined with Buster (Global Phasing, LTD, Cambridge, UK). For the CDH6 EC5/NOV0712 complex, the Rwork and Rfree values are 21.2% and 25.2%, respectively; and root-meansquare (r.m.s) deviation values of bond lengths and bond angles are 0.010 Å and 1.24°, respectively. For the CDH6 EC5/NOV0710 complex, the Rwork and Rfree values are 18.2% and 24.6%, respectively; and r.m.s deviation values of bond lengths and bond angles are 0.010 Å and 1.28°, respectively.

Residues of CDH6 EC5 that are in contact with NOV0712 or NOV0710 Fab, the types of interactions, and the buried surface areas are all identified by PISA (Krissinel et al., (2007) J Mol Biol. 372:774-97) and listed in Tables 12 and 13. For the structures that contain more than one copy of complex in the asymmetric unit (the smallest unique unit in the crystal), only those antibody-contacting residues that are common in all copies are listed as epitope residues.

Epitopes of NOV0712 and NOV0710 on CDH6

Overall Structures

Figure 4:
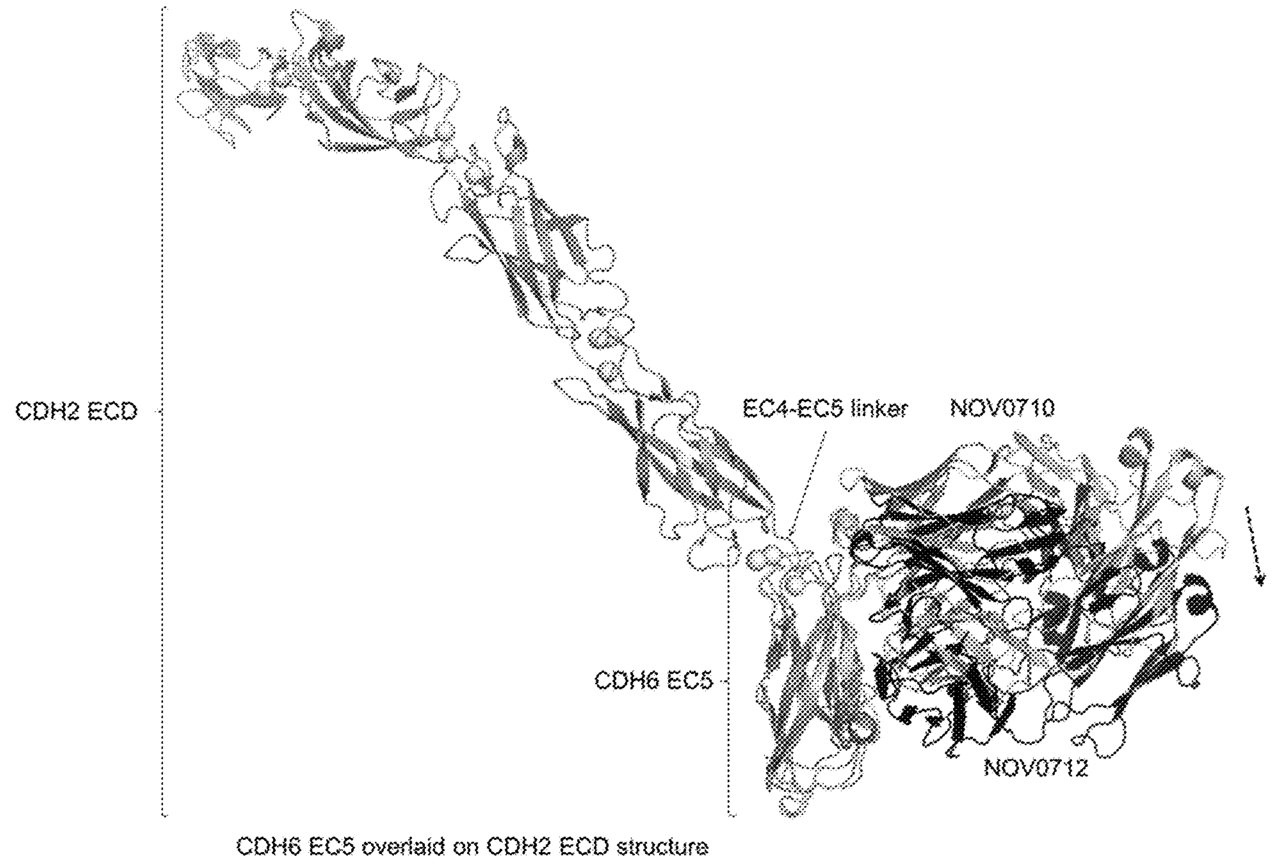
FIG. 4 is the crystal structure of NOV0710 binding to CDH6 EC5 domain overlaid onto the known structure of the CDH2 ECD.

There is no reported crystal structure of CDH6 EC5 at this time. The overall folding of CDH6 EC5 is similar to that of CDH2 (N-Cadherin) EC5, both composed by one three-strand β sheet stacking against another four-strand β sheet. Overlay of the two structures results in a small root-mean-square distance (RMSD) of 2.4 Å and similar orientation of the N- and C-terminus. Thus one can overlay the CDH6 EC5/Fab complex structure onto the full-length ECD structure of CDH2 based on the superposition of EC5 domains, in order to estimate the orientations and NOV0712 and NOV0710 Fab. As shown in FIG. 4, NOV0712 and NOV0710 bind the same side of CDH6 EC5, and share a significantly overlapped epitope. NOV0712 binds slightly shifted away from the EC4-EC5 linker compared to NOV0710.

Epitope of NOV0712

Figure 5:
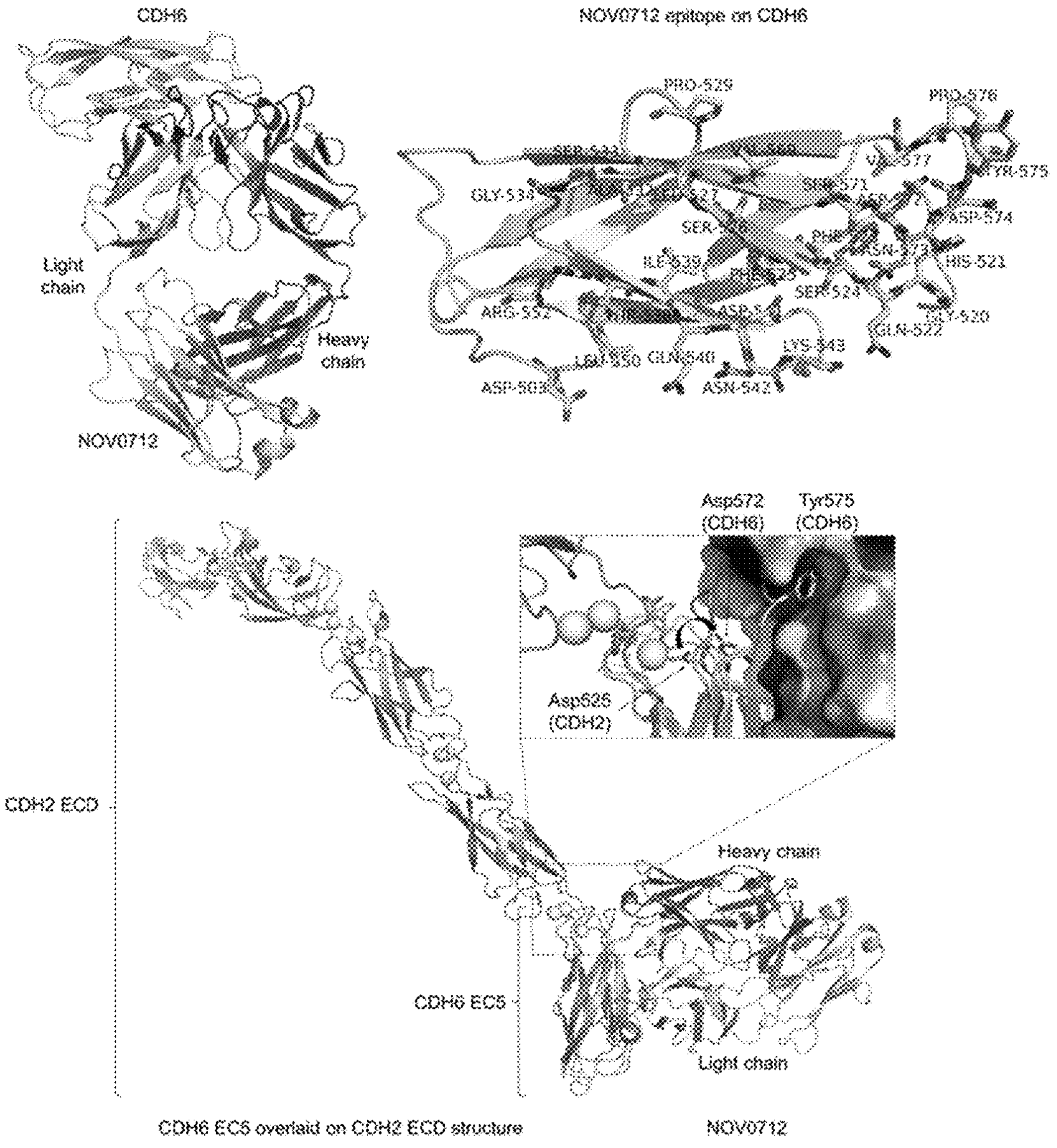
FIG. 5 depicts the crystal structure of NOV0712 binding to CDH6.

The crystal structure of the CDH6 EC5/NOV0712 complex is used to identify the NOV0712 epitope on CDH6. The interaction surface on CDH6 EC5 by NOV0712 Fab is formed by several continuous and discontinuous (i.e. non-contiguous) sequences: namely residues 503, 520-527, 529, 532-534, 538-543, 550, 552, 569, and 571-577, as detailed in Table 12. These residues form the three-dimensional conformational epitope that is recognized by NOV0712 Fab (FIG. 5 upper panel). This epitope defined by crystallography is in good agreement with that defined by hydrogen deuterium exchange mass spectrometry (HDx-MS), in which residues 572-586 are substantially protected by NOV0712. Interestingly, a potential Ca2+-binding loop of CDH6 EC5 (residues 571-579) has majority of it (8 out 10 residues) in contact with NOV0712, especially Tyr575 and Asn573 which are almost completely buried by the antibody (Table 12 and FIG. 5 lower panel). Compared with CDH2 structure, this Ca2+-binding loop of CDH6 EC5 is in an "out" conformation induced by NOV0712 binding (e.g. Asp572 of CDH6 is flipped out compared with its corresponding residue Asp525 in CDH2).

TABLE 12

NOV0712 epitope on CDH6. All residues of CDH6 that are in contact with NOV0712 in the crystal structure are identified by PISA, listed and sorted by their buried surface area by NOV0712. Types of interaction are also listed where applicable.

| Residue name | Residue number | Accessible surface area (ASA, Å$^2$) | Buried surface area (BSA) by heavy chain (Å$^2$) | BSA by light chain (Å$^2$) | Total BSA by NOV0712 (Å$^2$) | BSA/ ASA (%) | Type of interaction |
|---|---|---|---|---|---|---|---|
| TYR | 575 | 205.77 | 131.73 | 47.11 | 178.84 | 86.91 | H-SC[1], H-MC[2], Hydrophobic |
| ASN | 573 | 106.72 | 103.67 | 0 | 103.67 | 97.14 | H-SC, H-MC |
| LYS | 543 | 147.48 | 65.84 | 37.33 | 103.17 | 69.96 | Salt bridge |
| ARG | 552 | 148.25 | 0 | 78.9 | 78.9 | 53.22 | H-SC |
| ASP | 574 | 104.57 | 68.99 | 0 | 68.99 | 65.97 | H-SC, H-MC |
| GLN | 540 | 99.91 | 0 | 68.29 | 68.29 | 68.35 | H-SC |
| PRO | 529 | 122.44 | 0 | 65.25 | 65.25 | 53.29 | |
| ALA | 532 | 67.01 | 0 | 64.9 | 64.9 | 96.85 | H-MC |
| SER | 533 | 103.84 | 0 | 59.58 | 59.58 | 57.38 | H-SC |
| VAL | 577 | 97.82 | 53.24 | 0 | 53.24 | 54.43 | H-MC |
| SER | 526 | 52.04 | 0 | 47.12 | 47.12 | 90.55 | |
| ASP | 541 | 45.28 | 8.86 | 36.42 | 45.28 | 100.00 | H-MC |
| GLN | 522 | 100.04 | 45.14 | 0 | 45.14 | 45.12 | |
| SER | 524 | 43.52 | 26.98 | 16.54 | 43.52 | 100.00 | |
| GLY | 520 | 64.48 | 32.88 | 0 | 32.88 | 50.99 | H-MC |
| ASP | 503 | 113.22 | 0 | 32.06 | 32.06 | 28.32 | |
| ILE | 539 | 31.09 | 0 | 29.09 | 29.09 | 93.57 | H-MC |
| HIS | 521 | 104.3 | 23.91 | 0 | 23.91 | 22.92 | |
| THR | 538 | 39.69 | 0 | 23 | 23 | 57.95 | |
| LEU | 527 | 24.51 | 0 | 20.01 | 20.01 | 81.64 | H-MC |
| PRO | 576 | 111.16 | 17.57 | 0 | 17.57 | 15.81 | |
| ASN | 542 | 72.05 | 0 | 17.39 | 17.39 | 24.14 | |
| PHE | 525 | 15.47 | 0.95 | 14.52 | 15.47 | 100.00 | |
| SER | 571 | 16.16 | 6.96 | 7.1 | 14.06 | 87.00 | |
| VAL | 569 | 23.13 | 0 | 8.54 | 8.54 | 36.92 | |
| LEU | 550 | 23.71 | 0 | 7.9 | 7.9 | 33.32 | |
| GLY | 534 | 71.3 | 0 | 5.13 | 5.13 | 7.19 | |
| PHE | 523 | 9.81 | 4.5 | 0 | 4.5 | 45.87 | |
| ASP | 572 | 23.71 | 2.26 | 0 | 2.26 | 9.53 | |

[1]Hydrogen bond by side-chain atoms;

[2]Hydrogen bond by main-chain atoms

Epitope of NOV0710

Figure 6:
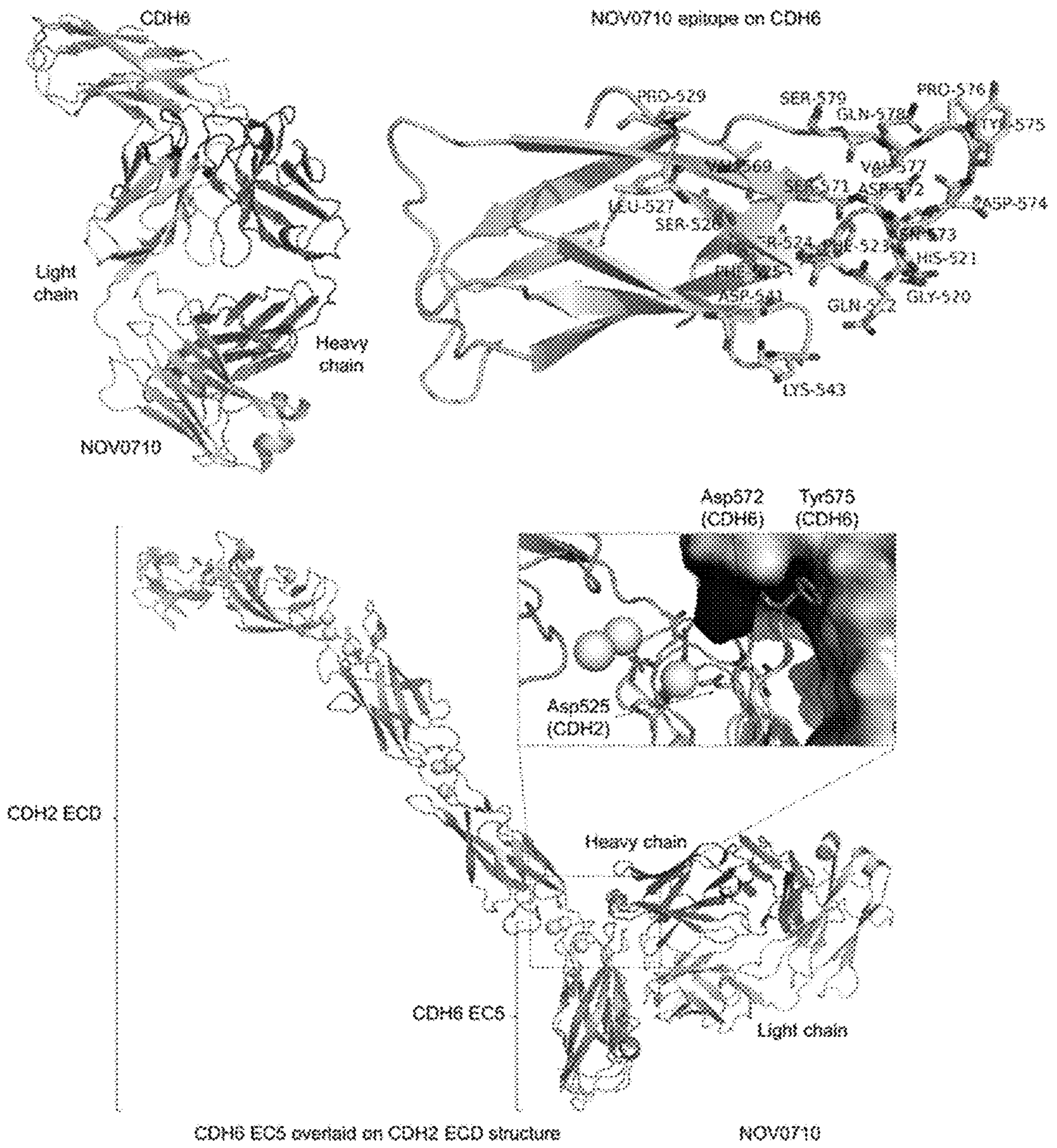
FIG. 6 depicts the crystal structure of NOV0710 binding to CDH6.

The crystal structure of the CDH6 EC5/NOV0710 complex is used to identify the NOV0710 epitope on CDH6. The interaction surface on CDH6 EC5 by NOV0712 Fab is formed by several continuous and discontinuous (i.e. non-contiguous) sequences: namely residues 520-527, 529, 541, 543, 569, and 571-579, as detailed in Table 13. These residues form the three-dimensional conformational epitope that is recognized by NOV0710 Fab (FIG. 6 upper panel). This epitope defined by crystallography is in good agreement with that defined by hydrogen deuterium exchange mass spectrometry (HDx-MS), in which residues 572-586 are substantially protected by NOV0710. Interestingly, similar as in the CDH6 EC5/NOV0712 complex structure, all residues in the potential Ca2+-binding loop of CDH6 EC5 (residues 571-579) are in contact with NOV0710; among which Tyr575, Asn573 and Asp574 are almost completely buried by the antibody (Table 13 and FIG. 6 lower panel). Compared with CDH2 structure, this Ca2+-binding loop of CDH6 EC5 is in an "out" conformation induced by NOV0710 binding (e.g. Asp572 of CDH6 is flipped out compared with its corresponding residue Asp525 in CDH2).

(Nunc) were coated overnight at 4° C. with 1 ug/ml, 100 ul/well of the appropriate recombinant human protein (CDH6 wt, CDH6-N573A, CDH6-D574A or CDH6-Y575A). All wells were then washed three times with PBS/0.1% Tween-20, blocked for one hour with PBS/1% BSA/0.1% Tween-20 and washed three times with PBS/0.1% Tween-20. A serial dilution of anti-CDH6 antibodies was added to the relevant wells (100 nM starting concentration; 5-fold serial dilution) and plates were incubated at room temperature for two hours. Plates were washed three times with PBS/0.1% Tween-20 prior to the addition of a goat anti-human peroxidase linked detection antibody (Pierce, #31412, Thermo, Rockford, Ill.). diluted 1/10000 in PBS/1% BSA/0.1% Tween-20. Plates were incubated at room temperature for one hour before washing three times with PBS/0.1% Tween-20. 100 μl TMB (3,3',5,5' tetramethyl benzidine) substrate solution (BioFx) was added to all wells for 6 minutes before stopping the reaction with 50 μl 2.5% H2SO4. The extent of CDH6 antibody binding to each recombinant protein was determined by measuring the OD450 using a SpectraMax plate reader (Molecular Devices). Dose response curves were analyzed using Graphpad Prism.

TABLE 13

NOV0710 epitope on CDH6. All residues of CDH6 that are in contact with NOV0710 in the crystal structure are identified by PISA, listed and sorted by their buried surface area by NOV0710. Types of interaction are also listed where applicable.

| Residue name | Residue number | Accessible surface area (ASA) ($Å^2$) | Buried surface area (BSA) by heavy chain ($Å^2$) | BSA by light chain ($Å^2$) | Total BSA by NOV0710 ($Å^2$) | BSA/ASA (%) | Type of interaction |
|---|---|---|---|---|---|---|---|
| TYR | 575 | 201.38 | 147.28 | 54.1 | 201.38 | 100.00 | H-MC[1], Hydrophobic |
| ASN | 573 | 128.75 | 116.17 | 4.34 | 120.51 | 93.60 | H-SC[2], H-MC |
| ASP | 574 | 95.9 | 87.31 | 0 | 87.31 | 91.04 | Salt bridge |
| LYS | 543 | 145.5 | 0 | 78.92 | 78.92 | 54.24 | H-SC |
| VAL | 577 | 93.73 | 21.59 | 52.36 | 73.95 | 78.90 | |
| PRO | 529 | 133.4 | 0 | 72.75 | 72.75 | 54.54 | |
| SER | 526 | 58.42 | 0 | 46.58 | 46.58 | 79.73 | |
| SER | 524 | 40.31 | 17.45 | 22.86 | 40.31 | 100.00 | H-SC |
| GLN | 522 | 108.66 | 29.79 | 0 | 29.79 | 27.42 | |
| SER | 571 | 28.68 | 0.34 | 24.21 | 24.55 | 85.60 | |
| PRO | 576 | 83.21 | 24.36 | 0 | 24.36 | 29.28 | H-MC |
| ASP | 541 | 33.17 | 0 | 22.2 | 22.2 | 66.93 | H-SC |
| GLY | 520 | 74.53 | 17.18 | 0 | 17.18 | 23.05 | |
| VAL | 569 | 26.11 | 0 | 16.9 | 16.9 | 64.73 | |
| SER | 579 | 82.89 | 0 | 13.6 | 13.6 | 16.41 | |
| GLN | 578 | 116.86 | 13.18 | 0 | 13.18 | 11.28 | |
| HIS | 521 | 84.59 | 10.25 | 0 | 10.25 | 12.12 | |
| LEU | 527 | 41.01 | 0 | 10.07 | 10.07 | 24.55 | |
| ASP | 572 | 18.64 | 6.51 | 0 | 6.51 | 34.92 | Salt bridge |
| PHE | 525 | 9.03 | 0 | 5.15 | 5.15 | 57.03 | |
| PHE | 523 | 15.28 | 0.31 | 0 | 0.31 | 2.03 | |

[1]Hydrogen bond by side-chain atoms;
[2]Hydrogen bond by main-chain atoms

Figure 7:
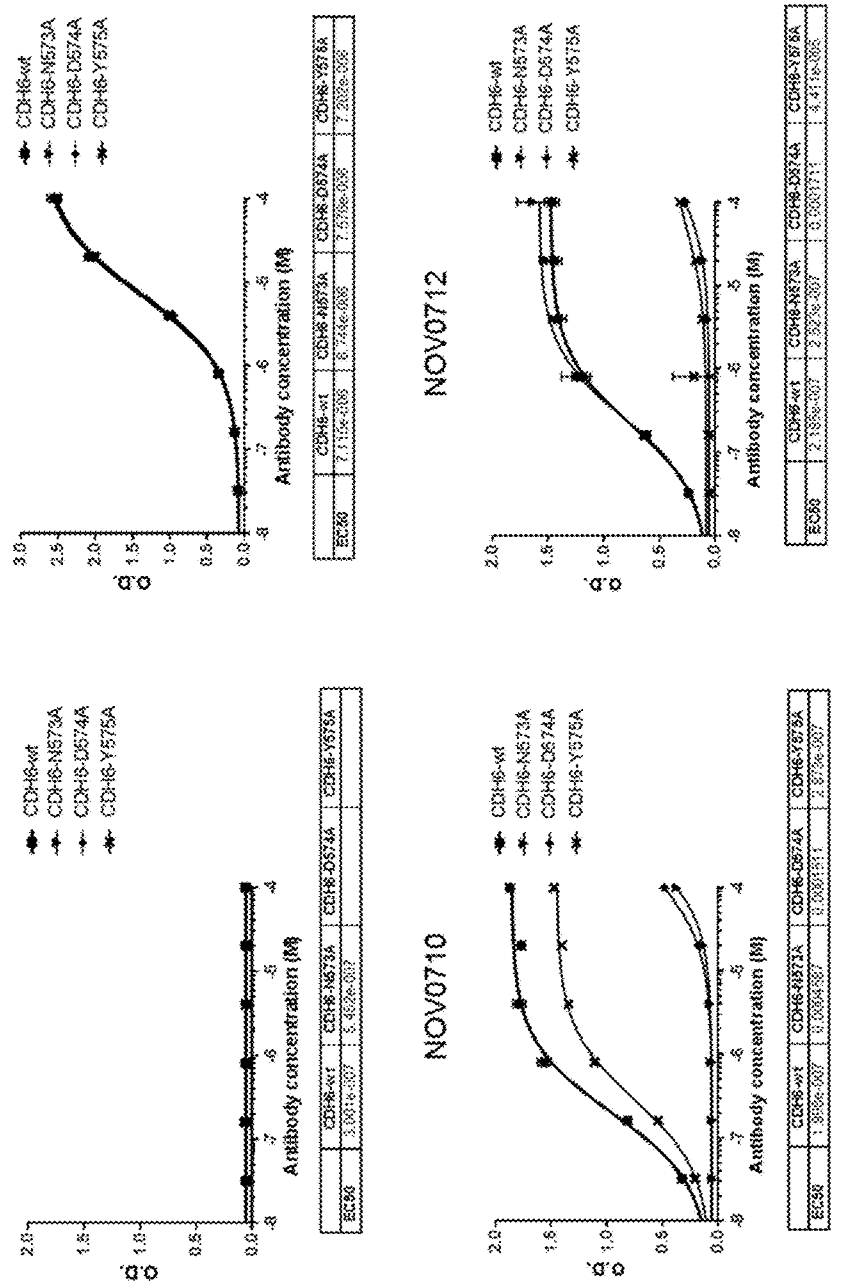
FIG. 7 is an ELISA assay showing the ability of three anti-CDH6 antibodies to bind to mutant forms of CDH6.

Example 8: ELISA Assay to Validate Co-Crystal Structure and Determine Binding of Anti-CDH6 Antibodies to Wild-Type and Mutant CDH6 Proteins Analysis of the CDH6 protein/NOV0710 or /NOV0712 crystal structures highlighted several amino acid residues (Asn573, Asp574 and Tyr575) with high buried surface values, suggesting they might be important for mediating the interaction of the antibodies with the CDH6 protein. We produced recombinant mutant CDH6 protein, replacing these residues by alanine (Table 11, SEQ ID NOs. 539, 540 and 541) and performed ELISA. 96-well Maxisorp plates As shown in FIG. 7, the D574A mutation abrogated binding of both NOV0710 and NOV712, confirming this residue is an essential component of a shared epitope of the two antibodies. Interestingly, the N573A mutant retains binding to NOV712 but not NOV0710, whereas the Y575A mutant retains binding to NOV0710 but not NOV0712. Of note, neither of these mutations impacted binding of the anti-CDH6 antibody NOV0720, which binds a distinct epitope (NOV0720 is the non-germlined version of NOV1132 in FIG. 2)—indicating the mutants did not alter overall architecture of the proteins. These data further validate the co-crystal structures and confirm that the two antibodies feature overlapping, yet distinct epitopes.

Example 9: Preparation of Antibody Drug Conjugates

Preparation of DM4 Conjugates by One-Step Process

An anti-CDH6 antibody, for example NOV7012, at a concentration of about 10.0 mg/mL, was mixed with DM4 (6.8-fold molar excess relative to the amount of antibody) and then with sulfo-SPDB (about 5.2-fold excess relative to the amount of antibody). The reaction was performed at 20° C. in 20 mM EPPS [4-(2-Hydroxyethyl)-1-piperazinepropanesulfonic acid] buffer (pH 8.1) containing 10% DMA for approximately 16 hours. The reaction was quenched by adding 1 M acetic acid to adjust the pH to 5.0. After pH adjustment, the reaction mixture was filtered through a multi-layer (0.45/0.22 μm) PVDF filter and purified and diafiltered into a 10 mM succinate buffer (pH 4.5) using Tangential Flow Filtration. An example of the instrument parameters for the Tangential Flow Filtration are listed in Table 14 below.

TABLE 14

Instrument parameters for the Tangential Flow Filtration

| TFF Parameter | TFF Set Point |
|---|---|
| Bulk Concentration (Cb - g/L) | 20 |
| TMP (psi) | 12-18 |
| Feed Flow rate (LMH) | 324 |
| Membrane Load (g/m2) | 50-150 |
| Diavolumes | 16 |
| Diafiltration Buffer | 20 mM Succinate, pH 4.5 |
| Temperature (° C.) | room temperature (20-25) |

Conjugates obtained from the process described above were analyzed by: UV spectroscopy for cytotoxic agent loading (Maytansinoid to Antibody Ratio, MAR); SEC-HPLC for determination of conjugate monomer; and reverse-phase HPLC or hydrophobic shielded phase (Hisep)-HPLC for free maytansinoid percentage.

Preparation of ADCs with the SPDB or Sulfo-SPDB Linker and DM4 Cytotoxic Agent

Anti-CDH6 antibodies, for example, antibody NOV0712, were combined with DM4 (6.8 and 10.2-fold molar excess) in 50 mM EPPS buffer (pH 8.1) containing ~10% DMA at 25° C. To this mixture was added N-succinimidyl 4-(2-pyridyldithio)butanoate (SPDB, 4.0 and 6.0-fold molar excess, respectively) such that the final antibody concentration was 4 mg/mL and the final DMA content was 10%. The reaction was allowed to proceed for ~16 hours at 25° C. in 50 EPPS buffer (pH 8.1). The conjugation reaction mixture was purified using a SEPHADEX™ G25 column equilibrated and eluted with 10 mM succinate, 250 mM glycine, 0.5% sucrose, 0.01% Tween 20, pH 5.5. Similar procedures were used to generate anti-CDH6-sulfo-SPDB-DM4 conjugates Either of the above methods is useful in the conjugation of antibodies with SPDB-DM4 or sulfo-SPDB-DM4. Table 15 below provides an example of CDH6 ADCs.

TABLE 15

Properties of DM4-conjugated antibodies

| Ab | MAR | Monomer % | Yield (%) | Free DM (%) |
|---|---|---|---|---|
| NOV0709 | 3.8 | 97 | 84 | 1.6 |
| NOV0691 | 3.6 | 96 | 97 | 1.5 |
| NOV0690 | 3.2 | 97 | 74 | 4.0 |
| NOV0689 | 3.3 | 99 | 96 | 2.0 |
| NOV0670 | 3.1 | 98 | 100 | 1.5 |
| NOV0720 | 3.3 | 99 | 78 | 2.0 |
| NOV0712 | 3.2 | 99 | 78 | 3.1 |
| NOV0674 | 3.2 | 99 | 78 | 2.6 |
| NOV0719 | 3.8 | 98 | 79 | 1.9 |

Preparation of SMCC-DM1 Conjugates by In Situ Process

The anti-CDH6 antibodies can also be conjugated with SMCC-DM1 using an in situ process according to the following procedures. CDH6 antibodies were conjugated to DM1 using the sulfosuccinimidyl 4-(N-maleimidomethyl) cyclohexane-1-carboxylate (sulfo-SMCC) linker. Stock solutions of DM1 and sulfo-SMCC heterobifunctional linker were prepared in DMA. Sulfo-SMCC and DM1 thiol were mixed together to react for 10 minutes at 25° C. in DMA containing 40% v/v of aqueous 50 mM succinate buffer, 2 mM EDTA, pH 5.0, at the ratio of DM1 to linker of 1.3:1 mole equivalent and a final concentration of DM1 of 1.95 mM. The antibody was then reacted with an aliquot of the above in situ generated SMCC-DM1 so that the final conjugation conditions included 2.5 mg/mL of Ab in 50 mM EPPS, pH 8.0, 10% DMA (v/v) and a molar ratio of SMCC:Ab around 6.5. After approximately 18 hours at 25° C., the conjugation reaction mixture was purified using a SEPHADEX® G25 column equilibrated with 10 mM succinate, 250 mM glycine, 0.5% sucrose, 0.01% Tween 20, pH 5.5.

Example 10: Validation of Anti-CDH6 Antibody and ADC Binding in a Panel of CHO Cell Lines Expressing CDH6 from Human, Cynomolgus, Rat or Mouse Origins To validate unconjugated anti-CDH6 antibody and anti-CDH6-ADC binding to cells featuring expression of CDH6 from different species, FACS (Fluorescence Activated Cell sorting) analysis was performed on on CHO cells engineered to express CDH6 from human, cynomolgus, rat and mouse origins. The generation of the CHO cell lines featuring CDH6 expression is described in Example 1; FACS methods are described in Example 3.

As shown in FIG. 8, non-conjugated CDH6 antibody NOV0712 features comparable cellular binding to CDH6 from human, cynomolgus, rat and mouse origin. The NOV0712-sulfo-SPDB-DM4 antibody drug conjugate features a comparable binding profile to non-conjugated NOV0712. This result indicates that the addition of a linker and payload does not interfere with binding affinity or specificity of anti-CDH6 antibodies.

Example 11: Assessment of CDH6 Expression and Cellular Binding of CDH6-Targeting Antibodies and ADCs in a Panel of Ovarian Cancer Cell Lines In preparation for evaluation of cellular activity of CDH6-targeting ADCs, the CDH6 cell surface expression levels were assessed in a panel of ovarian cancer cell lines by FACS. Specifically, a cell suspension was prepared by treating cells in culture with Accutase® Cell Dissociation Reagent (Gibco, #A1110501 Grand Island, N.Y.) according to the manufacturer's instructions followed by washing the cells in FACS buffer (RPMI/1% BSA, Gibco, Grand Island, N.Y.). Cells were resuspended in FACS buffer at $1\times10^6$ cells/ml and aliquoted into a 96-well round bottom plate at 100 μl/well (Corning #CLS3360 Tewksbury, Mass.). Primary antibodies (anti-CDH6-PE (R&D Systems, #FAB2715P Minneapolis, Minn.) and control mouse IgG1 PE conjugate (R&D Systems, #IC002P Minneapolis, Minn.) were diluted in FACS buffer at 5 μg/ml. Following three washes in 200 μl cold FACS buffer, cells were analyzed on a BD FACS Canto II® (BD Biosciences, San Jose, Calif.). Geomean of signal per sample was determined using FlowJo® software.

OVCAR3 endogenously express high levels of CDH6. To generate an isogenic cell line with suppressed CDH6 expression, OVCAR3 were transduced with a lentiviral vector delivering a shRNA targeting CDH6 according to the manufacturer's instructions (Mission shRNA bacterial glycerol stock, #TRCN0000054117, Sigma, St. Louis, Mo.). OVCAR8 cells do not express CDH6 endogenously. To generate an isogenic cell line featuring CDH6 expression, OVCAR8 cells were transduced with a lentiviral construct driving expression of a human CDH6 cDNA. Specifically, the cDNA for CDH6 was purchased from Genecopoeia (#Z2028, Genecopoeia, Rockville, Mass.) and cloned into pLenti6.3 using Gateway® cloning according to the manufacturer's instructions (Invitrogen, Carlsbad, Calif.).

Figure 9:
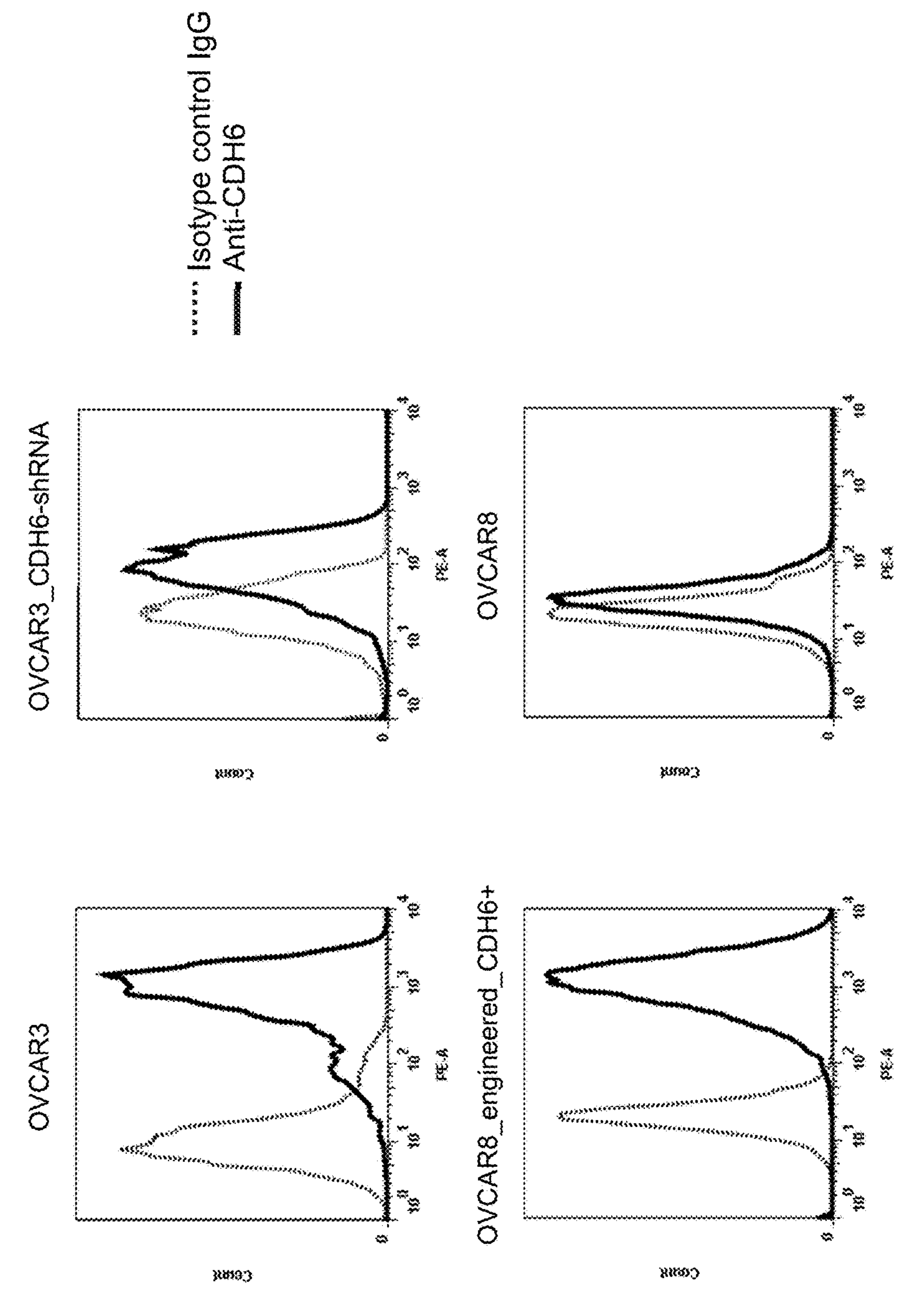
FIG. 9 are FACS graphics showing the levels of CDH6 expression on ovarian cancer cell lines, including CDH6 transfected lines and lines with CDH6 siRNA knockdown.

FACS analysis confirmed high levels of endogenous CDH6 expression in wild-type OVCAR3 and suppression of CDH6 in the OVCAR3 shRNACDH6 cell line. OVCAR8 cells were confirmed to be CDH6-negative, while high levels of exogenous expression of CDH6 were observed in the OVCAR8 engineered CDH6+ cells (FIG. 9).

Figure 10:
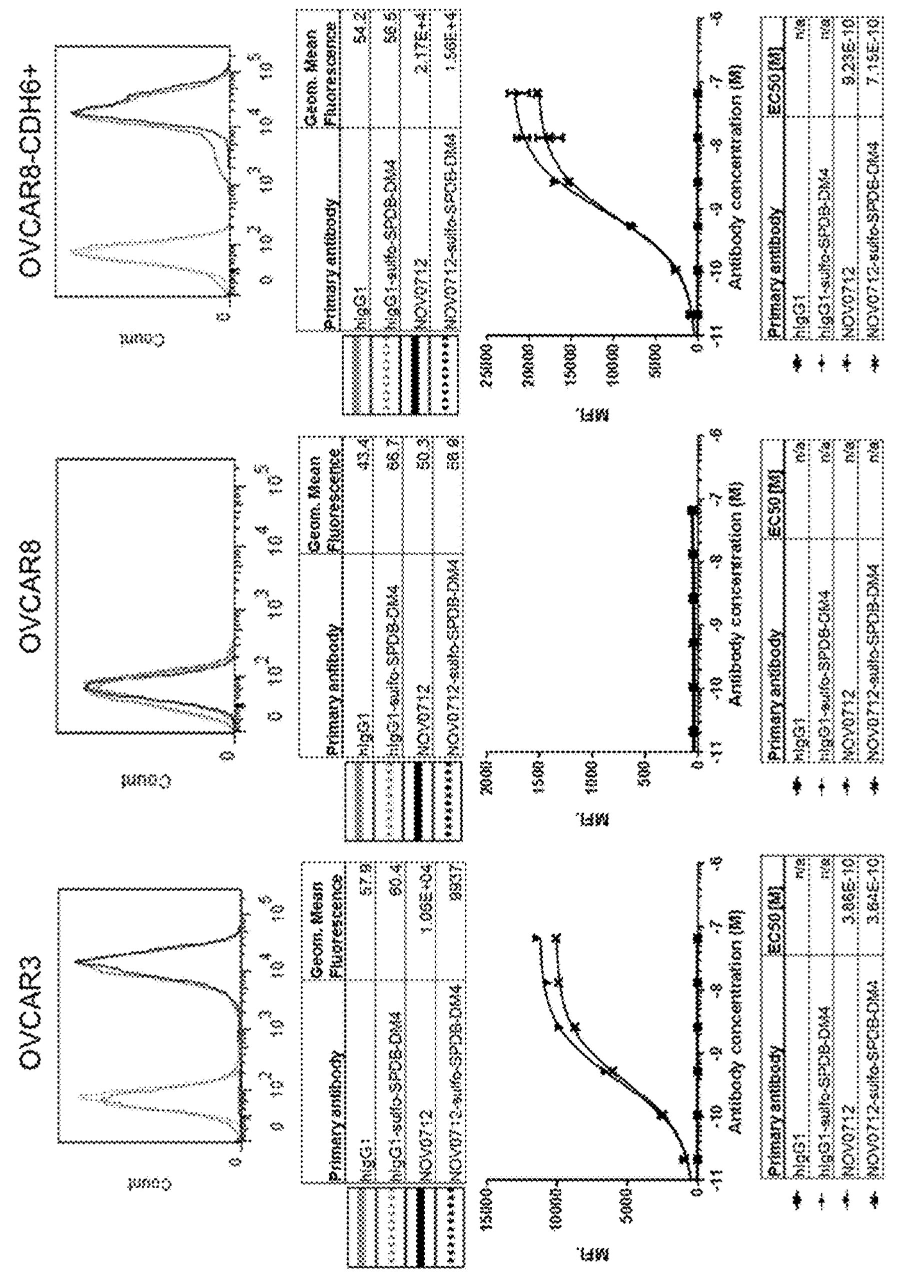
FIG. 10 shows anti-CDH6 antibodies either unconjugated or conjugated with a sulfo-SPDB-DM4 linker/payload in a panel of ovarian cancer cell lines.

FACS analysis further confirmed specific cellular binding of generated CDH6-targeting antibodies and ADCs. As shown in FIG. 10, a non-conjugated CDH6 antibody (NOV0712) features CDH6-specific binding pattern comparable to that of a sulfo-SPDB-DM4 conjugate using the same antibody and the sulfo-SPDB-DM4 linker/payload. A non-binding unconjugated IgG or ADC was included as control and found not to result in cell binding as expected. Again, indicating that the addition of a linker and payload does not interfere with affinity or specificity of anti-CDH6 antibodies.

Example 12: In Vitro Cellular Activity of CDH6-Targeting ADCs

In vitro cellular activity of SMCC-DM1 conjugates of a selection of anti-CDH6 antibodies was determined on a panel of cell lines comprising OVCAR3 (ovarian serous carcinoma, cultured in RPMI+20% FCS), JHOS4 (1:1 F12: DMEM+10% FBS), KNS42 (EMEM+10% FBS), NCIH661 (RPMI+10% FBS), SNU8 (RPMI+10% FBS) and OVCAR8 (RPMI+10% FBS). The OVCAR3 and NCIH661 cell lines were obtained from ATCC (#HTB-161 and #HTB-183, ATCC Manassas, Va.). JHOS4 were obtained from RIKEN (#RCB1678, RIKEN Cell Bank, RIKEN, Tsukuba, Japan). KNS42 were obtained from the Health Science Research Resources Bank HSRRB (#IFO50356, HSRRB, Osaka, Japan). SNU8 were obtained from the Korean Cell Line Bank KCLB (#00008, KCLB, Seoul, Korea). OVCAR8 were obtained from the NCI/DCTD Tumor/Cell Line Repository (NCI, Frederick, Mass.).

Cells in culture were counted and diluted in medium to a concentration of $1\times10^5$ cells/ml. 1000 cells/well were transferred to 384-well plates (Corning Costar#3707, Corning, Tewksbury, Mass.). The ADC stock solution was prepared in 1.4 ml Matrix tubes (Thermo, #3790, Rockford, Ill.). A 10-point, 1:3 serial dilution was prepared in a 384-well deep-well plate (Brandtech Scientific Inc #701355, Essex, Conn.) and 25 μl were transferred per assay plate (triplicates) to yield a highest starting concentration of the ADC of 33 nM. For controls, wells with cells only (=100% viability control) and cells incubated with an SMCC-DM1 conjugated non-targeting antibody (to check for non-target driven activity) were prepared. Plates were incubated for 120 h at 37° C. and 5% CO2. Cellular activity of the primary antibody/Fab-DM1 complexes was determined using CellTiter-Glo® reagent (Promega #G7571, Madison, Wis.) according to the manufacturer's instructions. Viability was normalized to the cells only control and data were plotted using Tibco Spotfire (Tibco Software Inc, Palo Alto, Calif.)

A subset of CDH6-targeting ADCs is able to inhibit proliferation of CDH6-positive cells at concentrations (1.22 nM) that are inactive on cells that lack CDH6 expression (OVCAR8), indicating target-dependent in vitro cellular activity of the CDH6-ADC (Table 16).

TABLE 16

In vitro cellular activity of anti-CDH6 SMCC-DM1 conjugates. Table shows percent inhibition at 1.22 nM ADC

| Antibody | OVCAR3 | JHOS4 | KNS42 | NCIH661 | SNU8 | OVCAR8 |
|---|---|---|---|---|---|---|
| NOV0670 | −29.97 | −27.88 | −18.63 | 5.14 | −15.57 | −23.77 |
| NOV0672 | −16.25 | −22.96 | −12.26 | −6.14 | −10.94 | −16.16 |
| NOV0674 | −10.29 | −11.94 | −6.82 | 3.9 | −1.42 | −8.97 |
| NOV0682 | 61.75 | 33.92 | 23.75 | 16.44 | 10.83 | −2.17 |
| NOV0685 | −20.65 | −14.67 | −14.65 | 2.08 | −0.1 | −11.51 |
| NOV0689 | 7.21 | 3.63 | −3.11 | −0.53 | 10.27 | −7.29 |
| NOV0690 | 84.8 | 50.97 | 56.81 | 14.55 | 18.39 | −15.8 |
| NOV0691 | −1.5 | −14.37 | −9.23 | −10.47 | −2.56 | −10.48 |
| NOV0692 | 88.01 | 62.3 | 57.32 | 14.77 | 15.66 | −10.83 |
| NOV0693 | 85.73 | 58.08 | 15.17 | 25.87 | 35.56 | −7.07 |
| NOV0695 | 89 | 66.94 | 66.31 | 18.69 | 21.56 | −7.04 |
| NOV0699 | n/a | n/a | n/a | n/a | n/a | n/a |
| NOV0705 | 68.57 | 40.35 | −13.35 | −3.15 | 6.4 | −22.58 |
| NOV0709 | 46.88 | 4.5 | −4.2 | 5.91 | −7.7 | −8.34 |
| NOV0710 | 90.84 | 69.01 | 56.98 | 38.7 | 42.4 | 6.53 |
| NOV0712 | 87.62 | 67.56 | 56.82 | 32.46 | 31.35 | 1.68 |
| NOV0713 | −3.55 | −6.22 | −17.26 | −9.74 | 7.79 | −0.08 |
| NOV0718 | −3.8 | −5.03 | 3.5 | 2.51 | 3.35 | 6.64 |
| NOV0719 | 76.05 | 27.25 | 40.97 | −9.87 | 3.18 | −2 |
| NOV0720 | 80.72 | 43.52 | 56.97 | 1.94 | 3.56 | −3.9 |

Figure 11:
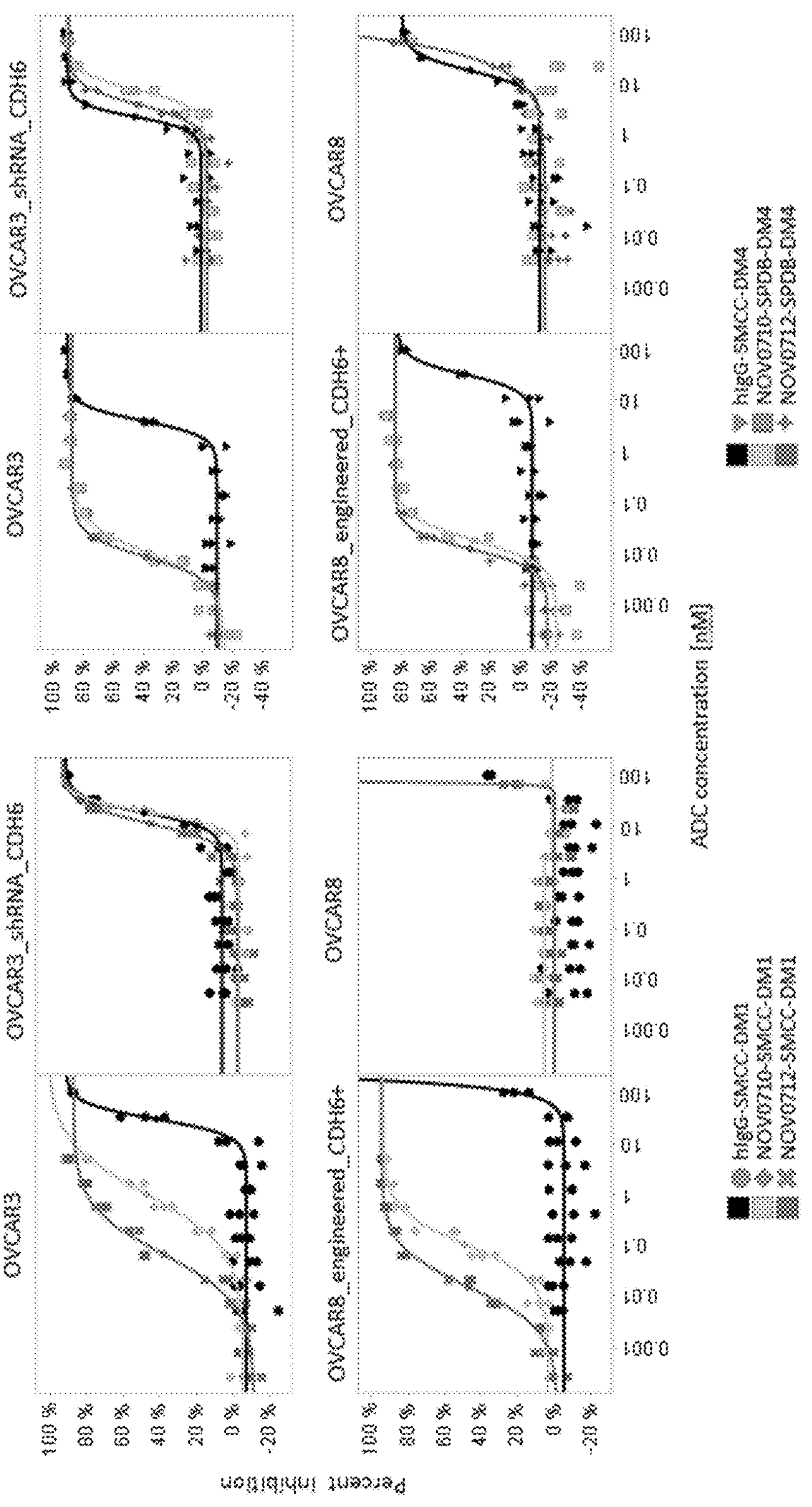
FIG. 11 shows in vitro activity of anti-CDH6 antibodies when conjugated to DM1 or DM4 on ovarian cancer cell lines.

Example 13: In Vitro Cellular Activity of Anti-CDH6 ADCs as SMCC-DM1 and SPDB-DM4 Conjugates on Ovarian Cancer Cell Lines In vitro cellular activity of anti-CDH6 ADCs as SMCC-DM1 and SPDB-DM4 conjugates was evaluated on a panel of ovarian cancer cell lines (FIG. 11 and Table 17). To assess target-dependent and specific activity of the anti-CDH6 ADCs, isogenic cell line pairs were generated for the OVCAR3 and OVCAR8 cell lines as described in Example 11.

CDH6-targeting ADCs in both SMCC-DM1 and SPDB-DM4 formats exhibited target and dose-dependent cellular activity as indicated by inhibition of proliferation in CDH6 expressing cell lines compared to the non-expressing isogenic cell line pair and isotype control ADCs (FIG. 11 and Table 17). The cellular activity assay was performed and analyzed as disclosed in Example 12.

TABLE 17

In vitro cellular activity of anti-CDH6 ADCs as SMCC-DMI and SPDB-DM4 conjugates on ovarian cancer cell lines.

| | | OVCAR3 | | OVCAR3 shRNA_CDH6 | | OVCAR8 | | OVCAR8 (engineered CDH6+) | |
|---|---|---|---|---|---|---|---|---|---|
| Compound | Linker/ Payload | IP [nM] | Amax (%) | IP [nM] | Amax (%) | IP [nM] | Amax (%) | IP [nM] | Amax (%) |
| me-DM1 | free payload | 0.002 | 90 | 0.002 | 89 | 0.104 | 85 | 0.087 | 84 |
| hIgG | SMCC-DM1 | 29.993 | 91 | 18.468 | 92 | 33 | n/a | 33 | n/a |
| hIgG | SPDB-DM4 | 3.966 | 91 | 2.168 | 91 | 17.79 | 79 | 32.728 | 83 |
| NOV0710 | SMCC-DM1 | 1.034 | 101 | 18.52 | 93 | 33 | 5 | 0.102 | 94 |
| NOV0710 | SPDB-DM4 | 0.01 | 88 | 7.543 | 91 | 33 | n/a | 0.018 | 85 |
| NOV0712 | SMCC-DM1 | 0.065 | 88 | 11.249 | 94 | 33 | n/a | 0.015 | 95 |
| NOV0712 | SPDB-DM4 | 0.008 | 88 | 3.785 | 90 | 33 | n/a | 0.012 | 84 |

Figure 12:
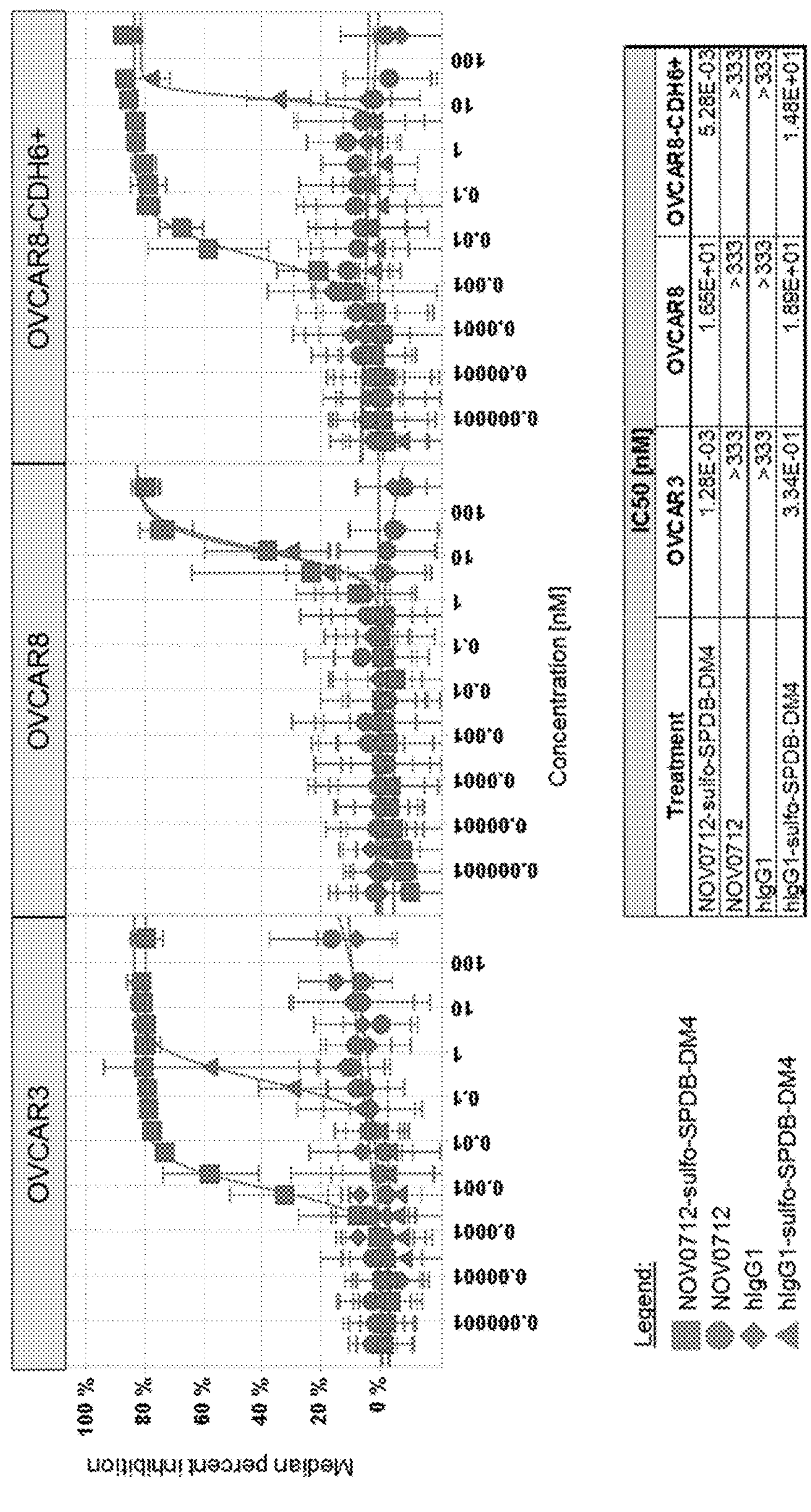
FIG. 12 shows in vitro activity of unconjugated anti-CDH6 antibodies or anti-CDH6 antibodies conjugated to sulfo-SPDB-DM4.

Example 14: In Vitro Cellular Activity of CDH6-Targeting Antibodies or Control IgG in Either Non-Conjugated Form or as Sulfo-SPDB-DM4 Antibody Drug Conjugate Cellular activity of the CDH6 antibody NOV0712 as either non-conjugated IgG or sulfo-SPDB-DM4 conjugate was assessed in a panel of ovarian cancer cell lines (see Example 11). A non-targeting isotype control antibody in either non-conjugated form or as sulfo-SPDB-DM4 conjugate was further included. As shown in FIG. 12, the CDH6-targeting antibody drug conjugate NOV0712-sulfo-SPDB-DM4 exhibited target and dose-dependent cellular activity as indicated by inhibition of proliferation in CDH6 expressing cell lines (OVCAR3 and OVCAR8-CDH6+) compared to the non-expressing cell line (OVCAR8). No cellular activity was observed with non-conjugated NOV0712 antibody or a non-targeting IgG control. Marginal activity at concentrations understood to result in non-specific cytotoxicity were seen with a control IgG-sulfo-SPDB-DM4 conjugate. The cellular activity assay was performed and analyzed as disclosed in Example 9.

Figure 13:
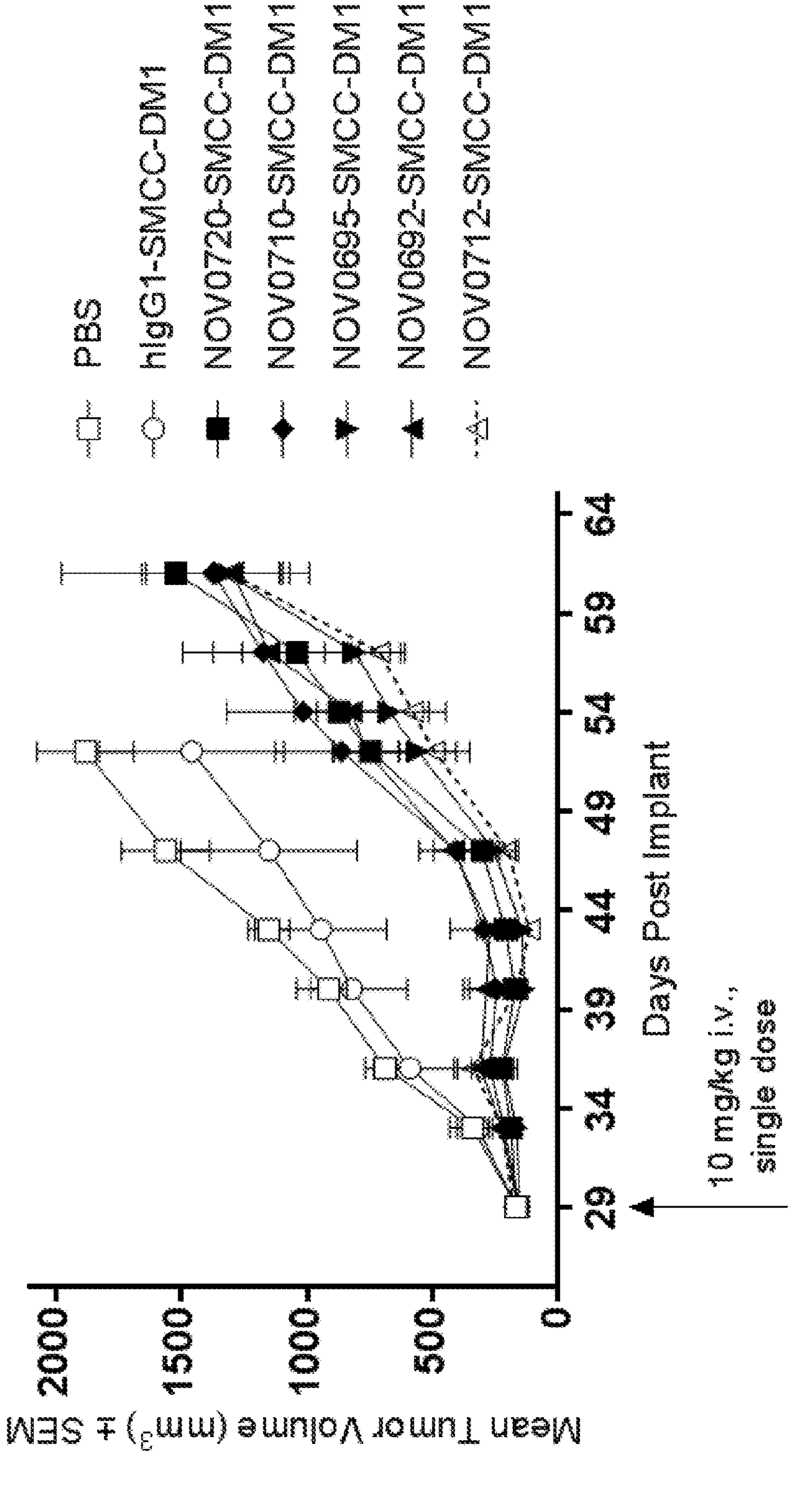
FIG. 13 demonstrates the efficacy of anti-CDH6 antibodies when conjugated to DM1 and tested in an ovarian cancer xenograft mouse model.

Example 15: In Vivo Efficacy of Anti-CDH6 Antibodies as SMCC-DM1 Conjugates in a Xenograft Mouse Model of Ovarian Cancer The anti-tumor activity of a selection of anti-CDH6 ADCs were evaluated in the OVCAR-3 ovarian xenograft model. Female NOD-scid-gamma mice were implanted subcutaneously on the right flank with $10\times10^6$ OVCAR-3 cells containing 50% Matrigel™ (BD Biosciences) in phosphate buffer solution (PBS). The total injection volume containing cells in suspension was 200 μl. Mice were enrolled in the study 29 days post implantation with average tumor volume of 165 $mm^3$. After being randomly assigned to one of seven groups (n=4/group), mice were administered a single i.v. dose of PBS (10 ml/kg), a non-target isotype control hIgG1-SMCC-DM1 (10 mg/kg), or one of five anti-CDH6-SMCC-DM1 (10 mg/kg). Tumor volumes and body weights were measured twice weekly. Each anti-CDH6-SMCC-DM1 ADC elicited an inhibitory effect upon tumor growth following a single dose of 10 mg/kg, when compared to control arms (FIG. 13).

Figure 14:
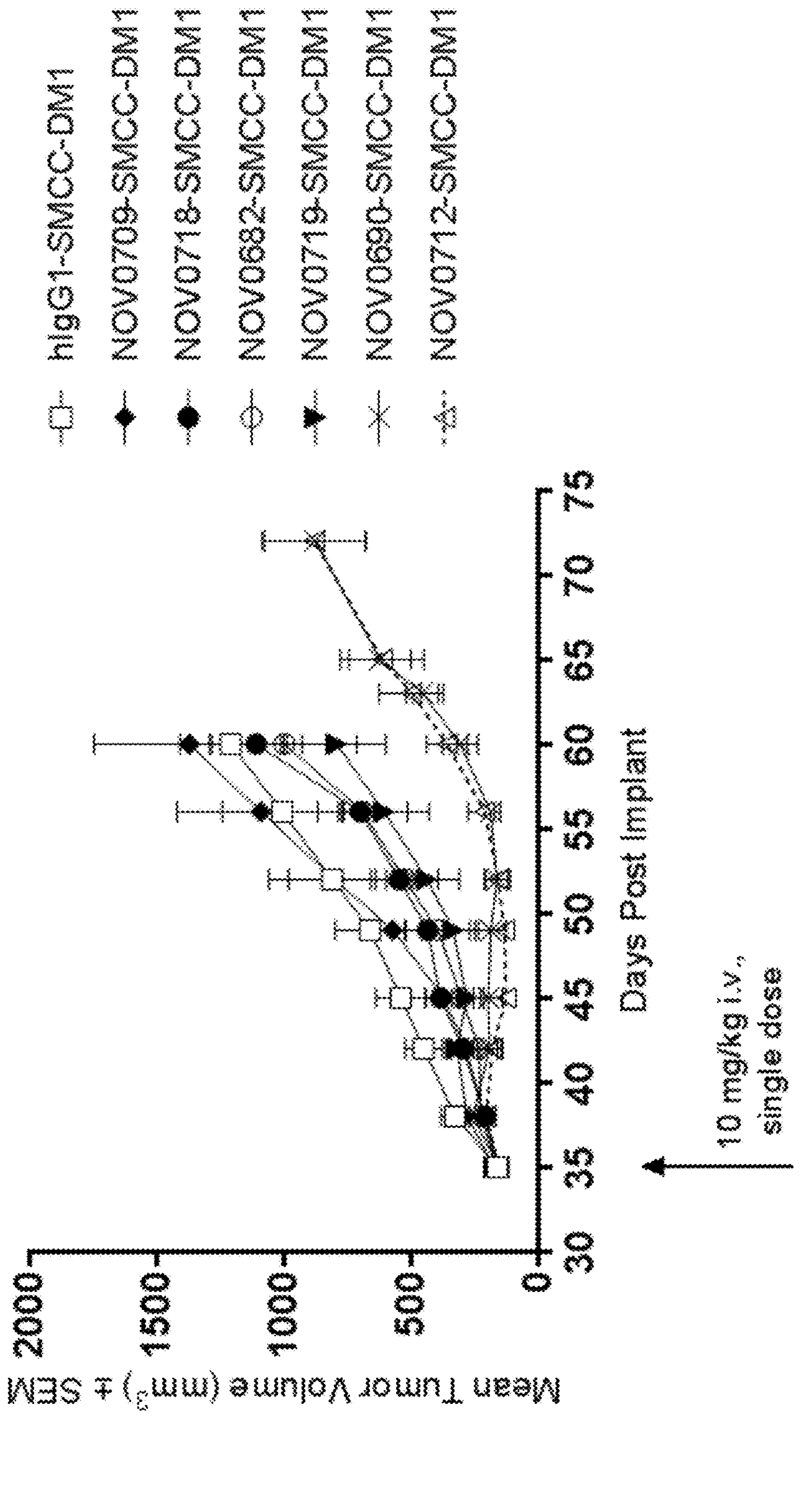
FIG. 14 demonstrates the efficacy of anti-CDH6 antibodies when conjugated to DM1 and tested in an ovarian cancer xenograft mouse model.

The anti-tumor activity of a second selection of anti-CDH6 ADCs were evaluated in the OVCAR-3 ovarian xenograft model. Female NOD-scid-gamma mice were implanted subcutaneously on the right flank with $10\times10^6$ OVCAR-3 cells containing 50% Matrigel™ (BD Biosciences, San Jose, Calif.) in PBS. The total injection volume containing cells in suspension was 200 μl. Mice were enrolled in the study 35 days post implantation with average tumor volume of 166 $mm^3$. After being randomly assigned to one of seven groups (n=4/group), mice were administered a single i.v. dose of PBS (10 ml/kg), a non-target isotype control hIgG1-SMCC-DM1 (10 mg/kg), or one of five anti-CDH6-SMCC-DM1 (10 mg/kg) plus NOV0712-SMCC-DM1 which had been dosed in the previous OVCAR3 triage. Tumor volumes and body weights were measured twice weekly. None of the mice showed a decrease in body weight, indicating that the ADC was well tolerated (data not shown). Of the five anti-CDH6-SMCC-DM1, only NOV0690 elicited a response comparable to that of NOV0712-SMCC-DM1 (FIG. 14).

Figure 15:
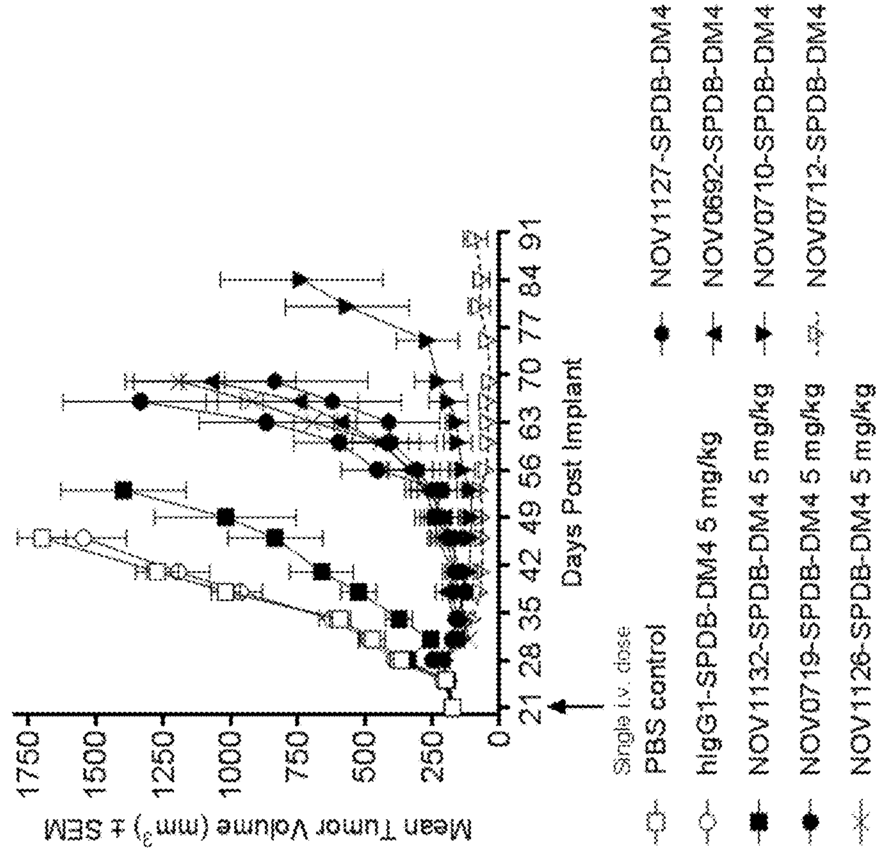
FIG. 15 shows the efficacy of anti-CDH6 antibodies when SPDB-DM4 conjugated and tested in an ovarian cancer xenograft mouse model.

Example 16: In Vivo Efficacy of Anti-CDH6 Antibodies as SPDB-DM4 Conjugates in a Xenograft Mouse Model of Ovarian Cancer The anti-tumor activity of a selection of anti-CDH6 ADCs were evaluated in the OVCAR-3 ovarian xenograft model. Female NOD-scid-gamma mice were implanted subcutaneously on the right flank with $10\times10^6$ OVCAR-3 cells containing 50% Matrigel™ (BD Biosciences, San Jose, Calif.) in PBS. The total injection volume containing cells in suspension was 200 μl. Mice were enrolled in the study 21 days post implantation with average tumor volume of 174 $mm^3$. After being randomly assigned to one of nine groups (n=5/group), mice were administered a single i.v. dose of PBS, (10 ml/kg), a non-target isotype control hIgG1-SPDB-DM4 (5 mg/kg), a non-target isotype control hIgG1-SMCC-DM1 (5 mg/kg), NOV0712-SMCC-DM1 (5 mg/kg), or one of seven anti-CDH6-SPDB-DM4 (5 mg/kg). Tumor volumes and body weights were measured 1-2 times weekly. None of the mice showed a decrease in body weight, indicating that the ADC was well tolerated at this dosage (data not shown). Of all the anti-CDH6-SPDB-DM4 agents, NOV0712-SPDB-DM4 elicited the greatest anti-tumor effect with regression 70 days post dose. NOV0710-SPDB-DM4 was the second most active anti-CDH6-SPDB-DM4 in this study (FIG. 15).

Figure 16:
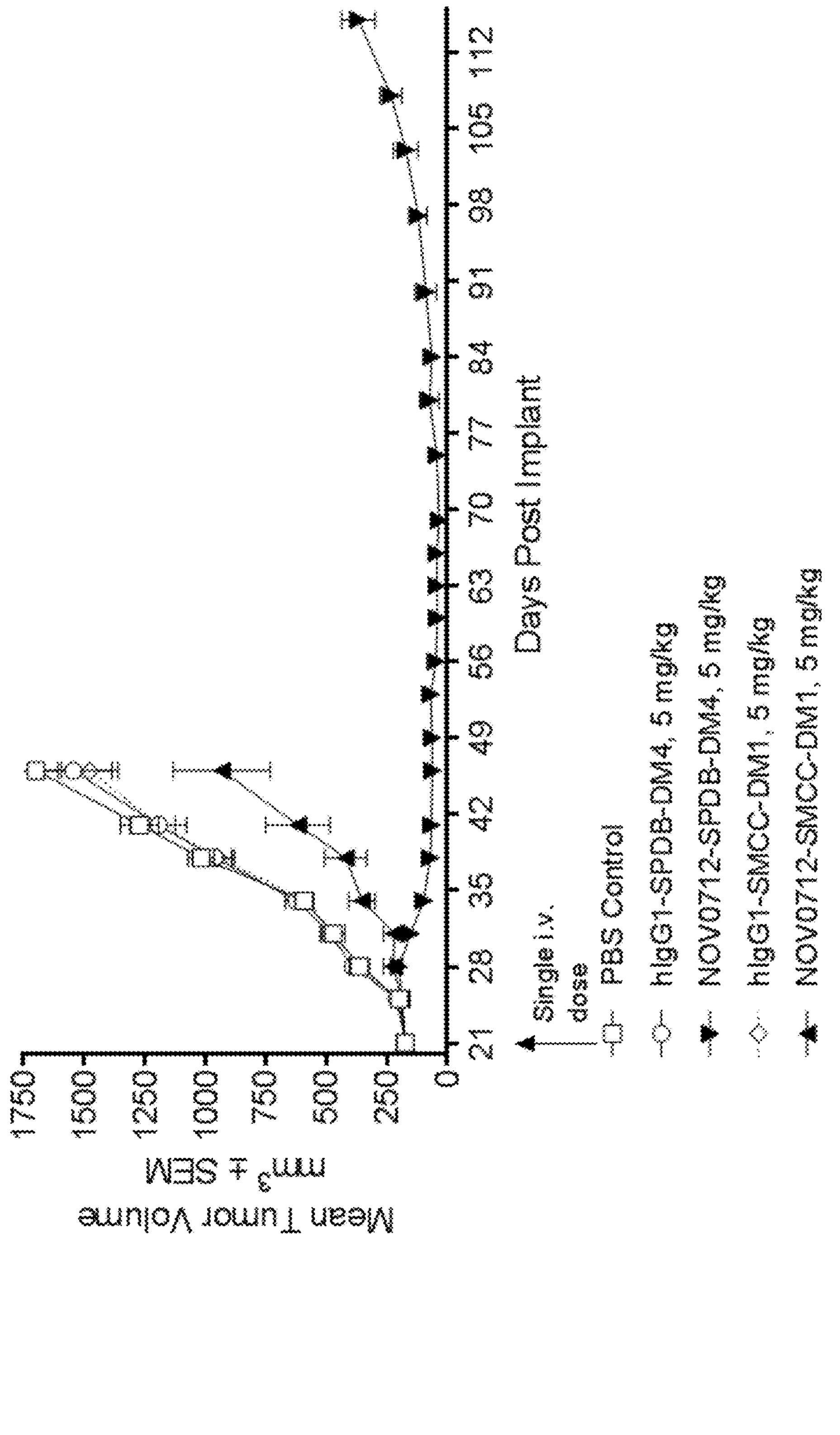
FIG. 16 compares the efficacy of NOV0712-SPDB-DM4 and NOV0712-SMCC-DM1 in an ovarian cancer xenograft mouse model.

Example 17: In Vivo Efficacy of Anti-CDH6 Antibodies as SMCC-DM1 or SPDB-DM4 Conjugates in a Xenograft Mouse Model of Ovarian Cancer The anti-tumor activity of a selection of anti-CDH6 ADC NOV0712 in different linker-payload formats were evaluated in the OVCAR-3 ovarian xenograft model. Female NOD-scid-gamma mice were implanted subcutaneously on the right flank with $10\times10^6$ OVCAR-3 cells containing 50% Matrigel™ (BD Biosciences, San Jose, Calif.) in PBS. The total injection volume containing cells in suspension was 200 μl. Mice were enrolled in the study 21 days post implantation with average tumor volume of 174 $mm^3$. After being randomly assigned to one of five groups (n=5/group), mice were administered a single i.v. dose of PBS, (10 ml/kg), a non-target isotype control hIgG1-SPDB-DM4 (5 mg/kg), a non-target isotype control hIgG1-SMCC-DM1 (5 mg/kg), NOV0712-SMCC-DM1 (5 mg/kg), or NOV0712-SPDB-DM4 (5 mg/kg). Tumor volumes and body weights were measured 1-2 times weekly. None of the mice showed a decrease in body weight (data not shown). Both L/P formats of NOV0712 elicited an antitumor effect, but the SPDB-DM4 format was much more potent leading to a durable regression for over 70 days post dose (FIG. 16). Pharmacokinetic sampling indicates the two agents have similar PK profiles (data not shown).

Figure 17:
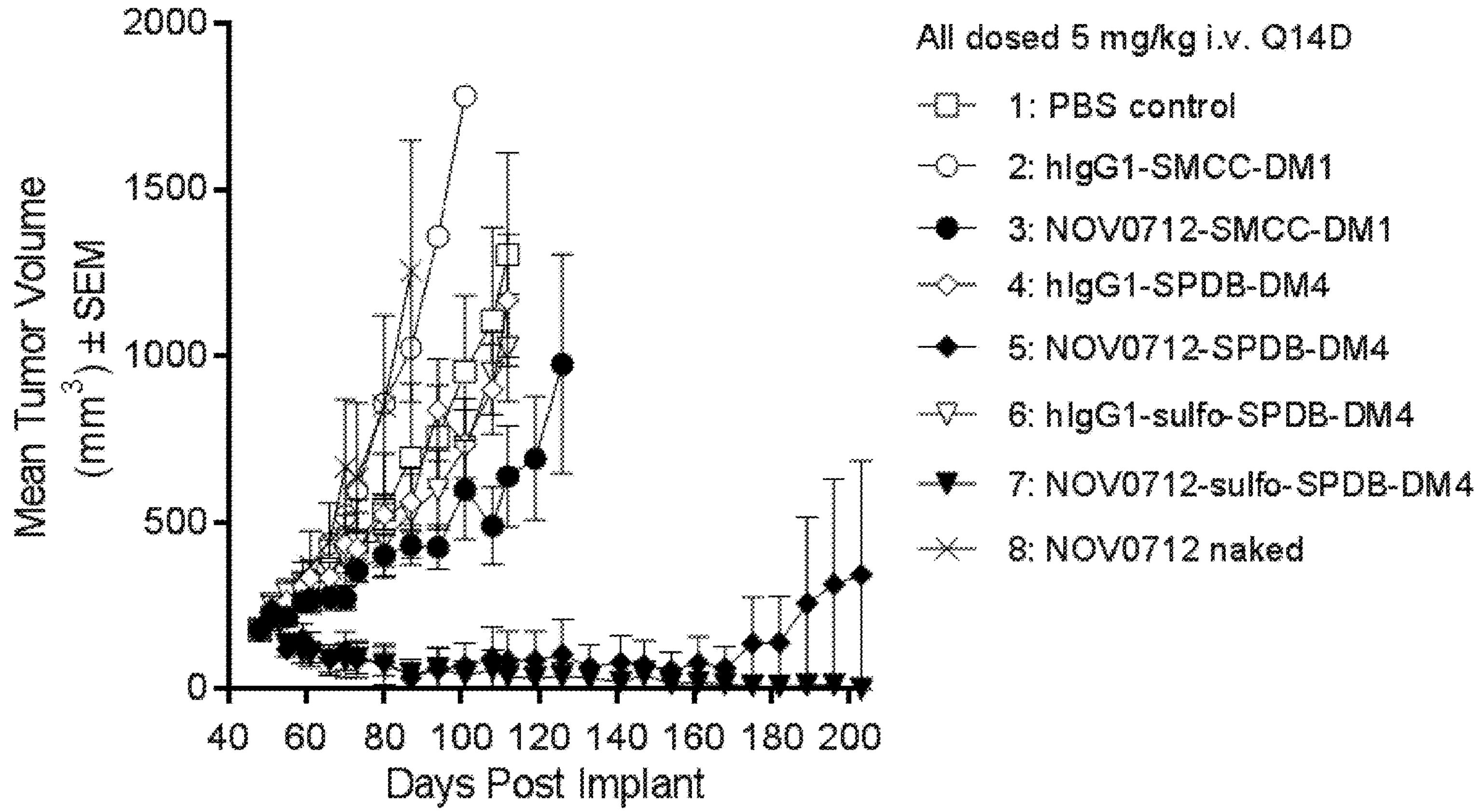
FIG. 17 compares the efficacy of NOV0712 with SPDB-DM4, sulfo-SPDB-DM4 and SMCC-DM1 linker/payload combinations in patient-derived primary tumor xenograft (PTX) mouse model of ovarian cancer.

Example 18: In Vivo Efficacy of Anti-CDH6 ADCs with Different Linker/Payload Formats in a Patient-Derived Primary Tumor Xenograft Mouse Model of Ovarian Cancer The anti-tumor activity of different linker payload formats of the anti-CDH6 ADC NOV0712 were evaluated in CDH6 expressing primary (patient derived) ovarian tumors xenografted into mice. Human primary xenograft models were established by direct implantation of primary human tumor tissue subcutaneously into nu/nu nude mice. The resulting xenografts were serially passaged between 4 and 10 times prior to use in this study. Athymic nude mice were implanted with fragments of tumor approximately 27 $mm^3$ in size, subcutaneously on the right flank. Mice were enrolled in the study 48 days post implant with a mean tumor volume of 178 $mm^3$. After being randomized into one of eight groups (n=5/group) Mice were administered a single i.v. dose every 14 days (Q14D), of PBS (10 ml/kg), a non-target isotype control hIgG1 linker payload format (-SMCC-DM1, -SPDB-DM4, -sulfo-SPDB-DM4), a NOV0712 linker payload format (-SMCC-DM1, -SPDB-DM4, -sulfo-SPDB-DM4) or NOV0712 as a naked antibody. All groups were dosed at 5 mg/kg. Tumor volumes and bodyweights were measured 1-2 times weekly. None of the mice showed a decrease in body weight (data not shown). NOV0712 as a naked antibody had no inhibitory effect upon tumor growth. NOV0712-SMCC-DM1 treatment did not result in regression in this model. Each cleavable format of NOV0712 resulted in regressions. NOV0712-sulfo-SPDB-DM4 at 5 mg/kg Q14D (single dose every 14 days) was the most potent treatment arm with durable tumor regression lasting over 150 days post first dose (FIG. 17).

Figure 18:
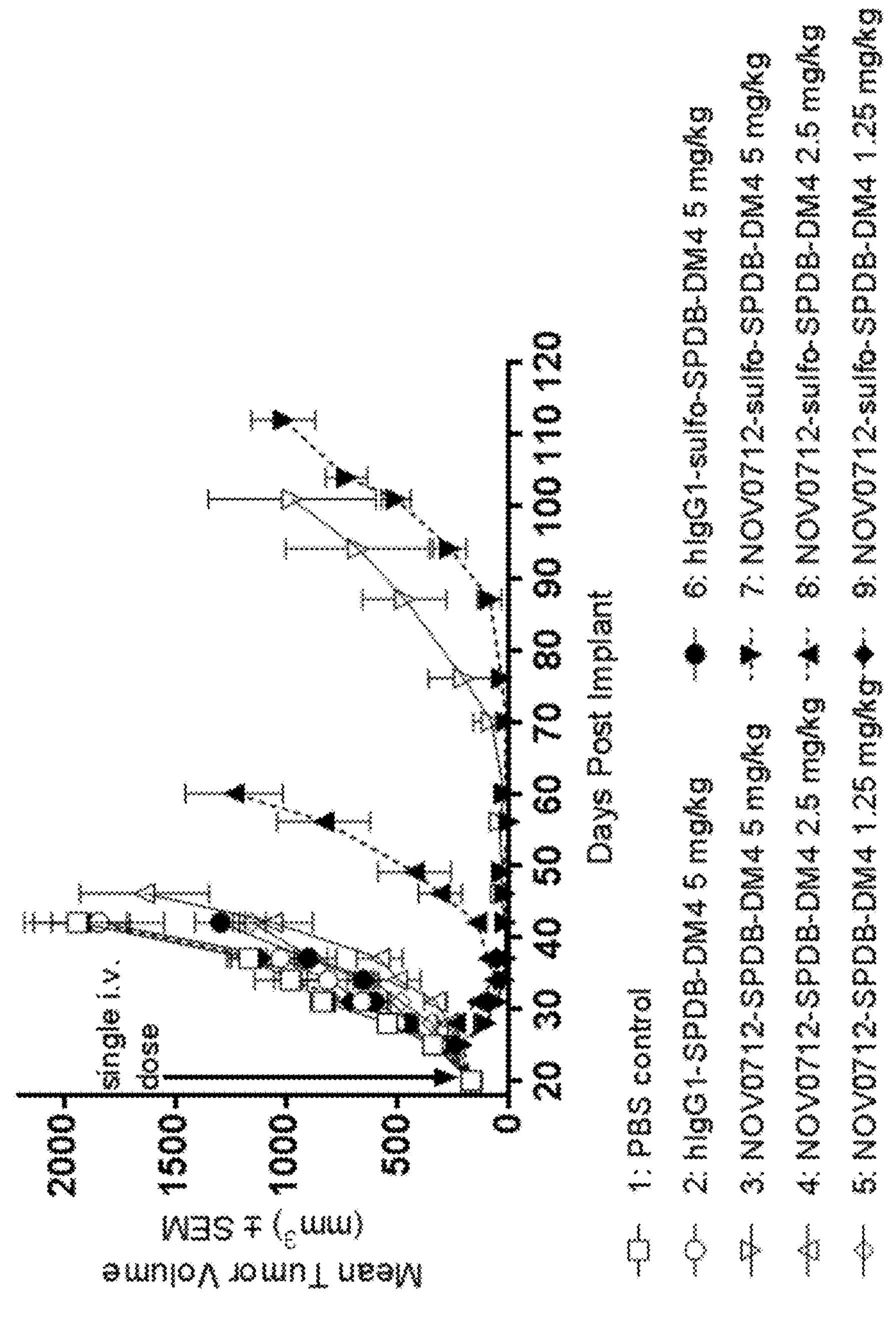
FIG. 18 shows the efficacy of different doses of NOV0712 when conjugated to SPDB-DM4 or sulfo-SPDB-DM4 in an ovarian cancer xenograft mouse model.

Example 19: In Vivo Efficacy of Anti-CDH6 ADCs with Different Linker/Payload Formats in a Xenograft Mouse Model of Ovarian Cancer The anti-tumor activity of a selection of anti-CDH6 ADCs were evaluated in the OVCAR-3 ovarian xenograft model. Female NOD-scid-gamma mice were implanted subcutaneously on the right flank with $10\times10^6$ OVCAR-3 cells containing 50% Matrigel™ (BD Biosciences, San Jose Calif.) in PBS. The total injection volume containing cells in suspension was 200 μl. Mice were enrolled in the study 20 days post implantation with average tumor volume of 172 $mm^3$. After being randomized into one of eight groups (n=5/group) mice were administered a single i.v. dose of PBS (10 ml/kg), a non-target isotype control hIgG1-SPDB-DM4 (5 mg/kg), a non-target isotype control hIgG1-sulfo-SPDB-DM4 (5 mg/kg), NOV0712-SPDB-DM4 (1.25, 2.5 and 5 mg/kg), or NOV0712-sulfo-SPDB-DM4 (1.25, 2.5 and 5 mg/kg). Tumor volumes and bodyweights were measured 1-2 times weekly throughout the duration of the study. None of the mice showed a decrease in body weight, indicating that the ADC was well tolerated (data not shown). NOV0712-sulfo-SPDB-DM4 was more efficacious than NOV0712-SPDB at both the 2.5 mg/kg and 5 mg/kg dose levels. A single 2.5 mg/kg dose of NOV0712-sulfo-SPDB-DM4 lead to regression. A single 5 mg/kg dose of each format led to regression, but the effect of the sulfo-SPDB-DM4 dose outlasted that of the -SPDB-DM4 dose. Overall these data show the sulfo-SPDB-DM4 format is the most active format for targeting CDH6 using ADCs out of the panel assessed (FIG. 18).

Figure 19:
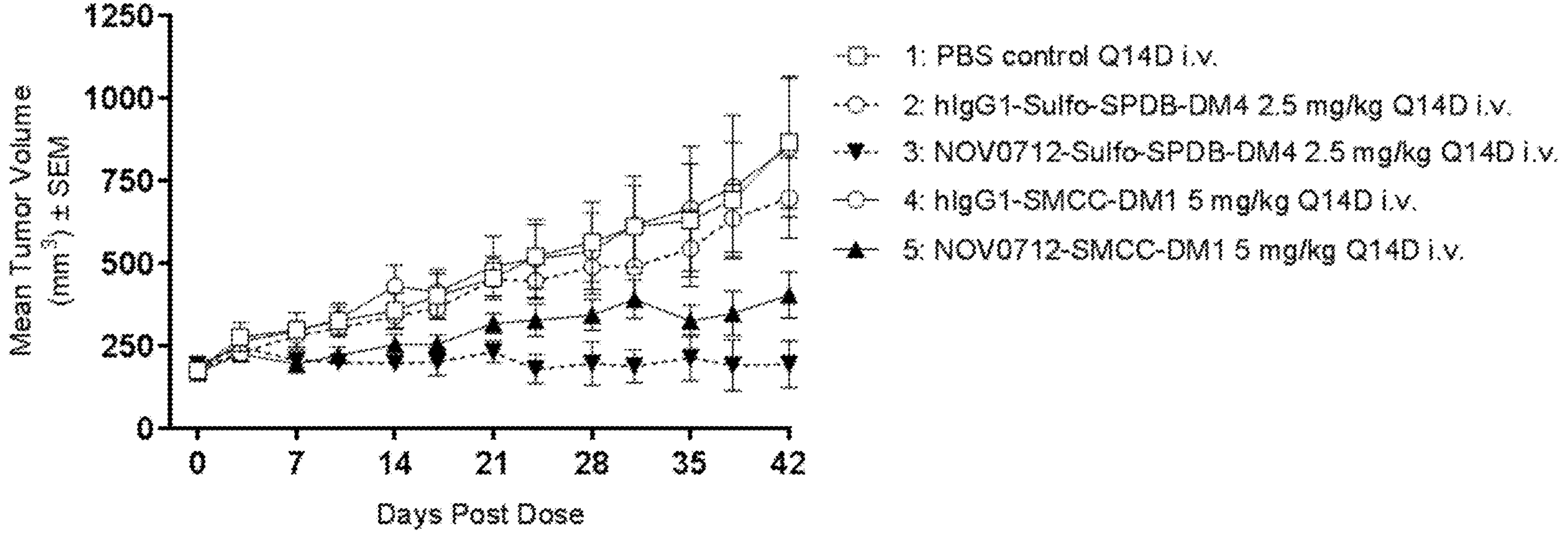
FIG. 19 compares NOV0712 with sulfo-SPDB-DM4 with SMCC-DM1 linker payload combinations in a patient-derived primary ovarian tumor xenograft mouse model.

Example 20: In Vivo Efficacy of Anti-CDH6 ADCs with Different Linker/Payload Formats in a Patient-Derived Primary Tumor Xenograft Mouse Model of Ovarian Cancer The anti-tumor activity of different linker payload formats of the anti-CDH6 ADC NOV0712 were evaluated in CDH6 expressing primary (patient derived) ovarian tumors xenografted into mice. Human primary xenograft models were established by direct implantation of primary human tumor tissue subcutaneously into nu/nu nude mice. The resulting xenografts were serially passaged between 4 and 10 times prior to use in this study. Athymic nude mice were implanted with fragments of tumor approximately 27 $mm^3$ in size, subcutaneously on the right flank. Due to the variable latencies in the growth kinetics of the primary tumors, mice were entered into the study in a rolling fashion. Tumors were assigned to a group when upon reaching an appropriate volume, between 147 $mm^3$ and 244 $mm^3$ (the mean size at enrollment was 180 $mm^3$) The first 5 mice were assigned to groups 1 through 5, the next 5 mice were assigned to groups 5 through 1, and so on until 5 groups (n=5/group) were filled. Upon enrollment each mouse was administered with an i.v. dose every 2 weeks (Q14D), of PBS (10 ml/kg), a non-target isotype control hIgG1-SMCC-DM1 (5 mg/kg), NOV0712-SMCC-DM1 (5 mg/kg), non-target isotype control hIgG1-sulfo-SPDB-DM4 (2.5 mg/kg) or NOV0712-sulfo-SPDB-DM4 (2.5 mg/kg). Tumor volumes and bodyweights were measured twice weekly. None of the mice showed a decrease in body weight, indicating that the ADC was well tolerated (data not shown). NOV0712-SMCC-DM1 5 mg/kg Q14D is able to reduce tumor growth in this model. NOV0712-sulfo-SPDB-DM4 2.5 mg/kg Q14D is efficacious in halting tumor growth in this model for 42 days (FIG. 19).

Example 21: In Vivo Efficacy of an Anti-CDH6 ADC in a Panel of Patient-Derived Primary Tumor Xenograft Mouse Models of Ovarian Cancer The anti-tumor activity of an anti-CDH6 ADC (NOV0712-sulfo-SPDB-DM4) was assessed in a panel of 28 ovarian primary tumor xenograft (PTX) models in a 1×1×1 design (1PTX×1 animal×1 treatment). Human primary xenograft models were established by direct implantation of primary human tumor tissue subcutaneously into nu/nu nude mice. The resulting xenografts were serially passaged between 4 and 10 times prior to use in this study. Female nude mice were implanted subcutaneously in the axillary region, with a 3×3×3 mm tumor fragment using a 12 gauge trocar. Once a tumor measured 200-250 $mm^3$ the mouse was enrolled into the study and treatment started. Upon enrollment each mouse was administered with an i.v. dose every 2 weeks (Q14D), of NOV0712-sulfo-SPDB-DM4 (5 mg/kg). None of the mice showed a decrease in body weight, indicating that the ADC was well tolerated (data not shown). Tumor volumes and bodyweights were measured twice weekly. For visualization of anti-tumor activity, the percent tumor volume change over time was plotted using Tibco Spotfire (Tibco Software, Palo Alto, Calif.).

CDH6 expression in the PTX samples was assessed using immunohistochemistry (IHC) on samples from untreated PTX tumors. Specifically, at sacrifice, tumors were immediately excised, collected into histology cassettes and fixed in 10% buffered formalin for 24 hours. Cassettes were then transferred into 70% EtOH and processed and embedded in paraffin using routine histological procedures. Experimental FFPE blocks were cut at 3.5 μm as whole sections on slides. A rabbit polyclonal anti human CDH6 antibody obtained from Sigma-Aldrich (Cat # HPA007047, Sigma Aldrich, St. Louis, Mo.) and used as the primary immunohistochemistry (IHC) antibody. The antibody was detected using Ventana Biotin-free DAB Detection Systems on the Ventana DISCOVERY XT Biomarker Platform (Tucson, Ariz.).

The optimized protocol included standard exposure to Ventana Cell Conditioning #1 antigen retrieval reagent (Cat #950-124). The primary antibody was diluted to a concentration of 1:200 in DAKO Cytomation Antibody Diluent (Cat # S0809), applied in 100 μl volume and incubated for 60 minutes at 37° C. Subsequently incubation with Ventana OmniMap prediluted HRP-conjugated anti-rabbit secondary antibody (Cat #760-4311) was performed for 4 minutes. The secondary antibody was then detected using the ChromoMap DAB kit (Cat #760-159) and slides were counterstained for 4 minutes with Ventana Hematoxylin (Cat #760-2021), followed by Ventana Bluing Reagent (Cat #760-2037) for 4 minutes. Slides were dehydrated in increasing concentrations of ethanol (95-100%), then in xylenes, followed by coverslipping. Coverslipped slides were evaluated by light microscopy and scanned by Leica/Aperio ScanScope slide scanner (Vista, Calif.). Scanned images of the stained slides were launched in Indica Labs HALO (Corrales, N. Mex.) opening from integrated Leica eSlide Manager/Aperio Spectrum (Vista, Calif.). Digital images were viewed, annotated and analyzed using Area Quantification Algorithm (Area Quantification v1.0) either with Classifier Module (CDH6 Loose Tumor 2, CDH6 Neg Tumor 2 & CDH6 Tumor & CDH6 tumor2) for tumor detection or without Classifier Module. Image analysis algorithms were used to detect any intensity.

Figure 20:
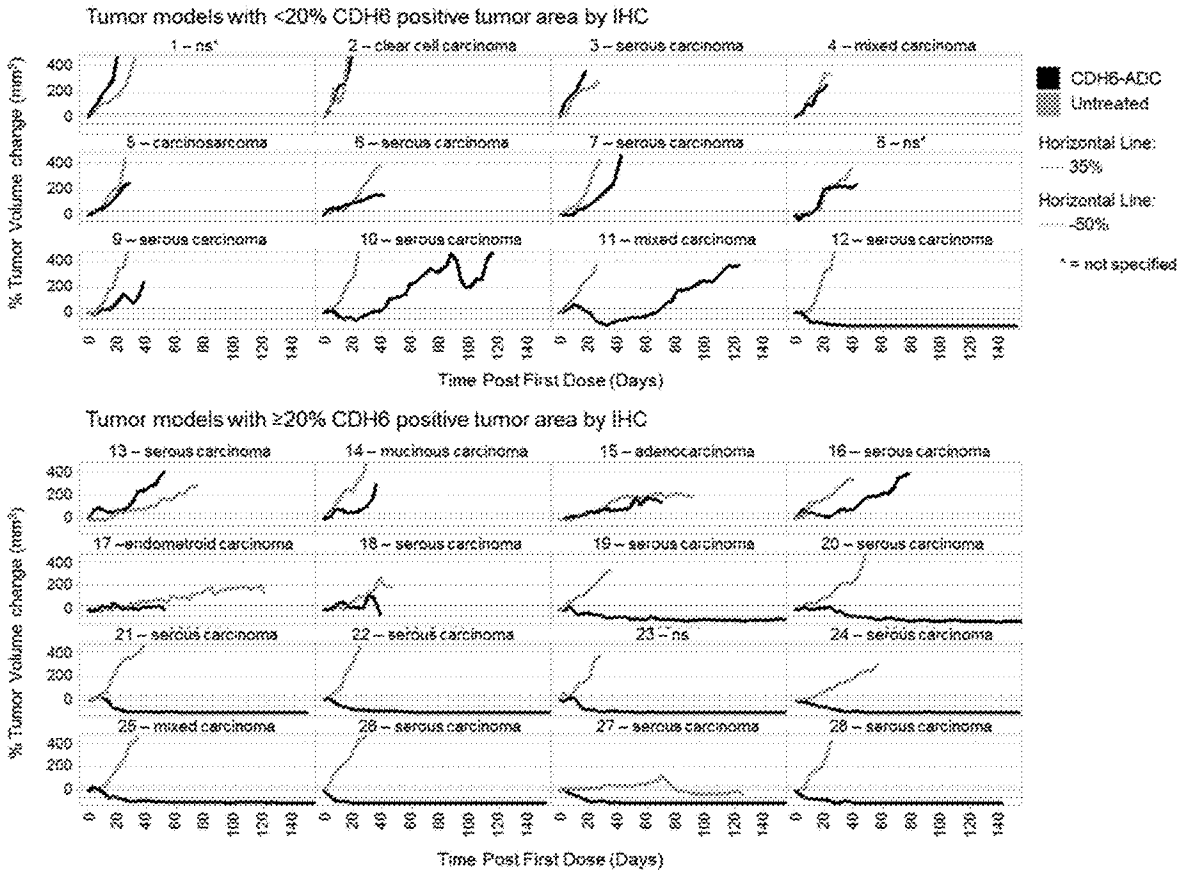
FIG. 20 demonstrates the in vivo efficacy of anti-CDH6 antibodies conjugated to sulfo-SPDB-DM4 in a patient derived primary xenograft mouse model of ovarian cancer.

As illustrated in FIG. 20, efficacy of anti-CDH6 ADC was observed in the PTX models, particularly amongst tumor models featuring greater than twenty percent CDH6 positive tumor area by IHC. Of special note, 11/28 (39%) of the PTX models responded with complete tumor regression lasting in excess of 150 days.

Figure 21:
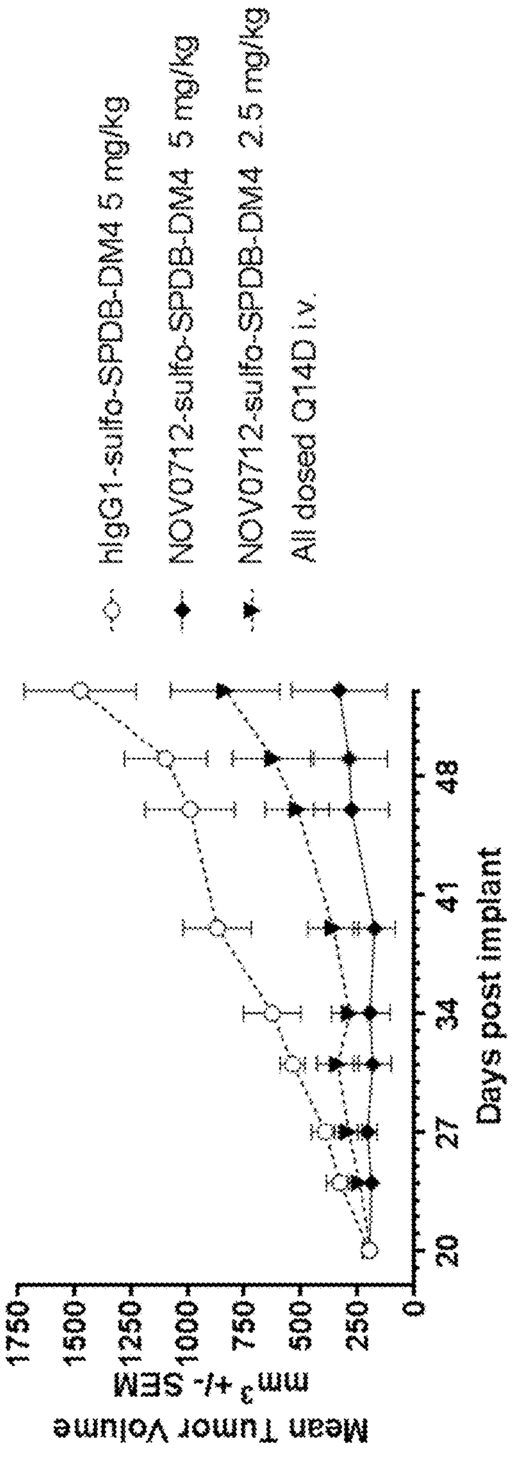
FIG. 21 shows in vivo efficacy of anti-CDH6 antibodies conjugated to sulfo-SPDB-DM4 in a patient derived primary xenograft mouse model of renal cancer.

Example 22: In Vivo Efficacy of an Anti-CDH6 ADC Dosed Either at 2.5 mg/kg i.v., Q14D or 5 mg/kg i.v. Q14D in a Patient-Derived Primary Tumor Xenograft Mouse Model of Renal Cancer The anti-tumor activity of an anti-CDH6 ADC (NOV0712-sulfo-SPDB-DM4, dosed either at 5 mg/kg Q14D or 2.5 mg/kg, Q14D) was assessed in a renal primary tumor xenograft (PTX) model. Human primary xenograft models were established by direct implantation of primary human tumor tissue subcutaneously into nu/nu nude mice. The resulting xenografts were serially passaged between 4 and 10 times prior to use in this study. Female nude mice were implanted subcutaneously in the axillary region, with a 3×3×3 mm tumor fragment using a 12 gauge trocar. Animals were randomized into treatment groups on day 20 following tumor fragment implantation, when the average tumor volume was 195 $mm^3$ (range 115-282 $mm^3$) Treatments were initiated on Day 20. Anti-tumor activity was determined on day 53 post tumor cell implant, 33 days post initiation of treatment, the last day when all animals remained on study. A non-targeting ADC was included as control for determining CDH6-specific anti-tumor activity. None of the mice showed a decrease in body weight, indicating that the ADC was well tolerated (data not shown). As with the ovarian cancer models, efficacy of anti-CDH6 ADC was observed in renal PTX models featuring greater than twenty percent CDH6 positive tumor area by IHC. As shown in FIG. 21, anti-CDH6 ADC treatment was efficacious against primary human tumors in a renal PTX model.

Figure 22:
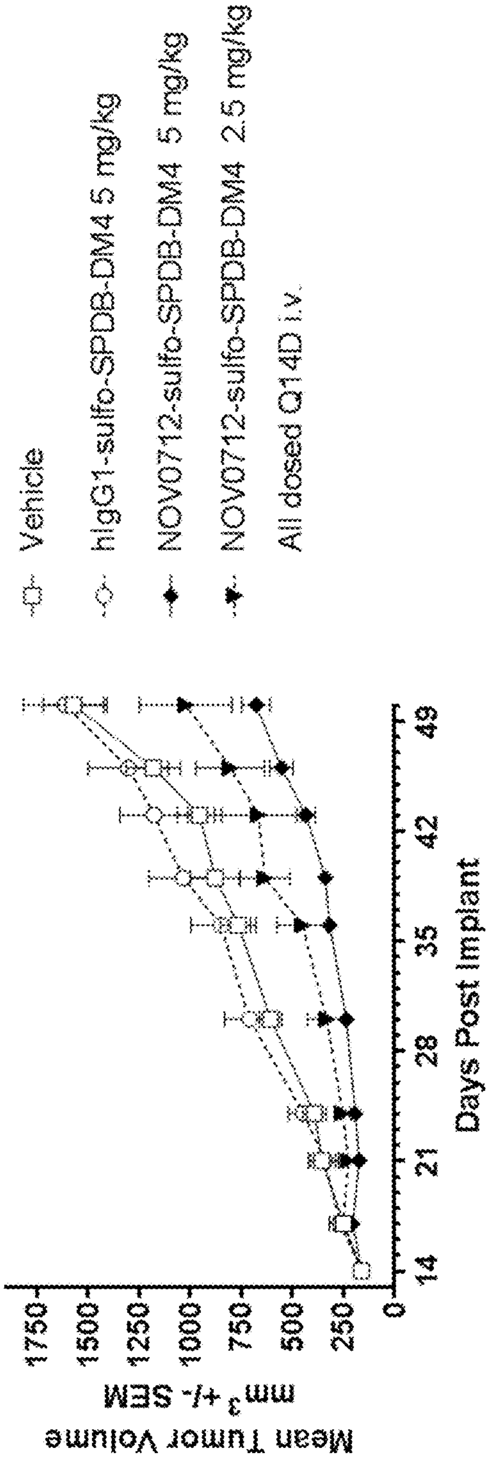
FIG. 22 shows in vivo efficacy of anti-CDH6 antibodies conjugated to sulfo-SPDB-DM4 in a patient derived primary xenograft mouse model of renal cancer.

Example 23: In Vivo Efficacy of an Anti-CDH6 ADC Dosed Either at 2.5 mg/kg, Q14D i.v. Or 5 mg/kg iv. Q14D in a Patient-Derived Primary Tumor Xenograft Mouse Model of Renal Cancer The anti-tumor activity of an anti-CDH6 ADC (NOV0712-sulfo-SPDB-DM4) was assessed in a renal primary tumor xenograft (PTX) model. Human primary xenograft models were established by direct implantation of primary human tumor tissue subcutaneously into nu/nu mice. The resulting xenografts were serially passaged between 4 and 10 times prior to use in this study. Female nude mice were implanted subcutaneously in the axillary region, with a 3x3x3 mm tumor fragment using a 12 gauge trocar. Animals were randomized into treatment groups on day 14 following tumor fragment implantation, when the average tumor volume was 160 $mm^3$ (range 113-245 $mm^3$) Treatments were initiated on Day 14. Anti-tumor activity was determined on day 50 post tumor cell implant. None of the mice showed a decrease in body weight, indicating that the ADC was well tolerated (data not shown). As with the ovarian cancer models, efficacy of anti-CDH6 ADC was observed in renal PTX models featuring greater than twenty percent CDH6 positive tumor area by IHC. As shown in FIG. 22, anti-CDH6 ADC treatment was efficacious against primary human tumors in a renal PTX model.

Figure 23:
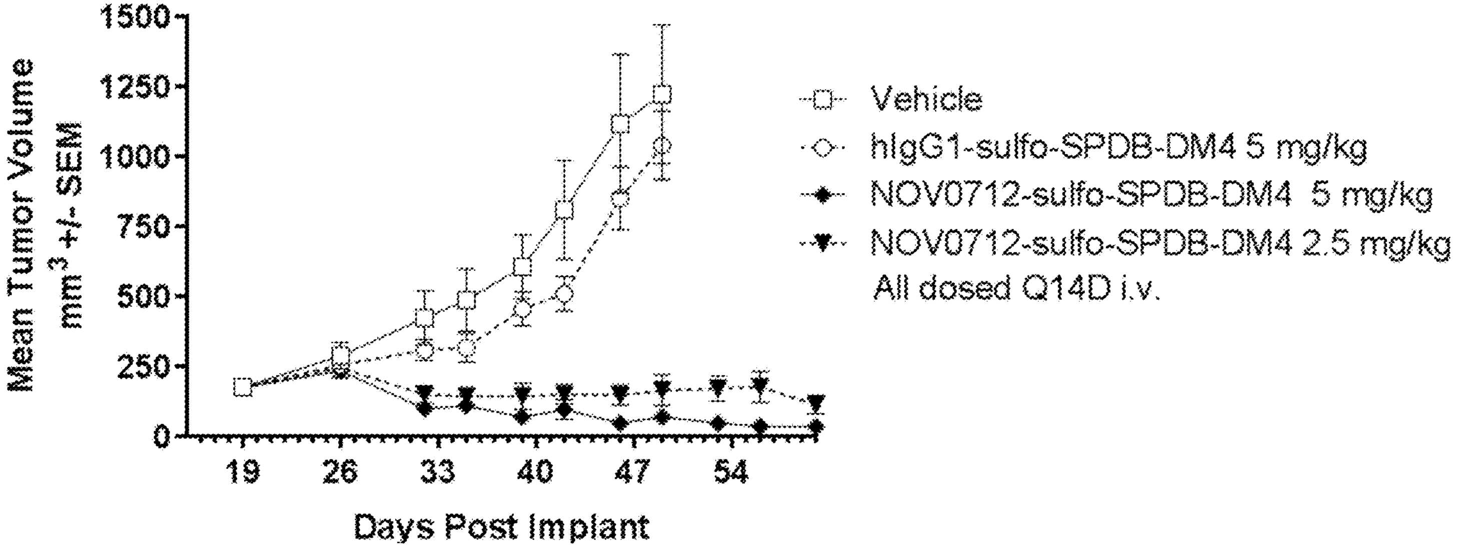
FIG. 23 shows in vivo efficacy of anti-CDH6 antibodies conjugated to sulfo-SPDB-DM4 in a patient derived primary xenograft mouse model of renal cancer.

Example 24: In Vivo Efficacy of an Anti-CDH6 ADC Dosed Either at 2.5 mg/kg, Q14D or 5 mg/kg Q14D in a Patient-Derived Primary Tumor Xenograft Mouse Model of Renal Cancer The anti-tumor activity of an anti-CDH6 ADC (NOV0712-sulfo-SPDB-DM4) was assessed in a renal primary tumor xenograft (PTX) model. Human primary xenograft models were established by direct implantation of primary human tumor tissue subcutaneously into nu/nu nude mice. The resulting xenografts were serially passaged between 4 and 10 times prior to use in this study. Female nude mice were implanted subcutaneously in the axillary region, with a 3x3x3 mm tumor fragment using a 12 gauge trocar. Animals were randomized into treatment groups on day 19 following tumor fragment implantation, when the average tumor volume was 176 $mm^3$ (range 123-267 $mm^3$) Treatments were initiated on Day 19. Anti-tumor activity was determined on day 49 post tumor cell implant. None of the mice showed a decrease in body weight, indicating that the ADC was well tolerated (data not shown). As with the ovarian cancer models, efficacy of anti-CDH6 ADC was observed in renal PTX models featuring greater than twenty percent CDH6 positive tumor area by IHC. As shown in FIG. 23, anti-CDH6 ADC treatment was efficacious against primary human tumors in a renal PTX model at both the 5 mg/kg and 2.5 mg/kg dosage.

Example 25: Anti-CDH6 ADC in Combination Therapy

Anti CDH6 ADCs can be combined with small molecule inhibitors or other antibodies. Using either the Chalice software (Zalicus, Cambridge Mass.) or ComboExplorer application (Novartis, Basel CH), the response of the combination is compared to its single agents, against the widely used Loewe model for drug-with-itself dose-additivity (Lehar et al. Nat. Biotechnol. (2009) 27: 659-666; Zimmermann et al., Drug Discov. Today (2007) 12: 34-42). Excess inhibition compared to additivity can be plotted as a full dose-matrix chart to visualize the drug concentrations where synergies occur. Table 18 shows several anti-CDH6 ADC/compound combinations.

Cell viability can be determined by measuring cellular ATP content using the CellTiter Glo® luminescence assay (Promega, Madison Wis.). One day before drug addition, 250-500 cells are plated into 384-well plates (Greiner, Monroe, N.C.) in 20 μl growth media. Cells are then incubated for 120 h with various concentrations of anti-CDH6 ADC (Table 18), as a single agent, single agent compounds or anti-CDH6 ADC/compound combinations before CellTiter Glo® reagent is added to each well and luminescence recorded on an Envision® plate reader (Perkin Elmer, Waltham Mass.). Luminescence values are used to calculate the inhibition of cell viability relative to DMSO-treated cells (0% inhibition).

TABLE 18 anti-CDH6 ADC combinations

| Target of compound | anti-CDH6 ADC in combination with: | Structure |
|---|---|---|
| RTKi | Glivec ® | Imatinib |
| RTKi | Sutent ® | Sunitinib |
| RTKi | Votrient ® | pazopanib |
| IAPi | NVP-LCL161 | 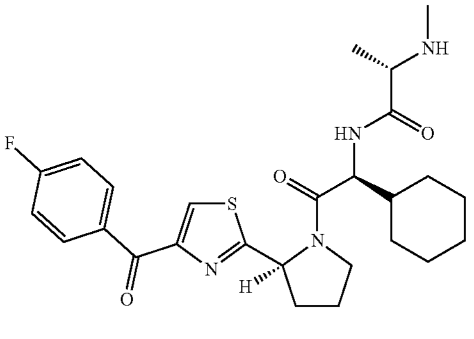 [SMILES: CN[C@@H](C)C(=O)N[C@H](C(=O)N1CCC[C@H]1c1nc(C(=O)c2ccc(F)cc2)cs1)C1CCCCC1] |

TABLE 18-continued
anti-CDH6 ADC combinations
| Target of compound | anti-CDH6 ADC in combination with: | Structure |
|---|---|---|
| PI3K fam. | NVP-BEZ235 | 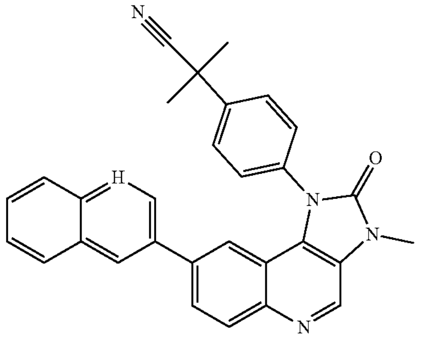 |
| pan PI3Ki | NVP-BKM120 | 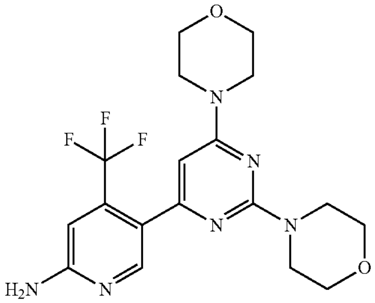 [SMILES: Nc1cc(C(F)(F)F)c(-c2cc(N3CCOCC3)nc(N3CCOCC3)n2)cn1] |
| PI3K | NVP-BYL719 | 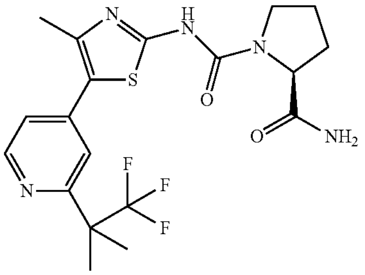 [SMILES: Cc1nc(NC(=O)N2CCC[C@H]2C(N)=O)sc1-c1ccnc(C(C)(C)C(F)(F)F)c1] |
| mTORi (cat.) | NVP-CCG168 | 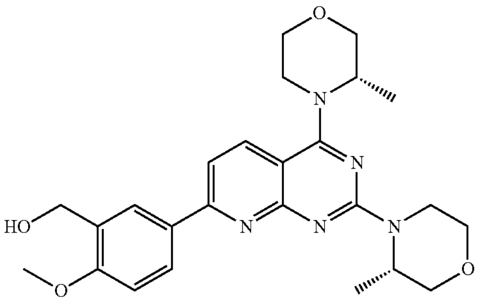 [SMILES: COc1ccc(-c2ccc3c(N4CCOC[C@@H]4C)nc(N4CCOC[C@@H]4C)nc3n2)cc1CO] |
| mTORi (allo.) | Afinitor ® | Everolimus |

TABLE 18-continued
| anti-CDH6 ADC combinations | | |
|---|---|---|
| Target of compound | anti-CDH6 ADC in combination with: | Structure |
| HSP90i | NVP-HSP990 | 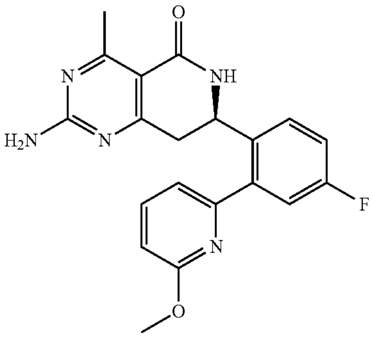 [SMILES: COc1cccc(-c2cc(F)ccc2[C@H]2Cc3nc(N)nc(C)c3C(=O)N2)n1] |
| JAK2 | NVP-BVB808 | 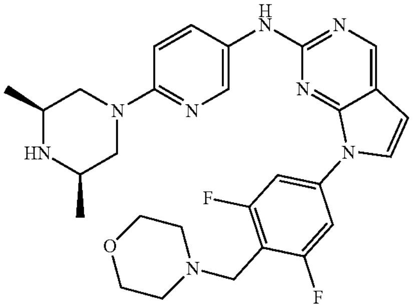 [SMILES: C[C@@H]1CN(c2ccc(Nc3ncc4ccn(-c5cc(F)c(CN6CCOCC6)c(F)c5)c4n3)cn2)C[C@H](C)N1] |
| BCL2/BCL-X1 | ABT263 | 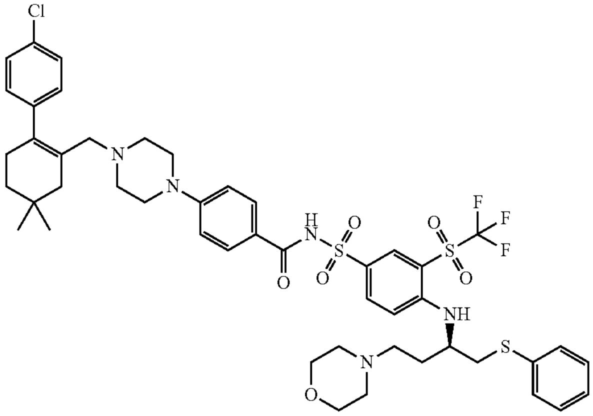 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |
| BCL-X1 | WEHI-539 | 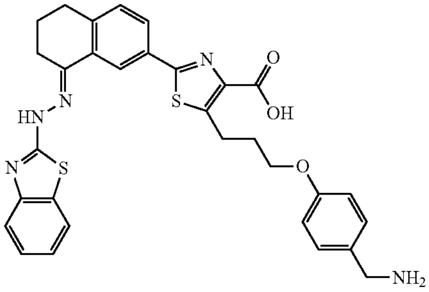 [SMILES: NCc1ccc(OCCCc2sc(-c3ccc4c(c3)/C(=N/Nc3nc5ccccc5s3)CCC4)nc2C(=O)O)cc1] |

TABLE 18-continued

| anti-CDH6 ADC combinations | | |
|---|---|---|
| Target of compound | anti-CDH6 ADC in combination with: | Structure |
| BCL2 | ABT199 | 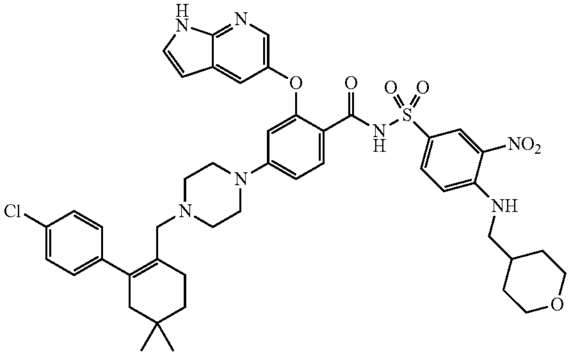 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] |
| HDAC | Farydak ® | panobinostat |
| CDH4/6 | NVP-LEE011 | 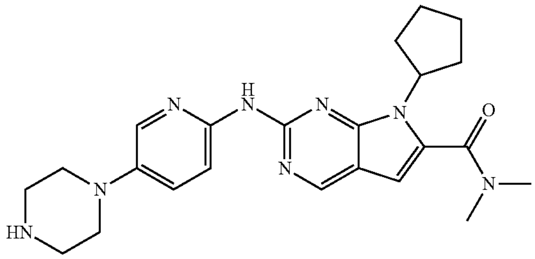 [SMILES: CN(C)C(=O)c1cc2cnc(Nc3ccc(N4CCNCC4)cn3)nc2n1C1CCCC1] |
| MEK | Mekinist ® | Trametinib |
| RAF | Tafinlar ® | Dabrafinib |
| DNA | Paraplatin ® | carboplatin |
| HDM2 | NVP-HDM201 | 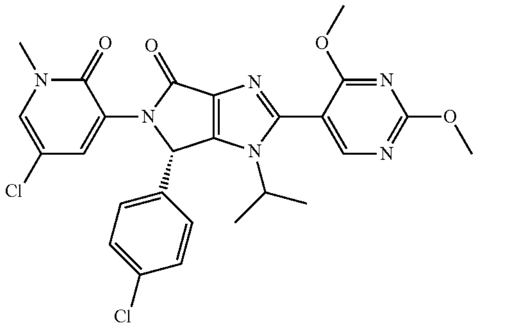 [SMILES: COc1ncc(-c2nc3c(n2C(C)C)[C@H](c2ccc(Cl)cc2)N(c2cc(Cl)cn(C)c2=O)C3=O)c(OC)n1] |
| Tubulin | Taxol ® | paclitaxel |
| HER3 | NVP-LJM716 | anti-HER3 antibody (Garner et al., Cancer Res 2013 73(19):6024-35) |

FIG. 24 is an example of anti-CDH6 ADC in combination with small molecule inhibitors. SNU-8 ovarian cancer cells were grown as described in Example 12 and treated with titrations of an anti-CDH6 ADC (NOV0712-sulfo-SPDB-DM4) and either a Bcl2/Bcl-Xl inhibitor (ABT-263), a Bcl-Xl inhibitor (WEHI-539), an IAP inhibitor (NVP-LCL161) or a MEK inhibitor (trametinib). Potent synergy is seen with an anti-CDH6 ADC (NOV0712-sulfo-SPDB-DM4) in combination with Bcl2/Bcl-Xl, Bcl-Xl, MEK and IAP inhibitors. Self-self combinations of ADC, for example, (CDH6-ADC+CDH6-ADC) or self-self combinations of a small molecule, for example, (NVP-LCL161+NVP-LCL161) were included to distinguish dose additivity from true synergy and these scores are reported in FIG. 24. As FIG. 24 indicates, the CDH6-ADC plus small molecule combinations feature significantly higher Loewe Synergy Scores compared to the self-self combinations.

This data indicates that the combination of an ADC with an anti-mitotic payload (for example, sulfo-SPDB-DM4, SPDB-DM4, SMCC-DM1) or other payloads with a pro-apoptotic small molecule inhibitor (for example, ABT-261, ABT-199, WEHI-539 or IAP inhibitors like NVP-LCL161) or MAPK pathway inhibitors (i.e. trametinib) results in more effective execution of apoptosis following initial G2/M arrest or damage induced by the anti-mitotic/cytotoxic ADC payload alone.

In addition, CDH6-ADC combinations can further be assessed by in vivo combination treatment. CDH6-ADCs can synergize with immuno-modulatory agents targeting the PD/PD-L1 pathway such as Keytruda® (pembrolizumab) or Opdivo® (nivolumab). In summary, the anti-CDH6 ADCs disclosed herein can exert synergistic effects when used in combination with other molecules to lead to more options for treatment.

Example 26: CDH6 Expression in Tumor Indications

Figure 25:
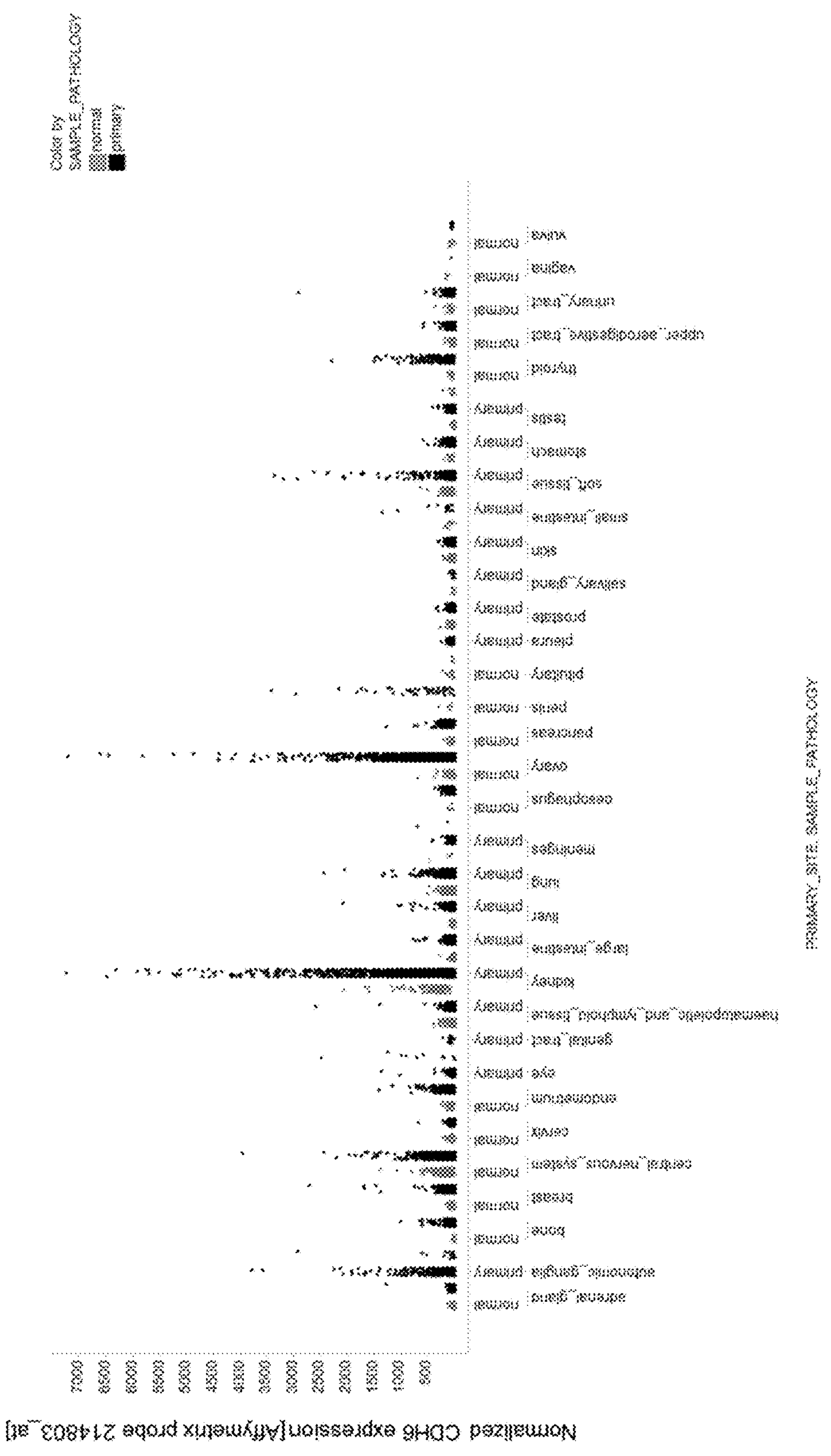
FIG. 25 is a graphic representation of CDH6 mRNA expression in cancerous tissues.

CDH6 is over-expressed in several tumor indications including ovarian cancer, renal cancer, soft tissue cancer, CNS cancers, thyroid cancer and cholangiocarcinoma. CDH6 mRNA expression was assessed using the Affymetrix GeneChip® platform (Santa Clara, Calif.). Specifically, a Novartis-internal mRNA expression database comprising data on human tumor and normal tissue samples was queried using the CDH6 probeset 214803_at and the data were plotted using Tibco Spotfire (Palo Alto, Calif.). Each point on the graph represents an individual tumor or normal tissue sample. As illustrated in FIG. 25, CDH6 features a restricted normal tissue expression and is significantly overexpressed in ovarian cancer, renal cancer, CNS cancers, soft tissue cancers and thyroid cancer and cholangiocarcinoma.

Figure 26:
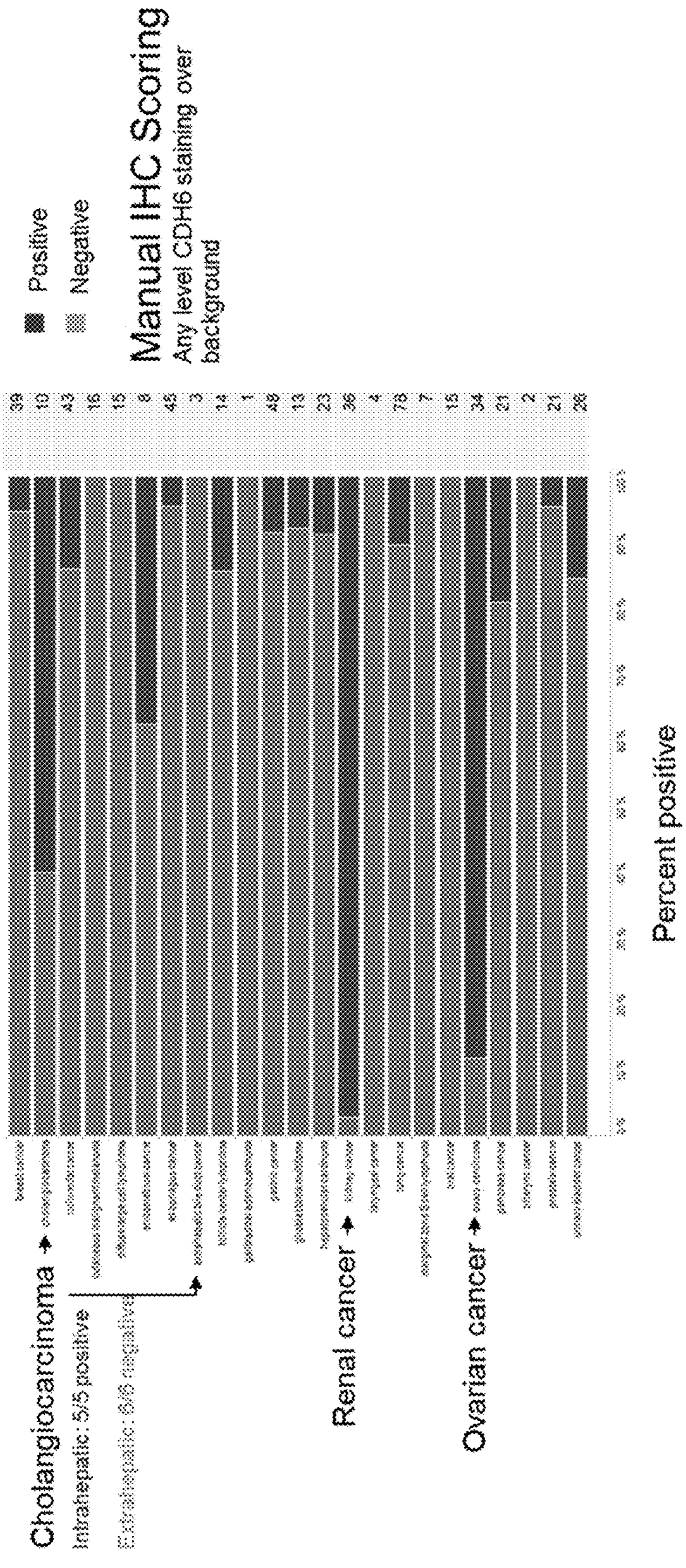
FIG. 26 is a graphical representation of CDH6 protein expression by immunohistochemistry in ovarian cancer, endometrial cancer, renal cancer and cholangiocarcinoma tissue.

CDH6 expression was further assessed in acollection of human primary tumor samples by immuno-histochemistry using the protocol described in Example 21. As shown in FIG. 26, CDH6 protein expression was observed in the majority of ovarian cancer and renal cancer samples. CDH6 expression was also frequently detected in endometrial cancer as well as cholangiocarcinoma. Interestingly, CDH6 expression within cholangiocarcinoma was enriched amongst the intra-hepatic sub-type.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. An antibody drug conjugate of the formula $$Ab\text{-}(L\text{-}(D)_m)_n$$

or a pharmaceutically acceptable salt thereof; wherein

Ab is an antibody or antigen binding fragment thereof comprising: a light chain variable region that comprises (a) a LCDR1 (CDR-Complementarity Determining Region) of SEQ ID NO:224, (b) a LCDR2 of SEQ ID NO:225, (c) a LCDR3 of SEQ ID NO:226; and a heavy chain variable region that comprises: (d) a HCDR1 of SEQ ID NO: 227, (e) a HCDR2 of SEQ ID NO: 228, and (f) a HCDR3 of SEQ ID NO:229 that specifically binds to an epitope of human CDH6;

L is a linker;

D is a drug moiety;

m is an integer from 1 to 8; and n is an integer from 1 to 10.

2. The antibody drug conjugate of claim 1, wherein said n is 3 or 4.

3. The antibody drug conjugate of claim 1, wherein said antibody or antigen binding fragment thereof comprises: a heavy chain variable region (vH) that comprises SEQ ID NO: 230, and a light chain variable region (vL) that comprises SEQ ID NO:231.

4. The antibody drug conjugate of claim 1, wherein said antibody or antigen binding fragment thereof comprises: a heavy chain that comprises SEQ ID NO: 234, and a light chain that comprises SEQ ID NO:235.

5. The antibody drug conjugate of claim 3, that retains at least 90, 91, 92, 93, 94, 95, 96, 97, 98 or 99% identity over either the variable light or variable heavy region.

6. The antibody drug conjugate of claim 1, wherein said linker (L) is selected from the group consisting of a cleavable linker, a non-cleavable linker, a hydrophilic linker, a procharged linker and a dicarboxylic acid based linker.

7. The antibody drug conjugate of claim 6, wherein the linker is derived from a cross-linking reagent selected from the group consisting of: N-succinimidyl-4-(2-pyridyldithio) 2-sulfo-butanoate (sulfo-SPDB), N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

8. The antibody drug conjugate of claim 7, wherein said linker is derived from N-succinimidyl-4-(2-pyridyldithio)2-sulfo-butanoate (sulfo-SPDB).

9. The antibody drug conjugate of claim 1, wherein said drug moiety (D) is selected from a group consisting of: a maytansinoid, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

10. The antibody drug conjugate of claim 9, wherein the drug moiety is a maytansinoid.

11. The antibody drug conjugate of claim 10, wherein the maytansinoid is N(2')-deacetyl-N2-(4-mercapto-4-methyl-1-oxopentyl)-maytansine (DM4) or N(2')-deacetyl-N(2')-(3-mercapto-1-oxopropyl)-maytansine (DM1).

12. The antibody drug conjugate of claim 1 in combination with another therapeutic agent.

13. The antibody drug conjugate of claim 1 in combination with a therapeutic agent listed in Table 18.

14. The antibody drug conjugate of claim 13 in combination with a BCL2 inhibitor, a BCL-XL inhibitor, a BCL2/BCL-XL inhibitor, an IAP inhibitor or a MEK inhibitor.

15. The antibody drug conjugate of claim 1 in combination with an immune modulatory molecule.

16. An antibody drug conjugate of the formula:

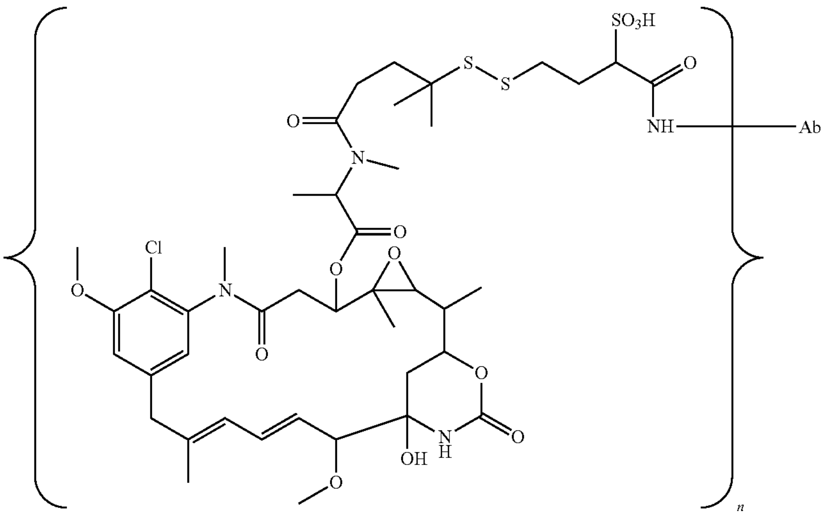

Ab-sulfo-SPDB-DM4 or a pharmaceutically acceptable salt thereof; wherein;

Ab is an antibody or antigen binding fragment comprising a light chain variable region that comprises (a) a LCDR1 (CDR-Complementarity Determining Region) of SEQ ID NO:224, (b) a LCDR2 of SEQ ID NO:225, (c) a LCDR3 of SEQ ID NO:226; and a heavy chain variable region that comprises: (d) a HCDR1 of SEQ ID NO: 227, (e) a HCDR2 of SEQ ID NO: 228, and (f) a HCDR3 of SEQ ID NO:229 thereof that specifically binds to human CDH6, and n is an integer from 1 to 10.

17. The antibody drug conjugate of claim 16 in combination with a BCL2 inhibitor, a BCL-XL inhibitor, a BCL2/BCL-XL inhibitor, an IAP inhibitor or a MEK inhibitor.

18. The antibody drug conjugate of claim 16 in combination with an immune modulatory molecule.

19. A pharmaceutical composition comprising the antibody drug conjugate of claim 1 and a pharmaceutically acceptable carrier.

20. The pharmaceutical composition of claim 19 wherein said composition is prepared as a lyophilisate.

* * * * *

SEQUENCE LISTING

```
<160> NUMBER OF SEQ ID NOS: 541

<210> SEQ ID NO 1
<211> LENGTH: 2988
<212> TYPE: DNA
<213> ORGANISM: Homo sapiens

<400> SEQUENCE: 1

acttcattca cttgcaaatc agtgtgtgcc cacaagagcc agctctcccg agcccgtaac     60

cttcgcatcc caagagctgc agtttcagcc gcgacagcaa gaacggcaga gccggcgacc    120

gcggcggcgg cggcggcgga ggcaggagca gcctgggcgg gtcgcagggt ctccgcgggc    180

gcaggaaggc gagcagagat atcctctgag agccaagcaa agaacattaa ggaaggaagg    240

aggaatgagg ctggatacgg tgcagtgaaa aaggcacttc caagagtggg gcactcacta    300

cgcacagact cgacggtgcc atcagcatga gaacttaccg ctacttcttg ctgctctttt    360

gggtgggcca gccctaccca actctctcaa ctccactatc aaagaggact agtggtttcc    420

cagcaaagaa aagggccctg gagctctctg gaaacagcaa aaatgagctg aaccgttcaa    480

aaaggagctg gatgtggaat cagttctttc tcctggagga atacacagga tccgattatc    540

agtatgtggg caagttacat tcagaccagg atagaggaga tggatcactt aaatatatcc    600

tttcaggaga tggagcagga gatctcttca ttattaatga aaacacaggc gacatacagg    660

ccaccaagag gctggacagg gaagaaaaac ccgtttacat ccttcgagct caagctataa    720

acagaaggac agggagaccc gtggagcccg agtctgaatt catcatcaag atccatgaca    780

tcaatgacaa tgaaccaata ttcaccaagg aggtttacac agccactgtc cctgaaatgt    840

ctgatgtcgg tacatttgtt gtccaagtca ctgcgacgga tgcagatgat ccaacatatg    900

ggaacagtgc taaagttgtc tacagtattc tacagggaca gccctatttt tcagttgaat    960

cagaaacagg tattatcaag acagctttgc tcaacatgga tcgagaaaac agggagcagt   1020

accaagtggt gattcaagcc aaggatatgg gcggccagat gggaggatta tctgggacca   1080

ccaccgtgaa catcacactg actgatgtca acgacaaccc tccccgattc cccccagagta  1140

cataccagtt taaaactcct gaatcttctc caccggggac accaattggc agaatcaaag   1200

ccagcgatgc tgatgtggga gaaaatgctg aaattgagta cagcatcaca gacggtgagg   1260
```

```
ggctggatat gtttgatgtc atcaccgacc aggaaaccca ggaagggatt ataactgtca   1320
aaaagctctt ggactttgaa aagaagaaag tgtataccct taaagtggaa gcctccaatc   1380
cttatgttga gccacgattt ctctacttgg ggcctttcaa agattcagcc acggttagaa   1440
ttgtggtgga ggatgtagat gagccacctg tcttcagcaa actggcctac atcttacaaa   1500
taagagaaga tgctcagata aacaccacaa taggctccgt cacagcccaa gatccagatg   1560
ctgccaggaa tcctgtcaag tactctgtag atcgacacac agatatggac agaatattca   1620
acattgattc tggaaatggt tcgattttta catcgaaact tcttgaccga gaaacactgc   1680
tatggcacaa cattacagtg atagcaacag agatcaataa tccaaagcaa agtagtcgag   1740
tacctctata tattaaagtt ctagatgtca atgacaacgc cccagaattt gctgagttct   1800
atgaaacttt tgtctgtgaa aaagcaaagg cagatcagtt gattcagacc ttgcatgctg   1860
ttgacaagga tgacccttat agtgggcacc aattttcgtt ttccttggcc cctgaagcag   1920
ccagtggctc aaactttacc attcaagaca acaaagacaa cacggcggga atcttaactc   1980
ggaaaaatgg ctataataga cacgagatga gcacctatct cttgcctgtg gtcatttcag   2040
acaacgacta cccagttcaa agcagcactg ggacagtgac tgtccgggtc tgtgcatgtg   2100
accaccacgg gaacatgcaa tcctgccacg cggaggcgct catccacccc acgggactga   2160
gcacgggggc tctggttgcc atccttctgt gcatcgtgat cctactagtg acagtggtgc   2220
tgtttgcagc tctgaggcgg cagcgaaaaa aagagccttt gatcatttcc aaagaggaca   2280
tcagagataa cattgtcagt tacaacgacg aaggtggtgg agaggaggac acccaggctt   2340
ttgatatcgg caccctgagg aatcctgaag ccatagagga caacaaatta cgaagggaca   2400
ttgtgcccga agccctttc ctacccgac ggactccaac agctcgcgac aacaccgatg   2460
tcagagattt cattaaccaa aggttaaagg aaaatgacac ggaccccact gccccgccat   2520
acgactcctt ggccacttac gcctatgaag gcactggctc cgtggcggat tccctgagct   2580
cgctggagtc agtgaccacg gatgcagatc aagactatga ttaccttagt gactggggac   2640
ctcgattcaa aaagcttgca gatatgtatg gaggagtgga cagtgacaaa gactcctaat   2700
ctgttgcctt tttcattttc caatacgaca ctgaaatatg tgaagtggct atttctttat   2760
atttatccac tactccgtga aggcttctct gttctacccg ttccaaaagc caatggctgc   2820
agtccgtgtg gatccaatgt tagagacttt tttctagtac acttttatga gcttccaagg   2880
ggcaaatttt tattttttag tgcatccagt taaccaagtc agcccaacag gcaggtgccg   2940
gaggggagga cagggaacag tatttccact tgttctcagg gcagcgtg                2988
```

<210> SEQ ID NO 2
<211> LENGTH: 790
<212> TYPE: PRT
<213> ORGANISM: Homo sapiens

<400> SEQUENCE: 2

```
Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
```

-continued

```
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Pro Gly Thr Pro Ile Gly
        275                 280                 285

Arg Ile Lys Ala Ser Asp Ala Asp Val Gly Glu Asn Ala Glu Ile Glu
    290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
    450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495
```

Cys Glu Lys Ala Lys Ala Asp Gln Leu Ile Gln Thr Leu His Ala Val
500 505 510

Asp Lys Asp Asp Pro Tyr Ser Gly His Gln Phe Ser Phe Ser Leu Ala
515 520 525

Pro Glu Ala Ala Ser Gly Ser Asn Phe Thr Ile Gln Asp Asn Lys Asp
530 535 540

Asn Thr Ala Gly Ile Leu Thr Arg Lys Asn Gly Tyr Asn Arg His Glu
545 550 555 560

Met Ser Thr Tyr Leu Leu Pro Val Val Ile Ser Asp Asn Asp Tyr Pro
565 570 575

Val Gln Ser Ser Thr Gly Thr Val Thr Val Arg Val Cys Ala Cys Asp
580 585 590

His His Gly Asn Met Gln Ser Cys His Ala Glu Ala Leu Ile His Pro
595 600 605

Thr Gly Leu Ser Thr Gly Ala Leu Val Ala Ile Leu Leu Cys Ile Val
610 615 620

Ile Leu Leu Val Thr Val Val Leu Phe Ala Ala Leu Arg Arg Gln Arg
625 630 635 640

Lys Lys Glu Pro Leu Ile Ile Ser Lys Glu Asp Ile Arg Asp Asn Ile
645 650 655

Val Ser Tyr Asn Asp Glu Gly Gly Gly Glu Glu Asp Thr Gln Ala Phe
660 665 670

Asp Ile Gly Thr Leu Arg Asn Pro Glu Ala Ile Glu Asp Asn Lys Leu
675 680 685

Arg Arg Asp Ile Val Pro Glu Ala Leu Phe Leu Pro Arg Arg Thr Pro
690 695 700

Thr Ala Arg Asp Asn Thr Asp Val Arg Asp Phe Ile Asn Gln Arg Leu
705 710 715 720

Lys Glu Asn Asp Thr Asp Pro Thr Ala Pro Pro Tyr Asp Ser Leu Ala
725 730 735

Thr Tyr Ala Tyr Glu Gly Thr Gly Ser Val Ala Asp Ser Leu Ser Ser
740 745 750

Leu Glu Ser Val Thr Thr Asp Ala Asp Gln Asp Tyr Asp Tyr Leu Ser
755 760 765

Asp Trp Gly Pro Arg Phe Lys Lys Leu Ala Asp Met Tyr Gly Gly Val
770 775 780

Asp Ser Asp Lys Asp Ser
785 790

<210> SEQ ID NO 3
<211> LENGTH: 233
<212> TYPE: PRT
<213> ORGANISM: Homo sapiens

<400> SEQUENCE: 3

Ser Trp Met Trp Asn Gln Phe Phe Leu Leu Glu Glu Tyr Thr Gly Ser
1 5 10 15

Asp Tyr Gln Tyr Val Gly Lys Leu His Ser Asp Gln Asp Arg Gly Asp
20 25 30

Gly Ser Leu Lys Tyr Ile Leu Ser Gly Asp Gly Ala Gly Asp Leu Phe
35 40 45

Ile Ile Asn Glu Asn Thr Gly Asp Ile Gln Ala Thr Lys Arg Leu Asp
50 55 60

Arg Glu Glu Lys Pro Val Tyr Ile Leu Arg Ala Gln Ala Ile Asn Arg 65 70 75 80

Arg Thr Gly Arg Pro Val Glu Pro Glu Ser Glu Phe Ile Ile Lys Ile
85 90 95

His Asp Ile Asn Asp Asn Glu Pro Ile Phe Thr Lys Glu Val Tyr Thr
100 105 110

Ala Thr Val Pro Glu Met Ser Asp Val Gly Thr Phe Val Val Gln Val
115 120 125

Thr Ala Thr Asp Ala Asp Asp Pro Thr Tyr Gly Asn Ser Ala Lys Val
130 135 140

Val Tyr Ser Ile Leu Gln Gly Gln Pro Tyr Phe Ser Val Glu Ser Glu
145 150 155 160

Thr Gly Ile Ile Lys Thr Ala Leu Leu Asn Met Asp Arg Glu Asn Arg
165 170 175

Glu Gln Tyr Gln Val Val Ile Gln Ala Lys Asp Met Gly Gly Gln Met
180 185 190

Gly Gly Leu Ser Gly Thr Thr Thr Val Asn Ile Thr Leu Thr Asp Gly
195 200 205

Gly Gly Gly Ser Glu Phe Arg His Asp Ser Gly Leu Asn Asp Ile Phe
210 215 220

Glu Ala Gln Lys Ile Glu Trp His Glu
225 230

<210> SEQ ID NO 4
<211> LENGTH: 562
<212> TYPE: PRT
<213> ORGANISM: Homo sapiens

<400> SEQUENCE: 4

Ser Trp Met Trp Asn Gln Phe Phe Leu Leu Glu Glu Tyr Thr Gly Ser
1 5 10 15

Asp Tyr Gln Tyr Val Gly Lys Leu His Ser Asp Gln Asp Arg Gly Asp
20 25 30

Gly Ser Leu Lys Tyr Ile Leu Ser Gly Asp Gly Ala Gly Asp Leu Phe
35 40 45

Ile Ile Asn Glu Asn Thr Gly Asp Ile Gln Ala Thr Lys Arg Leu Asp
50 55 60

Arg Glu Glu Lys Pro Val Tyr Ile Leu Arg Ala Gln Ala Ile Asn Arg
65 70 75 80

Arg Thr Gly Arg Pro Val Glu Pro Glu Ser Glu Phe Ile Ile Lys Ile
85 90 95

His Asp Ile Asn Asp Asn Glu Pro Ile Phe Thr Lys Glu Val Tyr Thr
100 105 110

Ala Thr Val Pro Glu Met Ser Asp Val Gly Thr Phe Val Val Gln Val
115 120 125

Thr Ala Thr Asp Ala Asp Asp Pro Thr Tyr Gly Asn Ser Ala Lys Val
130 135 140

Val Tyr Ser Ile Leu Gln Gly Gln Pro Tyr Phe Ser Val Glu Ser Glu
145 150 155 160

Thr Gly Ile Ile Lys Thr Ala Leu Leu Asn Met Asp Arg Glu Asn Arg
165 170 175

Glu Gln Tyr Gln Val Val Ile Gln Ala Lys Asp Met Gly Gly Gln Met
180 185 190

Gly Gly Leu Ser Gly Thr Thr Thr Val Asn Ile Thr Leu Thr Asp Val
195 200 205

```
Asn Asp Asn Pro Pro Arg Phe Pro Gln Ser Thr Tyr Gln Phe Lys Thr
    210                 215                 220

Pro Glu Ser Ser Pro Pro Gly Thr Pro Ile Gly Arg Ile Lys Ala Ser
225                 230                 235                 240

Asp Ala Asp Val Gly Glu Asn Ala Glu Ile Glu Tyr Ser Ile Thr Asp
                245                 250                 255

Gly Glu Gly Leu Asp Met Phe Asp Val Ile Thr Asp Gln Glu Thr Gln
            260                 265                 270

Glu Gly Ile Ile Thr Val Lys Lys Leu Leu Asp Phe Glu Lys Lys Lys
        275                 280                 285

Val Tyr Thr Leu Lys Val Glu Ala Ser Asn Pro Tyr Val Glu Pro Arg
    290                 295                 300

Phe Leu Tyr Leu Gly Pro Phe Lys Asp Ser Ala Thr Val Arg Ile Val
305                 310                 315                 320

Val Glu Asp Val Asp Glu Pro Pro Val Phe Ser Lys Leu Ala Tyr Ile
                325                 330                 335

Leu Gln Ile Arg Glu Asp Ala Gln Ile Asn Thr Thr Ile Gly Ser Val
            340                 345                 350

Thr Ala Gln Asp Pro Asp Ala Ala Arg Asn Pro Val Lys Tyr Ser Val
        355                 360                 365

Asp Arg His Thr Asp Met Asp Arg Ile Phe Asn Ile Asp Ser Gly Asn
    370                 375                 380

Gly Ser Ile Phe Thr Ser Lys Leu Leu Asp Arg Glu Thr Leu Leu Trp
385                 390                 395                 400

His Asn Ile Thr Val Ile Ala Thr Glu Ile Asn Asn Pro Lys Gln Ser
                405                 410                 415

Ser Arg Val Pro Leu Tyr Ile Lys Val Leu Asp Val Asn Asp Asn Ala
            420                 425                 430

Pro Glu Phe Ala Glu Phe Tyr Glu Thr Phe Val Cys Glu Lys Ala Lys
        435                 440                 445

Ala Asp Gln Leu Ile Gln Thr Leu His Ala Val Asp Lys Asp Asp Pro
    450                 455                 460

Tyr Ser Gly His Gln Phe Ser Phe Ser Leu Ala Pro Glu Ala Ala Ser
465                 470                 475                 480

Gly Ser Asn Phe Thr Ile Gln Asp Asn Lys Asp Asn Thr Ala Gly Ile
                485                 490                 495

Leu Thr Arg Lys Asn Gly Tyr Asn Arg His Glu Met Ser Thr Tyr Leu
            500                 505                 510

Leu Pro Val Val Ile Ser Asp Asn Asp Tyr Pro Val Gln Ser Ser Thr
        515                 520                 525

Gly Thr Val Thr Val Arg Val Cys Ala Cys Asp His His Gly Asn Met
    530                 535                 540

Gln Ser Cys His Ala Glu Ala Leu Ile His Pro Thr Gly Leu Ser Thr
545                 550                 555                 560

Gly Ala
```

<210> SEQ ID NO 5
<211> LENGTH: 585
<212> TYPE: PRT
<213> ORGANISM: Homo sapiens
<220> FEATURE:
<221> NAME/KEY: MOD_RES
<222> LOCATION: (580)..(580)
<223> OTHER INFORMATION: Lys(BIOTIN)

<400> SEQUENCE: 5

```
Ser Trp Met Trp Asn Gln Phe Phe Leu Leu Glu Glu Tyr Thr Gly Ser
1               5                   10                  15

Asp Tyr Gln Tyr Val Gly Lys Leu His Ser Asp Gln Asp Arg Gly Asp
            20                  25                  30

Gly Ser Leu Lys Tyr Ile Leu Ser Gly Asp Gly Ala Gly Asp Leu Phe
        35                  40                  45

Ile Ile Asn Glu Asn Thr Gly Asp Ile Gln Ala Thr Lys Arg Leu Asp
    50                  55                  60

Arg Glu Glu Lys Pro Val Tyr Ile Leu Arg Ala Gln Ala Ile Asn Arg
65                  70                  75                  80

Arg Thr Gly Arg Pro Val Glu Pro Glu Ser Glu Phe Ile Ile Lys Ile
                85                  90                  95

His Asp Ile Asn Asp Asn Glu Pro Ile Phe Thr Lys Glu Val Tyr Thr
            100                 105                 110

Ala Thr Val Pro Glu Met Ser Asp Val Gly Thr Phe Val Val Gln Val
        115                 120                 125

Thr Ala Thr Asp Ala Asp Asp Pro Thr Tyr Gly Asn Ser Ala Lys Val
    130                 135                 140

Val Tyr Ser Ile Leu Gln Gly Gln Pro Tyr Phe Ser Val Glu Ser Glu
145                 150                 155                 160

Thr Gly Ile Ile Lys Thr Ala Leu Leu Asn Met Asp Arg Glu Asn Arg
                165                 170                 175

Glu Gln Tyr Gln Val Val Ile Gln Ala Lys Asp Met Gly Gly Gln Met
            180                 185                 190

Gly Gly Leu Ser Gly Thr Thr Thr Val Asn Ile Thr Leu Thr Asp Val
        195                 200                 205

Asn Asp Asn Pro Pro Arg Phe Pro Gln Ser Thr Tyr Gln Phe Lys Thr
    210                 215                 220

Pro Glu Ser Ser Pro Pro Gly Thr Pro Ile Gly Arg Ile Lys Ala Ser
225                 230                 235                 240

Asp Ala Asp Val Gly Glu Asn Ala Glu Ile Glu Tyr Ser Ile Thr Asp
                245                 250                 255

Gly Glu Gly Leu Asp Met Phe Asp Val Ile Thr Asp Gln Glu Thr Gln
            260                 265                 270

Glu Gly Ile Ile Thr Val Lys Lys Leu Leu Asp Phe Glu Lys Lys Lys
        275                 280                 285

Val Tyr Thr Leu Lys Val Glu Ala Ser Asn Pro Tyr Val Glu Pro Arg
    290                 295                 300

Phe Leu Tyr Leu Gly Pro Phe Lys Asp Ser Ala Thr Val Arg Ile Val
305                 310                 315                 320

Val Glu Asp Val Asp Glu Pro Pro Val Phe Ser Lys Leu Ala Tyr Ile
                325                 330                 335

Leu Gln Ile Arg Glu Asp Ala Gln Ile Asn Thr Thr Ile Gly Ser Val
            340                 345                 350

Thr Ala Gln Asp Pro Asp Ala Ala Arg Asn Pro Val Lys Tyr Ser Val
        355                 360                 365

Asp Arg His Thr Asp Met Asp Arg Ile Phe Asn Ile Asp Ser Gly Asn
    370                 375                 380

Gly Ser Ile Phe Thr Ser Lys Leu Leu Asp Arg Glu Thr Leu Leu Trp
385                 390                 395                 400

His Asn Ile Thr Val Ile Ala Thr Glu Ile Asn Asn Pro Lys Gln Ser
                405                 410                 415
```

```
Ser Arg Val Pro Leu Tyr Ile Lys Val Leu Asp Val Asn Asp Asn Ala
            420                 425                 430

Pro Glu Phe Ala Glu Phe Tyr Glu Thr Phe Val Cys Glu Lys Ala Lys
        435                 440                 445

Ala Asp Gln Leu Ile Gln Thr Leu His Ala Val Asp Lys Asp Asp Pro
    450                 455                 460

Tyr Ser Gly His Gln Phe Ser Phe Ser Leu Ala Pro Glu Ala Ala Ser
465                 470                 475                 480

Gly Ser Asn Phe Thr Ile Gln Asp Asn Lys Asp Asn Thr Ala Gly Ile
                485                 490                 495

Leu Thr Arg Lys Asn Gly Tyr Asn Arg His Glu Met Ser Thr Tyr Leu
            500                 505                 510

Leu Pro Val Val Ile Ser Asp Asn Asp Tyr Pro Val Gln Ser Ser Thr
        515                 520                 525

Gly Thr Val Thr Val Arg Val Cys Ala Cys Asp His His Gly Asn Met
    530                 535                 540

Gln Ser Cys His Ala Glu Ala Leu Ile His Pro Thr Gly Leu Ser Thr
545                 550                 555                 560

Gly Ala Gly Ser Glu Phe Arg His Asp Ser Gly Leu Asn Asp Ile Phe
                565                 570                 575

Glu Ala Gln Lys Ile Glu Trp His Glu
            580                 585


<210> SEQ ID NO 6
<211> LENGTH: 791
<212> TYPE: PRT
<213> ORGANISM: Homo sapiens

<400> SEQUENCE: 6

Ser Trp Met Trp Asn Gln Phe Phe Leu Leu Glu Glu Tyr Thr Gly Ser
1               5                   10                  15

Asp Tyr Gln Tyr Val Gly Lys Leu His Ser Asp Gln Asp Arg Gly Asp
            20                  25                  30

Gly Ser Leu Lys Tyr Ile Leu Ser Gly Asp Gly Ala Gly Asp Leu Phe
        35                  40                  45

Ile Ile Asn Glu Asn Thr Gly Asp Ile Gln Ala Thr Lys Arg Leu Asp
    50                  55                  60

Arg Glu Glu Lys Pro Val Tyr Ile Leu Arg Ala Gln Ala Ile Asn Arg
65                  70                  75                  80

Arg Thr Gly Arg Pro Val Glu Pro Glu Ser Glu Phe Ile Ile Lys Ile
                85                  90                  95

His Asp Ile Asn Asp Asn Glu Pro Ile Phe Thr Lys Glu Val Tyr Thr
            100                 105                 110

Ala Thr Val Pro Glu Met Ser Asp Val Gly Thr Phe Val Val Gln Val
        115                 120                 125

Thr Ala Thr Asp Ala Asp Asp Pro Thr Tyr Gly Asn Ser Ala Lys Val
    130                 135                 140

Val Tyr Ser Ile Leu Gln Gly Gln Pro Tyr Phe Ser Val Glu Ser Glu
145                 150                 155                 160

Thr Gly Ile Ile Lys Thr Ala Leu Leu Asn Met Asp Arg Glu Asn Arg
                165                 170                 175

Glu Gln Tyr Gln Val Val Ile Gln Ala Lys Asp Met Gly Gly Gln Met
            180                 185                 190

Gly Gly Leu Ser Gly Thr Thr Thr Val Asn Ile Thr Leu Thr Asp Val
        195                 200                 205
```

```
Asn Asp Asn Pro Pro Arg Phe Pro Gln Ser Thr Tyr Gln Phe Lys Thr
    210                 215                 220

Pro Glu Ser Ser Pro Pro Gly Thr Pro Ile Gly Arg Ile Lys Ala Ser
225                 230                 235                 240

Asp Ala Asp Val Gly Glu Asn Ala Glu Ile Glu Tyr Ser Ile Thr Asp
                245                 250                 255

Gly Glu Gly Leu Asp Met Phe Asp Val Ile Thr Asp Gln Glu Thr Gln
            260                 265                 270

Glu Gly Ile Ile Thr Val Lys Lys Leu Leu Asp Phe Glu Lys Lys Lys
        275                 280                 285

Val Tyr Thr Leu Lys Val Glu Ala Ser Asn Pro Tyr Val Glu Pro Arg
    290                 295                 300

Phe Leu Tyr Leu Gly Pro Phe Lys Asp Ser Ala Thr Val Arg Ile Val
305                 310                 315                 320

Val Glu Asp Val Asp Glu Pro Pro Val Phe Ser Lys Leu Ala Tyr Ile
                325                 330                 335

Leu Gln Ile Arg Glu Asp Ala Gln Ile Asn Thr Thr Ile Gly Ser Val
            340                 345                 350

Thr Ala Gln Asp Pro Asp Ala Ala Arg Asn Pro Val Lys Tyr Ser Val
        355                 360                 365

Asp Arg His Thr Asp Met Asp Arg Ile Phe Asn Ile Asp Ser Gly Asn
    370                 375                 380

Gly Ser Ile Phe Thr Ser Lys Leu Leu Asp Arg Glu Thr Leu Leu Trp
385                 390                 395                 400

His Asn Ile Thr Val Ile Ala Thr Glu Ile Asn Asn Pro Lys Gln Ser
                405                 410                 415

Ser Arg Val Pro Leu Tyr Ile Lys Val Leu Asp Val Asn Asp Asn Ala
            420                 425                 430

Pro Glu Phe Ala Glu Phe Tyr Glu Thr Phe Val Cys Glu Lys Ala Lys
        435                 440                 445

Ala Asp Gln Leu Ile Gln Thr Leu His Ala Val Asp Lys Asp Asp Pro
    450                 455                 460

Tyr Ser Gly His Gln Phe Ser Phe Ser Leu Ala Pro Glu Ala Ala Ser
465                 470                 475                 480

Gly Ser Asn Phe Thr Ile Gln Asp Asn Lys Asp Asn Thr Ala Gly Ile
                485                 490                 495

Leu Thr Arg Lys Asn Gly Tyr Asn Arg His Glu Met Ser Thr Tyr Leu
            500                 505                 510

Leu Pro Val Val Ile Ser Asp Asn Asp Tyr Pro Val Gln Ser Ser Thr
        515                 520                 525

Gly Thr Val Thr Val Arg Val Cys Ala Cys Asp His His Gly Asn Met
    530                 535                 540

Gln Ser Cys His Ala Glu Ala Leu Ile His Pro Thr Gly Leu Ser Thr
545                 550                 555                 560

Gly Ala Gly Ser Asp Lys Thr His Thr Cys Pro Pro Cys Pro Ala Pro
                565                 570                 575

Glu Leu Leu Gly Gly Pro Ser Val Phe Leu Phe Pro Pro Lys Pro Lys
            580                 585                 590

Asp Thr Leu Met Ile Ser Arg Thr Pro Glu Val Thr Cys Val Val Val
        595                 600                 605

Asp Val Ser His Glu Asp Pro Glu Val Lys Phe Asn Trp Tyr Val Asp
    610                 615                 620
```

Gly Val Glu Val His Asn Ala Lys Thr Lys Pro Arg Glu Glu Gln Tyr
625 630 635 640

Asn Ser Thr Tyr Arg Val Val Ser Val Leu Thr Val Leu His Gln Asp
645 650 655

Trp Leu Asn Gly Lys Glu Tyr Lys Cys Lys Val Ser Asn Lys Ala Leu
660 665 670

Pro Ala Pro Ile Glu Lys Thr Ile Ser Lys Ala Lys Gly Gln Pro Arg
675 680 685

Glu Pro Gln Val Tyr Thr Leu Pro Pro Ser Arg Glu Glu Met Thr Lys
690 695 700

Asn Gln Val Ser Leu Thr Cys Leu Val Lys Gly Phe Tyr Pro Ser Asp
705 710 715 720

Ile Ala Val Glu Trp Glu Ser Asn Gly Gln Pro Glu Asn Asn Tyr Lys
725 730 735

Thr Thr Pro Pro Val Leu Asp Ser Asp Gly Ser Phe Phe Leu Tyr Ser
740 745 750

Lys Leu Thr Val Asp Lys Ser Arg Trp Gln Gln Gly Asn Val Phe Ser
755 760 765

Cys Ser Val Met His Glu Ala Leu His Asn His Tyr Thr Gln Lys Ser
770 775 780

Leu Ser Leu Ser Pro Gly Lys
785 790

<210> SEQ ID NO 7
<211> LENGTH: 585
<212> TYPE: PRT
<213> ORGANISM: Macaca fascicularis

<400> SEQUENCE: 7

Ser Trp Met Trp Asn Gln Phe Phe Leu Leu Glu Glu Tyr Thr Gly Ser
1 5 10 15

Asp Tyr Gln Tyr Val Gly Lys Leu His Ser Asp Gln Asp Arg Gly Asp
20 25 30

Gly Ser Leu Lys Tyr Ile Leu Ser Gly Asp Gly Ala Gly Asp Leu Phe
35 40 45

Ile Ile Asn Glu Asn Thr Gly Asp Ile Gln Ala Thr Lys Arg Leu Asp
50 55 60

Arg Glu Glu Lys Pro Val Tyr Ile Leu Arg Ala Gln Ala Ile Asn Arg
65 70 75 80

Arg Thr Gly Arg Pro Val Glu Pro Glu Ser Glu Phe Ile Ile Lys Ile
85 90 95

His Asp Ile Asn Asp Asn Glu Pro Ile Phe Thr Lys Glu Val Tyr Thr
100 105 110

Ala Thr Val Pro Glu Met Ser Asp Val Gly Thr Phe Val Val Gln Val
115 120 125

Thr Ala Thr Asp Ala Asp Asp Pro Thr Tyr Gly Asn Ser Ala Lys Val
130 135 140

Val Tyr Ser Ile Leu Gln Gly Gln Pro Tyr Phe Ser Val Glu Ser Glu
145 150 155 160

Thr Gly Ile Ile Lys Thr Ala Leu Leu Asn Met Asp Arg Glu Asn Arg
165 170 175

Glu Gln Tyr Gln Val Val Ile Gln Ala Lys Asp Met Gly Gly Gln Met
180 185 190

Gly Gly Leu Ser Gly Thr Thr Thr Val Asn Ile Thr Leu Thr Asp Val
195 200 205

Asn Asp Asn Pro Pro Arg Phe Pro Gln Ser Thr Tyr Gln Phe Lys Thr
    210                 215                 220

Pro Glu Ser Ser Pro Pro Gly Thr Pro Ile Gly Arg Ile Lys Ala Ser
225                 230                 235                 240

Asp Ala Asp Val Gly Glu Asn Ala Glu Ile Glu Tyr Ser Ile Thr Asp
                245                 250                 255

Gly Glu Gly Leu Asp Met Phe Asp Val Ile Thr Asp Gln Glu Thr Gln
            260                 265                 270

Glu Gly Ile Ile Thr Val Lys Lys Leu Leu Asp Phe Glu Lys Lys Lys
        275                 280                 285

Val Tyr Thr Leu Lys Val Glu Ala Ser Asn Pro His Val Glu Pro Arg
    290                 295                 300

Phe Leu Tyr Leu Gly Pro Phe Lys Asp Ser Ala Thr Val Arg Ile Val
305                 310                 315                 320

Val Glu Asp Val Asp Glu Pro Pro Val Phe Ser Lys Leu Ala Tyr Ile
                325                 330                 335

Leu Gln Ile Arg Glu Asp Ala Gln Ile Asn Thr Thr Ile Gly Ser Val
            340                 345                 350

Thr Ala Gln Asp Pro Asp Ala Ala Arg Asn Pro Val Lys Tyr Ser Val
        355                 360                 365

Asp Arg His Thr Asp Met Asp Arg Ile Phe Asn Ile Asp Ser Gly Asn
    370                 375                 380

Gly Ser Ile Phe Thr Ser Lys Leu Leu Asp Arg Glu Thr Leu Leu Trp
385                 390                 395                 400

His Asn Ile Thr Val Ile Ala Thr Glu Ile Asn Asn Pro Lys Gln Ser
                405                 410                 415

Ser Arg Val Pro Leu Tyr Ile Lys Val Leu Asp Val Asn Asp Asn Ala
            420                 425                 430

Pro Glu Phe Ala Glu Phe Tyr Glu Thr Phe Val Cys Glu Lys Ala Lys
        435                 440                 445

Ala Asp Gln Leu Ile Gln Thr Leu Arg Ala Val Asp Lys Asp Asp Pro
    450                 455                 460

Tyr Ser Gly His Gln Phe Ser Phe Ser Leu Ala Pro Glu Ala Ala Ser
465                 470                 475                 480

Gly Ser Asn Phe Thr Ile Gln Asp Asn Lys Asp Asn Thr Ala Gly Ile
                485                 490                 495

Leu Thr Arg Lys Asn Gly Tyr Asn Arg His Glu Met Ser Thr Tyr Leu
            500                 505                 510

Leu Pro Val Val Ile Ser Asp Asn Asp Tyr Pro Val Gln Ser Ser Thr
        515                 520                 525

Gly Thr Val Thr Val Arg Val Cys Ala Cys Asp His His Gly Asn Met
    530                 535                 540

Gln Ser Cys His Ala Glu Ala Leu Ile His Pro Thr Gly Leu Ser Thr
545                 550                 555                 560

Gly Ala Gly Ser Glu Phe Arg His Asp Ser Gly Leu Asn Asp Ile Phe
                565                 570                 575

Glu Ala Gln Lys Ile Glu Trp His Glu
            580                 585

<210> SEQ ID NO 8
<211> LENGTH: 585
<212> TYPE: PRT
<213> ORGANISM: Mus musculus

<400> SEQUENCE: 8

Ser Trp Met Trp Asn Gln Phe Phe Leu Leu Glu Glu Tyr Thr Gly Ser
1 5 10 15

Asp Tyr Gln Tyr Val Gly Lys Leu His Ser Asp Gln Asp Arg Gly Asp
20 25 30

Gly Ser Leu Lys Tyr Ile Leu Ser Gly Asp Gly Ala Gly Asp Leu Phe
35 40 45

Ile Ile Asn Glu Asn Thr Gly Asp Ile Gln Ala Thr Lys Arg Leu Asp
50 55 60

Arg Glu Glu Lys Pro Val Tyr Ile Leu Arg Ala Gln Ala Val Asn Arg
65 70 75 80

Arg Thr Gly Arg Pro Val Glu Pro Glu Ser Glu Phe Ile Ile Lys Ile
85 90 95

His Asp Ile Asn Asp Asn Glu Pro Ile Phe Thr Lys Asp Val Tyr Thr
100 105 110

Ala Thr Val Pro Glu Met Ala Asp Val Gly Thr Phe Val Val Gln Val
115 120 125

Thr Ala Thr Asp Ala Asp Asp Pro Thr Tyr Gly Asn Ser Ala Lys Val
130 135 140

Val Tyr Ser Ile Leu Gln Gly Gln Pro Tyr Phe Ser Val Glu Ser Glu
145 150 155 160

Thr Gly Ile Ile Lys Thr Ala Leu Leu Asn Met Asp Arg Glu Asn Arg
165 170 175

Glu Gln Tyr Gln Val Val Ile Gln Ala Lys Asp Met Gly Gly Gln Met
180 185 190

Gly Gly Leu Ser Gly Thr Thr Thr Val Asn Ile Thr Leu Thr Asp Val
195 200 205

Asn Asp Asn Pro Pro Arg Phe Pro Gln Ser Thr Tyr Gln Phe Lys Thr
210 215 220

Pro Glu Ser Ser Pro Pro Gly Thr Pro Ile Gly Arg Ile Lys Ala Ser
225 230 235 240

Asp Ala Asp Val Gly Glu Asn Ala Glu Ile Glu Tyr Ser Ile Thr Asp
245 250 255

Gly Glu Gly His Glu Met Phe Asp Val Ile Thr Asp Gln Glu Thr Gln
260 265 270

Glu Gly Ile Ile Thr Val Lys Lys Leu Leu Asp Phe Glu Lys Lys Lys
275 280 285

Val Tyr Thr Leu Lys Val Glu Ala Ser Asn Pro His Val Glu Pro Arg
290 295 300

Phe Leu Tyr Leu Gly Pro Phe Lys Asp Ser Ala Thr Val Arg Ile Val
305 310 315 320

Val Asp Asp Val Asp Glu Pro Pro Val Phe Ser Lys Leu Ala Tyr Ile
325 330 335

Leu Gln Ile Arg Glu Asp Ala Arg Ile Asn Thr Thr Ile Gly Ser Val
340 345 350

Ala Ala Gln Asp Pro Asp Ala Ala Arg Asn Pro Val Lys Tyr Ser Val
355 360 365

Asp Arg His Thr Asp Met Asp Arg Ile Phe Asn Ile Asp Ser Gly Asn
370 375 380

Gly Ser Ile Phe Thr Ser Lys Leu Leu Asp Arg Glu Thr Leu Leu Trp
385 390 395 400

His Asn Ile Thr Val Ile Ala Thr Glu Ile Asn Asn Pro Lys Gln Ser
405 410 415

```
Ser Arg Val Pro Leu Tyr Ile Lys Val Leu Asp Val Asn Asp Asn Ala
            420                 425                 430

Pro Glu Phe Ala Glu Phe Tyr Glu Thr Phe Val Cys Glu Lys Ala Lys
        435                 440                 445

Ala Asp Gln Leu Ile Gln Thr Leu Arg Ala Val Asp Lys Asp Asp Pro
    450                 455                 460

Tyr Ser Gly His Gln Phe Ser Phe Ser Leu Ala Pro Glu Ala Ala Ser
465                 470                 475                 480

Ser Ser Asn Phe Thr Ile Gln Asp Asn Lys Asp Asn Thr Ala Gly Ile
                485                 490                 495

Leu Thr Arg Lys Asn Gly Tyr Asn Arg His Glu Met Ser Thr Tyr Leu
            500                 505                 510

Leu Pro Val Val Ile Ser Asp Asn Asp Tyr Pro Val Gln Ser Ser Thr
        515                 520                 525

Gly Thr Val Thr Val Arg Val Cys Ala Cys Asp His His Gly Asn Met
    530                 535                 540

Gln Ser Cys His Ala Glu Ala Leu Ile His Pro Thr Gly Leu Ser Thr
545                 550                 555                 560

Gly Ala Gly Ser Glu Phe Arg His Asp Ser Gly Leu Asn Asp Ile Phe
                565                 570                 575

Glu Ala Gln Lys Ile Glu Trp His Glu
            580                 585


<210> SEQ ID NO 9
<211> LENGTH: 585
<212> TYPE: PRT
<213> ORGANISM: Rattus norvegicus

<400> SEQUENCE: 9

Ser Trp Met Trp Asn Gln Phe Phe Leu Leu Glu Glu Tyr Thr Gly Ser
1               5                   10                  15

Asp Tyr Gln Tyr Val Gly Lys Leu His Ser Asp Gln Asp Arg Gly Asp
            20                  25                  30

Gly Ser Leu Lys Tyr Ile Leu Ser Gly Asp Gly Ala Gly Asp Leu Phe
        35                  40                  45

Ile Ile Asn Glu Asn Thr Gly Asp Ile Gln Ala Thr Lys Arg Leu Asp
    50                  55                  60

Arg Glu Glu Lys Pro Val Tyr Ile Leu Arg Ala Gln Ala Ile Asn Arg
65                  70                  75                  80

Arg Thr Gly Arg Pro Val Glu Pro Glu Ser Glu Phe Ile Ile Lys Ile
                85                  90                  95

His Asp Ile Asn Asp Asn Glu Pro Ile Phe Thr Lys Asp Val Tyr Thr
            100                 105                 110

Ala Thr Val Pro Glu Met Ala Asp Val Gly Thr Phe Val Val Gln Val
        115                 120                 125

Thr Ala Thr Asp Ala Asp Asp Pro Thr Tyr Gly Asn Ser Ala Lys Val
    130                 135                 140

Val Tyr Ser Ile Leu Gln Gly Gln Pro Tyr Phe Ser Val Glu Ser Glu
145                 150                 155                 160

Thr Gly Ile Ile Lys Thr Ala Leu Leu Asn Met Asp Arg Glu Asn Arg
                165                 170                 175

Glu Gln Tyr Gln Val Val Ile Gln Ala Lys Asp Met Gly Gly Gln Met
            180                 185                 190

Gly Gly Leu Ser Gly Thr Thr Thr Val Asn Ile Thr Leu Thr Asp Val
```

```
        195                 200                 205

Asn Asp Asn Pro Pro Arg Phe Pro Gln Ser Thr Tyr Gln Phe Lys Thr
    210                 215                 220

Pro Glu Ser Ser Pro Pro Gly Thr Pro Ile Gly Arg Ile Lys Ala Ser
225                 230                 235                 240

Asp Ala Asp Val Gly Glu Asn Ala Glu Ile Glu Tyr Ser Ile Thr Asp
                245                 250                 255

Gly Glu Gly His Asp Met Phe Asp Val Ile Thr Asp Gln Glu Thr Gln
            260                 265                 270

Glu Gly Ile Ile Thr Val Lys Lys Leu Leu Asp Phe Glu Lys Lys Arg
        275                 280                 285

Val Tyr Thr Leu Lys Val Glu Ala Ser Asn Pro His Ile Glu Pro Arg
    290                 295                 300

Phe Leu Tyr Leu Gly Pro Phe Lys Asp Ser Ala Thr Val Arg Ile Val
305                 310                 315                 320

Val Asp Asp Val Asp Glu Pro Pro Val Phe Ser Lys Leu Ala Tyr Ile
                325                 330                 335

Leu Gln Ile Arg Glu Asp Ala Gln Ile Asn Thr Thr Ile Gly Ser Val
            340                 345                 350

Ala Ala Gln Asp Pro Asp Ala Ala Arg Asn Pro Val Lys Tyr Ser Val
        355                 360                 365

Asp Arg His Thr Asp Met Asp Arg Ile Phe Asn Ile Asp Ser Gly Asn
    370                 375                 380

Gly Ser Ile Phe Thr Ser Lys Leu Leu Asp Arg Glu Thr Leu Leu Trp
385                 390                 395                 400

His Asn Ile Thr Val Ile Ala Thr Glu Ile Asn Asn Pro Lys Gln Ser
                405                 410                 415

Ser Arg Val Pro Leu Tyr Ile Lys Val Leu Asp Val Asn Asp Asn Ala
            420                 425                 430

Pro Glu Phe Ala Glu Phe Tyr Glu Thr Phe Val Cys Glu Lys Ala Lys
        435                 440                 445

Ala Asp Gln Leu Ile Gln Thr Leu His Ala Val Asp Lys Asp Asp Pro
    450                 455                 460

Tyr Ser Gly His Gln Phe Ser Phe Ser Leu Ala Pro Glu Ala Ala Ser
465                 470                 475                 480

Gly Ser Asn Phe Thr Ile Gln Asp Asn Lys Asp Asn Thr Ala Gly Ile
                485                 490                 495

Leu Thr Arg Lys Asn Gly Tyr Asn Arg His Glu Met Ser Thr Tyr Leu
            500                 505                 510

Leu Pro Val Val Ile Ser Asp Asn Asp Tyr Pro Val Gln Ser Ser Thr
        515                 520                 525

Gly Thr Val Thr Val Arg Val Cys Ala Cys Asp His His Gly Asn Met
    530                 535                 540

Gln Ser Cys His Ala Glu Ala Leu Ile His Pro Thr Gly Leu Ser Thr
545                 550                 555                 560

Gly Ala Gly Ser Glu Phe Arg His Asp Ser Gly Leu Asn Asp Ile Phe
                565                 570                 575

Glu Ala Gln Lys Ile Glu Trp His Glu
            580                 585
```

<210> SEQ ID NO 10
<211> LENGTH: 17
<212> TYPE: DNA
<213> ORGANISM: Artificial Sequence -continued
<220> FEATURE:
<221> NAME/KEY: source
<223> OTHER INFORMATION: /note="Description of Artificial Sequence:
Synthetic primer"

<400> SEQUENCE: 10
caggaaacag ctatgac 17

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 11
gataagcatg cgtaggagaa a 21

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 12
taatacgact cactataggg 20

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 13
ctctagcgcc accatgaaac a 21

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 14

Ser Gly Ser Ser Ser Asn Ile Gly Ser Gln Tyr Val Tyr
1 5 10

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 15

Tyr Asn Ser Glu Arg Pro Ser 1 5

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

Gln Thr Trp Asp Ala Ser Ser Gln Ser Phe Val
1 5 10

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Ser Tyr Ala Ile Ser
1 5

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Gly Ile Ile Pro Ile Phe Gly Thr Ala Asn Tyr Ala Gln Lys Phe Gln
1 5 10 15

Gly

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Lys Phe Pro Gly Arg Gly Pro Phe Ala Tyr
1 5 10

<210> SEQ ID NO 20
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

Gln Val Gln Leu Val Gln Ser Gly Ala Glu Val Lys Lys Pro Gly Ser
1 5 10 15

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Phe Pro Gly Arg Gly Pro Phe Ala Tyr Trp Gly Gln Gly
            100                 105                 110

Thr Leu Val Thr Val Ser Ser
        115
```

<210> SEQ ID NO 21
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Gln
            20                  25                  30

Tyr Val Tyr Trp Tyr Gln Gln Leu Pro Gly Thr Ala Pro Lys Leu Leu
        35                  40                  45

Ile Tyr Tyr Asn Ser Glu Arg Pro Ser Gly Met Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Thr Trp Asp Ala Ser Ser
                85                  90                  95

Gln Ser Phe Val Phe Gly Gly Gly Thr Lys Leu Thr Val Leu
            100                 105                 110
```

<210> SEQ ID NO 22
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
caggtgcaat tggtgcagag cggtgccgaa gtgaaaaaac cgggcagcag cgtgaaagtt     60

agctgcaaag catccggagg gacgttttct tcttacgcta tctcttgggt gcgccaggcc    120

ccgggccagg gcctcgagtg gatgggcggt atcatcccga tcttcggcac tgcgaactac    180

gcccagaaat ttcagggccg ggtgaccatt accgccgatg aaagcaccag caccgcctat    240

atggaactga gcagcctgcg cagcgaagat acggccgtgt attattgcgc gcgtaaattc    300

ccgggtcgtg gtccgttcgc ttactggggc caaggcaccc tggtgactgt tagctca       357
```

<210> SEQ ID NO 23
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23
gatatcgtgc tgacccagcc gccgagcgtg agcggtgcac cgggccagcg cgtgaccatt 60
agctgtagcg gcagcagcag caacattggt tctcagtacg tgtactggta ccagcagctg 120
ccgggcacgg cgccgaaact gctgatctac tacaactctg aacgcccgag cggcatgccg 180
gatcgcttta gcggatccaa aagcggcacc agcgccagcc tggcgattac cggcctgcaa 240
gcagaagacg aagcggatta ttactgccag acttgggacg cttcttctca gtctttcgtg 300
tttggcggcg gcacgaagtt aaccgtccta 330

<210> SEQ ID NO 24
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Lys Phe Pro Gly Arg Gly Pro Phe Ala Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 25
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Gln
            20                  25                  30

Tyr Val Tyr Trp Tyr Gln Gln Leu Pro Gly Thr Ala Pro Lys Leu Leu
        35                  40                  45

Ile Tyr Tyr Asn Ser Glu Arg Pro Ser Gly Met Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Thr Trp Asp Ala Ser Ser
                85                  90                  95

Gln Ser Phe Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
```

```
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 26
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26

caggtgcaat tggtgcagag cggtgccgaa gtgaaaaaac cgggcagcag cgtgaaagtt      60

agctgcaaag catccggagg gacgttttct tcttacgcta tctcttgggt gcgccaggcc     120

ccgggccagg gcctcgagtg gatgggcggt atcatcccga tcttcggcac tgcgaactac     180

gcccagaaat ttcagggccg ggtgaccatt accgccgatg aaagcaccag caccgcctat     240

atggaactga gcagcctgcg cagcgaagat acggccgtgt attattgcgc gcgtaaattc     300

ccgggtcgtg gtccgttcgc ttactggggc caaggcaccc tggtgactgt tagctcagcc     360

tccaccaagg gtccatcggt cttccccctg gcaccctcct ccaagagcac ctctgggggc     420

acagcggccc tgggctgcct ggtcaaggac tacttccccg aaccggtgac ggtgtcgtgg     480

aactcaggcg ccctgaccag cggcgtgcac accttcccgg ctgtcctaca gtcctcagga     540

ctctactccc tcagcagcgt ggtgaccgtg ccctccagca gcttgggcac ccagacctac     600

atctgcaacg tgaatcacaa gcccagcaac accaaggtgg acaagagagt tgagcccaaa     660

tcttgtgaca aaactcacac atgcccaccg tgcccagcac ctgaactcct ggggggaccg     720

tcagtcttcc tcttcccccc aaaacccaag gacaccctca tgatctcccg gacccctgag     780

gtcacatgcg tggtggtgga cgtgagccac gaagaccctg aggtcaagtt caactggtac     840

gtggacggcg tggaggtgca taatgccaag acaaagccgc gggaggagca gtacaacagc     900

acgtaccggg tggtcagcgt cctcaccgtc ctgcaccagg actggctgaa tggcaaggag     960

tacaagtgca aggtctccaa caaagccctc ccagccccca tcgagaaaac catctccaaa    1020

gccaaagggc agccccgaga accacaggtg tacaccctgc ccccatcccg ggaggagatg    1080

accaagaacc aggtcagcct gacctgcctg gtcaaaggct tctatcccag cgacatcgcc    1140

gtggagtggg agagcaatgg gcagccggag aacaactaca agaccacgcc tcccgtgctg    1200

gactccgacg gctccttctt cctctacagc aagctcaccg tggacaagag caggtggcag    1260

caggggaacg tcttctcatg ctccgtgatg catgaggctc tgcacaacca ctacacgcag    1320

aagagcctct ccctgtctcc gggtaaa                                        1347


<210> SEQ ID NO 27
<211> LENGTH: 648
<212> TYPE: DNA
```

<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 27
gatatcgtgc tgacccagcc gccgagcgtg agcggtgcac cgggccagcg cgtgaccatt 60
agctgtagcg gcagcagcag caacattggt tctcagtacg tgtactggta ccagcagctg 120
ccgggcacgg cgccgaaact gctgatctac tacaactctg aacgcccgag cggcatgccg 180
gatcgcttta gcggatccaa aagcggcacc agcgccagcc tggcgattac cggcctgcaa 240
gcagaagacg aagcggatta ttactgccag acttgggacg cttcttctca gtctttcgtg 300
tttggcggcg gcacgaagtt aaccgtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca 648

<210> SEQ ID NO 28
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 28

Thr Gly Thr Ser Ser Asp Val Gly Ala Tyr Asn Tyr Val Ser
1 5 10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 29

Gly Val Ser Lys Arg Pro Ser
1 5

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 30

Gln Ser Tyr Asp His Leu Leu His Val Val
1 5 10

<210> SEQ ID NO 31
<211> LENGTH: 5
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 31

Thr Tyr Gly Ile His
1 5

<210> SEQ ID NO 32
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 32

Tyr Ile His Tyr Ser Gly Ser Ser Thr Tyr Tyr Ala Asp Ser Val Lys
1 5 10 15

Gly

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 33

His Ala Tyr Gly Tyr Met Asp Phe
1 5

<210> SEQ ID NO 34
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 34

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Gly Ile His Trp Val Arg Gln Ala Pro Gly Lys Gly Leu Glu Trp Val
35 40 45

Ser Tyr Ile His Tyr Ser Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Ala Tyr Gly Tyr Met Asp Phe Trp Gly Gln Gly Thr Leu
100 105 110

Val Thr Val Ser Ser
115

<210> SEQ ID NO 35
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp His Leu
                85                  90                  95

Leu His Val Val Phe Gly Gly Gly Thr Lys Leu Thr Val Leu
            100                 105                 110
```

<210> SEQ ID NO 36
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

```
caggtgcaat tgctggaaag cggcggtggc ctggtgcagc cgggtggcag cctgcgtctg     60

agctgcgcgg cgtccggatt cacctttaac acttacggta tccattgggt gcgccaggcc    120

ccgggcaaag gtctcgagtg ggtttcctac atccattact ctggttcttc tacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtcatgct    300

tacggttaca tggatttctg gggccaaggc accctggtga ctgttagctc a             351
```

<210> SEQ ID NO 37
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
gatatcgcgc tgacccagcc ggcgagcgtg agcggtagcc cgggccagag cattaccatt     60

agctgcaccg gcaccagcag cgatgtgggc gcttacaact acgtgtcttg gtaccagcag    120

catccgggca aggcgccgaa actgatgatc tacggtgttt ctaaacgtcc gagcggcgtg    180

agcaaccgtt ttagcggatc caaaagcggc aacaccgcga gcctgaccat tagcggcctg    240

caagcggaag acgaagcgga ttattactgc cagtcttacg accatctgct gcatgttgtg    300
```

tttggcggcg gcacgaagtt aaccgtccta 330

<210> SEQ ID NO 38
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Gly Ile His Trp Val Arg Gln Ala Pro Gly Lys Gly Leu Glu Trp Val
35 40 45

Ser Tyr Ile His Tyr Ser Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Ala Tyr Gly Tyr Met Asp Phe Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 39
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp His Leu
                85                  90                  95

Leu His Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 40
<211> LENGTH: 1341
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic polynucleotide"

<400> SEQUENCE: 40
caggtgcaat tgctggaaag cggcggtggc ctggtgcagc cgggtggcag cctgcgtctg 60
agctgcgcgg cgtccggatt cacctttaac acttacggta tccattgggt gcgccaggcc 120
ccgggcaaag gtctcgagtg ggtttcctac atccattact ctggttcttc tacctactat 180
gcggatagcg tgaaaggccg ctttaccatc agccgcgata attcgaaaaa caccctgtat 240
ctgcaaatga acagcctgcg tgcggaagat acggccgtgt attattgcgc gcgtcatgct 300
tacggttaca tggatttctg ggccaaggc accctggtga ctgttagctc agcctccacc 360
aagggtccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660
gacaaaactc acacatgccc accgtgccca gcacctgaac tcctgggggg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacaa cagcacgtac 900
cgggtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggagga gatgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gctggactcc 1200
gacggctcct tcttcctcta cagcaagctc accgtggaca agagcaggtg gcagcagggg 1260
aacgtcttct catgctccgt gatgcatgag gctctgcaca accactacac gcagaagagc 1320
ctctccctgt ctccgggtaa a 1341

<210> SEQ ID NO 41
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 41
gatatcgcgc tgacccagcc ggcgagcgtg agcggtagcc cgggccagag cattaccatt 60
agctgcaccg gcaccagcag cgatgtgggc gcttacaact acgtgtcttg gtaccagcag 120
catccgggca aggcgccgaa actgatgatc tacggtgttt ctaaacgtcc gagcggcgtg 180
agcaaccgtt ttagcggatc caaaagcggc aacaccgcga gcctgaccat tagcggcctg 240
caagcggaag acgaagcgga ttattactgc cagtcttacg accatctgct gcatgttgtg 300
tttggcggcg gcacgaagtt aaccgtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca 648

<210> SEQ ID NO 42
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

Ser Gly Ser Ser Ser Asn Ile Gly Tyr Asn Tyr Val Ser
1 5 10

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

Arg Asp Asn Gln Arg Pro Ser
1 5

<210> SEQ ID NO 44
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

Ala Ala Trp Thr Ser Gly Ser Ile Gly Trp Val
1 5 10

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 45

Ser Tyr Ala Met Thr
1 5

<210> SEQ ID NO 46
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

Gly Ile Ser Gly Gly Gly Ser Asn Thr Tyr Tyr Ala Asp Ser Val Lys
1 5 10 15

Gly

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Gly Gly Gly Gln Tyr Phe Asp Tyr
1 5

<210> SEQ ID NO 48
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Thr Trp Val Arg Gln Ala Pro Gly Lys Gly Leu Glu Trp Val
35 40 45

Ser Gly Ile Ser Gly Gly Gly Ser Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Gly Gln Tyr Phe Asp Tyr Trp Gly Gln Gly Thr Leu
100 105 110

Val Thr Val Ser Ser
115

<210> SEQ ID NO 49
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Asp Ile Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Tyr Asn
20 25 30

Tyr Val Ser Trp Tyr Gln Gln Leu Pro Gly Thr Ala Pro Lys Leu Leu
35 40 45

Ile Tyr Arg Asp Asn Gln Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Ala Ala Trp Thr Ser Gly Ser
85 90 95

Ile Gly Trp Val Phe Gly Gly Gly Thr Lys Leu Thr Val Leu
100 105 110

<210> SEQ ID NO 50
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50
caggtgcaat tgctggaaag cggcggtggc ctggtgcagc cgggtggcag cctgcgtctg 60
agctgcgcgg cgtccggatt caccttttct tcttacgcta tgacttgggt gcgccaggcc 120
ccgggcaaag gtctcgagtg ggtttccggt atctctggtg gtggttctaa cacctactat 180
gcggatagcg tgaaaggccg ctttaccatc agccgcgata attcgaaaaa caccctgtat 240
ctgcaaatga acagcctgcg tgcggaagat acggccgtgt attattgcgc gcgtggtggt 300
ggtcagtact tcgattactg gggccaaggc accctggtga ctgttagctc a 351

<210> SEQ ID NO 51
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51
gatatcgtgc tgacccagcc gccgagcgtg agcggtgcac cgggccagcg cgtgaccatt 60
agctgtagcg gcagcagcag caacattggt tacaactacg tgtcttggta ccagcagctg 120
ccgggcacgg cgccgaaact gctgatctac cgtgacaacc agcgcccgag cggcgtgccg 180
gatcgcttta gcggatccaa aagcggcacc agcgccagcc tggcgattac cggcctgcaa 240
gcagaagacg aagcggatta ttactgcgct gcttggactt ctggttctat cggttgggtg 300
tttggcggcg gcacgaagtt aaccgtccta 330

<210> SEQ ID NO 52
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Thr Trp Val Arg Gln Ala Pro Gly Lys Gly Leu Glu Trp Val
35 40 45

```
Ser Gly Ile Ser Gly Gly Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Gln Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 53
<211> LENGTH: 216
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Tyr Asn
            20                  25                  30

Tyr Val Ser Trp Tyr Gln Gln Leu Pro Gly Thr Ala Pro Lys Leu Leu
        35                  40                  45

Ile Tyr Arg Asp Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ala Ala Trp Thr Ser Gly Ser
                85                  90                  95

Ile Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 54
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

```
caggtgcaat tgctggaaag cggcggtggc ctggtgcagc cgggtggcag cctgcgtctg     60

agctgcgcgg cgtccggatt caccttttct tcttacgcta tgacttgggt gcgccaggcc    120

ccgggcaaag gtctcgagtg ggtttccggt atctctggtg gtggttctaa cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtggtggt    300

ggtcagtact tcgattactg gggccaaggc accctggtga ctgttagctc agcctccacc    360

aagggtccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540
```

```
tccctcagca gcgtggtgac cgtgccctcc agcagcttgg gcacccagac ctacatctgc    600

aacgtgaatc acaagcccag caacaccaag gtggacaaga gagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgggtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                             1341
```

<210> SEQ ID NO 55
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 55

```
gatatcgtgc tgacccagcc gccgagcgtg agcggtgcac cgggccagcg cgtgaccatt     60

agctgtagcg gcagcagcag caacattggt tacaactacg tgtcttggta ccagcagctg    120

ccgggcacgg cgccgaaact gctgatctac cgtgacaacc agcgcccgag cggcgtgccg    180

gatcgcttta gcggatccaa aagcggcacc agcgccagcc tggcgattac cggcctgcaa    240

gcagaagacg aagcggatta ttactgcgct gcttggactt ctggttctat cggttgggtg    300

tttggcggcg gcacgaagtt aaccgtccta ggtcagccca aggctgcccc ctcggtcact    360

ctgttcccgc cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tatctgagcc tgacgcctga gcagtggaag tcccacagaa gctacagctg ccaggtcacg    600

catgaaggga gcaccgtgga gaagacagtg gcccctacag aatgttca                 648
```

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 56

```
Arg Ala Ser Gln Thr Ile Asn Ser Tyr Leu Asn
1               5                   10
```

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 57

Arg Ala Ser Asn Leu Gln Ser
1 5

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 58

Gln Gln Gly Asp Ser Ser Trp Thr
1 5

<210> SEQ ID NO 59
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 59

Ser Tyr Ala Ile Ser
1 5

<210> SEQ ID NO 60
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 60

Phe Ile Lys Ser Asn Ala Asp Gly Tyr Thr Thr Asn Tyr Ala Ala Pro
1 5 10 15

Val Lys Gly

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 61

Ile Arg Tyr Phe Arg Asn Trp Asp Tyr
1 5

<210> SEQ ID NO 62
<211> LENGTH: 120

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Gly Phe Ile Lys Ser Asn Ala Asp Gly Tyr Thr Thr Asn Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ile Arg Tyr Phe Arg Asn Trp Asp Tyr Trp Gly Gln
            100                 105                 110

Gly Thr Leu Val Thr Val Ser Ser
        115                 120


<210> SEQ ID NO 63
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Ser Trp Thr
                85                  90                  95

Phe Gly Gln Gly Thr Lys Val Glu Ile Lys
            100                 105


<210> SEQ ID NO 64
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64

caggtgcaat tggtggaaag cggcggtggc ctggtgaaac caggcggcag cctgcgcctg     60
```

agctgcgccg cctccggatt caccttttct tcttacgcta tctcttgggt gcgccaggcc 120
ccgggcaaag gtctcgagtg ggtgggcttc atcaaatcta acgctgacgg ttacactact 180
aactatgccg ccccagtgaa aggccgcttt accattagcc gcgatgattc gaaaaacacc 240
ctgtatctgc aaatgaacag cctgaaaacc gaagatacgg ccgtgtatta ttgcgcgcgt 300
atccgttact tccgtaactg ggattactgg ggccaaggca ccctggtgac tgttagctca 360

<210> SEQ ID NO 65
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65
gatatccaga tgacccagag cccgagcagc ctgagcgcca gcgtgggcga tcgcgtgacc 60
attacctgca gagccagcca gactattaac tcttacctga actggtacca gcagaaaccg 120
ggcaaagcgc cgaaactatt aatctaccgt gcttctaacc tgcaaagcgg cgtgccgagc 180
cgctttagcg gcagcggatc cggcaccgat ttcaccctga ccattagctc tctgcaaccg 240
gaagactttg cgacctatta ttgccagcag ggtgactctt cttggacctt tggccagggc 300
acgaaagttg aaattaaa 318

<210> SEQ ID NO 66
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Gly Phe Ile Lys Ser Asn Ala Asp Gly Tyr Thr Thr Asn Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ile Arg Tyr Phe Arg Asn Trp Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 67
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Asn Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Ser Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 68
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

```
caggtgcaat tggtggaaag cggcggtggc ctggtgaaac caggcggcag cctgcgcctg      60

agctgcgccg cctccggatt caccttttct tcttacgcta tctcttgggt gcgccaggcc     120

ccgggcaaag gtctcgagtg ggtgggcttc atcaaatcta acgctgacgg ttacactact     180

aactatgccg ccccagtgaa aggccgcttt accattagcc gcgatgattc gaaaaacacc     240

ctgtatctgc aaatgaacag cctgaaaacc gaagatacgg ccgtgtatta ttgcgcgcgt     300

atccgttact tccgtaactg ggattactgg ggccaaggca ccctggtgac tgttagctca     360

gcctccacca agggtccatc ggtcttcccc ctggcaccct cctccaagag cacctctggg     420

ggcacagcgg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgacc gtgccctcca gcagcttggg cacccagacc     600

tacatctgca acgtgaatca caagcccagc aacaccaagg tggacaagag agttgagccc     660

aaatcttgtg acaaaactca cacatgccca ccgtgcccag cacctgaact cctgggggga     720

ccgtcagtct tcctcttccc cccaaaaccc aaggacaccc tcatgatctc ccggacccct     780

gaggtcacat gcgtggtggt ggacgtgagc cacgaagacc ctgaggtcaa gttcaactgg     840

tacgtggacg gcgtggaggt gcataatgcc aagacaaagc cgcgggagga gcagtacaac     900

agcacgtacc gggtggtcag cgtcctcacc gtcctgcacc aggactggct gaatggcaag     960

gagtacaagt gcaaggtctc caacaaagcc ctcccagccc ccatcgagaa aaccatctcc    1020

aaagccaaag ggcagccccg agaaccacag gtgtacaccc tgcccccatc ccgggaggag    1080

atgaccaaga accaggtcag cctgacctgc ctggtcaaag gcttctatcc cagcgacatc    1140
```

```
gccgtggagt gggagagcaa tgggcagccg gagaacaact acaagaccac gcctcccgtg   1200

ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                     1350


<210> SEQ ID NO 69
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69

gatatccaga tgacccagag cccgagcagc ctgagcgcca gcgtgggcga tcgcgtgacc     60

attacctgca gagccagcca gactattaac tcttacctga actggtacca gcagaaaccg    120

ggcaaagcgc cgaaactatt aatctaccgt gcttctaacc tgcaaagcgg cgtgccgagc    180

cgctttagcg gcagcggatc cggcaccgat ttcaccctga ccattagctc tctgcaaccg    240

gaagactttg cgacctatta ttgccagcag ggtgactctt cttggacctt tggccagggc    300

acgaaagttg aaattaaacg tacggtggcc gctcccagcg tgttcatctt cccccccagc    360

gacgagcagc tgaagagcgg caccgccagc gtggtgtgcc tgctgaacaa cttctacccc    420

cgggaggcca aggtgcagtg gaaggtggac aacgccctgc agagcggcaa cagccaggaa    480

agcgtcaccg agcaggacag caaggactcc acctacagcc tgagcagcac cctgaccctg    540

agcaaggccg actacgagaa gcacaaggtg tacgcctgcg aggtgaccca ccagggcctg    600

tccagccccg tgaccaagag cttcaaccgg ggcgagtgt                           639


<210> SEQ ID NO 70
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ser Gly Ser Ser Ser Asn Ile Gly Ser Tyr Tyr Val Ser
1               5                   10


<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Tyr Asn Thr Lys Arg Pro Ser
1               5


<210> SEQ ID NO 72
<211> LENGTH: 11
<212> TYPE: PRT
<213> ORGANISM: Artificial Sequence
<220> FEATURE:
```

<221> NAME/KEY: source
<223> OTHER INFORMATION: /note="Description of Artificial Sequence:
Synthetic peptide"

<400> SEQUENCE: 72

Gln Ser Trp Asp Lys Leu Gly Lys Gly Tyr Val
1 5 10

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 73

Gly Asn Ser Ala Ala Trp Asn
1 5

<210> SEQ ID NO 74
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 74

Ile Ile Tyr Tyr Arg Ser Lys Trp Tyr Asn Asp Tyr Ala Val Ser Val
1 5 10 15

Lys Ser

<210> SEQ ID NO 75
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 75

Ser Ser Tyr Ser Gly Gly Phe Asp Tyr
1 5

<210> SEQ ID NO 76
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 76

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Gly Asn
20 25 30

Ser Ala Ala Trp Asn Trp Ile Arg Gln Ser Pro Ser Arg Gly Leu Glu
35 40 45

Trp Leu Gly Ile Ile Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Ser Ser Tyr Ser Gly Gly Phe Asp Tyr Trp Gly
100 105 110

Gln Gly Thr Leu Val Thr Val Ser Ser
115 120

<210> SEQ ID NO 77
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

Asp Ile Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Ser Tyr
20 25 30

Tyr Val Ser Trp Tyr Gln Gln Leu Pro Gly Thr Ala Pro Lys Leu Leu
35 40 45

Ile Tyr Tyr Asn Thr Lys Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Gln Ser Trp Asp Lys Leu Gly
85 90 95

Lys Gly Tyr Val Phe Gly Gly Gly Thr Lys Leu Thr Val Leu
100 105 110

<210> SEQ ID NO 78
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78
caggtgcaat tgcagcagag cggtccgggc ctggtgaaac cgagccagac cctgagcctg 60
acctgcgcga tttccggaga tagcgtgagc ggtaactctg ctgcttggaa ctggattcgt 120
cagagcccga gccgtggcct cgagtggctg ggcatcatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgttcttctt actctggtgg tttcgattac tggggccaag gcaccctggt gactgttagc 360
tca 363

<210> SEQ ID NO 79
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 79

```
gatatcgtgc tgacccagcc gccgagcgtg agcggtgcac cgggccagcg cgtgaccatt    60
agctgtagcg gcagcagcag caacattggt tcttactacg tgtcttggta ccagcagctg   120
ccgggcacgg cgccgaaact gctgatctac tacaacacta aacgcccgag cggcgtgccg   180
gatcgcttta gcggatccaa aagcggcacc agcgccagcc tggcgattac cggcctgcaa   240
gcagaagacg aagcggatta ttactgccag tcttgggaca aactgggtaa aggttacgtg   300
tttggcggcg gcacgaagtt aaccgtccta                                    330
```

<210> SEQ ID NO 80
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 80

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Gly Asn
             20                  25                  30

Ser Ala Ala Trp Asn Trp Ile Arg Gln Ser Pro Ser Arg Gly Leu Glu
         35                  40                  45

Trp Leu Gly Ile Ile Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Ser Ser Tyr Ser Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 81
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Tyr
            20                  25                  30

Tyr Val Ser Trp Tyr Gln Gln Leu Pro Gly Thr Ala Pro Lys Leu Leu
        35                  40                  45

Ile Tyr Tyr Asn Thr Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Lys Leu Gly
                85                  90                  95

Lys Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 82
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82

caggtgcaat tgcagcagag cggtccgggc ctggtgaaac cgagccagac cctgagcctg     60

acctgcgcga tttccggaga tagcgtgagc ggtaactctg ctgcttggaa ctggattcgt    120

cagagcccga gccgtggcct cgagtggctg ggcatcatct actaccgtag caaatggtac    180

aacgactatg ccgtgagcgt gaaaagccgc attaccatta acccggatac ttcgaaaaac    240

cagtttagcc tgcaactgaa cagcgtgacc ccggaagata cggccgtgta ttattgcgcg    300

cgttcttctt actctggtgg tttcgattac tggggccaag gcaccctggt gactgttagc    360

tcagcctcca ccaagggtcc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gagagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggag   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                 1353


<210> SEQ ID NO 83
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 83
gatatcgtgc tgacccagcc gccgagcgtg agcggtgcac cgggccagcg cgtgaccatt 60
agctgtagcg gcagcagcag caacattggt tcttactacg tgtcttggta ccagcagctg 120
ccgggcacgg cgccgaaact gctgatctac tacaacacta aacgcccgag cggcgtgccg 180
gatcgcttta gcggatccaa aagcggcacc agcgccagcc tggcgattac cggcctgcaa 240
gcagaagacg aagcggatta ttactgccag tcttgggaca aactgggtaa aggttacgtg 300
tttggcggcg gcacgaagtt aaccgtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca 648

<210> SEQ ID NO 84
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

Ser Gly Ser Ser Ser Asn Ile Gly Ser Asn Phe Val Ser
1 5 10

<210> SEQ ID NO 85
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 85

Asp Asn Ser Asn Arg Pro Ser
1 5

<210> SEQ ID NO 86
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

Ser Ser Tyr Asp Ser Phe Asp His Ser Trp Val
1 5 10

<210> SEQ ID NO 87
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 87

Ser Phe Ala Met Asn
1 5

<210> SEQ ID NO 88
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 88

Val Ile Ser Ser Ser Gly Ser Asn Thr Asn Tyr Ala Asp Ser Val Lys
1 5 10 15

Gly

<210> SEQ ID NO 89
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 89

Pro Ser Tyr Phe Gln Ala Met Asp Tyr
1 5

<210> SEQ ID NO 90
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Phe
20 25 30

Ala Met Asn Trp Val Arg Gln Ala Pro Gly Lys Gly Leu Glu Trp Val
35 40 45

Ser Val Ile Ser Ser Ser Gly Ser Asn Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Pro Ser Tyr Phe Gln Ala Met Asp Tyr Trp Gly Gln Gly Thr
100 105 110

Leu Val Thr Val Ser Ser
115

<210> SEQ ID NO 91
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Tyr Asp Ser Phe Asp
                85                  90                  95

His Ser Trp Val Phe Gly Gly Gly Thr Lys Leu Thr Val Leu
            100                 105                 110
```

<210> SEQ ID NO 92
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
caggtgcaat tgctggaaag cggcggtggc ctggtgcagc cgggtggcag cctgcgtctg     60

agctgcgcgg cgtccggatt caccttttct tctttcgcta tgaactgggt gcgccaggcc    120

ccgggcaaag gtctcgagtg ggtttccgtt atctcttctt ctggttctaa caccaactat    180

gcggatagcg tgaaaggccg ctttaccatc agccgcgata attcgaaaaa caccctgtat    240

ctgcaaatga acagcctgcg tgcggaagat acggccgtgt attattgcgc gcgtccgtct    300

tacttccagg ctatggatta ctggggccaa ggcaccctgg tgactgttag ctca          354
```

<210> SEQ ID NO 93
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gatatcgtgc tgacccagcc gccgagcgtg agcggtgcac cgggccagcg cgtgaccatt     60

agctgtagcg gcagcagcag caacattggt tctaacttcg tgtcttggta ccagcagctg    120

ccgggcacgg cgccgaaact gctgatctac gacaactcta accgcccgag cggcgtgccg    180

gatcgcttta gcggatccaa aagcggcacc agcgccagcc tggcgattac cggcctgcaa    240

gcagaagacg aagcggatta ttactgctct tcttacgact ctttcgacca ttcttgggtg    300

tttggcggcg gcacgaagtt aaccgtccta                                     330
```

<210> SEQ ID NO 94
<211> LENGTH: 448

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Asn Trp Val Arg Gln Ala Pro Gly Lys Gly Leu Glu Trp Val
        35                  40                  45

Ser Val Ile Ser Ser Ser Gly Ser Asn Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Ser Tyr Phe Gln Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
```

```
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 95
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Tyr Asp Ser Phe Asp
                85                  90                  95

His Ser Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 96
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
```

caggtgcaat tgctggaaag cggcggtggc ctggtgcagc cgggtggcag cctgcgtctg 60
agctgcgcgg cgtccggatt caccttttct tctttcgcta tgaactgggt gcgccaggcc 120
ccgggcaaag gtctcgagtg ggtttccgtt atctcttctt ctggttctaa caccaactat 180
gcggatagcg tgaaaggccg ctttaccatc agccgcgata attcgaaaaa caccctgtat 240
ctgcaaatga acagcctgcg tgcggaagat acggccgtgt attattgcgc gcgtccgtct 300
tacttccagg ctatggatta ctggggccaa ggcaccctgg tgactgttag ctcagcctcc 360
accaagggtc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgggtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctacagcaag ctcaccgtgg acaagagcag gtggcagcag 1260
gggaacgtct tctcatgctc cgtgatgcat gaggctctgc acaaccacta cacgcagaag 1320
agcctctccc tgtctccggg taaa 1344

<210> SEQ ID NO 97
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97
gatatcgtgc tgacccagcc gccgagcgtg agcggtgcac cgggccagcg cgtgaccatt 60
agctgtagcg gcagcagcag caacattggt tctaacttcg tgtcttggta ccagcagctg 120
ccgggcacgg cgccgaaact gctgatctac gacaactcta accgcccgag cggcgtgccg 180
gatcgcttta gcggatccaa aagcggcacc agcgccagcc tggcgattac cggcctgcaa 240
gcagaagacg aagcggatta ttactgctct tcttacgact ctttcgacca ttcttgggtg 300
tttggcggcg gcacgaagtt aaccgtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca 648

<210> SEQ ID NO 98
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 98

Ser Gly Asp Ala Ile Gly Thr Lys Phe Ala His
1 5 10

<210> SEQ ID NO 99
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

Tyr Asp His Glu Arg Pro Ser
1 5

<210> SEQ ID NO 100
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 100

Tyr Ser Arg Ala Ser Ser Asn Leu Val
1 5

<210> SEQ ID NO 101
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 101

Asp His Ala Ile Asp
1 5

<210> SEQ ID NO 102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 102

Val Ile Ala Gly Asp Gly Ser Ile Thr Tyr Tyr Ala Asp Ser Val Lys
1 5 10 15

Gly

<210> SEQ ID NO 103
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 103

Asp Thr Gly Val Tyr Arg Glu Tyr Met Asp Val
1 5 10

<210> SEQ ID NO 104
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 104

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Ala Ile Asp Trp Val Arg Gln Ala Pro Gly Lys Gly Leu Glu Trp Val
35 40 45

Ser Val Ile Ala Gly Asp Gly Ser Ile Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Thr Gly Val Tyr Arg Glu Tyr Met Asp Val Trp Gly Gln
100 105 110

Gly Thr Leu Val Thr Val Ser Ser
115 120

<210> SEQ ID NO 105
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

Asp Ile Glu Leu Thr Gln Pro Pro Ser Val Ser Val Ser Pro Gly Gln
1 5 10 15

Thr Ala Ser Ile Thr Cys Ser Gly Asp Ala Ile Gly Thr Lys Phe Ala
20 25 30

His Trp Tyr Gln Gln Lys Pro Gly Gln Ala Pro Val Leu Val Ile Tyr
35 40 45

Tyr Asp His Glu Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Tyr Ser Arg Ala Ser Ser Asn Leu Val

```
                85                  90                  95

Phe Gly Gly Gly Thr Lys Leu Thr Val Leu
            100                 105


<210> SEQ ID NO 106
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106

caggtgcaat tgctggaaag cggcggtggc ctggtgcagc cgggtggcag cctgcgtctg      60

agctgcgcgg cgtccggatt caccttttct gaccatgcta tcgactgggt gcgccaggcc     120

ccgggcaaag gtctcgagtg ggtttccgtt atcgctggtg acggttctat cacctactat     180

gcggatagcg tgaaaggccg ctttaccatc agccgcgata attcgaaaaa caccctgtat     240

ctgcaaatga acagcctgcg tgcggaagat acggccgtgt attattgcgc gcgtgacact     300

ggtgtttacc gtgaatacat ggatgtttgg ggccaaggca ccctggtgac tgttagctca     360


<210> SEQ ID NO 107
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107

gatatcgaac tgacccagcc gccgagcgtg agcgtgagcc cgggccagac cgcgagcatt      60

acctgtagcg gcgatgctat cggtactaaa ttcgctcatt ggtaccagca gaaaccgggc     120

caggcgccgg tgctggtgat ctactacgac catgaacgtc cgagcggcat cccggaacgt     180

tttagcggat ccaacagcgg caacaccgcg accctgacca ttagcggcac ccaggcggaa     240

gacgaagcgg attattactg ctactctcgt gcttcttcta acctggtgtt tggcggcggc     300

acgaagttaa ccgtccta                                                   318


<210> SEQ ID NO 108
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Ala Ile Asp Trp Val Arg Gln Ala Pro Gly Lys Gly Leu Glu Trp Val
        35                  40                  45

Ser Val Ile Ala Gly Asp Gly Ser Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Thr Gly Val Tyr Arg Glu Tyr Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 109
<211> LENGTH: 212
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 109

```
Asp Ile Glu Leu Thr Gln Pro Pro Ser Val Ser Val Ser Pro Gly Gln
1               5                   10                  15

Thr Ala Ser Ile Thr Cys Ser Gly Asp Ala Ile Gly Thr Lys Phe Ala
            20                  25                  30

His Trp Tyr Gln Gln Lys Pro Gly Gln Ala Pro Val Leu Val Ile Tyr
        35                  40                  45

Tyr Asp His Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Tyr Ser Arg Ala Ser Ser Asn Leu Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 110
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110

```
caggtgcaat tgctggaaag cggcggtggc ctggtgcagc cgggtggcag cctgcgtctg     60

agctgcgcgg cgtccggatt caccttttct gaccatgcta tcgactgggt gcgccaggcc    120

ccgggcaaag gtctcgagtg ggtttccgtt atcgctggtg acggttctat cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgacact    300

ggtgtttacc gtgaatacat ggatgtttgg ggccaaggca ccctggtgac tgttagctca    360

gcctccacca agggtccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600
```

tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gggtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

<210> SEQ ID NO 111
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111
gatatcgaac tgacccagcc gccgagcgtg agcgtgagcc cgggccagac cgcgagcatt 60
acctgtagcg gcgatgctat cggtactaaa ttcgctcatt ggtaccagca gaaaccgggc 120
caggcgccgg tgctggtgat ctactacgac catgaacgtc cgagcggcat cccggaacgt 180
tttagcggat ccaacagcgg caacaccgcg accctgacca ttagcggcac ccaggcggaa 240
gacgaagcgg attattactg ctactctcgt gcttcttcta acctggtgtt tggcggcggc 300
acgaagttaa ccgtcctagg tcagcccaag gctgccccct cggtcactct gttcccgccc 360
tcctctgagg agcttcaagc caacaaggcc acactggtgt gtctcataag tgacttctac 420
ccgggagccg tgacagtggc ctggaaggca gatagcagcc ccgtcaaggc gggagtggag 480
accaccacac cctccaaaca aagcaacaac aagtacgcgg ccagcagcta tctgagcctg 540
acgcctgagc agtggaagtc ccacagaagc tacagctgcc aggtcacgca tgaagggagc 600
accgtggaga agacagtggc ccctacagaa tgttca 636

<210> SEQ ID NO 112
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 112

Thr Gly Thr Ser Ser Asp Val Gly Arg Tyr Asn Phe Val Ser
1 5 10

<210> SEQ ID NO 113
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Arg Val Ser Asn Arg Pro Ser
1               5


<210> SEQ ID NO 114
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Gln Ser Trp Thr Thr Tyr Ser Asn Val Val
1               5                   10


<210> SEQ ID NO 115
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ser Tyr Ala Leu Asn
1               5


<210> SEQ ID NO 116
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Arg Ile Lys Ser Lys Thr Tyr Gly Gly Ser Thr Asp Tyr Ala Ala Pro
1               5                   10                  15

Val Lys Gly


<210> SEQ ID NO 117
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Asp Arg Gly Gly Tyr Val Gly Phe Asp Ser
1               5                   10


<210> SEQ ID NO 118
<211> LENGTH: 121
<212> TYPE: PRT
<213> ORGANISM: Artificial Sequence
```

<220> FEATURE:
<221> NAME/KEY: source
<223> OTHER INFORMATION: /note="Description of Artificial Sequence:
Synthetic polypeptide"

<400> SEQUENCE: 118

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Asn Trp Val Arg Gln Ala Pro Gly Lys Gly Leu Glu Trp Val
        35                  40                  45

Gly Arg Ile Lys Ser Lys Thr Tyr Gly Gly Ser Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Gly Gly Tyr Val Gly Phe Asp Ser Trp Gly
            100                 105                 110

Gln Gly Thr Leu Val Thr Val Ser Ser
        115                 120
```

<210> SEQ ID NO 119
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 119

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Phe Val Ser Trp Tyr Gln Gln His Pro Gly Lys Ala Pro Lys Leu
        35                  40                  45

Met Ile Tyr Arg Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Thr Thr Tyr
                85                  90                  95

Ser Asn Val Val Phe Gly Gly Gly Thr Lys Leu Thr Val Leu
            100                 105                 110
```

<210> SEQ ID NO 120
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 120

```
caggtgcaat tggtggaaag cggcggtggc ctggtgaaac caggcggcag cctgcgcctg     60

agctgcgccg cctccggatt cacctttct tcttacgctc tgaactgggt gcgccaggcc    120
```

```
ccgggcaaag gtctcgagtg ggtgggccgt atcaaatcta aaacttacgg tggttctact    180

gactatgccg ccccagtgaa aggccgcttt accattagcc gcgatgattc gaaaaacacc    240

ctgtatctgc aaatgaacag cctgaaaacc gaagatacgg ccgtgtatta ttgcgcgcgt    300

gaccgtggtg gttacgttgg tttcgattct tggggccaag gcaccctggt gactgttagc    360

tca                                                                   363
```

```
<210> SEQ ID NO 121
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121

gatatcgcgc tgacccagcc ggcgagcgtg agcggtagcc cgggccagag cattaccatt     60

agctgcaccg gcaccagcag cgatgtgggc cgttacaact tcgtgtcttg gtaccagcag    120

catccgggca aggcgccgaa actgatgatc taccgtgttt ctaaccgtcc gagcggcgtg    180

agcaaccgtt ttagcggatc caaaagcggc aacaccgcga gcctgaccat tagcggcctg    240

caagcggaag acgaagcgga ttattactgc cagtcttgga ctacttactc taacgttgtg    300

tttggcggcg gcacgaagtt aaccgtccta                                    330
```

```
<210> SEQ ID NO 122
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Asn Trp Val Arg Gln Ala Pro Gly Lys Gly Leu Glu Trp Val
        35                  40                  45

Gly Arg Ile Lys Ser Lys Thr Tyr Gly Gly Ser Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Gly Gly Tyr Val Gly Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 123
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Phe Val Ser Trp Tyr Gln Gln His Pro Gly Lys Ala Pro Lys Leu
        35                  40                  45

Met Ile Tyr Arg Val Ser Asn Arg Pro Ser Gly Val Ser Asn Arg Phe
    50                  55                  60
```

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Thr Thr Tyr
                85                  90                  95

Ser Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 124
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124

caggtgcaat tggtggaaag cggcggtggc ctggtgaaac caggcggcag cctgcgcctg     60

agctgcgccg cctccggatt caccttttct tcttacgctc tgaactgggt gcgccaggcc    120

ccgggcaaag gtctcgagtg ggtgggccgt atcaaatcta aaacttacgg tggttctact    180

gactatgccg ccccagtgaa aggccgcttt accattagcc gcgatgattc gaaaaacacc    240

ctgtatctgc aaatgaacag cctgaaaacc gaagatacgg ccgtgtatta ttgcgcgcgt    300

gaccgtggtg gttacgttgg tttcgattct tggggccaag gcaccctggt gactgttagc    360

tcagcctcca ccaagggtcc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gagagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggag   1080

gagatgacca agaaccaggt cagcctgacc tgcctggtca aaggcttcta tcccagcgac   1140
```

atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa 1353

<210> SEQ ID NO 125
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125
gatatcgcgc tgacccagcc ggcgagcgtg agcggtagcc cgggccagag cattaccatt 60
agctgcaccg gcaccagcag cgatgtgggc cgttacaact tcgtgtcttg gtaccagcag 120
catccgggca aggcgccgaa actgatgatc taccgtgttt ctaaccgtcc gagcggcgtg 180
agcaaccgtt ttagcggatc caaaagcggc aacaccgcga gcctgaccat tagcggcctg 240
caagcggaag acgaagcgga ttattactgc cagtcttgga ctacttactc taacgttgtg 300
tttggcggcg gcacgaagtt aaccgtccta ggtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tatctgagcc tgacgcctga gcagtggaag tcccacagaa gctacagctg ccaggtcacg 600
catgaaggga gcaccgtgga gaagacagtg gcccctacag aatgttca 648

<210> SEQ ID NO 126
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Ser Gly Asp Ser Ile Gly Ser Lys Tyr Ala Gln
1 5 10

<210> SEQ ID NO 127
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 127

Tyr Asn Ser Glu Arg Pro Ser
1 5

<210> SEQ ID NO 128
<211> LENGTH: 11
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 128

Gln Ser Trp Asp Gly Gln Ser Thr Ile Arg Val
1 5 10

<210> SEQ ID NO 129
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 129

Arg Tyr Trp Met Asp
1 5

<210> SEQ ID NO 130
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 130

Arg Ile Lys Ser Lys Ala Asn Gly Gly Ile Thr Asp Tyr Ala Ala Pro
1 5 10 15

Val Lys Gly

<210> SEQ ID NO 131
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 131

Gly Met Thr Phe Leu Gly Ile
1 5

<210> SEQ ID NO 132
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 132

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Arg Tyr
20 25 30

Trp Met Asp Trp Val Arg Gln Ala Pro Gly Lys Gly Leu Glu Trp Val
35 40 45

Gly Arg Ile Lys Ser Lys Ala Asn Gly Gly Ile Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Gly Met Thr Phe Leu Gly Ile Trp Gly Gln Gly Thr
100 105 110

Leu Val Thr Val Ser Ser
115

<210> SEQ ID NO 133
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 133

Asp Ile Glu Leu Thr Gln Pro Pro Ser Val Ser Val Ser Pro Gly Gln
1 5 10 15

Thr Ala Ser Ile Thr Cys Ser Gly Asp Ser Ile Gly Ser Lys Tyr Ala
20 25 30

Gln Trp Tyr Gln Gln Lys Pro Gly Gln Ala Pro Val Leu Val Ile Tyr
35 40 45

Tyr Asn Ser Glu Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Asp Gly Gln Ser Thr Ile
85 90 95

Arg Val Phe Gly Gly Gly Thr Lys Leu Thr Val Leu
100 105

<210> SEQ ID NO 134
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134
caggtgcaat tggtggaaag cggcggtggc ctggtgaaac caggcggcag cctgcgcctg 60
agctgcgccg cctccggatt cacctttttct cgttactgga tggactgggt gcgccaggcc 120
ccgggcaaag gtctcgagtg ggtgggccgt atcaaatcta aagctaacgg tggtatcact 180
gactatgccg ccccagtgaa aggccgcttt accattagcc gcgatgattc gaaaaacacc 240
ctgtatctgc aaatgaacag cctgaaaacc gaagatacgg ccgtgtatta ttgcgcgcgt 300
ggtatgactt tcctgggtat ctggggccaa ggcaccctgg tgactgttag ctca 354

<210> SEQ ID NO 135
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 135
gatatcgaac tgacccagcc gccgagcgtg agcgtgagcc cgggccagac cgcgagcatt 60
acctgtagcg gcgattctat cggttctaaa tacgctcagt ggtaccagca gaaaccgggc 120
caggcgccgg tgctggtgat ctactacaac tctgaacgtc cgagcggcat cccggaacgt 180
tttagcggat ccaacagcgg caacaccgcg accctgacca ttagcggcac ccaggcggaa 240
gacgaagcgg attattactg ccagtcttgg gacggtcagt ctactatccg tgtgtttggc 300
ggcggcacga agttaaccgt ccta 324

<210> SEQ ID NO 136
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 136

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Arg Tyr
20 25 30

Trp Met Asp Trp Val Arg Gln Ala Pro Gly Lys Gly Leu Glu Trp Val
35 40 45

Gly Arg Ile Lys Ser Lys Ala Asn Gly Gly Ile Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Gly Met Thr Phe Leu Gly Ile Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala

```
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 137
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Asp Ile Glu Leu Thr Gln Pro Pro Ser Val Ser Val Ser Pro Gly Gln
1               5                   10                  15

Thr Ala Ser Ile Thr Cys Ser Gly Asp Ser Ile Gly Ser Lys Tyr Ala
            20                  25                  30

Gln Trp Tyr Gln Gln Lys Pro Gly Gln Ala Pro Val Leu Val Ile Tyr
        35                  40                  45

Tyr Asn Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Gln Ser Thr Ile
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

```
Tyr Ser Cys Gln Val Thr His Glu Gly Ser Thr Val Glu Lys Thr Val
        195                 200                 205

Ala Pro Thr Glu Cys Ser
    210


<210> SEQ ID NO 138
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 138

caggtgcaat tggtggaaag cggcggtggc ctggtgaaac caggcggcag cctgcgcctg      60

agctgcgccg cctccggatt caccttttct cgttactgga tggactgggt gcgccaggcc     120

ccgggcaaag gtctcgagtg ggtgggccgt atcaaatcta aagctaacgg tggtatcact     180

gactatgccg ccccagtgaa aggccgcttt accattagcc gcgatgattc gaaaaacacc     240

ctgtatctgc aaatgaacag cctgaaaacc gaagatacgg ccgtgtatta ttgcgcgcgt     300

ggtatgactt tcctgggtat ctggggccaa ggcaccctgg tgactgttag ctcagcctcc     360

accaagggtc catcggtctt ccccctggca ccctcctcca agagcacctc tgggggcaca     420

gcggccctgg gctgcctggt caaggactac ttccccgaac cggtgacggt gtcgtggaac     480

tcaggcgccc tgaccagcgg cgtgcacacc ttcccggctg tcctacagtc ctcaggactc     540

tactccctca gcagcgtggt gaccgtgccc tccagcagct tgggcaccca gacctacatc     600

tgcaacgtga atcacaagcc cagcaacacc aaggtggaca agagagttga gcccaaatct     660

tgtgacaaaa ctcacacatg cccaccgtgc ccagcacctg aactcctggg gggaccgtca     720

gtcttcctct tccccccaaa acccaaggac accctcatga tctcccggac ccctgaggtc     780

acatgcgtgg tggtggacgt gagccacgaa gaccctgagg tcaagttcaa ctggtacgtg     840

gacggcgtgg aggtgcataa tgccaagaca aagccgcggg aggagcagta caacagcacg     900

taccgggtgg tcagcgtcct caccgtcctg caccaggact ggctgaatgg caaggagtac     960

aagtgcaagg tctccaacaa agccctccca gcccccatcg agaaaaccat ctccaaagcc    1020

aaagggcagc cccgagaacc acaggtgtac accctgcccc catcccggga ggagatgacc    1080

aagaaccagg tcagcctgac ctgcctggtc aaaggcttct atcccagcga catcgccgtg    1140

gagtgggaga gcaatgggca gccggagaac aactacaaga ccacgcctcc cgtgctggac    1200

tccgacggct ccttcttcct ctacagcaag ctcaccgtgg acaagagcag gtggcagcag    1260

gggaacgtct tctcatgctc cgtgatgcat gaggctctgc acaaccacta cacgcagaag    1320

agcctctccc tgtctccggg taaa                                           1344


<210> SEQ ID NO 139
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 139

gatatcgaac tgacccagcc gccgagcgtg agcgtgagcc cgggccagac cgcgagcatt      60
```

```
acctgtagcg gcgattctat cggttctaaa tacgctcagt ggtaccagca gaaaccgggc    120

caggcgccgg tgctggtgat ctactacaac tctgaacgtc cgagcggcat cccggaacgt    180

tttagcggat ccaacagcgg caacaccgcg accctgacca ttagcggcac ccaggcggaa    240

gacgaagcgg attattactg ccagtcttgg gacggtcagt ctactatccg tgtgtttggc    300

ggcggcacga agttaaccgt cctaggtcag cccaaggctg ccccctcggt cactctgttc    360

ccgccctcct ctgaggagct tcaagccaac aaggccacac tggtgtgtct cataagtgac    420

ttctacccgg gagccgtgac agtggcctgg aaggcagata gcagccccgt caaggcggga    480

gtggagacca ccacaccctc caaacaaagc aacaacaagt acgcggccag cagctatctg    540

agcctgacgc ctgagcagtg gaagtcccac agaagctaca gctgccaggt cacgcatgaa    600

gggagcaccg tggagaagac agtggcccct acagaatgtt ca                       642


<210> SEQ ID NO 140
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Arg Ala Ser Gln Ser Ile Ser Phe Tyr Leu Ala
1               5                   10


<210> SEQ ID NO 141
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Gly Ala Ser Thr Leu Gln Ser
1               5


<210> SEQ ID NO 142
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

His Gln Tyr Ser Tyr Trp Leu Arg Thr
1               5


<210> SEQ ID NO 143
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ser Tyr Ala Leu His
1               5
```

<210> SEQ ID NO 144
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 144

Tyr Ile Phe Tyr Asp Ser Ser Ser Thr Tyr Tyr Ala Asp Ser Val Lys
1 5 10 15

Gly

<210> SEQ ID NO 145
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 145

Phe Leu Tyr Ser Ala Tyr Gly Val Ala Asn
1 5 10

<210> SEQ ID NO 146
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 146

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Leu His Trp Val Arg Gln Ala Pro Gly Lys Gly Leu Glu Trp Val
35 40 45

Ser Tyr Ile Phe Tyr Asp Ser Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Phe Leu Tyr Ser Ala Tyr Gly Val Ala Asn Trp Gly Gln Gly
100 105 110

Thr Leu Val Thr Val Ser Ser
115

<210> SEQ ID NO 147
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 147

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Phe Tyr
20 25 30

Leu Ala Trp Tyr Gln Gln Lys Pro Gly Lys Ala Pro Lys Leu Leu Ile
35 40 45

Tyr Gly Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Tyr Ser Tyr Trp Leu Arg
85 90 95

Thr Phe Gly Gln Gly Thr Lys Val Glu Ile Lys
100 105

<210> SEQ ID NO 148
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 148
caggtgcaat tgctggaaag cggcggtggc ctggtgcagc cgggtggcag cctgcgtctg 60
agctgcgcgg cgtccggatt caccttttct tcttacgctc tgcattgggt gcgccaggcc 120
ccgggcaaag gtctcgagtg ggtttcctac atcttctacg actcttcttc tacctactat 180
gcggatagcg tgaaaggccg ctttaccatc agccgcgata attcgaaaaa caccctgtat 240
ctgcaaatga acagcctgcg tgcggaagat acggccgtgt attattgcgc gcgtttcctg 300
tactctgctt acggtgttgc taactggggc caaggcaccc tggtgactgt tagctca 357

<210> SEQ ID NO 149
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 149
gatatccaga tgacccagag cccgagcagc ctgagcgcca gcgtgggcga tcgcgtgacc 60
attacctgca gagccagcca gtctatttct ttctacctgg cttggtacca gcagaaaccg 120
ggcaaagcgc cgaaactatt aatctacggt gcttctactc tgcaaagcgg cgtgccgagc 180
cgctttagcg gcagcggatc cggcaccgat ttcaccctga ccattagctc tctgcaaccg 240
gaagactttg cgacctatta ttgccatcag tactcttact ggctgcgtac ctttggccag 300
ggcacgaaag ttgaaattaa a 321

<210> SEQ ID NO 150
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 150

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Leu His Trp Val Arg Gln Ala Pro Gly Lys Gly Leu Glu Trp Val
35 40 45

Ser Tyr Ile Phe Tyr Asp Ser Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Phe Leu Tyr Ser Ala Tyr Gly Val Ala Asn Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 151
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Phe Tyr
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ser Tyr Trp Leu Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 152
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
caggtgcaat tgctggaaag cggcggtggc ctggtgcagc cgggtggcag cctgcgtctg     60
```

-continued

```
agctgcgcgg cgtccggatt caccttttct tcttacgctc tgcattgggt gcgccaggcc    120

ccgggcaaag gtctcgagtg ggtttcctac atcttctacg actcttcttc tacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtttcctg    300

tactctgctt acggtgttgc taactggggc caaggcaccc tggtgactgt tagctcagcc    360

tccaccaagg gtccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagagagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccggg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggaggagatg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

```
<210> SEQ ID NO 153
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 153

gatatccaga tgacccagag cccgagcagc ctgagcgcca gcgtgggcga tcgcgtgacc     60

attacctgca gagccagcca gtctatttct ttctacctgg cttggtacca gcagaaaccg    120

ggcaaagcgc cgaaactatt aatctacggt gcttctactc tgcaaagcgg cgtgccgagc    180

cgctttagcg gcagcggatc cggcaccgat ttcaccctga ccattagctc tctgcaaccg    240

gaagactttg cgacctatta ttgccatcag tactcttact ggctgcgtac ctttggccag    300

ggcacgaaag ttgaaattaa acgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gaaagcgtca ccgagcagga cagcaaggac tccacctaca gcctgagcag caccctgacc    540

ctgagcaagg ccgactacga gaagcacaag gtgtacgcct gcgaggtgac ccaccagggc    600

ctgtccagcc ccgtgaccaa gagcttcaac cggggcgagt gt                        642
```

```
<210> SEQ ID NO 154
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Arg Ala Ser Gln Gly Ile Phe Thr Tyr Leu Asn
1               5                   10


<210> SEQ ID NO 155
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ala Ala Ser Thr Leu Gln Ser
1               5


<210> SEQ ID NO 156
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Gln Gln Tyr Tyr Ser Thr Ser Leu Thr
1               5


<210> SEQ ID NO 157
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Ser Asn Ser Ala Ala Trp Asn
1               5


<210> SEQ ID NO 158
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Arg Ile Tyr Tyr Arg Ser Lys Trp Tyr Asn Asp Tyr Ala Val Ser Val
1               5                   10                  15

Lys Ser


<210> SEQ ID NO 159
<211> LENGTH: 10
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Glu Arg Ser Tyr Arg Asp Tyr Phe Asp Tyr
1               5                   10

<210> SEQ ID NO 160
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Arg Ser Tyr Arg Asp Tyr Phe Asp Tyr Trp
            100                 105                 110

Gly Gln Gly Thr Leu Val Thr Val Ser Ser
        115                 120

<210> SEQ ID NO 161
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Phe Thr Tyr
            20                  25                  30

Leu Asn Trp Tyr Gln Gln Lys Pro Gly Lys Ala Pro Lys Leu Leu Ile
        35                  40                  45

Ser Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Ser Leu
                85                  90                  95

Thr Phe Gly Gln Gly Thr Lys Val Glu Ile Lys 100 105

<210> SEQ ID NO 162
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 162
caggtgcaat tgcagcagag cggtccgggc ctggtgaaac cgagccagac cctgagcctg 60
acctgcgcga tttccggaga tagcgtgagc tctaactctg ctgcttggaa ctggattcgt 120
cagagcccga gccgtggcct cgagtggctg ggccgtatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgtgaacgtt cttaccgtga ctacttcgat tactggggcc aaggcaccct ggtgactgtt 360
agctca 366

<210> SEQ ID NO 163
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 163
gatatccaga tgacccagag cccgagcagc ctgagcgcca gcgtgggcga tcgcgtgacc 60
attacctgca gagccagcca gggtattttc acttacctga actggtacca gcagaaaccg 120
ggcaaagcgc cgaaactatt aatctctgct gcttctactc tgcaaagcgg cgtgccgagc 180
cgctttagcg gcagcggatc cggcaccgat ttcaccctga ccattagctc tctgcaaccg 240
gaagactttg cgacctatta ttgccagcag tactactcta cttctctgac ctttggccag 300
ggcacgaaag ttgaaattaa a 321

<210> SEQ ID NO 164
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 164

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Ile Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Arg Ser Tyr Arg Asp Tyr Phe Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly Lys
450

<210> SEQ ID NO 165
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 165

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Phe Thr Tyr
20 25 30

Leu Asn Trp Tyr Gln Gln Lys Pro Gly Lys Ala Pro Lys Leu Leu Ile
35 40 45

Ser Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ser Thr Ser Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 166
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 166
caggtgcaat tgcagcagag cggtccgggc ctggtgaaac cgagccagac cctgagcctg 60
acctgcgcga tttccggaga tagcgtgagc tctaactctg ctgcttggaa ctggattcgt 120
cagagcccga gccgtggcct cgagtggctg ggccgtatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgtgaacgtt cttaccgtga ctacttcgat tactggggcc aaggcaccct ggtgactgtt 360
agctcagcct ccaccaaggg tccatcggtc ttccccctgg caccctcctc caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga caagagagtt 660
gagcccaaat cttgtgacaa aactcacaca tgcccaccgt gcccagcacc tgaactcctg 720
gggggaccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgcg ggaggagcag 900
tacaacagca cgtaccgggt ggtcagcgtc ctcaccgtcc tgcaccagga ctggctgaat 960
ggcaaggagt acaagtgcaa ggtctccaac aaagccctcc cagcccccat cgagaaaacc 1020
atctccaaag ccaaagggca gccccgagaa ccacaggtgt acaccctgcc cccatcccgg 1080
gaggagatga ccaagaacca ggtcagcctg acctgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctacagca agctcaccgt ggacaagagc 1260
aggtggcagc aggggaacgt cttctcatgc tccgtgatgc atgaggctct gcacaaccac 1320
tacacgcaga agagcctctc cctgtctccg ggtaaa 1356

<210> SEQ ID NO 167
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 167
gatatccaga tgacccagag cccgagcagc ctgagcgcca gcgtgggcga tcgcgtgacc 60
attacctgca gagccagcca gggtattttc acttacctga actggtacca gcagaaaccg 120
ggcaaagcgc cgaaactatt aatctctgct gcttctactc tgcaaagcgg cgtgccgagc 180
cgctttagcg gcagcggatc cggcaccgat ttcaccctga ccattagctc tctgcaaccg 240
gaagactttg cgacctatta ttgccagcag tactactcta cttctctgac ctttggccag 300
ggcacgaaag ttgaaattaa acgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gaaagcgtca ccgagcagga cagcaaggac tccacctaca gcctgagcag caccctgacc 540
ctgagcaagg ccgactacga gaagcacaag gtgtacgcct gcgaggtgac ccaccagggc 600
ctgtccagcc ccgtgaccaa gagcttcaac cggggcgagt gt 642

<210> SEQ ID NO 168
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 168

Ser Gly Asp Asn Ile Arg Lys Tyr Val Val His
1               5                   10

<210> SEQ ID NO 169
<211> LENGTH: 7
<212> TYPE: PRT

-continued

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Arg Asp Asn Asn Arg Pro Ser
1               5

<210> SEQ ID NO 170
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Gln Ser Trp Asp Ser Phe Leu Ala Val Val
1               5                   10

<210> SEQ ID NO 171
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Ser Tyr Ala Met His
1               5

<210> SEQ ID NO 172
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Phe Ile Ser Ser Leu Gly Ser Tyr Thr Tyr Tyr Ala Asp Ser Val Lys
1               5                   10                  15

Gly

<210> SEQ ID NO 173
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Glu Thr Ala Gly Tyr Gly Tyr Ala Phe Asp Pro
1               5                   10

<210> SEQ ID NO 174
<211> LENGTH: 120
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 174

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Phe Ile Ser Ser Leu Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Ala Gly Tyr Gly Tyr Ala Phe Asp Pro Trp Gly Gln
            100                 105                 110

Gly Thr Leu Val Thr Val Ser Ser
        115                 120
```

<210> SEQ ID NO 175
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 175

```
Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Lys Tyr Val Val
            20                  25                  30

His Trp Tyr Gln Gln Lys Pro Gly Gln Ala Pro Val Leu Val Ile Tyr
        35                  40                  45

Arg Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Ser Phe Leu Ala Val
                85                  90                  95

Val Phe Gly Gly Gly Thr Lys Leu Thr Val Leu
            100                 105
```

<210> SEQ ID NO 176
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 176

```
caggtgcaat tgctggaaag cggcggtggc ctggtgcagc cgggtggcag cctgcgtctg     60

agctgcgcgg cgtccggatt caccttttct tcttacgcta tgcattgggt gcgccaggcc    120
```

```
ccgggcaaag gtctcgagtg ggtttccttc atctcttctc tgggttctta cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaact    300

gctggttacg gttacgcttt cgatccgtgg ggccaaggca ccctggtgac tgttagctca    360


<210> SEQ ID NO 177
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177

gatatcgaac tgacccagcc gccgagcgtg agcgtgagcc cgggccagac cgcgagcatt     60

acctgtagcg gcgataacat ccgtaaatac gttgttcatt ggtaccagca gaaaccgggc    120

caggcgccgg tgctggtgat ctaccgtgac aacaaccgtc cgagcggcat cccggaacgt    180

tttagcggat ccaacagcgg caacaccgcg accctgacca ttagcggcac ccaggcggaa    240

gacgaagcgg attattactg ccagtcttgg gactctttcc tggctgttgt gtttggcggc    300

ggcacgaagt taaccgtcct a                                              321


<210> SEQ ID NO 178
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Phe Ile Ser Ser Leu Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Ala Gly Tyr Gly Tyr Ala Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 179
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Lys Tyr Val Val
            20                  25                  30

His Trp Tyr Gln Gln Lys Pro Gly Gln Ala Pro Val Leu Val Ile Tyr
        35                  40                  45

Arg Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80
```

Asp Glu Ala Asp Tyr Tyr Cys Gln Ser Trp Asp Ser Phe Leu Ala Val
85 90 95

Val Phe Gly Gly Gly Thr Lys Leu Thr Val Leu Gly Gln Pro Lys Ala
100 105 110

Ala Pro Ser Val Thr Leu Phe Pro Pro Ser Ser Glu Glu Leu Gln Ala
115 120 125

Asn Lys Ala Thr Leu Val Cys Leu Ile Ser Asp Phe Tyr Pro Gly Ala
130 135 140

Val Thr Val Ala Trp Lys Ala Asp Ser Ser Pro Val Lys Ala Gly Val
145 150 155 160

Glu Thr Thr Thr Pro Ser Lys Gln Ser Asn Asn Lys Tyr Ala Ala Ser
165 170 175

Ser Tyr Leu Ser Leu Thr Pro Glu Gln Trp Lys Ser His Arg Ser Tyr
180 185 190

Ser Cys Gln Val Thr His Glu Gly Ser Thr Val Glu Lys Thr Val Ala
195 200 205

Pro Thr Glu Cys Ser
210

<210> SEQ ID NO 180
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 180
caggtgcaat tgctggaaag cggcggtggc ctggtgcagc cgggtggcag cctgcgtctg 60
agctgcgcgg cgtccggatt caccttttct tcttacgcta tgcattgggt gcgccaggcc 120
ccgggcaaag gtctcgagtg ggtttccttc atctcttctc tgggttctta cacctactat 180
gcggatagcg tgaaaggccg ctttaccatc agccgcgata attcgaaaaa caccctgtat 240
ctgcaaatga acagcctgcg tgcggaagat acggccgtgt attattgcgc gcgtgaaact 300
gctggttacg gttacgcttt cgatccgtgg ggccaaggca ccctggtgac tgttagctca 360
gcctccacca agggtccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gggtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

<210> SEQ ID NO 181
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 181
gatatcgaac tgacccagcc gccgagcgtg agcgtgagcc cgggccagac cgcgagcatt 60
acctgtagcg gcgataacat ccgtaaatac gttgttcatt ggtaccagca gaaaccgggc 120
caggcgccgg tgctggtgat ctaccgtgac aacaaccgtc cgagcggcat cccggaacgt 180
tttagcggat ccaacagcgg caacaccgcg accctgacca ttagcggcac ccaggcggaa 240
gacgaagcgg attattactg ccagtcttgg gactctttcc tggctgttgt gtttggcggc 300
ggcacgaagt taaccgtcct aggtcagccc aaggctgccc cctcggtcac tctgttcccg 360
ccctcctctg aggagcttca agccaacaag gccacactgg tgtgtctcat aagtgacttc 420
tacccgggag ccgtgacagt ggcctggaag gcagatagca gccccgtcaa ggcgggagtg 480
gagaccacca caccctccaa acaaagcaac aacaagtacg cggccagcag ctatctgagc 540
ctgacgcctg agcagtggaa gtcccacaga agctacagct gccaggtcac gcatgaaggg 600
agcaccgtgg agaagacagt ggcccctaca gaatgttca 639

<210> SEQ ID NO 182
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 182

Ser Gly Ser Ser Ser Asn Ile Gly Leu Asp Tyr Val Asn
1 5 10

<210> SEQ ID NO 183
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 183

Arg Asn Lys Gln Arg Pro Ser
1 5

<210> SEQ ID NO 184
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 184

Gln Ala Trp Ala Gly Arg Thr Asn Tyr Val Val
1 5 10

<210> SEQ ID NO 185
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 185

Asn Tyr Trp Ile Gly
1 5

<210> SEQ ID NO 186
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 186

Phe Ile Asp Pro Gly Val Ser Tyr Thr Arg Tyr Ser Pro Ser Phe Gln
1 5 10 15

Gly

<210> SEQ ID NO 187
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 187

Val Leu Ala His Ser Thr Glu Tyr Asn Trp Pro Ala Phe
1 5 10

<210> SEQ ID NO 188
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 188

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Trp Ile Gly Trp Val Arg Gln Met Pro Gly Lys Gly Leu Glu Trp Met
35 40 45

Gly Phe Ile Asp Pro Gly Val Ser Tyr Thr Arg Tyr Ser Pro Ser Phe
50 55 60

Gln Gly Gln Val Thr Ile Ser Ala Asp Lys Ser Ile Ser Thr Ala Tyr
65 70 75 80

```
Leu Gln Trp Ser Ser Leu Lys Ala Ser Asp Thr Ala Met Tyr Tyr Cys
                85                  90                  95

Ala Arg Val Leu Ala His Ser Thr Glu Tyr Asn Trp Pro Ala Phe Trp
            100                 105                 110

Gly Gln Gly Thr Leu Val Thr Val Ser Ser
        115                 120


<210> SEQ ID NO 189
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Leu Asp
            20                  25                  30

Tyr Val Asn Trp Tyr Gln Gln Leu Pro Gly Thr Ala Pro Lys Leu Leu
        35                  40                  45

Ile Tyr Arg Asn Lys Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ala Trp Ala Gly Arg Thr
                85                  90                  95

Asn Tyr Val Val Phe Gly Gly Gly Thr Lys Leu Thr Val Leu
            100                 105                 110


<210> SEQ ID NO 190
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190

caggtgcaat tggtgcagag cggtgcggaa gtgaaaaaac cgggcgaaag cctgaaaatt      60

agctgcaaag gctccggata tagcttcact aactactgga tcggttgggt gcgccagatg     120

ccgggcaaag gtctcgagtg gatgggcttc atcgacccgg gtgttagcta cacccgttat     180

agcccgagct ttcagggcca ggtgaccatt agcgcggata aaagcatcag caccgcgtat     240

ctgcaatgga gcagcctgaa agcgagcgat accgcgatgt attattgcgc gcgtgttctg     300

gctcattcta ctgaatacaa ctggccggct ttctggggcc aaggcaccct ggtgactgtt     360

agctca                                                                 366


<210> SEQ ID NO 191
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 191

```
gatatcgtgc tgacccagcc gccgagcgtg agcggtgcac cgggccagcg cgtgaccatt     60

agctgtagcg gcagcagcag caacattggt ctggactacg tgaactggta ccagcagctg    120

ccgggcacgg cgccgaaact gctgatctac cgtaacaaac agcgcccgag cggcgtgccg    180

gatcgcttta gcggatccaa aagcggcacc agcgccagcc tggcgattac cggcctgcaa    240

gcagaagacg aagcggatta ttactgccag gcttgggctg gtcgtactaa ctacgttgtg    300

tttggcggcg gcacgaagtt aaccgtccta                                     330
```

<210> SEQ ID NO 192
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Phe Ile Asp Pro Gly Val Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Leu Ala His Ser Thr Glu Tyr Asn Trp Pro Ala Phe Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly Lys
450

<210> SEQ ID NO 193
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 193

Asp Ile Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Leu Asp
20 25 30

Tyr Val Asn Trp Tyr Gln Gln Leu Pro Gly Thr Ala Pro Lys Leu Leu
35 40 45

Ile Tyr Arg Asn Lys Gln Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Gln Ala Trp Ala Gly Arg Thr
85 90 95

Asn Tyr Val Val Phe Gly Gly Gly Thr Lys Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 194
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194

caggtgcaat tggtgcagag cggtgcggaa gtgaaaaaac cgggcgaaag cctgaaaatt     60

agctgcaaag gctccggata tagcttcact aactactgga tcggttgggt gcgccagatg    120

ccgggcaaag gtctcgagtg gatgggcttc atcgacccgg gtgttagcta cacccgttat    180

agcccgagct ttcagggcca ggtgaccatt agcgcggata aaagcatcag caccgcgtat    240

ctgcaatgga gcagcctgaa agcgagcgat accgcgatgt attattgcgc gcgtgttctg    300

gctcattcta ctgaatacaa ctggccggct ttctggggcc aaggcaccct ggtgactgtt    360

agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaactcctg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356


<210> SEQ ID NO 195
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195
```

```
gatatcgtgc tgacccagcc gccgagcgtg agcggtgcac cgggccagcg cgtgaccatt      60

agctgtagcg gcagcagcag caacattggt ctggactacg tgaactggta ccagcagctg     120

ccgggcacgg cgccgaaact gctgatctac cgtaacaaac agcgcccgag cggcgtgccg     180

gatcgcttta gcggatccaa aagcggcacc agcgccagcc tggcgattac cggcctgcaa     240

gcagaagacg aagcggatta ttactgccag gcttgggctg gtcgtactaa ctacgttgtg     300

tttggcggcg gcacgaagtt aaccgtccta ggtcagccca aggctgcccc ctcggtcact     360

ctgttcccgc cctcctctga ggagcttcaa gccaacaagg ccacactggt gtgtctcata     420

agtgacttct acccgggagc cgtgacagtg gcctggaagg cagatagcag ccccgtcaag     480

gcgggagtgg agaccaccac accctccaaa caaagcaaca acaagtacgc ggccagcagc     540

tatctgagcc tgacgcctga gcagtggaag tcccacagaa gctacagctg ccaggtcacg     600

catgaaggga gcaccgtgga gaagacagtg gcccctacag aatgttca                  648


<210> SEQ ID NO 196
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Thr Gly Thr Ser Ser Asp Val Gly Ser Tyr Asn Tyr Val Ser
1               5                   10


<210> SEQ ID NO 197
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Tyr Val Ser Asn Arg Pro Ser
1               5


<210> SEQ ID NO 198
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Ala Ser Tyr Thr His Gln Gly Ser Trp Val
1               5                   10


<210> SEQ ID NO 199
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199
```

Thr Tyr Tyr Met His
1               5

<210> SEQ ID NO 200
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 200

Val Ile Ser Ser Asp Gly Ser Phe Thr Phe Tyr Ala Asp Ser Val Lys
1               5                   10                  15

Gly

<210> SEQ ID NO 201
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 201

His Gly Tyr Gly Ala Phe Asp Tyr
1               5

<210> SEQ ID NO 202
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 202

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Tyr Met His Trp Val Arg Gln Ala Pro Gly Lys Gly Leu Glu Trp Val
        35                  40                  45

Ser Val Ile Ser Ser Asp Gly Ser Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Ala Phe Asp Tyr Trp Gly Gln Gly Thr Leu
            100                 105                 110

Val Thr Val Ser Ser
        115

<210> SEQ ID NO 203
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 203

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Asn Tyr Val Ser Trp Tyr Gln Gln His Pro Gly Lys Ala Pro Lys Leu
35 40 45

Met Ile Tyr Tyr Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ala Ser Tyr Thr His Gln
85 90 95

Gly Ser Trp Val Phe Gly Gly Gly Thr Lys Leu Thr Val Leu
100 105 110

<210> SEQ ID NO 204
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 204
caggtgcaat tgctggaaag cggcggtggc ctggtgcagc cgggtggcag cctgcgtctg 60
agctgcgcgg cgtccggatt caccttttct acttactaca tgcattgggt gcgccaggcc 120
ccgggcaaag gtctcgagtg ggtttccgtt atctcttctg acggttcttt caccttctat 180
gcggatagcg tgaaaggccg ctttaccatc agccgcgata attcgaaaaa caccctgtat 240
ctgcaaatga acagcctgcg tgcggaagat acggccgtgt attattgcgc gcgtcatggt 300
tacggtgctt tcgattactg gggccaaggc accctggtga ctgttagctc a 351

<210> SEQ ID NO 205
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 205
gatatcgcgc tgacccagcc ggcgagcgtg agcggtagcc cgggccagag cattaccatt 60
agctgcaccg gcaccagcag cgatgtgggc tcttacaact acgtgtcttg gtaccagcag 120
catccgggca aggcgccgaa actgatgatc tactacgttt ctaaccgtcc gagcggcgtg 180
agcaaccgtt ttagcggatc caaaagcggc aacaccgcga gcctgaccat tagcggcctg 240
caagcggaag acgaagcgga ttattactgc gcttcttaca ctcatcaggg ttcttgggtg 300
tttggcggcg gcacgaagtt aaccgtccta 330

<210> SEQ ID NO 206
<211> LENGTH: 447
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic polypeptide"

<400> SEQUENCE: 206

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Tyr Met His Trp Val Arg Gln Ala Pro Gly Lys Gly Leu Glu Trp Val
        35                  40                  45

Ser Val Ile Ser Ser Asp Gly Ser Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 207
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Ser Trp Tyr Gln Gln His Pro Gly Lys Ala Pro Lys Leu
        35                  40                  45

Met Ile Tyr Tyr Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Thr His Gln
                85                  90                  95

Gly Ser Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 208
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 208

caggtgcaat tgctggaaag cggcggtggc ctggtgcagc cgggtggcag cctgcgtctg      60
```

-continued

```
agctgcgcgg cgtccggatt caccttttct acttactaca tgcattgggt gcgccaggcc    120

ccgggcaaag gtctcgagtg ggtttccgtt atctcttctg acggttcttt caccttctat    180

gcggatagcg tgaaaggccg ctttaccatc agccgcgata attcgaaaaa caccctgtat    240

ctgcaaatga acagcctgcg tgcggaagat acggccgtgt attattgcgc gcgtcatggt    300

tacggtgctt tcgattactg gggccaaggc accctggtga ctgttagctc agcctccacc    360

aagggtccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgggtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                             1341
```

```
<210> SEQ ID NO 209
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 209

gatatcgcgc tgacccagcc ggcgagcgtg agcggtagcc cgggccagag cattaccatt     60

agctgcaccg gcaccagcag cgatgtgggc tcttacaact acgtgtcttg gtaccagcag    120

catccgggca aggcgccgaa actgatgatc tactacgttt ctaaccgtcc gagcggcgtg    180

agcaaccgtt ttagcggatc caaaagcggc aacaccgcga gcctgaccat tagcggcctg    240

caagcggaag acgaagcgga ttattactgc gcttcttaca ctcatcaggg ttcttgggtg    300

tttggcggcg gcacgaagtt aaccgtccta ggtcagccca aggctgcccc ctcggtcact    360

ctgttcccgc cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tatctgagcc tgacgcctga gcagtggaag tcccacagaa gctacagctg ccaggtcacg    600

catgaaggga gcaccgtgga gaagacagtg gcccctacag aatgttca                 648
```

<210> SEQ ID NO 210
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 210

Arg Ala Ser Gln Ser Ile Ser Leu Trp Leu Asn
1 5 10

<210> SEQ ID NO 211
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Ala Ala Ser Thr Leu Gln Ser
1 5

<210> SEQ ID NO 212
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Gln Gln Tyr Tyr Thr Ser Pro Tyr Thr
1 5

<210> SEQ ID NO 213
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 213

Ser Tyr Ala Met Ser
1 5

<210> SEQ ID NO 214
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 214

Val Ile Arg Ser Ser Gly Ser Ser Thr Tyr Tyr Ala Asp Ser Val Lys
1 5 10 15

Gly

<210> SEQ ID NO 215
<211> LENGTH: 7

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 215

Gly Gly Gly Tyr Phe Asp Tyr
1               5

<210> SEQ ID NO 216
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 216

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Arg Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Tyr Phe Asp Tyr Trp Gly Gln Gly Thr Leu Val
            100                 105                 110

Thr Val Ser Ser
        115

<210> SEQ ID NO 217
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Leu Trp
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Ser Pro Tyr
                85                  90                  95

Thr Phe Gly Gln Gly Thr Lys Val Glu Ile Lys 100 105

<210> SEQ ID NO 218
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 218
caggtgcagc tgctggaatc aggcggcgga ctggtgcaac ctggcggatc cctgaggctg 60
agctgcgctg ctagtggctt caccttctct agctacgcta tgagctgggt ccgccaggcc 120
cctggtaaag gcctcgagtg ggtgtcagtg attagatcta gcggctctag cacctactac 180
gccgatagcg tgaagggccg gttcactatc tctagggata actctaagaa caccctgtac 240
ctgcagatga actccctgag ggccgaggac accgccgtct actactgcgc tagaggcgga 300
ggctacttcg actactgggg tcaaggcacc ctggtcaccg tgtctagc 348

<210> SEQ ID NO 219
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 219
gatattcaga tgactcagtc acctagtagc ctgagcgcta gtgtgggcga tagagtgact 60
atcacctgta gagcctctca gtctattagc ctgtggctga actggtatca gcagaagccc 120
ggtaaagccc ctaagctgct gatctacgcc gcctctaccc tgcagtcagg cgtgccctct 180
aggtttagcg gtagcggtag tggcaccgac ttcaccctga ctatctctag cctgcagccc 240
gaggacttcg ctacctacta ctgtcagcag tactacacta gcccctacac cttcggtcag 300
ggcactaagg tcgagattaa g 321

<210> SEQ ID NO 220
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 220

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Val Ile Arg Ser Ser Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Arg Gly Gly Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 221
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 221

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Leu Trp
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 222
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222

caggtgcagc tgctggaatc aggcggcgga ctggtgcaac ctggcggatc cctgaggctg     60

agctgcgctg ctagtggctt caccttctct agctacgcta tgagctgggt ccgccaggcc    120

cctggtaaag gcctcgagtg ggtgtcagtg attagatcta gcggctctag cacctactac    180

gccgatagcg tgaagggccg gttcactatc tctagggata actctaagaa caccctgtac    240

ctgcagatga actccctgag ggccgaggac accgccgtct actactgcgc tagaggcgga    300

ggctacttcg actactgggg tcaaggcacc ctggtcaccg tgtctagcgc tagcactaag    360

ggcccaagtg tgtttcccct ggcccccagc agcaagtcta cttccggcgg aactgctgcc    420

ctgggttgcc tggtgaagga ctacttcccc gagcccgtga cagtgtcctg gaactctggg    480

gctctgactt ccggcgtgca caccttcccc gccgtgctgc agagcagcgg cctgtacagc    540

ctgagcagcg tggtgacagt gccctccagc tctctgggaa cccagaccta tatctgcaac    600

gtgaaccaca agcccagcaa caccaaggtg gacaagagag tggagcccaa gagctgcgac    660

aagacccaca cctgcccccc ctgcccagct ccagaactgc tgggagggcc ttccgtgttc    720

ctgttccccc ccaagcccaa ggacaccctg atgatcagca ggacccccga ggtgacctgc    780
```

gtggtggtgg acgtgtccca cgaggaccca gaggtgaagt tcaactggta cgtggacggc 840
gtggaggtgc acaacgccaa gaccaagccc agagaggagc agtacaacag cacctacagg 900
gtggtgtccg tgctgaccgt gctgcaccag gactggctga acggcaaaga atacaagtgc 960
aaagtctcca acaaggccct gccagcccca atcgaaaaga caatcagcaa ggccaagggc 1020
cagccacggg agccccaggt gtacaccctg ccccccagcc gggaggagat gaccaagaac 1080
caggtgtccc tgacctgtct ggtgaagggc ttctacccca gcgatatcgc cgtggagtgg 1140
gagagcaacg gccagcccga gaacaactac aagaccaccc ccccagtgct ggacagcgac 1200
ggcagcttct tcctgtacag caagctgacc gtggacaagt ccaggtggca gcagggcaac 1260
gtgttcagct gcagcgtgat gcacgaggcc ctgcacaacc actacaccca gaagtccctg 1320
agcctgagcc ccggcaag 1338

<210> SEQ ID NO 223
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 223
gatattcaga tgactcagtc acctagtagc ctgagcgcta gtgtgggcga tagagtgact 60
atcacctgta gagcctctca gtctattagc ctgtggctga actggtatca gcagaagccc 120
ggtaaagccc ctaagctgct gatctacgcc gcctctaccc tgcagtcagg cgtgccctct 180
aggtttagcg gtagcggtag tggcaccgac ttcaccctga ctatctctag cctgcagccc 240
gaggacttcg ctacctacta ctgtcagcag tactacacta gcccctacac cttcggtcag 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 224
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 224

Arg Ala Ser Gln Ser Ile Ser Ser Tyr Leu Asn
1               5                   10

<210> SEQ ID NO 225
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 225

Ala Val Ser Thr Leu Gln Ser
1 5

<210> SEQ ID NO 226
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 226

Gln Gln Ser Gly Thr Phe Pro Pro Thr Thr
1 5 10

<210> SEQ ID NO 227
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 227

Ser His Gly Met His
1 5

<210> SEQ ID NO 228
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 228

Val Ile Ser Gly Ser Gly Ser Asn Thr Gly Tyr Ala Asp Ser Val Lys
1 5 10 15

Gly

<210> SEQ ID NO 229
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 229

Gln Trp Gly Ser Tyr Ala Phe Asp Ser
1 5

<210> SEQ ID NO 230
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 230

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ser Val Ile Ser Gly Ser Gly Ser Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Trp Gly Ser Tyr Ala Phe Asp Ser Trp Gly Gln Gly Thr
            100                 105                 110

Leu Val Thr Val Ser Ser
        115

<210> SEQ ID NO 231
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Thr Phe Pro Pro
                85                  90                  95

Thr Thr Phe Gly Gln Gly Thr Lys Val Glu Ile Lys
            100                 105

<210> SEQ ID NO 232
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 232
caggtgcagc tgctggaatc aggcggcgga ctggtgcagc ctggcggatc cctgaggctg 60
agctgcgctg ctagtggctt cacctttagc tctcacggaa tgcactgggt ccgccaggcc 120
cctggtaaag gcctcgagtg ggtgtcagtg attagcggta gcggctctaa caccggctac 180
gccgatagcg tgaagggccg gttcactatc tctagggata actctaagaa caccctgtac 240
ctgcagatga actccctgag ggccgaggac accgccgtct actactgcgc tagacagtgg 300
ggctcctacg ccttcgatag ctggggtcaa ggcaccctgg tcaccgtgtc tagc 354

<210> SEQ ID NO 233
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 233
gatattcaga tgactcagtc acctagtagc ctgagcgcta gtgtgggcga tagagtgact 60
atcacctgta gagcctctca gtctatctct agctacctga actggtatca gcagaagccc 120
ggtaaagccc ctaagctgct gatctacgcc gtgtctaccc tgcagtcagg cgtgccctct 180
aggtttagcg gtagcggtag tggcaccgac ttcaccctga ctattagtag cctgcagccc 240
gaggacttcg ctacctacta ctgtcagcag tcaggcacct tccccctac taccttcggt 300 cagggcacta aggtcgagat taag 324

<210> SEQ ID NO 234
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 234

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Gly Met His Trp Val Arg Gln Ala Pro Gly Lys Gly Leu Glu Trp Val
35 40 45

Ser Val Ile Ser Gly Ser Gly Ser Asn Thr Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Trp Gly Ser Tyr Ala Phe Asp Ser Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr

```
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 235
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Val Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Thr Phe Pro Pro
                85                  90                  95

Thr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 236
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236

caggtgcagc tgctggaatc aggcggcgga ctggtgcagc ctggcggatc cctgaggctg      60

agctgcgctg ctagtggctt cacctttagc tctcacggaa tgcactgggt ccgccaggcc     120

cctggtaaag gcctcgagtg ggtgtcagtg attagcggta gcggctctaa caccggctac     180

gccgatagcg tgaagggccg gttcactatc tctagggata actctaagaa caccctgtac     240

ctgcagatga actccctgag ggccgaggac accgccgtct actactgcgc tagacagtgg     300

ggctcctacg ccttcgatag ctggggtcaa ggcaccctgg tcaccgtgtc tagcgctagc     360

actaagggcc caagtgtgtt tcccctggcc cccagcagca agtctacttc cggcggaact     420

gctgccctgg gttgcctggt gaaggactac ttccccgagc ccgtgacagt gtcctggaac     480

tctggggctc tgacttccgg cgtgcacacc ttccccgccg tgctgcagag cagcggcctg     540

tacagcctga gcagcgtggt gacagtgccc tccagctctc tgggaaccca gacctatatc     600

tgcaacgtga accacaagcc cagcaacacc aaggtggaca agagagtgga gcccaagagc     660

tgcgacaaga cccacacctg ccccccctgc ccagctccag aactgctggg agggccttcc     720

gtgttcctgt tccccccaa gcccaaggac accctgatga tcagcaggac ccccgaggtg     780

acctgcgtgg tggtggacgt gtcccacgag gacccagagg tgaagttcaa ctggtacgtg     840

gacggcgtgg aggtgcacaa cgccaagacc aagcccagag aggagcagta caacagcacc     900

tacagggtgg tgtccgtgct gaccgtgctg caccaggact ggctgaacgg caaagaatac     960

aagtgcaaag tctccaacaa ggccctgcca gccccaatcg aaaagacaat cagcaaggcc    1020

aagggccagc cacgggagcc ccaggtgtac accctgcccc ccagccggga ggagatgacc    1080

aagaaccagg tgtccctgac ctgtctggtg aagggcttct accccagcga tatcgccgtg    1140

gagtgggaga gcaacggcca gcccgagaac aactacaaga ccaccccccc agtgctggac    1200

agcgacggca gcttcttcct gtacagcaag ctgaccgtgg acaagtccag gtggcagcag    1260

ggcaacgtgt tcagctgcag cgtgatgcac gaggccctgc acaaccacta cacccagaag    1320

tccctgagcc tgagccccgg caag                                           1344


<210> SEQ ID NO 237
```

<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 237
gatattcaga tgactcagtc acctagtagc ctgagcgcta gtgtgggcga tagagtgact 60
atcacctgta gagcctctca gtctatctct agctacctga actggtatca gcagaagccc 120
ggtaaagccc ctaagctgct gatctacgcc gtgtctaccc tgcagtcagg cgtgccctct 180
aggtttagcg gtagcggtag tggcaccgac ttcaccctga ctattagtag cctgcagccc 240
gaggacttcg ctacctacta ctgtcagcag tcaggcacct tcccccctac taccttcggt 300
cagggcacta aggtcgagat taagcgtacg gtggccgctc ccagcgtgtt catcttcccc 360
cccagcgacg agcagctgaa gagcggcacc gccagcgtgg tgtgcctgct gaacaacttc 420
tacccccggg aggccaaggt gcagtggaag gtggacaacg ccctgcagag cggcaacagc 480
caggagagcg tcaccgagca ggacagcaag gactccacct acagcctgag cagcaccctg 540
accctgagca aggccgacta cgagaagcat aaggtgtacg cctgcgaggt gacccaccag 600
ggcctgtcca gccccgtgac caagagcttc aacaggggcg agtgc 645

<210> SEQ ID NO 238
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 238

Ser Gly Asp Asn Leu Arg Ser Tyr Tyr Val His
1 5 10

<210> SEQ ID NO 239
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 239

Gly Asn Asn Lys Arg Pro Ser
1 5

<210> SEQ ID NO 240
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 240

Gly Val Tyr Thr Leu Ser Ser Val Val
1 5

<210> SEQ ID NO 241

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 241

Ser Asn Ser Ala Ala Trp Asn
1               5

<210> SEQ ID NO 242
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 242

Arg Ile Tyr Tyr Arg Ser Lys Trp Tyr Asn Asp Tyr Ala Val Ser Val
1               5                   10                  15

Lys Ser

<210> SEQ ID NO 243
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Gly Leu Val Gly Arg Tyr Gly Gln Pro Tyr His Phe Asp Val
1               5                   10

<210> SEQ ID NO 244
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 244

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Leu Val Gly Arg Tyr Gly Gln Pro Tyr His
            100                 105                 110

Phe Asp Val Trp Gly Gln Gly Thr Leu Val Thr Val Ser Ser

```
        115                 120                 125


<210> SEQ ID NO 245
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Arg Ser Tyr Tyr Val
            20                  25                  30

His Trp Tyr Gln Gln Lys Pro Gly Gln Ala Pro Val Leu Val Ile Tyr
        35                  40                  45

Gly Asn Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Val Tyr Thr Leu Ser Ser Val Val
                85                  90                  95

Phe Gly Gly Gly Thr Lys Leu Thr Val Leu
            100                 105


<210> SEQ ID NO 246
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246

caggtgcaat tgcagcagag cggtccgggc ctggtgaaac cgagccagac cctgagcctg     60

acctgcgcga tttccggaga tagcgtgagc tctaactctg ctgcttggaa ctggattcgt    120

cagagcccga gccgtggcct cgagtggctg ggccgtatct actaccgtag caaatggtac    180

aacgactatg ccgtgagcgt gaaaagccgc attaccatta acccggatac ttcgaaaaac    240

cagtttagcc tgcaactgaa cagcgtgacc ccggaagata cggccgtgta ttattgcgcg    300

cgtggtctgg ttggtcgtta cggtcagccg taccatttcg atgtttgggg ccaaggcacc    360

ctggtgactg ttagctca                                                  378


<210> SEQ ID NO 247
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247

gatatcgaac tgacccagcc gccgagcgtg agcgtgagcc cgggccagac cgcgagcatt     60

acctgtagcg gcgataacct gcgttcttac tacgttcatt ggtaccagca gaaaccgggc    120

caggcgccgg tgctggtgat ctacggtaac aacaaacgtc cgagcggcat cccggaacgt    180
```

```
tttagcggat ccaacagcgg caacaccgcg accctgacca ttagcggcac ccaggcggaa    240

gacgaagcgg attattactg cggtgtttac actctgtctt ctgttgtgtt tggcggcggc    300

acgaagttaa ccgtccta                                                  318
```

<210> SEQ ID NO 248
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 248

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Leu Val Gly Arg Tyr Gly Gln Pro Tyr His
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

```
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 249
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Arg Ser Tyr Tyr Val
            20                  25                  30

His Trp Tyr Gln Gln Lys Pro Gly Gln Ala Pro Val Leu Val Ile Tyr
        35                  40                  45

Gly Asn Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Val Tyr Thr Leu Ser Ser Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 250
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 250
caggtgcaat tgcagcagag cggtccgggc ctggtgaaac cgagccagac cctgagcctg 60
acctgcgcga tttccggaga tagcgtgagc tctaactctg ctgcttggaa ctggattcgt 120
cagagcccga gccgtggcct cgagtggctg ggccgtatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgtggtctgg ttggtcgtta cggtcagccg taccatttcg atgtttgggg ccaaggcacc 360
ctggtgactg ttagctcagc ctccaccaag ggtccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtgca caccttcccg 540
gctgtcctac agtcctcagg actctactcc ctcagcagcg tggtgaccgt gccctccagc 600
agcttgggca cccagaccta catctgcaac gtgaatcaca agcccagcaa caccaaggtg 660
gacaagagag ttgagcccaa atcttgtgac aaaactcaca catgcccacc gtgcccagca 720
cctgaactcc tggggggacc gtcagtcttc ctcttccccc caaaacccaa ggacaccctc 780
atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgg gtggtcagcg tcctcaccgt cctgcaccag 960
gactggctga atggcaagga gtacaagtgc aaggtctcca acaaagccct cccagccccc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctacag caagctcacc 1260
gtggacaaga gcaggtggca gcaggggaac gtcttctcat gctccgtgat gcatgaggct 1320
ctgcacaacc actacacgca gaagagcctc tccctgtctc cgggtaaa 1368

<210> SEQ ID NO 251
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 251
gatatcgaac tgacccagcc gccgagcgtg agcgtgagcc cgggccagac cgcgagcatt 60
acctgtagcg gcgataacct gcgttcttac tacgttcatt ggtaccagca gaaaccgggc 120
caggcgccgg tgctggtgat ctacggtaac aacaaacgtc cgagcggcat cccggaacgt 180
tttagcggat ccaacagcgg caacaccgcg accctgacca ttagcggcac ccaggcggaa 240

```
gacgaagcgg attattactg cggtgtttac actctgtctt ctgttgtgtt tggcggcggc    300

acgaagttaa ccgtcctagg tcagcccaag gctgccccct cggtcactct gttcccgccc    360

tcctctgagg agcttcaagc caacaaggcc acactggtgt gtctcataag tgacttctac    420

ccgggagccg tgacagtggc ctggaaggca gatagcagcc ccgtcaaggc gggagtggag    480

accaccacac cctccaaaca aagcaacaac aagtacgcgg ccagcagcta tctgagcctg    540

acgcctgagc agtggaagtc ccacagaagc tacagctgcc aggtcacgca tgaagggagc    600

accgtggaga agacagtggc ccctacagaa tgttca                              636


<210> SEQ ID NO 252
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Ser Gly Asp Lys Ile Pro Thr Tyr Thr Val His
1               5                   10


<210> SEQ ID NO 253
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Asp Asp Asn Lys Arg Pro Ser
1               5


<210> SEQ ID NO 254
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Gln Ser Thr Ala Ser Gly Thr Val Val
1               5


<210> SEQ ID NO 255
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Ser Tyr Ala Leu His
1               5


<210> SEQ ID NO 256
<211> LENGTH: 19
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic peptide"

<400> SEQUENCE: 256

Arg Ile Lys Ser Lys Thr Asn Gly Gly Thr Thr Asp Tyr Ala Ala Pro
1 5 10 15

Val Lys Gly

<210> SEQ ID NO 257
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 257

Val Asp Ala Thr Tyr Ser Tyr Ser Gly Tyr Tyr Tyr Pro Met Asp Tyr
1 5 10 15

<210> SEQ ID NO 258
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 258

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Asn Ser Tyr
20 25 30

Ala Leu His Trp Val Arg Gln Ala Pro Gly Lys Gly Leu Glu Trp Val
35 40 45

Gly Arg Ile Lys Ser Lys Thr Asn Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Val Asp Ala Thr Tyr Ser Tyr Ser Gly Tyr Tyr Tyr
100 105 110

Pro Met Asp Tyr Trp Gly Gln Gly Thr Leu Val Thr Val Ser Ser
115 120 125

<210> SEQ ID NO 259
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 259

Asp Ile Glu Leu Thr Gln Pro Pro Ser Val Ser Val Ser Pro Gly Gln
1 5 10 15

Thr Ala Ser Ile Thr Cys Ser Gly Asp Lys Ile Pro Thr Tyr Thr Val

```
            20                  25                  30

His Trp Tyr Gln Gln Lys Pro Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Thr Ala Ser Gly Thr Val Val
                85                  90                  95

Phe Gly Gly Gly Thr Lys Leu Thr Val Leu
            100                 105
```

<210> SEQ ID NO 260
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 260

```
caggtgcaat tggtggaaag cggcggtggc ctggtgaaac caggcggcag cctgcgcctg     60

agctgcgccg cctccggatt cacctttaac tcttacgctc tgcattgggt gcgccaggcc    120

ccgggcaaag gtctcgagtg ggtgggccgt atcaaatcta aaactaacgg tggtactact    180

gactatgccg ccccagtgaa aggccgcttt accattagcc gcgatgattc gaaaaacacc    240

ctgtatctgc aaatgaacag cctgaaaacc gaagatacgg ccgtgtatta ttgcgcgcgt    300

gttgacgcta cttactctta ctctggttac tactacccga tggattactg gggccaaggc    360

accctggtga ctgttagctc a                                               381
```

<210> SEQ ID NO 261
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 261

```
gatatcgaac tgacccagcc gccgagcgtg agcgtgagcc cgggccagac cgcgagcatt     60

acctgtagcg gcgataaaat cccgacttac actgttcatt ggtaccagca gaaaccgggc    120

caggcgccgg tgctggtgat ctacgacgac aacaaacgtc cgagcggcat cccggaacgt    180

tttagcggat ccaacagcgg caacaccgcg accctgacca ttagcggcac ccaggcggaa    240

gacgaagcgg attattactg ccagtctact gcttctggta ctgttgtgtt tggcggcggc    300

acgaagttaa ccgtccta                                                   318
```

<210> SEQ ID NO 262
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 262

-continued

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ser Tyr
            20                  25                  30

Ala Leu His Trp Val Arg Gln Ala Pro Gly Lys Gly Leu Glu Trp Val
        35                  40                  45

Gly Arg Ile Lys Ser Lys Thr Asn Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Asp Ala Thr Tyr Ser Tyr Ser Gly Tyr Tyr Tyr
            100                 105                 110

Pro Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
```

```
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455


<210> SEQ ID NO 263
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 263

Asp Ile Glu Leu Thr Gln Pro Pro Ser Val Ser Val Ser Pro Gly Gln
1               5                   10                  15

Thr Ala Ser Ile Thr Cys Ser Gly Asp Lys Ile Pro Thr Tyr Thr Val
            20                  25                  30

His Trp Tyr Gln Gln Lys Pro Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Thr Ala Ser Gly Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210


<210> SEQ ID NO 264
<211> LENGTH: 1371
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264

caggtgcaat tggtggaaag cggcggtggc ctggtgaaac caggcggcag cctgcgcctg      60

agctgcgccg cctccggatt cacctttaac tcttacgctc tgcattgggt gcgccaggcc     120

ccgggcaaag gtctcgagtg ggtgggccgt atcaaatcta aaactaacgg tggtactact     180
```

```
gactatgccg ccccagtgaa aggccgcttt accattagcc gcgatgattc gaaaaacacc    240

ctgtatctgc aaatgaacag cctgaaaacc gaagatacgg ccgtgtatta ttgcgcgcgt    300

gttgacgcta cttactctta ctctggttac tactacccga tggattactg gggccaaggc    360

accctggtga ctgttagctc agcctccacc aagggtccat cggtcttccc cctggcaccc    420

tcctccaaga gcacctctgg gggcacagcg gccctgggct gcctggtcaa ggactacttc    480

cccgaaccgg tgacggtgtc gtggaactca ggcgccctga ccagcggcgt gcacaccttc    540

ccggctgtcc tacagtcctc aggactctac tccctcagca gcgtggtgac cgtgccctcc    600

agcagcttgg gcacccagac ctacatctgc aacgtgaatc acaagcccag caacaccaag    660

gtggacaaga gagttgagcc caaatcttgt gacaaaactc acacatgccc accgtgccca    720

gcacctgaac tcctgggggg accgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgggtggtca gcgtcctcac cgtcctgcac    960

caggactggc tgaatggcaa ggagtacaag tgcaaggtct ccaacaaagc cctcccagcc   1020

cccatcgaga aaaccatctc caaagccaaa gggcagcccc gagaaccaca ggtgtacacc   1080

ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta cagcaagctc   1260

accgtggaca agagcaggtg gcagcagggg aacgtcttct catgctccgt gatgcatgag   1320

gctctgcaca accactacac gcagaagagc ctctccctgt ctccgggtaa a            1371
```

<210> SEQ ID NO 265
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 265

```
gatatcgaac tgacccagcc gccgagcgtg agcgtgagcc cgggccagac cgcgagcatt     60

acctgtagcg gcgataaaat cccgacttac actgttcatt ggtaccagca gaaaccgggc    120

caggcgccgg tgctggtgat ctacgacgac aacaaacgtc cgagcggcat cccggaacgt    180

tttagcggat ccaacagcgg caacaccgcg accctgacca ttagcggcac ccaggcggaa    240

gacgaagcgg attattactg ccagtctact gcttctggta ctgttgtgtt tggcggcggc    300

acgaagttaa ccgtcctagg tcagcccaag gctgccccct cggtcactct gttcccgccc    360

tcctctgagg agcttcaagc caacaaggcc acactggtgt gtctcataag tgacttctac    420

ccgggagccg tgacagtggc ctggaaggca gatagcagcc ccgtcaaggc gggagtggag    480

accaccacac cctccaaaca aagcaacaac aagtacgcgg ccagcagcta tctgagcctg    540

acgcctgagc agtggaagtc ccacagaagc tacagctgcc aggtcacgca tgaagggagc    600

accgtggaga agacagtggc ccctacagaa tgttca                              636
```

<210> SEQ ID NO 266
<211> LENGTH: 11
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 266

Arg Ala Ser Gln Ser Ile Val Ser Tyr Leu Asn
1 5 10

<210> SEQ ID NO 267
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 267

Asp Ala Ser Ser Leu Gln Ser
1 5

<210> SEQ ID NO 268
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 268

Gln Gln Ser Gly Ser His Ser Ile Thr
1 5

<210> SEQ ID NO 269
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 269

Ser His Trp Val His
1 5

<210> SEQ ID NO 270
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 270

Val Ile Ser Tyr Met Gly Ser Ser Thr Tyr Tyr Ala Asp Ser Val Lys
1 5 10 15

Gly

<210> SEQ ID NO 271
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 271

Gly Ser Tyr Asp Met Ala Phe Asp Val
1 5

<210> SEQ ID NO 272
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 272

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Trp Val His Trp Val Arg Gln Ala Pro Gly Lys Gly Leu Glu Trp Val
35 40 45

Ser Val Ile Ser Tyr Met Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Ser Tyr Asp Met Ala Phe Asp Val Trp Gly Gln Gly Thr
100 105 110

Leu Val Thr Val Ser Ser
115

<210> SEQ ID NO 273
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 273

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Val Ser Tyr
20 25 30

Leu Asn Trp Tyr Gln Gln Lys Pro Gly Lys Ala Pro Lys Leu Leu Ile
35 40 45

Tyr Asp Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Gly Ser His Ser Ile
85 90 95

Thr Phe Gly Gln Gly Thr Lys Val Glu Ile Lys
100 105

<210> SEQ ID NO 274
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 274
caggtgcagc tgctggaatc aggcggcgga ctggtgcagc ctggcggtag cctgagactg 60
agctgcgctg ctagtggctt cacctttagc tctcactggg tgcactgggt cagacaggcc 120
cctggtaaag gcctggagtg ggtgtcagtg attagctata tgggctctag cacctactac 180
gccgatagcg tgaagggccg gttcactatc tctagggata actctaagaa caccctgtac 240
ctgcagatga atagcctgag agccgaggac accgccgtct actactgcgc tagaggctcc 300
tacgatatgg ccttcgacgt gtggggtcag ggcaccctgg tcaccgtgtc tagc 354

<210> SEQ ID NO 275
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 275
gatattcaga tgactcagtc acctagtagc ctgagcgcta gtgtgggcga tagagtgact 60
atcacctgta gagcctctca gtctatcgtc agctacctga actggtatca gcagaagccc 120
ggtaaagccc ctaagctgct gatctacgac gcctctagcc tgcagtcagg cgtgccctct 180
aggtttagcg gtagcggtag tggcaccgac ttcaccctga ctattagtag cctgcagccc 240
gaggacttcg ctacctacta ctgtcagcag tcaggctctc actctatcac cttcggtcag 300
ggcactaagg tcgagattaa g 321

<210> SEQ ID NO 276
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 276

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Trp Val His Trp Val Arg Gln Ala Pro Gly Lys Gly Leu Glu Trp Val
35 40 45

Ser Val Ile Ser Tyr Met Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Ser Tyr Asp Met Ala Phe Asp Val Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 277
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 277

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Ser Ile Val Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser His Ser Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 278
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 278

```
caggtgcagc tgctggaatc aggcggcgga ctggtgcagc ctggcggtag cctgagactg     60

agctgcgctg ctagtggctt cacctttagc tctcactggg tgcactgggt cagacaggcc    120

cctggtaaag gcctggagtg ggtgtcagtg attagctata tgggctctag cacctactac    180

gccgatagcg tgaagggccg gttcactatc tctagggata actctaagaa caccctgtac    240

ctgcagatga atagcctgag agccgaggac accgccgtct actactgcgc tagaggctcc    300

tacgatatgg ccttcgacgt gtggggtcag ggcaccctgg tcaccgtgtc tagcgctagc    360

actaagggcc caagtgtgtt tcccctggcc cccagcagca agtctacttc cggcggaact    420

gctgccctgg gttgcctggt gaaggactac ttccccgagc ccgtgacagt gtcctggaac    480

tctggggctc tgacttccgg cgtgcacacc ttccccgccg tgctgcagag cagcggcctg    540

tacagcctga gcagcgtggt gacagtgccc tccagctctc tgggaaccca gacctatatc    600

tgcaacgtga accacaagcc cagcaacacc aaggtggaca agagagtgga gcccaagagc    660

tgcgacaaga cccacacctg ccccccctgc ccagctccag aactgctggg agggccttcc    720

gtgttcctgt tcccccccaa gcccaaggac accctgatga tcagcaggac ccccgaggtg    780

acctgcgtgg tggtggacgt gtcccacgag gacccagagg tgaagttcaa ctggtacgtg    840
```

```
gacggcgtgg aggtgcacaa cgccaagacc aagcccagag aggagcagta caacagcacc    900

tacagggtgg tgtccgtgct gaccgtgctg caccaggact ggctgaacgg caaagaatac    960

aagtgcaaag tctccaacaa ggccctgcca gccccaatcg aaaagacaat cagcaaggcc   1020

aagggccagc cacgggagcc ccaggtgtac accctgcccc ccagccggga ggagatgacc   1080

aagaaccagg tgtccctgac ctgtctggtg aagggcttct accccagcga tatcgccgtg   1140

gagtgggaga gcaacggcca gcccgagaac aactacaaga ccaccccccc agtgctggac   1200

agcgacggca gcttcttcct gtacagcaag ctgaccgtgg acaagtccag gtggcagcag   1260

ggcaacgtgt tcagctgcag cgtgatgcac gaggccctgc acaaccacta cacccagaag   1320

tccctgagcc tgagccccgg caag                                          1344
```

<210> SEQ ID NO 279
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 279

```
gatattcaga tgactcagtc acctagtagc ctgagcgcta gtgtgggcga tagagtgact     60

atcacctgta gagcctctca gtctatcgtc agctacctga actggtatca gcagaagccc    120

ggtaaagccc ctaagctgct gatctacgac gcctctagcc tgcagtcagg cgtgccctct    180

aggtttagcg gtagcggtag tggcaccgac ttcaccctga ctattagtag cctgcagccc    240

gaggacttcg ctacctacta ctgtcagcag tcaggctctc actctatcac cttcggtcag    300

ggcactaagg tcgagattaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

<210> SEQ ID NO 280
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 280

```
Ser Gly Asp Asn Ile Gly Ser Met Thr Ala His
1               5                   10
```

<210> SEQ ID NO 281
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 281

```
Asp Lys Asn Glu Arg Pro Ser
1               5


<210> SEQ ID NO 282
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Gln Ser Trp Asp Asp Ser Tyr Asn Ser Val Val
1               5                   10


<210> SEQ ID NO 283
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Ser Asn Ser Ala Gly Trp Asn
1               5


<210> SEQ ID NO 284
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Arg Ile Tyr Tyr Arg Ser Lys Trp Tyr Asn Asp Tyr Ala Val Ser Val
1               5                   10                  15

Lys Ser


<210> SEQ ID NO 285
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Glu Lys Tyr Thr Val Ser Phe Tyr Asp Phe Phe Asp Tyr
1               5                   10


<210> SEQ ID NO 286
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 286

Gln Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Asn
            20                  25                  30

Ser Ala Gly Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Lys Tyr Thr Val Ser Phe Tyr Asp Phe Phe
            100                 105                 110

Asp Tyr Trp Gly Gln Gly Thr Leu Val Thr Val Ser Ser
        115                 120                 125


<210> SEQ ID NO 287
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 287

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser Met Thr Ala
            20                  25                  30

His Trp Tyr Gln Gln Lys Pro Gly Gln Ala Pro Val Leu Val Ile Tyr
        35                  40                  45

Asp Lys Asn Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Asp Ser Tyr Asn Ser
                85                  90                  95

Val Val Phe Gly Gly Gly Thr Lys Leu Thr Val Leu
            100                 105


<210> SEQ ID NO 288
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 288

caggtgcaat tgcagcagag cggtccgggc ctggtgaaac cgagccagac cctgagcctg      60

acctgcgcga tttccggaga tagcgtgagc tctaactctg ctggttggaa ctggattcgt     120

cagagcccga gccgtggcct cgagtggctg ggccgtatct actaccgtag caaatggtac     180

aacgactatg ccgtgagcgt gaaaagccgc attaccatta acccggatac ttcgaaaaac     240

cagtttagcc tgcaactgaa cagcgtgacc ccggaagata cggccgtgta ttattgcgcg     300

cgtgaaaaat acactgtttc tttctacgac ttcttcgatt actggggcca aggcaccctg     360
```

gtgactgtta gctca 375

<210> SEQ ID NO 289
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 289
gatatcgaac tgacccagcc gccgagcgtg agcgtgagcc cgggccagac cgcgagcatt 60
acctgtagcg gcgataacat cggttctatg actgctcatt ggtaccagca gaaaccgggc 120
caggcgccgg tgctggtgat ctacgacaaa aacgaacgtc cgagcggcat cccggaacgt 180
tttagcggat ccaacagcgg caacaccgcg accctgacca ttagcggcac ccaggcggaa 240
gacgaagcgg attattactg ccagtcttgg gacgactctt acaactctgt tgtgtttggc 300
ggcggcacga agttaaccgt ccta 324

<210> SEQ ID NO 290
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 290

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Gly Trp Asn Trp Ile Arg Gln Ser Pro Ser Arg Gly Leu Glu
35 40 45

Trp Leu Gly Arg Ile Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Lys Tyr Thr Val Ser Phe Tyr Asp Phe Phe
100 105 110

Asp Tyr Trp Gly Gln Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

Glu Leu Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly Lys
450 455

<210> SEQ ID NO 291
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 291

Asp Ile Glu Leu Thr Gln Pro Pro Ser Val Ser Val Ser Pro Gly Gln
1 5 10 15

Thr Ala Ser Ile Thr Cys Ser Gly Asp Asn Ile Gly Ser Met Thr Ala
20 25 30

His Trp Tyr Gln Gln Lys Pro Gly Gln Ala Pro Val Leu Val Ile Tyr
35 40 45

Asp Lys Asn Glu Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Asp Asp Ser Tyr Asn Ser
85 90 95

Val Val Phe Gly Gly Gly Thr Lys Leu Thr Val Leu Gly Gln Pro Lys
100 105 110

```
Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 292
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 292

```
caggtgcaat tgcagcagag cggtccgggc ctggtgaaac cgagccagac cctgagcctg     60

acctgcgcga tttccggaga tagcgtgagc tctaactctg ctggttggaa ctggattcgt    120

cagagcccga gccgtggcct cgagtggctg ggccgtatct actaccgtag caaatggtac    180

aacgactatg ccgtgagcgt gaaaagccgc attaccatta acccggatac ttcgaaaaac    240

cagtttagcc tgcaactgaa cagcgtgacc ccggaagata cggccgtgta ttattgcgcg    300

cgtgaaaaat acactgtttc tttctacgac ttcttcgatt actggggcca aggcaccctg    360

gtgactgtta gctcagcctc caccaagggt ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaactcctgg ggggaccgtc agtcttcctc ttccccccaa aacccaagga caccctcatg    780

atctcccgga cccctgaggt cacatgcgtg gtggtggacg tgagccacga agaccctgag    840

gtcaagttca actggtacgt ggacggcgtg gaggtgcata atgccaagac aaagccgcgg    900

gaggagcagt acaacagcac gtaccgggtg gtcagcgtcc tcaccgtcct gcaccaggac    960

tggctgaatg gcaaggagta caagtgcaag gtctccaaca aagccctccc agcccccatc   1020

gagaaaacca tctccaaagc caaagggcag ccccgagaac cacaggtgta caccctgccc   1080

ccatcccggg aggagatgac caagaaccag gtcagcctga cctgcctggt caaaggcttc   1140

tatcccagcg acatcgccgt ggagtgggag agcaatgggc agccggagaa caactacaag   1200

accacgcctc ccgtgctgga ctccgacggc tccttcttcc tctacagcaa gctcaccgtg   1260

gacaagagca ggtggcagca ggggaacgtc ttctcatgct ccgtgatgca tgaggctctg   1320

cacaaccact acacgcagaa gagcctctcc ctgtctccgg gtaaa                   1365
```

<210> SEQ ID NO 293
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 293
gatatcgaac tgacccagcc gccgagcgtg agcgtgagcc cgggccagac cgcgagcatt 60
acctgtagcg gcgataacat cggttctatg actgctcatt ggtaccagca gaaaccgggc 120
caggcgccgg tgctggtgat ctacgacaaa aacgaacgtc cgagcggcat cccggaacgt 180
tttagcggat ccaacagcgg caacaccgcg accctgacca ttagcggcac ccaggcggaa 240
gacgaagcgg attattactg ccagtcttgg gacgactctt acaactctgt tgtgtttggc 300
ggcggcacga agttaaccgt cctaggtcag cccaaggctg ccccctcggt cactctgttc 360
ccgccctcct ctgaggagct tcaagccaac aaggccacac tggtgtgtct cataagtgac 420
ttctacccgg gagccgtgac agtggcctgg aaggcagata gcagccccgt caaggcggga 480
gtggagacca ccacaccctc caaacaaagc aacaacaagt acgcggccag cagctatctg 540
agcctgacgc ctgagcagtg gaagtcccac agaagctaca gctgccaggt cacgcatgaa 600
gggagcaccg tggagaagac agtggcccct acagaatgtt ca 642

<210> SEQ ID NO 294
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 294

Ser Gly Asp Ala Ile Gly Thr Lys Phe Ala His
1 5 10

<210> SEQ ID NO 295
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 295

Tyr Asp His Glu Arg Pro Ser
1 5

<210> SEQ ID NO 296
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 296

Tyr Ser Arg Ala Ser Ser Asn Leu Val
1 5

<210> SEQ ID NO 297
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 297

Asp His Ala Ile Asp
1 5

<210> SEQ ID NO 298
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 298

Val Ile Ala Gly Ser Gly Ser Ile Thr Tyr Tyr Ala Asp Ser Val Lys
1 5 10 15

Gly

<210> SEQ ID NO 299
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 299

Asp Thr Gly Val Tyr Arg Glu Tyr Met Asp Val
1 5 10

<210> SEQ ID NO 300
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 300

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Ala Ile Asp Trp Val Arg Gln Ala Pro Gly Lys Gly Leu Glu Trp Val
35 40 45

Ser Val Ile Ala Gly Ser Gly Ser Ile Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Thr Gly Val Tyr Arg Glu Tyr Met Asp Val Trp Gly Gln
100 105 110

```
Gly Thr Leu Val Thr Val Ser Ser
        115                 120


<210> SEQ ID NO 301
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 301

Ser Tyr Glu Leu Thr Gln Pro Leu Ser Val Ser Val Ala Leu Gly Gln
1               5                   10                  15

Thr Ala Arg Ile Thr Cys Ser Gly Asp Ala Ile Gly Thr Lys Phe Ala
            20                  25                  30

His Trp Tyr Gln Gln Lys Pro Gly Gln Ala Pro Val Leu Val Ile Tyr
        35                  40                  45

Tyr Asp His Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Tyr Ser Arg Ala Ser Ser Asn Leu Val
                85                  90                  95

Phe Gly Gly Gly Thr Lys Leu Thr Val Leu
            100                 105


<210> SEQ ID NO 302
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302

gaagtgcaat tgctggaaag cggcggtggc ctggtgcagc cgggtggcag cctgcgtctg     60

agctgcgcgg cgtccggatt caccttttct gaccatgcta tcgactgggt gcgccaggcc    120

ccgggcaaag gtctcgagtg ggtttccgtt atcgctggta gcggttctat cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgacact    300

ggtgtttacc gtgaatacat ggatgtttgg ggccaaggca ccctggtgac tgttagctca    360


<210> SEQ ID NO 303
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303

agctatgaac tgacccagcc gctgagcgtg agcgtggcgc tgggccagac cgcgcgcatt     60

acctgtagcg gcgatgctat cggtactaaa ttcgctcatt ggtaccagca gaaaccgggc    120

caggcgccgg tgctggtgat ctactacgac catgaacgtc cgagcggcat cccggaacgt    180
```

tttagcggat ccaacagcgg caacaccgcg accctgacca ttagccgcgc gcaggcgggc 240
gacgaagcgg attattactg ctactctcgt gcttcttcta acctggtgtt tggcggcggc 300
acgaagttaa ccgtccta 318

<210> SEQ ID NO 304
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 304

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Ala Ile Asp Trp Val Arg Gln Ala Pro Gly Lys Gly Leu Glu Trp Val
35 40 45

Ser Val Ile Ala Gly Ser Gly Ser Ile Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Thr Gly Val Tyr Arg Glu Tyr Met Asp Val Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu

```
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 305
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 305

Ser Tyr Glu Leu Thr Gln Pro Leu Ser Val Ser Val Ala Leu Gly Gln
1               5                   10                  15

Thr Ala Arg Ile Thr Cys Ser Gly Asp Ala Ile Gly Thr Lys Phe Ala
            20                  25                  30

His Trp Tyr Gln Gln Lys Pro Gly Gln Ala Pro Val Leu Val Ile Tyr
        35                  40                  45

Tyr Asp His Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Tyr Ser Arg Ala Ser Ser Asn Leu Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 306
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 306
gaagtgcaat tgctggaaag cggcggtggc ctggtgcagc cgggtggcag cctgcgtctg 60
agctgcgcgg cgtccggatt caccttttct gaccatgcta tcgactgggt gcgccaggcc 120
ccgggcaaag gtctcgagtg ggtttccgtt atcgctggta gcggttctat cacctactat 180
gcggatagcg tgaaaggccg ctttaccatc agccgcgata attcgaaaaa caccctgtat 240
ctgcaaatga acagcctgcg tgcggaagat acggccgtgt attattgcgc gcgtgacact 300
ggtgtttacc gtgaatacat ggatgtttgg ggccaaggca ccctggtgac tgttagctca 360
gcctccacca agggtccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gggtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

<210> SEQ ID NO 307
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 307
agctatgaac tgacccagcc gctgagcgtg agcgtggcgc tgggccagac cgcgcgcatt 60
acctgtagcg gcgatgctat cggtactaaa ttcgctcatt ggtaccagca gaaaccgggc 120
caggcgccgg tgctggtgat ctactacgac catgaacgtc cgagcggcat cccggaacgt 180
tttagcggat ccaacagcgg caacaccgcg accctgacca ttagccgcgc gcaggcgggc 240

```
gacgaagcgg attattactg ctactctcgt gcttcttcta acctggtgtt tggcggcggc    300

acgaagttaa ccgtcctagg tcagcccaag gctgcccct cggtcactct gttcccgccc    360

tcctctgagg agcttcaagc caacaaggcc acactggtgt gtctcataag tgacttctac    420

ccgggagccg tgacagtggc ctggaaggca gatagcagcc ccgtcaaggc gggagtggag    480

accaccacac cctccaaaca aagcaacaac aagtacgcgg ccagcagcta tctgagcctg    540

acgcctgagc agtggaagtc ccacagaagc tacagctgcc aggtcacgca tgaagggagc    600

accgtggaga agacagtggc ccctacagaa tgttca                              636
```

```
<210> SEQ ID NO 308
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Arg Ala Ser Gln Gly Ile Phe Thr Tyr Leu Asn
1               5                   10


<210> SEQ ID NO 309
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Ala Ala Ser Thr Leu Gln Ser
1               5


<210> SEQ ID NO 310
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Gln Gln Tyr Tyr Ser Thr Ser Leu Thr
1               5


<210> SEQ ID NO 311
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ser Gln Ser Ala Ala Trp Asn
1               5


<210> SEQ ID NO 312
<211> LENGTH: 18
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic peptide"

<400> SEQUENCE: 312

Arg Ile Tyr Tyr Arg Ser Lys Trp Tyr Asn Asp Tyr Ala Val Ser Val
1 5 10 15

Lys Ser

<210> SEQ ID NO 313
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 313

Glu Arg Ser Tyr Arg Asp Tyr Phe Asp Tyr
1 5 10

<210> SEQ ID NO 314
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 314

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Gln
20 25 30

Ser Ala Ala Trp Asn Trp Ile Arg Gln Ser Pro Ser Arg Gly Leu Glu
35 40 45

Trp Leu Gly Arg Ile Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Arg Ser Tyr Arg Asp Tyr Phe Asp Tyr Trp
100 105 110

Gly Gln Gly Thr Leu Val Thr Val Ser Ser
115 120

<210> SEQ ID NO 315
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 315

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Phe Thr Tyr

```
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Ser Leu
                85                  90                  95

Thr Phe Gly Gln Gly Thr Lys Val Glu Ile Lys
            100                 105
```

<210> SEQ ID NO 316
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 316

```
caggtgcagc tgcagcagtc aggccctggc ctggtcaagc ctagtcagac cctgagcctg     60

acctgcgcta ttagcggcga tagtgtgtct agtcagtcag ccgcctggaa ctggattaga    120

cagtcaccct ctaggggcct ggagtggctg ggtagaatct actataggtc taagtggtat    180

aacgactacg ccgtcagcgt gaagtctagg atcactatta accccgacac ctctaagaat    240

cagtttagcc tgcagctgaa tagcgtgacc cccgaggaca ccgccgtcta ctactgcgct    300

agagagcggt cctatagaga ctacttcgac tactggggtc agggcaccct ggtcaccgtg    360

tctagc                                                               366
```

<210> SEQ ID NO 317
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 317

```
gatattcaga tgactcagtc acctagtagc ctgagcgcta gtgtgggcga tagagtgact     60

atcacctgta gagcctctca gggaatcttc acctacctga actggtatca gcagaagccc    120

ggtaaagccc ctaagctgct gatctacgcc gcctctaccc tgcagtcagg cgtgccctct    180

aggtttagcg gtagcggtag tggcaccgac ttcaccctga ctatctctag cctgcagccc    240

gaggacttcg ctacctacta ctgtcagcag tactactcta ctagcctgac cttcggtcag    300

ggcactaagg tcgagattaa g                                              321
```

<210> SEQ ID NO 318
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 318

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Arg Ser Tyr Arg Asp Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
```

```
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 319
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Phe Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Ser Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 320
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 320

caggtgcagc tgcagcagtc aggccctggc ctggtcaagc ctagtcagac cctgagcctg      60

acctgcgcta ttagcggcga tagtgtgtct agtcagtcag ccgcctggaa ctggattaga     120

cagtcaccct ctaggggcct ggagtggctg ggtagaatct actataggtc taagtggtat     180
```

aacgactacg ccgtcagcgt gaagtctagg atcactatta accccgacac ctctaagaat 240
cagtttagcc tgcagctgaa tagcgtgacc cccgaggaca ccgccgtcta ctactgcgct 300
agagagcggt cctatagaga ctacttcgac tactggggtc agggcaccct ggtcaccgtg 360
tctagcgcta gcactaaggg cccaagtgtg tttcccctgg cccccagcag caagtctact 420
tccggcggaa ctgctgccct gggttgcctg gtgaaggact acttccccga gcccgtgaca 480
gtgtcctgga actctggggc tctgacttcc ggcgtgcaca ccttccccgc cgtgctgcag 540
agcagcggcc tgtacagcct gagcagcgtg gtgacagtgc cctccagctc tctgggaacc 600
cagacctata tctgcaacgt gaaccacaag cccagcaaca ccaaggtgga caagagagtg 660
gagcccaaga gctgcgacaa gacccacacc tgcccccct gcccagctcc agaactgctg 720
ggagggcctt ccgtgttcct gttcccccc aagcccaagg acaccctgat gatcagcagg 780
acccccgagg tgacctgcgt ggtggtggac gtgtcccacg aggacccaga ggtgaagttc 840
aactggtacg tggacggcgt ggaggtgcac aacgccaaga ccaagcccag agaggagcag 900
tacaacagca cctacagggt ggtgtccgtg ctgaccgtgc tgcaccagga ctggctgaac 960
ggcaaagaat acaagtgcaa agtctccaac aaggccctgc cagccccaat cgaaaagaca 1020
atcagcaagg ccaagggcca gccacgggag ccccaggtgt acaccctgcc ccccagccgg 1080
gaggagatga ccaagaacca ggtgtccctg acctgtctgg tgaagggctt ctaccccagc 1140
gatatcgccg tggagtggga gagcaacggc cagcccgaga acaactacaa gaccaccccc 1200
ccagtgctgg acagcgacgg cagcttcttc ctgtacagca agctgaccgt ggacaagtcc 1260
aggtggcagc agggcaacgt gttcagctgc agcgtgatgc acgaggccct gcacaaccac 1320
tacacccaga agtccctgag cctgagcccc ggcaag 1356

<210> SEQ ID NO 321
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 321
gatattcaga tgactcagtc acctagtagc ctgagcgcta gtgtgggcga tagagtgact 60
atcacctgta gagcctctca gggaatcttc acctacctga actggtatca gcagaagccc 120
ggtaaagccc ctaagctgct gatctacgcc gcctctaccc tgcagtcagg cgtgccctct 180
aggtttagcg gtagcggtag tggcaccgac ttcaccctga ctatctctag cctgcagccc 240
gaggacttcg ctacctacta ctgtcagcag tactactcta ctagcctgac cttcggtcag 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 322
<211> LENGTH: 11
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 322

Ser Gly Asp Asn Ile Gly Ser Met Thr Ala His
1 5 10

<210> SEQ ID NO 323
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 323

Asp Lys Asn Glu Arg Pro Ser
1 5

<210> SEQ ID NO 324
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 324

Gln Ser Trp Asp Asp Ser Tyr Thr Ser Val Val
1 5 10

<210> SEQ ID NO 325
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 325

Ser Gln Ser Ala Gly Trp Asn
1 5

<210> SEQ ID NO 326
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 326

Arg Ile Tyr Tyr Arg Ser Lys Trp Tyr Asn Asp Tyr Ala Val Ser Val
1 5 10 15

Lys Ser

<210> SEQ ID NO 327
<211> LENGTH: 13
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 327

```
Glu Lys Tyr Thr Val Ser Phe Tyr Asp Phe Phe Asp Tyr
1               5                   10
```

<210> SEQ ID NO 328
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 328

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Gly Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Lys Tyr Thr Val Ser Phe Tyr Asp Phe Phe
            100                 105                 110

Asp Tyr Trp Gly Gln Gly Thr Leu Val Thr Val Ser Ser
        115                 120                 125
```

<210> SEQ ID NO 329
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 329

```
Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Met Thr Ala
            20                  25                  30

His Trp Tyr Gln Gln Lys Pro Gly Gln Ala Pro Val Leu Val Ile Tyr
        35                  40                  45

Asp Lys Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp Asp Ser Tyr Thr Ser
                85                  90                  95

Val Val Phe Gly Gly Gly Thr Lys Leu Thr Val Leu
            100                 105
```

<210> SEQ ID NO 330
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 330
caggtgcaat tgcagcagag cggtccgggc ctggtgaaac cgagccagac cctgagcctg 60
acctgcgcga tttccggaga tagcgtgagc tctcagtctg ctggttggaa ctggattcgt 120
cagagcccga gccgtggcct cgagtggctg ggccgtatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgtgaaaaat acactgtttc tttctacgac ttcttcgatt actggggcca aggcaccctg 360
gtgactgtta gctca 375

<210> SEQ ID NO 331
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 331
agctatgaac tgacccagcc gctgagcgtg agcgtggcgc tgggccagac cgcgcgcatt 60
acctgtagcg gcgataacat cggttctatg actgctcatt ggtaccagca gaaaccgggc 120
caggcgccgg tgctggtgat ctacgacaaa aacgaacgtc cgagcggcat cccggaacgt 180
tttagcggat ccaacagcgg caacaccgcg accctgacca ttagccgcgc gcaggcgggc 240
gacgaagcgg attattactg ccagtcttgg gacgactctt acacctctgt tgtgtttggc 300
ggcggcacga agttaaccgt ccta 324

<210> SEQ ID NO 332
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 332

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Gln
20 25 30

Ser Ala Gly Trp Asn Trp Ile Arg Gln Ser Pro Ser Arg Gly Leu Glu
35 40 45

Trp Leu Gly Arg Ile Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

```
Tyr Tyr Cys Ala Arg Glu Lys Tyr Thr Val Ser Phe Tyr Asp Phe Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 333
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 333

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Met Thr Ala
            20                  25                  30

His Trp Tyr Gln Gln Lys Pro Gly Gln Ala Pro Val Leu Val Ile Tyr
        35                  40                  45

Asp Lys Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp Asp Ser Tyr Thr Ser
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 334
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 334
caggtgcaat tgcagcagag cggtccgggc ctggtgaaac cgagccagac cctgagcctg 60
acctgcgcga tttccggaga tagcgtgagc tctcagtctg ctggttggaa ctggattcgt 120
cagagcccga gccgtggcct cgagtggctg ggccgtatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgtgaaaaat acactgtttc tttctacgac ttcttcgatt actggggcca aggcaccctg 360
gtgactgtta gctcagcctc caccaagggt ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaactcctgg ggggaccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgggtg gtcagcgtcc tcaccgtcct gcaccaggac 960
tggctgaatg gcaaggagta caagtgcaag gtctccaaca aagccctccc agcccccatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctacagcaa gctcaccgtg 1260
gacaagagca ggtggcagca ggggaacgtc ttctcatgct ccgtgatgca tgaggctctg 1320
cacaaccact acacgcagaa gagcctctcc ctgtctccgg gtaaa 1365

<210> SEQ ID NO 335
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 335
agctatgaac tgacccagcc gctgagcgtg agcgtggcgc tgggccagac cgcgcgcatt 60
acctgtagcg gcgataacat cggttctatg actgctcatt ggtaccagca gaaaccgggc 120
caggcgccgg tgctggtgat ctacgacaaa aacgaacgtc cgagcggcat cccggaacgt 180
tttagcggat ccaacagcgg caacaccgcg accctgacca ttagccgcgc gcaggcgggc 240
gacgaagcgg attattactg ccagtcttgg gacgactctt acacctctgt tgtgtttggc 300
ggcggcacga agttaaccgt cctaggtcag cccaaggctg ccccctcggt cactctgttc 360
ccgccctcct ctgaggagct tcaagccaac aaggccacac tggtgtgtct cataagtgac 420
ttctacccgg gagccgtgac agtggcctgg aaggcagata gcagccccgt caaggcggga 480
gtggagacca ccacaccctc caaacaaagc aacaacaagt acgcggccag cagctatctg 540
agcctgacgc ctgagcagtg gaagtcccac agaagctaca gctgccaggt cacgcatgaa 600
gggagcaccg tggagaagac agtggcccct acagaatgtt ca 642

<210> SEQ ID NO 336
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 336

Val Thr Ala Thr Asp Ala Asp Asp Pro Thr Tyr Gly Asn Ser Ala Lys
1               5                   10                  15

Val Val Tyr

<210> SEQ ID NO 337
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 337

Ile Gln Thr Leu His Ala Val Asp Lys Asp Asp Pro Tyr Ser Gly His
1 5 10 15

Gln Phe Ser Phe
20

<210> SEQ ID NO 338
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 338

Phe Leu Leu Glu Glu Tyr Thr Gly Ser Asp
1 5 10

<210> SEQ ID NO 339
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 339

Ala Lys Val Val Tyr Ser Ile Leu
1 5

<210> SEQ ID NO 340
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 340

Gln Gly Gln Pro Tyr Phe Ser Val Glu Ser Glu Thr Gly Ile Ile Lys
1 5 10 15

Thr Ala Leu

<210> SEQ ID NO 341
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 341

Asp Arg Glu Asn Arg Glu Gln Tyr Gln Val Val Ile Gln
1 5 10

<210> SEQ ID NO 342
<211> LENGTH: 28
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 342

Phe Lys Thr Pro Glu Ser Ser Pro Pro Gly Thr Pro Ile Gly Arg Ile
1 5 10 15

Lys Ala Ser Asp Ala Asp Val Gly Glu Asn Ala Glu
20 25

<210> SEQ ID NO 343
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 343

Ile Glu Tyr Ser Ile Thr Asp Gly Glu Gly Leu Asp Met
1 5 10

<210> SEQ ID NO 344
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 344

Phe Asp Val Ile Thr Asp Gln Glu Thr Gln Glu Gly Ile Ile Thr
1 5 10 15

<210> SEQ ID NO 345
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 345

Val Lys Lys Leu Leu Asp
1 5

<210> SEQ ID NO 346
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 346

Phe Glu Lys Lys Lys Val Tyr Thr Leu Lys Val Glu Ala Ser Asn Pro
1 5 10 15

Tyr Val Glu Pro Arg Phe
20

<210> SEQ ID NO 347

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Phe Glu Lys Lys Lys Val Tyr Thr Leu
1               5


<210> SEQ ID NO 348
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Val Arg Ile Val Val Glu Asp
1               5


<210> SEQ ID NO 349
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Ala Gln Asp Pro Asp Ala Ala Arg Asn Pro Val Lys Tyr Ser Val Asp
1               5                   10                  15

Arg His Thr Asp Met
            20


<210> SEQ ID NO 350
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 350

Ile Ala Thr Glu Ile Asn Asn Pro Lys Gln Ser Ser Arg Val Pro Leu
1               5                   10                  15

Tyr Ile Lys Val Leu Asp Val Asn Asp Asn Ala Pro Glu Phe
            20                  25                  30


<210> SEQ ID NO 351
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Tyr Leu Leu Pro Val Val Ile Ser Asp Asn Asp Tyr Pro Val Gln Ser
1               5                   10                  15
```

```
Ser Thr Gly Thr Val Thr Val
            20


<210> SEQ ID NO 352
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Ala Asp Val Gly Glu Asn Ala Glu Ile Glu Tyr Ser Ile Thr Asp Gly
1               5                   10                  15

Glu Gly Leu Asp Met
            20


<210> SEQ ID NO 353
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Tyr Glu Thr Phe Val Cys Glu Lys Ala Lys Ala Asp Gln Leu
1               5                   10


<210> SEQ ID NO 354
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Thr Arg Lys Asn Gly Tyr Asn Arg His Glu Met Ser Thr
1               5                   10


<210> SEQ ID NO 355
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Asp Asn Asp Tyr Pro Val Gln Ser Ser Thr Gly Thr Val Thr Val
1               5                   10                  15


<210> SEQ ID NO 356
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

His Ala Val Asp Lys Asp Asp Pro Tyr Ser Gly His Gln Phe Ser Phe
```

1 5 10 15

<210> SEQ ID NO 357
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 357

Asn Lys Asp Asn Thr Ala Gly Ile Leu
1 5

<210> SEQ ID NO 358
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 358

Cys Asp His His Gly Asn Met Gln Ser Cys His Ala Glu Ala
1 5 10

<210> SEQ ID NO 359
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 359

Val Asp Lys Asp Asp Pro Tyr Ser Gly His Gln
1 5 10

<210> SEQ ID NO 360
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 360

Leu Glu Glu Tyr Thr Gly Ser Asp
1 5

<210> SEQ ID NO 361
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 361

Tyr Gln Tyr Val Gly Lys Leu
1 5

<210> SEQ ID NO 362

<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 362

```
Tyr Gln Tyr Val Gly Lys Leu His Ser Asp Gln Asp Arg Gly Asp Gly
1               5                   10                  15

Ser Leu
```

<210> SEQ ID NO 363
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 363

```
Tyr Gln Tyr Val Gly Lys Leu His Ser Asp Gln Asp Arg Gly Asp Gly
1               5                   10                  15

Ser Leu Lys Tyr Ile Leu Ser Gly Asp Gly Ala Gly Asp Leu
            20                  25                  30
```

<210> SEQ ID NO 364
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 364

```
Tyr Ile Leu Ser Gly Asp Gly Ala Gly Asp Leu
1               5                   10
```

<210> SEQ ID NO 365
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 365

```
Phe Ile Ile Asn Glu Asn Thr Gly Asp Ile Gln Ala
1               5                   10
```

<210> SEQ ID NO 366
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 366

```
Phe Ile Ile Asn Glu Asn Thr Gly Asp Ile Gln Ala Thr Lys Arg Leu
1               5                   10                  15

Asp Arg Glu Glu Lys Pro Val Tyr
```

20

<210> SEQ ID NO 367
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 367

Phe Ile Ile Asn Glu Asn Thr Gly Asp Ile Gln Ala Thr Lys Arg Leu
1 5 10 15

Asp Arg Glu Glu Lys Pro Val Tyr Ile Leu
20 25

<210> SEQ ID NO 368
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 368

Phe Ile Ile Asn Glu Asn Thr Gly Asp Ile Gln Ala Thr Lys Arg Leu
1 5 10 15

Asp Arg Glu Glu Lys Pro Val Tyr Ile Leu Arg Ala
20 25

<210> SEQ ID NO 369
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 369

Ile Ile Asn Glu Asn Thr Gly Asp Ile Gln Ala Thr Lys Arg Leu Asp
1 5 10 15

Arg Glu Glu Lys Pro Val Tyr
20

<210> SEQ ID NO 370
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 370

Asn Thr Gly Asp Ile Gln Ala Thr Lys Arg Leu Asp Arg Glu Glu Lys
1 5 10 15

Pro Val Tyr

<210> SEQ ID NO 371
<211> LENGTH: 21
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 371

Asn Thr Gly Asp Ile Gln Ala Thr Lys Arg Leu Asp Arg Glu Glu Lys
1 5 10 15

Pro Val Tyr Ile Leu
20

<210> SEQ ID NO 372
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 372

Thr Lys Arg Leu Asp Arg Glu Glu Lys Pro Val Tyr
1 5 10

<210> SEQ ID NO 373
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 373

Ile Leu Arg Ala Gln Ala Ile Asn Arg Arg Thr Gly Arg Pro Val Glu
1 5 10 15

Pro Glu Ser Glu
20

<210> SEQ ID NO 374
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 374

Ile Leu Arg Ala Gln Ala Ile Asn Arg Arg Thr Gly Arg Pro Val Glu
1 5 10 15

Pro Glu Ser Glu Phe
20

<210> SEQ ID NO 375
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 375

Arg Ala Gln Ala Ile Asn Arg Arg Thr Gly Arg Pro Val Glu Pro Glu
1 5 10 15

Ser Glu

<210> SEQ ID NO 376
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 376

Arg Ala Gln Ala Ile Asn Arg Arg Thr Gly Arg Pro Val Glu Pro Glu
1 5 10 15

Ser Glu Phe

<210> SEQ ID NO 377
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 377

Gln Ala Ile Asn Arg Arg Thr Gly Arg Pro Val Glu Pro Glu Ser Glu
1 5 10 15

<210> SEQ ID NO 378
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 378

Gln Ala Ile Asn Arg Arg Thr Gly Arg Pro Val Glu Pro Glu Ser Glu
1 5 10 15

Phe

<210> SEQ ID NO 379
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 379

Phe Ile Ile Lys Ile His Asp Ile Asn Asp Asn Glu Pro Ile Phe
1 5 10 15

<210> SEQ ID NO 380
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 380

Phe Ile Ile Lys Ile His Asp Ile Asn Asp Asn Glu Pro Ile Phe Thr
1 5 10 15

Lys Glu

<210> SEQ ID NO 381
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 381

Ile Ile Lys Ile His Asp Ile Asn Asp Asn Glu Pro Ile Phe
1 5 10

<210> SEQ ID NO 382
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 382

Ile Ile Lys Ile His Asp Ile Asn Asp Asn Glu Pro Ile Phe Thr
1 5 10 15

<210> SEQ ID NO 383
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 383

Ile Ile Lys Ile His Asp Ile Asn Asp Asn Glu Pro Ile Phe Thr Lys
1 5 10 15

<210> SEQ ID NO 384
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 384

Thr Lys Glu Val Tyr Thr Ala Thr Val Pro Glu Met Ser Asp Val Gly
1 5 10 15

Thr

<210> SEQ ID NO 385
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 385

Thr Lys Glu Val Tyr Thr Ala Thr Val Pro Glu Met Ser Asp Val Gly
1 5 10 15

Thr Phe

<210> SEQ ID NO 386
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 386

Val Tyr Thr Ala Thr Val Pro Glu Met Ser Asp Val Gly Thr Phe
1 5 10 15

<210> SEQ ID NO 387
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 387

Phe Val Val Gln Val Thr Ala Thr
1 5

<210> SEQ ID NO 388
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 388

Val Val Gln Val Thr Ala Thr
1 5

<210> SEQ ID NO 389
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 389

Val Val Gln Val Thr Ala Thr Asp Ala Asp Asp Pro Thr Tyr Gly Asn
1 5 10 15

Ser

<210> SEQ ID NO 390
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 390

Val Val Gln Val Thr Ala Thr Asp Ala Asp Asp Pro Thr Tyr Gly Asn
1 5 10 15

Ser Ala Lys Val Val Tyr
20

<210> SEQ ID NO 391
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 391

Asp Ala Asp Asp Pro Thr Tyr Gly Asn Ser Ala Lys Val Val Tyr
1 5 10 15

<210> SEQ ID NO 392
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 392

Ser Ile Leu Gln Gly Gln Pro Tyr Phe
1 5

<210> SEQ ID NO 393
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 393

Gln Gly Gln Pro Tyr Phe Ser Val Glu
1 5

<210> SEQ ID NO 394
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 394

Ser Val Glu Ser Glu Thr Gly Ile Ile Lys Thr Ala Leu
1 5 10

<210> SEQ ID NO 395
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 395

Ser Glu Thr Gly Ile Ile Lys Thr Ala Leu
1 5 10

<210> SEQ ID NO 396
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 396

Thr Gly Ile Ile Lys Thr Ala Leu Leu
1 5

<210> SEQ ID NO 397
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 397

Leu Asn Met Asp Arg Glu Asn Arg Glu Gln Tyr
1 5 10

<210> SEQ ID NO 398
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 398

Leu Asn Met Asp Arg Glu Asn Arg Glu Gln Tyr Gln
1 5 10

<210> SEQ ID NO 399
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 399

Asp Arg Glu Asn Arg Glu Gln Tyr Gln
1 5

<210> SEQ ID NO 400
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 400

Phe Lys Thr Pro Glu Ser Ser Pro Pro Gly Thr Pro Ile Gly Arg Ile
1 5 10 15

Lys Ala Ser Asp
20

<210> SEQ ID NO 401
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 401

Phe Lys Thr Pro Glu Ser Ser Pro Pro Gly Thr Pro Ile Gly Arg Ile
1 5 10 15

Lys Ala Ser Asp Ala Asp Val Gly Glu Asn
20 25

<210> SEQ ID NO 402
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 402

Tyr Ser Ile Thr Asp Gly Glu Gly Leu Asp Met
1 5 10

<210> SEQ ID NO 403
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 403

Ser Ile Thr Asp Gly Glu Gly Leu Asp Met
1 5 10

<210> SEQ ID NO 404
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 404

Phe Asp Val Ile Thr Asp Gln Glu Thr Gln Glu
1 5 10

<210> SEQ ID NO 405
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 405

Phe Asp Val Ile Thr Asp Gln Glu Thr Gln Glu Gly Ile Ile Thr Val
1 5 10 15

Lys Lys Leu Leu Asp
20

<210> SEQ ID NO 406
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 406

```
Phe Asp Val Ile Thr Asp Gln Glu Thr Gln Glu Gly Ile Ile Thr Val
1               5                   10                  15

Lys Lys Leu Leu Asp Phe
            20
```

<210> SEQ ID NO 407
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 407

```
Phe Asp Val Ile Thr Asp Gln Glu Thr Gln Glu Gly Ile Ile Thr Val
1               5                   10                  15

Lys Lys Leu Leu Asp Phe Glu Lys Lys Lys Val Tyr Thr Leu
            20                  25                  30
```

<210> SEQ ID NO 408
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 408

```
Asp Val Ile Thr Asp Gln Glu Thr Gln Glu Gly Ile Ile Thr Val Lys
1               5                   10                  15

Lys Leu Leu Asp
            20
```

<210> SEQ ID NO 409
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 409

```
Asp Val Ile Thr Asp Gln Glu Thr Gln Glu Gly Ile Ile Thr Val Lys
1               5                   10                  15

Lys Leu Leu Asp Phe
            20
```

<210> SEQ ID NO 410
<211> LENGTH: 20
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 410

Val Ile Thr Asp Gln Glu Thr Gln Glu Gly Ile Ile Thr Val Lys Lys
1               5                   10                  15

Leu Leu Asp Phe
            20


<210> SEQ ID NO 411
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Gly Ile Ile Thr Val Lys Lys Leu Leu Asp
1               5                   10


<210> SEQ ID NO 412
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Gly Ile Ile Thr Val Lys Lys Leu Leu Asp Phe
1               5                   10


<210> SEQ ID NO 413
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Val Lys Lys Leu Leu Asp Phe Glu Lys Lys Lys Val Tyr Thr Leu Lys
1               5                   10                  15

Val Glu Ala Ser Asn Pro Tyr Val Glu Pro Arg Phe
            20                  25


<210> SEQ ID NO 414
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Glu Lys Lys Lys Val Tyr Thr Leu
1               5


<210> SEQ ID NO 415
<211> LENGTH: 13
<212> TYPE: PRT
```

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 415

Lys Val Glu Ala Ser Asn Pro Tyr Val Glu Pro Arg Phe
1 5 10

<210> SEQ ID NO 416
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 416

Val Arg Ile Val Val Glu Asp Val Asp Glu Pro Pro Val Phe Ser Lys
1 5 10 15

Leu

<210> SEQ ID NO 417
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 417

Asp Val Asp Glu Pro Pro Val Phe
1 5

<210> SEQ ID NO 418
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 418

Asp Val Asp Glu Pro Pro Val Phe Ser Lys Leu
1 5 10

<210> SEQ ID NO 419
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 419

Val Asp Glu Pro Pro Val Phe
1 5

<210> SEQ ID NO 420
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 420

Val Asp Glu Pro Pro Val Phe Ser Lys Leu
1 5 10

<210> SEQ ID NO 421
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 421

Ala Arg Asn Pro Val Lys Tyr Ser Val Asp Arg His Thr Asp Met
1 5 10 15

<210> SEQ ID NO 422
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 422

Ser Val Asp Arg His Thr Asp Met
1 5

<210> SEQ ID NO 423
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 423

Asp Arg Ile Phe Asn Ile Asp Ser Gly Asn Gly Ser Ile Phe
1 5 10

<210> SEQ ID NO 424
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 424

Thr Ser Lys Leu Leu Asp Arg Glu Thr Leu
1 5 10

<210> SEQ ID NO 425
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 425

Leu Asp Arg Glu Thr Leu Leu
1 5

<210> SEQ ID NO 426
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 426

Ile Ala Thr Glu Ile Asn Asn Pro Lys Gln Ser Ser Arg Val Pro Leu
1 5 10 15

Tyr

<210> SEQ ID NO 427
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 427

Thr Glu Ile Asn Asn Pro Lys Gln Ser Ser Arg Val Pro Leu
1 5 10

<210> SEQ ID NO 428
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 428

Thr Glu Ile Asn Asn Pro Lys Gln Ser Ser Arg Val Pro Leu Tyr
1 5 10 15

<210> SEQ ID NO 429
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 429

Glu Ile Asn Asn Pro Lys Gln Ser Ser Arg Val Pro Leu
1 5 10

<210> SEQ ID NO 430
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 430

Glu Ile Asn Asn Pro Lys Gln Ser Ser Arg Val Pro Leu Tyr
1 5 10

<210> SEQ ID NO 431
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 431

Glu Ile Asn Asn Pro Lys Gln Ser Ser Arg Val Pro Leu Tyr Ile Lys
1 5 10 15

Val Leu Asp Val Asn Asp Asn Ala Pro Glu Phe
20 25

<210> SEQ ID NO 432
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 432

Ile Asn Asn Pro Lys Gln Ser Ser Arg Val Pro Leu Tyr
1 5 10

<210> SEQ ID NO 433
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 433

Tyr Ile Lys Val Leu Asp Val Asn Asp Asn Ala Pro Glu Phe
1 5 10

<210> SEQ ID NO 434
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 434

Ile Lys Val Leu Asp Val Asn Asp Asn Ala Pro Glu Phe
1 5 10

<210> SEQ ID NO 435
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 435

Val Cys Glu Lys Ala Lys Ala Asp Gln Leu 1 5 10

<210> SEQ ID NO 436
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 436

Ile Gln Thr Leu His Ala Val Asp Lys Asp Asp Pro Tyr Ser Gly His
1 5 10 15

Gln

<210> SEQ ID NO 437
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 437

His Ala Val Asp Lys Asp Asp Pro Tyr Ser Gly His Gln
1 5 10

<210> SEQ ID NO 438
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 438

His Ala Val Asp Lys Asp Asp Pro Tyr Ser Gly His Gln Phe Ser
1 5 10 15

<210> SEQ ID NO 439
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 439

Val Asp Lys Asp Asp Pro Tyr Ser Gly His Gln Phe Ser Phe
1 5 10

<210> SEQ ID NO 440
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 440

Arg Val Cys Ala Cys Asp His His Gly Asn Met Gln Ser Cys His Ala
1 5 10 15

<210> SEQ ID NO 441
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 441

Cys Asp His His Gly Asn Met Gln Ser Cys His Ala
1 5 10

<210> SEQ ID NO 442
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 442

Gln Phe Lys Thr Pro Glu Ser Ser Pro Pro
1 5 10

<210> SEQ ID NO 443
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 443

Phe Lys Thr Pro Glu Ser Ser Pro Pro Gly Thr Pro Ile Gly Arg Ile
1 5 10 15

Lys Ala Ser Asp
20

<210> SEQ ID NO 444
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 444

Phe Lys Thr Pro Glu Ser Ser Pro Pro Gly Thr Pro Ile Gly Arg Ile
1 5 10 15

Lys Ala Ser Asp Ala
20

<210> SEQ ID NO 445
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 445

Pro Pro Gly Thr Pro Ile Gly Arg Ile Lys Ala Ser Asp 1 5 10

<210> SEQ ID NO 446
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 446

Ala Asp Val Gly Glu Asn Ala Glu
1 5

<210> SEQ ID NO 447
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 447

Ile Glu Tyr Ser Ile Thr Asp Gly Glu Gly
1 5 10

<210> SEQ ID NO 448
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 448

Ser Ile Thr Asp Gly Glu Gly
1 5

<210> SEQ ID NO 449
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 449

Thr Asp Gly Glu Gly Leu Asp Met
1 5

<210> SEQ ID NO 450
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 450

Phe Asp Val Ile Thr Asp Gln Glu
1 5

<210> SEQ ID NO 451

<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 451

Phe Asp Val Ile Thr Asp Gln Glu Thr Gln Glu
1 5 10

<210> SEQ ID NO 452
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 452

Phe Asp Val Ile Thr Asp Gln Glu Thr Gln Glu Gly Ile Ile Thr Val
1 5 10 15

Lys Lys Leu Leu Asp
20

<210> SEQ ID NO 453
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 453

Phe Asp Val Ile Thr Asp Gln Glu Thr Gln Glu Gly Ile Ile Thr Val
1 5 10 15

Lys Lys Leu Leu Asp Phe
20

<210> SEQ ID NO 454
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 454

Asp Val Ile Thr Asp Gln Glu Thr Gln Glu Gly Ile Ile Thr
1 5 10

<210> SEQ ID NO 455
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 455

Asp Val Ile Thr Asp Gln Glu Thr Gln Glu Gly Ile Ile Thr Val Lys
1 5 10 15

Lys Leu Leu Asp
20

<210> SEQ ID NO 456
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 456

Val Ile Thr Asp Gln Glu Thr Gln Glu Gly Ile Ile Thr Val Lys Lys
1 5 10 15

Leu Leu Asp

<210> SEQ ID NO 457
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 457

Thr Asp Gln Glu Thr Gln Glu
1 5

<210> SEQ ID NO 458
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 458

Asp Gln Glu Thr Gln Glu Gly Ile Ile Thr Val Lys Lys Leu Leu Asp
1 5 10 15

<210> SEQ ID NO 459
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 459

Asp Gln Glu Thr Gln Glu Gly Ile Ile Thr Val Lys Lys Leu Leu Asp
1 5 10 15

Phe

<210> SEQ ID NO 460
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 460

Glu Thr Gln Glu Gly Ile Ile Thr Val Lys Lys Leu Leu Asp
1 5 10

<210> SEQ ID NO 461
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 461

Thr Gln Glu Gly Ile Ile Thr Val Lys Lys Leu Leu Asp
1 5 10

<210> SEQ ID NO 462
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 462

Gly Ile Ile Thr Val Lys Lys Leu Leu Asp
1 5 10

<210> SEQ ID NO 463
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 463

Gly Ile Ile Thr Val Lys Lys Leu Leu Asp Phe
1 5 10

<210> SEQ ID NO 464
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 464

Ile Ile Thr Val Lys Lys Leu Leu Asp Phe
1 5 10

<210> SEQ ID NO 465
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 465

Ile Thr Val Lys Lys Leu Leu Asp
1 5

<210> SEQ ID NO 466
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 466

Ile Thr Val Lys Lys Leu Leu Asp Phe
1 5

<210> SEQ ID NO 467
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 467

Thr Val Lys Lys Leu Leu Asp
1 5

<210> SEQ ID NO 468
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 468

Thr Val Lys Lys Leu Leu Asp Phe
1 5

<210> SEQ ID NO 469
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 469

Val Lys Lys Leu Leu Asp Phe
1 5

<210> SEQ ID NO 470
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 470

Phe Glu Lys Lys Lys Val Tyr Thr
1 5

<210> SEQ ID NO 471
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 471

Glu Lys Lys Lys Val Tyr Thr Leu
1 5

<210> SEQ ID NO 472
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 472

Lys Val Glu Ala Ser Asn Pro Tyr Val Glu Pro Arg Phe
1 5 10

<210> SEQ ID NO 473
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 473

Glu Ala Ser Asn Pro Tyr Val Glu Pro Arg Phe
1 5 10

<210> SEQ ID NO 474
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 474

Leu Tyr Leu Gly Pro Phe Lys Asp Ser Ala Thr
1 5 10

<210> SEQ ID NO 475
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 475

Leu Tyr Leu Gly Pro Phe Lys Asp Ser Ala Thr Val
1 5 10

<210> SEQ ID NO 476
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 476

Leu Gly Pro Phe Lys Asp Ser Ala Thr
1 5

<210> SEQ ID NO 477
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 477

Val Arg Ile Val Val Glu Asp Val Asp Glu Pro Pro Val Phe
1 5 10

<210> SEQ ID NO 478
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 478

Val Arg Ile Val Val Glu Asp Val Asp Glu Pro Pro Val Phe Ser Lys
1 5 10 15

Leu

<210> SEQ ID NO 479
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 479

Val Val Glu Asp Val Asp Glu Pro Pro Val Phe
1 5 10

<210> SEQ ID NO 480
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 480

Asp Val Asp Glu Pro Pro Val Phe
1 5

<210> SEQ ID NO 481
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 481

Asp Val Asp Glu Pro Pro Val Phe Ser Lys Leu
1 5 10

<210> SEQ ID NO 482
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 482

Asp Val Asp Glu Pro Pro Val Phe Ser Lys Leu Ala Tyr
1 5 10

<210> SEQ ID NO 483
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 483

Val Asp Glu Pro Pro Val Phe
1 5

<210> SEQ ID NO 484
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 484

Val Asp Glu Pro Pro Val Phe Ser Lys Leu
1 5 10

<210> SEQ ID NO 485
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 485

Ala Gln Asp Pro Asp Ala Ala Arg Asn Pro Val Lys Tyr
1 5 10

<210> SEQ ID NO 486
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 486

Ala Arg Asn Pro Val Lys Tyr Ser Val Asp Arg His Thr Asp Met
1 5 10 15

<210> SEQ ID NO 487
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 487

Val Asp Arg His Thr Asp Met
1 5

<210> SEQ ID NO 488
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 488

Asp Arg Ile Phe Asn Ile Asp Ser Gly Asn Gly Ser Ile Phe
1 5 10

<210> SEQ ID NO 489
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 489

Thr Ser Lys Leu Leu Asp Arg Glu Thr Leu
1 5 10

<210> SEQ ID NO 490
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 490

Leu Asp Arg Glu Thr Leu Leu
1 5

<210> SEQ ID NO 491
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 491

Ile Ala Thr Glu Ile Asn Asn Pro Lys Gln Ser Ser Arg Val Pro Leu
1 5 10 15

<210> SEQ ID NO 492
<211> LENGTH: 17
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 492

Ile Ala Thr Glu Ile Asn Asn Pro Lys Gln Ser Ser Arg Val Pro Leu
1 5 10 15

Tyr

<210> SEQ ID NO 493
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 493

Thr Glu Ile Asn Asn Pro Lys Gln Ser Ser Arg Val Pro Leu Tyr
1 5 10 15

<210> SEQ ID NO 494
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 494

Thr Glu Ile Asn Asn Pro Lys Gln Ser Ser Arg Val Pro Leu Tyr Ile
1 5 10 15

Lys Val

<210> SEQ ID NO 495
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 495

Glu Ile Asn Asn Pro Lys Gln Ser Ser Arg Val Pro Leu
1 5 10

<210> SEQ ID NO 496
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 496

Glu Ile Asn Asn Pro Lys Gln Ser Ser Arg Val Pro Leu Tyr
1 5 10

<210> SEQ ID NO 497
<211> LENGTH: 13
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 497

Ile Asn Asn Pro Lys Gln Ser Ser Arg Val Pro Leu Tyr
1 5 10

<210> SEQ ID NO 498
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 498

Asn Asn Pro Lys Gln Ser Ser Arg Val Pro Leu
1 5 10

<210> SEQ ID NO 499
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 499

Asn Asn Pro Lys Gln Ser Ser Arg Val Pro Leu Tyr Ile
1 5 10

<210> SEQ ID NO 500
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 500

Tyr Ile Lys Val Leu Asp Val Asn Asp Asn Ala Pro Glu Phe
1 5 10

<210> SEQ ID NO 501
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 501

Ile Lys Val Leu Asp Val Asn Asp
1 5

<210> SEQ ID NO 502
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 502

Ile Lys Val Leu Asp Val Asn Asp Asn Ala Pro Glu Phe
1 5 10

<210> SEQ ID NO 503
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 503

Lys Val Leu Asp Val Asn Asp Asn Ala Pro Glu Phe
1 5 10

<210> SEQ ID NO 504
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 504

Leu Asp Val Asn Asp Asn Ala Pro Glu Phe
1 5 10

<210> SEQ ID NO 505
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 505

Phe Val Cys Glu Lys Ala Lys Ala Asp Gln Leu
1 5 10

<210> SEQ ID NO 506
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 506

Val Cys Glu Lys Ala Lys Ala Asp Gln Leu
1 5 10

<210> SEQ ID NO 507
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 507

Lys Ala Lys Ala Asp Gln Leu
1               5

<210> SEQ ID NO 508
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 508

Ile Gln Thr Leu His Ala Val Asp
1               5

<210> SEQ ID NO 509
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 509

Ile Gln Thr Leu His Ala Val Asp Lys Asp Asp Pro Tyr Ser Gly His
1               5                   10                  15

Gln

<210> SEQ ID NO 510
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 510

Ile Gln Thr Leu His Ala Val Asp Lys Asp Asp Pro Tyr Ser Gly His
1               5                   10                  15

Gln Phe Ser

<210> SEQ ID NO 511
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 511

Ile Gln Thr Leu His Ala Val Asp Lys Asp Asp Pro Tyr Ser Gly His
1               5                   10                  15

Gln Phe Ser Phe
            20

<210> SEQ ID NO 512
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 512

His Ala Val Asp Lys Asp Asp Pro Tyr Ser Gly His Gln
1 5 10

<210> SEQ ID NO 513
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 513

His Ala Val Asp Lys Asp Asp Pro Tyr Ser Gly His Gln Phe Ser
1 5 10 15

<210> SEQ ID NO 514
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 514

Val Asp Lys Asp Asp Pro Tyr Ser Gly His Gln Phe Ser Phe
1 5 10

<210> SEQ ID NO 515
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 515

Ile Leu Thr Arg Lys Asn Gly Tyr Asn Arg His Glu Met Ser Thr
1 5 10 15

<210> SEQ ID NO 516
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 516

Arg Lys Asn Gly Tyr Asn Arg His Glu Met Ser Thr
1 5 10

<210> SEQ ID NO 517
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 517

Tyr Leu Leu Pro Val Val Ile Ser 1 5

<210> SEQ ID NO 518
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 518

Tyr Leu Leu Pro Val Val Ile Ser Asp Asn Asp Tyr
1 5 10

<210> SEQ ID NO 519
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 519

Tyr Leu Leu Pro Val Val Ile Ser Asp Asn Asp Tyr Pro Val Gln
1 5 10 15

<210> SEQ ID NO 520
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 520

Pro Val Val Ile Ser Asp Asn Asp Tyr Pro Val Gln Ser Ser Thr Gly
1 5 10 15

Thr Val Thr Val
20

<210> SEQ ID NO 521
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 521

Arg Val Cys Ala Cys Asp His His Gly Asn Met Gln Ser Cys
1 5 10

<210> SEQ ID NO 522
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 522

Arg Val Cys Ala Cys Asp His His Gly Asn Met Gln Ser Cys His Ala
1 5 10 15

<210> SEQ ID NO 523
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 523

Cys Asp His His Gly Asn Met Gln Ser Cys
1 5 10

<210> SEQ ID NO 524
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 524

Cys Asp His His Gly Asn Met Gln Ser Cys His Ala
1 5 10

<210> SEQ ID NO 525
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 525

Asp His His Gly Asn Met Gln Ser Cys His Ala
1 5 10

<210> SEQ ID NO 526
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 526

Leu Ile His Pro Thr Gly Leu Ser Thr Gly Ala Gly Ser Glu
1 5 10

<210> SEQ ID NO 527
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 527

Phe Arg His Asp Ser Gly Leu
1 5

<210> SEQ ID NO 528
<211> LENGTH: 9

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 528

Phe Arg His Asp Ser Gly Leu Asn Asp
1 5

<210> SEQ ID NO 529
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 529

Glu Ala Gln Lys Ile Glu Trp His
1 5

<210> SEQ ID NO 530
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 530

Glu Ala Gln Lys Ile Glu Trp His Glu
1 5

<210> SEQ ID NO 531
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 531

Glu Phe Arg His Asp Ser
1 5

<210> SEQ ID NO 532
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 532

Leu Glu Val Leu Phe Gln Gly Pro
1 5

<210> SEQ ID NO 533
<211> LENGTH: 790
<212> TYPE: PRT
<213> ORGANISM: Homo sapiens

<400> SEQUENCE: 533

-continued

```
Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Pro Gly Thr Pro Ile Gly
        275                 280                 285

Arg Ile Lys Ala Ser Asp Ala Asp Val Gly Glu Asn Ala Glu Ile Glu
    290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415
```

-continued

```
Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
    450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
    610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Gly Glu Glu Asp Thr Gln Ala Phe
            660                 665                 670

Asp Ile Gly Thr Leu Arg Asn Pro Glu Ala Ile Glu Asp Asn Lys Leu
        675                 680                 685

Arg Arg Asp Ile Val Pro Glu Ala Leu Phe Leu Pro Arg Arg Thr Pro
    690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
        755                 760                 765

Asp Trp Gly Pro Arg Phe Lys Lys Leu Ala Asp Met Tyr Gly Gly Val
    770                 775                 780

Asp Ser Asp Lys Asp Ser
785                 790
```

<210> SEQ ID NO 534
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 534

Glu Phe Tyr Glu Thr Phe Val Cys Glu Lys Ala Lys Ala Asp Gln Leu
1 5 10 15

Ile Gln Thr Leu His Ala Val Asp Lys Asp Asp Pro Tyr Ser Gly His
20 25 30

Gln Phe Ser Phe Ser Leu Ala Pro Glu Ala Ala Ser Gly Ser Asn Phe
35 40 45

Thr Ile Gln Asp Asn Lys Asp Asn Thr Ala Gly Ile Leu Thr Arg Lys
50 55 60

Asn Gly Tyr Asn Arg His Glu Met Ser Thr Tyr Leu Leu Pro Val Val
65 70 75 80

Ile Ser Asp Asn Asp Tyr Pro Val Gln Ser Ser Thr Gly Thr Val Thr
85 90 95

Val Arg Val Cys Ala Cys Asp His His Gly Asn Met Gln Ser Cys His
100 105 110

Ala Glu Ala Leu Ile His Pro
115

<210> SEQ ID NO 535
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 535

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Gly Met His Trp Val Arg Gln Ala Pro Gly Lys Gly Leu Glu Trp Val
35 40 45

Ser Val Ile Ser Gly Ser Gly Ser Asn Thr Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Trp Gly Ser Tyr Ala Phe Asp Ser Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His
225

<210> SEQ ID NO 536
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 536

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Val Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Gly Thr Phe Pro Pro
85 90 95

Thr Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 537
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 537

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

```
Ala Met Ser Trp Val Arg Gln Ala Pro Gly Lys Gly Leu Glu Trp Val
        35                  40                  45

Ser Val Ile Arg Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220


<210> SEQ ID NO 538
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 538

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Leu Trp
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 539
<211> LENGTH: 790
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 539

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Pro Gly Thr Pro Ile Gly
        275                 280                 285

Arg Ile Lys Ala Ser Asp Ala Asp Val Gly Glu Asn Ala Glu Ile Glu
    290                 295                 300
```

```
Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
    450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
    610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Gly Glu Glu Asp Thr Gln Ala Phe
            660                 665                 670

Asp Ile Gly Thr Leu Arg Asn Pro Glu Ala Ile Glu Asp Asn Lys Leu
        675                 680                 685

Arg Arg Asp Ile Val Pro Glu Ala Leu Phe Leu Pro Arg Arg Thr Pro
    690                 695                 700

Thr Ala Arg Asp Asn Thr Asp Val Arg Asp Phe Ile Asn Gln Arg Leu
705                 710                 715                 720
```

```
Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
        755                 760                 765

Asp Trp Gly Pro Arg Phe Lys Lys Leu Ala Asp Met Tyr Gly Gly Val
    770                 775                 780

Asp Ser Asp Lys Asp Ser
785                 790


<210> SEQ ID NO 540
<211> LENGTH: 790
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 540

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Pro Gly Thr Pro Ile Gly
```

-continued

```
        275                 280                 285

Arg Ile Lys Ala Ser Asp Ala Asp Val Gly Glu Asn Ala Glu Ile Glu
    290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
    450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
    610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Gly Glu Glu Asp Thr Gln Ala Phe
            660                 665                 670

Asp Ile Gly Thr Leu Arg Asn Pro Glu Ala Ile Glu Asp Asn Lys Leu
        675                 680                 685

Arg Arg Asp Ile Val Pro Glu Ala Leu Phe Leu Pro Arg Arg Thr Pro
    690                 695                 700
```

Thr Ala Arg Asp Asn Thr Asp Val Arg Asp Phe Ile Asn Gln Arg Leu
705 710 715 720

Lys Glu Asn Asp Thr Asp Pro Thr Ala Pro Pro Tyr Asp Ser Leu Ala
725 730 735

Thr Tyr Ala Tyr Glu Gly Thr Gly Ser Val Ala Asp Ser Leu Ser Ser
740 745 750

Leu Glu Ser Val Thr Thr Asp Ala Asp Gln Asp Tyr Asp Tyr Leu Ser
755 760 765

Asp Trp Gly Pro Arg Phe Lys Lys Leu Ala Asp Met Tyr Gly Gly Val
770 775 780

Asp Ser Asp Lys Asp Ser
785 790

<210> SEQ ID NO 541
<211> LENGTH: 790
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 541

Met Arg Thr Tyr Arg Tyr Phe Leu Leu Leu Phe Trp Val Gly Gln Pro
1 5 10 15

Tyr Pro Thr Leu Ser Thr Pro Leu Ser Lys Arg Thr Ser Gly Phe Pro
20 25 30

Ala Lys Lys Arg Ala Leu Glu Leu Ser Gly Asn Ser Lys Asn Glu Leu
35 40 45

Asn Arg Ser Lys Arg Ser Trp Met Trp Asn Gln Phe Phe Leu Leu Glu
50 55 60

Glu Tyr Thr Gly Ser Asp Tyr Gln Tyr Val Gly Lys Leu His Ser Asp
65 70 75 80

Gln Asp Arg Gly Asp Gly Ser Leu Lys Tyr Ile Leu Ser Gly Asp Gly
85 90 95

Ala Gly Asp Leu Phe Ile Ile Asn Glu Asn Thr Gly Asp Ile Gln Ala
100 105 110

Thr Lys Arg Leu Asp Arg Glu Glu Lys Pro Val Tyr Ile Leu Arg Ala
115 120 125

Gln Ala Ile Asn Arg Arg Thr Gly Arg Pro Val Glu Pro Glu Ser Glu
130 135 140

Phe Ile Ile Lys Ile His Asp Ile Asn Asp Asn Glu Pro Ile Phe Thr
145 150 155 160

Lys Glu Val Tyr Thr Ala Thr Val Pro Glu Met Ser Asp Val Gly Thr
165 170 175

Phe Val Val Gln Val Thr Ala Thr Asp Ala Asp Asp Pro Thr Tyr Gly
180 185 190

Asn Ser Ala Lys Val Val Tyr Ser Ile Leu Gln Gly Gln Pro Tyr Phe
195 200 205

Ser Val Glu Ser Glu Thr Gly Ile Ile Lys Thr Ala Leu Leu Asn Met
210 215 220

Asp Arg Glu Asn Arg Glu Gln Tyr Gln Val Val Ile Gln Ala Lys Asp
225 230 235 240

Met Gly Gly Gln Met Gly Gly Leu Ser Gly Thr Thr Thr Val Asn Ile
245 250 255

-continued

```
Thr Leu Thr Asp Val Asn Asp Asn Pro Pro Arg Phe Pro Gln Ser Thr
            260                 265                 270

Tyr Gln Phe Lys Thr Pro Glu Ser Ser Pro Pro Gly Thr Pro Ile Gly
        275                 280                 285

Arg Ile Lys Ala Ser Asp Ala Asp Val Gly Glu Asn Ala Glu Ile Glu
    290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
    450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
    610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655
```

-continued

```
Val Ser Tyr Asn Asp Glu Gly Gly Gly Glu Glu Asp Thr Gln Ala Phe
            660                 665                 670

Asp Ile Gly Thr Leu Arg Asn Pro Glu Ala Ile Glu Asp Asn Lys Leu
        675                 680                 685

Arg Arg Asp Ile Val Pro Glu Ala Leu Phe Leu Pro Arg Arg Thr Pro
    690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
        755                 760                 765

Asp Trp Gly Pro Arg Phe Lys Lys Leu Ala Asp Met Tyr Gly Gly Val
    770                 775                 780

Asp Ser Asp Lys Asp Ser
785                 790
```